(12) United States Patent
Sakai et al.

(10) Patent No.: US 8,273,741 B2
(45) Date of Patent: Sep. 25, 2012

(54) IMIDAZO-PYRIDAZINYL COMPOUNDS AND USES THEREOF

(75) Inventors: Nozomu Sakai, Osaka (JP); Shinichi Imamura, Ibaraki (JP); Naoki Miyamoto, Ibaraki (JP); Takaharu Hirayama, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 519 days.

(21) Appl. No.: 12/263,949

(22) Filed: Nov. 3, 2008

(65) Prior Publication Data

US 2010/0273788 A1 Oct. 28, 2010

Related U.S. Application Data

(63) Continuation of application No. 12/064,903, filed as application No. PCT/JP2007/065681 on Aug. 3, 2007, now Pat. No. 8,044,049.

(30) Foreign Application Priority Data

Aug. 4, 2006 (JP) ................................. 2006-213981
Dec. 7, 2006 (JP) ................................. 2006-331230
May 30, 2007 (JP) ................................. 2007-144072

(51) Int. Cl.
C07D 487/04 (2006.01)
A01N 43/58 (2006.01)
A61P 35/00 (2006.01)

(52) U.S. Cl. ...................................... 514/248; 544/236
(58) Field of Classification Search .................. 544/236; 514/248

See application file for complete search history.

(56) References Cited

U.S. PATENT DOCUMENTS 7,723,336 B2 * 5/2010 Vaccaro et al. ................ 514/248
2010/0216798 A1 * 8/2010 Nakai et al. .................... 514/248

FOREIGN PATENT DOCUMENTS

| EP | 1 153 920 | | 11/2001 |
|---|---|---|---|
| EP | 1 415 987 | | 5/2004 |
| JP | 08020584 | * | 1/1996 |
| WO | 89/01333 | | 2/1989 |
| WO | 89/01478 | | 2/1989 |
| WO | WO 8901333 | * | 2/1989 |
| WO | WO 8901478 | * | 2/1989 |
| WO | 98/35958 | | 8/1998 |
| WO | 00/42012 | | 7/2000 |
| WO | 00/43366 | | 7/2000 |
| WO | 01/32651 | | 5/2001 |
| WO | 01/60814 | | 8/2001 |
| WO | 02/32872 | | 4/2002 |
| WO | WO 2005066177 | * | 7/2005 |
| WO | 2007/013673 | | 2/2007 |
| WO | WO 2007013673 | * | 2/2007 |
| WO | 2007/025090 | | 3/2007 |
| WO | 2007/025540 | | 3/2007 |
| WO | 2007/038314 | | 4/2007 |
| WO | WO 2007038314 | * | 7/2007 |
| WO | 2008/016131 | | 2/2008 |

OTHER PUBLICATIONS

Barlin, et al., Austral. J. Chem. (1996), 49(4), 443-449 [Barlin (III)].*
Stanovnik, et al., Tetrahedron (1967), 23(1), 387-95.*
Mourad, et al., J. Het. Chem. (1993), 30(5), 1365-72.*
Ishikawa, et al., J. Antibiot. (2001), 54(3), 257-277.*
Registry Compound, Oct. 2008.
Bullock, et al., "Structural Basis of Inhibitor Specificity of the Human Protooncogene Proviral Insertion Site in Moloney Murine Leukemia Virus (PIM-1) Kinase", J. Med. Chem. 2005, 48, 7604-7614.
Mourad, et al., "Synthesis of Imidazo[1,2-b]pyridazines: Fenbendazole, Oxifenbendazole Analogs and Related Derivatives", J. Heterocyclic Chem., 30, 1365-1372, Oct.-Nov. 1993.
Barlin, et al., "Imidazo[1,2-b]pyridazines. II 6-Alkylthio- and 6-Arylthio-3-methoxy-2-phenylimidazo [1,2-b-]pyridazines" Aust. J. Chem., 1987, 40, 1491-7.
Bailin, et al., "Imidazo[1,2-b]pyridazlines IV Syntheses and Central Nervous System Activities of Some 3-Methoxy-6-phenoxy(substituted phenoxy and naphthylocy)-2-phenylimidazo[1,2-b]pyridazines", Aust. J. Chem, 1988, 41, 1735-42.
Trebše, et al., "A Direct Conversion of 5,6,7,8-Tetrahydro-2H-1-Benzo-Pyran-2,5-Diones into Substituted 1-Amion-5,6,7,8-Tetra-Hydroquinoline-2,5-Diones", Heterocycles, vol. 59, No. 1, 129-136, 2003. Trebše, et al., "Transformation of 5-Oxo Substituted Fused Pyran-2-ones. Lactam Versus Hydrazone Formation", Synthetic Communications, 27(15), 2637-2644, 1997.
Golič Grdadolnik, et al., "Structural Investigation of 5-Hydrazono-5,6,7,8-tetrahydro-2H-1-benzopyran-2-ones and 5,6,7,8-Tetrahydroquinoline-2,5(1H)-diones", J. Chem. Inf. Comput. Sci. 1997, 37, 489-494.
Ishikawa, et al., "Synthesis and Antibacterial Activity of 7 β-[2-(5-Amino-1,2,4-thiadiazol-3-yl)-2(Z)-alkoxyiminoacetamido]-3-[(E)-2-(1-alkylimidazo[1,2-b]pyridazinium-6-yl)thiovinyl]-3-cephem-4-carboxylates and Related Compounds", The Journal of Antibiotics, 54(3), 257-277, Mar. 2001.
Matter, Alex, "Tumor angiogenesis as a therapeutic target", DDT vol. 6, No. 19, Oct. 2001, pp. 1005-1024.
Ferrara, et al., "The Biology of Vascular Endothelial Growth Factor", Endocrine Reviews, vol. 18, No. 1, Feb. 1997, pp. 4-25.
Folkamn, Judah, "Tumor Angiogenesis: Therapeutic Implications", The New England Journal of Medicine, vol. 285, No. 21, Nov. 1971, pp. 1182-1186.

* cited by examiner

*Primary Examiner* — James O Wilson
*Assistant Examiner* — Cecilia M Jaisle
(74) *Attorney, Agent, or Firm* — Hamre, Schumann, Mueller & Larson, P.C.

(57) ABSTRACT

The present invention provides a fused heterocyclic derivative having a potent kinase inhibitory activity and use thereof. A compound represented by the formula (I):

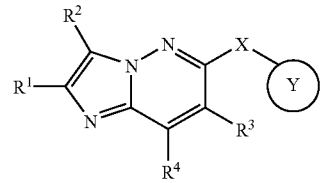

wherein each symbol is as defined in the specification, except a particular compound, or a salt thereof, and a pharmaceutical agent containing the compound or a prodrug thereof, which is a kinase (VEGFR, VEGFR2, PDGFR, Raf) inhibitor, an angiogenesis inhibitor, an agent for the prophylaxis or treatment of cancer, a cancer growth inhibitor or a cancer metastasis suppressor.

23 Claims, No Drawings

SEQUENCE LISTING

```
<160> NUMBER OF SEQ ID NOS: 6

<210> SEQ ID NO 1
<211> LENGTH: 69
<212> TYPE: DNA
<213> ORGANISM: Artificial
<220> FEATURE:
<223> OTHER INFORMATION: Designed oligonucleotide primer to amplify DNA
``` encoding human VEGFR2

<400> SEQUENCE: 1
aattaagtcg acatggacta caaggatgac gatgacaaga agcgggccaa tggaggggaa    60
ctgaagaca                                                           69

<210> SEQ ID NO 2
<211> LENGTH: 42
<212> TYPE: DNA
<213> ORGANISM: Artificial
<220> FEATURE:
<223> OTHER INFORMATION: Designed oligonucleotide primer to amplify DNA
      encoding human VEGFR2

<400> SEQUENCE: 2
aattaagcat gcttaaacag gaggagagct cagtgtggtc cc                       42

<210> SEQ ID NO 3
<211> LENGTH: 64
<212> TYPE: DNA
<213> ORGANISM: Artificial
<220> FEATURE:
<223> OTHER INFORMATION: Designed oligonucleotide primer to amplify DNA
      encoding human BRAF

<400> SEQUENCE: 3
aaagaattca ccatggacta caaggacgac gatgacaaga ccccccctgc ctcattacct    60
ggct                                                                64

<210> SEQ ID NO 4
<211> LENGTH: 35
<212> TYPE: DNA
<213> ORGANISM: Artificial
<220> FEATURE:
<223> OTHER INFORMATION: Designed oligonucleotide primer to amplify DNA
      encoding human BRAF

<400> SEQUENCE: 4
aaaagtcgac tcagtggaca ggaaacgcac catat                               35

<210> SEQ ID NO 5
<211> LENGTH: 29
<212> TYPE: DNA
<213> ORGANISM: Artificial
<220> FEATURE:
<223> OTHER INFORMATION: Designed oligonucleotide primer to introduce
      V600E mutation

<400> SEQUENCE: 5
ggtctagcta cagagaaatc tcgatggag                                      29

<210> SEQ ID NO 6
<211> LENGTH: 29
<212> TYPE: DNA
<213> ORGANISM: Artificial
<220> FEATURE:
<223> OTHER INFORMATION: Designed oligonucleotide primer to introduce
      V600E mutation

<400> SEQUENCE: 6
ctccatcgag atttctctgt agctagacc                                      29

IMIDAZO-PYRIDAZINYL COMPOUNDS AND USES THEREOF

CROSS REFERENCE TO RELATED APPLICATIONS

This application is a Continuation of application Ser. No. 12/064,903, filed Feb. 26, 2008, which is a U.S. National Stage of PCT/JP2007/065681 filed Aug. 3, 2007, which applications are incorporated herein by reference.

TECHNICAL FIELD

The present invention relates to fused heterocyclic derivatives and use thereof. More particularly, the present invention relates to imidazopyridazine derivatives having potent kinase inhibitory activity and useful for the prophylaxis or treatment of cancer and the like.

BACKGROUND OF THE INVENTION

For a solid tumor to grow to a certain size or above, angiogenesis is essential for ensuring sufficient supply of nutrition and oxygen to cancer cell (see, for example, New England Journal of Medicine, 1971, vol. 285, No. 21, pp. 1182-1186). One of the important factors causing angiogenesis toward tumor, a vascular endothelial growth factor (VEGF) is known. VEGF is bound to a vascular endothelial growth factor receptor (VEGFR) expressed on vascular endothelial cells and transmits signal for cell growth (see, for example, Endocrine Reviews, 1997, vol. 18, No. 1, pp. 4-25). Accordingly, inhibition of the VEGF-VEGFR signal transduction system is considered to enable suppression of angiogenesis and tumor growth (see, for example, Drug Discovery Today, 2001, vol. 6, No. 19, pp. 1005-1024). Moreover, since tumor blood vessels are involved in cancer hematogenous metastasis, inhibition of angiogenesis is considered to be effective for suppression of cancer metastasis.

As compounds inhibiting receptor-type tyrosine kinase including VEGFR, phthalazine derivatives (see, for example, WO 98/35958), pyrrole-substituted 2-indolinone derivatives see, for example, WO 01/60814), quinazoline derivatives (see, for example, WO 01/32651), ω-carboxyaryl-substituted diphenylurea derivatives (see, for example, WO 00/42012), quinoline derivatives and quinazoline derivatives (see, for example, WO 00/43366), nitrogen-containing aromatic ring derivatives (see, for example, WO 02/32872) and the like are known.

DISCLOSURE OF THE INVENTION

A kinase inhibitor superior in the affinity for kinase, efficacy expression, pharmacokinetics, solubility, interaction with other pharmaceutical products, safety and stability is expected to show a therapeutically superior effect. At present, however, such inhibitor superior in the affinity for kinase, and sufficiently satisfactory in the efficacy expression, pharmacokinetics, solubility, interaction with other pharmaceutical products, safety and stability has not been found. Thus, there is a demand for the development of a compound having a superior kinase inhibitory activity, and sufficiently satisfactory as a pharmaceutical product. Accordingly, an object of the present invention is to provide a compound having a superior kinase inhibitory activity, low toxic and sufficiently satisfactory as a pharmaceutical product.

The present inventors have conducted intensive studies in an attempt to solve the above-mentioned problems and found that a compound represented by the following formula or a salt thereof has a superior kinase inhibitory activity, which resulted in the completion of the present invention.

Accordingly, the present invention provides the following.

[1] A compound represented by the formula (I):

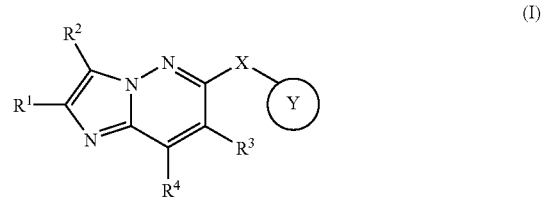

wherein ring Y is an optionally substituted cyclic group;

X is —O—, —S—, —S(O)—, —S(O)$_2$— or —NR— (wherein R is a hydrogen atom or a substituent);

$R^1$ is a hydrogen atom or a substituent;

$R^2$ is a hydrogen atom or a substituent;

$R^3$ is a hydrogen atom or a substituent;

$R^4$ is a hydrogen atom or a substituent;

provided that when $R^1$ is other than an optionally substituted amino, ring Y is a cyclic group substituted by an optionally substituted amino, wherein the cyclic group is optionally further substituted, and that methyl [6-(phenylthio)imidazo[1,2-b]pyridazin-2-yl]carbamate, methyl [6-(phenylsulfinyl)imidazo[1,2-b]pyridazin-2-yl]carbamate, ethyl 6-(4-acetamidophenoxy)imidazo[1,2-b]pyridazine-2-carboxylate, ethyl 6-[4-(4-acetylpiperazin-1-yl)phenoxy]imidazo[1,2-b]pyridazine-2-carboxylate, N-[1-(imidazo[1,2-b]pyridazin-6-ylamino)-2,5-dioxo-1,2,5,6,7,8-hexahydroquinolin-3-yl]benzamide, N-[1-(imidazo[1,2-b]pyridazin-6-ylamino)-7,7-dimethyl-2,5-dioxo-1,2,5,6,7,8-hexahydroquinolin-3-yl]benzamide, N-[1-(imidazo[1,2-b]pyridazin-6-ylamino)-2,5-dioxo-2,5,6,7-tetrahydro-1H-cyclopenta[b]pyridin-3-yl]benzamide, N-[1-(imidazo[1,2-b]pyridazin-6-ylamino)-7-methyl-2,5-dioxo-1,2,5,6,7,8-hexahydroquinolin-3-yl]benzamide, N-[(5E)-5-(imidazo[1,2-b]pyridazin-6-ylhydrazono)-7-methyl-2-oxo-4a,5,6,7,8,8a-hexahydro-2H-chromen-3-yl]benzamide, 4-methoxybenzyl (6R,7R)-3-(imidazo[1,2-b]pyridazin-6-ylthio)-8-oxo-7-[(phenylacetyl)amino]-5-thia-1-azabicyclo[4.2.0]oct-2-ene-2-carboxylate, 4-[(3-methoxy-2-phenylimidazo[1,2-b]pyridazin-6-yl)thio]-N,N-dimethylaniline, 3-methoxy-6-(3-nitrophenoxy)-2-phenylimidazo[1,2-b]pyridazine, 3-[(3-methoxy-2-phenylimidazo[1,2-b]pyridazin-6-yl)oxy]aniline, and 3-[(3-methoxy-2-phenylimidazo[1,2-b]pyridazin-6-yl)oxy]-N,N-dimethylaniline are excluded, or a salt thereof.

[2] The compound of the above-mentioned [1], wherein a compound represented by the formula (II):

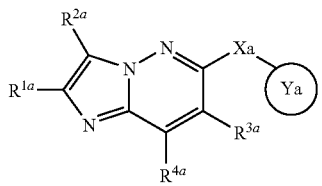

wherein
ring Ya is an optionally substituted cyclic group;
Xa is —O—, —S—, —S(O)—, —S(O)$_2$— or —NR$^a$— (wherein R$^a$ is a hydrogen atom or a substituent);
R$^{1a}$ is an optionally substituted amino;
R$^{2a}$ is a hydrogen atom or a substituent;
R$^{3a}$ is a hydrogen atom or a substituent;
R$^{4a}$ is a hydrogen atom or a substituent;
provided that
methyl [6-(phenylthio)imidazo[1,2-b]pyridazin-2-yl]carbamate and
methyl [6-(phenylsulfinyl)imidazo[1,2-b]pyridazin-2-yl] carbamate are excluded,
or a salt thereof.
[3] The compound of the above-mentioned [2], wherein R$^{1a}$ is
(1) amino,
(2) optionally substituted alkylcarbonylamino,
(3) optionally substituted alkenylcarbonylamino,
(4) optionally substituted alkynylcarbonylamino,
(5) optionally substituted cycloalkylcarbonylamino,
(6) optionally substituted cycloalkyl-alkylcarbonylamino,
(7) optionally substituted 6-membered heterocyclyl-carbonylamino,
(8) optionally substituted aminocarbonylamino,
(9) optionally substituted alkoxycarbonylamino,
(10) optionally substituted alkylsulfonylamino,
(11) optionally substituted cycloalkylsulfonylamino,
(12) optionally substituted arylamino, or
(13) optionally substituted heterocyclylamino.
[4] The compound of the above-mentioned [2], wherein R$^{1a}$ is
(1) amino,
(2) C$_{1-4}$ alkyl-carbonylamino optionally substituted by 1 to 3 substituents selected from
  (a) a halogen atom,
  (b) hydroxy,
  (c) C$_{1-4}$ alkoxy,
  (d) C$_{1-4}$ alkyl-carbonyloxy,
  (e) C$_{1-4}$ alkylamino,
  (f) di-C$_{1-4}$ alkylamino,
  (g) C$_{1-4}$ alkylsulfonyl, and
  (h) a 6-membered heterocyclic group optionally having 1 to 3 C$_{1-4}$ alkyl,
(3) C$_{2-4}$ alkenyl-carbonylamino optionally having C$_{1-4}$ alkoxy,
(4) C$_{2-4}$ alkynyl-carbonylamino,
(5) C$_{3-6}$ cycloalkyl-carbonylamino optionally substituted by 1 to 4 substituents selected from
  (a) a halogen atom,
  (b) hydroxy,
  (c) C$_{1-4}$ alkyl optionally having hydroxy,
  (d) C$_{1-4}$ alkoxy,
  (e) C$_{1-4}$ alkoxy-carbonyl, and
  (f) C$_{1-4}$ alkyl-carbonyloxy,
(6) C$_{3-6}$ cycloalkyl-C$_{1-4}$ alkyl-carbonylamino,
(7) 6-membered heterocyclyl-carbonylamino optionally substituted by 1 to 3 substituents selected from
  (a) a halogen atom,
  (b) cyano, and
  (c) C$_{1-4}$ alkyl optionally having 1 to 3 halogen atoms,
(8) aminocarbonylamino optionally substituted by 1 or 2 substituents selected from
  (a) C$_{1-4}$ alkyl optionally having 1 to 3 C$_{1-4}$ alkoxy optionally having 1 to 3 hydroxy, and
  (b) C$_{1-4}$ alkoxy,
(9) C$_{1-4}$ alkoxy-carbonylamino optionally substituted by 1 to 3 halogen atoms,
(10) C$_{1-4}$ alkylsulfonylamino,
(11) C$_{3-6}$ cycloalkylsulfonylamino,
(12) C$_{6-10}$ arylamino, or
(13) heterocyclylamino optionally substituted by 1 to 3 substituents selected from
  (a) a halogen atom, and
  (b) C$_{1-4}$ alkylamino.
[5] The compound of the above-mentioned [2], wherein R$^{2a}$ is a hydrogen atom.
[6] The compound of the above-mentioned [2], wherein R$^{3a}$ is a hydrogen atom.
[7] The compound of the above-mentioned [2], wherein R$^{4a}$ is a hydrogen atom.
[8] The compound of the above-mentioned [2], wherein Xa is —O—, —S— or —NH—.
[9] The compound of the above-mentioned [2], wherein ring Ya is an optionally substituted aromatic hydrocarbon group or an optionally substituted aromatic heterocyclic group.
[10] The compound of the above-mentioned [2], wherein ring Ya is
(1) C$_{6-10}$ aryl optionally substituted by 1 to 3 substituents selected from
  (a) a halogen atom,
  (b) C$_{1-4}$ alkyl,
  (c) C$_{1-4}$ alkoxy,
  (d) amino optionally substituted by the substituents selected from
    (i) C$_{1-4}$ alkyl optionally substituted by a 5-membered aromatic heterocyclic group optionally substituted by 1 to 3 C$_{1-4}$ alkyl,
    (ii) C$_{1-4}$ alkyl-carbonyl optionally substituted by 1 to 3 substituents selected from
      (i') hydroxy,
      (ii') C$_{1-4}$ alkylsulfonyl, and
      (iii') a 6-membered aromatic heterocyclic group,
    (iii) C$_{2-4}$ alkenyl-carbonyl optionally substituted by C$_{6-10}$ aryl,
    (iv) C$_{2-4}$ alkynyl-carbonyl optionally substituted by C$_{6-10}$ aryl,
    (v) C$_{3-6}$ cycloalkyl-carbonyl,
    (vi) C$_{3-6}$ cycloalkenyl-carbonyl,
    (vii) C$_{6-10}$ aryl-carbonyl optionally substituted by 1 to 3 substituents selected from
      (i') a halogen atom,
      (ii') C$_{1-4}$ alkyl optionally substituted by 1 to 3 substituents selected from a halogen atom, cyano, hydroxy and C$_{3-6}$ cycloalkyl,
      (iii') C$_{3-6}$ cycloalkyl optionally substituted by cyano,
      (iv') C$_{1-4}$ alkoxy optionally substituted by 1 to 5 halogen atoms,
      (v') C$_{1-4}$ alkoxy-carbonyl, and
      (vi') a 5- or 6-membered heterocyclic group optionally substituted by cyano or oxo,
    (viii) 5- or 6-membered heterocyclyl-carbonyl containing, as ring-constituting atom, 1 to 3 heteroatoms selected from oxygen atom, sulfur atom and nitrogen atom besides carbon atoms, which is optionally substituted by 1 to 3 substituents selected from
(i') a halogen atom,
(ii') $C_{1-4}$ alkyl optionally substituted by 1 to 3 substituents selected from a halogen atom, cyano, hydroxy and $C_{1-4}$ alkoxy,
(iii') $C_{6-10}$ aryl,
(iv') $C_{6-10}$ aryl-$C_{1-4}$ alkyl,
(v') $C_{1-4}$ alkoxy optionally substituted by $C_{1-4}$ alkoxy,
(vi') $C_{1-4}$ alkylsulfonyl,
(vii') $C_{1-4}$ alkyl-carbonyl, and
(viii') oxo,
(ix) aromatic fused heterocyclyl-carbonyl,
(x) $C_{1-4}$ alkyl-aminocarbonyl,
(xi) $C_{6-10}$ aryl-aminocarbonyl optionally substituted by $C_{1-4}$ alkyl optionally substituted by 1 to 3 halogen atoms,
(xii) $C_{1-4}$ alkoxy-aminocarbonyl,
(xiii) 5-membered heterocyclyl-aminocarbonyl optionally substituted by 1 to 3 substituents selected from $C_{1-4}$ alkyl and $C_{6-10}$ aryl,
(xiv) aminothiocarbonyl optionally substituted by $C_{6-10}$ aryl-$C_{1-4}$ alkyl-carbonyl, and
(xv) 5-membered aromatic heterocyclyl-sulfonyl optionally substituted by 1 to 3 $C_{1-4}$ alkyl,
(e) $C_{1-4}$ alkyl-aminocarbonyl optionally having $C_{6-10}$ aryl,
(f) 5-membered heterocyclyl-aminocarbonyl optionally substituted by 1 to 3 substituents selected from $C_{1-4}$ alkyl and $C_{6-10}$ aryl,
(g) $C_{6-10}$ aryl-aminocarbonyl optionally substituted by $C_{1-4}$ alkyl optionally substituted by 1 to 3 substituents selected from a halogen atom and cyano,
(h) carboxy, and
(i) nitro,
(2) monocyclic aromatic heterocycle optionally substituted by 1 to 3 substituents selected from
(a) a halogen atom, and
(b) $C_{6-10}$ aryl-carbonylamino optionally substituted by $C_{1-4}$ alkyl optionally substituted by 1 to 3 halogen atoms, or
(3) fused aromatic heterocycle optionally substituted by 1 to 3 substituents selected from
(a) $C_{1-4}$ alkyl, and
(b) $C_{6-10}$ arylamino optionally substituted by $C_{1-4}$ alkyl optionally substituted by 1 to 3 halogen atoms.

[11] A compound selected from the group consisting of:
N-{3-[(2-{[2-(methylamino)pyrimidin-4-yl]amino}imidazo[1,2-b]pyridazin-6-yl)oxy]phenyl}-3-(trifluoromethyl)benzamide;
N-[2-chloro-5-({2-[(cyclopropylcarbonyl)amino]imidazo[1,2-b]pyridazin-6-yl}oxy)phenyl]-1,3-dimethyl-1H-pyrazole-5-carboxamide;
N-[5-({2-[(cyclopropylcarbonyl)amino]imidazo[1,2-b]pyridazin-6-yl}oxy)-2-methylphenyl]-1,3-dimethyl-1H-pyrazole-5-carboxamide;
N-[3-({2-[(cyclopropylcarbonyl)amino]imidazo[1,2-b]pyridazin-6-yl}oxy)phenyl]-2,4-dimethyl-1,3-thiazole-5-carboxamide;
N-[3-({2-[(cyclopropylcarbonyl)amino]imidazo[1,2-b]pyridazin-6-yl}oxy)phenyl]-2,5-dimethyl-1,3-oxazole-4-carboxamide;
N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide;
N-[3-({2-[(N,N-dimethylglycyl)amino]imidazo[1,2-b]pyridazin-6-yl}oxy)phenyl]-1,3-dimethyl-1H-pyrazole-5-carboxamide;
N-[3-({2-[(cyclopropylcarbonyl)amino]imidazo[1,2-b]pyridazin-6-yl}sulfanyl)phenyl]-1,3-dimethyl-1H-pyrazole-5-carboxamide;
N-[5-({2-[(cyclopropylcarbonyl)amino]imidazo[1,2-b]pyridazin-6-yl}oxy)-2-fluorophenyl]-1-ethyl-3-methyl-1H-pyrazole-4-carboxamide;
N-[3-({2-[(cyclopropylcarbonyl)amino]imidazo[1,2-b]pyridazin-6-yl}oxy)phenyl]benzamide;
N-[5-({2-[(cyclopropylcarbonyl)amino]imidazo[1,2-b]pyridazin-6-yl}oxy)-2-fluorophenyl]-1,3-dimethyl-1H-pyrazole-4-carboxamide;
N-[5-({2-[(cyclopropylcarbonyl)amino]imidazo[1,2-b]pyridazin-6-yl}oxy)-2-fluorophenyl]-1-ethyl-1H-pyrazole-5-carboxamide;
N-[5-({2-[(cyclopropylcarbonyl)amino]imidazo[1,2-b]pyridazin-6-yl}oxy)-2-fluorophenyl]-3-methoxy-1-methyl-1H-pyrazole-5-carboxamide;
N-[5-({2-[(cyclopropylcarbonyl)amino]imidazo[1,2-b]pyridazin-6-yl}oxy)-2-fluorophenyl]-3-ethyl-1-methyl-1H-pyrazole-5-carboxamide;
N-[2-chloro-5-({2-[(cyclopropylcarbonyl)amino]imidazo[1,2-b]pyridazin-6-yl}oxy)phenyl]-1-ethyl-3-methyl-1H-pyrazole-4-carboxamide;
N-[5-({2-[(cyclopropylcarbonyl)amino]imidazo[1,2-b]pyridazin-6-yl}oxy)-2-fluorophenyl]-1-methyl-1H-pyrazole-5-carboxamide;
N-[5-({2-[(cyclopropylcarbonyl)amino]imidazo[1,2-b]pyridazin-6-yl}oxy)-2-fluorophenyl]-2,4-dimethyl-1,3-oxazole-5-carboxamide;
N-[5-({2-[(cyclopropylcarbonyl)amino]imidazo[1,2-b]pyridazin-6-yl}oxy)-2-fluorophenyl]-2-ethyl-4-methyl-1,3-oxazole-5-carboxamide;
N-[3-({2-[(cyclopropylcarbonyl)amino]imidazo[1,2-b]pyridazin-6-yl}oxy)phenyl]-3-(trifluoromethyl)benzamide;
3-(1-cyano-1-methylethyl)-N-[5-({2-[(cyclopropylcarbonyl)amino]imidazo[1,2-b]pyridazin-6-yl}oxy)-2-methylphenyl]benzamide;
N-[3-({2-[(N,N-dimethylglycyl)amino]imidazo[1,2-b]pyridazin-6-yl}oxy)phenyl]-3-(trifluoromethyl)benzamide;
N-[3-({2-[(cyclopropylcarbonyl)amino]imidazo[1,2-b]pyridazin-6-yl}thio)phenyl]-3-(trifluoromethyl)benzamide; and
N-{6-[3-({[3-(trifluoromethyl)phenyl]carbamoyl}amino)phenoxy]imidazo[1,2-b]pyridazin-2-yl}cyclopropanecarboxamide,
or a salt thereof.

[12] The compound of the above-mentioned [1], which is a compound of the formula (III):

$$\text{(III)}$$

wherein
ring Yb is a cyclic group substituted by an optionally substituted amino, wherein the cyclic group is optionally further substituted;

Xb is —O—, —S—, —S(O)—, —S(O)$_2$— or —NR$^b$— (wherein R$^b$ is a hydrogen atom or a substituent);

R$^{1b}$ is a hydrogen atom or a substituent (provided that an optionally substituted amino is excluded);

R$^{2b}$ is a hydrogen atom or a substituent;

R$^{3b}$ is a hydrogen atom or a substituent;

R$^{4b}$ is a hydrogen atom or a substituent;

provided that ethyl 6-(4-acetamidophenoxy)imidazo[1,2-b]pyridazine-2-carboxylate, ethyl 6-[4-(4-acetylpiperazin-1-yl)phenoxy]imidazo[1,2-b]pyridazine-2-carboxylate, N-[1-(imidazo[1,2-b]pyridazin-6-ylamino)-2,5-dioxo-1,2,5,6,7,8-hexahydroquinolin-3-yl]benzamide, N-[1-(imidazo[1,2-b]pyridazin-6-ylamino)-7,7-dimethyl-2,5-dioxo-1,2,5,6,7,8-hexahydroquinolin-3-yl]benzamide, N-[1-(imidazo[1,2-b]pyridazin-6-ylamino)-2,5-dioxo-2,5,6,7-tetrahydro-1H-cyclopenta[b]pyridin-3-yl]benzamide, N-[1-(imidazo[1,2-b]pyridazin-6-ylamino)-7-methyl-2,5-dioxo-1,2,5,6,7,8-hexahydroquinolin-3-yl]benzamide, N-[(5E)-5-(imidazo[1,2-b]pyridazin-6-ylhydrazono)-7-methyl-2-oxo-4a,5,6,7,8,8a-hexahydro-2H-chromen-3-yl]benzamide, 4-methoxybenzyl (6R,7R)-3-(imidazo[1,2-b]pyridazin-6-ylthio)-8-oxo-7-[(phenylacetyl)amino]-5-thia-1-azabicyclo[4.2.0]oct-2-ene-2-carboxylate, 4-[(3-methoxy-2-phenylimidazo[1,2-b]pyridazin-6-yl)thio]-N,N-dimethylaniline, 3-methoxy-6-(3-nitrophenoxy)-2-phenylimidazo[1,2-b]pyridazine, 3-[(3-methoxy-2-phenylimidazo[1,2-b]pyridazin-6-yl)oxy]aniline, and 3-[(3-methoxy-2-phenylimidazo[1,2-b]pyridazin-6-yl)oxy]-N,N-dimethylaniline are excluded, or a salt thereof.

[13] A prodrug of the compound of the above-mentioned [1].

[14] A pharmaceutical agent comprising the compound of the above-mentioned [1] or a prodrug thereof.

[15] The pharmaceutical agent of the above-mentioned [14], which is a kinase inhibitor.

[16] The pharmaceutical agent of the above-mentioned [14], which is an inhibitor of vascular endothelial growth factor receptor (VEGFR).

[17] The pharmaceutical agent of the above-mentioned [14], which is an inhibitor of vascular endothelial growth factor receptor (VEGFR) 2.

[18] The pharmaceutical agent of the above-mentioned [14], which is an inhibitor of platelet-derived growth factor receptor (PDGFR).

[19] The pharmaceutical agent of the above-mentioned [14], which is a Raf inhibitor.

[20] The pharmaceutical agent of the above-mentioned [14], which is an angiogenesis inhibitor.

[21] The pharmaceutical agent of the above-mentioned [14], which is an agent for the prophylaxis or treatment of cancer.

[22] The pharmaceutical agent of the above-mentioned [14], which is a cancer growth inhibitor.

[23] The pharmaceutical agent of the above-mentioned [14], which is a cancer metastasis suppressor.

[24] A method for the prophylaxis or treatment of cancer, which comprises administering an effective amount of a compound of the formula (I):

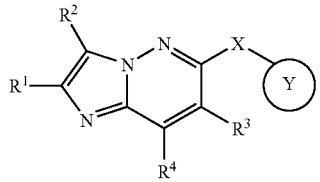

(I)

wherein ring Y is an optionally substituted cyclic group;

X is —O—, —S—, —S(O)—, —S(O)$_2$— or —NR— (wherein R is a hydrogen atom or a substituent);

R$^1$ is a hydrogen atom or a substituent;

R$^2$ is a hydrogen atom or a substituent;

R$^3$ is a hydrogen atom or a substituent;

R$^4$ is a hydrogen atom or a substituent;

provided that when R$^1$ is other than an optionally substituted amino, ring Y is a cyclic group substituted by an optionally substituted amino, wherein the cyclic group is optionally further substituted, and that methyl [6-(phenylthio)imidazo[1,2-b]pyridazin-2-yl]carbamate, methyl [6-(phenylsulfinyl)imidazo[1,2-b]pyridazin-2-yl]carbamate, ethyl 6-(4-acetamidophenoxy)imidazo[1,2-b]pyridazine-2-carboxylate, ethyl 6-[4-(4-acetylpiperazin-1-yl)phenoxy]imidazo[1,2-b]pyridazine-2-carboxylate, N-[1-(imidazo[1,2-b]pyridazin-6-ylamino)-2,5-dioxo-1,2,5,6,7,8-hexahydroquinolin-3-yl]benzamide, N-[1-(imidazo[1,2-b]pyridazin-6-ylamino)-7,7-dimethyl-2,5-dioxo-1,2,5,6,7,8-hexahydroquinolin-3-yl]benzamide, N-[1-(imidazo[1,2-b]pyridazin-6-ylamino)-2,5-dioxo-2,5,6,7-tetrahydro-1H-cyclopenta[b]pyridin-3-yl]benzamide, N-[1-(imidazo[1,2-b]pyridazin-6-ylamino)-7-methyl-2,5-dioxo-1,2,5,6,7,8-hexahydroquinolin-3-yl]benzamide, N-[(5E)-5-(imidazo[1,2-b]pyridazin-6-ylhydrazono)-7-methyl-2-oxo-4a,5,6,7,8,8a-hexahydro-2H-chromen-3-yl]benzamide, 4-methoxybenzyl (6R,7R)-3-(imidazo[1,2-b]pyridazin-6-ylthio)-8-oxo-7-[(phenylacetyl)amino]-5-thia-1-azabicyclo[4.2.0]oct-2-ene-2-carboxylate, 4-[(3-methoxy-2-phenylimidazo[1,2-b]pyridazin-6-yl)thio]-N,N-dimethylaniline, 3-methoxy-6-(3-nitrophenoxy)-2-phenylimidazo[1,2-b]pyridazine, 3-[(3-methoxy-2-phenylimidazo[1,2-b]pyridazin-6-yl)oxy]aniline, and 3-[(3-methoxy-2-phenylimidazo[1,2-b]pyridazin-6-yl)oxy]-N,N-dimethylaniline are excluded, or a salt thereof or a prodrug thereof to the mammal.

[25] Use of a compound of the formula (I) for the production of an agent for the prophylaxis or treatment of cancer:

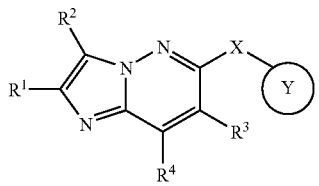

wherein ring Y is an optionally substituted cyclic group;
X is —O—, —S—, —S(O)—, —S(O)$_2$— or —NR— (wherein R is a hydrogen atom or a substituent);
$R^1$ is a hydrogen atom or a substituent;
$R^2$ is a hydrogen atom or a substituent;
$R^3$ is a hydrogen atom or a substituent;
$R^4$ is a hydrogen atom or a substituent;
provided that
when $R^1$ is other than an optionally substituted amino, ring Y is a cyclic group substituted by an optionally substituted amino, wherein the cyclic group is optionally further substituted, and that
methyl [6-(phenylthio)imidazo[1,2-b]pyridazin-2-yl]carbamate, methyl [6-(phenylsulfinyl)imidazo[1,2-b]pyridazin-2-yl]carbamate,
ethyl 6-(4-acetamidophenoxy)imidazo[1,2-b]pyridazine-2-carboxylate,
ethyl 6-[4-(4-acetylpiperazin-1-yl)phenoxy]imidazo[1,2-b]pyridazine-2-carboxylate,
N-[1-(imidazo[1,2-b]pyridazin-6-ylamino)-2,5-dioxo-1,2,5,6,7,8-hexahydroquinolin-3-yl]benzamide,
N-[1-(imidazo[1,2-b]pyridazin-6-ylamino)-7,7-dimethyl-2,5-dioxo-1,2,5,6,7,8-hexahydroquinolin-3-yl]benzamide,
N-[1-(imidazo[1,2-b]pyridazin-6-ylamino)-2,5-dioxo-2,5,6,7-tetrahydro-1H-cyclopenta[b]pyridin-3-yl]benzamide,
N-[1-(imidazo[1,2-b]pyridazin-6-ylamino)-7-methyl-2,5-dioxo-1,2,5,6,7,8-hexahydroquinolin-3-yl]benzamide,
N-[(5E)-5-(imidazo[1,2-b]pyridazin-6-ylhydrazono)-7-methyl-2-oxo-4a,5,6,7,8,8a-hexahydro-2H-chromen-3-yl]benzamide,
4-methoxybenzyl (6R,7R)-3-(imidazo[1,2-b]pyridazin-6-ylthio)-8-oxo-7-[(phenylacetyl)amino]-5-thia-1-azabicyclo[4.2.0]oct-2-ene-2-carboxylate,
4-[(3-methoxy-2-phenylimidazo[1,2-b]pyridazin-6-yl)thio]-N,N-dimethylaniline, 3-methoxy-6-(3-nitrophenoxy)-2-phenylimidazo[1,2-b]pyridazine,
3-[(3-methoxy-2-phenylimidazo[1,2-b]pyridazin-6-yl)oxy]aniline, and
3-[(3-methoxy-2-phenylimidazo[1,2-b]pyridazin-6-yl)oxy]-N,N-dimethylaniline are excluded,
or a salt thereof or a prodrug thereof.

The present invention also includes the following.
[26] A compound of the formula (IV):

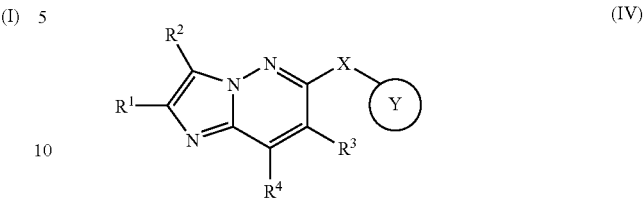

wherein ring Y is an optionally substituted cyclic group;
X is —O—, —S—, —S(O)—, —S(O)$_2$— or —NR— (wherein R is a hydrogen atom or a substituent);
$R^1$ is a hydrogen atom or a substituent;
$R^2$ is a hydrogen atom or a substituent;
$R^3$ is a hydrogen atom or a substituent;
$R^4$ is a hydrogen atom or a substituent;
provided that
where $R^1$ is other than an optionally substituted amino, ring Y is a cyclic group substituted by an optionally substituted amino, wherein the cyclic group is optionally further substituted,
or a salt thereof.
[27] A kinase inhibitor, which comprises the compound of the above-mentioned [26] or a prodrug thereof.
[28] The kinase inhibitor of the above-mentioned [27], wherein the kinase is a vascular endothelial growth factor receptor (VEGFR).
[29] The kinase inhibitor of the above-mentioned [27], wherein the kinase is a vascular endothelial growth factor receptor (VEGFR) 2.
[30] The kinase inhibitor of the above-mentioned [27], wherein the kinase is a platelet-derived growth factor receptor (PDGFR).
[31] The kinase inhibitor of the above-mentioned [27], wherein the kinase is a Raf.
[32] An angiogenesis inhibitor, which comprises the compound of the above-mentioned [26] or a prodrug thereof.
[33] An agent for the prophylaxis or treatment of cancer, which comprises the compound of the above-mentioned [26] or a prodrug thereof.
[34] A cancer growth inhibitor, which comprises the compound of the above-mentioned [26] or a prodrug thereof.
[35] A cancer metastasis suppressor, which comprises the compound of the above-mentioned [26] or a prodrug thereof.
[36] A method for the prophylaxis or treatment of cancer, which comprises administering an effective amount of the compound of the above-mentioned [26] or a prodrug thereof to the mammal.
[37] Use of the compound of the above-mentioned [26] or a prodrug thereof for the production of an agent for the prophylaxis or treatment of cancer.

EFFECT OF THE INVENTION

The compounds represented by the formulas (I) to (IV) of the present invention or salts thereof or prodrugs thereof have strong inhibitory activity against kinases such as vascular endothelial growth factor receptor, platelet-derived growth factor receptor and the like, and have strong angiogenesis inhibitory activity. Therefore, they can provide a clinically useful agent for the prophylaxis or treatment of cancer, a cancer growth inhibitor, or a cancer metastasis suppressor. Furthermore, compounds represented by the formulas (I) to (IV) of the present invention or salts thereof or prodrugs thereof can provide clinically useful agents for the prophylaxis or treatment for applications on diseases other than cancer such as chronic rheumatism, diabetic retinopathy and the like, and have excellent efficacy expression, pharmacokinetics, solubility, interaction with other pharmaceutical products, safety and stability.

Hereinafter the present invention is explained in detail.

A compound represented by the formula (I) (hereinafter to be referred to as compound (I)) and a compound represented by the formula (IV) (hereinafter to be referred to as compound (IV)) of the present invention are explained.

In compounds (I) and (IV), examples of the "cyclic group" of the "optionally substituted cyclic group" for ring Y include aromatic hydrocarbon group, aromatic heterocyclic group (e.g., monocyclic aromatic heterocyclic group, fused aromatic heterocyclic group), non-aromatic cyclic hydrocarbon group, non-aromatic heterocyclic group, fused ring group thereof and the like.

Examples of the aromatic hydrocarbon group include $C_{6-14}$ aryl and the like. Specifically, phenyl, 1-naphthyl, 2-naphthyl, biphenylyl, anthryl, phenanthryl, acenaphthylenyl and the like can be mentioned.

Examples of the monocyclic aromatic heterocyclic group include 5- to 7-membered monocyclic aromatic heterocyclic group containing, as ring-constituting atom, 1 to 4 heteroatoms selected from oxygen atom, sulfur atom and nitrogen atom besides carbon atoms, and the like.

Examples of the monocyclic aromatic heterocyclic group specifically include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl, oxazolyl (e.g., 2-oxazolyl, 4-oxazolyl, 5-oxazolyl), isoxazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl and the like.

Examples of the fused aromatic heterocyclic group include a group formed by fusion of 5- to 7-membered monocyclic aromatic heterocyclic group containing, as ring-constituting atom, 1 to 4 heteroatoms selected from oxygen atom, sulfur atom and nitrogen atom besides carbon atoms, and the like, and $C_{6-14}$ aryl and the like; a group formed by fusion of the above-mentioned 5- to 7-membered monocyclic aromatic heterocyclic groups, and the like.

Examples of the fused aromatic heterocyclic group specifically include quinolyl (e.g., 2-quinolyl, 3-quinolyl, 4-quinolyl, isoquinolyl), quinazolinyl (e.g., 2-quinazolinyl, 4-quinazolinyl), quinoxalinyl (e.g., 2-quinoxalinyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-1-yl, benzimidazol-2-yl, benzimidazol-5-yl, benzimidazol-6-yl), indolyl (e.g., indol-1-yl, indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl, benzotriazolyl, pyrazolopyridyl, pyrazolothienyl, pyrazolotriazinyl and the like.

Examples of the non-aromatic cyclic hydrocarbon group include cycloalkyl, cycloalkenyl, cycloalkadienyl and the like, each of which is optionally fused with benzene ring.

Examples of the non-aromatic cyclic hydrocarbon group specifically include $C_{3-10}$ cycloalkyl (e.g., cyclopropyl, cyclobutyl, cyclopentyl, cyclohexyl, cycloheptyl, cyclooctyl, cyclononyl, cyclodecyl), $C_{3-10}$ cycloalkenyl (e.g., cyclopropenyl, cyclobutenyl, cyclopentenyl, cyclohexenyl, cycloheptenyl, cyclooctenyl, cyclononenyl, cyclodecenyl), $C_{4-10}$ cycloalkadienyl (e.g., cyclobutadienyl, cyclopentadienyl, cyclohexadienyl, cycloheptadienyl, cyclooctadienyl, cyclononadienyl, cyclodecadienyl), fused ring formed by fusion of these groups and benzene ring (e.g., indanyl (e.g., 1-indanyl), tetrahydronaphthyl (e.g., 1,2,3,4-tetrahydronaphthalen-1-yl), fluorenyl (e.g., 9-fluorenyl) etc.), and the like.

Examples of the non-aromatic heterocyclic group include 3- to 8-membered (preferably 5- or 6-membered) saturated or unsaturated (preferably saturated) non-aromatic heterocyclic group and the like.

Examples of the non-aromatic heterocyclic group specifically include oxiranyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azocanyl, oxocanyl, thiocanyl, oxazocanyl, thiazocanyl, dioxinyl and the like.

As the "cyclic group" of the "optionally substituted cyclic group" for ring Y, aromatic hydrocarbon group, aromatic heterocyclic group are preferable. As the aromatic hydrocarbon group, $C_{6-14}$ aryl is preferable, $C_{6-10}$ aryl is more preferable, and phenyl is particularly preferable. As the aromatic heterocyclic group, monocyclic heterocyclic group or fused aromatic heterocyclic group is preferable, pyridine ring, or fused aromatic heterocyclic group formed by fusion of 5-membered monocyclic aromatic heterocyclic group containing, as ring-constituting atom, 1 or 2 heteroatoms selected from sulfur atom and nitrogen atom, besides carbon atoms, and benzene ring (e.g., benzothiazolyl, benzimidazolyl, indolyl etc.) is more preferable, and benzothiazolyl (e.g., 5-benzothiazolyl, 6-benzothiazolyl), benzimidazolyl (e.g., benzimidazol-5-yl, benzimidazol-6-yl), indolyl (e.g., indol-4-yl, indol-5-yl, indol-6-yl) and the like are particularly preferable.

The "optionally substituted cyclic group" for ring Y may have 1 to the acceptable maximum number of substituents at any substitutable positions. Where the cyclic group is substituted by two or more substituents, the substituents may be the same or different, and it is preferable to optionally have 1 to 5, more preferably 1 to 3, particularly preferably 1 or 2 substituents.

As the "substituent" of the "optionally substituted cyclic group" for ring Y, for example,
(i) halogen atom (e.g., fluorine, chlorine, bromine, iodine),
(ii) cyano,
(iii) nitro,
(iv) optionally substituted hydrocarbon group,
(v) hydroxy,
(vi) optionally substituted hydrocarbon-oxy,
(vii) optionally substituted aminosulfonyl,
(viii) optionally substituted aminocarbonyl,
(ix) acyl,
(x) optionally substituted amino,
(xi) optionally substituted sulfanyl,
(xii) optionally substituted heterocyclic group,
(xiii) optionally substituted heterocyclyl-oxy,
(xiv) oxo,
(xv) optionally substituted sulfinyl, (xvi) optionally substituted aminothiocarbonyl,
(xvii) optionally esterified carboxy,
and the like (in the present specification, to be referred to as Substituent Group (1)) can be mentioned.

Hereinafter the substituents listed in Substituent Group (1) are explained.

As the "optionally substituted hydrocarbon group" in Substituent Group (1)(iv), alkyl, alkenyl, alkynyl, cycloalkyl, cycloalkenyl, aryl, cycloalkyl-alkyl, cycloalkenyl-alkyl, arylalkyl, cycloalkanedienyl and the like, each of which is optionally substituted, can be mentioned.

In the present specification, examples of the "alkyl" may include linear or branched chain alkyl having 1 to 8, preferably 1 to 6, more preferably 1 to 4 carbons and the like, specifically methyl, ethyl, propyl, isopropyl, butyl, isobutyl, sec-butyl, tert-butyl, pentyl, isopentyl, tert-pentyl, neopentyl, hexyl, isohexyl, heptyl, octyl and the like. The "alkyl" may have, for example, at any substitutable position thereof, 1 to the acceptable maximum number of the substituents selected from the group of the following substituents (hereinafter abbreviated to as "Substituent Group (2)"):

(1) halogen atom (e.g., fluorine, chlorine, bromine, iodine);
(2) cyano;
(3) nitro;
(4) hydroxy;
(5) $C_{1-6}$ alkoxy (e.g., methoxy, ethoxy, propoxy, isopropoxy, butoxy, isobutoxy, tert-butoxy etc.) optionally substituted by 1 to 3 substituents selected from halogen atom (e.g., fluorine, chlorine, bromine, iodine) and $C_{1-6}$ alkoxy (e.g., methoxy, ethoxy, propoxy, isopropoxy, butoxy, isobutoxy, tert-butoxy etc.);
(6) $C_{2-6}$ alkenyloxy (e.g., ethenyloxy, propenyloxy, butenyloxy, pentenyloxy, hexenyloxy etc.) optionally having 1 to 3 halogen atoms (e.g., fluorine, chlorine, bromine, iodine);
(7) $C_{2-6}$ alkynyloxy (e.g., ethynyloxy, propynyloxy, butynyloxy, pentynyloxy, hexynyloxy etc.) optionally having 1 to 3 halogen atoms (e.g., fluorine, chlorine, bromine, iodine);
(8) $C_{3-6}$ cycloalkyl-oxy (e.g., cyclopropyloxy, cyclobutyloxy, cyclopentyloxy, cyclohexyloxy) optionally having 1 to 3 halogen atoms (e.g., fluorine, chlorine, bromine, iodine);
(9) $C_{3-6}$ cycloalkenyloxy (e.g., cyclopropenyloxy, cyclobutenyloxy, cyclopentenyloxy, cyclohexenyloxy etc.) optionally having 1 to 3 halogen atoms (e.g., fluorine, chlorine, bromine, iodine);
(10) $C_{6-10}$ aryloxy (e.g., phenyloxy, 1-naphthyloxy, 2-naphthyloxy etc.) optionally having 1 to 3 halogen atoms (e.g., fluorine, chlorine, bromine, iodine);
(11) $C_{3-6}$ cycloalkyl-$C_{1-6}$ alkoxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 halogen atoms (e.g., fluorine, chlorine, bromine, iodine);
(12) $C_{3-6}$ cycloalkenyl-$C_{1-6}$ alkoxy (e.g., cyclopentenylmethyloxy, cyclohexenylmethyloxy, cyclohexenylethyloxy, cyclohexenylpropyloxy etc.) optionally having 1 to 3 halogen atoms (e.g., fluorine, chlorine, bromine, iodine);
(13) $C_{6-10}$ aryl-$C_{1-6}$ alkoxy (e.g., phenylmethyloxy, phenylethyloxy etc.) optionally having 1 to 3 halogen atoms (e.g., fluorine, chlorine, bromine, iodine);
(14) $C_{1-6}$ alkyl-aminosulfonyl (e.g., methylaminosulfonyl, ethylaminosulfonyl, propylaminosulfonyl etc.);
(15) di-$C_{1-6}$ alkyl-aminosulfonyl (e.g., dimethylaminosulfonyl, diethylaminosulfonyl, dipropylaminosulfonyl etc.);
(16) $C_{1-6}$ alkyl-aminocarbonyl (e.g., methylaminocarbonyl, ethylaminocarbonyl, propylaminocarbonyl etc.);
(17) di-$C_{1-6}$ alkyl-aminocarbonyl (e.g., dimethylaminocarbonyl, diethylaminocarbonyl, dipropylaminocarbonyl etc.);
(18) formyl;
(19) $C_{1-6}$ alkyl-carbonyl (e.g., acetyl, ethylcarbonyl, propylcarbonyl, isopropylcarbonyl etc.);
(20) $C_{2-6}$ alkenyl-carbonyl (e.g., ethenylcarbonyl, propenylcarbonyl, butenylcarbonyl, pentenylcarbonyl, hexenylcarbonyl etc.);
(21) $C_{2-6}$ alkynyl-carbonyl (e.g., ethynylcarbonyl, propynylcarbonyl, butynylcarbonyl, pentynylcarbonyl, hexynylcarbonyl etc.);
(22) $C_{3-6}$ cycloalkyl-carbonyl (e.g., cyclopropylcarbonyl, cyclobutylcarbonyl, cyclopentylcarbonyl, cyclohexylcarbonyl);
(23) $C_{3-6}$ cycloalkenyl-carbonyl (e.g., cyclopropenylcarbonyl, cyclobutenylcarbonyl, cyclopentenylcarbonyl, cyclohexenylcarbonyl etc.);
(24) $C_{6-10}$ aryl-carbonyl (e.g., benzoyl, 1-naphthylcarbonyl, 2-naphthylcarbonyl etc.);
(25) $C_{3-6}$ cycloalkyl-$C_{1-6}$ alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl etc.);
(26) $C_{3-6}$ cycloalkenyl-$C_{1-6}$ alkyl-carbonyl (e.g., cyclopentenylmethylcarbonyl, cyclohexenylmethylcarbonyl, cyclohexenylethylcarbonyl, cyclohexenylpropylcarbonyl etc.);
(27) $C_{6-10}$ aryl-$C_{1-6}$ alkyl-carbonyl (e.g., benzylcarbonyl, phenylethylcarbonyl etc.);
(28) 5- or 6-membered monocyclic aromatic heterocyclyl-carbonyl (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl etc.);
(29) 8- to 12-membered fused aromatic heterocyclyl-carbonyl (e.g., benzofurylcarbonyl, isobenzofurylcarbonyl, benzothienylcarbonyl, isobenzothienylcarbonyl, indolylcarbonyl, isoindolylcarbonyl, 1H-indazolylcarbonyl, benzimidazolylcarbonyl, benzoxazolylcarbonyl etc.);
(30) 5- or 6-membered non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidinylcarbonyl etc.);
(31) $C_{1-6}$ alkylsulfonyl (e.g., methylsulfonyl, ethylsulfonyl etc.);
(32) $C_{2-6}$ alkenylsulfonyl (e.g., ethenylsulfonyl, propenylsulfonyl etc.);
(33) $C_{2-6}$ alkynylsulfonyl (e.g., ethynylsulfonyl, propynylsulfonyl, butynylsulfonyl, pentynylsulfonyl, hexynylsulfonyl etc.);
(34) $C_{3-6}$ cycloalkylsulfonyl (e.g., cyclopropylsulfonyl, cyclobutylsulfonyl etc.);
(35) $C_{3-6}$ cycloalkenylsulfonyl (e.g., cyclopropenylsulfonyl, cyclobutenylsulfonyl etc.);
(36) $C_{6-10}$ arylsulfonyl (e.g., phenylsulfonyl etc.);
(37) $C_{3-6}$ cycloalkyl-$C_{1-6}$ alkyl-sulfonyl (e.g., cyclopropylmethylsulfonyl etc.);
(38) $C_{3-6}$ cycloalkenyl-$C_{1-6}$ alkyl-sulfonyl (e.g., cyclopentenylmethylsulfonyl etc.);
(39) $C_{6-10}$ aryl-$C_{1-6}$ alkyl-sulfonyl (e.g., benzylsulfonyl etc.);
(40) 5- or 6-membered monocyclic aromatic heterocyclyl-sulfonyl (e.g., furylsulfonyl, thienylsulfonyl, pyridylsulfonyl etc.);
(41) 8- to 12-membered fused aromatic heterocyclyl-sulfonyl (e.g., benzofurylsulfonyl, isobenzofurylsulfonyl etc.);
(42) 5- or 6-membered non-aromatic heterocyclyl-sulfonyl (e.g., oxiranylsulfonyl, azetidinylsulfonyl etc.);

(43) amino;
(44) mono-$C_{1-6}$ alkylamino (e.g., methylamino, ethylamino, propylamino, isopropylamino, butylamino, isobutylamino, tert-butylamino etc.);
(45) di-$C_{1-6}$ alkylamino (e.g., dimethylamino, diethylamino, dipropylamino, diisopropylamino, dibutylamino, diisobutylamino, di-tert-butylamino etc.);
(46) mono-($C_{1-6}$ alkyl-carbonyl)amino (e.g., acetylamino, ethylcarbonylamino, propylcarbonylamino, tert-butylcarbonylamino etc.) optionally having 1 to 3 halogen atoms (e.g., fluorine, chlorine, bromine, iodine);
(47) mono-($C_{3-6}$ cycloalkyl-carbonyl)amino (e.g., cyclopropylcarbonylamino, cyclobutylcarbonylamino, cyclopentylcarbonylamino, cyclohexylcarbonylamino etc.);
(48) mono-($C_{6-10}$ aryl-carbonyl)amino (e.g., benzoylamino etc.) optionally having 1 to 3 halogen atoms (e.g., fluorine, chlorine, bromine, iodine);
(49) mono-(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, pyridylcarbonylamino, pyrazolylcarbonylamino etc.);
(50) mono-(8- to 12-membered fused aromatic heterocyclyl-carbonyl)amino (e.g., benzofurylcarbonylamino, isobenzofurylcarbonylamino, benzothienylcarbonylamino, isobenzothienylcarbonylamino etc.);
(51) mono-(5- or 6-membered non-aromatic heterocyclyl-carbonyl)amino (e.g., oxiranylcarbonylamino, azetidinylcarbonylamino, oxetanylcarbonylamino etc.);
(52) thiol;
(53) $C_{1-6}$ alkylsulfanyl (e.g., methylsulfanyl, ethylsulfanyl etc.);
(54) $C_{2-6}$ alkenylsulfanyl (e.g., ethenylsulfanyl, propenylsulfanyl etc.);
(55) $C_{2-6}$ alkynylsulfanyl (e.g., ethynylsulfanyl, propynylsulfanyl, butynylsulfanyl, pentynylsulfanyl, hexynylsulfanyl etc.);
(56) $C_{3-6}$ cycloalkylsulfanyl (e.g., cyclopropylsulfanyl, cyclobutylsulfanyl etc.);
(57) $C_{3-6}$ cycloalkenylsulfanyl (e.g., cyclopropenylsulfanyl, cyclobutenylsulfanyl etc.);
(58) $C_{6-10}$ arylsulfanyl (e.g., phenylsulfanyl etc.);
(59) $C_{3-6}$ cycloalkyl-$C_{1-6}$ alkyl-sulfanyl (e.g., cyclopropylmethylsulfanyl etc.);
(60) $C_{3-6}$ cycloalkenyl-$C_{1-6}$ alkyl-sulfanyl (e.g., cyclopentenylmethylsulfanyl etc.);
(61) 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.) optionally having 1 to 3 $C_{1-4}$ alkyl (e.g., methyl, ethyl etc.);
(62) 8- to 12-membered fused aromatic heterocyclic group (e.g., benzofuryl, isobenzofuryl, benzothienyl, isobenzothienyl, indolyl, isoindolyl, 1H-indazolyl, benzimidazolyl, benzoxazolyl etc.);
(63) 5- or 6-membered non-aromatic heterocyclic group (e.g., oxiranyl, azetidinyl, oxetanyl, thietanyl, pyrrolidinyl, tetrahydrofuryl, thiolanyl, piperidinyl etc.);
(64) 5- or 6-membered monocyclic aromatic heterocyclyl-oxy (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy etc.);
(65) 8- to 12-membered fused aromatic heterocyclyl-oxy (e.g., benzofuryloxy, isobenzofuryloxy, benzothienyloxy, isobenzothienyloxy, indolyloxy, isoindolyloxy, 1H-indazolyloxy, benzimidazolyloxy, benzoxazolyloxy etc.);
(66) 5- or 6-membered non-aromatic heterocyclyl-oxy (e.g., oxiranyloxy, azetidinyloxy, oxetanyloxy, thietanyloxy, pyrrolidinyloxy, tetrahydrofuryloxy, thiolanyloxy, piperidinyloxy etc.);
(67) oxo;
(68) $C_{1-6}$ alkylsulfinyl (e.g., methylsulfinyl, ethylsulfinyl etc.);
(69) $C_{2-6}$ alkenylsulfinyl (e.g., ethenylsulfinyl, propenylsulfinyl etc.);
(70) $C_{2-6}$ alkynylsulfinyl (e.g., ethynylsulfinyl, propynylsulfinyl, butynylsulfinyl, pentynylsulfinyl, hexynylsulfinyl etc.);
(71) $C_{3-6}$ cycloalkylsulfinyl (e.g., cyclopropylsulfinyl, cyclobutylsulfinyl etc.);
(72) $C_{3-6}$ cycloalkenylsulfinyl (e.g., cyclopropenylsulfinyl, cyclobutenylsulfinyl etc.);
(73) $C_{6-10}$ arylsulfinyl (e.g., phenylsulfinyl etc.);
(74) $C_{3-6}$ cycloalkyl-$C_{1-6}$ alkyl-sulfinyl (e.g., cyclopropylmethylsulfinyl etc.);
(75) $C_{3-6}$ cycloalkenyl-$C_{1-6}$ alkyl-sulfinyl (e.g., cyclopentenylmethylsulfinyl etc.);
(76) aminothiocarbonyl substituted by $C_{1-6}$ alkyl or $C_{6-10}$ aryl-$C_{1-4}$ alkyl-carbonyl (e.g., methylaminothiocarbonyl, ethylaminothiocarbonyl, propylaminothiocarbonyl, benzylcarbonylaminothiocarbonyl etc.);
(77) di-$C_{1-6}$ alkyl-aminothiocarbonyl (e.g., dimethylaminothiocarbonyl, diethylaminothiocarbonyl, dipropylaminothiocarbonyl etc.);
(78) carboxy;
(79) $C_{1-6}$ alkoxycarbonyl (e.g., methoxycarbonyl, ethoxycarbonyl, propoxycarbonyl, isopropoxycarbonyl, butoxycarbonyl, isobutoxycarbonyl, tert-butoxycarbonyl etc.);
(80) $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl etc.);
(81) $C_{2-6}$ alkynyloxy-carbonyl (e.g., ethynyloxycarbonyl, propynyloxycarbonyl, butynyloxycarbonyl, pentynyloxycarbonyl, hexynyloxycarbonyl etc.);
(82) $C_{3-6}$ cycloalkyl-oxy-carbonyl (e.g., cyclopropyloxycarbonyl, cyclobutyloxycarbonyl, cyclopentyloxycarbonyl, cyclohexyloxycarbonyl etc.);
(83) $C_{3-6}$ cycloalkenyloxy-carbonyl (e.g., cyclopropenyloxycarbonyl, cyclobutenyloxycarbonyl, cyclopentenyloxycarbonyl, cyclohexenyloxycarbonyl etc.);
(84) $C_{6-10}$ aryloxy-carbonyl (e.g., phenyloxycarbonyl, 1-naphthyloxycarbonyl, 2-naphthyloxycarbonyl etc.);
(85) $C_{3-6}$ cycloalkyl-$C_{1-6}$ alkoxy-carbonyl (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl etc.);
(86) $C_{3-6}$ cycloalkenyl-$C_{1-6}$ alkoxy-carbonyl (e.g., cyclopentenylmethyloxycarbonyl, cyclohexenylmethyloxycarbonyl, cyclohexenylethyloxycarbonyl, cyclohexenylpropyloxycarbonyl etc.); and
(87) $C_{6-10}$ aryl-$C_{1-6}$ alkoxy-carbonyl (e.g., phenylmethyloxycarbonyl, phenylethyloxycarbonyl etc.).

Where the alkyl is substituted by two or more substituents, the substituents may be the same or different, and preferable number of the substituents is 1 to 5, and more preferably 1 to 3.

As the "alkenyl", for example, linear or branched chain alkenyl having 2 to 8, preferably 2 to 4 carbons and the like can be mentioned, and ethenyl, propenyl, butenyl, pentenyl, hexenyl, heptenyl, octenyl, butadienyl and the like can be specifically mentioned. The "alkenyl" may have, at any substitutable positions, 1 to the acceptable maximum number of substituents selected from the above-mentioned Substituent Group (2) and $C_{6-10}$ aryl (e.g., phenyl etc.). Where the alkenyl is substituted by two or more substituents, the substituents may be the same or different, and preferable number of the substituents is 1 to 5, more preferably 1 to 3.

As the "alkynyl", for example, linear or branched chain alkynyl having 2 to 8, preferably 2 to 4 carbons and the like can be mentioned, and ethynyl, propynyl, butynyl, pentynyl, hexynyl, heptynyl, octynyl and the like can be specifically mentioned. The "alkynyl" may have, at any substitutable positions, 1 to the acceptable maximum number of substituents selected from the above-mentioned Substituent Group (2) and $C_{6-10}$ aryl (e.g., phenyl etc.). Where the alkynyl is substituted by two or more substituents, the substituents may be the same or different, and preferable number of the substituents is 1 to 5, more preferably 1 to 3.

As the "cycloalkyl", for example, cycloalkyl having 3 to 8, preferably 3 to 6 carbons and the like can be mentioned, and cyclopropyl, cyclobutyl, cyclopentyl, cyclohexyl, cycloheptyl and cyclooctyl and the like can be specifically mentioned. The "cycloalkyl" may have, at any substitutable positions, 1 to the acceptable maximum number of substituents selected from (a) $C_{1-6}$ alkyl (e.g., methyl, ethyl, propyl, isopropyl, butyl, isobutyl, tert-butyl etc.) optionally having 1 to 3 substituents selected from halogen atom (e.g., fluorine, chlorine, bromine, iodine) and hydroxy, and (b) substituent selected from the above-mentioned Substituent Group (2). Where the cycloalkyl is substituted by two or more substituents, the substituents may be the same or different, and preferable number of the substituents is 1 to 5, more preferably 1 to 3.

As the "cycloalkenyl", for example, cycloalkenyl having 3 to 8, preferably 3 to 6 carbons and the like can be mentioned, and cyclopropenyl, cyclobutenyl, cyclopentenyl, cyclohexenyl, cycloheptenyl, cyclooctenyl and the like can be specifically mentioned. The "cycloalkenyl" may have, at any substitutable positions, 1 to the acceptable maximum number of substituents selected from $C_{1-6}$ alkyl (e.g., methyl, ethyl, propyl, isopropyl, butyl, isobutyl, tert-butyl etc.) optionally having 1 to 3 halogen atoms (e.g., fluorine, chlorine, bromine, iodine), and substituent selected from the above-mentioned Substituent Group (2). Where the cycloalkenyl is substituted by two or more substituents, the substituents may be the same or different, and preferable number of the substituents is 1 to 5, more preferably 1 to 3.

As the "aryl", for example, aryl having 6 to 18, preferably 6 to 14, more preferably 6 to 10, particularly preferably 6 carbons and the like can be mentioned, and phenyl, 1-naphthyl, 2-naphthyl, biphenylyl, 2-anthryl, phenanthryl, acenaphthylenyl and the like can be specifically mentioned. The "aryl" may have, at any substitutable positions, 1 to the acceptable maximum number of substituents selected from (a) $C_{1-4}$ alkyl (e.g., methyl, ethyl, propyl, isopropyl, butyl, isobutyl, tert-butyl etc.) optionally having 1 to 3 substituents selected from halogen atom (e.g., fluorine, chlorine, bromine, iodine), cyano, hydroxy and $C_{3-6}$ cycloalkyl (e.g., cyclopropyl etc.), and (b) substituent selected from the above-mentioned Substituent Group (2) (except for oxo). Where the aryl is substituted by two or more substituents, the substituents may be the same or different, and preferable number of the substituents is 1 to 5, more preferably 1 to 3.

As the "cycloalkyl-alkyl", for example, group in which cycloalkyl group having 3 to 8, preferably 3 to 6 carbons and the like, is bonded to linear or branched chain alkyl having 1 to 6, preferably 1 to 4 carbon atoms (e.g., $C_{3-8}$ cycloalkyl-$C_{1-4}$ alkyl) and the like can be mentioned, and cyclopropylmethyl, cyclopropylethyl, cyclobutylmethyl, cyclopentylmethyl, cyclohexylmethyl, cyclohexylethyl and the like can be specifically mentioned. The "cycloalkyl-alkyl" may have, at any substitutable positions, 1 to the acceptable maximum number of substituents selected from $C_{1-6}$ alkyl (e.g., methyl, ethyl, propyl, isopropyl, butyl, isobutyl, tert-butyl etc.) optionally having 1 to 3 halogen atoms (e.g., fluorine, chlorine, bromine, iodine) and substituent selected from the above-mentioned Substituent Group (2). Where the cycloalkyl-alkyl is substituted by two or more substituents, the substituents may be the same or different, and preferable number of the substituents is 1 to 5, more preferably 1 to 3.

As the "cycloalkenyl-alkyl", for example, group in which cycloalkenyl having 3 to 8, preferably 3 to 6 carbons is bonded to linear or branched chain alkyl having 1 to 6, preferably 1 to 4 carbon atoms (e.g., $C_{3-8}$ cycloalkenyl-$C_{1-4}$ alkyl group) can be mentioned, and cyclopentenylmethyl, cyclohexenylmethyl, cyclohexenylethyl, cyclohexenylpropyl, cycloheptenylmethyl, cycloheptenylethyl and the like can be specifically mentioned. The "cycloalkenyl-alkyl" may have, at any substitutable positions, 1 to the acceptable maximum number of substituents selected from $C_{1-6}$ alkyl (e.g., methyl, ethyl, propyl, isopropyl, butyl, isobutyl, tert-butyl etc.) optionally having 1 to 3 halogen atoms (e.g., fluorine, chlorine, bromine, iodine) and substituent selected from the above-mentioned Substituent Group (2). Where the cycloalkenyl-alkyl is substituted by two or more substituents, the substituents may be the same or different, and preferable number of the substituents is 1 to 5, more preferably 1 to 3.

As the "aryl-alkyl", for example, group in which aryl having 6 to 18, more preferably 6 to 10, particularly preferably 6 carbons is bonded to linear or branched chain alkyl having 1 to 6, preferably 1 to 4 carbon atoms (e.g., $C_{6-18}$ aryl-$C_{1-4}$ alkyl) and the like can be mentioned, and phenylmethyl (benzyl), phenylethyl (phenethyl) and the like can be specifically mentioned. The "aryl-alkyl" may have, at any substitutable positions, 1 to the acceptable maximum number of substituents selected from $C_{1-6}$ alkyl (e.g., methyl, ethyl, propyl, isopropyl, butyl, isobutyl, tert-butyl etc.) optionally having 1 to 3 halogen atoms (e.g., fluorine, chlorine, bromine, iodine) and substituent selected from the above-mentioned Substituent Group (2). Where the aryl-alkyl is substituted by two or more substituents, the substituents may be the same or different, and preferable number of the substituents is 1 to 5, more preferably 1 to 3.

As the "cycloalkanedienyl", for example, $C_{4-6}$ cycloalkanedienyl group such as 2,4-cyclopentadien-1-yl, 2,4-cyclohexadien-1-yl, 2,5-cyclohexadien-1-yl and the like, and the like can be mentioned. The "cycloalkanedienyl" may have, at any substitutable positions, 1 to the acceptable maximum number of substituents selected from $C_{1-6}$ alkyl (e.g., methyl, ethyl, propyl, isopropyl, butyl, isobutyl, tert-butyl etc.) optionally having 1 to 3 halogen atoms (e.g., fluorine, chlorine, bromine, iodine) and substituent selected from the above-mentioned Substituent Group (2). Where the cycloalkanedienyl is substituted by two or more substituents, the substituents may be the same or different, and preferable number of the substituents is 1 to 5, more preferably 1 to 3.

As the "optionally substituted hydrocarbon-oxy" in Substituent Group (1)(vi), alkyl-oxy, alkenyl-oxy, alkynyl-oxy, cycloalkyl-oxy, cycloalkenyl-oxy, aryl-oxy, cycloalkyl-alkyl-oxy, cycloalkenyl-alkyl-oxy, aryl-alkyl-oxy and the like, each of which is optionally substituted, can be mentioned. As the "alkyl" for alkyl-oxy, the "alkenyl" for alkenyl-oxy, the "alkynyl" for alkynyl-oxy, the "cycloalkyl" for cycloalkyl-oxy, the "cycloalkenyl" for cycloalkenyl-oxy, the "aryl" for aryl-oxy, the "cycloalkyl-alkyl" for cycloalkyl-alkyl-oxy, the "cycloalkenyl-alkyl" for cycloalkenyl-alkyl-oxy, the "aryl-alkyl" for aryl-alkyl-oxy, similar groups to those exemplified as the "hydrocarbon group" of the "optionally substituted hydrocarbon group" in the aforementioned Substituent Group (1)(iv) can be respectively mentioned.

The "optionally substituted aminosulfonyl" in Substituent Group (1) (vii) may have 1 or 2 substituents. Where the aminosulfonyl is substituted by two substituents, the substituents may be the same or different.

As the "substituent" of the "optionally substituted aminosulfonyl", for example, similar groups to those exemplified as the "hydrocarbon group" of the "optionally substituted hydrocarbon group" in the aforementioned Substituent Group (1)(iv) and the below-mentioned groups as the "optionally substituted heterocyclic group" in the aforementioned Substituent Group (1)(xii) can be mentioned.

The "optionally substituted aminocarbonyl" in Substituent Group (1) (viii) may have 1 or 2 substituents. Where the aminocarbonyl is substituted by two substituents, the substituents may be the same or different.

As the "substituent" of the "optionally substituted aminocarbonyl", for example, those similar to group exemplified as the "optionally substituted hydrocarbon group" in the aforementioned Substituent Group (1)(iv), group exemplified as the "optionally substituted hydrocarbon-oxy" in the aforementioned Substituent Group (1)(vi), and group below-mentioned as "optionally substituted heterocycle" in the aforementioned Substituent Group (1)(xii) can be mentioned.

As the "acyl" in Substituent Group (1)(ix), for example, optionally substituted hydrocarbon-carbonyl, optionally substituted heterocyclyl-carbonyl, optionally substituted hydrocarbon-sulfonyl, optionally substituted heterocyclyl-sulfonyl and the like can be mentioned.

As the "optionally substituted hydrocarbon" of the "optionally substituted hydrocarbon-carbonyl", those similar to the group exemplified as the "optionally substituted hydrocarbon group" in the above-mentioned Substituent Group (1)(iv) can be mentioned.

As the "optionally substituted hydrocarbon" of the "optionally substituted hydrocarbon-sulfonyl", those similar to the group exemplified as the "optionally substituted hydrocarbon group" in the above-mentioned Substituent Group (1)(iv) can be mentioned.

As the "optionally substituted heterocycle" of the "optionally substituted heterocyclyl-carbonyl" and "optionally substituted heterocyclyl-sulfonyl", those similar to the group below-mentioned as the "optionally substituted heterocyclic group" in the aforementioned Substituent Group (1)(xii) can be mentioned.

The "optionally substituted-amino" in Substituent Group (1)(x) may have 1 or 2 substituents. Where the amino is substituted by two substituents, the substituents may be the same or different. As the "substituent" of the "optionally substituted amino", for example, those similar to the group exemplified as the "optionally substituted hydrocarbon group" in the aforementioned Substituent Group (1)(iv), the group exemplified as the "optionally substituted aminocarbonyl" in the aforementioned Substituent Group (1)(viii), the group exemplified as the "acyl" in the aforementioned Substituent Group (1)(ix), the group below-mentioned as the "optionally substituted heterocyclic group" in the aforementioned Substituent Group (1)(xii), and group selected from the "optionally esterified carboxy" in the aforementioned Substituent Group (1)(xvii) can be mentioned.

As the "substituent" of the "optionally substituted sulfanyl" in Substituent Group (1)(xi), for example, those similar to the group exemplified as the "optionally substituted hydrocarbon group" in the aforementioned Substituent Group (1) (iv) can be mentioned.

As the "heterocyclic group" of the "optionally substituted heterocyclic group" in Substituent Group (1)(xii), aromatic heterocyclic group (e.g., monocyclic aromatic heterocyclic group, fused aromatic heterocyclic group), non-aromatic heterocyclic group, and the like can be mentioned, and for example, 5- to 12-membered aromatic heterocyclic group (monocyclic aromatic heterocyclic group or fused aromatic heterocyclic group etc.), saturated or unsaturated non-aromatic heterocycle, and the like having, as ring-constituting atom, 1 or more (preferably 1 to 4, more preferably 1 or 2) of 1 to 3, preferably 1 or 2 kinds of heteroatoms selected from oxygen atom, optionally oxidized sulfur atom and nitrogen atom and the like (preferably oxygen atom, sulfur atom and nitrogen atom etc.) besides carbon atoms, can be mentioned.

As the monocyclic aromatic heterocyclic group, for example, 5- or 6-membered monocyclic aromatic heterocyclic group and the like can be mentioned.

As the monocyclic aromatic heterocyclic group, furyl, thienyl, pyrrolyl, oxazolyl, isoxazolyl, thiazolyl, isothiazolyl, imidazolyl, pyrazolyl, oxadiazolyl (e.g., 1,2,3-oxadiazolyl, 1,2,4-oxadiazolyl, 1,3,4-oxadiazolyl), furazanyl, thiadiazolyl (e.g., 1,2,3-thiadiazolyl, 1,2,4-thiadiazolyl, 1,3,4-thiadiazolyl), triazolyl (e.g., 1,2,3-triazolyl, 1,2,4-triazolyl), tetrazolyl, pyridyl, pyridazinyl, pyrimidinyl, pyrazinyl, triazinyl and the like can be specifically mentioned.

As the fused aromatic heterocyclic group, for example, 8- to 12-membered fused aromatic heterocyclic group can be mentioned, and heterocyclic group formed by fusion of the aforementioned 5- or 6-membered monocyclic aromatic heterocyclic group and benzene ring or heterocyclic group formed by fusion of the same or different two of the aforementioned 5- or 6-membered monocyclic aromatic heterocyclic groups can be particularly mentioned.

Examples of fused aromatic heterocyclic group specifically include benzofuryl, isobenzofuryl, benzothienyl, isobenzothienyl, indolyl, isoindolyl, 1H-indazolyl, benzimidazolyl, benzoxazolyl, 1,2-benzisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

Examples of non-aromatic heterocyclic group include 3- to 8-membered (preferably 5- or 6-membered) saturated or unsaturated (preferably saturated) non-aromatic heterocyclic group and the like.

Examples of non-aromatic heterocyclic group specifically include oxiranyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azocanyl, oxocanyl, thiocanyl, oxazocanyl, thiazocanyl, dioxinyl and the like.

Alternatively, the non-aromatic heterocyclic group may be fused to benzene ring or the above-mentioned monocyclic aromatic heterocyclic group to form fused non-aromatic heterocyclic group. As the fused non-aromatic heterocyclic group formed by fusion of non-aromatic heterocyclic group and benzene ring, for example, benzodioxinyl, tetrahydroisoquinolyl and the like can be mentioned.

The "optionally substituted heterocyclic group" may have, at any substitutable positions, 1 to the acceptable maximum number of substituents. Where the heterocyclic group is substituted by two or more substituents, the substituents may be the same or different, and preferable number of the substituents is 1 to 5, more preferably 1 to 3.

Examples of the "substituent" of the "optionally substituted heterocyclic group" may include (a) $C_{1-6}$ alkyl (e.g., methyl, ethyl, propyl, isopropyl, butyl, isobutyl, tert-butyl etc.) optionally having 1 to 3 substituents selected from halogen atom (e.g., fluorine, chlorine, bromine, iodine), cyano, hydroxy and $C_{1-4}$ alkoxy (e.g., methoxy), (b) $C_{6-10}$ aryl (e.g., phenyl), (c) $C_{6-10}$ aryl-$C_{1-4}$ alkyl (e.g., benzyl etc.) and (d) those similar to the group selected from the aforementioned Substituent Group (2).

For example, among the heterocyclic groups substituted by oxo in the aforementioned Substituent Group (2), as the specific examples of the non-aromatic heterocyclic group substituted by oxo, 2-oxoazetidinyl, 2-oxopyrrolidinyl, 2-oxopiperidinyl, 2-oxoazepanyl, 2-oxoazocanyl, 2-oxotetrahydrofuryl, 2-oxotetrahydropyranyl, 2-oxothiolanyl, 2-oxothianyl, 2-oxopiperazinyl, 2-oxooxepanyl, 2-oxooxazepanyl, 2-oxothiepanyl, 2-oxothiazepanyl, 2-oxooxocanyl, 2-oxothiocanyl, 2-oxooxazocanyl, 2-oxothiazocanyl, 2-oxodioxinyl and the like can be mentioned.

As the "optionally substituted heterocycle" of the "optionally substituted heterocyclyl-oxy" in Substituent Group (1) (xiii), those similar to the group exemplified as the "optionally substituted heterocycle" in the aforementioned Substituent Group (1)(xii) can be mentioned.

As the "substituent" of the "optionally substituted sulfinyl" in Substituent Group (1)(xv), for example, those similar to the group exemplified as the "optionally substituted hydrocarbon group" in the aforementioned Substituent Group (1)(iv) can be mentioned.

The "optionally substituted aminothiocarbonyl" in Substituent Group (1) (xvi) may have 1 or 2 substituents. Where the aminothiocarbonyl is substituted by 2 substituents, the substituents may be the same or different.

As the "substituent" of the "optionally substituted aminothiocarbonyl", for example, 1 or 2 groups similar to the group exemplified as the "optionally substituted hydrocarbon group" in the aforementioned Substituent Group (1)(iv) can be mentioned.

As the "optionally esterified carboxy" in Substituent Group (1)(xvii), for example, carboxy optionally esterified by the group exemplified as the "optionally substituted hydrocarbon group" in the aforementioned Substituent Group (1) (iv) can be mentioned.

The "substituent" of the "optionally substituted cyclic group" for ring Y is preferably
(1) halogen atom (e.g., fluorine, chlorine, bromine, iodine),
(2) optionally substituted alkyl,
(3) optionally substituted alkoxy,
(4) optionally substituted aminocarbonyl,
(5) optionally substituted amino,
(6) optionally esterified carboxy,
(7) nitro,
and the like.
Of these,
(1) halogen atom (e.g., fluorine, chlorine, bromine, iodine),
(2) optionally substituted alkyl,
(3) optionally substituted amino,
and the like are preferable.

Hereinafter the above-mentioned preferable examples of the "substituent" of the "optionally substituted cyclic group" for ring Y are exemplified in detail.

(1) As the halogen atom, fluorine, chlorine, bromine and the like are preferable.
(2) As the optionally substituted alkyl, optionally substituted $C_{1-8}$ alkyl is preferable, optionally substituted $C_{1-4}$ alkyl is more preferable, and unsubstituted $C_{1-4}$ alkyl is much more preferable. Specifically, methyl, ethyl and the like are preferable.
(3) As the optionally substituted alkoxy, optionally substituted $C_{1-8}$ alkoxy is preferable, optionally substituted $C_{1-4}$ alkoxy is more preferable, unsubstituted $C_{1-4}$ alkoxy is much more preferable. Specifically, methoxy and the like are preferable.
(4) As the "substituent" for the optionally substituted aminocarbonyl, for example, $C_{1-8}$ alkyl, $C_{2-8}$ alkenyl, $C_{2-8}$ alkynyl, $C_{3-8}$ cycloalkyl, $C_{3-8}$ cycloalkenyl, $C_{3-8}$ cycloalkynyl, $C_{6-18}$ aryl, heterocyclic group and the like, each of which is optionally substituted, are preferable. Of these, optionally substituted $C_{1-4}$ alkyl, optionally substituted $C_{6-12}$ aryl and optionally substituted 5-membered heterocyclic group and the like are preferable. Particularly, (a) $C_{1-4}$ alkyl (e.g., methyl, ethyl) optionally having $C_{6-12}$ aryl (e.g., phenyl) (Specific examples are benzyl, ethyl), (b) 5-membered heterocyclic group (e.g., pyrazolyl) optionally substituted by 1 to 3 substituents selected from $C_{1-4}$ alkyl (e.g., methyl) and $C_{6-12}$ aryl (e.g., phenyl), (c) $C_{6-12}$ aryl optionally substituted by $C_{1-4}$ alkyl (e.g., methyl) optionally substituted by 1 to 3 substituents selected from halogen atom (e.g., fluorine) and cyano (specific examples: trifluoromethyl, tert-butyl, 1-cyano-1-methylethyl) are preferable.
(5) As the "substituent" for the optionally substituted amino, optionally substituted alkyl, optionally substituted aminocarbonyl, acyl, optionally substituted aminothiocarbonyl and the like are preferable.

As the optionally substituted amino, amino optionally substituted by 1 or 2 substituents selected from (a) optionally substituted alkyl, (b) optionally substituted aminocarbonyl, (c) acyl and (d) optionally substituted aminothiocarbonyl is preferable.

As the optionally substituted alkyl, optionally substituted $C_{1-4}$ alkyl is preferable. Of these, $C_{1-4}$ alkyl (e.g., methyl) optionally substituted by 5-membered heterocyclic group (e.g., pyrazolyl) optionally substituted by 1 to 3 $C_{1-4}$ alkyl (e.g., methyl) (specific example: 1,3-dimethyl-1H-pyrazol-5-ylmethyl) is preferable.

As the optionally substituted aminocarbonyl, $C_{1-8}$ alkyl-aminocarbonyl, $C_{6-18}$ aryl-aminocarbonyl, $C_{6-18}$ aryl-$C_{1-4}$ alkyl-aminocarbonyl, heterocyclyl-aminocarbonyl, $C_{3-8}$ cycloalkyl-aminocarbonyl, $C_{1-8}$ alkoxy-aminocarbonyl and the like, each of which is optionally substituted, are preferable. Of these, optionally substituted $C_{1-8}$ alkyl-aminocarbonyl, optionally substituted $C_{6-18}$ aryl-aminocarbonyl, optionally substituted heterocyclyl-aminocarbonyl, optionally substituted $C_{1-8}$ alkoxy-aminocarbonyl and the like are preferable. Particularly, (i) $C_{1-4}$ alkyl-aminocarbonyl (e.g., ethylaminocarbonyl), (ii) $C_{6-10}$ aryl-aminocarbonyl (e.g., phenylaminocarbonyl) optionally substituted by $C_{1-4}$ alkyl (e.g., methyl) optionally substituted by 1 to 3 halogen atom (e.g., fluorine) (specific examples: phenylaminocarbonyl, 3-(trifluoromethyl)phenylcarbonyl), (iii) $C_{1-4}$ alkoxy-aminocarbonyl (e.g., methoxyaminocarbonyl, isobutoxyaminocarbonyl), (iv) 5-membered heterocyclyl-aminocarbonyl (e.g., pyrazolyl-aminocarbonyl) optionally substituted by 1 to 3 substituents selected from $C_{1-4}$ alkyl (e.g., methyl) and $C_{6-10}$ aryl (specific example: 1,3-dimethyl-1H-pyrazol-5-yl-aminocarbonyl) and the like are preferable.

As the acyl, $C_{1-8}$ alkyl-carbonyl, $C_{2-8}$ alkenyl-carbonyl, $C_{2-8}$ alkynyl-carbonyl, $C_{3-8}$ cycloalkyl-carbonyl, $C_{3-8}$ cycloalkenyl-carbonyl, $C_{6-18}$ aryl-carbonyl, $C_{6-18}$ aryl-$C_{1-4}$ alkyl-carbonyl, $C_{1-8}$ alkylsulfonyl, $C_{6-18}$ aryl-sulfonyl, heterocyclyl-carbonyl, heterocyclyl-sulfonyl and the like, each of which is optionally substituted, are preferable. Of these, $C_{1-8}$ alkyl-carbonyl, $C_{2-8}$ alkenyl-carbonyl, $C_{2-8}$ alkynyl-carbonyl, $C_{3-8}$ cycloalkyl-carbonyl, $C_{3-8}$ cycloalkenyl-carbonyl, $C_{6-18}$ aryl-carbonyl, heterocyclyl-carbonyl, each of which is optionally substituted, are preferable.

As the optionally substituted $C_{1-8}$ alkyl-carbonyl, optionally substituted $C_{1-4}$ alkyl-carbonyl is preferable. Particularly, $C_{1-4}$ alkyl-carbonyl (e.g., methylcarbonyl, tert-butylcarbonyl, 3-methylbutanoyl) optionally substituted by 1 to 3 substituents selected from (a) hydroxy, (b) $C_{1-4}$ alkylsulfonyl (e.g., methylsulfonyl) and (c) 6-membered heterocyclic group (e.g., pyridyl) (specific examples: methylsulfonylmethylcarbonyl, 2-pyridylmethylcarbonyl, tert-butylcarbonyl, 3-hydroxy-3-methylbutanoyl) is preferable.

As the optionally substituted $C_{2-8}$ alkenyl-carbonyl, optionally substituted $C_{2-4}$ alkenyl-carbonyl is preferable. Particularly, $C_{2-4}$ alkenyl-carbonyl (e.g., 3-methyl-2-butenoyl) optionally substituted by $C_{6-10}$ aryl (e.g., phenyl) (specific example: 3-methyl-2-butenoyl) is preferable.

As the optionally substituted $C_{2-8}$ alkynyl-carbonyl, optionally substituted $C_{2-4}$ alkynyl-carbonyl is preferable. Particularly, $C_{2-4}$ alkynyl-carbonyl (e.g., 2-butynoyl) optionally substituted by $C_{6-10}$ aryl (e.g., phenyl) (specific example: 2-butynoyl) is preferable.

As the optionally substituted $C_{3-8}$ cycloalkyl-carbonyl, $C_{3-6}$ cycloalkyl-carbonyl is preferable, and cyclopropylcarbonyl, cyclopentylcarbonyl and cyclohexylcarbonyl are specifically preferable.

As the optionally substituted $C_{3-8}$ cycloalkenyl-carbonyl, $C_{3-6}$ cycloalkenyl-carbonyl (e.g., cyclopentenecarbonyl) (specific example: 1-cyclopentenecarbonyl) is preferable.

As the optionally substituted $C_{6-18}$ aryl-carbonyl, optionally substituted $C_{6-10}$ aryl-carbonyl is preferable. Particularly, $C_{6-10}$ aryl-carbonyl (e.g., benzoyl) optionally substituted by 1 to 3 substituents selected from (a) halogen atom (e.g., fluorine), (b) $C_{1-4}$ alkyl (e.g., methyl, ethyl, isopropyl, tert-butyl) optionally substituted by 1 to 3 substituents selected from halogen atom (e.g., fluorine), cyano, hydroxy and $C_{3-6}$ cycloalkyl (e.g., cyclopropyl) (specific example: trifluoromethyl), (c) $C_{3-6}$ cycloalkyl (e.g., cyclopropyl, cyclobutyl, cyclohexyl) optionally substituted by cyano, (d) $C_{1-4}$ alkoxy (e.g., isopropoxy, tert-butoxy) optionally substituted by 1 to 5 halogen atoms (e.g., fluorine), (e) $C_{1-4}$ alkoxy-carbonyl (e.g., methoxycarbonyl), and (f) 5 or 6-membered heterocyclic group (e.g., tetrahydropyranyl, pyrrolidinyl) optionally substituted by cyano or oxo is preferable. Specifically, phenylcarbonyl (benzoyl), 3-(trifluoromethyl)phenylcarbonyl, 4-(trifluoromethyl)phenylcarbonyl, 3-fluorophenylcarbonyl, 3-chlorophenylcarbonyl, 3-(1-cyanocyclopropyl)phenylcarbonyl, 3-(1-cyanocyclobutyl)phenylcarbonyl, 3-(1-cyanocyclohexyl)phenylcarbonyl, 2-fluoro-3-(trifluoromethyl)phenylcarbonyl, 2-fluoro-5-(trifluoromethyl)phenylcarbonyl, 3-fluoro-5-(trifluoromethyl)phenylcarbonyl, 4-chloro-3-(trifluoromethyl)phenylcarbonyl, 2-chloro-3-(trifluoromethyl)phenylcarbonyl, 2-chloro-5-(trifluoromethyl)phenylcarbonyl, 3-isopropoxyphenylcarbonyl, 3-(tert-butoxy)phenylcarbonyl, 3-(1-cyano-1-methylethyl)phenylcarbonyl, 3-methoxyphenylcarbonyl, 3-methoxycarbonylphenylcarbonyl, 3-(trifluoromethoxy)carbonylphenylcarbonyl, 3-(1,1,2,2-tetrafluoroethoxy)phenylcarbonyl, 3-(4-cyanotetrahydropyran-4-yl)phenylcarbonyl, 3,5-di(trifluoromethyl)phenylcarbonyl, 3-(2-oxopyrrolidin-1-yl)phenylcarbonyl, 4-(tert-butyl)phenylcarbonyl, 3-(1-cyanoethyl)phenylcarbonyl, 3-(1-cyano-2-cyclopropyl-1-methylethyl)phenylcarbonyl and the like are preferable.

As the optionally substituted $C_{6-18}$ aryl-$C_{1-4}$ alkyl-carbonyl, $C_{6-10}$ aryl-$C_{1-4}$ alkyl-carbonyl is preferable.

As the optionally substituted $C_{1-8}$ alkylsulfonyl, $C_{1-4}$ alkylsulfonyl are preferable.

As the optionally substituted $C_{6-18}$ aryl-sulfonyl, $C_{6-10}$ aryl-sulfonyl is preferable.

As the "heterocycle" moiety for the optionally substituted heterocyclyl-carbonyl, 5- or 6-membered monocyclic heterocyclic group containing, as ring-constituting atom, 1 to 3 hetero atoms selected from oxygen atom, sulfur atom and nitrogen atom besides carbon atoms, and the like are preferable, and pyridyl, furyl, tetrahydrofuryl, thienyl, pyrazolyl, imidazolyl, thiazolyl, oxazolyl, isoxazolyl, 1,2,3-triazolyl, 1,2,3-thiadiazolyl, dihydrooxazolyl, pyridazinyl, pyrazinyl, dihydropyrazolyl, pyrrolyl, pyrrolidinyl, pyrimidinyl and the like are specifically preferable. As the "substituent" for the optionally substituted heterocyclyl-carbonyl, (1) halogen atom (e.g., chlorine), (2) $C_{1-4}$ alkyl (e.g., methyl, ethyl, isopropyl, tert-butyl) optionally substituted by 1 to 3 substituents selected from halogen atom (e.g., fluorine), cyano, hydroxy and $C_{1-4}$ alkoxy (e.g., methoxy) (specific examples: methyl, trifluoromethyl, ethyl, methoxyethyl, 2,2,2-trifluoroethyl, isopropyl, tert-butyl), (3) $C_{6-18}$ aryl (e.g., phenyl), (4) $C_{6-10}$ aryl-$C_{1-4}$ alkyl (e.g., benzyl), (5) $C_{1-4}$ alkoxy (e.g., methoxy, ethoxy) optionally substituted by $C_{1-4}$ alkoxy (e.g., methoxy) (specific examples: methoxy, ethoxy, methoxyethoxy), (6) $C_{1-4}$ alkylsulfonyl (e.g., methylsulfonyl, ethylsulfonyl), (7) $C_{1-4}$ alkylcarbonyl (e.g., acetyl), (8) oxo, and the like are preferable.

As the optionally substituted heterocyclyl-carbonyl, 2-pyridylcarbonyl, 3-pyridylcarbonyl, 4-pyridylcarbonyl, 2-methyl-6-pyridylcarbonyl, 3-methyl-2-pyridylcarbonyl, 4-methyl-2-pyridylcarbonyl, 2-methyl-3-pyridylcarbonyl, 2-(trifluoromethyl)-3-pyridylcarbonyl, 2-(trifluoromethyl)-4-pyridylcarbonyl, 2-(trifluoromethyl)-6-pyridylcarbonyl, 2-chloro-6-methyl-4-pyridylcarbonyl, 2,6-dichloro-4-pyridylcarbonyl, 2-furylcarbonyl, 2,5-dimethylfuran-3-carbonyl, 5-methyl-2-(trifluoromethyl)-3-furancarbonyl, 3-methylthiophene-2-carbonyl, 5-acetylsulfonylthiophene-2-carbonyl, 5-ethylsulfonylthiophene-2-carbonyl, 4-methyl-1,2,3-thiadiazole-5-carbonyl, isoxazole-5-carbonyl, 1H-pyrazole-5-carbonyl, 1-methyl-1H-pyrazole-3-carbonyl, 1-methyl-1H-pyrazole-5-carbonyl, 1-ethyl-1H-pyrazole-3-carbonyl, 1-ethyl-1H-pyrazole-5-carbonyl, 3-methyl-1H-pyrazole-5-carbonyl, 3-chloro-1-methyl-1H-pyrazole-5-carbonyl, 4-chloro-1-methyl-1H-pyrazole-3-carbonyl, 1-methyl-3-methoxy-1H-pyrazole-5-carbonyl, 1-methyl-3-(trifluoromethyl)-1H-pyrazole-5-carbonyl, 3-methoxy-1-methyl-1H-pyrazole-4-carbonyl, 3-methoxy-1-methyl-1H-pyrazole-5-carbonyl, 3-ethoxy-1-methyl-1H-pyrazole-5-carbonyl, 3-(2-methoxyethoxy)-1-methyl-1H-pyrazole-5-carbonyl, 1-ethyl-3-methyl-1H-pyrazole-4-carbonyl, 1-ethyl-3-methyl-1H-pyrazole-5-carbonyl, 3-methyl-1-phenyl-1H-pyrazole-5-carbonyl, 5-methyl-1-phenyl-1H-pyrazole-3-carbonyl, 3-ethyl-1-methyl-1H-pyrazole-5-carbonyl, 3-isopropyl-1-methyl-1H-pyrazole-5-carbonyl, 3-methoxy-1-methyl-1H-pyrazole-5-carbonyl, 1-tert-butyl-3-methyl-1H-pyrazole-5-carbonyl, 3-tert-butyl-1-methyl-1H-pyrazole-5-carbonyl, 1-methoxyethyl-3-methyl-1H-pyrazole-5-carbonyl, 1,3-dimethyl-1H-pyrazole-4-carbonyl, 1,3-dimethyl-1H-pyrazole-5-carbonyl, 1,4-dimethyl-1H-pyrazole-3-carbonyl, 1,4-dimethyl-1H-pyrazole-5-carbonyl, 1,5-dimethyl-1H-pyrazole-3-carbonyl, 3-methylisoxazole-4-carbonyl, 3-methylisoxazole-5-carbonyl, 5-methylisoxazole-3-carbonyl, 5-methylisoxazole-4-carbonyl, 3,5-dimethylisoxazole-4-carbonyl, 1,3-thiazole-2-carbonyl, 2-methyl-1,3-thiazole-4-carbonyl, 4-methyl-1,3-thiazole-5-carbonyl, 5-methyl-1,3-thiazole-4-carbonyl, 2,4-dimethyl-1,3-thiazole-5-carbonyl, 2-chloro-4-methyl-1,3-thiazole-5-carbonyl, 4-methoxy-2-methyl-1,3-thiazole-5-carbonyl, 2-(1-hydroxy-1-methylethyl)-1,3-thiazole-5-carbonyl, 2-(1-cyano-1-methylethyl)-1,3-thiazole-5-carbonyl, 2-methyl-1,3-oxazole-4-carbonyl, 4-methyl-1,3-oxazole-5-carbonyl, 2-ethyl-4-methyl-1,3-oxazole-5-carbonyl, 2,4-dimethyl-1,3-oxazole-5-carbonyl, 2,5-dimethyl-1,3-oxazole-4-carbonyl, 1-methyl-1H-1,2,3-triazole-5-carbonyl, 1-methyl-1H-1,2,3-triazole-4-carbonyl, 1-methyl-1H-imidazole-2-carbonyl, 1-methyl-1H-imidazole-5-carbonyl, 2-pyrazinylcarbonyl, 1-methylpyrrole-2-carbonyl, 1-benzylpyrrole-3-carbonyl, 1,2,5-trimethylpyrrole-3-carbonyl, 1-methylpyrrolidine-2-carbonyl, 2-(trifluoromethyl)pyrimidine-4-carbonyl and the like are specifically preferable.

As the "heterocycle" moiety for the optionally substituted heterocyclyl-sulfonyl, 5- or 6-membered monocyclic aromatic heterocyclic group containing, as ring-constituting atom, 1 to 3 heteroatoms selected from oxygen atom, sulfur atom and nitrogen atom besides carbon atoms, and the like are preferable, and thiazolyl and the like are specifically preferable. As the "substituent" for the optionally substituted heterocyclyl-carbonyl, $C_{1-4}$ alkyl (e.g., methyl) and the like are preferable.

As the optionally substituted heterocyclyl-sulfonyl, 2,5-dimethyl-1,3-thiazole-4-sulfonyl and the like are specifically preferable.

As the optionally substituted aminothiocarbonyl, aminothiocarbonyl optionally substituted by $C_{6-18}$ aryl-$C_{1-4}$ alkyl-carbonyl (e.g., benzylcarbonyl) and the like are preferable.

(6) As the optionally esterified carboxy, carboxy and $C_{1-6}$ alkoxy-carbonyl (e.g., methoxycarbonyl) are preferable.

Preferably, ring Y is (1) $C_{6-10}$ aryl (e.g., phenyl) optionally substituted by 1 to 3 substituents selected from
  (a) halogen atom (e.g., fluorine, chlorine, bromine),
  (b) $C_{1-4}$ alkyl (e.g., methyl, ethyl),
  (c) $C_{1-4}$ alkoxy (e.g., methoxy),
  (d) amino optionally substituted by substituents selected from
    (i) $C_{1-4}$ alkyl (e.g., methyl) optionally substituted by 5-membered aromatic heterocyclic group (e.g., pyrazolyl) optionally substituted by 1 to 3 $C_{1-4}$ alkyl (e.g., methyl),
    (ii) $C_{1-4}$ alkyl-carbonyl (e.g., methylcarbonyl, isobutylcarbonyl, tert-butylcarbonyl) optionally substituted by 1 to 3 substituents selected from
      (i') hydroxy,
      (ii') $C_{1-4}$ alkylsulfonyl (e.g., methylsulfonyl), and
      (iii') 6-membered aromatic heterocyclic group (e.g., pyridyl),
    (iii) $C_{2-4}$ alkenyl-carbonyl (e.g., 2-methyl-1-propenylcarbonyl, vinylcarbonyl) optionally substituted by $C_{6-10}$ aryl (e.g., phenyl),
    (iv) $C_{2-4}$ alkynyl-carbonyl (e.g., acetylenecarbonyl, 1-propynylcarbonyl) optionally substituted by $C_{6-10}$ aryl (e.g., phenyl),
    (v) $C_{3-6}$ cycloalkyl-carbonyl (e.g., cyclopropylcarbonyl, cyclopentylcarbonyl, cyclohexylcarbonyl),
    (vi) $C_{3-6}$ cycloalkenyl-carbonyl (e.g., cyclopentenylcarbonyl),
    (vii) $C_{6-10}$ aryl-carbonyl (e.g., benzoyl) optionally substituted from
      (i') halogen atom (e.g., fluorine, chlorine),
      (ii') $C_{1-4}$ alkyl (e.g., methyl, ethyl, isopropyl, tert-butyl) optionally substituted by 1 to 3 substituents selected from halogen atom (e.g., fluorine), cyano, hydroxy and $C_{3-6}$ cycloalkyl (e.g., cyclopropyl),
      (iii') $C_{3-6}$ cycloalkyl (e.g., cyclopropyl, cyclobutyl, cyclohexyl) optionally substituted by cyano,
      (iv') $C_{1-4}$ alkoxy (e.g., methoxy, ethoxy, isopropoxy, tert-butoxy) optionally substituted by 1 to 5 halogen atoms (e.g., fluorine),
      (v') $C_{1-4}$ alkoxy-carbonyl (e.g., methoxycarbonyl), and
      (vi') 5- or 6-membered heterocyclic group (e.g., tetrahydropyranyl, pyrrolidinyl) optionally substituted by cyano or oxo,
    (viii) 5- or 6-membered heterocyclyl-carbonyl containing, as ring-constituting atom, 1 to 3 heteroatoms selected from oxygen atom, sulfur atom and nitrogen atom besides carbon atoms (e.g., furylcarbonyl, tetrahydrofurylcarbonyl, thienylcarbonyl, pyrrolylcarbonyl, pyrrolidinylcarbonyl, imidazolylcarbonyl, thiazolylcarbonyl, thiadiazolylcarbonyl, dihydrooxazolylcarbonyl, oxazolylcarbonyl, isoxazolylcarbonyl, pyrazolylcarbonyl, dihydropyrazolylcarbonyl, triazolylcarbonyl, pyridylcarbonyl, pyrimidinylcarbonyl, pyrazinylcarbonyl, pyridazinylcarbonyl) optionally substituted by 1 to 3 substituents selected from
      (i') halogen atom (e.g., chlorine),
      (ii') $C_{1-4}$ alkyl (e.g., methyl, ethyl, isopropyl, tert-butyl) optionally substituted by 1 to 3 substituents selected from halogen atom (e.g., fluorine), cyano, hydroxy and $C_{1-4}$ alkoxy (e.g., methoxy),
      (iii') $C_{6-10}$ aryl (e.g., phenyl),
      (iv') $C_{6-10}$ aryl-$C_{1-4}$ alkyl (e.g., benzyl),
      (v') $C_{1-4}$ alkoxy (e.g., methoxy, ethoxy) optionally substituted by $C_{1-4}$ alkoxy (e.g., methoxy),
      (vi') $C_{1-4}$ alkylsulfonyl (e.g., methylsulfonyl, ethylsulfonyl),
      (vii') $C_{1-4}$ alkyl-carbonyl (e.g., acetyl), and
      (viii') oxo,
    (ix) aromatic fused heterocyclyl-carbonyl (e.g., benzopyrazolylcarbonyl, indolylcarbonyl),
    (x) $C_{1-4}$ alkyl-aminocarbonyl (e.g., ethylaminocarbonyl),
    (xi) $C_{6-10}$ aryl-aminocarbonyl (e.g., phenylaminocarbonyl) optionally substituted by $C_{1-4}$ alkyl (e.g., methyl) optionally substituted by 1 to 3 halogen atoms (e.g., fluorine),
    (xii) $C_{1-4}$ alkoxy-aminocarbonyl (e.g., methoxyaminocarbonyl, isobutoxyaminocarbonyl),
    (xiii) 5-membered heterocyclyl-aminocarbonyl (e.g., isoxazolylaminocarbonyl, pyrazolylaminocarbonyl) optionally substituted by 1 to 3 substituents selected from $C_{1-4}$ alkyl (e.g., methyl, tert-butyl) and $C_{6-10}$ aryl (e.g., phenyl),
    (xiv) aminothiocarbonyl optionally substituted by $C_{6-10}$ aryl-$C_{1-4}$ alkyl-carbonyl (e.g., benzylcarbonyl), and
    (xv) 5-membered aromatic heterocyclyl-sulfonyl (e.g., thiazolylsulfonyl) optionally substituted by 1 to 3 $C_{1-4}$ alkyl (e.g., methyl),
  (e) $C_{1-4}$ alkyl-aminocarbonyl (e.g., methylaminocarbonyl) optionally having $C_{6-10}$ aryl (e.g., phenyl),
  (f) 5-membered heterocyclyl-aminocarbonyl (e.g., pyrazolylaminocarbonyl) optionally substituted by 1 to 3 substituents selected from $C_{1-4}$ alkyl (e.g., methyl) and $C_{6-10}$ aryl, (g) $C_{6-10}$ aryl-aminocarbonyl (e.g., phenylaminocarbonyl) optionally substituted by $C_{1-4}$ alkyl (e.g., methyl, isopropyl, tert-butyl) optionally substituted by 1 to 3 substituents selected from halogen atom (e.g., fluorine) and cyano,
(h) carboxy, and
(i) nitro,
(2) monocyclic aromatic heterocycle (e.g., pyridyl) optionally substituted by 1 to 3 substituents selected from
    (a) halogen atom (e.g., bromine), and
    (b) $C_{6-10}$ aryl-carbonylamino (e.g., benzoylamino) optionally substituted by $C_{1-4}$ alkyl (e.g., methyl) optionally substituted by 1 to 3 halogen atoms (e.g., fluorine), or
(3) fused aromatic heterocycle (e.g., indolyl, benzothiazolyl, benzimidazolyl) optionally substituted by 1 to 3 substituents selected from
    (a) $C_{1-4}$ alkyl (e.g., methyl), and
    (b) $C_{6-10}$ arylamino (e.g., phenylamino) optionally substituted by $C_{1-4}$ alkyl (e.g., methyl) optionally substituted by 1 to 3 halogen atoms (e.g., fluorine),
and the like.

As ring Y, 3-[(1,3-dimethyl-1H-pyrazol-5-yl) aminocarbonyl]phenyl, 3-aminophenyl, 4-aminophenyl, 3-{[(ethylamino)carbonyl]amino}phenyl, 4-{[(phenylamino)carbonyl]amino}phenyl, 3-{[(phenylamino)carbonyl]amino}phenyl, 3-({[3 -(trifluoromethylpheny)amino] carbonyl}amino)phenyl, 3 -({[4-(trifluoromethylpheny) amino]carbonyl}amino)phenyl, 3-[(tert-butylcarbonyl) amino]phenyl, 3-[(cyclopropylcarbonyl)amino]phenyl, 3-[(cyclohexylcarbony)amino]phenyl, 3-[(phenylcarbonyl) amino]phenyl, 3-{[3-(trifluoromethylphenyl) carbonyl] amino}phenyl, 3-{[3-(fluorophenyl)carbonyl] amino}phenyl, 3-{[3-(chlorophenyl)carbonyl] amino}phenyl, 3-{[3-(pyridyl)carbonyl]amino}phenyl, 3-{[2-(furyl)carbonyl]amino}phenyl, 3-{[3-(2,5-dimethylfuran)carbonyl]amino}phenyl, 3-{[2-(3-methylthiophene) carbonyl]amino}phenyl, 3-{[5-(4-methyl-1,2,3-thiadiazole) carbonyl]amino}phenyl, 3-{[5-(isoxazole)carbonyl] amino}phenyl, 3-{[5-(1,3-dimethyl-1H-pyrazole)carbonyl] amino}phenyl, 3-{[5-(3-methylisoxazole)carbonyl] amino}phenyl, 3-{[3-(5-methylisoxazole)carbonyl] amino}phenyl, 3-({5-[1-methyl-3-(trifluoromethyl)-1H -pyrazole]carbonyl}amino)phenyl, 5-methyl-2-(trifluoromethyl)-3-furancarbonylaminophenyl, 3-{[5-(2,4- dimethyl-1, 3-thiazole)carbonyl]amino}phenyl, 3-{[4-(2,5-dimethyl-1,3 -oxazole)carbonyl]amino}phenyl, 3-{[5-(1-methyl-1 H -pyrazole)carbonyl]amino}phenyl,
3-{[3-(1,5-dimethyl-1H-pyrazole)carbonyl]amino}phenyl, 3-{[4-(3,5-dimethylisoxazole)carbonyl]amino}phenyl, 3-{[5-(1-methyl-1H-1,2,3-triazole)carbonyl]amino}phenyl, 3-{[4-(1-methyl-1H-1,2,3-triazole)carbonyl]amino}phenyl, 3-{[2-(1-methyl-1H-imidazole)carbonyl]amino}phenyl, 3-{[5-(1-methyl-1H-imidazole)carbonyl]amino}phenyl, 1H-indol6-yl, 2-methyl-1H-indol6-yl, 1,2-dimethyl-1H-benzimidazol-5-yl, 1H-indol-4-yl, 2-methyl-1,3-benzothiazol-5-yl, 2-methyl-1,3-benzothiazol-6-yl, 5-amino-2-methylphenyl, 3-amino-2-methylphenyl, 3-amino-4-methylphenyl, 3-amino-4-chlorophenyl, 5-amino-2-chlorophenyl, 5-amino-2-methoxyphenyl, 6-methyl-3-{[5-(1,3-dimethyl-1H-pyrazole)carbonyl]amino}phenyl, 2-methyl-3-{[5-(1,3-dimethyl-1H-pyrazole)carbonyl] amino}phenyl, 4-methyl-3-{[5-(1,3-dimethyl-1H-pyrazole) carbonyl]amino}phenyl, 4-chloro-3-{[5-(1,3-dimethyl-1H-pyrazole)carbonyl]amino}phenyl, 6-chloro-3-{[5-(1,3-dimethyl-1H-pyrazole)carbonyl]amino}phenyl, 4-fluoro-3-{[5-(1,3-dimethyl-1H- pyrazole)carbonyl]amino}phenyl, 6-methoxy-3-{[5-(1,3-dimethyl-1H-pyrazole)carbonyl] amino}phenyl, 4-chloro-3- (cyclopropylcarbonylamino)phenyl, 3-amino-4-fluorophenyl, 4-fluoro-3-[4-(1-ethyl-3-methyl-1H-pyrazole)carbonyl] amino}phenyl and the like can be specifically mentioned.

In the compounds (I) and (IV), as the substituent for R of NR defined by X, those similar to the group exemplified as the "optionally substituted hydrocarbon group" in the aforementioned Substituent Group (1)(iv), the group exemplified as the "optionally substituted aminocarbonyl" in the aforementioned Substituent Group (1)(viii), the group exemplified as the "acyl" in the aforementioned Substituent Group (1)(ix) and the group exemplified as the "optionally substituted heterocyclic group" in the aforementioned Substituent Group (1)(xii) can be mentioned.

As the substituent for R, optionally substituted hydrocarbon group and the like are preferable.

X is preferably —O—, —S— or —NH—, more preferably —O— or —S—, and particularly preferably —O—.

In the compounds (I) and (IV), $R^1$ is hydrogen atom or substituent (provided that when $R^1$ is other than an optionally substituted amino, ring Y is a cyclic group substituted by an optionally substituted amino, wherein the cyclic group is optionally further substituted).

As the "substituent" for $R^1$, those similar to the substituent of the aforementioned Substituent Group (1) can be mentioned. Of these, optionally substituted amino, optionally substituted aminocarbonyl, optionally substituted alkyl and the like are preferable.

Preferable $R^1$ is
(1) hydrogen atom,
(2) amino,
(3) optionally substituted alkylcarbonylamino,
(4) optionally substituted alkenylcarbonylamino,
(5) optionally substituted alkynylcarbonylamino,
(6) optionally substituted cycloalkylcarbonylamino,
(7) optionally substituted cycloalkyl-alkylcarbonylamino,
(8) optionally substituted 6-membered heterocyclyl-carbonylamino,
(9) optionally substituted aminocarbonylamino,
(10) optionally substituted alkoxycarbonylamino,
(11) optionally substituted alkylsulfonylamino,
(12) optionally substituted cycloalkylsulfonylamino,
(13) optionally substituted arylamino,
(14) optionally substituted heterocyclylamino,
(15) optionally substituted aminocarbonyl,
(16) optionally substituted alkyl,
(17) optionally esterified carboxy, and the like.

Of these, preferable $R^1$ are
(1) hydrogen atom,
(2) amino,
(3) $C_{1-4}$ alkyl-carbonylamino (e.g., acetylamino, ethylcarbonylamino, isopropylcarbonylamino, isobutylcarbonylamino, tert-butylcarbonylamino) optionally substituted by 1 to 3 substituents selected from (a) halogen atom (e.g., chlorine), (b) hydroxy, (c) $C_{1-4}$ alkoxy (e.g., methoxy), (d) $C_{1-4}$ alkyl-carbonyloxy (e.g., methylcarbonyloxy), (e) $C_{1-4}$ alkylamino (e.g., methylamino), (f) di-$C_{1-4}$ alkylamino (e.g., dimethylamino), (g) $C_{1-4}$ alkylsulfonyl (e.g., methylsulfonyl), and (h) 6-membered heterocyclic group (e.g., piperazinyl, morpholinyl) optionally having 1 to 3 $C_{1-4}$ alkyl (e.g., methyl),
(4) $C_{2-4}$ alkenyl-carbonylamino (e.g., vinylcarbonylamino, 2-methyl-1-propenylcarbonylamino) optionally having $C_{1-4}$ alkoxy (e.g., methoxy),
(5) $C_{2-4}$ alkynyl-carbonylamino (e.g., 1-propenylcarbonylamino),
(6) $C_{3-6}$ cycloalkyl-carbonylamino (e.g., cyclopropylcarbonylamino, cyclobutylcarbonylamino, cyclopentylcarbonylamino, cyclohexylcarbonylamino) optionally substituted by 1 to 4 substituents selected from (a) halogen atom (e.g., fluorine), (b) hydroxy, (c) $C_{1-4}$ alkyl (e.g., methyl, isopropyl) optionally having hydroxy, (d) $C_{1-4}$ alkoxy (e.g., methoxy), (e) $C_{1-4}$ alkoxy-carbonyl (e.g., methoxycarbonyl), and (f) $C_{1-4}$ alkyl-carbonyloxy (e.g., acetoxy),
(7) $C_{3-6}$ cycloalkyl-$C_{1-4}$ alkyl-carbonylamino (e.g., cyclopropylmethylcarbonylamino),
(8) 6-membered heterocyclyl-carbonylamino (e.g., tetrahydropyranylcarbonylamino, pyridylcarbonylamino, pyrimidinylcarbonylamino, morpholinylcarbonylamino, piperazinylcarbonylamino) optionally substituted by 1 to 3 substituents selected from (a) halogen atom (e.g., fluorine, chlorine), (b) cyano, and (c) $C_{1-4}$ alkyl (e.g., methyl) optionally having 1 to 3 halogen atoms (e.g., fluorine),
(9) aminocarbonylamino optionally substituted by 1 or 2 substituents selected from (a) $C_{1-4}$ alkyl (e.g., ethyl) optionally having 1 to 3 $C_{1-4}$ alkoxy (e.g., ethoxy) optionally having 1 to 3 hydroxy, and (b) $C_{1-4}$ alkoxy (e.g., methoxy),
(10) $C_{1-4}$ alkoxy-carbonylamino (e.g., methoxycarbonylamino, ethoxycarbonylamino, tert-butoxycarbonylamino) optionally substituted by 1 to 3 halogen atoms (e.g., chlorine),
(11) $C_{1-4}$ alkylsulfonylamino (e.g., methylsulfonylamino),
(12) $C_{3-6}$ cycloalkylsulfonylamino (e.g., cyclopropylsulfonylamino),
(13) $C_{6-10}$ arylamino (e.g., phenylamino),
(14) heterocyclylamino (e.g., thiazolylamino, pyrimidinylamino) optionally substituted by 1 to 3 substituents selected from (a) halogen atom (e.g., chlorine), and (b) $C_{1-4}$ alkylamino (e.g., methylamino),
(15) aminocarbonyl optionally substituted by $C_{1-4}$ alkyl (e.g., methyl),
(16) $C_{1-4}$ alkyl (e.g., methyl) optionally substituted by hydroxy,
(17) carboxy,
(18) $C_{1-6}$ alkoxy-carbonyl (e.g., ethoxycarbonyl),
and the like.

Specific $R^1$ may include hydrogen atom, amino, acetylamino, chloroacetylamino, 4-morpholinylacetylamino, methylcarbonyloxymethylcarbonylamino, methylaminomethylcarbonylamino, hydroxymethylcarbonylamino, methoxymethylcarbonylamino, ethylcarbonylamino, isopropylcarbonylamino, dimethylaminomethylcarbonylamino, 4-methylpiperazin-1-ylacetylamino, methylsulfonylmethylcarbonylamino, 3-hydroxy-3-methylbutanoylamino, hydroxyethylcarbonylamino, 3-methyl-2-butenoylamino, 3-methoxy-2-propencylamino, 2-butynoylamino, (cyclopropylcarbonyl)amino, (1-methoxycarbonylcyclopropylcarbonyl)amino, (1-hydroxycyclopropylcarbonyl)amino, (2-methylcyclopropylcarbonyl)amino, (2-methoxycyclopropylcarbonyl)amino, (2-methylcarbonylcyclopropylcarbonyl)amino, (2-hydroxymethylcarbonylcyclopropylcarbonyl)amino, (2-(1-hydroxy-1-methylethyl)cyclopropyl)carbonylamino, (2,2-dimethylcyclopropylcarbonyl)amino, (2,2-difluorocyclopropylcarbonyl)amino, (2,2,3,3-tetramethylcyclopropylcarbonyl)amino, (cyclobutylcarbonyl)amino, (cyclopentylcarbonyl)amino, (cyclohexylcarbonyl)amino, cyclopropylmethylcarbonylamino, (tetrahydro-2H-pyran-4-ylcarbonyl)amino, (3-pyridylcarbonyl)amino, (4-pyridylcarbonyl)amino, (6-methyl-3-pyridylcarbonyl)amino, (6-fluoro-3-pyridylcarbonyl)amino, (6-chloro-3-pyridylcarbonyl)amino, (6-cyano-3-pyridylcarbonyl)amino, (6-(trifluoromethyl)-3-pyridylcarbonyl)amino, (5-pyrimidinylcarbonyl)amino, 4-morpholinylcarbonylamino, methoxyureido, ethylureido, 2-hydroxyethoxyethylureido, methoxycarbonylamino, ethoxycarbonylamino, 2,2,2-trichloroethoxycarbonylamino, tert-butoxycarbonylamino, methylsulfonylamino, (cyclopropylsulfonyl)amino, phenylamino, 2-methylaminopyrimidin-4-ylamino, 2-chloropyrimidin-4-ylamino, 1,3-thiazol-2-ylamino, methylaminocarbonyl, hydroxymethyl, carboxy, ethoxycarbonyl and the like can be mentioned.

In the compounds (I) and (IV), as the "substituent" for $R^2$, those similar to the substituents of the aforementioned Substituent Group (1) can be mentioned.

Of these, preferable $R^2$ is hydrogen atom.

In the compounds (I) and (IV), as the "substituent" for $R^3$, those similar to the substituents of the aforementioned Substituent Group (1) can be mentioned.

Of these, preferable $R^3$ is hydrogen atom.

In the compounds (I) and (IV), as the "substituent" for $R^4$, those similar to the substituents of the aforementioned Substituent Group (1) can be mentioned.

Of these, preferable $R^4$ is hydrogen atom.

As preferable examples of the compounds (I) and (IV), for example, the following compounds can be mentioned.

A compound wherein
ring Y is
(1) $C_{6-10}$ aryl optionally substituted by 1 to 3 substituents selected from
 (a) halogen atom,
 (b) $C_{1-4}$ alkyl,
 (c) $C_{1-4}$ alkoxy,
 (d) amino optionally substituted by the substituents selected from
  (i) $C_{1-4}$ alkyl optionally substituted by a 5-membered aromatic heterocyclic group optionally substituted by 1 to 3 $C_{1-4}$ alkyl,
  (ii) $C_{1-4}$ alkyl-carbonyl optionally substituted by 1 to 3 substituents selected from
   (i') hydroxy,
   (ii') $C_{1-4}$ alkylsulfonyl, and
   (iii') 6-membered aromatic heterocyclic group,
  (iii) $C_{2-4}$ alkenyl-carbonyl optionally substituted by $C_{6-10}$ aryl,
  (iv) $C_{2-6}$ alkynyl-carbonyl optionally substituted by $C_{6-10}$ aryl,
  (v) $C_{3-6}$ cycloalkyl-carbonyl,
  (vi) $C_{3-6}$ cycloalkenyl-carbonyl,
  (vii) $C_{6-10}$ aryl-carbonyl optionally substituted by 1 to 3 substituents selected from
   (i') halogen atom,
   (ii') $C_{1-4}$ alkyl optionally substituted by 1 to 3 substituents selected from halogen atom, cyano, hydroxy and $C_{3-6}$ cycloalkyl,
   (iii') $C_{3-6}$ cycloalkyl optionally substituted by cyano,
   (iv') $C_{1-4}$ alkoxy optionally substituted by 1 to 5 halogen atoms,
   (v') $C_{1-4}$ alkoxy-carbonyl, and
   (vi') 5- or 6-membered heterocyclic group optionally substituted by cyano or oxo,
  (viii) 5- or 6-membered heterocyclyl-carbonyl containing, as ring-constituting atom, 1 to 3 heteroatoms selected from oxygen atom, sulfur atom and nitrogen atom besides carbon atoms, which is optionally substituted by 1 to 3 substituents selected from
   (i') halogen atom,
   (ii') $C_{1-4}$ alkyl optionally substituted by 1 to 3 substituents selected from halogen atom, cyano, hydroxy and $C_{1-4}$ alkoxy,
   (iii') $C_{6-10}$ aryl,
   (iv') $C_{6-10}$ aryl-$C_{1-4}$ alkyl, (v') C$_{1-4}$ alkoxy optionally substituted by C$_{1-4}$ alkoxy,
(vi') C$_{1-4}$ alkylsulfonyl,
(vii') C$_{1-4}$ alkyl-carbonyl, and
(viii') oxo,
(ix) aromatic fused heterocyclyl-carbonyl,
(x) C$_{1-4}$ alkyl-aminocarbonyl,
(xi) C$_{6-10}$ aryl-aminocarbonyl optionally substituted by C$_{1-4}$ alkyl optionally substituted by 1 to 3 halogen atoms,
(xii) C$_{1-4}$ alkoxy-aminocarbonyl,
(xiii) 5-membered heterocyclyl-aminocarbonyl optionally substituted by 1 to 3 substituents selected from C$_{1-4}$ alkyl and C$_{6-10}$ aryl,
(xiv) aminothiocarbonyl optionally substituted by C$_{6-10}$ aryl-C$_{1-4}$ alkyl-carbonyl, and
(xv) 5-membered aromatic heterocyclyl-sulfonyl optionally substituted by 1 to 3 C$_{1-4}$ alkyl,
(e) C$_{1-4}$ alkyl-aminocarbonyl optionally having C$_{6-10}$ aryl,
(f) 5-membered heterocyclyl-aminocarbonyl optionally substituted by 1 to 3 substituents selected from C$_{1-4}$ alkyl and C$_{6-10}$ aryl,
(g) C$_{6-10}$ aryl-aminocarbonyl optionally substituted by C$_{1-4}$ alkyl optionally substituted by 1 to 3 substituents selected from halogen atom and cyano,
(h) carboxy, and
(i) nitro,
(2) monocyclic aromatic heterocycle optionally substituted by 1 to 3 substituents selected from
(a) halogen atom, and
(b) C$_{6-10}$ aryl-carbonylamino optionally substituted by C$_{1-4}$ alkyl optionally substituted by 1 to 3 halogen atoms, or
(3) fused aromatic heterocycle optionally substituted by 1 to 3 substituents selected from
(a) C$_{1-4}$ alkyl, and
(b) C$_{6-10}$ arylamino optionally substituted by C$_{1-4}$ alkyl optionally substituted by 1 to 3 halogen atoms;
X is —O—, —S— or —NH— (more preferably —O— or —S—, particularly preferably —O—);
R$^1$ is
(1) hydrogen atom,
(2) amino,
(3) C$_{1-4}$ alkyl-carbonylamino optionally substituted by 1 to 3 substituents selected from
(a) halogen atom,
(b) hydroxy,
(c) C$_{1-4}$ alkoxy,
(d) C$_{1-4}$ alkyl-carbonyloxy,
(e) C$_{1-4}$ alkylamino,
(f) di-C$_{1-4}$ alkylamino,
(g) C$_{1-4}$ alkylsulfonyl, and
(h) 6-membered heterocyclic group optionally having 1 to 3 C$_{1-4}$ alkyl,
(4) C$_{2-4}$ alkenyl-carbonylamino optionally having C$_{1-4}$ alkoxy,
(5) C$_{2-4}$ alkynyl-carbonylamino,
(6) C$_{3-6}$ cycloalkyl-carbonylamino optionally substituted by 1 to 4 substituents selected from
(a) halogen atom,
(b) hydroxy,
(c) C$_{1-4}$ alkyl optionally having hydroxy,
(d) C$_{1-4}$ alkoxy,
(e) C$_{1-4}$ alkoxy-carbonyl, and
(f) C$_{1-4}$ alkyl-carbonyloxy,
(7) C$_{3-6}$ cycloalkyl-C$_{1-4}$ alkyl-carbonylamino,
(8) 6-membered heterocyclyl-carbonylamino optionally substituted by 1 to 3 substituents selected from
(a) halogen atom,
(b) cyano, and
(c) C$_{1-4}$ alkyl optionally having 1 to 3 halogen atom,
(9) aminocarbonylamino optionally substituted by 1 or 2 substituents selected from
(a) C$_{1-4}$ alkyl optionally having 1 to 3 C$_{1-4}$ alkoxy optionally having 1 to 3 hydroxy, and
(b) C$_{1-4}$ alkoxy,
(10) C$_{1-4}$ alkoxy-carbonylamino optionally substituted by 1 to 3° halogen atoms,
(11) C$_{1-4}$ alkylsulfonylamino,
(12) C$_{3-6}$ cycloalkylsulfonylamino,
(13) C$_{6-10}$ arylamino,
(14) heterocyclylamino optionally substituted by 1 to 3 substituents selected from
(a) halogen atom, and
(b) C$_{1-4}$ alkylamino,
(15) aminocarbonyl substituted by C$_{1-4}$ alkyl (e.g., methyl etc.),
(16) C$_{1-4}$ alkyl (e.g., methyl) optionally substituted by hydroxy,
(17) carboxy, or
(18) C$_{1-6}$ alkoxy-carbonyl (e.g., ethoxycarbonyl); and
R$^2$, R$^3$ and R$^4$ are each hydrogen atom.

As specific examples of the compounds (I) and (IV), for example, compounds of Examples 1 to 440, 442 and 445 can be mentioned.

Particularly preferable examples may include the following compounds or salts thereof.

N-{3-[(2-{[2-(methylamino)pyrimidin-4-yl]amino}imidazol[1,2-b]pyridazin-6-yl)oxy]phenyl}-3-(trifluoromethyl)benzamide (Example 70);

N-[2-chloro-5-({2-[(cyclopropylcarbonyl)amino]imidazol[1,2-b]pyridazin-6-yl}oxy)phenyl]-1,3-dimethyl-1H-pyrazole-5-carboxamide (Example 97);

N-[5-({2-[(cyclopropylcarbonyl)amino]imidazo[1,2-b]pyridazin-6-yl}oxy)-2-methylphenyl]-1,3-dimethyl-1H-pyrazole-5-carboxamide (Example 111);

N-[3-({2-[(cyclopropylcarbonyl)amino]imidazo[1,2-b]pyridazin-6-yl}oxy)phenyl]-2,4-dimethyl-1,3-thiazole-5-carboxamide (Example 114);

N-[3-({2-[(cyclopropylcarbonyl)amino]imidazo[1,2-b]pyridazin-6-yl}oxy)phenyl]-2,5-dimethyl-1,3-oxazole-4-carboxamide (Example 117);

N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide (Example 148);

N-[3-({2-[(N,N-dimethylglycyl)amino]imidazo[1,2-b]pyridazin-6-yl}oxy)phenyl]-1,3-dimethyl-1H-pyrazole-5-carboxamide (Example 149);

N-[3-({2-[(cyclopropylcarbonyl)amino]imidazo[1,2-b]pyridazin-6-yl}sulfanyl)phenyl]-1,3-dimethyl-1H-pyrazole-5-carboxamide (Example 150);

N-[5-({2-[(cyclopropylcarbonyl)amino]imidazo[1,2-b]pyridazin-6-yl}oxy)-2-fluorophenyl]-1-ethyl-3-methyl-1H-pyrazole-4-carboxamide (Example 161);

N-[3-({2-[(cyclopropylcarbonyl)amino]imidazo[1,2-b]pyridazin-6-yl}oxy)phenyl]benzamide (Example 165);

N-[5-({2-[(cyclopropylcarbonyl)amino]imidazo[1,2-b]pyridazin-6-yl}oxy)-2-fluorophenyl]-1,3-dimethyl-1H-pyrazole-4-carboxamide (Example 173);

N-[5-({2-[(cyclopropylcarbonyl)amino]imidazo[1,2-b]pyridazin-6-yl}oxy)-2-fluorophenyl]-1-ethyl-1H-pyrazole-5-carboxamide (Example 174);

N-[5-({2-[(cyclopropylcarbonyl)amino]imidazo[1,2-b]pyridazin-6-yl}oxy)-2-fluorophenyl]-3-methoxy-1-methyl-1H-pyrazole-5-carboxamide (Example 180);

N-[5-({2-[(cyclopropylcarbonyl)amino]imidazo[1,2-b]pyridazin-6-yl}oxy)-2-fluorophenyl]-3-ethyl-1-methyl-1H-pyrazole-5-carboxamide (Example 208);

N-[2-chloro-5-({2-[(cyclopropylcarbonyl)amino]imidazo[1,2-b]pyridazin-6-yl}oxy)phenyl]-1-ethyl-3-methyl-1H-pyrazole-4-carboxamide (Example 254);

N-[5-({2-[(cyclopropylcarbonyl)amino]imidazo[1,2-b]pyridazin-6-yl}oxy)-2-fluorophenyl]-1-methyl-1H-pyrazole-5-carboxamide (Example 287);

N-[5-({2-[(cyclopropylcarbonyl)amino]imidazo[1,2-b]pyridazin-6-yl}oxy)-2-fluorophenyl]-2,4-dimethyl-1,3-oxazole-5-carboxamide (Example 289);

N-[5-({2-[(cyclopropylcarbonyl)amino]imidazo[1,2-b]pyridazin-6-yl}oxy)-2-fluorophenyl]-2-ethyl-4-methyl-1,3-oxazole-5-carboxamide (Example 314);

N-[3-({2-[(cyclopropylcarbonyl)amino]imidazo[1,2-b]pyridazin-6-yl}oxy)phenyl]-3-(trifluoromethyl)benzamide (Example 319);

3-(1-cyano-1-methylethyl)-N-[5-({2-[(cyclopropylcarbonyl)amino]imidazo[1,2-b]pyridazin-6-yl}oxy)-2-methylphenyl]benzamide (Example 330);

N-[3-({2-[(N,N-dimethylglycyl)amino]imidazo[1,2-b]pyridazin-6-yl}oxy)phenyl]-3-(trifluoromethyl)benzamide (Example 398);

N-[3-({2-[(cyclopropylcarbonyl)amino]imidazo[1,2-b]pyridazin-6-yl}thio)phenyl]-3-(trifluoromethyl)benzamide (Example 427);

N-{6-[3-({[3-(trifluoromethyl)phenyl]carbamoyl}amino)phenoxy]imidazo[1,2-b]pyridazin-2-yl}cyclopropanecarboxamide (Example 431).

The compound represented by the formula (II) (hereinafter compound (II)) of the present invention is explained.

As the "cyclic group" of the "optionally substituted cyclic group" for ring Ya, those similar to the group exemplified as the "cyclic group" of the "optionally substituted cyclic group" for ring Y of compound (I) can be mentioned.

As the "cyclic group" of the "optionally substituted cyclic group" shown by ring Ya, aromatic hydrocarbon group, aromatic heterocyclic group are preferable. As the aromatic hydrocarbon group, $C_{6-14}$ aryl is preferable, $C_{6-10}$ aryl is more preferable, and phenyl is particularly preferable. As the aromatic heterocyclic group, monocyclic aromatic heterocyclic group, fused aromatic heterocyclic group are preferable, pyridine ring, and, fused aromatic heterocyclic group formed by fusion of benzene ring and 5-membered monocyclic aromatic heterocyclic group containing, as ring-constituting atom, 1 or 2 hetero atoms selected from sulfur atom and nitrogen atom besides carbon atoms (e.g., benzothiazolyl, benzimidazolyl, indolyl etc.) is more preferable, and benzothiazolyl (e.g., 5-benzothiazolyl, 6-benzothiazolyl), benzimidazolyl (e.g., benzimidazol-5-yl, benzimidazol-6-yl), indolyl (e.g., indol-4-yl, indol-5-yl, indol-6-yl) and the like are particularly preferable.

The "optionally substituted cyclic group" for ring Ya may have 1 to the acceptable maximum number of substituents at any substitutable positions. Where the cyclic group is substituted by two or more substituents, the substituents may be the same or different, and the cyclic group optionally has preferably 1 to 5, more preferably 1 to 3 substituents.

As the "substituent" of the "optionally substituted cyclic group" for ring Ya, those similar to the group exemplified as the "substituent" of the "optionally substituted cyclic group" for ring Y of compound (I) can be mentioned.

The "substituent" of the "optionally substituted cyclic group" for ring Ya is preferably
(1) halogen atom (e.g., fluorine, chlorine, bromine, iodine),
(2) optionally substituted alkyl,
(3) optionally substituted alkoxy,
(4) optionally substituted aminocarbonyl,
(5) optionally substituted amino,
(6) carboxyl,
and the like.

Of these,
(1) halogen atom (e.g., fluorine, chlorine, bromine, iodine),
(2) optionally substituted alkyl,
(3) optionally substituted amino,
and the like are preferable.

Hereinafter the above-mentioned preferable examples of the "substituent" of the "optionally substituted cyclic group" for ring Ya are explained in detail.

(1) As the halogen atom, fluorine, chlorine, bromine and the like are preferable.

(2) As the optionally substituted alkyl, optionally substituted $C_{1-8}$ alkyl is preferable, optionally substituted $C_{1-4}$ alkyl is more preferable, and unsubstituted $C_{1-4}$ alkyl is more preferable. Specifically, methyl, ethyl and the like are preferable.

(3) As the optionally substituted alkoxy, optionally substituted $C_{1-8}$ alkoxy is preferable, optionally substituted $C_{1-4}$ alkoxy is more preferable, unsubstituted $C_{1-4}$ alkoxy is much more preferable. Specifically, methoxy and the like are preferable.

(4) As the "substituent" for the optionally substituted aminocarbonyl, for example, $C_{1-8}$ alkyl, $C_{2-8}$ alkenyl, $C_{2-8}$ alkynyl, $C_{3-8}$ cycloalkyl, $C_{3-8}$ cycloalkenyl, $C_{3-8}$ cycloalkynyl, $C_{6-18}$ aryl, heterocyclic group and the like, each of which is optionally substituted, are preferable. Of these, optionally substituted $C_{1-4}$ alkyl, optionally substituted $C_{6-12}$ aryl and optionally substituted 5-membered heterocyclic group and the like are preferable. Particularly, $C_{6-12}$ aryl optionally substituted by $C_{1-4}$ alkyl optionally substituted by 1 to 3 substituents selected from (a) $C_{1-4}$ alkyl optionally having $C_{6-12}$ aryl, (b) 5-membered heterocyclic group optionally substituted by 1 to 3 substituents selected from $C_{1-4}$ alkyl and $C_{6-12}$ aryl, (c) halogen atom and (d) cyano is preferable.

(5) As the "substituent" for the optionally substituted amino, optionally substituted alkyl, optionally substituted aminocarbonyl, acyl, optionally substituted aminothiocarbonyl, optionally substituted heterocyclyl-sulfonyl and the like are preferable.

As the optionally substituted amino, amino optionally substituted by 1 or 2 substituents selected from (a) optionally substituted alkyl, (b) optionally substituted aminocarbonyl, (c) acyl, (d) optionally substituted aminothiocarbonyl, and (e) optionally substituted heterocyclyl-sulfonyl is preferable.

As the optionally substituted alkyl, optionally substituted $C_{1-4}$ alkyl is preferable. Of these, $C_{1-4}$ alkyl optionally substituted by 5-membered heterocyclic group optionally substituted by 1 to 3 $C_{1-4}$ alkyl is preferable.

As the optionally substituted aminocarbonyl, $C_{1-8}$ alkyl-aminocarbonyl, $C_{6-18}$ aryl-aminocarbonyl, $C_{6-18}$ aryl-$C_{1-4}$-alkyl-aminocarbonyl, heterocyclyl-aminocarbonyl, $C_{3-8}$ cycloalkyl-aminocarbonyl, $C_{1-8}$ alkoxy-aminocarbonyl and the like, each of which is optionally substituted, are preferable. Of these, optionally substituted $C_{1-8}$ alkyl-aminocarbonyl, optionally substituted $C_{6-18}$ aryl-aminocarbonyl, optionally substituted heterocyclyl-aminocarbonyl, optionally substituted $C_{1-8}$ alkoxy-aminocarbonyl and the like are preferable. Particularly, (i) $C_{1-4}$ alkyl-aminocarbonyl, (ii) $C_{6-10}$ aryl-aminocarbonyl optionally substituted by $C_{1-4}$ alkyl optionally substituted by 1 to 3 halogen atoms, (iii) $C_{1-4}$ alkoxy-aminocarbonyl, (iv) 5-membered heterocyclyl-aminocarbonyl optionally substituted by 1 to 3 substituents selected from $C_{1-4}$ alkyl and $C_{6-10}$ aryl, and the like are preferable.

As the acyl, $C_{1-8}$ alkyl-carbonyl, $C_{2-8}$ alkenyl-carbonyl, $C_{2-8}$ alkynyl-carbonyl, $C_{3-8}$ cycloalkyl-carbonyl, $C_{3-8}$ cycloalkenyl-carbonyl, $C_{6-18}$ aryl-carbonyl, $C_{6-18}$ aryl-$C_{1-4}$ alkyl-carbonyl, $C_{1-8}$ alkylsulfonyl, $C_{6-18}$ aryl-sulfonyl, heterocyclyl-carbonyl, heterocyclyl-sulfonyl and the like, each of which is optionally substituted, are preferable. Of these, $C_{1-8}$ alkyl-carbonyl, $C_{2-8}$ alkenyl-carbonyl, $C_{2-8}$ alkynyl-carbonyl, $C_{3-8}$ cycloalkyl-carbonyl, $C_{3-8}$ cycloalkenyl-carbonyl, $C_{6-18}$ aryl-carbonyl, heterocyclyl-carbonyl, each of which is optionally substituted, are preferable.

As the optionally substituted $C_{1-8}$ alkyl-carbonyl, optionally substituted $C_{1-4}$ alkyl-carbonyl is preferable. Particularly, $C_{1-4}$ alkyl-carbonyl (e.g., methylcarbonyl, tert-butylcarbonyl, 3-methylbutanoyl) optionally substituted by 1 to 3 substituents selected from (a) hydroxy, (b) $C_{1-4}$ alkylsulfonyl (e.g., methylsulfonyl) and (c) 6-membered heterocyclic group (e.g., pyridyl) (specific examples: methylsulfonylmethylcarbonyl, 2-pyridylmethylcarbonyl, tert-butylcarbonyl, 3-hydroxy-3-methylbutanoyl) is preferable.

As the optionally substituted $C_{2-8}$ alkenyl-carbonyl, optionally substituted $C_{2-4}$ alkenyl-carbonyl is preferable. Particularly, $C_{2-4}$ alkenyl-carbonyl (e.g., 3-methyl-2-butenoyl) optionally substituted by $C_{6-10}$ aryl (e.g., phenyl) (specific examples: 3-methyl-2-butenoyl) is preferable.

As the optionally substituted $C_{2-8}$ alkynyl-carbonyl, optionally substituted $C_{2-4}$ alkynyl-carbonyl is preferable. Particularly, $C_{2-4}$ alkynyl-carbonyl (e.g., 2-butynoyl) optionally substituted by $C_{6-10}$ aryl (e.g., phenyl) (specific example: 2-butynoyl) is preferable.

As the optionally substituted $C_{3-8}$ cycloalkyl-carbonyl, $C_{3-6}$ cycloalkyl-carbonyl is preferable, and cyclopropylcarbonyl, cyclopentylcarbonyl, cyclohexylcarbonyl and the like are specifically preferable.

As the optionally substituted $C_{3-8}$ cycloalkenyl-carbonyl, $C_{3-6}$ cycloalkenyl-carbonyl (e.g., cyclopentenecarbonyl) (specific example: 1-cyclopentenecarbonyl) is preferable.

As the optionally substituted $C_{6-18}$ aryl-carbonyl, optionally substituted $C_{6-10}$ aryl-carbonyl is preferable. Particularly, $C_{6-10}$ aryl-carbonyl (e.g., benzoyl) optionally substituted by 1 to 3 substituents selected from (a) halogen atom (e.g., fluorine), (b) $C_{1-4}$ alkyl (e.g., methyl, ethyl, isopropyl, tert-butyl) optionally substituted by 1 to 3 substituents selected from halogen atom (e.g., fluorine), cyano, hydroxy and $C_{3-6}$ cycloalkyl (e.g., cyclopropyl) (specific example: trifluoromethyl), (c) $C_{3-6}$ cycloalkyl (e.g., cyclopropyl, cyclobutyl, cyclohexyl) optionally substituted by cyano, (d) $C_{1-4}$ alkoxy (e.g., isopropoxy, tert-butoxy) optionally substituted by 1 to 5 halogen atoms (e.g., fluorine), (e) $C_{1-4}$ alkoxy-carbonyl (e.g., methoxycarbonyl), and (f) 5 or 6-membered heterocyclic group (e.g., tetrahydropyranyl, pyrrolidinyl) optionally substituted by cyano or oxo is preferable. Specifically, phenylcarbonyl(benzoyl), 3-(trifluoromethyl)phenylcarbonyl, 4-(trifluoromethyl)phenylcarbonyl, 3-fluorophenylcarbonyl, 3-chlorophenylcarbonyl, 3-(1-cyanocyclopropyl)phenylcarbonyl, 3-(1-cyanocyclobutyl)phenylcarbonyl, 3-(1-cyanocyclohexyl)phenylcarbonyl, 2-fluoro-3-(trifluoromethyl)phenylcarbonyl, 2-fluoro-5-(trifluoromethyl)phenylcarbonyl, 3-fluoro-5-(trifluoromethyl)phenylcarbonyl, 4-chloro-3-(trifluoromethyl)phenylcarbonyl, 2-chloro-3-(trifluoromethyl)phenylcarbonyl, 2-chloro-5-(trifluoromethyl)phenylcarbonyl, 3-isopropoxyphenylcarbonyl, 3-(tert-butoxy)phenylcarbonyl, 3-(1-cyano-1-methylethyl)phenylcarbonyl, 3-methoxyphenylcarbonyl, 3-methoxycarbonylphenylcarbonyl, 3-(trifluoromethoxy)carbonylphenylcarbonyl, 3-(1,1,2,2-tetrafluoroethoxy)phenylcarbonyl, 3-(4-cyanotetrahydropyran-4-yl)phenylcarbonyl, 3,5-di(trifluoromethyl)phenylcarbonyl, 3-(2-oxopyrrolidin-1-yl)phenylcarbonyl, 4-(tert-butyl)phenylcarbonyl, 3-(1-cyanoethyl)phenylcarbonyl, 3-(1-cyano-2-cyclopropyl-1-methylethyl)phenylcarbonyl and the like are preferable.

As the optionally substituted $C_{6-18}$ aryl-$C_{1-4}$ alkyl-carbonyl, $C_{6-10}$ aryl-$C_{1-4}$ alkyl-carbonyl is preferable.

As the optionally substituted $C_{1-8}$ alkylsulfonyl, $C_{1-4}$ alkylsulfonyl are preferable.

As the optionally substituted $C_{6-18}$ aryl-sulfonyl, $C_{6-10}$ aryl-sulfonyl is preferable.

As the "heterocycle" moiety for the optionally substituted heterocyclyl-carbonyl, 5- or 6-membered monocyclic heterocyclic group containing, as ring-constituting atom, 1 to 3 hetero atoms selected from oxygen atom, sulfur atom and nitrogen atom besides carbon atoms, and the like are preferable, and pyridyl, furyl, tetrahydrofuryl, thienyl, pyrazolyl, imidazolyl, thiazolyl, oxazolyl, isoxazolyl, 1,2,3-triazolyl, 1,2,3-thiadiazolyl, dihydrooxazolyl, pyridazinyl, pyrazinyl, dihydropyrazolyl, pyrrolyl, pyrrolidinyl, pyrimidinyl and the like are specifically preferable. As the "substituent" for the optionally substituted heterocyclyl-carbonyl, (1) halogen atom (e.g., chlorine), (2) $C_{1-4}$ alkyl (e.g., methyl, ethyl, isopropyl, tert-butyl) optionally substituted by 1 to 3 substituents selected from halogen atom (e.g., fluorine), cyano, hydroxy and $C_{1-4}$ alkoxy (e.g., methoxy) (specific examples: methyl, trifluoromethyl, ethyl, methoxyethyl, 2,2,2-trifluoroethyl, isopropyl, tert-butyl), (3) $C_{6-18}$ aryl (e.g., phenyl), (4) $C_{6-10}$ aryl-$C_{1-4}$ alkyl (e.g., benzyl), (5) $C_{1-4}$ alkoxy (e.g., methoxy, ethoxy) optionally substituted by $C_{1-4}$ alkoxy (e.g., methoxy) (specific examples: methoxy, ethoxy, methoxyethoxy), (6) $C_{1-4}$ alkylsulfonyl (e.g., methylsulfonyl, ethylsulfonyl), (7) $C_{1-4}$ alkylcarbonyl (e.g., acetyl), (8) oxo, and the like are preferable.

As the optionally substituted heterocyclyl-carbonyl, the above-mentioned 5- or 6-membered monocyclic aromatic heterocyclyl-carbonyl and the like optionally substituted by optionally halogenated $C_{1-4}$ alkyl and the like are preferable. Specifically, 2-pyridylcarbonyl, 3-pyridylcarbonyl, 4-pyridylcarbonyl, 2-methyl-6-pyridylcarbonyl, 3-methyl-2-pyridylcarbonyl, 4-methyl-2-pyridylcarbonyl, 2-methyl-3-pyridylcarbonyl, 2-(trifluoromethyl)-3-pyridylcarbonyl, 2-(trifluoromethyl)-4-pyridylcarbonyl, 2-(trifluoromethyl)-6-pyridylcarbonyl, 2-chloro-6-methyl-4-pyridylcarbonyl, 2,6-dichloro-4-pyridylcarbonyl, 2-furylcarbonyl, 2,5-dimethylfuran-3-carbonyl, 5-methyl-2-(trifluoromethyl)-3-furancarbonyl, 3-methylthiophene-2-carbonyl, 5-acetylsulfonylthiophene-2-carbonyl, 5-ethylsulfonylthiophene-2-carbonyl, 4-methyl-1,2,3-thiadiazole-5-carbonyl, isoxazole-5-carbonyl, 1H-pyrazole-5-carbonyl, 1-methyl-1H-pyrazole-3-carbonyl, 1-methyl-1H-pyrazole-5-carbonyl, 1-ethyl-1H-pyrazole-3-carbonyl, 1-ethyl-1H-pyrazole-5-carbonyl, 3-methyl-1H-pyrazole-5-carbonyl, 3-chloro-1-methyl-1H-pyrazole-5-carbonyl, 4-chloro-1-methyl-1H-pyrazole-3-carbonyl, 1-methyl-3-methoxy-1H-pyrazole-5-carbonyl, 1-methyl-3-(trifluoromethyl)-1H-pyrazole-5-carbonyl, 3-methoxy-1-methyl-1H-pyrazole-4-carbonyl, 3-methoxy-1-methyl-1H-pyrazole-5-carbonyl, 3-ethoxy-1-methyl-1H-pyrazole-5-carbonyl, 3-(2-methoxyethoxy)-1-methyl-1H-pyrazole-5-carbonyl, 1-ethyl-3-methyl-1H-pyrazole-4-carbonyl, 1-ethyl-3-methyl-1H-pyrazole-5-carbonyl, 3-methyl-1-phenyl-1H-pyrazole-5-carbonyl, 5-methyl-1-phenyl-1H-pyrazole-3-carbonyl, 3-ethyl-1-methyl-1H-pyrazole-5-carbonyl, 3-isopropyl-1-methyl-1H-pyrazole-5-carbonyl, 3-methoxy-1-methyl-1H-pyrazole-5-carbonyl, 1-tert-butyl-3-methyl-1H-pyrazole-5-carbonyl, 3-tert-butyl-1- methyl-1H-pyrazole-5-carbonyl, 1-methoxyethyl-3-methyl-1H-pyrazole-5-carbonyl, 1,3-dimethyl-1H-pyrazole-4-carbonyl, 1,3-dimethyl-1H-pyrazole-5-carbonyl, 1,4-dimethyl-1H-pyrazole-3-carbonyl, 1,4-dimethyl-1H-pyrazole-5-carbonyl, 1,5-dimethyl-1H-pyrazole-3-carbonyl, 3-methylisoxazole-4-carbonyl, 3-methylisoxazole-5-carbonyl, 5-methylisoxazole-3-carbonyl, 5-methylisoxazole-4-carbonyl, 3,5-dimethylisoxazole-4-carbonyl, 1,3-thiazole-2-carbonyl, 2-methyl-1,3-thiazole-4-carbonyl, 4-methyl-1,3-thiazole-5-carbonyl, 5-methyl-1,3-thiazole-4-carbonyl, 2,4-dimethyl-1,3-thiazole-5-carbonyl, 2-chloro-4-methyl-1,3-thiazole-5-carbonyl, 4-methoxy-2-methyl-1,3-thiazole-5-carbonyl, 2-(1-hydroxy-1-methylethyl)-1,3-thiazole-5-carbonyl, 2-(1-cyano-1-methylethyl)-1,3-thiazole-5-carbonyl, 2-methyl-1,3-oxazole-4-carbonyl, 4-methyl-1,3-oxazole-5-carbonyl, 2-ethyl-4-methyl-1,3-oxazole-5-carbonyl, 2,4-dimethyl-1,3-oxazole-5-carbonyl, 2,5-dimethyl-1,3-oxazole-4-carbonyl, 1-methyl-1H-1,2,3-triazole-5-carbonyl, 1-methyl-1H-1,2,3-triazole-4-carbonyl, 1-methyl-1H-imidazole-2-carbonyl, 1-methyl-1H-imidazole-5-carbonyl, 2-pyrazinylcarbonyl, 1-methylpyrrole-2-carbonyl, 1-benzylpyrrole-3-carbonyl, 1,2,5-trimethylpyrrole-3-carbonyl, 1-methylpyrrolidine-2-carbonyl, 2-(trifluoromethyl)pyrimidine-4-carbonyl and the like are preferable.

As the "heterocycle" moiety for the optionally substituted heterocyclyl-sulfonyl, 5- or 6-membered monocyclic aromatic heterocyclic group containing, as ring-constituting atom, 1 to 3 heteroatoms selected from oxygen atom, sulfur atom and nitrogen atom besides carbon atoms, and the like are preferable, and thiazolyl and the like are specifically preferable. As the "substituent" for the optionally substituted heterocyclyl-carbonyl, $C_{1-4}$ alkyl (e.g., methyl) and the like are preferable.

As the optionally substituted heterocyclyl-sulfonyl, 2,5-dimethyl-1,3-thiazole-4-sulfonyl and the like are specifically preferable.

As the optionally substituted aminothiocarbonyl, aminothiocarbonyl optionally substituted by $C_{6-18}$ aryl-$C_{1-4}$ alkyl-carbonyl (e.g., benzylcarbonyl) and the like are preferable.

Preferably, ring Ya is
(1) $C_{6-10}$ aryl (e.g., phenyl) optionally substituted by 1 to 3 substituents selected from
  (a) halogen atom (e.g., fluorine, chlorine, bromine),
  (b) $C_{1-4}$ alkyl (e.g., methyl, ethyl),
  (c) $C_{1-4}$ alkoxy (e.g., methoxy),
  (d) amino optionally substituted by substituents selected from
    (i) $C_{1-4}$ alkyl (e.g., methyl) optionally substituted by 5-membered aromatic heterocyclic group (e.g., pyrazolyl) optionally substituted by 1 to 3 $C_{1-4}$ alkyl (e.g., methyl),
    (ii) $C_{1-4}$ alkyl-carbonyl (e.g., methylcarbonyl, isobutylcarbonyl, tert-butylcarbonyl) optionally substituted by 1 to 3 substituents selected from
      (i') hydroxy,
      (ii') $C_{1-4}$ alkylsulfonyl (e.g., methylsulfonyl), and
      (iii') 6-membered aromatic heterocyclic group (e.g., pyridyl),
    (iii) $C_{2-4}$ alkenyl-carbonyl (e.g., 2-methyl-1-propenylcarbonyl, vinylcarbonyl) optionally substituted by $C_{6-10}$ aryl (e.g., phenyl),
    (iv) $C_{2-4}$ alkynyl-carbonyl (e.g., acetylenecarbonyl, 1-propynylcarbonyl) optionally substituted by $C_{6-10}$ aryl (e.g., phenyl),
    (v) $C_{3-6}$ cycloalkyl-carbonyl (e.g., cyclopropylcarbonyl, cyclopentylcarbonyl, cyclohexylcarbonyl),
    (vi) $C_{3-6}$ cycloalkenyl-carbonyl (e.g., cyclopentenylcarbonyl),
    (vii) $C_{6-10}$ aryl-carbonyl (e.g., benzoyl) optionally substituted by 1 to 3 substituents selected from
      (i') halogen atom (e.g., fluorine, chlorine),
      (ii') $C_{1-4}$ alkyl (e.g., methyl, ethyl, isopropyl, tert-butyl) optionally substituted by 1 to 3 substituents selected from halogen atom (e.g., fluorine), cyano, hydroxy and $C_{3-6}$ cycloalkyl (e.g., cyclopropyl),
      (iii') $C_{3-6}$ cycloalkyl (e.g., cyclopropyl, cyclobutyl, cyclohexyl) optionally substituted by cyano,
      (iv') $C_{1-4}$ alkoxy (e.g., methoxy, ethoxy, isopropoxy, tert-butoxy) optionally substituted by 1 to 5 halogen atoms (e.g., fluorine),
      (v') $C_{1-4}$ alkoxy-carbonyl (e.g., methoxycarbonyl), and
      (vi') 5- or 6-membered heterocyclic group (e.g., tetrahydropyranyl, pyrrolidinyl) optionally substituted by cyano or oxo,
    (viii) 5- or 6-membered heterocyclyl-carbonyl containing, as ring-constituting atom, 1 to 3 heteroatoms selected from oxygen atom, sulfur atom and nitrogen atom besides carbon atoms (e.g., furylcarbonyl, tetrahydrofurylcarbonyl, thienylcarbonyl, pyrrolylcarbonyl, pyrrolidinylcarbonyl, imidazolylcarbonyl, thiazolylcarbonyl, thiadiazolylcarbonyl, dihydrooxazolylcarbonyl, oxazolylcarbonyl, isoxazolylcarbonyl, pyrazolylcarbonyl, dihydropyrazolylcarbonyl, triazolylcarbonyl, pyridylcarbonyl, pyrimidinylcarbonyl, pyrazinylcarbonyl) optionally substituted by 1 to 3 substituents selected from
      (i') halogen atom (e.g., chlorine),
      (ii') $C_{1-4}$ alkyl (e.g., methyl, ethyl, isopropyl, tert-butyl) optionally substituted by 1 to 3 substituents selected from halogen atom (e.g., fluorine), cyano, hydroxy and $C_{1-4}$ alkoxy (e.g., methoxy),
      (iii') $C_{6-10}$ aryl (e.g., phenyl),
      (iv') $C_{6-10}$ aryl-$C_{1-4}$ alkyl (e.g., benzyl),
      (v') $C_{1-4}$ alkoxy (e.g., methoxy, ethoxy) optionally substituted by $C_{1-4}$ alkoxy (e.g., methoxy),
      (vi') $C_{1-4}$ alkylsulfonyl (e.g., methylsulfonyl, ethylsulfonyl),
      (vii') $C_{1-4}$ alkyl-carbonyl (e.g., acetyl), and
      (viii') oxo,
    (ix) aromatic fused heterocyclyl-carbonyl (e.g., benzopyrazolylcarbonyl, indolylcarbonyl),
    (x) $C_{1-4}$ alkyl-aminocarbonyl (e.g., ethylaminocarbonyl),
    (xi) $C_{6-10}$ aryl-aminocarbonyl (e.g., phenylaminocarbonyl) optionally substituted by $C_{1-4}$ alkyl (e.g., methyl) optionally substituted by 1 to 3 halogen atoms (e.g., fluorine),
    (xii) $C_{1-4}$ alkoxy-aminocarbonyl (e.g., methoxyaminocarbonyl, isobutoxyaminocarbonyl),
    (xiii) 5-membered heterocyclyl-aminocarbonyl (e.g., isoxazolylaminocarbonyl, pyrazolylaminocarbonyl) optionally substituted by 1 to 3 substituents selected from $C_{1-4}$ alkyl (e.g., methyl, tert-butyl) and $C_{6-10}$ aryl (e.g., phenyl),
    (xiv) aminothiocarbonyl optionally substituted by $C_{6-10}$ aryl-$C_{1-4}$ alkyl-carbonyl (e.g., benzylcarbonyl), and
    (xv) 5-membered aromatic heterocyclyl-sulfonyl (e.g., thiazolylsulfonyl) optionally substituted by 1 to 3 $C_{1-4}$ alkyl (e.g., methyl), (e) C$_{1-4}$ alkyl-aminocarbonyl (e.g., methylaminocarbonyl) optionally having C$_{6-10}$ aryl (e.g., phenyl),
(f) 5-membered heterocyclyl-aminocarbonyl (e.g., pyrazolylaminocarbonyl) optionally substituted by 1 to 3 substituents selected from C$_{1-4}$ alkyl (e.g., methyl) and C$_{6-10}$ aryl,
(g) C$_{6-10}$ aryl-aminocarbonyl (e.g., phenylaminocarbonyl) optionally substituted by C$_{1-4}$ alkyl (e.g., methyl, isopropyl, tert-butyl) optionally substituted by 1 to 3 substituents selected from halogen atom (e.g., fluorine) and cyano,
(h) carboxy, and
(i) nitro,
(2) monocyclic aromatic heterocycle (e.g., pyridyl) optionally substituted by 1 to 3 substituents selected from
  (a) halogen atom (e.g., bromine), and
  (b) C$_{6-10}$ aryl-carbonylamino (e.g., benzoylamino) optionally substituted by C$_{1-4}$ alkyl (e.g., methyl) optionally substituted by 1 to 3 halogen atoms (e.g., fluorine), or
(3) fused aromatic heterocycle (e.g., indolyl, benzothiazolyl, benzimidazolyl) optionally substituted by 1 to 3 substituents selected from
  (a) C$_{1-4}$ alkyl (e.g., methyl), and,
  (b) C$_{6-10}$ arylamino (e.g., phenylamino) optionally substituted by C$_{1-4}$ alkyl (e.g., methyl) optionally substituted by 1 to 3 halogen atoms (e.g., fluorine).

As ring Ya, (1,3-dimethyl-1H-pyrazol-5-yl)aminocarbonyl-3-phenyl, 3-aminophenyl, 4-aminophenyl, 3-{[(ethylamino)carbonyl]amino}phenyl, 4-{[(phenylamino)carbonyl]amino}phenyl, 3-{[(phenylamino)carbonyl]amino}phenyl, 3-({[3-(trifluoromethylphenyl)amino]carbonyl}amino)phenyl, 3-({[4-(trifluoromethylphenyl)amino]carbonyl}amino)phenyl, 3-[(tert-butylcarbonyl)amino]phenyl, 3-[(cyclopropylcarbonyl)amino]phenyl, 3-[(cyclohexylcarbonyl)amino]phenyl, 3-[(phenylcarbonyl)amino]phenyl, 3-{[3-(trifluoromethylphenyl)carbonyl]amino}phenyl, 3-{[3-(fluorophenyl)carbonyl]amino}phenyl, 3-{[3-(chlorophenyl)carbonyl]amino}phenyl, 3-{[3-(pyridyl)carbonyl]amino}phenyl, 3-{[2-(furyl)carbonyl]amino}phenyl, 3-{[3-(2,5-dimethylfuran)carbonyl]amino}phenyl, 3-{[2-(3-methylthiophene)carbonyl]amino}phenyl, 3-{[5-(4-methyl-1,2,3-thiadiazole)carbonyl]amino}phenyl, 3-{[5-(isoxazole)carbonyl]amino}phenyl, 3-{[5-(1,3-dimethyl-1H-pyrazole)carbonyl]amino}phenyl, 3-{[5-(3-methylisoxazole)carbonyl]amino}phenyl, 3-{[3-(5-methylisoxazole)carbonyl]amino}phenyl, 3-({5-[1-methyl-3-(trifluoromethyl)-1H-pyrazole]carbonyl}amino)phenyl, 5-methyl-2-(trifluoromethyl)-3-furancarbonylaminophenyl, 3-{[5-(2,4-dimethyl-1,3-thiazole)carbonyl]amino}phenyl, 3-{[4-(2,5-dimethyl-1,3-oxazole)carbonyl]amino}phenyl, 3-{[5-(1-methyl-1H-pyrazole)carbonyl]amino}phenyl, 3-{[3-(1,5-dimethyl-1H-pyrazole)carbonyl]amino}phenyl, 3-{[4-(3,5-dimethylisoxazole)carbonyl]amino}phenyl, 3-{[5-(1-methyl-1H-1,2,3-triazole)carbonyl]amino}phenyl, 3-{[4-(1-methyl-1H-1,2,3-triazole)carbonyl]amino}phenyl, 3-{[2-(1-methyl-1H-imidazole)carbonyl]amino}phenyl, 3-{[5-(1-methyl-1H-imidazole)carbonyl]amino}phenyl, 1H-indol-6-yl, 2-methyl-1H-indol-6-yl, 1,2-dimethyl-1H-benzimidazol-5-yl, 1H-indol-4-yl, 2-methyl-1,3-benzothiazol-5-yl, 2-methyl-1,3-benzothiazol-6-yl, 5-amino-2-methylphenyl, 3-amino-2-methylphenyl, 3-amino-4-methylphenyl, 3-amino-4-chlorophenyl, 5-amino-2-chlorophenyl, 5-amino-2-methoxyphenyl, 6-methyl-3-{[5-(1,3-dimethyl-1H-pyrazole)carbonyl]amino}phenyl, 2-methyl-3-{[5-(1,3-dimethyl-1H-pyrazole)carbonyl]amino}phenyl, 4-methyl-3-{[5-(1,3-dimethyl-1H-pyrazole)carbonyl]amino}phenyl, 4-chloro-3-{[5-(1,3-dimethyl-1H-pyrazole)carbonyl]amino}phenyl, 6-chloro-3-{[5-(1,3-dimethyl-1H-pyrazole)carbonyl]amino}phenyl, 4-fluoro-3-{[5-(1,3-dimethyl-1H-pyrazole)carbonyl]amino}phenyl, 6-methoxy-3-{[5-(1,3-dimethyl-1H-pyrazole)carbonyl]amino}phenyl, 4-chloro-3-(cyclopropylcarbonylamino)phenyl, 3-amino-4-fluorophenyl, 4-fluoro-3-{[4-(1-ethyl-3-methyl-1H-pyrazole)carbonyl]amino}phenyl and the like can be specifically mentioned.

In the compound (II), as the substituent for R$^a$ of NR$^a$ defined by Xa, those similar to the substituent selected from the group exemplified as the "optionally substituted hydrocarbon group" for the aforementioned Substituent Group (1)(iv), the group exemplified as the "optionally substituted aminocarbonyl" for the aforementioned Substituent Group (1)(viii), the group exemplified as the "acyl" for the aforementioned Substituent Group (1)(ix) and the group exemplified as the "optionally substituted heterocyclic group" for the aforementioned Substituent Group (1)(xii) can be mentioned.

As the substituent for R$^a$, optionally substituted hydrocarbon group and the like are preferable.

Xa is preferably —O—, —S— or —NH—, more preferably —O— or —S—, and particularly preferably —O—.

As the "optionally substituted amino" for R$^{1a}$ in the compound (II), those similar to the "optionally substituted amino" exemplified in the aforementioned Substituent Group (1)(x) can be mentioned.

As the "optionally substituted amino" for R$^{1a}$, (1) amino, (2) optionally substituted alkylcarbonylamino, (3) optionally substituted alkenylcarbonylamino, (4) optionally substituted alkynylcarbonylamino, (5) optionally substituted cycloalkylcarbonylamino, (6) optionally substituted cycloalkyl-alkylcarbonylamino, (7) optionally substituted 6-membered heterocyclyl-carbonylamino, (8) optionally substituted aminocarbonylamino, (9) optionally substituted alkoxycarbonylamino, (10) optionally substituted alkylsulfonylamino, (11) optionally substituted cycloalkylsulfonylamino, (12) optionally substituted arylamino and (13) optionally substituted heterocyclylamino are preferable.

Of these, preferable R$^{1a}$ are
(1) amino,
(2) C$_{1-4}$ alkyl-carbonylamino (e.g., acetylamino, ethylcarbonylamino, isopropylcarbonylamino, isobutylcarbonylamino, tert-butylcarbonylamino) optionally substituted by 1 to 3 substituents selected from (a) halogen atom (e.g., chlorine), (b) hydroxy, (c) C$_{1-4}$ alkoxy (e.g., methoxy), (d) C$_{1-4}$ alkyl-carbonyloxy (e.g., methylcarbonyloxy), (e) C$_{1-4}$ alkylamino (e.g., methylamino), (f) di-C$_{1-4}$ alkylamino (e.g., dimethylamino), (g) C$_{1-4}$ alkylsulfonyl (e.g., methylsulfonyl), and (h) 6-membered heterocyclic group (e.g., piperazinyl, morpholinyl) optionally substituted by 1 to 3 C$_{1-4}$ alkyl (e.g., methyl),
(3) C$_{2-4}$ alkenyl-carbonylamino (e.g., vinylcarbonylamino, 2-methyl-1-propenylcarbonylamino) optionally having C$_{1-4}$ alkoxy (e.g., methoxy),
(4) C$_{2-4}$ alkynyl-carbonylamino (e.g., 1-propenylcarbonylamino),
(5) C$_{3-6}$ cycloalkyl-carbonylamino (e.g., cyclopropylcarbonylamino, cyclobutylcarbonylamino, cyclopentylcarbonylamino, cyclohexylcarbonylamino) optionally substituted by 1 to 4 substituents selected from (a) halogen atom (e.g., fluorine), (b) hydroxy, (c) C$_{1-4}$ alkyl (e.g., methyl, isopropyl) optionally having hydroxy, (d) C$_{1-4}$ alkoxy (e.g., methoxy), (e) C$_{1-4}$ alkoxy-carbonyl (e.g., methoxycarbonyl), and (f) C$_{1-4}$ alkyl-carbonyloxy (e.g., acetoxy), (6) $C_{3-6}$ cycloalkyl-$C_{1-4}$ alkyl-carbonylamino (e.g., cyclopropylmethylcarbonylamino),
(7) 6-membered heterocyclyl-carbonylamino (e.g., tetrahydropyranylcarbonylamino, pyridylcarbonylamino, pyrimidinylcarbonylamino, morpholinylcarbonylamino) optionally substituted by 1 to 3 substituents selected from (a) halogen atom (e.g., fluorine, chlorine), (b) cyano, and (c) $C_{1-4}$ alkyl (e.g., methyl) optionally having 1 to 3 halogen atom (e.g., fluorine),
(8) aminocarbonylamino optionally substituted by 1 or 2 substituents selected from (a) $C_{1-4}$ alkyl (e.g., ethyl) optionally having 1 to 3 $C_{1-4}$ alkoxy (e.g., ethoxy) optionally having 1 to 3 hydroxy, and (b) $C_{1-4}$ alkoxy (e.g., methoxy),
(9) $C_{1-4}$ alkoxy-carbonylamino (e.g., methoxycarbonylamino, ethoxycarbonylamino, tert-butoxycarbonylamino) optionally substituted by 1 to 3 halogen atom (e.g., chlorine),
(10) $C_{1-4}$ alkylsulfonylamino (e.g., methylsulfonylamino),
(11) $C_{3-6}$ cycloalkylsulfonylamino (e.g., cyclopropylsulfonylamino),
(12) $C_{6-10}$ arylamino (e.g., phenylamino), and
(13) heterocyclylamino (e.g., thiazolylamino, pyrimidinylamino) optionally substituted by 1 to 3 substituents selected from (a) halogen atom (e.g., chlorine), and (b) $C_{1-4}$ alkylamino (e.g., methylamino), and the like.

As $R^{1a}$, amino, acetylamino, chloroacetylamino, 4-morpholinylacetylamino, methylcarbonyloxymethylcarbonylamino, methylaminomethylcarbonylamino, hydroxymethylcarbonylamino, methoxymethylcarbonylamino, ethylcarbonylamino, isopropylcarbonylamino, dimethylaminomethylcarbonylamino, 4-methylpiperazin-1-ylacetylamino, methylsulfonylmethylcarbonylamino, 3-hydroxy-3-methylbutanoylamino, hydroxyethylcarbonylamino, 3-methyl-2-butenoylamino, 3-methoxy-2-propenoylamino, 2-butynoylamino, (cyclopropylcarbonyl)amino, (1-methoxycarbonylcyclopropylcarbonyl)amino, (1-hydroxycyclopropylcarbonyl)amino, (2-methylcyclopropylcarbonyl)amino, (2-methoxycyclopropylcarbonyl)amino, (2-methylcarbonylcyclopropylcarbonyl)amino, (2-hydroxymethylcarbonylcyclopropylcarbonyl)amino, (2-(1-hydroxy-1-methylethyl)cyclopropyl)carbonylamino, (2,2-dimethylcyclopropylcarbonyl)amino, (2,2-difluorocyclopropylcarbonyl)amino, (2,2,3,3-tetramethylcyclopropylcarbonyl)amino, (cyclobutylcarbonyl)amino, (cyclopentylcarbonyl)amino, (cyclohexylcarbonyl)amino, cyclopropylmethylcarbonylamino, (tetrahydro-2H-pyran-4-ylcarbonyl)amino, (3-pyridylcarbonyl)amino, (4-pyridylcarbonyl)amino, (6-methyl-3-pyridylcarbonyl)amino, (6-fluoro-3-pyridylcarbonyl)amino, (6-chloro-3-pyridylcarbonyl)amino, (6-cyano-3-pyridylcarbonyl)amino, (6-(trifluoromethyl)-3-pyridylcarbonyl)amino, (5-pyrimidinylcarbonyl)amino, 4-morpholinylcarbonylamino, methoxyureido, ethylureido, 2-hydroxyethoxyethylureido, methoxycarbonylamino, ethoxycarbonylamino, 2,2,2-trichloroethoxycarbonylamino, tert-butoxycarbonylamino, methylsulfonylamino, (cyclopropylsulfonyl)amino, phenylamino, 2-methylaminopyrimidin-4-ylamino, 2-chloropyrimidin-4-ylamino, 1,3-thiazol-2-ylamino and the like can be specifically mentioned.

In the compound (II), as the "substituent" for $R^{2a}$, those similar to the substituents of the aforementioned Substituent Group (1) can be mentioned.

Of these, preferable $R^{2a}$ is hydrogen atom.

In the compound (II), as the "substituent" for $R^{3a}$, those similar to the substituents of the aforementioned Substituent Group (1) can be mentioned.

Of these, preferable $R^{3a}$ is hydrogen atom.

In the compound (II), as the "substituent" for $R^{4a}$, those similar to the substituents of the aforementioned Substituent Group (1) can be mentioned.

Of these, preferable $R^{4a}$ is hydrogen atom.

As preferable examples of the compound (II), for example, the following compounds can be mentioned.

A compound wherein
ring Ya is
(1) $C_{6-10}$ aryl optionally substituted by 1 to 3 substituents selected from
  (a) halogen atom,
  (b) $C_{1-4}$ alkyl,
  (c) $C_{1-4}$ alkoxy,
  (d) amino optionally substituted by the substituents selected from
    (i) $C_{1-4}$ alkyl optionally substituted by a 5-membered aromatic heterocyclic group optionally substituted by 1 to 3 $C_{1-4}$ alkyl,
    (ii) $C_{1-4}$ alkyl-carbonyl optionally substituted by 1 to 3 substituents selected from
      (i') hydroxy,
      (ii') $C_{1-4}$ alkylsulfonyl, and
      (iii') 6-membered aromatic heterocyclic group,
    (iii) $C_{2-4}$ alkenyl-carbonyl optionally substituted by $C_{6-10}$ aryl,
    (iv) $C_{2-4}$ alkynyl-carbonyl optionally substituted by $C_{6-10}$ aryl,
    (v) $C_{3-6}$ cycloalkyl-carbonyl,
    (vi) $C_{3-6}$ cycloalkenyl-carbonyl,
    (vii) $C_{6-10}$ aryl-carbonyl optionally substituted by 1 to 3 substituents selected from
      (i') halogen atom,
      (ii') $C_{1-4}$ alkyl optionally substituted by 1 to 3 substituents selected from halogen atom, cyano, hydroxy and $C_{3-6}$ cycloalkyl,
      (iii') $C_{3-6}$ cycloalkyl optionally substituted by cyano,
      (iv') $C_{1-4}$ alkoxy optionally substituted by 1 to 5 halogen atoms,
      (v') $C_{1-4}$ alkoxy-carbonyl, and
      (vi') 5- or 6-membered heterocyclic group optionally substituted by cyano or oxo,
    (viii) 5- or 6-membered heterocyclyl-carbonyl containing, as ring-constituting atom, 1 to 3 heteroatoms selected from oxygen atom, sulfur atom and nitrogen atom besides carbon atoms, which is optionally substituted by 1 to 3 substituents selected from
      (i') halogen atom,
      (ii') $C_{1-4}$ alkyl optionally substituted by 1 to 3 substituents selected from halogen atom, cyano, hydroxy and $C_{1-4}$ alkoxy,
      (iii') $C_{6-10}$ aryl,
      (iv') $C_{6-10}$ aryl-$C_{1-4}$ alkyl,
      (v') $C_{1-4}$ alkoxy optionally substituted by $C_{1-4}$ alkoxy,
      (vi') $C_{1-4}$ alkylsulfonyl,
      (vii') $C_{1-4}$ alkyl-carbonyl, and
      (viii') oxo,
    (ix) aromatic fused heterocyclyl-carbonyl,
    (x) $C_{1-4}$ alkyl-aminocarbonyl,
    (xi) $C_{6-10}$ aryl-aminocarbonyl optionally substituted by $C_{1-4}$ alkyl optionally substituted by 1 to 3 halogen atoms,
    (xii) $C_{1-4}$ alkoxy-aminocarbonyl,
    (xiii) 5-membered heterocyclyl-aminocarbonyl optionally substituted by 1 to 3 substituents selected from $C_{1-4}$ alkyl and $C_{6-10}$ aryl, (xiv) aminothiocarbonyl optionally substituted by $C_{6-10}$ aryl-$C_{1-4}$ alkyl-carbonyl, and
(xv) 5-membered aromatic heterocyclyl-sulfonyl optionally substituted by 1 to 3 $C_{1-4}$ alkyl,
(e) $C_{1-4}$ alkyl-aminocarbonyl optionally having $C_{6-10}$ aryl,
(f) 5-membered heterocyclyl-aminocarbonyl optionally substituted by 1 to 3 substituents selected from $C_{1-4}$ alkyl and $C_{6-10}$ aryl,
(g) $C_{6-10}$ aryl-aminocarbonyl optionally substituted by $C_{1-4}$ alkyl optionally substituted by 1 to 3 substituents selected from halogen atom and cyano,
(h) carboxy, and
(i) nitro,
(2) monocyclic aromatic heterocycle optionally substituted by 1 to 3 substituents selected from
(a) halogen, and
(b) $C_{6-10}$ aryl-carbonylamino optionally substituted by $C_{1-4}$ alkyl optionally substituted by 1 to 3 halogen atoms, or
(3) fused aromatic heterocycle optionally substituted by 1 to 3 substituents selected from
(a) $C_{1-4}$ alkyl, and
(b) $C_{6-10}$ arylamino optionally substituted by $C_{1-4}$ alkyl optionally substituted by 1 to 3 halogen atoms;
Xa is —O—, —S— or —NH— (more preferably —O— or —S—, particularly preferably —O—);
$R^{1a}$ is
(1) amino,
(2) $C_{1-4}$ alkyl-carbonylamino optionally substituted by 1 to 3 substituents selected from
(a) halogen atom,
(b) hydroxy,
(c) $C_{1-4}$ alkoxy,
(d) $C_{1-4}$ alkyl-carbonyloxy,
(e) $C_{1-4}$ alkylamino,
(f) di-$C_{1-4}$ alkylamino,
(g) $C_{1-4}$ alkylsulfonyl, and
(h) 6-membered heterocyclic group optionally having 1 to 3 $C_{1-4}$ alkyl,
(3) $C_{2-4}$ alkenyl-carbonylamino optionally having $C_{1-4}$ alkoxy,
(4) $C_{2-4}$ alkynyl-carbonylamino,
(5) $C_{3-6}$ cycloalkyl-carbonylamino optionally substituted by 1 to 4 substituents selected from
(a) halogen atom,
(b) hydroxy,
(c) $C_{1-4}$ alkyl optionally having hydroxy,
(d) $C_{1-4}$ alkoxy, and
(e) $C_{1-4}$ alkoxy-carbonyl,
(6) $C_{3-6}$ cycloalkyl-$C_{1-4}$ alkyl-carbonylamino,
(7) 6-membered heterocyclyl-carbonylamino optionally substituted by 1 to 3 substituents selected from
(a) halogen atom,
(b) cyano, and
(c) $C_{1-4}$ alkyl optionally having 1 to 3 halogen atoms,
(8) aminocarbonylamino optionally substituted by 1 or 2 substituents selected from
(a) $C_{1-4}$ alkyl optionally having 1 to 3 $C_{1-4}$ alkoxy optionally having 1 to 3 hydroxy, and
(b) $C_{1-4}$ alkoxy,
(9) $C_{1-4}$ alkoxy-carbonylamino optionally substituted by 1 to 3 halogen atoms,
(10) $C_{1-4}$ alkylsulfonylamino,
(11) $C_{3-6}$ cycloalkylsulfonylamino,
(12) $C_{6-10}$ arylamino, and
(13) heterocyclylamino optionally substituted by 1 to 3 substituents selected from
(a) halogen atom, and
(b) $C_{1-4}$ alkylamino; and
$R^{2a}$, $R^{3a}$ and $R^{4a}$ are each hydrogen atom.

As the specific examples of the compound (II), for example, compounds of Examples 1 to 60, 64, 66 to 72, 74 to 123, 126 to 138 and 147 to 439 can be mentioned.

Of these, the following compounds or salts thereof are preferable.

N-{3-[(2-{[2-(methylamino)pyrimidin-4-yl]amino}imidazo[1,2-b]pyridazin-6-yl)oxy]phenyl}-3-(trifluoromethyl)benzamide (Example 70);

N-[2-chloro-5-({2-[(cyclopropylcarbonyl)amino]imidazo[1,2-b]pyridazin-6-yl}oxy)phenyl]-1,3-dimethyl-1H-pyrazole-5-carboxamide (Example 97);

N-[5-({2-[(cyclopropylcarbonyl)amino]imidazo[1,2-b]pyridazin-6-yl}oxy)-2-methylphenyl]-1,3-dimethyl-1H-pyrazole-5-carboxamide (Example 111);

N-[3-({2-[(cyclopropylcarbonyl)amino]imidazo[1,2-b]pyridazin-6-yl}oxy)phenyl]-2,4-dimethyl-1,3-thiazole-5-carboxamide (Example 114);

N-[3-({2-[(cyclopropylcarbonyl)amino]imidazo[1,2-b]pyridazin-6-yl}oxy)phenyl]-2,5-dimethyl-1,3-oxazole-4-carboxamide (Example 117);

N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide (Example 148);

N-[3-({2-[(N,N-dimethylglycyl)amino]imidazo[1,2-b]pyridazin-6-yl}oxy)phenyl]-1,3-dimethyl-1H-pyrazole-5-carboxamide (Example 149);

N-[3-({2-[(cyclopropylcarbonyl)amino]imidazo[1,2-b]pyridazin-6-yl}sulfanyl)phenyl]-1,3-dimethyl-1H-pyrazole-5-carboxamide (Example 150);

N-[5-({2-[(cyclopropylcarbonyl)amino]imidazo[1,2-b]pyridazin-6-yl}oxy)-2-fluorophenyl]-1-ethyl-3-methyl-1H-pyrazole-4-carboxamide (Example 161);

N-[3-({2-[(cyclopropylcarbonyl)amino]imidazo[1,2-b]pyridazin-6-yl}oxy)phenyl]benzamide (Example 165);

N-[5-({2-[(cyclopropylcarbonyl)amino]imidazo[1,2-b]pyridazin-6-yl}oxy)-2-fluorophenyl]-1,3-dimethyl-1H-pyrazole-4-carboxamide (Example 173);

N-[5-({2-[(cyclopropylcarbonyl)amino]imidazo[1,2-b]pyridazin-6-yl}oxy)-2-fluorophenyl]-1-ethyl-1H-pyrazole-5-carboxamide (Example 174);

N-[5-({2-[(cyclopropylcarbonyl)amino]imidazo[1,2-b]pyridazin-6-yl}oxy)-2-fluorophenyl]-3-methoxy-1-methyl-1H-pyrazole-5-carboxamide (Example 180);

N-[5-({2-[(cyclopropylcarbonyl)amino]imidazo[1,2-b]pyridazin-6-yl}oxy)-2-fluorophenyl]-3-ethyl-1-methyl-1H-pyrazole-5-carboxamide (Example 208);

N-[2-chloro-5-({2-[(cyclopropylcarbonyl)amino]imidazo[1,2-b]pyridazin-6-yl}oxy)phenyl]-1-ethyl-3-methyl-1H-pyrazole-4-carboxamide (Example 254);

N-[5-({2-[(cyclopropylcarbonyl)amino]imidazo[1,2-b]pyridazin-6-yl}oxy)-2-fluorophenyl]-1-methyl-1H-pyrazole-5-carboxamide (Example 287);

N-[5-({2-[(cyclopropylcarbonyl)amino]imidazo[1,2-b]pyridazin-6-yl}oxy)-2-fluorophenyl]-2,4-dimethyl-1,3-oxazole-5-carboxamide (Example 289);

N-[5-({2-[(cyclopropylcarbonyl)amino]imidazo[1,2-b]pyridazin-6-yl}oxy)-2-fluorophenyl]-2-ethyl-4-methyl-1,3-oxazole-5-carboxamide (Example 314);

N-[3-({2-[(cyclopropylcarbonyl)amino]imidazo[1,2-b]pyridazin-6-yl}oxy)phenyl]-3-(trifluoromethyl)benzamide (Example 319);

3-(1-cyano-1-methylethyl)-N-[5-({2-[(cyclopropylcarbonyl)amino]imidazo[1,2-b]pyridazin-6-yl}oxy)-2-methylphenyl]benzamide (Example 330);

N-[3-({2-[(N,N-dimethylglycyl)amino]imidazo[1,2-b]pyridazin-6-yl}oxy)phenyl]-3-(trifluoromethyl)benzamide (Example 398);

N-[3-({2-[(cyclopropylcarbonyl)amino]imidazo[1,2-b]pyridazin-6-yl}thio)phenyl]-3-(trifluoromethyl)benzamide (Example 427);

N-{6-[3-({[3-(trifluoromethyl)phenyl]carbamoyl}amino)phenoxy]imidazo[1,2-b]pyridazin-2-yl}cyclopropanecarboxamide (Example 431).

The compound represented by the formula (III) (hereinafter compound (III)) of the present invention is explained below.

As the "cyclic group" of the "cyclic group substituted by an optionally substituted amino, wherein the cyclic group is optionally further substituted", for ring Yb, those similar to the groups exemplified as the "cyclic group" of the "optionally substituted cyclic group" for ring Y of compound (I) can be mentioned.

As the "cyclic group" of the "cyclic group substituted by an optionally substituted amino, wherein the cyclic group is optionally further substituted" for ring Yb, aromatic hydrocarbon group, aromatic heterocyclic group are preferable. As the aromatic hydrocarbon group, $C_{6-14}$ aryl is preferable, $C_{6-10}$ aryl is more preferable, and phenyl is particularly preferable. As the aromatic heterocyclic group, fused aromatic heterocyclic group is preferable, fused aromatic heterocyclic group formed by fusion of 5-membered monocyclic aromatic heterocyclic group containing, as ring-constituting atom, 1 or 2 heteroatoms selected from sulfur atom and nitrogen atom, besides carbon atoms, and benzene ring (e.g., benzothiazolyl, benzimidazolyl, indolyl etc.) is more preferable, and benzothiazolyl (e.g., 5-benzothiazolyl, 6-benzothiazolyl), benzimidazolyl (e.g., benzimidazol-5-yl, benzimidazol-6-yl), indolyl (e.g., indol-4-yl, indol-5-yl, indol-6-yl) and the like are particularly preferable.

The "cyclic group substituted by an optionally substituted amino, wherein the cyclic group is optionally further substituted" for ring Yb is substituted, at its any substitutable position, by optionally substituted amino that may further have 1 to the acceptable maximum number, preferably 1 to 5, more preferably 1 to 3, substituents at any substitutable position(s). Where the cyclic group is substituted by two or more substituents, the substituents may be the same or different.

As the "optionally substituted amino" of the "cyclic group substituted by an optionally substituted amino, wherein the cyclic group is optionally further substituted" for ring Yb, those similar to the group exemplified as the "optionally substituted amino" (Substituent Group (1)(x)) among the groups exemplified as the "substituent" of the "optionally substituted cyclic group" for ring Y of compound (I). As the substituent that may be used for the further substitution, those similar to the group exemplified as the "substituent" of the "optionally substituted cyclic group" for ring Y of compound (I) can be mentioned.

As the "substituent" of the "optionally substituted amino" in the "cyclic group substituted by an optionally substituted amino, wherein the cyclic group is optionally further substituted" for ring Yb, the "optionally substituted aminocarbonyl" of the aforementioned Substituent Group (1)(viii), and the "acyl" of the aforementioned Substituent Group (1)(ix) are preferable among the substituents referenced and exemplified above. Of these, (1) $C_{6-18}$ aryl-aminocarbonyl (e.g., phenylaminocarbonyl etc.) optionally substituted by $C_{1-4}$ alkyl (e.g., methyl) optionally having halogen atom (e.g., fluorine) (specific examples: phenylaminocarbonyl, 3-trifluoromethylphenylaminocarbonyl, 4-trifluoromethylphenylaminocarbonyl etc.), (2) $C_{6-18}$ aryl-carbonyl (e.g., phenylcarbonyl etc.) optionally substituted by $C_{1-4}$ alkyl (e.g., methyl) optionally having halogen atom (e.g., fluorine) (specific examples: phenylcarbonyl, 3-trifluoromethylphenylcarbonyl etc.) and (3) 5- or 6-membered monocyclic aromatic heterocycle (e.g., pyrazolyl etc.)-carbonyl containing, as ring-constituting atom, 1 to 3 heteroatoms selected from oxygen atom, sulfur atom and nitrogen atom besides carbon atoms, which is optionally substituted by $C_{1-4}$ alkyl (e.g., methyl) and the like (specific examples: 1,3-dimethyl-1H-pyrazole-5-carbonyl etc.), and the like are preferable.

Of the substituents referenced and exemplified above, the "substituent" by which the "cyclic group" is optionally substituted is preferably (1) halogen atom (e.g., fluorine, chlorine, bromine, iodine),
(2) optionally substituted alkyl,
(3) optionally substituted alkoxy,
(4) optionally substituted aminocarbonyl,
(5) optionally substituted amino,
and the like.

Of these,
(1) halogen atom (e.g., fluorine, chlorine, bromine, iodine),
(2) optionally substituted alkyl,
(3) optionally substituted amino,
and the like are preferable.

Hereinafter the above-mentioned preferable examples of the substituent by which the cyclic group is further substituted of the "cyclic group substituted by an optionally substituted amino, wherein the cyclic group is optionally further substituted" for ring Yb are exemplified in detail.

(1) As the halogen atom, fluorine, chlorine, bromine and the like are preferable.
(2) As the optionally substituted alkyl, optionally substituted $C_{1-8}$ alkyl is preferable, optionally substituted $C_{1-4}$ alkyl is more preferable, and unsubstituted $C_{1-4}$ alkyl is much more preferable. Specifically, methyl, ethyl and the like are preferable.
(3) As the optionally substituted alkoxy, optionally substituted $C_{1-8}$ alkoxy is preferable, optionally substituted $C_{1-4}$ alkoxy is more preferable, and unsubstituted $C_{1-4}$ alkoxy is more preferable. Specifically methoxy and the like are preferable.
(4) As the "substituent" for the optionally substituted aminocarbonyl, for example, $C_{1-8}$ alkyl, $C_{2-8}$ alkenyl, $C_{2-8}$ alkynyl, $C_{3-8}$ cycloalkyl, $C_{3-8}$ cycloalkenyl, $C_{3-8}$ cycloalkynyl, $C_{6-18}$ aryl, heterocyclic group and the like, each of which is optionally substituted, are preferable, optionally substituted heterocyclic group and the like are more preferable, and optionally substituted aromatic heterocyclic group is particularly preferable. As the optionally substituted aminocarbonyl, aminocarbonyl optionally substituted by aromatic heterocyclic group optionally substituted $C_{1-4}$ alkyl and the like are preferable, and 1,3-dimethyl-1H-pyrazol-5-yl-aminocarbonyl and the like are specifically preferable.
(5) As the "substituent" for the optionally substituted amino, optionally substituted aminocarbonyl, acyl and the like are preferable.

As the optionally substituted amino, unsubstituted amino; amino optionally substituted by optionally substituted aminocarbonyl; amino optionally substituted by acyl and the like are preferable.

As the optionally substituted aminocarbonyl, $C_{1-8}$ alkyl-aminocarbonyl, $C_{6-18}$ aryl-aminocarbonyl, $C_{6-18}$ aryl-$C_{1-4}$ alkyl-aminocarbonyl, heterocyclyl-aminocarbonyl, $C_{3-8}$ cycloalkyl-aminocarbonyl and the like, each of which is optionally substituted, are preferable. Of these, optionally substituted $C_{1-8}$ alkyl-aminocarbonyl and the like are preferable, and optionally substituted $C_{1-4}$ alkyl-aminocarbonyl is more preferable. Specifically, ethylaminocarbonyl and the like are preferable. Alternatively, optionally substituted $C_{6-18}$ aryl-aminocarbonyl and the like are preferable, optionally substituted $C_{6-10}$ aryl-aminocarbonyl is more preferable, and those wherein the aryl moiety is unsubstituted phenyl; phenyl optionally substituted by halogen atom (e.g., fluorine, chlorine), optionally halogenated $C_{1-4}$ alkyl (e.g., trifluoromethyl) and the like, and the like are particularly preferable. Specifically, phenylaminocarbonyl (anilinocarbonyl), 3-trifluoromethylphenylaminocarbonyl (3-trifluoromethylanilinocarbonyl), 4-trifluoromethylphenylaminocarbonyl (4-trifluoromethylanilinocarbonyl) and the like are preferable.

As the acyl, $C_{1-8}$ alkyl-carbonyl, $C_{6-18}$ aryl-carbonyl, $C_{6-18}$ aryl-$C_{1-4}$ alkyl-carbonyl, $C_{1-8}$ alkylsulfonyl, $C_{6-18}$ aryl-sulfonyl, heterocyclyl-carbonyl, heterocyclyl-sulfonyl, $C_{3-8}$ cycloalkyl-carbonyl and the like, each of which is optionally substituted, are preferable. Of these, $C_{1-8}$ alkyl-carbonyl, $C_{3-8}$ cycloalkyl-carbonyl, $C_{6-18}$ aryl-carbonyl, heterocyclyl-carbonyl, each of which is optionally substituted, are preferable.

As the optionally substituted $C_{1-8}$ alkyl-carbonyl, $C_{1-4}$ alkyl-carbonyl is preferable, and tert-butylcarbonyl and the like are specifically preferable.

As the optionally substituted $C_{3-8}$ cycloalkyl-carbonyl, $C_{3-6}$ cycloalkyl-carbonyl is preferable, and cyclopropylcarbonyl, cyclohexylcarbonyl and the like are specifically preferable.

As the optionally substituted $C_{6-18}$ aryl-carbonyl, optionally substituted $C_{6-10}$ aryl-carbonyl is preferable, and optionally substituted phenyl-carbonyl is more preferable. As the "substituent" for the optionally substituted $C_{6-18}$ aryl-carbonyl, halogen atom (e.g., fluorine, chlorine), optionally halogenated $C_{1-4}$ alkyl (e.g., trifluoromethyl) and the like are preferable. As the optionally substituted $C_{6-18}$ aryl-carbonyl, those wherein the "aryl" moiety is unsubstituted phenyl; phenyl optionally substituted by halogen atom (e.g., fluorine, chlorine), optionally halogenated $C_{1-4}$ alkyl (e.g., trifluoromethyl) and the like, and the like are preferable. Specifically, phenylcarbonyl(benzoyl), 3-trifluoromethylphenylcarbonyl, 3-fluorophenylcarbonyl, 3-chlorophenylcarbonyl and the like are preferable.

As the "heterocycle" moiety for the optionally substituted heterocyclyl-carbonyl, 5- or 6-membered monocyclic aromatic heterocyclic group containing, as ring-constituting atom, 1 to 3 heteroatoms selected from oxygen atom, sulfur atom and nitrogen atom besides carbon atoms and the like are preferable, and pyridyl, furyl, thienyl, pyrazolyl, imidazolyl, thiazolyl, oxazolyl, isoxazolyl, 1,2,3-triazolyl, 1,2,3-thiadiazolyl, pyridazinyl and the like are specifically preferable. As the "substituent" for the optionally substituted heterocyclyl-carbonyl, optionally halogenated $C_{1-4}$ alkyl (e.g., methyl, trifluoromethyl) and the like are preferable.

As the optionally substituted heterocyclyl-carbonyl, the above-mentioned 5- or 6-membered monocyclic aromatic heterocyclyl-carbonyl and the like optionally substituted by optionally halogenated $C_{1-4}$ alkyl and the like are preferable. specifically, 3-pyridylcarbonyl, 2-furylcarbonyl, 2,5-dimethylfuran-3-carbonyl, 3-methylthiophene-2-carbonyl, 4-methyl-1,2,3-thiadiazole-5-carbonyl, isoxazole-5-carbonyl, 1,3-dimethyl-1H-pyrazole-5-carbonyl, 3-methylisoxazole-5-carbonyl, 5-methylisoxazole-3-carbonyl, 1-methyl-3-(trifluoromethyl)-1H-pyrazole-5-carbonyl, 5-methyl-2-(trifluoromethyl)-3-furancarbonyl, 2,4-dimethyl-1,3-thiazole-5-carbonyl, 2,5-dimethyl-1,3-oxazole-4-carbonyl, 1-methyl-1H-pyrazole-5-carbonyl, 1,5-dimethyl-1H-pyrazole-3-carbonyl, 3,5-dimethylisoxazole-4-carbonyl, 1-methyl-1H-1,2,3-triazole-5-carbonyl, 1-methyl-1H-1,2,3-triazole-4-carbonyl, 1-methyl-1H-imidazole-2-carbonyl, 1-methyl-1H-imidazole-5-carbonyl and the like are preferable.

Preferably, ring Yb is
(1) $C_{6-14}$ aryl (e.g., phenyl etc.) substituted by amino optionally substituted by substituent selected from (1') $C_{6-18}$ aryl-aminocarbonyl (e.g., phenylaminocarbonyl etc.) optionally substituted by $C_{1-4}$ alkyl (e.g., methyl) optionally having halogen atom (e.g., fluorine) (specific examples: phenylaminocarbonyl, 3-trifluoromethylphenylaminocarbonyl, 4-trifluoromethylphenylaminocarbonyl etc.),
(2') $C_{6-18}$ aryl-carbonyl (e.g., phenylcarbonyl etc.) optionally substituted by $C_{1-4}$ alkyl (e.g., methyl) optionally having halogen atom (e.g., fluorine) (specific examples: phenylcarbonyl, 3-trifluoromethylphenylcarbonyl etc.), and
(3') 5- or 6-membered monocyclic aromatic heterocycle (e.g., pyrazolyl etc.)-carbonyl containing, as ring-constituting atom, 1 to 3 heteroatoms selected from oxygen atom, sulfur atom and nitrogen atom besides carbon atoms, which is optionally substituted by $C_{1-4}$ alkyl (e.g., methyl) and the like (specific examples: 1,3-dimethyl-1H-pyrazole-5-carbonyl etc.), wherein said $C_{6-14}$ aryl is optionally further substituted by 1 or 2 substituents selected from
(i) halogen atom (e.g., fluorine, chlorine, bromine, iodine etc.),
(ii) $C_{1-4}$ alkyl (e.g., methyl etc.),
(iii) $C_{1-4}$ alkoxy (e.g., methoxy etc.),
(iv) aminocarbonyl substituted by aromatic heterocyclic group (e.g., pyrazolyl etc.) optionally substituted by $C_{1-4}$ alkyl (e.g., methyl etc.), and
(v) amino optionally substituted by substituent selected from
  (a) $C_{1-4}$ alkyl-carbonyl (e.g., tert-butylcarbonyl etc.),
  (b) $C_{3-6}$ cycloalkyl-carbonyl (e.g., cyclopropylcarbonyl, cyclohexylcarbonyl etc.),
  (c) $C_{6-18}$ aryl-carbonyl (e.g., phenylcarbonyl etc.) optionally substituted by substituent selected from halogen atom (e.g., fluorine, chlorine) and optionally halogenated $C_{1-4}$ alkyl (e.g., trifluoromethyl) (specific examples: phenylcarbonyl (benzoyl), 3-trifluoromethylphenylcarbonyl, 3-fluorophenylcarbonyl, 3-chlorophenylcarbonyl etc.), and
  (d) 5- or 6-membered monocyclic aromatic heterocyclic group (e.g., pyridyl, furyl, thienyl, pyrazolyl, imidazolyl, thiazolyl, oxazolyl, isoxazolyl, 1,2,3-triazolyl, 1,2,3-thiadiazolyl, pyridazinyl etc.)-carbonyl containing, as ring-constituting atom, 1 to 3 heteroatoms selected from oxygen atom, sulfur atom and nitrogen atom besides carbon atoms, which is optionally substituted by $C_{1-4}$ alkyl (e.g., methyl) optionally having halogen atom (e.g., fluorine) and the like (specific examples: 3-pyridylcarbonyl, 2-furylcarbonyl, 2,5-dimethylfuran-3-carbonyl, 3-methylthiophene-2-carbonyl, 4-methyl-1,2,3-thiadiazole-5-carbonyl, isoxazole-5-carbonyl, 1,3-dimethyl-1H-pyrazole-5-carbonyl, 3-methylisoxazole-5-carbonyl, 5-methylisoxazole-3-carbonyl, 1-methyl-3-(trifluoromethyl)-1H-pyrazole-5-carbonyl, 5-methyl-2-(trifluoromethyl)-3-furancarbonyl, 2,4-dimethyl-1,3-thiazole-5-carbonyl, 2,5-dimethyl-1,3-oxazole-4-carbonyl, 1-methyl-1H-pyrazole-5-carbonyl, 1,5-dimethyl-1H-pyrazole-3-carbonyl, 3,5-dimethylisoxazole-4-carbonyl, 1-methyl-1H-1,2,3-triazole-5-carbonyl, 1-methyl-1H-1,2,3-triazole-4- carbonyl, 1-methyl-1H-imidazole-2-carbonyl, 1-methyl-1H-imidazole-5-carbonyl etc.),
and the like,
(2) fused aromatic heterocycle (e.g., benzothiazolyl (e.g., 5-benzothiazolyl, 6-benzothiazolyl), benzimidazolyl (e.g., benzimidazol-5-yl, benzimidazol-6-yl), indolyl (e.g., indol-4-yl, indol-5-yl, indol-6-yl) etc.) substituted by amino optionally substituted by (1') $C_{6-18}$ aryl-aminocarbonyl (e.g., phenylaminocarbonyl etc.) optionally substituted by $C_{1-4}$ alkyl (e.g., methyl) optionally having halogen atom (e.g., fluorine) (specific examples: phenylaminocarbonyl, 3-trifluoromethylphenylaminocarbonyl, 4-trifluoromethylphenylaminocarbonyl etc.), (2') $C_{6-18}$ aryl-carbonyl (e.g., phenylcarbonyl etc.) optionally substituted by $C_{1-4}$ alkyl (e.g., methyl) optionally having halogen atom (e.g., fluorine) (specific examples: phenylcarbonyl, 3-trifluoromethylphenylcarbonyl etc.), and (3') 5- or 6-membered monocyclic aromatic heterocycle (e.g., pyrazolyl etc.)-carbonyl containing, as ring-constituting atom, 1 to 3 heteroatoms selected from oxygen atom, sulfur atom and nitrogen atom besides carbon atoms, which is optionally substituted by $C_{1-4}$ alkyl (e.g., methyl) and the like (specific examples: 1,3-dimethyl-1H-pyrazole-5-carbonyl etc.), wherein said fused aromatic heterocycle further has 1 or 2 $C_{1-4}$ alkyl (e.g., methyl etc.), and the like.

Particularly, $C_{6-14}$ aryl (e.g., phenyl etc.) substituted by amino optionally substituted by (1) $C_{6-18}$ aryl-aminocarbonyl (e.g., phenylaminocarbonyl etc.) optionally substituted by $C_{1-4}$ alkyl (e.g., methyl) optionally having halogen atom (e.g., fluorine) (specific examples: phenylaminocarbonyl, 3-trifluoromethylphenylaminocarbonyl, 4-trifluoromethylphenylaminocarbonyl etc.), (2) $C_{6-18}$ aryl-carbonyl (e.g., phenylcarbonyl etc.) optionally substituted by $C_{1-4}$ alkyl (e.g., methyl) optionally having halogen atom (e.g., fluorine) (specific examples: phenylcarbonyl, 3-trifluoromethylphenylcarbonyl etc.), and (3) 5- or 6-membered monocyclic aromatic heterocycle (e.g., pyrazolyl etc.)-carbonyl containing, as ring-constituting atom, 1 to 3 heteroatoms selected from oxygen atom, sulfur atom and nitrogen atom besides carbon atoms, which is optionally substituted by $C_{1-4}$ alkyl (e.g., methyl) and the like (specific examples: 1,3-dimethyl-1H-pyrazole-5-carbonyl etc.), wherein said $C_{6-14}$ aryl does not have further substituent, is preferable.

As ring Yb, 3-aminophenyl, 4-aminophenyl, 3-{[(ethylamino)carbonyl]amino}phenyl, 4-{[(phenylamino)carbonyl]amino}phenyl, 3-{[(phenylamino)carbonyl]amino}phenyl, 3-({[3-(trifluoromethylphenyl)amino]carbonyl}amino)phenyl, 3-({[4-(trifluoromethylphenyl)amino]carbonyl}amino)phenyl, 3-[(tert-butylcarbonyl)amino]phenyl, 3-[(cyclopropylcarbonyl)amino]phenyl, 3-[(cyclohexylcarbonyl)amino]phenyl, 3-[(phenylcarbonyl)amino]phenyl, 3-{[3-(trifluoromethylphenyl)carbonyl]amino}phenyl, 3-{[3-(fluorophenyl)carbonyl]amino}phenyl, 3-{[3-(chlorophenyl)carbonyl]amino}phenyl, 3-{[3-(pyridyl)carbonyl]amino}phenyl, 3-{[2-(furyl)carbonyl]amino}phenyl, 3-{[3-(2,5-dimethylfuran)carbonyl]amino}phenyl, 3-{[2-(3-methylthiophene)carbonyl]amino}phenyl, 3-{[5-(4-methyl-1,2,3-thiadiazole)carbonyl]amino}phenyl, 3-{[5-(isoxazole)carbonyl]amino}phenyl, 3-{[5-(1,3-dimethyl-1H-pyrazole)carbonyl]amino}phenyl, 3-{[5-(3-methylisoxazole)carbonyl]amino}phenyl, 3-{[3-(5-methylisoxazole)carbonyl]amino}phenyl, 3-({5-[1-methyl-3-(trifluoromethyl)-1H-pyrazole]carbonyl}amino)phenyl, 5-methyl-2-(trifluoromethyl)-3-furancarbonylaminophenyl, 3-{[5-(2,4-dimethyl-1,3-thiazole)carbonyl]amino}phenyl, 3-{[4-(2,5-dimethyl-1,3-oxazole)carbonyl]amino}phenyl, 3-{[5-(1-methyl-1H-pyrazole)carbonyl]amino}phenyl, 3-{[3-(1,5-dimethyl-1H-pyrazole)carbonyl]amino}phenyl, 3-{[4-(3,5-dimethylisoxazole)carbonyl]amino}phenyl, 3-{[5-(1-methyl-1H-1,2,3-triazole)carbonyl]amino}phenyl, 3-{[4-(1-methyl-1H-1,2,3-triazole)carbonyl]amino}phenyl, 3-{[2-(1-methyl-1H-imidazole)carbonyl]amino}phenyl, 3-{[5-(1-methyl-1H-imidazole)carbonyl]amino}phenyl, 5-amino-2-methylphenyl, 3-amino-2-methylphenyl, 3-amino-4-methylphenyl, 3-amino-4-chlorophenyl, 5-amino-2-chlorophenyl, 5-amino-2-methoxyphenyl, 6-methyl-3-{[5-(1,3-dimethyl-1H-pyrazole)carbonyl]amino}phenyl, 2-methyl-3-{[5-(1,3-dimethyl-1H-pyrazole)carbonyl]amino}phenyl, 4-methyl-3-{[5-(1,3-dimethyl-1H-pyrazole)carbonyl]amino}phenyl, 4-chloro-3-{[5-(1,3-dimethyl-1H-pyrazole)carbonyl]amino}phenyl, 6-chloro-3-{[5-(1,3-dimethyl-1H-pyrazole)carbonyl]amino}phenyl, 4-fluoro-3-{[5-(1,3-dimethyl-1H-pyrazole)carbonyl]amino}phenyl, 6-methoxy-3-{[5-(1,3-dimethyl-1H-pyrazole)carbonyl]amino}phenyl, 4-chloro-3-(cyclopropylcarbonylamino)phenyl, 3-amino-4-fluorophenyl and the like can be specifically mentioned. Of these, 3-aminophenyl, 4-aminophenyl, 4-{[(phenylamino)carbonyl]amino}phenyl, 3-{[(phenylamino)carbonyl]amino}phenyl, 3-({[3-(trifluoromethylphenyl)amino]carbonyl}amino)phenyl, 3-({[4-(trifluoromethylphenyl)amino]carbonyl}amino)phenyl, 3-{[5-(1,3-dimethyl-1H-pyrazole)carbonyl]amino}phenyl, 4-fluoro-3-{[4-(1-ethyl-3-methyl-1H-pyrazole)carbonyl]amino}phenyl and the like are preferable.

In the compound (III), as the substituent for $R^b$ of NR defined by Xb, those similar to the substituent selected from the aforementioned Substituent Group (1) can be mentioned.

As the substituent for $R^b$, optionally substituted hydrocarbon group and the like are preferable.

Xb is preferably —O—, —S— or —NH—, and particularly preferably —O—.

As the "substituent (except for optionally substituted amino)" for $R^{1b}$, those similar to the group of the substituents of the aforementioned Substituent Group (1) except for the "optionally substituted amino" can be mentioned. Of these, optionally substituted aminocarbonyl and the like are preferable.

Preferable $R^{1b}$ are
(1) hydrogen atom,
(2) optionally substituted aminocarbonyl,
(3) optionally substituted alkyl,
(4) optionally esterified carboxy,
and the like.

Of these, more preferable $R^{1b}$ are
(1) hydrogen atom,
(2) aminocarbonyl optionally substituted by optionally substituted alkyl,
(3) alkyl optionally substituted by hydroxy,
(4) carboxy,
(5) $C_{1-6}$ alkoxy-carbonyl (e.g., ethoxycarbonyl),
and the like.

Hereinafter the preferable examples of the "substituent" for $R^{1b}$ are explained in detail.

As the "alkyl" of the "optionally substituted alkyl" of the above-mentioned (2), $C_{1-8}$ alkyl and the like are preferable, $C_{1-4}$ alkyl and the like are more preferable, and methyl and the like are specifically preferable.

As the "alkyl" of the "alkyl optionally substituted by hydroxy" of the above-mentioned (3), $C_{1-8}$ alkyl and the like are preferable, $C_{1-4}$ alkyl and the like are more preferable, and methyl and the like are specifically preferable.

As $R^b$, hydroxymethyl, —C(O)NH—CH$_3$, hydrogen atom, carboxy, ethoxycarbonyl and the like can be specifically mentioned.

In the compound (III), as the "substituent" for $R^{2b}$, those similar to the substituents of the aforementioned Substituent Group (1) can be mentioned.

Of these, preferable $R^{2b}$ is hydrogen atom.

In the compound (III), as the "substituent" for $R^{3b}$, those similar to the substituents of the aforementioned Substituent Group (1) can be mentioned.

Of these, preferable $R^{3b}$ is hydrogen atom.

In the compound (III), as the "substituent" for $R^{4b}$, those similar to the substituents of the aforementioned Substituent Group (1) can be mentioned.

Of these, preferable $R^{4b}$ is hydrogen atom.

As the preferable example of the compound (III), for example, the following compound can be mentioned.

A compound wherein
ring Yb is $C_{6-14}$ aryl (e.g., phenyl etc.) substituted by amino optionally substituted by (1) $C_{6-18}$ aryl-aminocarbonyl (e.g., phenylaminocarbonyl etc.) optionally substituted by $C_{1-4}$ alkyl (e.g., methyl) optionally having halogen atom (e.g., fluorine) (specific examples: phenylaminocarbonyl, 3-trifluoromethylphenylaminocarbonyl, 4-trifluoromethylphenylaminocarbonyl etc.), (2) $C_{6-18}$ aryl-carbonyl (e.g., phenylcarbonyl etc.) optionally substituted by $C_{1-4}$ alkyl (e.g., methyl) optionally having halogen atom (e.g., fluorine) (specific examples: phenylcarbonyl, 3-trifluoromethylphenylcarbonyl etc.), and (3) 5- or 6-membered monocyclic aromatic heterocycle (e.g., pyrazolyl etc.)-carbonyl containing, as ring-constituting atom, 1 to 3 heteroatoms selected from oxygen atom, sulfur atom and nitrogen atom besides carbon atoms, which is optionally substituted by $C_{1-4}$ alkyl (e.g., methyl) and the like (specific examples: 1,3-dimethyl-1H-pyrazole-5-carbonyl etc.), wherein said $C_{6-14}$ aryl does not have further substituent;
Xb is —O—, —S— or —NH— (preferably —O—);
$R^{1b}$ is
(1) hydrogen atom,
(2) —C(O)NH—CH$_3$, or
(3) hydroxymethyl; and
$R^{2b}$, $R^{3b}$ and $R^{4b}$ are each hydrogen atom.

Specific examples of the compound (III) include Examples 61 to 63, 65, 73, 124, 125, 139 to 146, 440, 442 and 445.

Examples of the salt of compounds (I)-(IV) include a metal salt, an ammonium salt, a salt with organic base, a salt with inorganic acid, a salt with organic acid, a salt with basic or acidic amino acid and the like. Preferable examples of the metal salt include alkali metal salt such as sodium salt, potassium salt and the like; alkaline earth metal salt such as calcium salt, magnesium salt, barium salt and the like; aluminum salt and the like. Preferable examples of the salt with the organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with the inorganic acid include a salt with hydrochloric acid, hydrobromic acid, nitric acid, sulfuric acid, phosphoric acid and the like. Preferable examples of the salt with the organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with the basic amino acid include a salt with arginine, lysine, ornithine and the like. Preferable examples of the salt with the acidic amino acid include a salt with aspartic acid, glutamic acid and the like.

Of these, pharmaceutically acceptable salt is preferable. For example, where the compound has an acidic functional group, inorganic salt such as alkali metal salt (e.g., sodium salt, potassium salt etc.), alkaline earth metal salt (e.g., calcium salt, magnesium salt etc.) and the like, ammonium salt and the like can be mentioned. Alternatively, where the compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like can be mentioned.

Hereinafter, the production methods of compounds (I)-(IV) of the present invention are explained.

The compounds (I)-(IV) of the present invention can be obtained, for example, according to the methods shown in the following Schemes or a method analogous thereto and the like (while the production methods of compounds (II) and (III) are exemplarily shown below, compounds (I) and (IV) can also be obtained according to a method shown by a similar Scheme or a method analogous thereto and the like).

Each compound in the following Schemes includes salts, and as such salts, for example, those similar to the salts of the compounds (I)-(IV) and the like can be used.

The compound obtained in each step can be used in the form of a reaction mixture or a crude product for the next reaction. In addition, the compound can be isolated from a reaction mixture according to a conventional method, and can be easily purified by a separation means such as recrystallization, distillation, chromatography and the like.

Schematic reaction formulas are shown in the following, wherein each symbol in the compounds is as defined above.

Moreover, the respective terms in the production methods mean the following.

The "halogen atom" means fluorine, chlorine, bromine or iodine.

The "optionally substituted alkylsulfonyl" means $C_{1-6}$ alkylsulfonyl (e.g., methylsulfonyl, ethylsulfonyl etc.) optionally substituted by substituent(s) selected from halogen atom, optionally halogenated $C_{1-6}$ alkyl (e.g., methyl, ethyl, trifluoromethyl) and nitro.

The "optionally substituted alkylsulfonyloxy" means $C_{1-6}$ alkylsulfonyloxy (e.g., methylsulfonyloxy, ethylsulfonyloxy etc.) optionally substituted by substituent(s) selected from halogen atom, optionally halogenated $C_{1-6}$ alkyl (e.g., methyl, ethyl, trifluoromethyl) and nitro.

The "optionally substituted arylsulfonyloxy" means $C_{6-14}$ arylsulfonyloxy (e.g., phenylsulfonyloxy etc.) optionally substituted by substituent(s) selected from halogen atom, optionally halogenated $C_{1-6}$ alkyl (e.g., methyl, ethyl, trifluoromethyl) and nitro.

The "optionally substituted aryloxy" means $C_{6-14}$ aryloxy (e.g., phenyloxy etc.) optionally substituted by substituent(s) selected from halogen atom, optionally halogenated $C_{1-6}$ alkyl (e.g., methyl, ethyl, trifluoromethyl) and nitro.

The "optionally substituted alkoxy" means $C_{1-6}$ alkoxy (e.g., methoxy, ethoxy etc.) optionally substituted by substituent(s) selected from halogen atom, optionally halogenated $C_{1-6}$ alkyl (e.g., methyl, ethyl, trifluoromethyl) and nitro.

[Production Method 1]

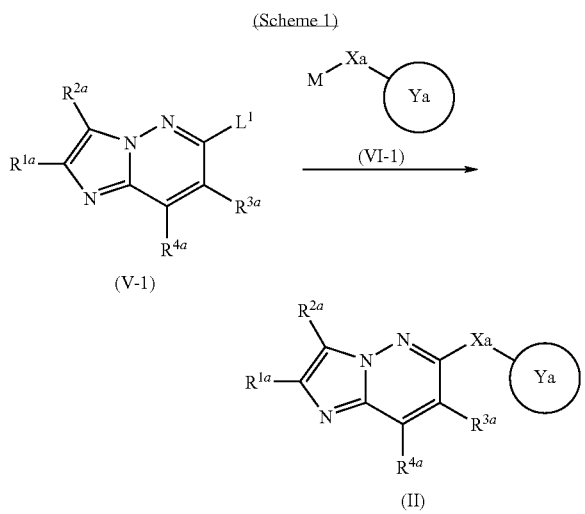

wherein $L^1$ is a leaving group, M is a hydrogen atom or a metal atom, and other symbols are as defined above.

As the leaving group for $L^1$, for example, a halogen atom, optionally substituted alkylsulfonyl, optionally substituted alkylsulfonyloxy, optionally substituted arylsulfonyloxy and the like can be used.

M is mainly a hydrogen atom, but may be an alkali metal such as lithium, sodium, potassium, cesium and the like, or an alkaline earth metal such as magnesium, calcium and the like.

Compound (II) can be produced by reacting compound (V-1) with compound (VI-1). Compound (VI-1) is used in 0.1 to 10 equivalents, preferably 0.3 to 3 equivalents, relative to compound (V-1). A base may be added as necessary. As the base, inorganic base or organic base and the like can be used. Specifically, for example, sodium hydroxide, potassium hydroxide, sodium carbonate, potassium carbonate, cesium carbonate, sodium bicarbonate, triethylamine, N-ethyldiisopropylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like can be mentioned. The base is used in 1 to 30 equivalents, preferably 1 to 10 equivalents, relative to compound (V-1). This reaction is advantageously carried out using a solvent inert to the reaction. While the solvent is not particularly limited as long as the reaction proceeds, for example, alcohols such as methanol, ethanol, 2-propanol, 2-methyl-2-propanol and the like, ethers such as diethyl ether, tetrahydrofuran, 1,4-dioxane, 1,2-dimethoxyethane and the like, hydrocarbons such as benzene, toluene, cyclohexane, hexane and the like, esters such as ethyl acetate and the like, ketones such as acetone, methyl ethyl ketone and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile and the like, sulfoxides such as dimethylsulfoxide and the like, pyridine, water and the like can be used alone or in mixture. While the reaction time varies depending on the kind of reagent and solvent to be used, it is generally 1 min to 200 hr, preferably 10 min to 100 hr. While the reaction temperature varies depending on the kind of reagent and solvent to be used, it is generally −100 to 250° C., preferably −78 to 200° C. The reaction can be carried out using a microwave synthesizer.

A compound within the scope of the present invention can also be produced by applying a means known per se to the obtained compound (II) of the present invention for introduction of substituents and conversion of functional groups. For conversion of substituents, a known conventional method can be used. For example, conversion to carboxy by hydrolysis of ester, conversion to carbamoyl by amidation of carboxy, conversion to hydroxymethyl by reduction of carboxy, conversion to alcohol compound by reduction or alkylation of carbonyl, reductive amination of carbonyl, oximation of carbonyl, acylation, ureation, sulfonylation or alkylation of amino, substitution and amination of active halogen by amine, amination of nitro by reduction, alkylation of hydroxy, substitution and amination of hydroxy and the like can be mentioned. When a reactive substituent that causes non-objective reaction is present during the introduction of substituents and conversion of functional groups, a protecting group is introduced in advance as necessary into the reactive substituent by a means known per se, and the protecting group is removed by a means known per se after the objective reaction, whereby the compound within the scope of the present invention can also be produced.

Compound (VI-1) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 2]

Compound (II) wherein Ya is substituted by optionally substituted amide, which is further optionally substituted, can also be produced for example, according to a method shown in Scheme 2. Compounds (II-1), (II-2) and (II-3) are encompassed in compound (II).

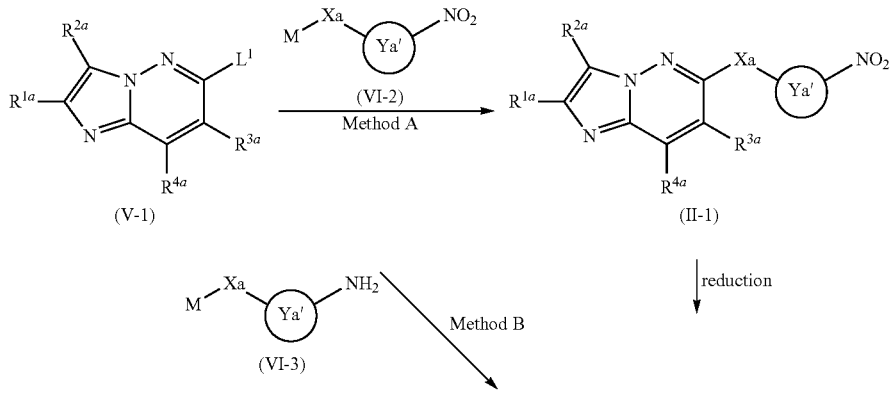

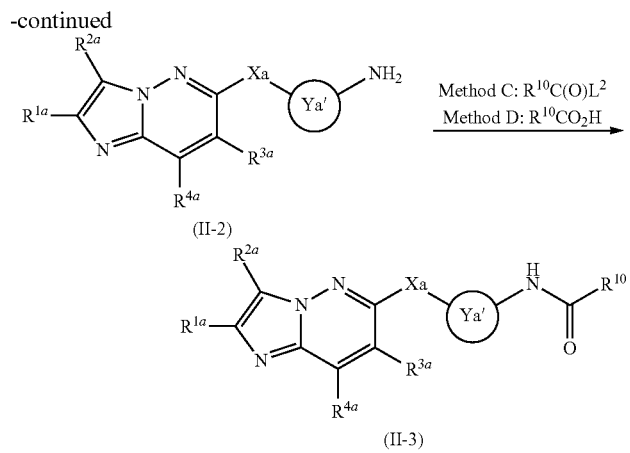

(II-2)

(II-3)

wherein $L^2$ is a leaving group, Ya' is a cyclic group of Ya, $R^{10}$ is a group shown by the moiety of acyl except for carbonyl moiety, which acyl is exemplified as the substituent of the "optionally substituted amino" which is one of the substituents of the "optionally substituted cyclic group" for ring Y of compound (I), and other symbols are as defined above.

As the leaving group for $L^2$, for example, halogen atom, optionally substituted aryloxy, optionally substituted alkoxy, 1-imidazolyl and the like can be used.

In Method A, compound (II-2) is produced by reacting compound (V-1) and compound (VI-2) in the presence of a base, and reducing the nitro of compound (II-1). Compound (VI-2) is used in 0.1 to 10 equivalents, preferably 0.3 to 3 equivalents, relative to compound (V-1). As the base, those similar to the base exemplified in Scheme 1 can be used. The base is used in 1 to 30 equivalents, preferably 1 to 10 equivalents, relative to compound (V-1). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VI-2) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto. The obtained compound (II-1) can be used as a reaction mixture or as a crude product in the next reaction. It can be isolated from a reaction mixture according to a conventional method. The reduction of nitro can be carried out according to a method known per se, for example, the methods described in the fourth series of experimental chemistry, vol. 20, 279-280 and the like, or a method analogous thereto.

In Method B, compound (II-2) is produced by reacting compound (V-1) with compound (VI-3) in the presence of a base. Compound (VI-3) is used in 0.1 to 10 equivalents, preferably 0.3 to 3 equivalents, relative to compound (V-1). As the base, those similar to the base exemplified in Scheme 1 can be used. The base is used in 1 to 30 equivalents, preferably 1 to 10 equivalents, relative to compound (V-1). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VI-3) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method C, compound (II-3) is produced by reacting compound (II-2) with a compound represented by the formula $R^{10}C(O)L^2$. The compound represented by the formula $R^{10}C(O)L^2$ is used in 0.1 to 10 equivalents, preferably 0.3 to 3 equivalents, relative to compound (II-2). A base may be used in 0.01 to 10 equivalents, preferably 0.03 to 5 equivalents, relative to compound (II-2). As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The compound represented by the formula $R^{10}C(O)L^2$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method D, (II-3) is produced by reacting compound (II-2) with carboxylic acid ($R^{10}CO_2H$) in the presence of a condensing agent. When Compound (II-2) is reacted with carboxylic acid ($R^{10}CO_2H$) in the presence of a condensing agent, carboxylic acid ($R^{10}CO_2H$) is used in 0.1 to 10 equivalents, preferably 0.3 to 3 equivalents, relative to compound (II-2). As the condensing agent, for example, 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate and the like can be used. The condensing agent is used in 1 to 10 equivalents, preferably 1 to 5 equivalents, relative to compound (II-2). Where necessary, a suitable condensation promoter (e.g., 1-hydroxybenzotriazole, N-hydroxysuccinimide etc.) can be used. The condensation promoter is used in 0.1 to 10 equivalents, preferably 0.3 to 3 equivalents, relative to compound (II-2). This reaction may proceed more smoothly when a base is added. As the base, those similar to the bases exemplified in Scheme 1 can be used. The base is used in 0.01 to 10 equivalents, preferably 0.03 to 5 equivalents, relative to compound (II-2). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Carboxylic acid ($R^{10}CO_2H$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 3]

In compound (II), when Ya is substituted by optionally substituted ureido, and optionally further substituted, for example, the compound can also be produced by the method shown in Scheme 3. Compounds (II-2), (II-4) and (II-5) are encompassed in compound (II).

This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Isocyanate derivative ($R^{11}NCO$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method F-1, compound (II-5) is produced by first reacting compound (II-2) with a compound represented by the formula $L^2C(O)L^3$ to give compound (II-4), and then reacting compound (II-4) with amine derivative ($R^{11}R^{12}NH$). The compound represented by the formula $L^2C(O)L^3$ is used in 0.1 to 10 equivalents, preferably 0.3 to 3 equivalents, relative to compound (II-2). A base may be used in 0.1 to 10 equivalents, preferably 0.3 to 3 equivalents. As the base, those similar to the base exemplified in Scheme 1 can be used. This reaction is advantageously carried out using a solvent inert to

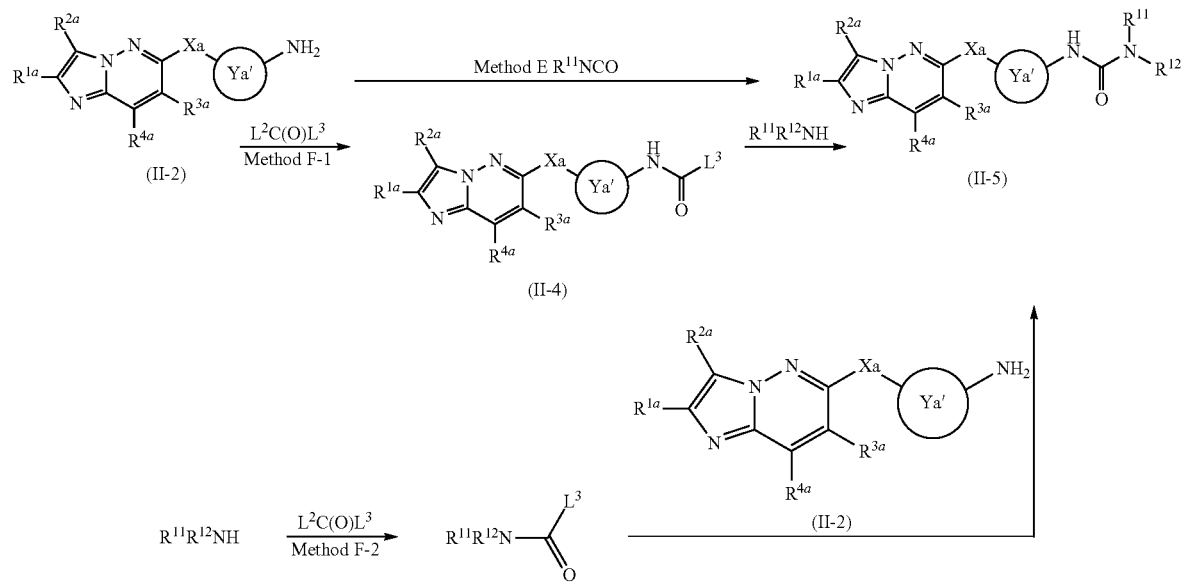

(Scheme 3)

wherein $L^3$ is a leaving group, $-NR^{11}R^{12}$ is a group shown by the moiety of optionally substituted aminocarbonyl except for carbonyl moiety, which optionally substituted aminocarbonyl is exemplified as the substituent of the "optionally substituted amino" which is one of the substituents of the "optionally substituted cyclic group" for ring Y of compound (I), and other symbols are as defined above.

As the leaving group for $L^3$, for example, a halogen atom, optionally substituted aryloxy, optionally substituted alkoxy, 1-imidazolyl and the like can be used.

In Method E, compound (II-5) wherein $R^{12}$ is H is produced by reacting compound (II-2) with the isocyanate derivative ($R^{11}NCO$). Isocyanate derivative ($R^{11}NCO$) is used in 0.1 to 10 equivalents, preferably 0.3 to 3 equivalents, relative to compound (II-2). A base may be used in 0.01 to 10 equivalents, preferably 0.01 to 3 equivalents. As the base, those similar to the base exemplified in Scheme 1 can be used.

the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The compound represented by the formula $L^2C(O)L^3$ may be commercially available, or can be produced by a method known per se. The obtained compound (II-4) can be used in the form of a reaction mixture or a crude product for the next reaction. It can also be used for the next reaction after isolation and purification from a reaction mixture according to a conventional method. The amine derivative ($R^{11}R^{12}NH$) is used in 0.1 to 10 equivalents, preferably 0.3 to 3 equivalents, relative to compound (II-4). In addition, a base may be used in 0.1 to 10 equivalents, preferably 0.3 to 3 equivalents. As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The amine derivative ($R^{11}R^{12}NH$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method F-2, compound (II-5) is produced by first reacting a compound represented by the formula $R^{11}R^{12}NH$ with a compound represented by the formula $L^2C(O)L^3$, successively compound (II-2) to give compound (II-5). The compound represented by the formula $L^2C(O)L^3$ is used in 0.1 to 10 equivalents, preferably 0.3 to 3 equivalents, relative to amine derivative ($R^{11}R^{12}NH$). A base may be used in 0.1 to 10 equivalents, preferably 0.3 to 3 equivalents. As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The amine derivative ($R^{11}R^{12}NH$) and the compound represented by the formula $L^2C(O)L^3$ may be commercially available, or can be produced by a method known per se for example, the methods described in "Advanced Organic Chemistry, 4th Ed." (Jerry March), "Comprehensive Organic Transformations, 2nd Ed." (Richard C. Larock) and the like or a method analogous thereto. The obtained compound represented by the formula $R^{11}R^{12}NC(O)L^3$ can be used in the form of a reaction mixture or a crude product for the next reaction. It can also be used for the next reaction after isolation and purification from a reaction mixture according to a conventional method. The compound (II-2) is used in 0.1 to 10 equivalents, preferably 0.3 to 3 equivalents, relative to the compound represented by the formula $R^{11}R^{12}NC(O)L^3$. In addition, a base may be used in 0.1 to 10 equivalents, preferably 0.3 to 3 equivalents. As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C.

[Production Method 4]

In compound (II), when Ya is substituted by optionally substituted sulfonamide, and optionally further substituted, for example, the compound can also be produced by the method shown in Scheme 4. Compound (II-6) is encompassed in compound (II).

(Scheme 4)

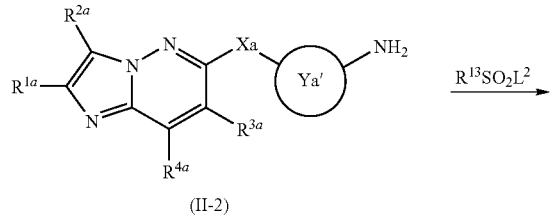

(II-2)

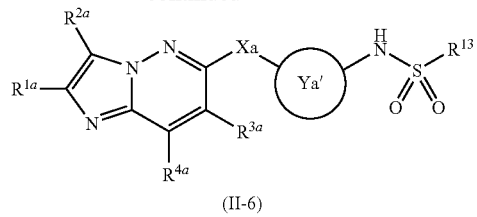

(II-6)

wherein $R^{13}$ is a group shown by the moiety of acyl except for carbonyl moiety, which acyl is exemplified as the substituent of the "optionally substituted amino" which is one of the substituents of the "optionally substituted cyclic group" for ring Y of compound (I), and other symbols are as defined above.

Compound (II-6) can be produced by reacting compound (II-2) with a reactive derivative of sulfonic acid ($R^{13}SO_2L^2$). The reactive derivative of sulfonic acid ($R^{13}SO_2L^2$) is used in 0.1 to 10 equivalents, preferably 0.3 to 3 equivalents, relative to compound (II-2). In the present method, the reaction is generally carried out in the presence of a base, though it is not always essential. As the base, those similar to the base exemplified in Scheme 1 can be used. A base may be used in 0.01 to 10 equivalents, preferably 0.03 to 5 equivalents, relative to compound (II-2). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The reactive derivative of sulfonic acid ($R^{13}SO_2L^2$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 5]

Compound (V-1) shown in Schemes 1 and 2 can be obtained, for example, by the method shown in the following Scheme or a method analogous thereto and the like. Compounds (V-2), (V-3) and (V-4) are encompassed in compound (V-1).

(Scheme 5)

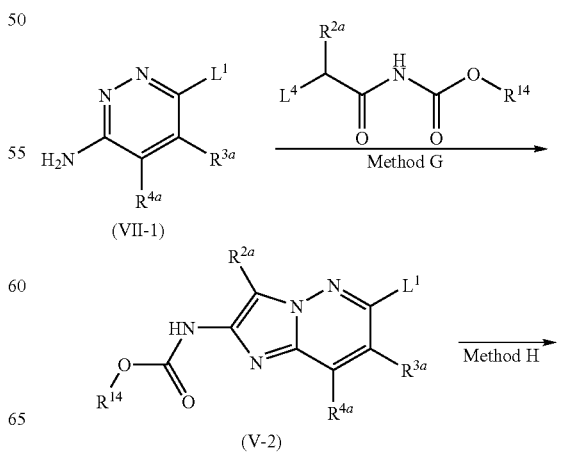

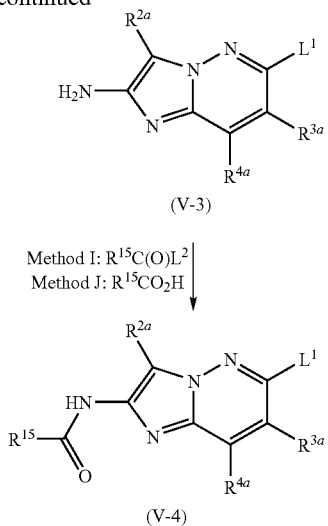

(V-3)

Method I: $R^{15}C(O)L^2$
Method J: $R^{15}CO_2H$ (V-4)

wherein $L^4$ is a leaving group, $R^{14}$ is an optionally substituted hydrocarbon group, $R^{15}$ is an optionally substituted hydrocarbon group or optionally substituted cyclic group, and other symbols are as defined above.

As the leaving group for $L^4$, chlorine, bromine, iodine and the like can be used.

Examples of the optionally substituted hydrocarbon group for $R^{14}$ include methyl, ethyl, propyl, isopropyl, tert-butyl and the like.

Examples of the optionally substituted hydrocarbon group, optionally substituted cyclic group for $R^{15}$ include a group shown by the moiety of acyl except for carbonyl group, which acyl is exemplified as the substituent of the "optionally substituted amino" for $R^{1a}$ of compound (II) and the like.

In Method G, compound (V-2) is produced by reacting compound (VII-1) with an acetylcarbamic acid derivative ($L^4CHR^{2a}C(O)NHC(O)OR^{14}$). The acetylcarbamic acid derivative is used in 0.1 to 10 equivalents, preferably 0.3 to 5 equivalents, relative to compound (VII-1). A base may be used in 0.1 to 10 equivalents, preferably 0.3 to 5 equivalents, relative to compound (VII-1). As the base, inorganic base or organic base and the like can be used, specifically, for example, sodium carbonate, potassium carbonate, cesium carbonate, sodium bicarbonate, disodium hydrogenphosphate, dipotassium hydrogenphosphate, calcium hydrogenphosphate, triethylamine, N-ethyldiisopropylamine, N-methylmorpholine, 1,8-diazabicyclo[5.4.0]undec-7-ene, pyridine, 4-(dimethylamino)pyridine, N,N-dimethylaniline and the like can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The acetylcarbamic acid derivative ($L^4CHR^{2a}C(O)NHC(O)OR^{14}$) may be commercially available, or can be produced according to a method known per se, for example, the methods described in "Journal of Organic Chemistry, 50, 2480-2499 (1985)" and the like or a method analogous thereto.

In Method H, compound (V-3) is produced by treating compound (V-2) with a base or acid. As the base, for example, sodium hydroxide, potassium hydroxide, cesium hydroxide, barium hydroxide and the like can be mentioned. A base is used in 0.01 to 10 equivalents, preferably 0.03 to 5 equivalents, relative to compound (V-2). As the acid, for example, hydrochloric acid, hydrobromic acid, hydroiodic acid, sulfuric acid, trifluoroacetic acid and the like can be used. An acid is used in 0.1 to 20 equivalents, preferably 0.3 to 10 equivalents, relative to compound (V-2). This reaction is advantageously carried out using a solvent inert to the reaction. As the solvent, those similar to the solvents exemplified in Scheme 1 can be used.

In Method I, compound (V-4) is produced by reacting compound (V-3) with a compound represented by the formula $R^{15}C(O)L^2$. The compound represented by the formula $R^{15}C(O)L^2$ is used in 0.1 to 10 equivalents, preferably 0.3 to 3 equivalents, relative to compound (V-3). As the base, those similar to the base exemplified in Scheme 1 can be used. A base may be used in 0.01 to 10 equivalents, preferably 0.03 to 5 equivalents, relative to compound (V-3). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The compound represented by the formula $R^{15}C(O)L^2$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method J, (V-4) is produced by reacting compound (V-3) with carboxylic acid ($R^{15}CO_2H$) in the presence of a condensing agent. When compound (V-3) is reacted with carboxylic acid ($R^{15}CO_2H$) in the presence of a condensing agent, carboxylic acid ($R^{15}CO_2H$) is used in 0.1 to 10 equivalents, preferably 0.3 to 3 equivalents, relative to compound (V-3). As the condensing agent, for example, 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate and the like can be used. These condensing agents are used in 1 to 10 equivalents, preferably 1 to 5 equivalents, relative to compound (V-3). Where necessary, a suitable condensation promoter (e.g., 1-hydroxybenzotriazole, N-hydroxysuccinimide etc.) can be used. These condensation promoters are used in 0.1 to 10 equivalents, preferably 0.3 to 3 equivalents, relative to compound (V-3). This reaction may proceed more smoothly when a base is added. As the base, those similar to the base exemplified in Scheme 1 can be used. These bases are used in 0.01 to 10 equivalents, preferably 0.03 to 5 equivalents, relative to compound (V-3). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Carboxylic acid ($R^{15}CO_2H$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 6]

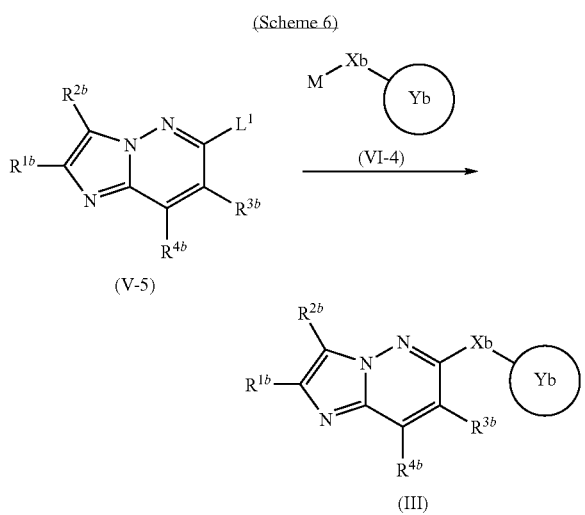

wherein each symbol is as defined above.

Compound (III) can be produced by reacting compound (V-5) with compound (VI-4). Compound (VI-4) is used in 0.1 to 10 equivalents, preferably 0.3 to 3 equivalents, relative to Compound (V-5). Where necessary, a base may be added. As the base, those similar to the base exemplified in Scheme 1 can be used. These bases are used in 1 to 30 equivalents, preferably 1 to 10 equivalents, relative to compound (V-5). This reaction is advantageously carried out using a solvent inert to the reaction. As the solvent, those similar to the solvents exemplified in Scheme 1 can be used. The reaction time varies depending on the kind of reagent and solvent to be used, and is generally 1 min to 200 hr, preferably 10 min to 100 hr. While the reaction temperature varies depending on the kind of reagent and solvent to be used, generally −100° C. to 250° C., preferably −78° C. to 200° C. The reaction may be carried out using a microwave synthesizer.

A compound within the scope of the present invention can also be produced by applying a means known per se to the obtained compound (III) of the present invention for introduction of substituents and conversion of functional groups. For conversion of substituents, a known conventional method can be used. For example, conversion to carboxy by hydrolysis of ester, conversion to carbamoyl by amidation of carboxy, conversion to hydroxymethyl by reduction of carboxy, conversion to alcohol compound by reduction or alkylation of carbonyl, reductive amination of carbonyl, oximation of carbonyl, acylation, ureation, sulfonylation or alkylation of amino, substitution and amination of active halogen by amine, alkylation of hydroxy, substitution and amination of hydroxy and the like can be mentioned. When a reactive substituent that causes non-objective reaction is present during the introduction of substituents and conversion of functional groups, a protecting group is introduced in advance as necessary into the reactive substituent by a means known per se, and the protecting group is removed by a means known per se after the objective reaction, whereby the compound within the scope of the present invention can also be produced.

Compound (VI-4) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production method 7]

In compound (III), when the substituent of optionally substituted amino for Yb is acyl, for example, the compound can also be produced by the method shown in Scheme 7. Compounds (III-2) and (III-3) are encompassed in compound (III).

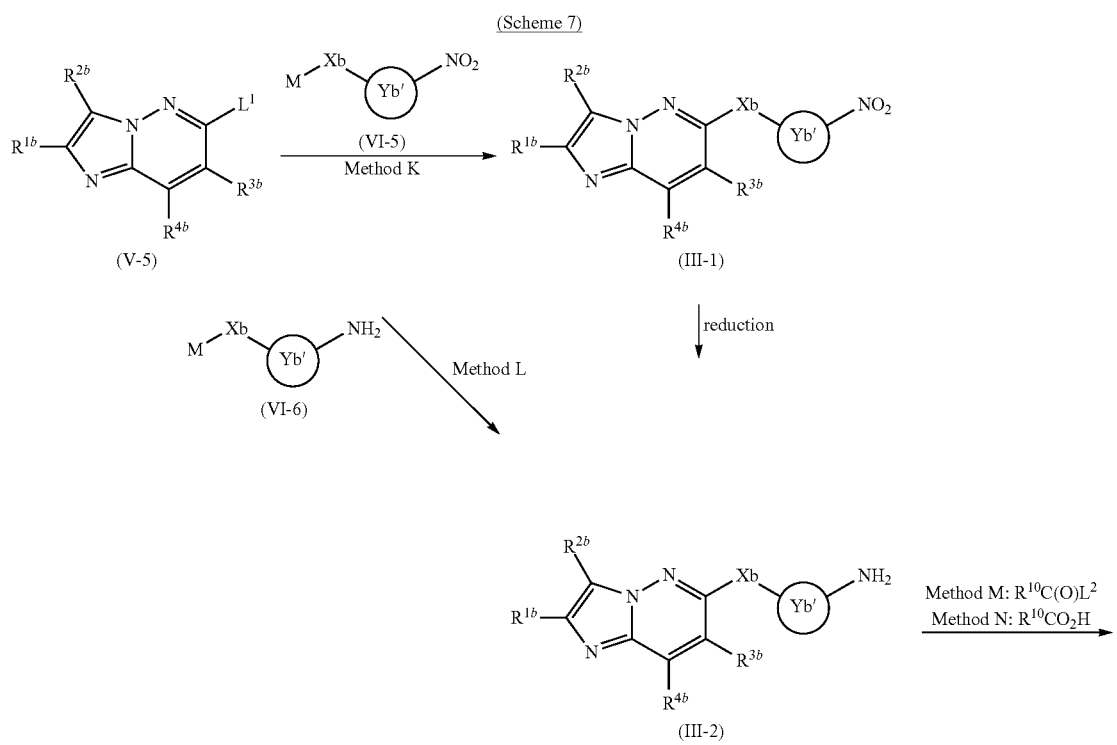

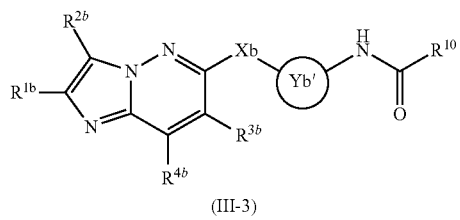

(III-3)

wherein Yb' is a cyclic group of Yb, and other symbols are as defined above.

In Method K, compound (III-2) is produced by first reacting compound (V-5) with compound (VI-5) in the presence of a base to give compound (III-1), and then reducing nitro of compound (III-1). Compound (VI-5) is used in 0.1 to 10 equivalents, preferably 0.3 to 3 equivalents, relative to compound (V-5). As the base, those similar to the base exemplified in Scheme 1 can be used. A base is used in 1 to 30 equivalents, preferably 1 to 10 equivalents, relative to compound (V-5). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VI-5) may be commercially available, or can be produced according to a method known per se, for example, the method described in "Advanced Organic Chemistry, 4th Ed." (Jerry March), "Comprehensive Organic Transformations, 2nd Ed." (Richard C. Larock) and the like, or a method analogous thereto. The obtained compound (III-1) can be used in the form of a reaction mixture or a crude product for the next reaction. Alternatively, it may be used for the next reaction after isolation and purification from the reaction mixture according to a conventional method. The reduction of nitro can be carried out by a method known per se, for example, the method described in the fourth series of experimental chemistry, vol. 20, 279-280 and the like, or a method analogous thereto.

In Method L, compound (III-2) is produced by reacting compound (V-5) with compound (VI-6) in the presence of a base. Compound (VI-6) is used in 0.1 to 10 equivalents, preferably 0.3 to 3 equivalents, relative to compound (V-5). As the base, those similar to the base exemplified in Scheme 1 can be used. A base is used in 1 to 5 equivalents, preferably 1 to 2 equivalents, relative to compound (V-5). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VI-6) may be commercially available, or can be produced according to a method known per se, for example, the method described in "Advanced Organic Chemistry, 4th Ed." (Jerry March), "Comprehensive Organic Transformations, 2nd Ed." (Richard C. Larock) and the like, or a method analogous thereto.

In Method M, compound (III-3) is produced by reacting compound (III-2) with a compound represented by the formula $R^{10}C(O)L^2$. The compound represented by the formula $R^{10}C(O)L^2$ is used in 0.1 to 10 equivalents, preferably 0.3 to 3 equivalents, relative to compound (III-2). A base may be used in 0.01 to 10 equivalents, preferably 0.03 to 5 equivalents, relative to compound (III-2). As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The compound represented by the formula $R^{10}C(O)L^2$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method N, compound (III-3) is produced by reacting compound (III-2) with carboxylic acid ($R^{10}CO_2H$) in the presence of a condensing agent. When Compound (III-2) is reacted with carboxylic acid ($R^{10}CO_2H$) in the presence of a condensing agent, carboxylic acid ($R^{10}CO_2H$) is used in 0.1 to 10 equivalents, preferably 0.3 to 3 equivalents, relative to compound (III-2). As the condensing agent, for example, 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N', N'-tetramethyluronium hexafluorophosphate and the like can be used. These condensing agents are used in 1 to 10 equivalents, preferably 1 to 5 equivalents, relative to compound (III-2). Where necessary, a suitable condensation promoter (e.g., 1-hydroxybenzotriazole, N-hydroxysuccinimide etc.) can be used. These condensation promoters are used in 0.1 to 10 equivalents, preferably 0.3 to 3 equivalents, relative to compound (III-2). This reaction may proceed more smoothly when a base is added. As the base, those similar to the base exemplified in Scheme 1 can be used. A base is used in 0.01 to 10 equivalents, preferably 0.03 to 5 equivalents, relative to compound (III-2). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Carboxylic acid ($R^{10}CO_2H$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 8]

Compound (III) wherein Yb is substituted by optionally substituted ureido, and optionally further substituted can also be produced, for example, by the method shown in Scheme 8. Compounds (III-2), (III-4) and (III-5) are encompassed in compound (III).

(Scheme 8)

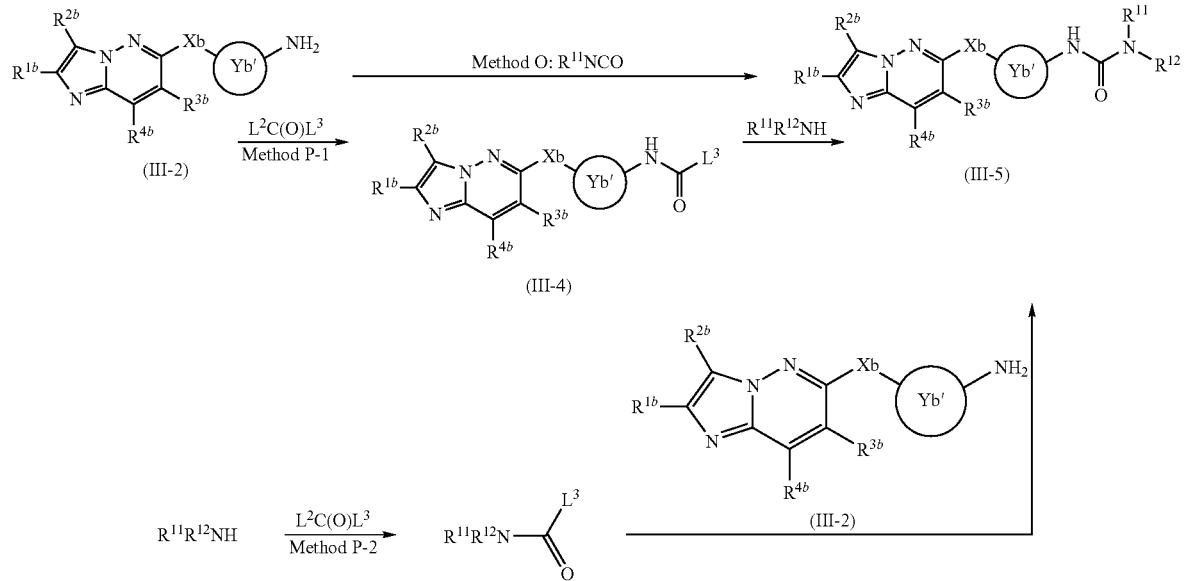

wherein each symbol is as defined above.

In Method O, compound (III-5) wherein $R^{12}$ is H is produced by reacting compound (III-2) with an isocyanate derivative ($R^{11}$NCO). The isocyanate derivative ($R^{11}$NCO) is used in 0.1 to 10 equivalents, preferably 0.3 to 3 equivalents, relative to compound (III-2). In addition, a base may be used in 0.01 to 10 equivalents, preferably 0.01 to 3 equivalents. As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. An isocyanate derivative ($R^{11}$NCO) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method P-1, compound (III-5) is produced by first reacting compound (III-2) with a compound represented by the formula $L^2C(O)L^3$ to give compound (III-4), and then reacting compound (III-4) with an amine derivative ($R^{11}R^{12}$NH). The compound represented by the formula $L^2C(O)L^3$ is used in 0.1 to 10 equivalents, preferably 0.3 to 3 equivalents, relative to compound (III-2). A base may be used in 0.1 to 10 equivalents, preferably 0.3 to 3 equivalents. As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The compound represented by the formula $L^2C(O)L^3$ may be commercially available, or can be produced by a method known per se. The obtained compound (III-4) can be used in the form of a reaction mixture or a crude product for the next reaction. It may be used for the next reaction after isolation and purification from the reaction mixture according to a conventional method. An amine derivative ($R^{11}R^{12}$NH) is used in 0.1 to 10 equivalents, preferably 0.3 to 3 equivalents, relative to compound (III-4). A base may be used in 0.1 to 10 equivalents, preferably 0.3 to 3 equivalents. As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The amine derivative ($R^{11}R^{12}$NH) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method P-2, compound (III-5) is produced by reacting amine derivative ($R^{11}R^{12}$NH) with a compound represented by the formula $L^2C(O)L^3$ successively with compound (III-2). The compound represented by the formula $L^2C(O)L^3$ is used in 0.1 to 10 equivalents, preferably 0.3 to 3 equivalents, relative to the amine derivative ($R^{11}R^{12}$NH). A base may be used in 0.1 to 10 equivalents, preferably 0.3 to 3 equivalents. As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The amine derivative ($R^{11}R^{12}$NH) and the compound represented by the formula $L^2C(O)L^3$ may be commercially available, or can be produced by a method known per se, for example, the methods described in "Advanced Organic Chemistry, 4th Ed." (Jerry March), "Comprehensive Organic Transformations, 2nd Ed." (Richard C. Larock) and the like or a method analogous thereto. The obtained compound represented by the formula $R^{11}R^{12}$NC(O)$L^3$ can be used in the form of a reaction mixture or a crude product for the next reaction. It may be used for the next reaction after isolation and purification from the reaction mixture according to a conventional method. The compound (III-2) is used in 0.1 to 10 equivalents, preferably 0.3 to 3 equivalents, relative to the compound represented by the formula $R^{11}R^{12}NC(O)L^3$. A base may be used in 0.1 to 10 equivalents, preferably 0.3 to 3 equivalents. As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C.

[Production Method 9]

Compound (III) wherein the substituent of the optionally substituted amino for Yb is sulfonyl can also be produced, for example, by the method shown in Scheme 9. Compound (III-6) is encompassed in compound (III).

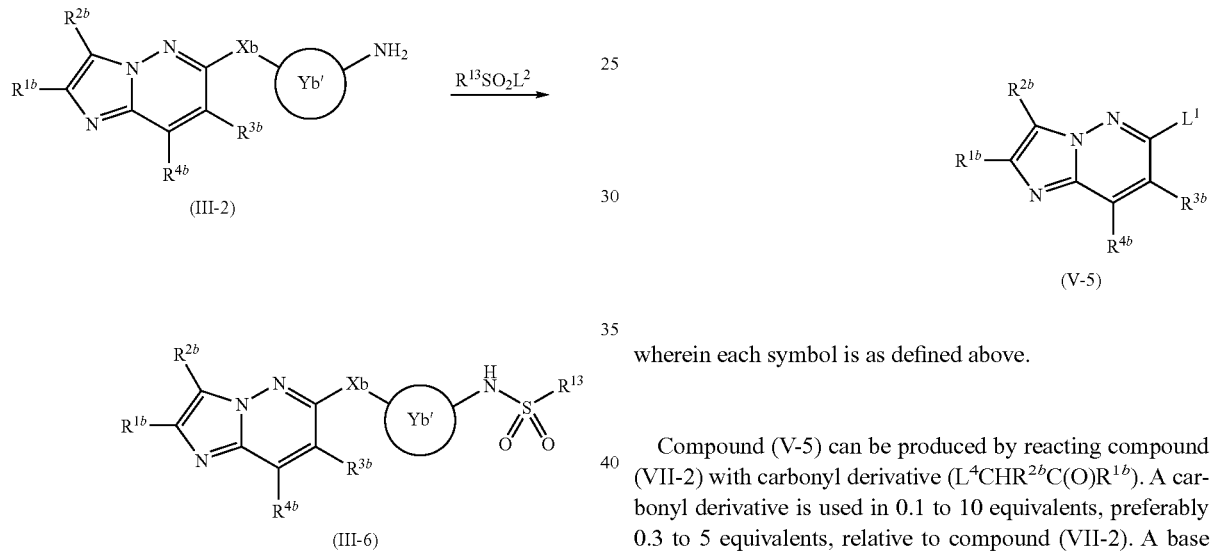

wherein each symbol is as defined above.

Compound (III-6) can be produced by reacting compound (III-2) with a reactive derivative of sulfonic acid ($R^{13}SO_2L^2$). The reactive derivative of sulfonic acid ($R^{13}SO_2L^2$) is used in 0.1 to 10 equivalents, preferably 0.3 to 3 equivalents, relative to compound (III-2). In the present method, the reaction is generally carried out in the presence of a base, which is not always essential. As the base, those similar to the base exemplified in Scheme 1 can be used. A base may be used in 0.01 to 10 equivalents, preferably 0.03 to 5 equivalents, relative to Compound (III-2). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The reactive derivative of sulfonic acid ($R^{13}SO_2L^2$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 10]

Compound (V-5) shown in Schemes 6 and 7 can be obtained, for example, by the method described in WO00/23450 or a method analogous thereto and the like.

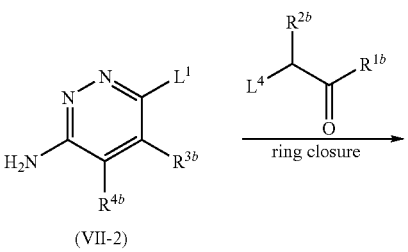

wherein each symbol is as defined above.

Compound (V-5) can be produced by reacting compound (VII-2) with carbonyl derivative ($L^4CHR^{2b}C(O)R^{1b}$). A carbonyl derivative is used in 0.1 to 10 equivalents, preferably 0.3 to 5 equivalents, relative to compound (VII-2). A base may be used in 0.1 to 10 equivalents, preferably 0.3 to 5 equivalents, relative to compound (VII-2). As the base, those similar to the bases exemplified in Scheme 5 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The carbonyl derivative ($L^4CHR^{2b}C(O)R^{1b}$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 11]

Compound (II) can also be produced by the method shown in Scheme 11. Compounds (IX-1), (IX-2) and (IX-3) are encompassed in compound (III), and compounds (II-7), (II-8), (II-9), (II-10), (II-11), (II-12) and (II-13) are encompassed in compound (II).

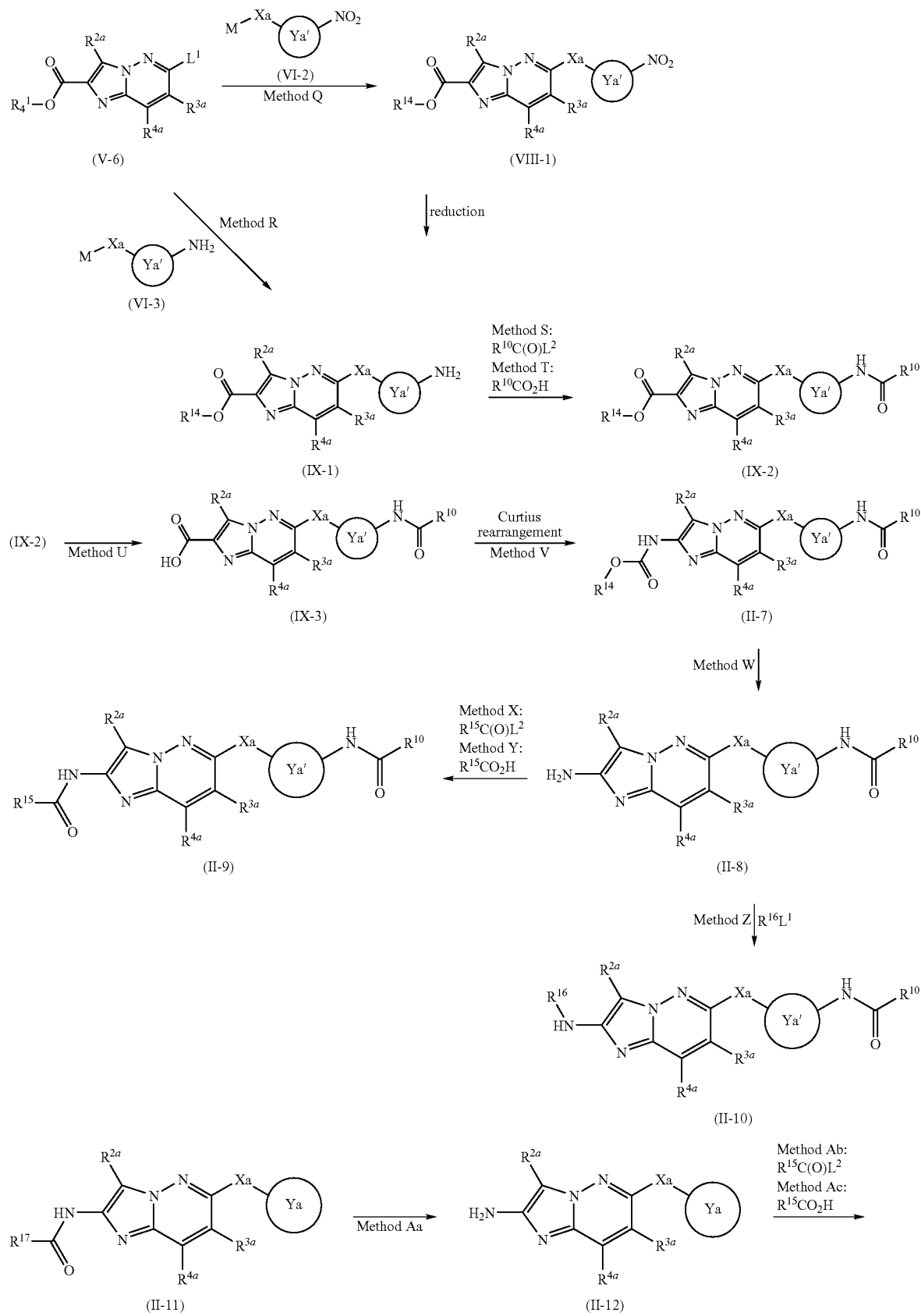

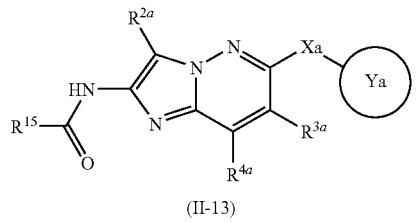

(II-13)

wherein $R^{16}$ is an optionally substituted aryl or optionally substituted heterocyclic group, $R^{17}$ is an optionally substituted alkyl or optionally substituted cycloalkyl, and other symbols are as defined above.

$R^{16}$ is a group to be, as $R^{16}NH$—, the "optionally substituted arylamino" or "optionally substituted heterocyclylamino" exemplified as a preferable substituent for the aforementioned $R^1$.

$R^{17}$ is a group to be, as $R^{17}CONH$—, the "optionally substituted alkylcarbonylamino" or "optionally substituted cycloalkylcarbonylamino" exemplified as a preferable substituent for the aforementioned $R^1$.

In Method Q, compound (IX-1) is produced by first reacting compound (V-6) with compound (VI-2) in the presence of a base to give compound (VIII-1), and then reducing the nitro group of compound (VIII-1). Compound (VI-2) is used in 0.1 to 10 equivalents, preferably 0.3 to 3 equivalents, relative to compound (V-6). As the base, those similar to the base exemplified in Scheme 1 can be used. A base is used in 1 to 30 equivalents, preferably 1 to 10 equivalents, relative to compound (V-6). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VI-2) may be commercially available, or can be produced by a method known per se. The obtained compound (VIII-1) can be used in the form of a reaction mixture or a crude product for the next reaction. It may be used for the next reaction after isolation and purification from the reaction mixture according to a conventional method. The nitro group can be reduced according to a method known per se, for example, the method described in the fourth series of experimental chemistry, vol. 20, 279-280 and the like, or a method analogous thereto.

In Method R, compound (IX-1) is produced by reacting compound (V-6) with compound (VI-3) in the presence of a base. Compound (VI-3) is used in 0.1 to 10 equivalents, preferably 0.3 to 3 equivalents, relative to compound (V-6). As the base, those similar to the base exemplified in Scheme 1 can be used. A base is used in 1 to 30 equivalents, preferably 1 to 10 equivalents, relative to compound (V-6). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VI-3) may be commercially available, or can be produced by a method known per se.

In Method S, compound (IX-2) is produced by reacting compound (IX-1) with a compound represented by the formula $R^{10}C(O)L^2$. The compound represented by the formula $R^{10}C(O)L^2$ is used in 0.1 to 10 equivalents, preferably 0.3 to 3 equivalents, relative to compound (IX-1). A base may be used in 0.01 to 10 equivalents, preferably 0.03 to 5 equivalents, relative to compound (IX-1). As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C. preferably −78° C. to 200° C. The compound represented by the formula $R^{10}C(O)L^2$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method T, compound (IX-2) is produced by reacting compound (IX-1) with carboxylic acid ($R^{10}CO_2H$) in the presence of a condensing agent. When compound (IX-1) is reacted with carboxylic acid ($R^{10}CO_2H$) in the presence of a condensing agent, carboxylic acid ($R^{10}CO_2H$) is used in 0.1 to 10 equivalents, preferably 0.3 to 3 equivalents, relative to compound (IX-1). As the condensing agent, for example, 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N', N'-tetramethyluronium hexafluorophosphate and the like can be used. These condensing agents are used in 1 to 10 equivalents, preferably 1 to 5 equivalents, relative to compound (IX-1). Where necessary, a suitable condensation promoter (e.g., 1-hydroxybenzotriazole, N-hydroxysuccinimide etc.) can be used. These condensation promoters are used in 0.1 to 10 equivalents, preferably 0.3 to 3 equivalents, relative to compound (IX-1). This reaction may proceed more smoothly when a base is added. As the base, those similar to the base exemplified in Scheme 1 can be used. A base is used in 0.01 to 10 equivalents, preferably 0.03 to 5 equivalents, relative to Compound (IX-1). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Carboxylic acid ($R^{10}CO_2H$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method U, compound (IX-3) is produced by treating compound (IX-2) with a base or acid. As the base, for example, sodium hydroxide, potassium hydroxide, cesium hydroxide, barium hydroxide and the like can be mentioned.

A base is used in 0.01 to 10 equivalents, preferably 0.03 to 5 equivalents, relative to compound (IX-2). As the acid, for example, hydrochloric acid, hydrobromic acid, hydroiodic acid, sulfuric acid, trifluoroacetic acid and the like can be used. An acid is used in 0.1 to 20 equivalents, preferably 0.3 to 10 equivalents, relative to compound (IX-2). This reaction is advantageously carried out using a solvent inert to the reaction. As the solvent, those similar to the solvents exemplified in Scheme 1 can be used.

In Method V, compound (II-7) is produced by reacting compound (IX-3) with diphenylphosphoryl azide in the presence of a base. Diphenylphosphoryl azide is used in 0.1 to 10 equivalents, preferably 0.3 to 5 equivalents, relative to compound (IX-3). As the base, those similar to the bases exemplified in Scheme 1 can be used. As the base for this method, for example, triethylamine, N-ethyldiisopropylamine, N-methylmorpholine, pyridine and the like are preferable. As the solvent for this reaction, those similar to the solvents exemplified in Scheme 1 can be used. For example, alcohols such as methanol, ethanol, 2-propanol, 2-methyl-2-propanol and the like are preferable. The reaction time is generally 1 min to 200 hr, preferably 10 min to 100 hr. The reaction temperature is generally $-100°$ C. to $250°$ C., preferably $-78°$ C. to $200°$ C.

In Method W, compound (II-8) is produced by treating compound (II-7) with a base or acid. As the base, for example, sodium hydroxide, potassium hydroxide, cesium hydroxide, barium hydroxide and the like can be mentioned. A base is used in 0.01 to 10 equivalents, preferably 0.03 to 5 equivalents, relative to compound (II-7). As the acid, for example, hydrochloric acid, hydrobromic acid, hydroiodic acid, sulfuric acid, trifluoroacetic acid and the like can be used. An acid is used in 0.1 to 20 equivalents, preferably 0.3 to 10 equivalents, relative to compound (II-7). This reaction is advantageously carried out using a solvent inert to the reaction. As the solvent, those similar to the solvents exemplified in Scheme 1 can be used.

In Method X, compound (II-9) is produced by reacting compound (II-8) with a compound represented by the formula $R^{15}C(O)L^2$. The compound represented by the formula $R^{15}C(O)L^2$ is used in 0.1 to 10 equivalents, preferably 0.3 to 3 equivalents, relative to compound (II-8). The base may be used in 0.01 to 10 equivalents, preferably 0.03 to 5 equivalents, relative to compound (II-8). As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally $-100°$ C. to $250°$ C., preferably $-78°$ C. to $200°$ C. The compound represented by the formula $R^{15}C(O)L^2$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method Y, compound (II-9) is produced by reacting compound (II-8) with carboxylic acid ($R^{15}CO_2H$) in the presence of a condensing agent. When compound (II-8) is reacted with carboxylic acid ($R^{15}CO_2H$) in the presence of a condensing agent, carboxylic acid ($R^{15}CO_2H$) is used in 0.1 to 10 equivalents, preferably 0.3 to 3 equivalents, relative to compound (II-8). As the condensing agent, for example, 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate and the like can be used. These condensing agents are used in 1 to 10 equivalents, preferably 1 to 5 equivalents, relative to compound (II-8). Where necessary, a suitable condensation promoter (e.g., 1-hydroxybenzotriazole, N-hydroxysuccinimide etc.) can be used. These condensation promoters are used in 0.1 to 10 equivalents, preferably 0.3 to 3 equivalents, relative to compound (II-8). This reaction may proceed more smoothly when a base is added. As the base, those similar to the base exemplified in Scheme 1 can be used. The base is used in 0.01 to 10 equivalents, preferably 0.03 to 5 equivalents, relative to compound (II-8). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally $-100°$ C. to $250°$ C., preferably $-78°$ C. to $200°$ C. Carboxylic acid ($R^{15}CO_2H$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method Z, compound (II-10) is produced by reacting compound (II-8) with a compound represented by the formula $R^{16}L^1$ in the presence of a base. The compound represented by the formula $R^{16}L^1$ is used in 0.1 to 10 equivalents, preferably 0.3 to 3 equivalents, relative to compound (II-8). As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally $-100°$ C. to $250°$ C., preferably $-78°$ C. to $200°$ C. The compound represented by the formula $R^{16}L^1$ may be commercially available, or can be produced according to a method known per se, for example, the method described in "Advanced Organic Chemistry, 4th Ed." (Jerry March), "Comprehensive Organic Transformations, 2nd Ed." (Richard C. Larock) and the like, or a method analogous thereto.

In Method Aa, compound (II-12) is produced by treating compound (II-11) with a base or acid. As the base, for example, sodium hydroxide, potassium hydroxide, cesium hydroxide, barium hydroxide and the like can be mentioned. A base is used in 0.01 to 10 equivalents, preferably 0.03 to 5 equivalents, relative to compound (II-11). As the acid, for example, hydrochloric acid, hydrobromic acid, hydroiodic acid, sulfuric acid, trifluoroacetic acid and the like can be used. An acid is used in 0.1 to 20 equivalents, preferably 0.3 to 10 equivalents, relative to compound (II-11). This reaction is advantageously carried out using a solvent inert to the reaction. As the solvent, those similar to the solvents exemplified in Scheme 1 can be used.

In Method Ab, compound (II-13) is produced by reacting compound (II-12) with a compound represented by the formula $R^{15}C(O)L^2$. The compound represented by the formula $R^{15}C(O)L^2$ is used in 0.1 to 10 equivalents, preferably 0.3 to 3 equivalents, relative to compound (II-12). A base may be used in 0.01 to 10 equivalents, preferably 0.03 to 5 equivalents, relative to compound (II-12). As the base, those similar to the base exemplified in Scheme 1 can be used. This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. a compound represented by the formula $R^{15}C(O)L^2$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

In Method Ac, (II-13) is produced by reacting compound (II-12) with carboxylic acid ($R^{15}CO_2H$) in the presence of a condensing agent. When compound (II-12) is reacted with carboxylic acid ($R^{15}CO_2H$) in the presence of a condensing agent, carboxylic acid ($R^{15}CO_2H$) is used in 0.1 to 10 equivalents, preferably 0.3 to 3 equivalents, relative to compound (II-12). As the condensing agent, for example, 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate and the like can be used. These condensing agents are used in 1 to 10 equivalents, preferably 1 to 5 equivalents, relative to compound (II-12). Where necessary, a suitable condensation promoter (e.g., 1-hydroxybenzotriazole, N-hydroxysuccinimide etc.) can be used. These condensation promoters are used in 0.1 to 10 equivalents, preferably 0.3 to 3 equivalents, relative to compound (II-12). This reaction may proceed more smoothly when a base is added. As the base, those similar to the base exemplified in Scheme 1 can be used. The base is used in 0.01 to 10 equivalents, preferably 0.03 to 5 equivalents, relative to compound (II-12). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Carboxylic acid ($R^{15}CO_2H$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 12]

Compound (II) wherein Ya is substituted by an optionally substituted aminocarbonyl group, and optionally further substituted can also be produced, for example, by the method shown in Scheme 12. Compounds (II-14), (II-15) and (II-16) are encompassed in compound (II).

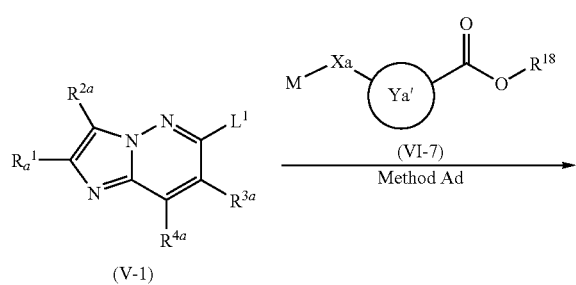

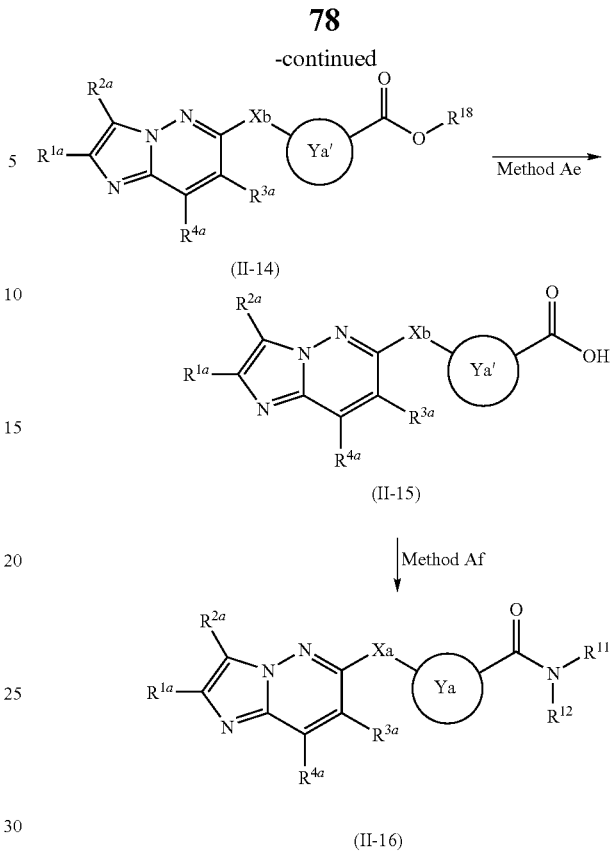

wherein $R^{18}$ is an alkyl group, and other symbols are as defined above.

As the alkyl for $R^{18}$, for example, methyl, ethyl, propyl, isopropyl, tert-butyl and the like can be mentioned.

In Method Ad, compound (II-14) can be produced by reacting compound (V-1) with compound (VI-7). Compound (VI-7) is used in 0.1 to 10 equivalents, preferably 0.3 to 3 equivalents, relative to compound (V-1). Where necessary, a base may be added. As the base, inorganic base or organic base and the like can be used. Specifically, for example, sodium carbonate, potassium carbonate, cesium carbonate, sodium bicarbonate, triethylamine, N-ethyldiisopropylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like can be used. These bases are used in 1 to 30 equivalents, preferably 1 to 10 equivalents, relative to compound (V-1). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VI-7) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto. The reaction may be carried out using a microwave synthesizer.

In Method Ae, compound (II-15) is produced by treating compound (II-14) with a base or acid. As the base, for example, sodium hydroxide, potassium hydroxide, cesium hydroxide, barium hydroxide and the like can be mentioned. A base is used in 0.01 to 10 equivalents, preferably 0.03 to 5 equivalents, relative to compound (II-14). As the acid, for example, hydrochloric acid, hydrobromic acid, hydroiodic acid, sulfuric acid, trifluoroacetic acid and the like can be used. An acid is used in 0.1 to 20 equivalents, preferably 0.3 to 10 equivalents, relative to compound (II-14). This reaction is advantageously carried out using a solvent inert to the reaction. As the solvent, those similar to the solvents exemplified in Scheme 1 can be used.

In Method Af, compound (II-16) is produced by reacting compound (II-15) with an amine derivative ($R^{11}R^{12}NH$) under a condensing agent. The amine derivative ($R^{11}R^{12}NH$) is used in 0.1 to 10 equivalents, preferably 0.3 to 3 equivalents, relative to compound (II-15). As the condensing agent, for example, 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate and the like can be used. These condensing agents are used in 1 to 10 equivalents, preferably 1 to 5 equivalents, relative to compound (II-15). Where necessary, a suitable condensation promoter (e.g., 1-hydroxybenzotriazole, N-hydroxysuccinimide etc.) can be used. These condensation promoters are used in 0.1 to 10 equivalents, preferably 0.3 to 3 equivalents, relative to compound (II-15). This reaction may proceed more smoothly when a base is added. As the base, those similar to the base exemplified in Scheme 1 can be used. These bases are used in 0.01 to 10 equivalents, preferably 0.03 to 5 equivalents, relative to compound (II-15). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The amine derivative ($R^{11}R^{12}NH$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 13]

Compound (II) wherein Ya is substituted by optionally substituted amide, and is optionally further substituted, can also be produced by the method shown in Production Method 2, as well as, for example, Scheme 13. Compounds (II-17) and (II-18) are encompassed in compound (II).

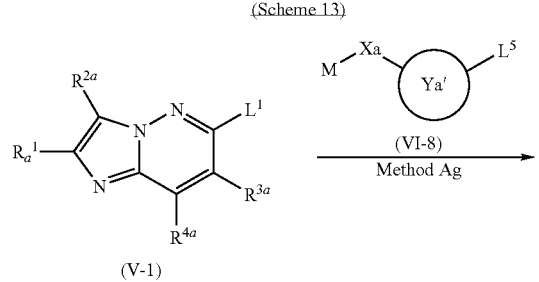

(Scheme 13)

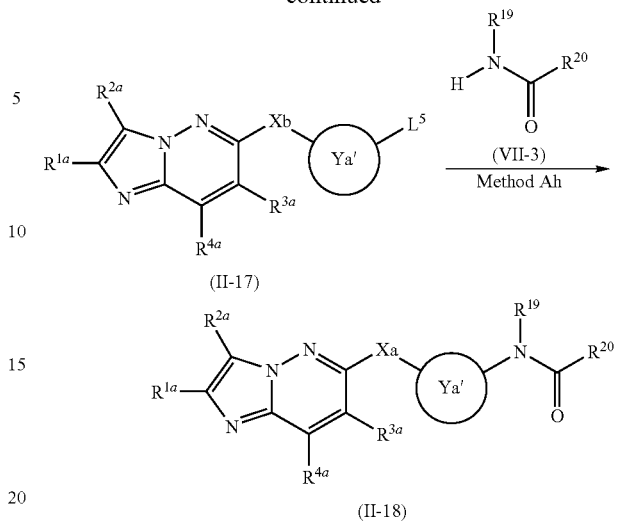

wherein $L^5$ is a leaving group, $R^{19}$ and $R^{20}$ are, as —$NR^{19}C(O)R^{20}$, each a group to be amino substituted by the "$C_{1-8}$ alkyl-carbonyl, $C_{2-8}$ alkenyl-carbonyl, $C_{2-8}$ alkynyl-carbonyl, $C_{3-8}$ cycloalkyl-carbonyl, $C_{3-6}$ cycloalkenyl-carbonyl, $C_{6-18}$ aryl-carbonyl, $C_{6-18}$ aryl-$C_{1-4}$ alkyl-carbonyl or heterocyclyl-carbonyl, each of which is optionally substituted" as the substituent on the aforementioned ring Y, and other symbols are as defined above.

As the leaving group for $L^5$, a halogen atom can be used.

In Method Ag, compound (II-17) can be produced by reacting compound (V-1) with compound (VI-8). Compound (VI-8) is used in 0.1 to 10 equivalents, preferably 0.3 to 3 equivalents, relative to compound (V-1). Where necessary, a base may be added. As the base, inorganic base or organic base and the like can be used. Specifically, for example, sodium carbonate, potassium carbonate, cesium carbonate, sodium bicarbonate, triethylamine, N-ethyldiisopropylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like can be mentioned. These bases are used in 1 to 30 equivalents, preferably 1 to 10 equivalents, relative to compound (V-1). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VI-8) may be commercially available, or can be produced according to a method known per se, for example, the method described in "Advanced Organic Chemistry, 4th Ed." (Jerry March), "Comprehensive Organic Transformations, 2nd Ed." (Richard C. Larock) and the like or a method analogous thereto. The reaction may be carried out using a microwave synthesizer.

In Method Ah, compound (II-18) can be produced by reacting compound (II-17) with compound (VII-3) under a copper catalyst. Compound (VII-3) is used in 0.1 to 10 equivalents, preferably 0.3 to 3 equivalents, relative to compound (II-17). As the copper catalyst, for example, copper iodide and copper (II) trifluoromethanesulfonate can be used. Where necessary, a base may be added. As the base, for example, sodium carbonate, potassium carbonate, cesium carbonate, sodium bicarbonate, sodium methoxide, sodium ethoxide, potassium tert-butoxide, sodium tert-butoxide, potassium phosphate tribasic, trans-1,2-cyclohexanediamine, 1,10-phenanthrolin, N,N-dimethylethylenediamine and the like can be used. These bases are used in 1 to 30 equivalents, preferably 1 to 10 equivalents, relative to compound (II-17). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. Compound (VII-3) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like or a method analogous thereto.

[Production Method 14]

Compound (II) wherein Ya is substituted by optionally substituted acylthioureido and optionally further substituted can also be produced, for example, by the method shown in Scheme 14. Compound (II-19) is encompassed in compound (II).

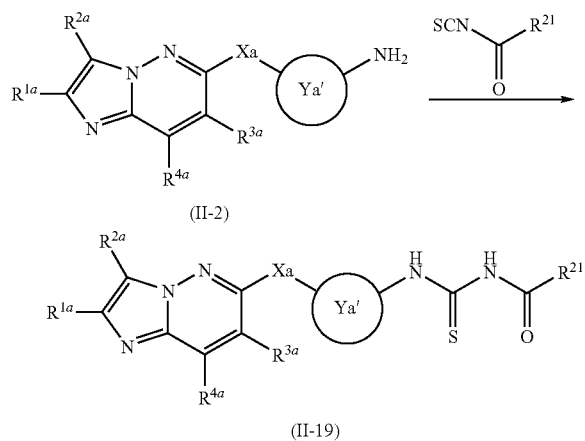

wherein $R^{21}$ is, as —C(S)NHC(O)$R^{21}$, a group that becomes the "amino substituted by optionally substituted aminothiocarbonyl" as the substituent on the aforementioned ring Y, and other symbols are as defined above.

Compound (II-19) can be produced by reacting compound (II-2) with an acylthiocyanate derivative ($R^{21}$C(O)NCS). The acylthiocyanate derivative ($R^{21}$C(O)NCS) is used in 0.1 to 10 equivalents, preferably 0.5 to 5 equivalents, relative to compound (II-19). This reaction is advantageously carried out using a solvent inert to the reaction. As the solvent, those similar to the solvents exemplified in Scheme 1 can be used. The reaction time is generally 1 min to 200 hr, preferably 10 min to 100 hr. The reaction temperature is generally −100° C. to 250° C., preferably −78° C. to 200° C. The acylthiocyanate derivative ($R^{21}$C(O)NCS) may be commercially available, or can be produced according to a method known per se.

It is also possible to produce a compound encompassed in the scope of the present invention by subjecting compounds (I)-(IV) (e.g., compound (II) and compound (III) obtained by the above-mentioned method) to introduction of substituents and functional group conversion by a means known per se.

For the substituent conversion, a known conventional method can be used. For example, conversion to carboxy by hydrolysis of ester, conversion to carbamoyl by amidation of carboxy, conversion to hydroxymethyl by reduction of carboxy, conversion to alcohol compound by reduction or alkylation of carbonyl, reductive amination of carbonyl, oximation of carbonyl, acylation, ureation, sulfonylation or alkylation of amino, substitution and amination of active halogen by amine, amination by reduction of nitro, alkylation of hydroxy, substitution and amination of hydroxy and the like can be mentioned. When a reactive substituent that causes non-objective reaction is present during the introduction of substituents and conversion of functional groups, a protecting group is introduced in advance as necessary into the reactive substituent by a means known per se, and the protecting group is removed by a means known per se after the objective reaction, whereby a compound within the scope of the present invention can also be produced.

Compounds (I)-(IV) (e.g., compound (II) and compound (III) obtained by the above-mentioned method) can be isolated and purified by a means known per se, such as phase transfer, concentration, solvent extraction, fractionation, liquid conversion, crystallization, recrystallization, chromatography and the like. When compounds (I)-(IV) are obtained as free compounds, they can be converted to desired salts by a method known per se or a modification thereof; conversely, when the compounds are obtained as salts, they can be converted to free forms or other desired salts by a method known per se or a modification thereof.

Compounds (I)-(IV) (hereinafter to be also referred to as compound (I) and the like) may be used as prodrugs. A prodrug of compound (I) and the like means a compound which is converted to compound (I) and the like by a reaction due to an enzyme, a gastric acid, etc. under the physiological condition in the living body, that is, a compound which is converted to compound (I) and the like by oxidation, reduction, hydrolysis, etc. due to an enzyme; a compound which is converted to compound (I) and the like by hydrolysis etc. due to gastric acid, and the like.

A prodrug of compound (I) and the like may be a compound obtained by subjecting an amino in compound (I) and the like to an acylation, alkylation or phosphorylation (e.g., a compound obtained by subjecting an amino in compound (I) and the like to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy in compound (I) and the like to an acylation, alkylation, phosphorylation or boration (e.g., a compound obtained by subjecting an hydroxy in compound (I) and the like to an acetylation, palmitoylation, propanoylation, pivaloylation, succinylation, fumarylation, alanylation or dimethylaminomethylcarbonylation); a compound obtained by subjecting a carboxy in compound (I) and the like to an esterification or amidation (e.g., a compound obtained by subjecting a carboxy in compound (I) and the like to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any one of these compounds can be produced from compound (I) and the like by a method known per se.

A prodrug of compound (I) and the like may also be one which is converted into compound (I) and the like under a physiological condition, such as those described in IYAKUHIN no KAIHATSU (Development of Pharmaceuticals), Vol.

7, Design of Molecules, p. 163-198, Published by HIROKAWA SHOTEN (1990).

When compound (I) and the like has isomers such as optical isomer, stereoisomer, positional isomer, rotational isomer and the like, any isomers and mixtures are encompassed in compound (I) and the like. For example, when compound (I) and the like has an optical isomer, an optical isomer separated from a racemate is also encompassed in compound (I) and the like. These isomers can be obtained as independent products by a synthesis means or a separation means (concentration, solvent extraction, column chromatography, recrystallization and the like) known per se.

The compound (I) and the like may be a crystal, and both a single crystal and crystal mixtures are encompassed in compound (I) and the like. Crystals can be produced by crystallization according to crystallization methods known per se.

The compound (I) and the like may be a co-crystal.

The compound (I) and the like may be a solvate (e.g., hydrate etc.) or a non-solvate, both of which are encompassed in compound (I) and the like.

A compound labeled with an isotope (e.g., $^{3}H$, $^{14}C$, $^{35}S$, $^{125}I$ etc.) is also encompassed in compound (I) and the like.

Compounds (I)-(IV) of the present invention, a salt thereof and a prodrug thereof (hereinafter sometimes to be abbreviated as the compound of the present invention) have, for example, phosphorylation-inhibitory activity against a kinase having such phosphorylating action. As used herein, kinase encompasses not only a substance having a phosphorylating action by itself as a whole, but also a substance a part of which has a phosphorylating action. The phosphorylating action possessed by kinases encompasses both a phosphorylating action on its own and that on other substances.

Examples of kinase include vascular endothelial growth factor receptor (VEGFR), platelet-derived growth factor receptor (PDGFR), Raf and the like. Examples of vascular endothelial growth factor receptor (VEGFR) include vascular endothelial growth factor receptor 1 (VEGFR1, Flt-1), vascular endothelial growth factor receptor 2 (VEGFR2, KDR, Flk-1), vascular endothelial growth factor receptor 3 (VEGFR3, Flt-4) and the like. Of these, vascular endothelial growth factor receptor 2 (VEGFR2) is preferable. Examples of platelet-derived growth factor receptor (PDGFR) include platelet-derived growth factor receptor α (PDGFRα), platelet-derived growth factor receptor β (PDGFRβ) and the like. Examples of Raf include A-Raf, B-Raf, C-Raf and the like. Particularly, as kinase, vascular endothelial growth factor receptor 2 (VEGFR2), platelet-derived growth factor receptor (PDGFR) and Raf are preferable.

Besides these, as kinase, tyrosine Kinase with Ig and EGF homology domains 2 (TIE2), fibroblast growth factor receptor 1 (FGFR1), fibroblast growth factor receptor 2 (FGFR2), fibroblast growth factor receptor 3 (FGFR3), fibroblast growth factor receptor 4 (FGFR4), stem cell factor receptor (c-Kit), Aurora A, Aurora B, CDK, MEK1, MEK2, Akt, ERK, MAPK, Src, MET, epithelial cell growth factor receptor (EGFR), human epithelial growth factor receptor 2 (HER2), human epithelial growth factor receptor 4 (HER4), Abl, Fgr, Fms and the like can also be used.

For example, the vascular endothelial growth factor receptor 2 inhibitory activity of the compound of the present invention can be determined according to Test Example 1, the vascular endothelial cell growth inhibitory activity can be determined according to Test Example 2, the antitumor activity can be determined according to Test Example 3, the platelet-derived growth factor receptor α inhibitory activity can be determined according to Test Example 4, the platelet-derived growth factor receptor β inhibitory activity can be determined according to Test Example 5, and the B-Raf inhibitory activity can be determined according to Test Example 6.

The compound of the present invention particularly shows potent inhibitory activity for vascular endothelial growth factor receptor (VEGFR), and specifically high selectivity for vascular endothelial growth factor receptor 2 (VEGFR2, KDR, Flk-1) and potent kinase inhibitory activity for VEGFR1, PDGFR, and Raf. In addition, since the compound of the present invention is also superior in the efficacy, pharmacokinetics (absorption, distribution, metabolism, excretion etc.), solubility (water-solubility etc.), interaction with other pharmaceutical products, safety (acute toxicity, chronic toxicity, genetic toxicity, reproductive toxicity, cardiotoxicity, carcinogenicity etc.) and stability (chemical stability, stability to enzyme etc.), it is useful as a pharmaceutical agent.

Accordingly, the compound of the present invention is useful as a kinase inhibitor, preferably a vascular endothelial growth factor receptor (VEGFR) inhibitor, a platelet-derived growth factor receptor (PDGFR) inhibitor, a Raf inhibitor, more preferably a vascular endothelial growth factor receptor 2 (VEGFR2, KDR, Flk-1) inhibitor for a mammal (e.g., mouse, rat, hamster, rabbit, cat, dog, bovine, sheep, monkey, human etc.). In addition, the compound of the present invention is useful as an angiogenesis inhibitor or a vascular endothelial cell growth inhibitor. The compound of the present invention is used as a pharmaceutical agent such as an agent for the prophylaxis or treatment of diseases possibly affected by a vascular endothelial growth factor, for example, cancer [e.g., colorectal cancer (e.g., familial colorectal cancer, hereditary nonpolyposis colorectal cancer, gastrointestinal stromal tumor, etc.), lung cancer (e.g., non-small cell lung cancer, small cell lung cancer, malignant mesothelioma, etc.), mesothelioma, pancreatic cancer (e.g., pancreatic duct cancer, etc.), gastric cancer (e.g., papillary adenocarcinoma, mucinous adenocarcinoma, adenosquamous cancer, etc.), breast cancer (e.g., invasive ductal carcinoma, ductal cancer in situ, inflammatory breast cancer, etc.), ovarian cancer (e.g., ovarian epithelial cancer, extragonadal germ cell tumor, ovarian germ cell tumor, ovarian low malignant potential tumor, etc.), prostate cancer (e.g., hormone-dependent prostate cancer, non-hormone dependent prostate cancer, etc.), liver cancer (e.g., primary liver cancer, extrahepatic bile duct cancer, etc.), thyroid cancer (e.g., medullary thyroid cancer, etc.), kidney cancer (e.g., renal cell carcinoma, renal pelvis and ureter transitional cell cancer, etc.), uterine cancer, brain tumor (e.g., pineal astrocytoma, pilocytic astrocytoma, diffuse astrocytoma, anaplastic astrocytoma, etc.), melanoma, sarcoma, bladder cancer, blood cancer including multiple myeloma etc.], diabetic retinopathy, rheumatoid arthritis, psoriasis, atherosclerosis, Kaposi's sarcoma, COPD, pain, asthma, endometriosis, nephritis, inflammation such as osteoarthritis and the like and hypertension, a cancer growth inhibitor, a cancer metastasis suppressor, an apoptosis promoter and the like. Of these, it is effective, for example, for colorectal cancer, lung cancer, pancreatic cancer, gastric cancer, breast cancer, ovary cancer, prostate cancer, liver cancer, thyroid cancer, kidney cancer, cerebral tumor, melanoma, bladder cancer and blood cancer. Particularly, the compound of the present invention is effective for patients with lung cancer, colorectal cancer, ovary cancer, prostate cancer or kidney cancer.

The compound of the present invention can be administered orally or parenterally as it is or in a mixture with a pharmacologically acceptable carrier.

The dosage form of the compound of the present invention for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method to produce the compound of the present invention in the above-mentioned dosage form, a known production method generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pertinent field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, microcrystalline cellulose, powdered glycyrrhiza, mannitol, sodium hydrogencarbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a coloring agent, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride and the like) and the like can be mentioned, and they can be used in combination with suitable dissolution aids, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with dissolution aids such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like can be mentioned. A prepared injection is generally filled in an ampoule.

While the content of the compound of the present invention in the pharmaceutical agent of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the pharmaceutical agent of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, pharmaceutical agents inhibiting the action of cell growth factors or cell growth factor receptors and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, epristeride, and the like), aderenal cortex hormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, capecitabine, and the like), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (BRM)" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, and the like.

Example of the "cell growth factor" in the "pharmaceutical agents inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα, and the like], (2) insulin or substances possessing substantially the same activity as insulin [e.g., insulin, IGF (insulin-like growth factor)-1, IGF-2, and the like], (3) FGF (fibroblast growth factor) or substances possessing substantially the same activity as FGF [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factorβ), HGF (hepatocyte growth factor), VEGF (vascular endothelial growth factor), heregulin, angiopoietin, and the like].

Examples of the "cell growth factor receptors" include any receptors capable of binding to the aforementioned growth factors, including EGF receptor, heregulin receptor (HER3, etc.), insulin receptor, IGF receptor-1, IGF receptor-2, FGF receptor-1 or FGF receptor-2, VEGF receptor, angiopoietin receptor (Tie2 etc.), PDGF receptor, and the like.

As the "pharmaceutical agents inhibiting the action of cell growth factors or cell growth factor receptors", EGF inhibitor, TGFα inhibitor, haregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK(MEK1/2) inhibitor, MET inhibitor, CDK inhibitor, Akt inhibitor, ERK inhibitor and the like are used. More specifically, anti-VEGF antibody (Bevacizumab etc.), anti-HER2 antibody (Trastuzumab, Pertuzumab etc.), anti-EGFR antibody (Cetuximab, Panitumumab, Matuzumab, Nimotuzumab etc.), anti-VEGFR antibody, Imatinib, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R),3-dihydroxypropyl]-3,4-difluoro-2-(2-fluoro-4-iodophenylamino)benzamide (PD-0325901) and the like are used.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), other angiogenesis inhibitors (e.g., humagillin, shark extract, COX-2 inhibitor, and the like), α-blockers (e.g., tamsulosin hydrochloride, and the like), bisphosphonic acids (pamidronate, zoledronate, and the like), thalidomide, 5 azacytidine, decitabine, bortezomib, antitumor antibody such as anti-CD20 antibody and the like, toxin labeled antibody and the like can also be used.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer,
(4) a sustained treatment effect can be designed,
(5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the administration amount clinically set, and can be appropriately selected depending on the administration subject, administration route, disease, combination and the like.

Examples of the administration mode of the combined use of the compound of the present invention and the concomitant drug include the following methods:
(1) The compound of the present invention and the concomitant drug are simultaneously produced to give a single preparation, which is then administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route at different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (for example, the compound of the present invention and the concomitant drug are administered in this order, or in the reverse order). The dose of the concomitant drug is determined in accordance with its clinical dose. And the ratio of the compound of the present invention and the concomitant drug is determined depending on the subject, administration route, disease, symptom, combination, and the like. For example, when the subject is human, the concomitant drug is used in 0.01 to 100 (w/w), relative to the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous, and the like). An injection can be administered directly to the lesion by intravenous, intramuscular, subcutaneous or intra-tissue administration.

As a pharmacologically acceptable carrier which may be used for preparing a preparation of the combination agent of the present invention, those similar to the aforementioned pharmacologically acceptable carriers, that can be used for the production of the pharmaceutical agent of the present invention, can be mentioned. Where necessary, the aforementioned additives that can be used for the production of the pharmaceutical agent of the present invention, such as preservatives, antioxidants, coloring agents, sweetening agents, adsorbents, wetting agents and the like can also be used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the preparation.

The content of additives in the combination agent of the present invention varies depending on the dosage form, and is usually from about 1 to 99.99% by weight, preferably from about 10 to 90% by weight, based on the preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH adjusting agent (e.g., hydrochloric acid, sodium hydroxide and the like), a preservative (e.g., ethyl p-oxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and the like and prepared into an oily injection, whereby an injection is afforded.

In addition, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxypropylcellulose and the like), a lubricant (e.g., talc, magnesium stearate, polyethylene glycol 6000 and the like) and the like may be added to the compound of the present invention or the concomitant drug according to a method known per se, and the mixture can be compression-molded, then if desirable, the molded product can be coated by a method known per se for the purpose of masking of taste, enteric property or durability, to give a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid-acrylic acid copolymer, manufactured by Rohm, Del.), pigment (e.g., iron oxide red, titanium dioxide, etc.) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. As the above-mentioned oily substrate, for example, glycerides of higher fatty acids [e.g., cacao butter, Witepsols (manufactured by Dynamit Nobel, Germany), etc.], glycerides of medium chain fatty acid [e.g., Miglyols (manufactured by Dynamit Nobel, Germany), etc.], or vegetable oils (e.g., sesame oil, soybean oil, cotton seed oil and the like), and the like are mentioned. Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned. The sustained release microcapsule can be produced by a method known per se, such as the method shown in the following [2].

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be specifically described below.

[1] Injection and Preparation Thereof.

An injection prepared by dissolving the compound of the present invention or the concomitant drug in water is preferable. This injection may contain a benzoate and/or salicylate.

The injection is obtained by dissolving the compound of the present invention or the concomitant drug, and if desirable, a benzoate and/or salicylate, in water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic bases such as tromethamol and the like, etc. are mentioned.

The concentration of the compound of the present invention or the concomitant drug in an injection is from 0.5 to 50 w/v %, preferably from about 3 to 20 w/v %. The concentration of a benzoate and/or salicylate is from 0.5 to 50 w/v %, preferably from about 3 to 20 w/v %.

The injection of the present invention can be appropriately mixed with an additive conventionally used for injection, such as a stabilizer (e.g., ascorbic acid, sodium pyrosulfite and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride and the like), a dispersing agent (e.g., hydroxypropylmethylcellulose, dextrin), a pH adjusting agent (e.g., hydrochloric acid, sodium hydroxide and the like), a preservative (e.g., ethyl p-oxybenzoate, benzoic acid and the like), a dissolving agent (e.g., conc. glycerin, meglumine and the like), a dissolution aid (e.g., propylene glycol, sucrose and the like), a soothing agent (e.g., glucose, benzyl alcohol and the like), and the like. These additives are generally blended in a proportion usually used for injections.

The pH of an injection is advantageously adjusted to pH 2 to 12, preferably pH 2.5 to 8.0, by addition of a pH adjusting agent.

An injection is obtained by dissolving, in water, the compound of the present invention or the concomitant drug and, if desirable, a benzoate and/or a salicylate, and if necessary, the above-mentioned additives. They may be dissolved in any order, and can be appropriately dissolved in the same manner as in a conventional production method of an injection.

An aqueous solution for injection may be advantageously heated, alternatively, for example, subjected to filter sterilization, high pressure heat sterilization and the like to give an injection, in the same manner as for usual injections.

An aqueous solution for injection may be advantageously subjected to high pressure heat sterilization at 100° C. to 121° C. for 5 to 30 min.

Furthermore, a preparation conferred with antibacterial property of a solution may also be produced to permit multiple administration in portions.

[2] Sustained Release Preparation or Immediate-Release Preparation, and Preparation Thereof A sustained release preparation is preferable, which is obtained, if desirable, by coating a nucleus containing the compound of the present invention or the concomitant drug with a film agent such as a water-insoluble substance, a swellable polymer and the like. For example, a sustained release preparation for oral administration of a one-day-one-time administration type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudoragit (Rohm Pharma) such as Eudoragit RS-100, RL-100, RS-30D, RL-30D, RL-PO, RS-PO (ethyl acrylate/methyl methacrylate/trimethyl methacryloyl chloride/ammoniumethyl copolymer), Eudoragit NE-30D (methyl methacrylate/ethyl acrylate copolymer), and the like, hydrogenated oils such as hydrogenated castor oil (e.g., Lubri wax (Freund Corporation) and the like), waxes such as carnauba wax, glycerin fatty acid ester, paraffin and the like, polyglycerin fatty acid esters, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid copolymers such as Carbomer 934P, 940, 941, 974P, 980, 1342 and the like, polycarbophil, calcium polycarbophil (all of which are manufactured by BF Goodrich), Hiviswako 103, 104, 105, 304 (all are manufactured by Wako Pure Chemical Industries, Ltd.), and the like, can be used.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drug as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to about 2000 μm, further preferably, from about 500 to about 1400 μm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 μm to about 1500 μm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl or carboxyalkyl are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). As the immediate-release preparation, oral agents and parenteral agents such as an injection and the like are used, and oral agents are preferable.

The immediate-release preparation, usually, may contain, in addition to an active component drug, also carriers, additives and excipients conventionally used in the production field (hereinafter, sometimes abbreviated as excipient). The excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 9.7 w/w %, based on the total amount of the immediate-release preparation.

The content of a drug in the immediate-release preparation can be appropriately selected in the range from about 0.5 to about 95%, preferably from about 1 to about 60% based on the total amount of the immediate-release preparation.

When the immediate-release preparation is an oral solid preparation, it usually contains, in addition to the above-mentioned components, also an integrating agent. As this integrating agent, for example, carboxymethylcellulose calcium (ECG-505, manufactured by Gotoku Yakuhin), croscarmelose sodium (for example, Actisol, manufactured by Asahi Kasei Corporation), crospovidone (for example, Kollidon CL, manufactured by BASF), low substituted hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the quick releasing agent.

When the immediate-release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (for example, Aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a coloring agent (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof.

Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased in vivo use efficiency, $\beta$-cyclodextrin or $\beta$-cyclodextrin derivatives (e.g., hydroxypropyl-$\beta$-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbophil, ascorbic acid, palmitates and the like are listed, and hydroxypropylmethylcellulose, polyacrylic acid, alginates, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include gelatins, dextrins, animal proteins or vegetable proteins such as soybean, wheat and psyllium seed protein and the like; rubber substances such as gum Arabic, guar gum, agar, xanthane gum and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, coloring agent, pH controlling agent, flavoring agent, sweetening agent, food taste masking agent and the like. As the suitable coloring agent, there are listed red, black and yellow iron oxides, and FD & C dyes such as FD & C Blue 2, FD &

C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of $\beta$-cyclodextrin or $\beta$-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to 5% by weight. The above-mentioned preparation may further contain additives such as a coloring agent, sweetening agent, preservative and the like, if necessary.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention and the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., $\beta$-lactam type such as pansporin and the like, macrolide type such as clarithromycin and the like etc.) for the complication with various infectious diseases, (ii) administration of total parenteral nutrition, amino acid preparation or general vitamin preparation for the improvement of malnutrition, (iii) administration of morphine for pain mitigation, (iv) administration of a pharmaceutical agent for improving side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administrated 1-time about 30 min to 24 hrs before the surgery, etc., or in 1 to 3 cycles about 3 months to 6 months before the surgery, etc. In this way, the surgery, etc. can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administrated repeatedly per a few weeks to 3 months, about 30 min to 24 hrs after the surgery, and the like. In this way, it enhances the effect of the surgery, etc. by administering the compound of the present invention or the combination agent of the present invention after the surgery, and the like.

EXAMPLES

The present invention is specifically explained in the following by way of Reference Examples, Examples, Formulation Examples, Experimental Examples and Test Examples, which are not to be construed as limitative.

The LC/MS analysis in the Examples was performed under the following conditions.

measurement tool: Waters Corporation ZQ column: manufactured by Shiseido Co., Ltd. CAPCELL PAK C18 UG120 S-33 µm, 35×1.5 mm solvent: SOLUTION A; 5 mM aqueous ammonium acetate/acetonitrile=98/2

SOLUTION B; 100 mM aqueous ammonium acetate/acetonitrile=5/95 gradient cycle: 0.00 min (SOLUTION A/SOLUTION B=100/0), 2.00 min (SOLUTION A/SOLUTION B=0/100), 3.00 min (SOLUTION A/SOLUTION B=0/100), 3.01 min (SOLUTION A/SOLUTION B=100/0), 3.80 min (SOLUTION A/SOLUTION B=100/0)

flow rate: 0.5 mL/min, Column temperature was room temperature with no temperature control.

ionization method: Electron Spray Ionization, ESI positive and negative ion peaks were detected.

The percentage of the peak area detected at UV: 220 nm of the resultant product peak was taken as the purity of the compound.

In the Examples, preparative HPLC was performed as in the following.

Preparative HPLC tools: Gilson, Inc. High-Throughput purification system column: YMC Combiprep Hydrosphere C18 S-55 µm, 12 nM. 50×20 mm solvent: SOLUTION A; water SOLUTION B; acetonitrile gradient cycle: 0.00 min (SOLUTION A/SOLUTION B=98/2), 1.10 min (SOLUTION A/SOLUTION B=98/2), 5.00 min (SOLUTION A/SOLUTION B=0/100), 6.40 min (SOLUTION A/SOLUTION B=0/100), 6.50 min (SOLUTION A/SOLUTION B=2/98), 6.52 min (SOLUTION A/SOLUTION B=2/98)

flow rate: 25 mL/min, detection method: UV 220 nm

Unless otherwise specified, the elution by column chromatography was performed under observation by TLC (thin layer chromatography) in Reference Examples and Examples. For TLC observation, 60F254 manufactured by Merck, or NH TLC plate manufactured by Fuji Silysia Chemical Ltd. was used as a TLC plate, and the solvent used as an elution solvent in column chromatography was used as a developing solvent. For detection, moreover, a UV detector was employed. As the silica gel for column chromatography, silica gel 60 (70-230 mesh) manufactured by Merck, NH silica gel (100-200 mesh) manufactured by Fuji Silysia Chemical Ltd. and the like were used. The room temperature generally means from about 10° C. to 35° C. For drying the extract, anhydrous sodium sulfate or anhydrous magnesium sulfate was used.

In Formulation Examples, the Japanese Pharmacopoeia 14th Edition or Japanese Pharmaceutical Excipients 2003 compatible products are used as the preparation additives (e.g., lactose, cornstarch, magnesium stearate, microcrystalline cellulose). Abbreviations in the Examples and Reference Examples mean the following.

LC: liquid chromatography
MS: mass spectrometry
ESI: electrospray ionization
FAB: fast atomic beam
M: molecular ion peak
NMR: nuclear magnetic resonance spectra
Hz: hertz
J: coupling constant
m: multiplet
q: quartet
t: triplet
d: doublet
s: singlet
br: broad
dt: double triplet
brs: broad singlet
wt %: weight percent
DMSO: dimethyl sulfoxide Reference Example 1

Production of tert-butyl (chloroacetyl)carbamate

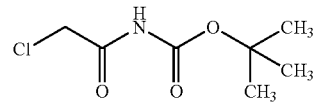

To a suspension of 2-chloroacetamide (25 g, 267 mmol) in 1,2-dichloroethane (125 mL) was added dropwise oxalyl chloride (28 mL, 321 mmol) at 0° C. After heating under reflux for 3 hr, the mixture was cooled to 0° C., tert-butyl alcohol/1,2-dichloroethane (75 mL, 1/1) was added to the mixture, and the mixture was stirred for 20 min. Saturated aqueous sodium hydrogencarbonate solution was added to the reaction mixture, and the mixture was extracted with 1,2-dichloroethane. After washing with saturated aqueous sodium hydrogencarbonate solution and water, the extract was dried over anhydrous magnesium sulfate and filtrated.

The solvent was evaporated under reduced pressure, and the residue was recrystallized from cyclohexane to give the title compound (25.6 g, 49%) as white crystals.

$^1$H-NMR (CDCl$_3$, 300 MHz) δ 1.58 (9H, s), 4.46 (2H, s), 7.59 (1H, br).

Reference Example 2

Production of tert-butyl (6-iodoimidazo[1,2-b]pyridazin-2-yl)carbamate

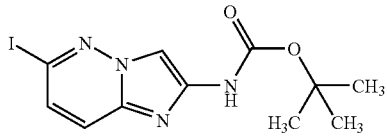

To a solution of 3-amino-6-iodopyridazine (10.0 g, 45.2 mmol) in N,N-dimethylacetamide (100 mL) were added tert-butyl (chloroacetyl)carbamate (14.0 g, 72.4 mmol) and disodium hydrogenphosphate (16.1 g, 113 mmol), and the mixture was stirred at 120° C. for 3 hr. After cooling the mixture to room temperature, water (400 mL) was added to the mixture, and the precipitated crystals were filtrated, and washed with acetonitrile and petroleum ether to give the title compound (10.2 g, 63%) as a green powder.

$^1$H-NMR (DMSO-d$_6$, 300 MHz) δ 1.49 (9H, s), 7.45 (1H, d, J=9.5 Hz), 7.69 (1H, d, J=9.5 Hz), 8.01 (1H, brs), 10.20 (1H, brs).

Reference Example 3

Production of ethyl (6-iodoimidazo[1,2-b]pyridazin-2-yl)carbamate

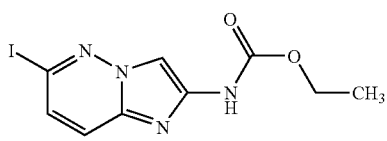

To a solution of 3-amino-6-iodopyridazine (27.0 g, 122 mmol) in N,N-dimethylacetamide (270 mL) were added ethyl (chloroacetyl)carbamate (32.4 g, 195 mmol) and disodium hydrogenphosphate (43.4 g, 305 mmol), and the mixture was stirred at 110° C. for 3 hr. After cooling the mixture to room temperature, water (810 mL) was added, and the precipitated crystals were filtrated, and washed with acetonitrile and ether to give the title compound (33.0 g, 81%) as a dark brown powder.

$^1$H-NMR (DMSO-d$_6$, 300 MHz) δ 1.26 (3H, t, J=7.1 Hz), 4.17 (2H, q, J=7.1 Hz), 7.47 (1H, d, J=9.2 Hz), 7.70 (1H, d, J=9.2 Hz), 8.06 (1H, s), 10.51 (1H, brs).

Reference Example 4-1

Production of 6-iodoimidazo[1,2-b]pyridazin-2-amine

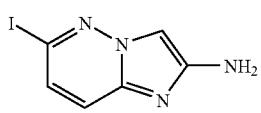

To a suspension of tert-butyl (6-iodoimidazo[1,2-b]pyridazin-2-yl)carbamate (10.2 g, 28.3 mmol) in ethyl acetate (50 mL) was added 4N hydrochloric acid/ethyl acetate (75 mL), and the mixture was stirred at room temperature for 4 hr. Diethyl ether (200 mL) was added to the reaction mixture, and the precipitate was filtrated. After washing with saturated aqueous sodium hydrogencarbonate solution, the filtrate was washed with water, acetonitrile and diethyl ether to give the title compound (4.9 g, 67%) as a green powder.

$^1$H-NMR (DMSO-d$_6$, 300 MHz) δ 5.61 (2H, s), 7.22 (1H, d, J=8.7 Hz), 7.36 (1H, s), 7.39 (1H, d, J=8.7 Hz).

Reference Example 4-2

Production of 6-iodoimidazo[1,2-b]pyridazin-2-amine

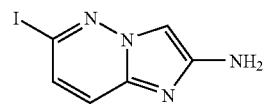

To barium hydroxide octahydrate (14.5 g, 46.1 mmol) was added water (240 mL), and the mixture was stirred at 80° C. for 15 min. A solution of ethyl (6-iodoimidazo[1,2-b]pyridazin-2-yl)carbamate (10.2 g, 30.7 mmol) in N-methylpyrrolidone (80 mL) was added to the mixture, and the mixture was stirred at 120° C. for 8 hr. After cooling the mixture to room temperature, water (480 mL) was added to the mixture, and the mixture was stirred for 1 hr. The mixture was extracted twice with ethyl acetate/tetrahydrofuran, washed with saturated brine, dried over anhydrous magnesium sulfate, and filtrated. The solvent was evaporated under reduced pressure, diisopropyl ether was added to the residue, and the precipitated crystals were collected by filtration to give the title compound (6.1 g, 76%) as a brown powder.

$^1$H-NMR (DMSO-d$_6$, 300 MHz) δ 5.61 (2H, s), 7.22 (1H, d, J=8.7 Hz), 7.36 (1H, s), 7.39 (1H, d, J=8.7 Hz).

Reference Example 5

Production of N-(6-iodoimidazo[1,2-b]pyridazin-2-yl)cyclopropanecarboxamide

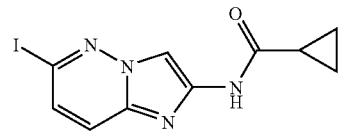

To a solution (10 mL) of 6-iodoimidazo[1,2-b]pyridazin-2-amine (1.0 g, 3.85 mmol) in N,N-dimethylacetamide was added cyclopropylcarbonyl chloride (0.38 mL, 4.23 mmol), and the mixture was stirred at room temperature for 4 hr. Water was added to the reaction mixture, and the mixture was extracted with ethyl acetate/tetrahydrofuran. The extract was washed with saturated brine, dried over anhydrous magnesium sulfate, and filtrated. The solvent was evaporated under reduced pressure, and the residue was washed with hexane/ethyl acetate (4/1) to give the title compound (1.01 g, 80%) as a dark brown powder.

$^1$H-NMR (DMSO-d$_6$, 300 MHz) δ 0.82-0.86 (4H, m), 1.90-2.00 (1H, m), 7.49 (1H, d, J=9.3 Hz), 7.73 (1H, d, J=9.3 Hz), 8.23 (1H, s), 11.20 (1H, s).

Reference Example 7

Production of 3-methyl-1-(2,2,2-trifluoroethyl)-1H-pyrazole-5-carboxylic acid

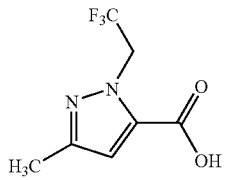

To a suspension of sodium hydride (1.62 g, 40.4 mmol) in N,N-dimethylformamide (250 mL) was added dropwise a solution of ethyl 3-methyl-1H-pyrazole-5-carboxylate (5660 mg, 36.8 mmol) in N,N-dimethylformamide (50 mL) over 10 min under ice-cooling. After the completion of the dropwise addition, the reaction mixture was stirred at 0° C. for 10 min and at room temperature for 40 min. To the mixture was added 2,2,2-trifluoroethyl trifluoromethanesulfonate (9.87 g, 40.4 mmol), and the mixture was stirred at room temperature for 3 hr. Under ice-cooling, 1N hydrochloric acid (36 mL) was added to the mixture, and the solvent was evaporated under reduced pressure. Ethyl acetate/tetrahydrofuran and saturated aqueous sodium hydrogencarbonate solution were added to the residue, and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was purified by silica gel column chromatography (ethyl acetate/hexane=5/95→60/40), and recrystallized from ethyl acetate/hexane to give ethyl 3-methyl-1-(2,2,2-trifluoroethyl)-1H-pyrazole-5-carboxylate (1.98 g, 23%) as white crystals.

To a solution of ethyl 3-methyl-1-(2,2,2-trifluoroethyl)-1H-pyrazole-5-carboxylate (1.74 g, 7.36 mmol) in tetrahydrofuran (5.0 mL) was added 8N sodium hydroxide (4.6 mL), and the mixture was stirred at room temperature for 2 hr. 6N hydrochloric acid (6.0 mL) was added to the mixture (pH=3), and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was filtrated, and washed with ethyl acetate/hexane to give the title compound (1.28 g, 84%) as a white powder.

$^1$H-NMR (DMSO-d$_6$, 300 MHz) δ 2.19 (3H, s), 5.36 (2H, q, J=9.0 Hz), 6.76 (1H, s), 13.66 (1H, brs).

Reference Example 8

Production of ethyl 6-iodoimidazo[1,2-b]pyridazine-2-carboxylate

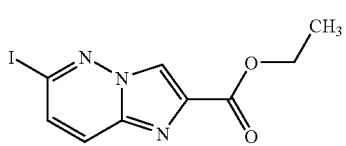

Using 3-amino-6-iodopyridazine (2.0 g, 9.05 mmol), N,N-dimethylacetamide (20 mL), ethyl 3-bromo-2-oxopropanate (1.82 mL, 14.5 mmol) and disodium hydrogenphosphate (3.21 g, 22.6 mmol), and in the same manner as in Reference Example 3, the title compound (1.2 g, 44%) was obtained as a green powder.

$^1$H-NMR (DMSO-d$_6$, 300 MHz) δ 1.33 (3H, t, J=7.1 Hz), 4.33 (2H, q, J=7.1 Hz), 7.65 (1H, d, J=9.5 Hz), 7.96 (1H, d, J=9.5 Hz), 8.88 (1H, s).

Reference Example 9

Production of 6-iodo-N-methylimidazo[1,2-b]pyridazine-2-carboxamide

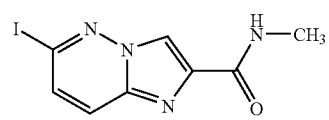

To a suspension of ethyl 6-iodoimidazo[1,2-b]pyridazine-2-carboxylate (4.5 g, 14.8 mmol) in methanol (13.5 mL) was added dropwise a solution of methylamine/tetrahydrofuran (2 mol/L, 37.1 mL, 74.2 mmol), and the mixture was stirred at room temperature for 96 hr. The solvent was evaporated under reduced pressure, and the residue was washed with ethyl acetate, saturated brine and water to give the title compound (3.2 g, 71%) as a dark brown powder.

$^1$H-NMR (DMSO-d$_6$, 300 MHz) δ 2.79 (3H, d, J=4.8 Hz), 7.62 (1H, d, J=9.6 Hz), 7.90 (1H, d, J=9.6 Hz), 8.46-8.55 (1H, m), 8.65 (1H, s).

Reference Example 10

Production of N-(6-iodoimidazo[1,2-b]pyridazin-2-yl)-2-methoxyacetamide

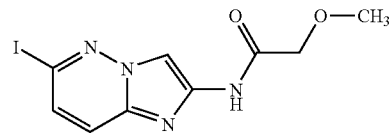

Using 6-iodoimidazo[1,2-b]pyridazin-2-amine (1.0 g, 3.85 mmol), N,N-dimethylacetamide (10 mL) and methoxyacetyl chloride (0.46 g, 4.23 mmol) as starting materials and in the same manner as in Reference Example 5, the title compound (1.01 g, 79%) was obtained as a dark brown powder.

$^1$H-NMR (DMSO-d$_6$, 300 MHz) δ 3.36 (3H, s), 4.09 (2H, s), 7.51 (1H, d, J=9.6 Hz), 7.75 (1H, d, J=9.6 Hz), 8.30 (1H, s), 10.73 (1H, s).

Reference Example 11

Production of N-(6-iodoimidazo[1,2-b]pyridazin-2-yl)-2-methylpropanamide

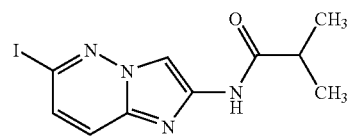

Using 6-iodoimidazo[1,2-b]pyridazin-2-amine (1.0 g, 3.85 mmol), N,N-dimethylacetamide (8.0 mL) and isobutyryl chloride (0.44 mL, 4.23 mmol) as starting materials and in the same manner as in Reference Example 5, the title compound (0.93 g, 73%) was obtained as a dark brown powder.
$^1$H-NMR (DMSO-$d_6$, 300 MHz) δ 1.10 (6H, d, J=6.6 Hz), 2.67-2.74 (1H, m), 7.49 (1H, d, J=9.3 Hz), 7.73 (1H, d, J=9.3 Hz), 8.27 (1H, s), 10.87 (1H, s).

Reference Example 12

Production of 1-methyl-1H-1,2,3-triazole-5-carboxylic acid

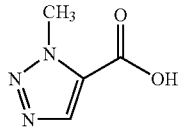

To a solution of ethyl 1-methyl-1H-1,2,3-triazole-5-carboxylate (1.15 g, 7.41 mmol) in methanol (17 mL) was added 1N sodium hydroxide (11.5 mL), and the mixture was stirred at room temperature for 1 hr. Methanol was evaporated under reduced pressure, 1N hydrochloric acid (12 mL) was added to the mixture, the precipitated crystals were collected by filtration and washed with water. The crystals were vacuum dried at 90° C. to give the title compound (148 mg, 16%) as a white powder.
$^1$H-NMR (DMSO-$d_6$, 300 MHz) δ 4.23 (3H, s), 8.20 (1H, s).

Reference Example 13

Production of 1-methyl-1H-1,2,3-triazole-4-carboxylic acid

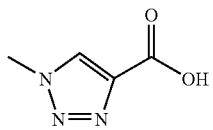

Using ethyl 1-methyl-1H-1,2,3-triazole-4-carboxylate (1.48 g, 9.54 mmol), methanol (22 mL), 1N sodium hydroxide (15 mL) and 1N hydrochloric acid (15 mL) as starting materials and in the same manner as in Reference Example 12, the title compound (605 mg, 50%) was obtained as a white powder.
$^1$H-NMR (DMSO-$d_6$, 300 MHz) δ 4.09 (3H, s), 8.62 (1H, s), 10.06 (1H, br).

Reference Example 14

Production of N-(6-iodoimidazo[1,2-b]pyridazin-2-yl)propaneamide

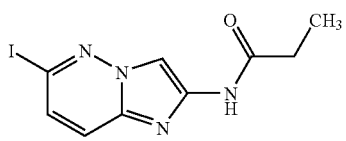

Using 6-iodoimidazo[1,2-b]pyridazin-2-amine (1.0 g, 3.85 mmol), N,N-dimethylacetamide (10 mL) and propionyl chloride (0.37 mL, 4.23 mmol) as starting materials and in the same manner as in Reference Example 5, the title compound (0.88 g, 72%) was obtained as a dark brown powder.
$^1$H-NMR (DMSO-$d_6$, 300 MHz) δ 1.08 (3H, d, J=7.5 Hz), 2.39 (2H, q, j=7.5 Hz), 7.48 (1H, d, J=9.3 Hz), 7.73 (1H, d, J=9.3 Hz), 8.26 (1H, s), 10.86 (1H, s).

Reference Example 15

Production of 3-amino-4-fluorophenol

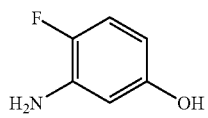

To a solution of 2-chloro-4-fluoro-5-nitrophenol (3.20 g, 16.7 mmol) in methanol (60 mL) was added 20 wt % palladium hydroxide on carbon (1.60 g) under nitrogen atmosphere. The reaction mixture was stirred at room temperature for 8 hr under hydrogen atmosphere. After nitrogen replacement, triethylamine (2.32 mL, 16.7 mmol) was added to the reaction mixture, and the mixture was filtered through a kiriyama funnel. Saturated brine was added to the filtrate, and the mixture was extracted twice with diethyl ether. The extract was dried over anhydrous magnesium sulfate, and filtrated. The solvent was evaporated under reduced pressure, and the residue was recrystallized from diethyl ether/hexane to give the title compound (1.40 g, 66%) as pale-brown crystals.
$^1$H-NMR (CDCl$_3$, 300 MHz) δ 3.70 (2H, brs), 4.50 (1H, s), 6.10 (1H, dt, J=8.7, 3.0 Hz), 6.26 (1H, dd, J=7.5, 3.0 Hz), 6.81 (1H, dd, J=10.8, 8.7 Hz).

Reference Example 16

Production of N-(6-iodoimidazo[1,2-b]pyridazin-2-yl)-N$^2$,N$^2$-dimethylglycinamide

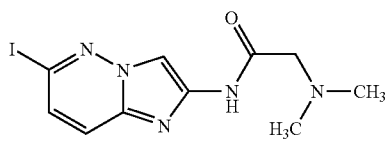

To a solution of 6-iodoimidazo[1,2-b]pyridazin-2-amine (1040 mg, 4.0 mmol) in N-methylpyrrolidone (5.0 mL) was added dimethylaminoacetyl chloride hydrochloride (948 mg, 6.0 mmol), and the mixture was stirred at room temperature for 6 hr. The reaction mixture was diluted with 1N aqueous sodium hydroxide solution, and extracted with ethyl acetate. The organic layer was concentrated under reduced pressure, and the residue was purified by silica gel column chromatography (ethyl acetate/methanol=100/0→70/30), and precipitated from diisopropyl ether to give the title compound (1019 mg, 74%) as a pale-yellow powder.

$^1$H-NMR (DMSO-d$_6$, 300 MHz) δ 2.28 (6H, s), 3.16 (2H, s), 7.51 (1H, d, J=9.2 Hz), 7.75 (1H, d, J=9.2 Hz), 8.29 (1H, s), 10.50 (1H, s).

Reference Example 17

Production of 2-cyclopropyl-N-(6-iodoimidazo[1,2-b]pyridazin-2-yl)acetamide

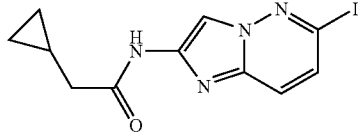

To a solution of cyclopropylacetic acid (441 mg, 4.4 mmol) in tetrahydrofuran (8.0 mL) were added N,N-dimethylformamide (1 drop) and thionyl chloride (0.32 mL, 4.4 mmol), and the mixture was stirred at room temperature for 2 hr. The reaction mixture was concentrated under reduced pressure, and dissolved in N,N-dimethylacetamide (2.0 mL). To a solution of 6-iodoimidazo[1,2-b]pyridazin-2-amine (1.04 g, 4.0 mmol) in N,N-dimethylacetamide (6.0 mL) was added dropwise the above-mentioned solution under ice-cooling. The mixture was stirred at room temperature for 2 hr. Under ice-cooling, aqueous sodium hydrogencarbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was purified by basic silica gel column chromatography (ethyl acetate/hexane=80/20→100/0), and recrystallized from ethyl acetate to give the title compound (982 mg, 72%) as pale-green crystals.

$^1$H-NMR (DMSO-d$_6$, 300 MHz) δ 0.10-0.25 (2H, m), 0.45-0.55 (2H, m), 1.00-1.15 (1H, m), 2.27 (2H, d, J=6.9 Hz), 7.48 (1H, d, J=9.4 Hz), 7.72 (1H, d, J=9.4 Hz), 8.28 (1H, s), 10.82 (1H, s).

Reference Example 18

Production of 3-amino-4-fluorophenyl methyl carbonate hydrochloride

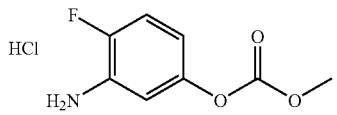

To a solution (20 mL) of 2-chloro-4-fluoro-5-nitrophenyl methyl carbonate (1.00 g, 4.0 mmol) in methanol was added 20% palladium hydroxide on carbon (0.4 g) under a nitrogen atmosphere. The reaction mixture was stirred under a hydrogen atmosphere at room temperature for 5 days. After nitrogen replacement, the catalyst was filtered off. The solvent was evaporated from the filtrate under reduced pressure, and the residue was recrystallized from diethyl ether to give the title compound (759 mg, 86%) as a pale-green powder.

$^1$H-NMR (CDCl$_3$, 300 MHz) δ 3.89 (3H, s), 6.75-6.85 (1H, m), 7.05-7.15 (2H, m).

Reference Example 19

Production of 3-{[(1,3-dimethyl-1H-pyrazol-5-yl)carbonyl]amino}-4-fluorophenyl methyl carbonate

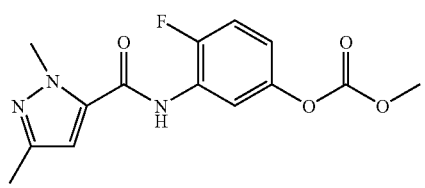

Using a solution of 3-amino-4-fluorophenyl methyl carbonate hydrochloride (740 mg, 3.34 mmol) and 1,3-dimethyl-1H-pyrazole-5-carbonylchloride (556 mg, 3.51 mmol) in N,N-dimethylacetamide (10 mL), and by a reaction in the same manner as in Example 148, the title compound (895 mg, 87%) was obtained as a white powder.

$^1$H-NMR (CDCl$_3$, 300 MHz) δ 2.30 (3H, s), 3.91 (3H, s), 4.14 (3H, s), 6.45 (1H, s), 6.85-6.95 (1H, m), 7.13 (1H, dd, J=9.0 Hz, 10.5 Hz), 7.83 (1H, br s), 8.33 (1H, dd, J=2.7 Hz, 6.6 Hz).

Reference Example 20

Production of N-(2-fluoro-5-hydroxyphenyl)-1,3-dimethyl-1H-pyrazole-5-carboxamide

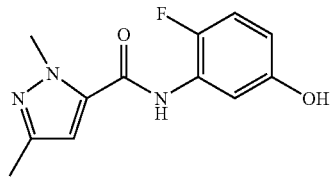

To a solution of 3-{[(1,3-dimethyl-1H-pyrazol-5-yl)carbonyl]amino}-4-fluorophenyl methyl carbonate (448 mg, 1.46 mmol) in methanol (10 mL) was added 1N aqueous sodium hydroxide solution (2 mL, 2 mmol) under ice-cooling, and the mixture was stirred at room temperature for 40 min. Under ice-cooling, 1N hydrochloric acid was added to the reaction mixture, and the mixture was extracted with ethyl acetate. The extract was washed with saturated brine, dried over anhydrous magnesium sulfate, and filtrated. The solvent was evaporated under reduced pressure, and the residue was recrystallized from diethyl ether/hexane to give the title compound (305 mg, 84%) as a white powder.

¹H-NMR (DMSO-d₆, 300 MHz) δ 2.19 (3H, s), 3.98 (3H, s), 6.56 (1H, m), 6.82 (1H, s), 6.97-7.10 (2H, m), 9.47 (1H, s), 9.85 (1H, s).

Reference Example 21

Production of 1,4-dimethyl-1H-pyrazole-3-carboxylic acid

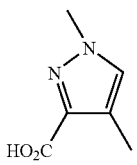

Using ethyl 1,4-dimethyl-1H-pyrazole-3-carboxylate (440 mg, 2.62 mmol), 1N aqueous sodium hydroxide solution (3 mL, 3 mmol) and ethanol (3 mL), and by a reaction in the same manner as in Reference Example 20, the title compound (152 mg, 41%) was obtained as pale-yellow crystals.

¹H-NMR (CDCl₃, 300 MHz) δ 2.30 (3H, s), 3.92 (3H, s), 7.21 (1H, s).

Reference Example 22

Production of 1,4-dimethyl-1H-pyrazole-5-carboxylic acid

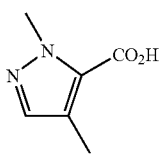

Using ethyl 1,4-dimethyl-1H-pyrazole-5-carboxylate (565 mg, 3.36 mmol), 1N aqueous sodium hydroxide solution (4 mL, 4 mmol) and ethanol (4 mL), and by a reaction in the same manner as in Reference Example 20, the title compound (261 mg, 55%) was obtained as colorless crystals.

¹H-NMR (CDCl₃, 300 MHz) δ 2.31 (3H, s), 4.16 (3H, s), 7.34 (1H, s).

Reference Example 23

Production of 3-{[(1,3-dimethyl-1H-pyrazol-5-yl)methyl]amino}-4-methylphenol

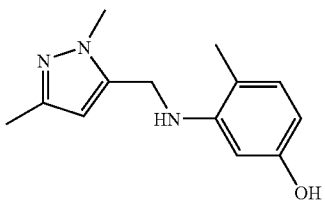

To a solution of 3-amino-4-methylphenol (930 mg, 7.5 mmol) in N,N-dimethylacetamide (10 mL) was added a solution of 1,3-dimethyl-1H-pyrazole-5-carbonylchloride (1370 mg, 8.7 mmol) in N, N-dimethylacetamide (5 mL), and the mixture was stirred at 0° C. for 20 min. To the mixture were added ethyl acetate/tetrahydrofuran, saturated aqueous sodium hydrogencarbonate solution, and the aqueous layer was extracted 4 times with ethyl acetate/tetrahydrofuran. Combined organic layer was washed with water and saturated brine, dried over anhydrous sodium sulfate, and filtrated. The filtrate was concentrated under reduced pressure, and the residue was washed with ethyl acetate/hexane to give N-(5-hydroxy-2-methylphenyl)-1,3-dimethyl-1H-pyrazole-5-carboxamide (1170 mg, 63%) as a white solid. To a suspension of lithium aluminum hydride (1130 mg, 24 mmol) in tetrahydrofuran (35 mL) was slowly added dropwise a solution of N-(5-hydroxy-2-methylphenyl)-1,3-dimethyl-1H-pyrazole-5-carboxamide (1170 mg, 4.8 mmol) in tetrahydrofuran (10 mL) under ice-cooling. After dropwise addition, the reaction mixture was heated under reflux for 5 hr. A saturated aqueous sodium sulfate solution was added to the mixture under cooling, magnesium sulfate was added and the insoluble material was filtrated. The filtrate was concentrated under reduced pressure, and the residue was washed with ethyl acetate/hexane to give the title compound (570 mg, 52%) as a white solid.

¹H-NMR (DMSO-d₆, 300 MHz) δ 1.98 (3H, s), 2.06 (3H, s), 3.72 (3H, s), 4.21 (2H, d, J=5.7 Hz), 5.23 (1H, t, J=5.7 Hz), 5.89 (1H, s), 5.93 (1H, dd, J=8.0, 2.3 Hz), 5.97 (1H, d, J=2.3 Hz), 6.71 (1H, d, J=8.3 Hz), 8.73 (1H, s).

Reference Example 24

Production of 2-methyl-1H-indole-6-ol

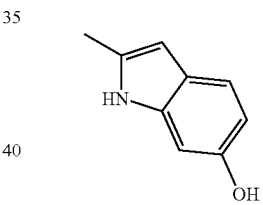

To a suspension of lithium aluminum hydride (3.7 g, 97 mmol) in 1,4-dioxane (97 mL) was slowly added dropwise a solution of methyl 6-methoxy-1H-indole-2-carboxylate (2.0 g, 9.8 mmol) in 1,4-dioxane (30 mL) under ice-cooling. After dropwise addition, the reaction mixture was heated under reflux for 24 hr. A saturated aqueous sodium sulfate solution was added to the mixture under cooling, magnesium sulfate was added and the insoluble material was filtrated. The filtrate was concentrated under reduced pressure, and the residue was recrystallized from hexane to give 6-methoxy-2-methyl-1H-indole (1.0 g, 6.5 mmol) as a yellow solid. To a solution of 6-methoxy-2-methyl-1H-indole (1.0 g, 6.2 mmol) in acetic acid (15 mL) was added 48% aqueous hydrogen bromide (31 mL) at room temperature, and the reaction mixture was heated under reflux for 3 hr. The solvent was evaporated under reduced pressure, ethyl acetate/tetrahydrofuran and saturated aqueous sodium hydrogencarbonate solution were added to the residue. The aqueous layer was extracted with ethyl acetate/tetrahydrofuran (×3). Combined organic layer was washed with saturated brine, dried over anhydrous sodium sulfate, and filtrated. The filtrate was concentrated under reduced pressure, and the residue was washed with ethyl acetate/hexane to give the title compound (600 mg, 65%) as a white solid.

$^1$H-NMR (DMSO-d$_6$, 300 MHz) δ 2.29 (3H, d, J=0.8 Hz), 5.88-5.95 (1H, m), 6.43 (1H, dd, J=8.3, 2.3 Hz), 6.63 (1H, d, J=2.3 Hz), 7.12 (1H, d, J=8.3 Hz), 8.70 (1H, s), 10.45 (1H, br, s).

Reference Example 25

Production of 4-chloro-3-{[(1,3-dimethyl-1H-pyrazol-5-yl)methyl]amino}phenol

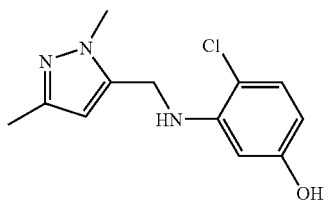

In the same manner as in Reference Example 23 and using 3-amino-4-chlorophenol (920 mg, 6.4 mmol), 1,3-dimethyl-1H-pyrazole-5-carbonylchloride (1170 mg, 7.4 mmol) and N,N-dimethylacetamide (13 mL) as starting materials, N-(2-chloro-5-hydroxyphenyl)-1,3-dimethyl-1H-pyrazole-5-carboxamide (1190 mg, 4.5 mmol) was obtained. Using lithium aluminum hydride (1060 mg, 22 mmol), N-(2-chloro-5-hydroxyphenyl)-1,3-dimethyl-1H-pyrazole-5-carboxamide (1190 mg, 4.5 mmol) and tetrahydrofuran (40 mL) as starting materials, the title compound (810 mg, 72%) was obtained as a brown solid.

$^1$H-NMR (DMSO-d$_6$, 300 MHz) δ 2.06 (3H, s), 3.72 (3H, s), 4.29 (2H, d, J=5.7 Hz), 5.73 (1H, t, J=5.7 Hz), 5.87 (1H, s), 6.02 (1H, dd, J=8.3, 2.7 Hz), 6.11 (1H, d, J=2.7 Hz), 6.99 (1H, d, J=8.3 Hz), 9.27 (1H, s).

Reference Example 26

Production of 1-(2-methoxyethyl)-3-methyl-1H-pyrazole-5-carboxylic acid

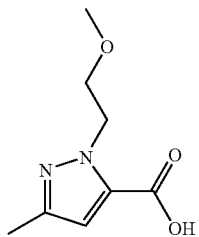

To a suspension of sodium hydride (310 mg, 7.8 mmol) in N,N-dimethylformamide (10 mL) was slowly added a solution of ethyl 3-methyl-1H-pyrazole-5-carboxylate (1000 mg, 6.5 mmol) in N,N-dimethylformamide (5 mL) under ice-cooling, and the mixture was stirred at 0° C. for 10 min, then at room temperature for 20 min. To the reaction mixture was added a solution of 1-bromo-2-methoxyethane (1090 mg, 7.8 mmol) in N,N-dimethylformamide (4 mL), and the mixture was stirred at room temperature for 7 hr. The solvent was evaporated under reduced pressure, and ethyl acetate/tetrahydrofuran and water were added to the residue. The aqueous layer was extracted with ethyl acetate/tetrahydrofuran (×3). Combined organic layer was washed with saturated brine, dried over anhydrous sodium sulfate, and filtrated. The filtrate was concentrated under reduced pressure, and the residue was purified by silica gel column chromatography (ethyl acetate/hexane=5/95→70/30) to give ethyl 1-(2-methoxyethyl)-3-methyl-1H-pyrazole-5-carboxylate (430 mg, 2.0 mmol) as a colorless liquid. To a solution of the obtained ethyl 1-(2-methoxyethyl)-3-methyl-1H-pyrazole-5-carboxylate (430 mg, 2.0 mmol) in tetrahydrofuran (6 mL) was added 8N aqueous sodium hydroxide solution (1.3 mL), and the mixture was stirred at room temperature for 3 hr. 1N Hydrochloric acid (13 mL) and ethyl acetate were added to the reaction mixture, and the aqueous layer was extracted with ethyl acetate (×3). Combined organic layer was washed with saturated brine, dried over anhydrous sodium sulfate, and filtrated. The filtrate was concentrated under reduced pressure, and the residue was washed with ethyl acetate/hexane to give the title compound (310 mg, 83%) as a white solid.

$^1$H-NMR (DMSO-d$_6$, 300 MHz) δ 2.15 (3H, s), 3.17 (3H, s), 3.61 (2H, t, J=5.8 Hz), 4.55 (2H, t, J=5.8 Hz), 6.56 (1H, s), 13.19 (1H, br. s).

Reference Example 27

Production of N-(3-aminophenyl)-1,3-dimethyl-1H-pyrazole-5-carboxamide

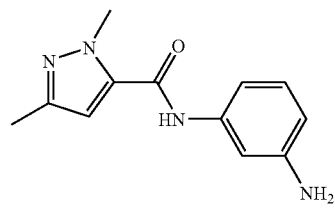

To a solution of 3-nitroaniline (1.0 g, 7.2 mmol) in N,N-dimethylacetamide (6 mL) was added a solution of 1,3-dimethyl-1H-pyrazole-5-carbonylchloride (1260 mg, 8.0 mmol) in N,N-dimethylacetamide (2 mL), and the mixture was stirred at room temperature for 30 min. Water (200 mL) was added to the mixture under ice-cooling, and the mixture was filtrated. The obtained solid was washed with water and diethyl ether to give 1,3-dimethyl-N-(3-nitrophenyl)-1H-pyrazole-5-carboxamide (1850 mg, 7.1 mmol). To a solution of the obtained 1,3-dimethyl-N-(3-nitrophenyl)-1H-pyrazole-5-carboxamide (1850 mg, 7.1 mmol) in ethanol (50 mL) was added 10% palladium/carbon (190 mg). Hydrazine monohydrate (1090 mg, 22 mmol) was slowly added to the mixture at room temperature and the mixture was stirred at 60° C. for 1 hr. The reaction mixture was filtrated, and the filtrate was evaporated under reduced pressure. To the residue were added ethyl acetate and water, and the aqueous layer was extracted with ethyl acetate (×4). Combined organic layer was washed with saturated brine, dried over anhydrous sodium sulfate, and filtrated. The filtrate was concentrated under reduced pressure, and the residue was washed with ethyl acetate/hexane to give the title compound (1650 mg, 99%) as a pale-yellow solid.

¹H-NMR (DMSO-d₆, 300 MHz) δ 2.19 (3H, s), 3.98 (3H, s), 5.09 (2H, s), 6.31 (1H, d, J=9.1 Hz), 6.76-6.83 (2H, m), 6.95 (1H, t, J=8.0 Hz), 7.03-7.08 (1H, m), 9.81 (1H, s).

Reference Example 28

Production of (2E)-N-(5-hydroxy-2-methylphenyl)but-2-ene amide

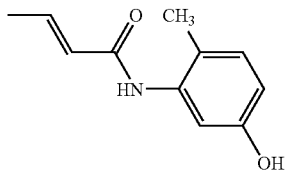

In the same manner as in Example 259 and using (2E)-but-2-enoic acid (1680 mg, 19 mmol), tetrahydrofuran (5 mL), N,N-dimethylformamide (1 drop), oxalyl chloride (1670 μL, 19 mmol), 3-amino-4-methylphenol (2000 mg, 16 mmol) and N,N-dimethylacetamide (35 mL) as starting materials, the title compound (1830 mg, 59%) was obtained as a white solid.

¹H-NMR (DMSO-d₆, 300 MHz) δ 1.85 (3H, dd, J=7.0, 1.7 Hz), 2.07 (3H, s), 6.22 (1H, d, J=15.5 Hz), 6.47 (1H, dd, J=8.3, 2.5 Hz), 6.68-6.83 (1H, m), 6.95 (1H, d, J=8.3 Hz), 7.02 (1H, s), 9.05 (1H, s), 9.16 (1H, s).

Reference Example 29

Production of N-(5-hydroxy-2-methylphenyl)-1,4-dimethyl-4,5-dihydro-1H-pyrazole-3-carboxamide

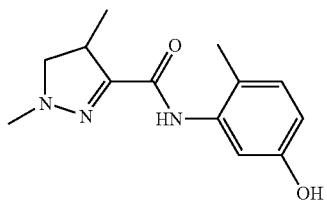

A mixture of (2E)-N-(5-hydroxy-2-methylphenyl)but-2-ene amide (1830 mg, 9.6 mmol) and 3-methyl-1,2,3-oxadiazol-3-ium-5-olate (4 mL) was stirred at 150° C. for 2 days. The reaction mixture was purified by silica gel column chromatography (ethyl acetate/hexane=5/95→60/40) to give the title compound (351 mg, 15%) as a pale-yellow solid.

¹H-NMR (DMSO-d₆, 300 MHz) δ 1.15 (3H, d, J=6.4 Hz), 2.07 (3H, s), 2.91 (3H, s), 3.04-3.11 (1H, m), 3.23-3.33 (2H, m), 6.47 (1H, dd, J=8.3, 2.7 Hz), 6.97 (1H, d, J=8.3 Hz), 7.13 (1H, d, J=2.7 Hz), 8.94 (1H, s), 9.22 (1H, s).

Reference Example 30

Production of methyl 3-(cyanomethyl)benzoate

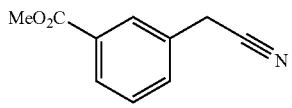

To a solution of methyl 3-(bromomethyl)benzoate (10.0 g, 44 mmol) in acetonitrile (100 mL) were added potassium cyanide (5.7 g, 87 mmol) and 18-crown-6 (1.0 g), and the mixture was stirred at room temperature for 3 days. The reaction mixture was filtrated, the solvent was evaporated under reduced pressure, and the residue was purified by silica gel column chromatography (ethyl acetate/hexane=5/95→30/70). The combined solution was concentrated under reduced pressure to give the title compound (7.0 g, 91%) as a colorless oil.

¹H-NMR (DMSO-d₆, 300 MHz) δ 3.88 (3H, s), 4.17 (2H, s), 7.57 (1H, t, J=7.6 Hz), 7.61-7.69 (1H, m), 7.88-7.95 (1H, m), 7.97 (1H, br s).

Reference Example 31

Production of methyl 3-(1-cyano-1-methylethyl)benzoate

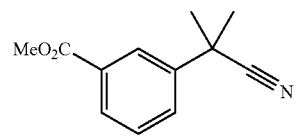

To a solution of methyl 3-(cyanomethyl)benzoate (7.0 g, 40 mmol) in dimethylsulfoxide (80 mL) was slowly added sodium hydride (60% in oil, 4.8 g, 120 mmol) under cooling at not more than 25° C. The reaction mixture was stirred at room temperature for 20 min. To the mixture was added methyl iodide (7.5 mL, 120 mmol), and the mixture was stirred at room temperature for 16 hr. Under ice-cooling, the reaction mixture was diluted with water. The mixture was extracted with ethyl acetate, and the organic layer was washed with water and saturated brine, dried over anhydrous sodium sulfate, and filtrated. The solvent was evaporated under reduced pressure, and the residue was purified by silica gel column chromatography (ethyl acetate/hexane=5/95→50/50). The combined solution was concentrated under reduced pressure to give the title compound (6.4 g, 79%) as a colorless oil.

¹H-NMR (DMSO-d₆, 300 MHz) δ 1.72 (6H, s), 3.89 (3H, s), 7.61 (1H, t, J=7.8 Hz), 7.84 (1H, ddd, J=7.8, 2.1, 1.2 Hz), 7.95 (1H, dt, J=7.8, 1.2 Hz), 8.08 (1H, t, J=1.5 Hz).

Reference Example 32

Production of 3-(1-cyano-1-methylethyl)benzoic acid

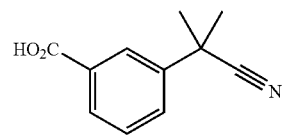

To a solution of methyl 3-(1-cyano-1-methylethyl)benzoate (2.8 g, 14 mmol) in tetrahydrofuran (30 mL) were added lithium hydroxide-monohydrate (0.98 g, 24 mmol), methanol (10 mL) and water (10 mL), and the mixture was stirred at room temperature for 18 hr. The solvent was evaporated under reduced pressure, and the residue was diluted with water (15 mL). The mixture was adjusted to pH 3 by slowly adding 1N hydrochloric acid. The precipitated white precipitate was collected by filtration, washed with water, and air-dried to give the title compound (2.5 g, 98%) as a white powder.

$^1$H-NMR (DMSO-d$_6$, 300 MHz) δ 1.72 (6H, s), 7.57 (1H, t, J=7.8 Hz), 7.78 (1H, dq, J=7.8, 1.5 Hz), 7.92 (1H, dt, J=7.8, 1.5 Hz), 8.08 (1H, t, J=1.5 Hz), 13.19 (1H, s).

Reference Example 33

Production of methyl 3-(4-cyanotetrahydro-2H-pyran-4-yl)benzoate

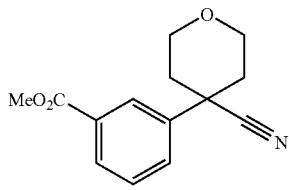

Using methyl 3-(cyanomethyl)benzoate (1.0 g, 5.7 mmol), sodium hydride (60% in oil, 0.69 g, 17 mmol), bis(2-bromoethyl)ether (1.8 g, 6.9 mmol) and dimethyl sulfoxide (12 mL) as starting materials and in the same manner as in Reference Example 31, the title compound (650 mg, 46%) was obtained as a colorless oil.

$^1$H-NMR (DMSO-d$_6$, 300 MHz) δ 2.02-2.21 (4H, m), 3.61-3.75 (2H, m), 3.89 (3H, s), 3.98-4.09 (2H, m), 7.64 (1H, t, J=7.8 Hz), 7.83-7.91 (1H, m), 7.93-8.01 (1H, m), 8.10 (1H, t, J=1.7 Hz).

Reference Example 34

Production of 3-(4-cyanotetrahydro-2H-pyran-4-yl)benzoic acid

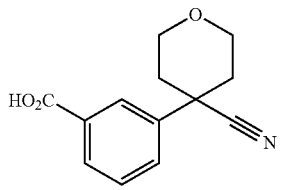

To a solution of methyl 3-(4-cyanotetrahydro-2H-pyran-4-yl)benzoate (0.62 g, 2.5 mmol) in tetrahydrofuran (6.0 mL) were added lithium hydroxide-monohydrate (0.18 g, 4.3 mmol), methanol (2.0 mL) and water (2.0 mL), and the mixture was stirred at room temperature for 12 hr. The solvent was evaporated under reduced pressure, and the residue was diluted with water (5.0 mL). The mixture was adjusted to pH 3 by slowly adding 1N hydrochloric acid. The mixture was extracted with ethyl acetate, and the organic layer was washed with water and saturated brine, dried over anhydrous sodium sulfate, and filtrated. The solvent was evaporated under reduced pressure to give the title compound (0.48 g, 83%) as a white powder.

$^1$H-NMR (DMSO-d$_6$, 300 MHz) δ 2.00-2.23 (4H, m), 3.57-3.77 (2H, m), 3.94-4.10 (2H, m), 7.61 (1H, t, J=7.8 Hz), 7.77-7.87 (1H, m), 7.90-8.00 (1H, m), 8.05-8.12 (1H, m), 13.20 (1H, br s).

Reference Example 35

Production of 5-bromopyridine-3-ol

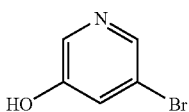

To a solution of 3-bromo-5-methoxypyridine (5.0 g, 27 mmol) in acetic acid (15 mL) was added 48% hydrobromic acid (23 mL), and the reaction mixture was heated under reflux for 16 hr. The mixture was allowed to cool to room temperature, and the solvent was evaporated under reduced pressure. The residue was adjusted to pH9-10 by adding 8N aqueous sodium hydroxide solution. The obtained aqueous solution was washed with diethyl ether, and the pH was adjusted to 5-6 by adding 6N hydrochloric acid. The obtained precipitate was collected by filtration, and washed with diisopropyl ether to give the title compound (2.8 g, 61%) as a pale-yellow powder.

$^1$H-NMR (DMSO-d$_6$, 300 MHz) δ 7.40 (1H, t, J=2.1 Hz), 8.12-8.15 (2H, m), 10.47 (1H, br. s).

Reference Example 36

Production of methyl 3-(1-cyanocyclopropyl)benzoate

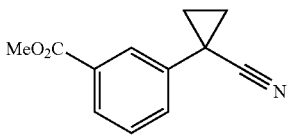

Using methyl 3-(cyanomethyl)benzoate (1.5 g, 8.6 mmol), sodium hydride (60% in oil, 1.0 g, 26 mmol), 1,2-dibromoethane (2.4 g, 13 mmol) and dimethyl sulfoxide (30 mL) as starting materials and in the same manner as in Reference Example 31, the title compound (1.3 g, 76%) was obtained as a colorless oil.

$^1$H-NMR (CDCl$_3$, 300 MHz) δ 1.38-1.56 (2H, m), 1.74-1.82 (2H, m), 3.93 (3H, s), 7.40-7.49 (1H, m), 7.55-7.62 (1H, m), 7.88 (1H, t, J=1.5 Hz), 7.96 (1H, dt, J=7.8, 1.5 Hz).

Reference Example 37

Production of 3-(1-cyanocyclopropyl)benzoic acid

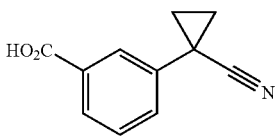

To a solution of methyl 3-(1-cyanocyclopropyl)benzoate (1.3 g, 6.4 mmol) in tetrahydrofuran (12 mL) were added lithium hydroxide-monohydrate (0.44 g, 11 mmol), methanol (4.0 mL) and water (6.0 mL), and the mixture was stirred at room temperature for 14 hr. The solvent was evaporated under reduced pressure, and the residue was diluted with water (5.0 mL). The mixture was adjusted to pH 5 by slowly adding 1N hydrochloric acid. The precipitated white precipitate was collected by filtration, washed with water, and air-dried to give the title compound (0.73 g, 61%) as a white powder.

$^1$H-NMR (DMSO-$d_6$, 300 MHz) δ 1.50-1.62 (2 H, m), 1.76-1.86 (2 H, m), 7.41-7.59 (2 H, m), 7.82-7.97 (2 H, m), 13.19 (1 H, br. s.).

Reference Example 38

Production of methyl 3-(1-cyanocyclohexyl)benzoate

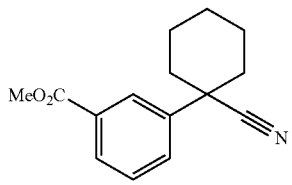

Using methyl 3-(cyanomethyl)benzoate (1.5 g, 8.6 mmol), sodium hydride (60% in oil, 1.0 g, 26 mmol), 1,5-dibromopentane (3.0 g, 13 mmol) and dimethyl sulfoxide (30 mL) as starting materials and in the same manner as in Reference Example 31, the title compound (1.4 g, 68%) was obtained as a colorless oil.

$^1$H-NMR (DMSO-$d_6$, 300 MHz) δ 1.23-1.46 (1H, m), 1.53-2.17 (9H, m), 3.88 (3 H, s), 7.61 (1H, t, J=7.8 Hz), 7.80-7.88 (1H, m), 7.95 (1H, dt, J=7.8, 1.2 Hz), 8.10 (1H, t, J=1.8 Hz).

Reference Example 39

Production of 3-(1-cyanocyclohexyl)benzoic acid

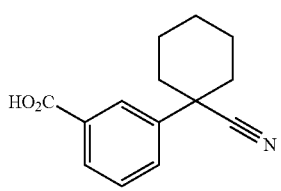

Using methyl 3-(1-cyanocyclohexyl)benzoate (1.3 g, 5.3 mmol), lithium hydroxide-monohydrate (0.52 g, 13 mmol), tetrahydrofuran (18 mL), methanol (6.0 mL) and water (6.0 mL) as starting materials and in the same manner as in Reference Example 37, the title compound (1.1 g, 88%) was obtained as a white powder.

$^1$H-NMR (DMSO-$d_6$, 300 MHz) δ 1.21-1.43 (1H, m), 1.52-2.17 (9H, m), 7.58 (1H, t, J=7.8 Hz), 7.80 (1H, dq, J=7.8, 1.2 Hz), 7.92 (1H, dt, J=7.8, 1.2 Hz), 8.09 (1H, t, J=1.8 Hz).

Reference Example 40

Production of methyl 3-(1-cyanocyclobutyl)benzoate

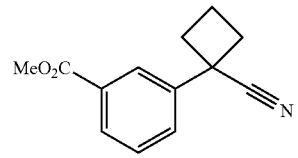

Using methyl 3-(cyanomethyl)benzoate (1.8 g, 10 mmol), sodium hydride (60% in oil, 1.2 g, 30 mmol), 1,3-dibromopropane (3.0 g, 15 mmol) and dimethyl sulfoxide (30 mL) as starting materials and in the same manner as in Reference Example 31, the title compound (0.91 g, 42%) was obtained as a colorless oil.

$^1$H-NMR (DMSO-$d_6$, 300 MHz) δ 1.92-2.12 (1H, m), 2.18-2.41 (1H, m), 2.56-2.91 (4H, m), 3.88 (3H, s), 7.59-7.66 (1H, m), 7.75-7.83 (1H, m), 7.91-8.02 (2H, m).

Reference Example 41

Production of 3-(1-cyanocyclobutyl)benzoic acid

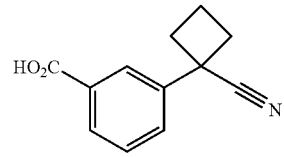

Using methyl 3-(1-cyanocyclobutyl)benzoate (0.9 g, 4.2 mmol), lithium hydroxide-monohydrate (0.26 g, 6.3 mmol), tetrahydrofuran (9.0 mL), methanol (3.0 mL) and water (4.0 mL) as starting materials and in the same manner as in Reference Example 37, the title compound (0.73 g, 86%) was obtained as a white powder.

$^1$H-NMR (DMSO-$d_6$, 300 MHz) δ 1.93-2.13 (1H, m), 2.20-2.42 (H, m), 2.56-2.90 (4H, m), 7.59 (1H, t, J=7.8 Hz), 7.68-7.81 (1H, m), 7.85-8.01 (2H, m).

Reference Example 42

Production of 2-methyl-2-(3-nitrophenyl)propanenitrile

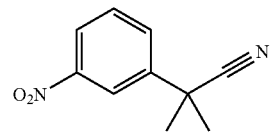

To a two-phase solution of (3-nitrophenyl)acetonitrile (5.0 g, 31 mmol) and tetraethylammoniumbromide (600 mg) in 2N aqueous sodium hydroxide (47 mL, 93 mmol) and methylene chloride (50 mL) was added methyl iodide (8.0 mL, 130 mmol), and the mixture was stirred at room temperature for 12 hr. The reaction mixture was diluted with water and extracted with ethyl acetate. The organic layer was washed with saturated brine, dried over anhydrous sodium sulfate, and filtrated. The solvent was evaporated under reduced pressure, and the residue was purified by silica gel column chromatography (ethyl acetate/hexane=2/98→10/90) to give the title compound (0.38 g, 6.5%) as a yellow oil.

$^1$H-NMR (DMSO-$d_6$, 300 MHz) δ 1.76 (6H, s), 7.76 (1H, t, J=8.0 Hz), 8.04 (1H, dd, J=7.8, 0.8 Hz), 8.24 (1H, d, J=8.3 Hz), 8.32 (1H, s).

Reference Example 43

Production of 2-(3-aminophenyl)-2-methylpropanenitrile

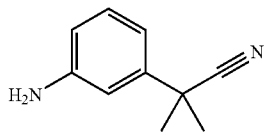

To a solution of 2-methyl-2-(3-nitrophenyl)propanenitrile (0.35 g, 1.8 mmol) in ethyl acetate (10 mL) was added 10% palladium/carbon (35 mg), and the mixture was stirred for 10 hr under hydrogen atmosphere. The residual catalyst was filtered through celite, and washed with ethyl acetate. The filtrate was concentrated under reduced pressure to give the title compound (0.35 g, 1.8 mmol) as a pale-yellow oil.

$^1$H-NMR (DMSO-$d_6$, 300 MHz) δ 1.61 (6H, s), 5.21 (2H, br. s), 6.46-6.55 (1H, m), 6.56-6.63 (1H, m), 6.71 (1H, t, J=2.1 Hz), 7.04 (1H, t, J=7.8 Hz).

Reference Example 44

Production of 2-methyl-2-(4-nitrophenyl)propanenitrile

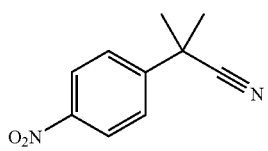

To a two-phase solution of (4-nitrophenyl)acetonitrile (5.0 g, 31 mmol) and tetraethylammoniumbromide (2.0 g) in 2N aqueous sodium hydroxide (75 mL, 150 mmol) and methylene chloride (50 mL) was added methyl iodide (9.6 mL, 150 mmol), and the mixture was stirred at room temperature for 4 hr. To the reaction mixture were added 2N aqueous sodium hydroxide solution (10 mL, 20 mmol) and methyl iodide (1.5 mL, 24 mmol), and the mixture was further stirred for 2 hr. The reaction mixture was diluted with water and extracted with ethyl acetate. The organic layer was washed with saturated brine, dried over anhydrous sodium sulfate, and filtrated. The solvent was evaporated under reduced pressure, and the residue was purified by silica gel column chromatography (ethyl acetate/hexane=5/95→10/90) to give the title compound (3.8 g, 65%) as a pale-yellow oil.

$^1$H-NMR (DMSO-$d_6$, 300 MHz) δ 1.75 (6H, s), 7.79-7.88 (2H, m), 8.25-8.34 (2H, m).

Reference Example 45

2-(4-aminophenyl)-2-methylpropanenitrile

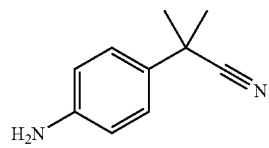

To a solution of 2-methyl-2-(4-nitrophenyl)propanenitrile (0.95 g, 5.0 mmol) in ethyl acetate (10 mL) was added 10% palladium/carbon (100 mg), and the mixture was stirred at room temperature for 14 hr under hydrogen atmosphere. The residual catalyst was filtered through celite, and washed with ethyl acetate. The filtrate was concentrated under reduced pressure to give the title compound (0.81 g, 99%) as a pale-yellow oil.

$^1$H-NMR (DMSO-$d_6$, 300 MHz) δ 1.59 (6H, s), 5.14 (2H, br. s), 6.57 (2H, d, J=8.7 Hz), 7.12 (2H, d, J=8.7 Hz).

Reference Example 46

Production of methyl 3-(1-cyanoethyl)benzoate

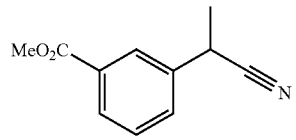

To a solution of 3-(1-cyanoethyl)benzoic acid (2.0 g, 11 mmol) in methanol (20 mL) was added conc. sulfuric acid (0.2 mL), and the mixture was stirred at 60° C. for 8 hr. The reaction mixture was concentrated under reduced pressure, and neutralized with saturated aqueous sodium hydrogencarbonate solution. The mixture was diluted with water and extracted with ethyl acetate. The organic layer was washed with saturated brine, dried over anhydrous sodium sulfate, and filtrated. The solvent was evaporated under reduced pressure to give the title compound (1.9 g, 89%) as a colorless oil.

$^1$H-NMR (DMSO-$d_6$, 300 MHz) δ 1.57 (3H, d, J=7.2 Hz), 3.88 (3H, s), 4.46 (1H, q, J=7.2 Hz), 7.59 (1H, t, J=7.8 Hz), 7.68-7.76 (1H, m), 7.94 (1H, dt, J=7.8, 1.5 Hz), 8.00 (1H, t, J=1.8 Hz).

Reference Example 47

Production of methyl 3-(1-cyano-2-cyclopropyl-1-methylethyl)benzoate

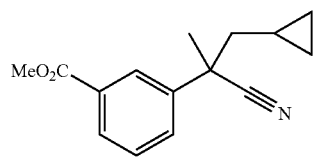

To a solution of methyl 3-(1-cyanoethyl)benzoate (1.5 g, 7.9=mol) in acetonitrile (20 mL) were added sodium methoxide (0.95 g, 17 mmol) and (bromomethyl)cyclopropane (1.3 g, 9.5 mmol), and the reaction mixture was stirred at room temperature for 30 min. To the reaction mixture was added sodium hydride (60% in oil, 0.7 g, 17 mmol) under ice-cooling, and the mixture was stirred at room temperature for 16 hr. The mixture was diluted with diethyl ether, and washed with 5% aqueous sodium hydrogencarbonate solution and saturated brine. The organic layer was dried over anhydrous sodium sulfate, and filtrated. The solvent was evaporated under reduced pressure, and the residue was purified by silica gel column chromatography (ethyl acetate/hexane=5/95→40/60) to give the title compound (129 mg, 6.7%) as a colorless oil.

$^1$H-NMR (DMSO-$d_6$, 300 MHz) δ −0.10-0.03 (1H, m), 0.21 (1H, dt, J=4.9, 9.1 Hz), 0.26-0.39 (1H, m), 0.39-0.50 (1H, m), 0.51-0.66 (1H, m), 1.70-1.77 (3H, m), 1.77-1.89 (1H, m), 1.92-2.03 (1H, m), 3.88 (3H, s), 7.55-7.67 (1H, m), 7.77-7.86 (1H, m), 7.95 (1H, d, J=7.7 Hz), 8.08-8.13 (1H, m).

Reference Example 48

Production of 3-(1-cyano-2-cyclopropyl-1-methylethyl)benzoic acid

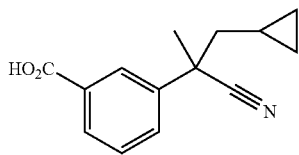

To a solution of methyl 3-(1-cyano-2-cyclopropyl-1-methylethyl)benzoate (120 mg, 0.49 mmol) in tetrahydrofuran/methanol/water (=3.0 mL/1.0 mL/1.0 mL) was added lithium hydroxide monohydrate (40 mg, 0.99 mmol), and the reaction mixture was stirred at room temperature for 4 hr. The mixture was concentrated under reduced pressure, and the obtained aqueous solution was adjusted to pH 5 by adding 1N hydrochloric acid. The mixture was concentrated under reduced pressure, and the residue was purified by silica gel column chromatography (ethyl acetate/hexane=50/50→100/0) to give the title compound (76 mg, 66%) as a colorless oil.

$^1$H NMR (DMSO-$d_6$, 300 MHz) δ −0.04-0.09 (1 H, m), 0.18-0.31 (1 H, m), 0.36-0.49 (1H, m), 0.49-0.62 (1H, m), 0.64-0.82 (1H, m), 1.73-1.87 (2H, m), 1.91-2.03 (2H, m), 7.44-7.63 (1H, m), 7.79-7.86 (1H, m), 8.09 (1H, d, J=7.9 Hz), 8.15-8.22 (1H, m), 11.25-12.45 (1H, br. s).

Reference Example 49

Production of ethyl 2-(cyanomethyl)-1,3-thiazole-4-carboxylate

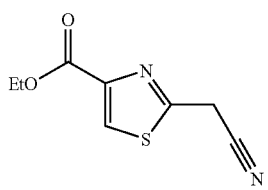

To a solution of ethyl 3-bromo-2-oxopropanate (21 g, 110 mmol) in N,N-dimethylformamide (50 mL) was added a solution of 2-cyanoethanethioamide (10 g, 100 mmol) in N,N-dimethylformamide (50 mL) under ice-cooling, and the reaction mixture was stirred at room temperature for 12 hr. The mixture was concentrated under reduced pressure, and the obtained residue was dissolved in ethyl acetate, and washed with 5% aqueous sodium hydrogencarbonate solution and saturated brine. The organic layer was dried over anhydrous sodium sulfate and filtrated. The solvent was evaporated under reduced pressure, and the residue was purified by silica gel column chromatography (ethyl acetate/hexane=20/80→60/40) to give the title compound (5.1 g, 26%) as a yellow powder.

$^1$H-NMR (DMSO-$d_6$, 300 MHz) δ 1.31 (3H, t, J=7.2 Hz), 4.31 (2H, q, J=7.2 Hz), 4.63 (2H, s), 8.53 (1H, s).

Reference Example 50

Production of ethyl 2-(1-cyano-1-methylethyl)-1,3-thiazole-4-carboxylate

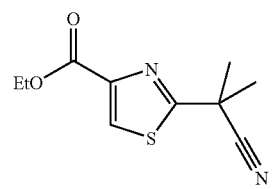

To a solution of ethyl 2-(cyanomethyl)-1,3-thiazole-4-carboxylate (2.0 g, 10 mmol) in dimethylsulfoxide (20 mL) was added sodium hydride (60% in oil, 1.6 g, 41 mmol), and the mixture was stirred at room temperature for 30 min. Under cooling, a solution of methyl iodide (2.5 mL, 41 mmol) in dimethylsulfoxide (10 mL) was added dropwise to the mixture, and the mixture was stirred at room temperature for 6 hr. Water was added to the mixture under cooling, and the mixture was extracted with ethyl acetate. The organic layer was washed with saturated brine, dried over anhydrous sodium sulfate, and filtrated. The solvent was evaporated under reduced pressure, and the residue was purified by silica gel column chromatography (ethyl acetate/hexane=5/95→50/50) to give the title compound (0.90 g, 39%) as a pale-yellow oil.

$^1$H-NMR (DMSO-$d_6$, 300 MHz) δ 1.31 (3H, t, J=7.2 Hz), 1.83 (6H, s), 4.33 (2H, q, J=7.2 Hz), 8.59 (1H, s).

Reference Example 51

Production of 2-(1-cyano-1-methylethyl)-1,3-thiazole-4-carboxylic acid

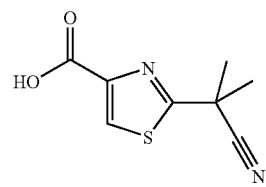

To a solution of ethyl 2-(1-cyano-1-methylethyl)-1,3-thiazole-4-carboxylate (0.9 g, 4.0 mmol) in tetrahydrofuran/methanol/water (=12 mL/4.0 mL/4.0 mL) was added lithium hydroxide monohydrate (330 mg, 8.0 mmol), and the reaction mixture was stirred at room temperature for 10 hr. The mixture was concentrated under reduced pressure, and the obtained aqueous solution was adjusted to pH 5 by adding 1N hydrochloric acid. The mixture was extracted with ethyl acetate, and the organic layer was washed with saturated brine, dried over anhydrous sodium sulfate, and filtrated. The solvent was evaporated under reduced pressure to give the title compound (256 mg, 53%) as a white powder.

$^1$H NMR (DMSO-d, 300 MHz$_6$) δ 1.82 (6H, s), 8.43 (1H, s).

Reference Example 52

Production of 5-amino-2-bromophenol

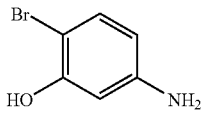

4-Bromo-3-methoxyaniline (5.0 g, 25 mmol) was added to 48% hydrobromic acid (20 mL), and the reaction mixture was stirred at 80° C. for 16 hr. After completion of the reaction, the mixture was allowed to cool to room temperature, and adjusted to pH 7-8 by adding 8N aqueous sodium hydroxide solution. The mixture was extracted with ethyl acetate, and the obtained organic layer was washed with water and saturated brine, dried over anhydrous sodium sulfate, and filtrated. The solvent was evaporated under reduced pressure, and the residue was purified by silica gel column chromatography (ethyl acetate/hexane=10/90→100/0) to give the title compound (2.0 g, 43%) as a white powder.

$^1$H-NMR (DMSO-d$_6$, 300 MHz) δ 5.10 (2H, s), 5.97 (1H, dd, J=8.4, 52.4 Hz), 6.19 (1H, d, J=2.4 Hz), 6.99 (1H, d, J=8.4 Hz), 9.64 (1H, s).

Reference Example 53

Production of 2,2,2-trichloroethyl (3-tert-butyl-1-phenyl-1H-pyrazol-5-yl)carbamate

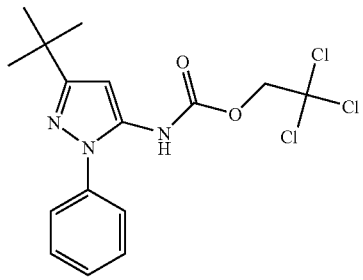

To a two-phase solution of 3-tert-butyl-1-phenyl-1H-pyrazol-5-amine (5.0 g, 23 mmol) in ethyl acetate (45 mL)/3N aqueous sodium hydroxide (20 mL) was added 2,2,2-trichloroethyl chlorocarbonate (4.5 mL, 33 mmol) under ice-cooling, and the mixture was stirred at room temperature for 2 hr. The obtained organic layer was washed with 5% aqueous sodium hydrogencarbonate, water and saturated brine, dried over anhydrous sodium sulfate, and filtrated. The solvent was evaporated under reduced pressure to give the title compound (5.0 g, 55%) as a white powder.

$^1$H-NMR (DMSO-d$_6$, 300 MHz) δ 1.28 (9H, s), 4.85 (2H, br. s), 6.30 (1H, s), 7.28-7.53 (5H, m).

Reference Example 54

Production of (6-iodoimidazo[1,2-b]pyridazin-2-yl)methanol

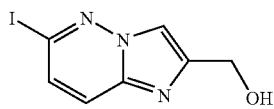

To a solution of 3-amino-6-iodopyridazine (2.0 g, 9.0 mmol) in ethanol (40 mL) was added 3-chloro-2-oxopropyl acetate (2.73 g, 18.1 mmol), and the mixture was heated under reflux for 24 hr. After cooling the mixture to room temperature, saturated aqueous sodium hydrogencarbonate solution was added to the mixture, and the mixture was extracted with ethyl acetate/tetrahydrofuran. The extract was washed with saturated brine, dried over anhydrous sodium sulfate, and filtrated. The solvent was evaporated under reduced pressure, and the residue was collected by filtration and washed with ethyl acetate/hexane to give the title compound (498 mg, 20%) as a white powder.

$^1$H-NMR (DMSO-d$_6$, 300 MHz) δ 4.62 (2H, d, J=5.6 Hz), 5.33 (1H, t, J=5.6 Hz), 7.49 (1H, d, J=9.3 Hz), 7.80 (1H, d, J=9.3 Hz), 8.14 (1H, s).

Reference Example 55

Production of methyl 5-methyl-1,3-thiazole-4-carboxylate

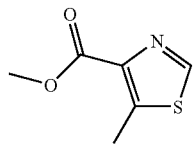

To a solution of methyl 2-amino-5-methyl-1,3-thiazole-4-carboxylate (2.15 g, 12.5 mmol) in tetrahydrofuran (60 mL) was slowly added tert-butyl nitrite (2.23 mL, 18.7 mmol) with stirring at 50° C., and the mixture was stirred at 60° C. for 2 hr. The mixture was diluted with water (100 mL), and extracted with ethyl acetate (100 mL×2). The organic layer was concentrated under reduced pressure, and the residue was purified by silica gel column chromatography (hexane/ethyl acetate=80/20→0/100) to give the title compound (1.17 g, yield 60%).

¹H-NMR (DMSO-d₆, 300 MHz) δ 2.72 (3H, s), 3.82 (3H, s), 8.90 (1H, s).

Reference Example 56

Production of 5-methyl-1,3-thiazole-4-carboxylic acid

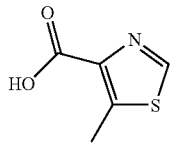

To a solution of methyl 5-methyl-1,3-thiazole-4-carboxylate (1.17 g, 7.4 mmol) in methanol (15 mL) was added 8N aqueous sodium hydroxide solution (2.00 mL), and the mixture was stirred at room temperature for 18 hr. 6N Hydrochloric acid (2.67 mL) was added to the mixture, and the mixture was concentrated under reduced pressure. Water was added to the residue, and the precipitate was collected by filtration, and washed with water. The precipitate was suspended in a mixed solvent of ethyl acetate (9 mL) and ethanol (1 mL), and the mixture was stirred at 80° C. for 3 min. After allowing to cool to room temperature, the precipitate was collected by filtration, washed with ethyl acetate, and dried under reduced pressure to give the title compound (531 mg, yield 50%) as a pale-yellow solid.

¹H-NMR (DMSO-d₆, 300 MHz) δ 2.71 (3H, s), 8.87 (1H, s), 12.88 (1H, br s).

Reference Example 57

Production of methyl 3-methoxy-1-methyl-1H-pyrazole-5-carboxylate

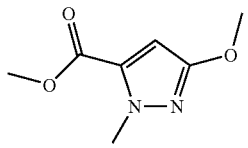

A mixture of methyl 3-hydroxy-1-methyl-1H-pyrazole-5-carboxylate (2.34 g, 15.0 mmol), iodomethane (3.19 g, 22.5 mmol), potassium carbonate (4.15 g, 30.0 mmol) and N,N-dimethylformamide (15 mL) was stirred at room temperature for 18 hr. The mixture was diluted with water (50 mL), and extracted with ethyl acetate (50 mL×3). The organic layer was washed with water (10 mL×2), and concentrated under reduced pressure. The residue was purified by silica gel column chromatography (hexane/ethyl acetate=100/0→50/50) to give the title compound (2.01 g, yield 79%) as a white solid.

¹H-NMR (DMSO-d₆, 300 MHz) δ 3.78 (3H, s), 3.81 (3H, s), 3.94 (3H, s), 6.27 (1H, s).

Reference Example 58

Production of 3-methoxy-1-methyl-1H-pyrazole-5-carboxylic acid

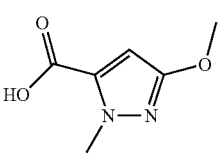

To a solution of methyl 3-methoxy-1-methyl-1H-pyrazole-5-carboxylate (2.01 g, 11.8 mmol) in methanol (15 mL) was added 8N aqueous sodium hydroxide solution (3.00 mL), and the mixture was stirred at room temperature for 18 hr. 6N Hydrochloric acid (4.00 mL) was added to the mixture, and the mixture was concentrated under reduced pressure. Water was added to the residue, and the precipitate was collected by filtration, washed with water and air-dried. The precipitate was suspended in diisopropyl ether, and the mixture was stirred at 80° C. for 15 min. After allowing to cool to room temperature, the precipitate was collected by filtration, washed with diisopropyl ether, and dried under reduced pressure to give the title compound (746 mg, yield 40%) as a white solid.

¹H-NMR (DMSO-d₆, 300 MHz) δ 3.77 (3H, s), 3.93 (3H, s), 6.20 (1H, s), 13.37 (1H, br s).

Reference Example 59

Production of methyl 3-ethoxy-1-methyl-1H-pyrazole-5-carboxylate

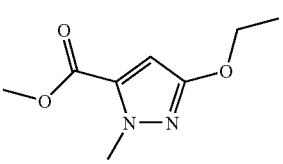

Using methyl 3-hydroxy-1-methyl-1H-pyrazole-5-carboxylate (2.34 g, 15.0 mmol), iodoethane (3.51 g, 22.5 mmol), potassium carbonate (4.15 g, 30.0 mmol) and N,N-dimethylformamide (15 mL), and in the same manner as in Reference Example 57, the title compound (2.59 g, yield 94%) was obtained.

Reference Example 60

Production of 3-ethoxy-1-methyl-1H-pyrazole-5-carboxylic acid

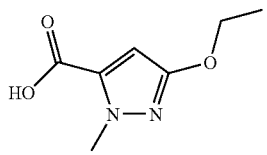

Using methyl 3-ethoxy-1-methyl-1H-pyrazole-5-carboxylate (2.59 g, 14.1 mmol), methanol (15 mL) and 8N aqueous sodium hydroxide solution (3.00 mL), and in the same manner as in Reference Example 58, the title compound (1.94 g, yield 81%) was obtained.

$^1$H-NMR (DMSO-$d_6$, 300 MHz) δ 1.28 (3H, t, J=7.0 Hz), 3.92 (3H, s), 4.09 (2H, q, J=7.0 Hz), 6.19 (1H, s), 13.37 (1H, br s).

Reference Example 61

Production of methyl 3-(2-methoxyethoxy)-1-methyl-1H-pyrazole-5-carboxylate

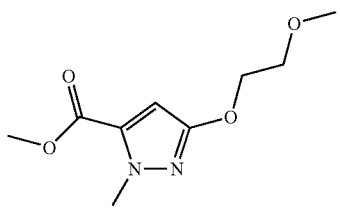

Using methyl 3-hydroxy-1-methyl-1H-pyrazole-5-carboxylate (2.34 g, 15.0 mmol), 1-bromo-2-methoxyethane (3.13 g, 22.5 mmol), potassium carbonate (4.15 g, 30.0 mmol) and N,N-dimethylformamide (15 mL), and in the same manner as in Reference Example 57, the title compound (3.03 g, yield 94%) was obtained.

$^1$H-NMR (DMSO-$d_6$, 300 MHz) δ 3.28 (3H, s), 3.57-3.64 (2H, m), 3.81 (3H, s), 3.93 (3H, s), 4.14-4.20 (2H, m), 6.28 (1H, s).

Reference Example 62

Production of 3-(2-methoxyethoxy)-1-methyl-1H-pyrazole-5-carboxylic acid

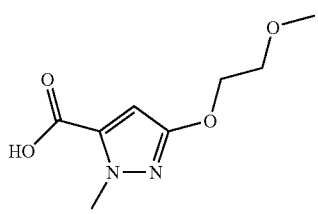

Using methyl 3-(2-methoxyethoxy)-1-methyl-1H-pyrazole-5-carboxylate (3.03 g, 14.1 mmol), methanol (15 mL) and 8N aqueous sodium hydroxide solution (3.00 mL), and in the same manner as in Reference Example 58, the title compound (2.72 g, yield 96%) was obtained.

$^1$H-NMR (DMSO-$d_6$, 300 MHz) δ 3.28 (3H, s), 3.57-3.63 (2H, m), 3.92 (3H, s), 4.13-4.19 (2H, m), 6.21 (1H, s), 13.39 (1H, br s).

Example 1

Production of N-[6-(3-aminophenoxy)imidazo[1,2-b]pyridazin-2-yl]tetrahydro-2H-pyran-4-carboxamide

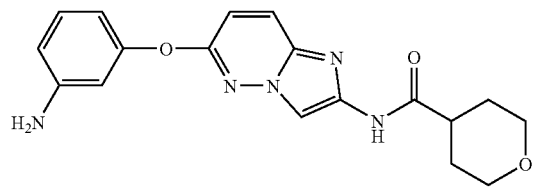

A mixture of 6-iodoimidazo[1,2-b]pyridazin-2-amine (550 mg, 2.11 mmol), tetrahydro-2H-pyran-4-carbonyl chloride (320 mg, 2.15 mmol) and N,N-dimethylacetamide (5.0 mL) was stirred at room temperature for 3 hr. The reaction mixture was poured into water, and the precipitated solid was collected by filtration, washed with water, and air-dried to give N-(6-iodoimidazo[1,2-b]pyridazin-2-yl)tetrahydro-2H-pyran-4-carboxamide as a white powder.

A mixture of N-(6-iodoimidazo[1,2-b]pyridazin-2-yl)tetrahydro-2H-pyran-4-carboxamide, 3-aminophenol (436 mg, 4.0 mmol), potassium carbonate (552 mg, 4.0 mmol) and N,N-dimethylformamide (5.0 mL) was stirred with heating at 180° C. for 15 min using a microwave synthesizer. After cooling, the reaction mixture was filtrated, and the filtrate was purified by preparative HPLC to give the title compound (364 mg, 49%) as a dark brown powder.

$^1$H-NMR (CDCl$_3$, 400 MHz) δ 1.67-1.81 (4H, m), 2.34-2.44 (1H, m), 3.25-3.34 (2H, m), 3.78 (2H, s), 3.86-3.94 (2H, m), 6.33-6.37 (1H, m), 6.37-6.43 (2H, m), 6.67 (1H, d, J=9.5 Hz), 7.02 (1H, t, J=8.1 Hz), 7.54 (1H, d, J=9.5 Hz), 7.89 (1H, s), 8.06 (1H, s).

In the same manner as in Example 1, the compounds of Examples 2 to 5 were synthesized. The structures of the compounds of Examples 2 to 5 are shown in Table 1.

TABLE 1

| Example No. | Chemical structural formula | MS (m/Z) |
|---|---|---|
| 2 | | 347 |
| 3 | | 284 |
| 4 | | 310 |
| 5 | | 352 |

Example 6

Production of N-(3-{[2-(acetylamino)imidazo[1,2-b]pyridazin-6-yl]oxy}phenyl)cyclopropanecarboxamide

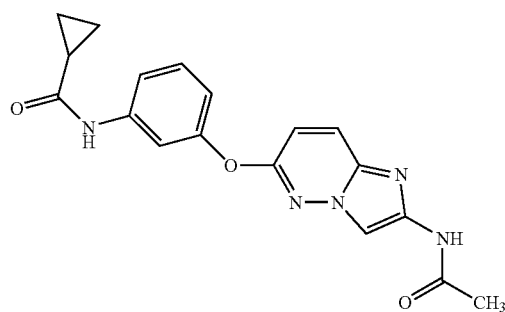

A mixture of N-[6-(3-aminophenoxy)imidazo[1,2-b]pyridazin-2-yl]acetamide (17 mg, 0.06 mmol), cyclopropanecarbonyl chloride (9.5 mg, 0.09 mmol) and N,N-dimethylacetamide (0.5 mL) was stirred at room temperature for 14 hr. The reaction mixture was purified by preparative HPLC to give the title compound (10.8 mg, 51%).

LC-MS 352 (M+H).

In the same manner as in Example 6, the compounds of Examples 7 to 51 were synthesized. The structures of the compounds of Examples 7 to 51 are shown in Tables 2 to 7.

TABLE 2

| Example No. | Chemical structural formula | MS (m/Z) |
|---|---|---|
| 7 | | 519 |
| 8 | | 469 |
| 9 | | 452 |
| 10 | | 526 |
| 11 | | 476 |

TABLE 2-continued

| Example No. | Chemical structural formula | MS (m/Z) |
|---|---|---|
| 12 | | 459 |
| 13 | | 394 |
| 14 | | 368 |

TABLE 3

| Example No. | Chemical structural formula | MS (m/Z) |
|---|---|---|
| 15 | | 378 |
| 16 | | 406 |
| 17 | | 408 |
| 18 | | 410 |
| 19 | | 422 |

TABLE 3-continued

| Example No. | Chemical structural formula | MS (m/Z) |
|---|---|---|
| 20 | | 406 |
| 21 | | 379 |
| 22 | | 378 |

TABLE 4

| Example No. | Chemical structural formula | MS (m/Z) |
|---|---|---|
| 23 | | 420 |
| 24 | | 394 |
| 25 | | 404 |
| 26 | | 432 |
| 27 | | 434 |

TABLE 4-continued

| Example No. | Chemical structural formula | MS (m/Z) |
|---|---|---|
| 28 | | 436 |
| 29 | | 448 |
| 30 | | 432 |

TABLE 5

| Example No. | Chemical structural formula | MS (m/Z) |
|---|---|---|
| 31 | | 405 |
| 32 | | 420 |
| 33 | | 462 |
| 34 | | 436 |

TABLE 5-continued
| Example No. | Chemical structural formula | MS (m/Z) |
|---|---|---|
| 35 | 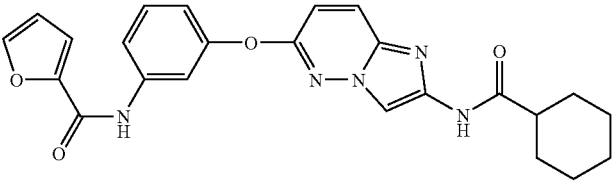 | 446 |
| 36 | 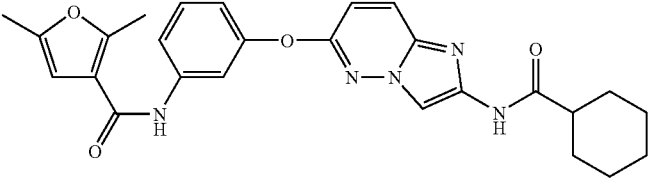 | 474 |
| 37 | 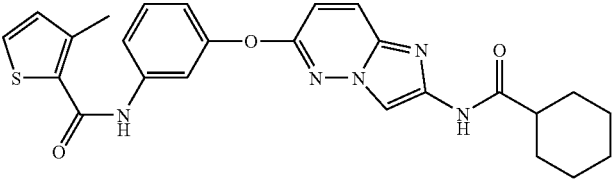 | 476 |
| 38 | 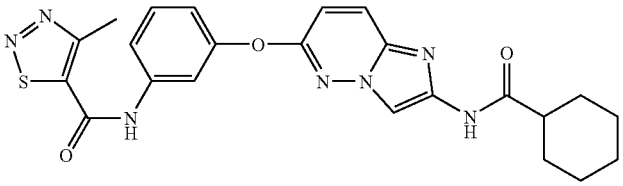 | 478 |
TABLE 6
| Example No. | Chemical structural formula | MS (m/Z) |
|---|---|---|
| 39 | 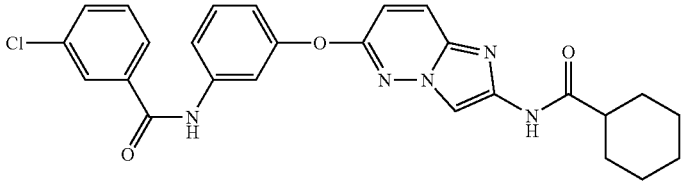 | 490 |
| 40 | 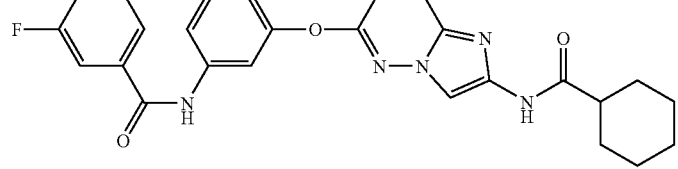 | 474 |
| 41 | 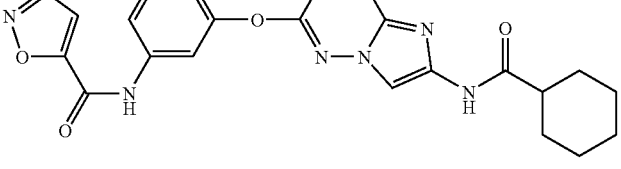 | 447 |

TABLE 6-continued

| Example No. | Chemical structural formula | MS (m/Z) |
|---|---|---|
| 42 | | 422 |
| 43 | | 464 |
| 44 | | 438 |
| 45 | | 448 |
| 46 | | 476 |

TABLE 7

| Example No. | Chemical structural formula | MS (m/Z) |
|---|---|---|
| 47 | | 478 |
| 48 | | 480 |

TABLE 7-continued

| Example No. | Chemical structural formula | MS (m/Z) |
|---|---|---|
| 49 | | 492 |
| 50 | | 449 |
| 51 | | 474 |

Example 52

Production of N-[3-({2-[(cyclopropylcarbonyl)amino]imidazo[1,2-b]pyridazin-6-yl}oxy)phenyl]-2-fluoro-3-(trifluoromethyl)benzamide

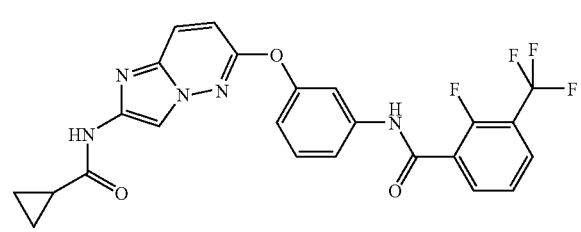

Using N-[6-(3-aminophenoxy)imidazo[1,2-b]pyridazin-2-yl]cyclopropanecarboxamide (309 mg, 1.00 mmol), 2-fluoro-3-(trifluoromethyl)benzoic acid (312 mg, 1.50 mmol), 1-hydroxybenzotriazole (203 mg, 1.50 mmol), 1-ethyl-3-(3-dimethylaminopropyl)carbodiimide hydrochloride (288 mg, 1.50 mmol) and N,N-dimethylformamide (5.0 mL) as starting materials and in the same manner as in Example 106, the title compound (380 mg, 76%) was obtained as a white powder.

$^1$H-NMR (DMSO-d$_6$, 300 MHz) δ 0.78-0.82 (4H, m), 1.88-1.95 (1H, m), 7.03-7.09 (2H, m), 7.45 (1H, t, J=8.1 Hz), 7.52-7.57 (2H, m), 7.66-7.67 (1H, m), 7.94-8.07 (4H, m), 10.79 (1H, s), 11.09 (1H, s).

Example 53

Production of N-[3-({2-[(cyclopropylcarbonyl)amino]imidazo[1,2-b]pyridazin-6-yl}oxy)phenyl]-3-fluoro-5-(trifluoromethyl)benzamide

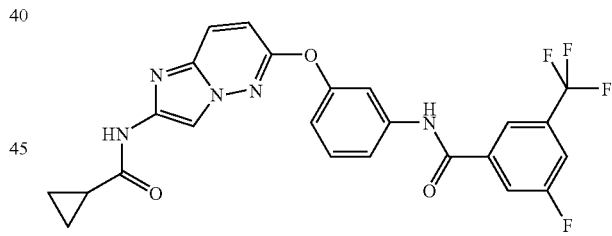

Using N-[6-(3-aminophenoxy)imidazo[1,2-b]pyridazin-2-yl]cyclopropanecarboxamide (309 mg, 1.00 mmol), 3-fluoro-5-(trifluoromethyl)benzoic acid (312 mg, 1.50 mmol), 1-hydroxybenzotriazole (203 mg, 1.50 mmol), 1-ethyl-3-(3-dimethylaminopropyl)carbodiimide hydrochloride (288 mg, 1.50 mmol) and N,N-dimethylformamide (5.0 mL) as starting materials and in the same manner as in Example 106, the title compound (437 mg, 88%) was obtained as a white powder.

$^1$H-NMR (DMSO-d$_6$, 300 MHz) δ 0.79-0.82 (4H, m), 1.88-1.97 (1H, m), 7.04-7.10 (2H, m), 7.47 (1H, t, J=8.4 Hz), 7.64-7.72 (2H, m), 7.96-8.15 (5H, m), 10.63 (1H, s), 11.10 (1H, s).

Example 54

Production of N-[5-({2-[(cyclopropylcarbonyl)amino]imidazo[1,2-b]pyridazin-6-yl}oxy)-2-fluorophenyl]-3-(trifluoromethyl)benzamide

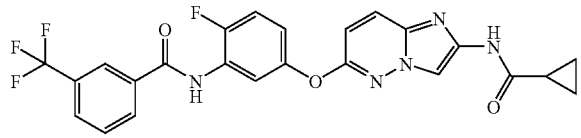

Using N-[6-(3-amino-4-fluorophenoxy)imidazo[1,2-b]pyridazin-2-yl]cyclopropanecarboxamide (163 mg, 0.50 mmol), 3-(trifluoromethyl)benzoic acid (950 mg, 5.00 mmol), 1-hydroxybenzotriazole (676 mg, 5.00 mmol), 1-ethyl-3-(3-dimethylaminopropyl)carbodiimide hydrochloride (959 mg, 5.00 mmol) and N,N-dimethylformamide (5.0 mL) as starting materials and in the same manner as in Example 106, the title compound (160 mg, 64%) was obtained as a white powder.

$^1$H-NMR (DMSO-$d_6$, 300 MHz) δ 0.79-0.81 (4H, m), 1.88-1.95 (1H, m), 7.08-7.25 (2H, m), 7.42 (1H, t, J=9.6 Hz), 7.60-7.79 (2H, m), 7.95-8.07 (3H, m), 8.25-8.30 (2H, m), 10.51 (1H, s), 11.08 (1H, s).

Example 55

Production of N-[3-({2-[(cyclopropylcarbonyl)amino]imidazo[1,2-b]pyridazin-6-yl}oxy)phenyl]-4-fluoro-3-(trifluoromethyl)benzamide

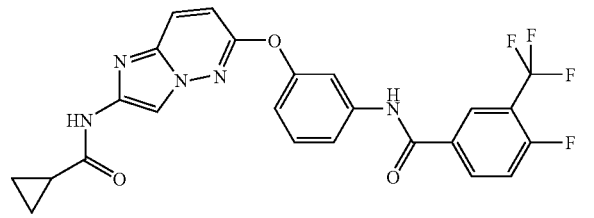

Using N-[6-(3-aminophenoxy)imidazo[1,2-b]pyridazin-2-yl]cyclopropanecarboxamide (309 mg, 1.00 mmol), 4-fluoro-3-(trifluoromethyl)benzoic acid (312 mg, 1.50 mmol), 1-hydroxybenzotriazole (203 mg, 1.50 mmol), 1-ethyl-3-(3-dimethylaminopropyl)carbodiimide hydrochloride (288 mg, 1.50 mmol) and N,N-dimethylformamide (5.0 mL) as starting materials and in the same manner as in Example 106, the title compound (380 mg, 76%) was obtained as a white powder.

$^1$H-NMR (DMSO-$d_6$, 300 MHz) δ 0.80-0.82 (4H, m), 1.88-1.96 (1H, m), 7.02-7.10 (2H, m), 7.46 (1H, t, J=8.1 Hz), 7.63-7.74 (3H, m), 7.98 (1H, s), 8.06-8.36 (3H, m), 10.59 (1H, s), 11.10 (1H, s).

Example 56

Production of N-[4-chloro-5-({2-[(cyclopropylcarbonyl)amino]imidazo[1,2-b]pyridazin-6-yl}oxy)-2-fluorophenyl]-3-(trifluoromethyl)benzamide

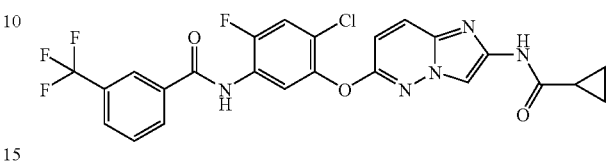

Using N-[6-(3-amino-6-chloro-4-fluorophenoxy)imidazo[1,2-b]pyridazin-2-yl]cyclopropanecarboxamide (181 mg, 0.50 mmol), 3-(trifluoromethyl)benzoic acid (114 mg, 0.60 mmol), 1-hydroxybenzotriazole (81 mg, 0.60 mmol), 1-ethyl-3-(3-dimethylaminopropyl)carbodiimide hydrochloride (115 mg, 0.60 mmol) and N,N-dimethylformamide (5.0 mL) as starting materials and in the same manner as in Example 106, the title compound (54 mg, 20%) was obtained as a white powder.

$^1$H-NMR (DMSO-$d_6$, 300 MHz) δ 0.79-0.82 (4H, m), 1.88-1.94 (1H, m), 7.17 (1H, d, J=9.6 Hz), 7.76-7.85 (3H, m), 7.92 (1H, s), 7.98-8.08 (2H, m), 8.24-8.30 (2H, m), 10.60 (1H, s), 11.08 (1H, s).

Example 57

Production of N-[3-({2-[(cyclopropylcarbonyl)amino]imidazo[1,2-b]pyridazin-6-yl}oxy)phenyl]-2-fluoro-5-(trifluoromethyl)benzamide

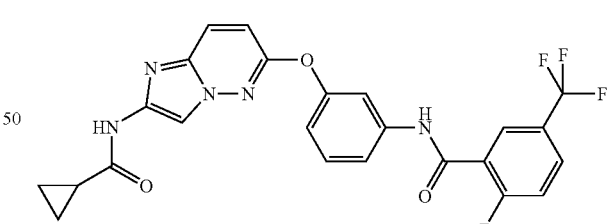

Using N-[6-(3-aminophenoxy)imidazo[1,2-b]pyridazin-2-yl]cyclopropanecarboxamide (309 mg, 1.00 mmol), 2-fluoro-5-(trifluoromethyl)benzoic acid (312 mg, 1.50 mmol), 1-hydroxybenzotriazole (203 mg, 1.50 mmol), 1-ethyl-3-(3-dimethylaminopropyl)carbodiimide hydrochloride (288 mg, 1.50 mmol) and N,N-dimethylformamide (5.0 mL) as starting materials and in the same manner as in Example 106, the title compound (198 mg, 40%) was obtained as a white powder.

$^1$H-NMR (DMSO-d$_6$, 300 MHz) δ 0.79-0.82 (4H, m), 1.88-1.94 (1H, m), 7.02-7.09 (2H, m), 7.43-7.68 (4H, m), 7.98-8.09 (4H, m), 10.76 (1H, s), 11.09 (1H, s).

Example 58

Production of N-[2-chloro-5-({2-[(cyclopropylcarbonyl)amino]imidazo[1,2-b]pyridazin-6-yl}oxy)phenyl]-3-(trifluoromethyl)benzamide

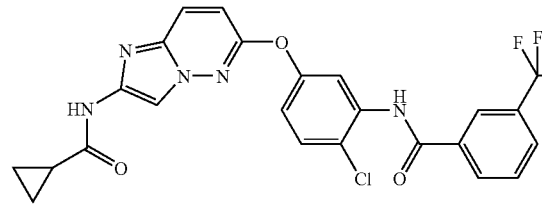

A mixture of N-[6-(3-amino-4-chlorophenoxy)imidazo[1,2-b]pyridazin-2-yl]cyclopropanecarboxamide (103 mg, 0.30 mmol), 3-(trifluoromethyl)benzoyl chloride (75 mg, 0.36 mmol) and N-methylpyrrolidone (3.0 mL) was heated to 50° C., and the mixture was stirred for 10 min. The reaction mixture was poured into saturated aqueous sodium hydrogencarbonate solution, and extracted with ethyl acetate. The extract was dried over anhydrous magnesium sulfate. The solvent was evaporated under reduced pressure, and the residue was purified by silica gel column chromatography (hexane/ethyl acetate=1/19→ethyl acetate) to give the title compound (131 mg, 85%) as a white powder.

$^1$H-NMR (DMSO-d$_6$, 300 MHz) δ 0.78-0.82 (4H, m), 1.90-1.94 (1H, m), 7.10 (1H, d, J=9.9 Hz), 7.27 (1H, dd, J=2.7 Hz, 8.7 Hz), 7.57 (1H, d, J=3.0 Hz), 7.65 (1H, d, J=8.7 Hz), 7.80 (1H, d, J=7.8 Hz), 7.97-8.01 (2H, m), 8.06 (1H, d, J=9.6 Hz), 8.26-8.31 (2H, m), 10.43 (1H, brs), 11.08 (1H, brs).

Example 59

Production of N-[3-({2-[(cyclopropylcarbonyl)amino]imidazo[1,2-b]pyridazin-6-yl}oxy)phenyl]-2-(trifluoromethyl)isonicotinamide

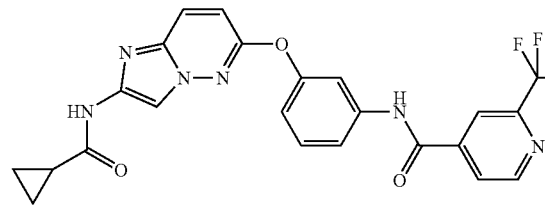

Using N-[6-(3-amino-4-chlorophenoxy)imidazo[1,2-b]pyridazin-2-yl]cyclopropanecarboxamide (103 mg, 0.30 mmol), 2-(trifluoromethyl)isonicotinic acid (86 mg, 0.45 mmol), 1-hydroxybenzotriazole (61 mg, 0.45 mmol), 1-ethyl-3-(3-dimethylaminopropyl)carbodiimide hydrochloride (86 mg, 0.45 mmol) and N,N-dimethylformamide (3.0 mL) as starting materials and in the same manner as in Example 106, the title compound (102 mg, 71%) was obtained as a light blue powder.

$^1$H-NMR (DMSO-d$_6$, 300 MHz) δ 0.78-0.81 (4H, m), 1.89-1.94 (1H, m), 7.05-7.10 (2H, m), 7.48 (1H, t, J=8.1 Hz), 7.64-7.72 (2H, m), 7.98 (1H, s), 8.07-8.35 (3H, m), 8.99 (1H, d, J=5.1 Hz), 10.80 (1H, s), 11.09 (1H, s).

Example 60

Production of N-[2-bromo-5-({2-[(cyclopropylcarbonyl)amino]imidazo[1,2-b]pyridazin-6-yl}oxy)phenyl]-3-(trifluoromethyl)benzamide

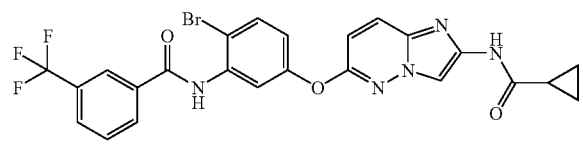

Using N-[6-(3-amino-4-bromophenoxy)imidazo[1,2-b]pyridazin-2-yl]cyclopropanecarboxamide (178 mg, 0.46 mmol), 3-(trifluoromethyl)benzoyl chloride (92 mg, 0.44 mmol), triethylamine (0.14 mL, 1.00 mmol) and tetrahydrofuran (5.0 mL) as starting materials and in the same manner as in Example 96, the title compound (67 mg, 24%) was obtained as a white powder.

$^1$H-NMR (DMSO-d$_6$, 300 MHz) δ 0.79-0.82 (4H, m), 1.90-1.95 (1H, m), 7.11-7.22 (2H, m), 7.54 (1H, d, J=2.7 Hz), 7.77-7.82 (2H, m), 7.97-8.08 (3H, m), 8.26-8.31 (2H, m), 10.43 (1H, s), 11.09 (1H, s).

Example 61

Production of ethyl 6-(3-aminophenoxy)imidazo[1,2-b]pyridazine-2-carboxylate

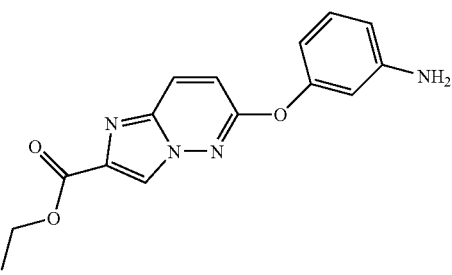

A mixture of ethyl 6-iodoimidazo[1,2-b]pyridazine-2-carboxylate (951 mg, 3.00 mmol), 3-aminophenol (655 mg, 6.00 mmol), potassium carbonate (622 mg, 4.50 mmol) and N,N-dimethylformamide (9.0 mL) was stirred at 150° C. for 6 hr. After allowing the reaction mixture to cool to room temperature, ethyl acetate and water were added to the mixture and the insoluble material was filtered through celite. The organic layer was collected from the filtrate, washed with saturated aqueous sodium hydrogencarbonate solution, and dried over anhydrous magnesium sulfate. The solvent was evaporated under reduced pressure, and the residue was purified by silica gel column chromatography (ethyl acetate/hexane=1/19→ethyl acetate alone) to give the title compound (350 mg, 39%).

¹H-NMR (DMSO-d₆, 300 MHz) δ 1.30 (3H, t, J=7.2 Hz), 4.29 (2H, q, J=7.2 Hz), 5.34 (2H, brs), 6.35-6.48 (3H, m), 7.07 (1H, t, J=8.1 Hz), 7.17 (1H, d, J=9.9 Hz), 8.20 (1H, d, J=9.6 Hz), 8.61 (1H, s).

Example 62

Production of ethyl 6-(3-{[3-(trifluoromethyl)benzoyl]amino}phenoxy)imidazo[1,2-b]pyridazine-2-carboxylate

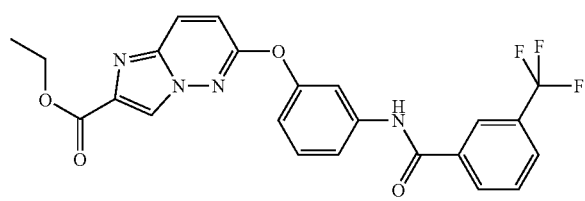

Using ethyl 6-(3-aminophenoxy)imidazo[1,2-b]pyridazine-2-carboxylate (350 mg, 1.17 mmol), 3-(trifluoromethyl)benzoic acid (342 mg, 1.80 mmol), 1-hydroxybenzotriazole (243 mg, 1.80 mmol), 1-ethyl-3-(3-dimethylaminopropyl)carbodiimide hydrochloride (345 mg, 1.80 mmol) and N,N-dimethylformamide (5.0 mL) as starting materials and in the same manner as in Example 106, the title compound (496 mg, 90%) was obtained as a white powder.

¹H-NMR (DMSO-d₆, 300 MHz) δ1.29 (3H, t, J=7.1 Hz), 4.29 (2H, q, J=7.1 Hz), 7.10 (1H, dd, J=1.5 Hz, 7.5 Hz), 7.29 (1H, d, J=9.9 Hz), 7.49 (1H, t, J=8.4 Hz), 7.68-7.82 (3H, m), 7.97-8.00 (1H, m), 8.25-8.28 (3H, m), 8.62 (1H, s), 10.63 (1H, s).

Example 63

Production of 6-(3-{[3-(trifluoromethyl)benzoyl]amino}phenoxy)imidazo[1,2-b]pyridazine-2-carboxylic acid

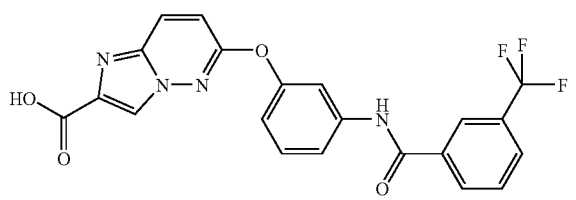

A mixture of ethyl 6-(3-{[3-(trifluoromethyl)benzoyl]amino}phenoxy)imidazo[1,2-b]pyridazine-2-carboxylate (470 mg, 1.00 mmol), 8N aqueous sodium hydroxide solution (2.0 mL) and methanol (6.0 mL) was stirred at room temperature for 4 hr. 6N Hydrochloric acid (2.7 mL) and water (25 mL) were added to the mixture, and the mixture was extracted with ethyl acetate (50 mL). The extract was dried over anhydrous magnesium sulfate, and the solvent was evaporated under reduced pressure to give the title compound (425 mg, 96%) as a white powder.

¹H-NMR (DMSO-d₆, 300 MHz) δ 7.10 (1H, dd, J=2.1 Hz, 7.8 Hz), 7.27 (1H, d, J=9.9 Hz), 7.48 (1H, t, J=7.8 Hz), 7.69-7.82 (3H, m), 7.98 (1H, d, J=7.5 Hz), 8.23-8.29 (3H, m), 8.52 (1H, s), 10.62 (1H, s), 12.85 (1H, brs).

Example 64

Production of tert-butyl [6-(3-{[3-(trifluoromethyl)benzoyl]amino}phenoxy)imidazo[1,2-b]pyridazin-2-yl]carbamate

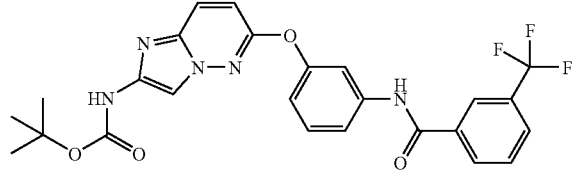

A suspension of 6-(3-{[3-(trifluoromethyl)benzoyl]amino}phenoxy)imidazo[1,2-b]pyridazine-2-carboxylic acid (111 mg, 0.25 mmol), diphenylphosphoryl azide (103 mg, 0.375 mmol), triethylamine (51 mg, 0.5 mmol) and tert-butanol (5.0 mL) was stirred at room temperature for 5 min, heated to 100° C. and stirred overnight. After allowing the reaction mixture to cool to room temperature, ethyl acetate was added to the mixture, and the mixture was washed with saturated aqueous sodium hydrogencarbonate solution, dried over anhydrous magnesium sulfate, and filtrated. The solvent was evaporated under reduced pressure, and the residue was purified by silica gel column chromatography (ethyl acetate/hexane=1/19→ethyl acetate alone) to give the title compound (79 mg, 39%) as a white solid.

¹H-NMR (DMSO-d₆, 300 MHz) δ 1.47 (9H, s), 7.00-7.05 (2H, m), 7.45 (1H, t, J=8.1 Hz), 7.65-7.81 (4H, m), 7.96-8.03 (2H, m), 8.24-8.28 (2H, m), 10.04 (1H, brs), 10.58 (1H, brs).

Example 65

Production of 6-(3-{[3-(1-cyano-1-methylethyl)benzoyl]amino}phenoxy)imidazo[1,2-b]pyridazine-2-carboxylic acid

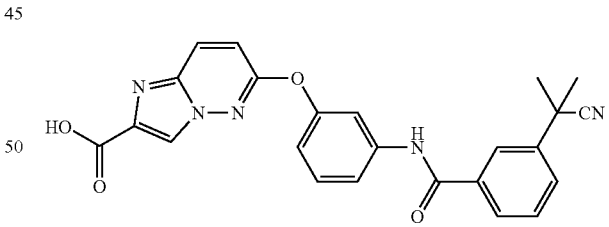

To a mixture of 3-(1-cyano-1-methylethyl)benzoic acid (454 mg, 2.40 mmol), tetrahydrofuran (10 mL) and N,N-dimethylformamide (0.01 mL) was added oxalyl chloride (366 mg, 2.88 mmol), and the mixture was stirred at room temperature for 2 hr. The solvent was evaporated under reduced pressure, tetrahydrofuran was added to the residue, and the mixture was azeotroped twice. The residue was dissolved in N-methylpyrrolidone (4 mL), added to a solution of ethyl 6-(3-aminophenoxy)imidazo[1,2-b]pyridazine-2-carboxylate (350 mg, 1.17 mmol) in N-methylpyrrolidone (6 mL), and the mixture was stirred at room temperature for 2 hr. Ethyl acetate was added to the reaction mixture, and the mixture was washed with saturated aqueous sodium hydrogencarbonate solution, dried over anhydrous magnesium sulfate, and filtrated. To the residue were added 8N aqueous sodium hydroxide solution (4.0 mL) and methanol (10.0 mL), and the mixture was stirred at room temperature for 10 min. 6N Hydrochloric acid (5.0 mL) and water (60 mL) were added to the mixture, and the mixture was extracted with ethyl acetate (150 mL). The extract was dried over anhydrous magnesium sulfate, and the solvent was evaporated under reduced pressure. The residue was washed with hexane to give the title compound (828 mg, 94%) as a white powder.

$^1$H-NMR (DMSO-$d_6$, 300 MHz) δ1.75 (6H, s), 7.08 (1H, dd, J=1.5 Hz, 8.4 Hz), 7.27 (1H, d, J=9.6 Hz), 7.47 (1H, t, J=7.8 Hz), 7.60-7.77 (4H, m), 7.92-8.03 (2H, m), 8.24 (1H, d, J=10.2 Hz), 8.52 (1H, s), 10.46 (1H, s), 12.81 (1H, brs).

Example 66

Production of tert-butyl [6-(3-{[3-(1-cyano-1-methylethyl)benzoyl]amino}phenoxy)imidazo[1,2-b]pyridazin-2-yl]carbamate

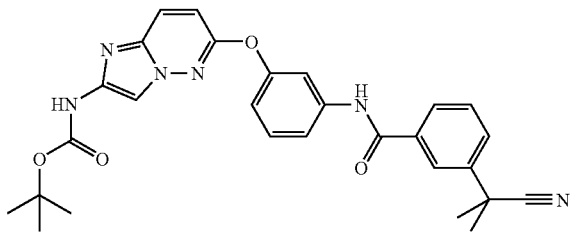

Using 6-(3-{[3-(1-cyano-1-methylethyl)benzoyl]amino}phenoxy)imidazo[1,2-b]pyridazine-2-carboxylic acid (826 mg, 1.87 mmol), diphenylphosphoryl azide (771 mg, 2.81 mmol), triethylamine (381 mg, 3.74 mmol) and tert-butanol (30.0 mL), and in the same manner as in Example 64, the title compound (682 mg, 71%) was obtained as a white powder.

$^1$H-NMR (DMSO-$d_6$, 300 MHz) δ 1.47 (9H, s), 1.74 (6H, s), 6.99-7.05 (2H, m), 7.44 (1H, t, J=8.4 Hz), 7.57-7.77 (5H, m), 7.91-7.94 (1H, m), 8.00-8.03 (2H, m), 10.04 (1H, brs), 10.43 (1H, s).

Example 67

Production of N-[6-(4-amino-3-nitrophenoxy)imidazo[1,2-b]pyridazin-2-yl]cyclopropanecarboxamide

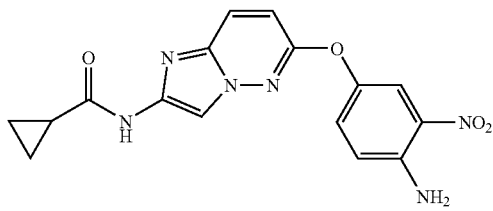

A mixture of N-(6-iodoimidazo[1,2-b]pyridazin-2-yl)cyclopropanecarboxamide (656 mg, 2.00 mmol), 4-amino-3-nitrophenol (616 mg, 4.00 mmol), potassium carbonate (411 mg, 3.00 mmol) and N,N-dimethylformamide (6.0 mL) was stirred at 150° C. for 3 hr. After allowing the reaction mixture to cool to room temperature, ethyl acetate (100 mL), tetrahydrofuran (40 mL) and water (40 mL) were added to the mixture, and the insoluble material was filtered through celite. The organic layer was collected from the filtrate, washed with saturated aqueous sodium hydrogencarbonate solution, dried over anhydrous magnesium sulfate, and filtrated. Dichloromethane (20 mL) was added to the residue, and the precipitate was collected by filtration to give the title compound (367 mg, 52%). The filtrate was evaporated under reduced pressure, and the residue was purified by silica gel column chromatography (ethyl acetate/hexane=1/19→ethyl acetate alone) to give the title compound (125 mg, 18%) as a white solid.

$^1$H-NMR (DMSO-$d_6$, 300 MHz) δ0.78-0.81 (4H, m), 1.84-1.91 (1H, m), 7.04 (1H, d, J=9.3 Hz), 7.11 (1H, d, J=9.3 Hz), 7.44 (1H, dd, J=3.0 Hz, 9.3 Hz), 7.51 (2H, m), 7.83 (1H, d, J=2.4 Hz), 7.91 (1H, s), 8.01 (1H, d, J=9.3 Hz), 11.04 (1H, s).

Example 68

Production of N-{6-[(2-{[4-(trifluoromethyl)phenyl]amino}-1H-benzimidazol-6-yl)oxy]imidazo[1,2-b]pyridazin-2-yl}cyclopropanecarboxamide

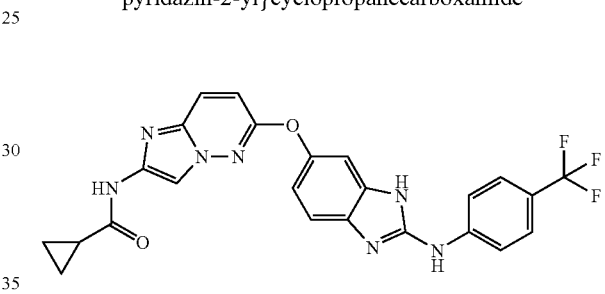

A suspension of N-[6-(4-amino-3-nitrophenoxy)imidazo[1,2-b]pyridazin-2-yl]cyclopropanecarboxamide (499 mg, 1.38 mmol), 10% palladium carbon (100 mg) and methanol (20.0 mL) was stirred under a hydrogen atmosphere (up to 1 atm) at room temperature overnight. The insoluble material was filtered through celite, and the filtrate was evaporated under reduced pressure. The residue was dissolved in methanol (10 mL), 4-(trifluoromethyl)phenylisothiocyanate (120 mg, 0.59 mmol) was added to the mixture, and the mixture was stirred at room temperature for 1 hr. Iron (III) chloride (177 mg, 1.1 mmol) was added to the reaction mixture, and the mixture was further stirred at room temperature for 1.5 hr. Ethyl acetate was added to the reaction mixture, and the mixture was washed with saturated aqueous sodium hydrogencarbonate solution, dried over anhydrous magnesium sulfate, and filtrated. Dichloromethane (20 mL) was added to the residue, and the precipitate was collected by filtration to give the title compound (367 mg, 52%). The filtrate was evaporated under reduced pressure, and the residue was purified by silica gel column chromatography (ethyl acetate alone→ethyl acetate/methanol=9:1). Ethyl acetate was added to the obtained oily substance, and the precipitate was collected by filtration to give the title compound (116 mg, 32%) as a pale-yellow solid.

¹H-NMR (DMSO-d₆, 300 MHz) δ 0.78-0.81 (4H, m), 1.88-1.94 (1H, m), 6.90-7.02 (2H, m), 7.22-7.39 (2H, m), 7.65-8.01 (6H, m), 9.98 (1H, d, J=8.1 Hz), 11.03 (1H, s), 11.20 (1H, d, J=16.2 Hz).

Example 69

Production of N-{3-[(2-aminoimidazo[1,2-b]pyridazin-6-yl)oxy]phenyl}-3-(trifluoromethyl)benzamide

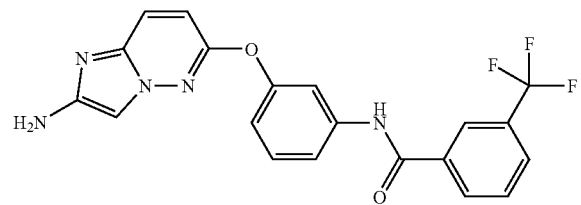

A mixture of tert-butyl [6-(3-{[3-(trifluoromethyl)benzoyl]amino}phenoxy)imidazo[1,2-b]pyridazin-2-yl]carbamate (2.37 g, 4.62 mmol), 4N hydrochloric acid-ethyl acetate solution (50 mL) and methanol (50 mL) was stirred at room temperature for 6 hr. The solvent was evaporated under reduced pressure, saturated aqueous sodium hydrogencarbonate solution was added to the residue, and the mixture was extracted with ethyl acetate. The extract was dried over anhydrous magnesium sulfate and evaporated under reduced pressure, and the residue was purified by silica gel column chromatography (ethyl acetate alone→ethyl acetate/methanol=4:1) to give the title compound (1.57 g, 82%) as a green solid.

¹H-NMR (DMSO-d₆, 300 MHz) δ 5.33 (2H, brs), 6.80 (1H, d, J=9.0 Hz), 6.94 (1H, m), 7.15 (1H, s), 7.42 (1H, t, J=7.8 Hz), 7.63-7.80 (4H, m), 7.97 (1H, d, J=7.5 Hz), 8.23-8.27 (2H, m), 10.54 (1H, s).

Example 70

Production of N-{3-[(2-{[2-(methylamino)pyrimidin-4-yl]amino}imidazo[1,2-b]pyridazin-6-yl)oxy]phenyl}-3-(trifluoromethyl)benzamide

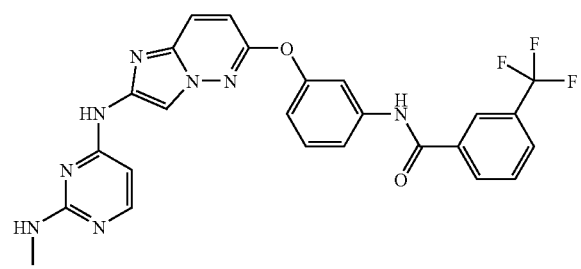

A mixture of N-[3-({2-[(2-chloropyrimidin-4-yl)amino]imidazo[1,2-b]pyridazin-6-yl}oxy)phenyl]-3-(trifluoromethyl)benzamide (122 mg, 0.23 mmol), 2M methylamine-tetrahydrofuran solution (3.0 mL) and ethanol (6.0 mL) was heated to 70° C., and the mixture was stirred overnight. Ethyl acetate was added to the reaction mixture, and the mixture was washed with saturated aqueous sodium hydrogencarbonate solution, dried over anhydrous magnesium sulfate, and filtrated, and the residue was purified by silica gel column chromatography (ethyl acetate alone→ethyl acetate/methanol=4:1). The obtained residue was washed with ethyl acetate-hexane to give the title compound (60 mg, 50%) as a yellow solid.

¹H-NMR (DMSO-d₆, 300 MHz) δ 2.76 (3H, m), 6.15 (1H, d, J=5.1 Hz), 6.85 (1H, m), 7.04-7.07 (2H, m), 7.47 (1H, t, J=8.1 Hz), 7.68-8.02 (6H, m), 8.24-8.28 (2H, m), 8.44 (1H, m), 9.96 (1H, brs), 10.59 (1H, s).

Example 71

Production of N-[3-({2-[(2-chloropyrimidin-4-yl)amino]imidazo[1,2-b]pyridazin-6-yl}oxy)phenyl]-3-(trifluoromethyl)benzamide

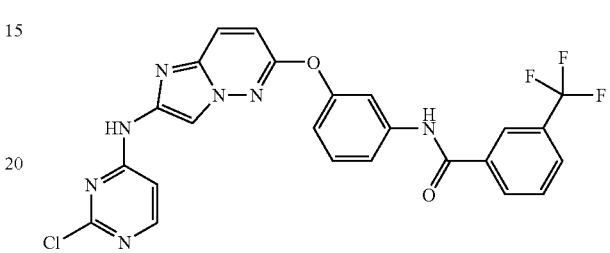

To a solution of N-{3-[(2-aminoimidazo[1,2-b]pyridazin-6-yl)oxy]phenyl}-3-(trifluoromethyl)benzamide (103 mg, 0.25 mmol) in tetrahydrofuran (15 mL) was added sodium hydride (60% in oil, 80 mg, 2.0 mmol), and the mixture was stirred at room temperature for 10 min. 2,4-Dichloropyrimidine (149 mg, 1.00 mmol) was added to the reaction mixture, and the mixture was heated to 60° C. After 1 hr, the reaction mixture was cooled to room temperature and ethyl acetate was added thereto. The mixture was washed with saturated aqueous sodium hydrogencarbonate solution, dried over anhydrous magnesium sulfate, and filtrated. The residue was purified by silica gel column chromatography (ethyl acetate/hexane=1/19→ethyl acetate alone) and the obtained solid was washed with ethyl acetate/hexane (=1/2) to give the title compound (27 mg, 21%) as a light blue solid.

¹H-NMR (DMSO-d₆, 300 MHz) δ 6.97-7.17 (3H, m), 7.48 (1H, t, J=8.1 Hz), 7.68-8.00 (4H, m), 8.08-8.29 (5H, m), 10.61 (1H, brs), 10.93 (1H, brs).

Example 72

Production of N-(3-{[2-(1,3-thiazol-2-ylamino)imidazo[1,2-b]pyridazin-6-yl]oxy}phenyl)-3-(trifluoromethyl)benzamide

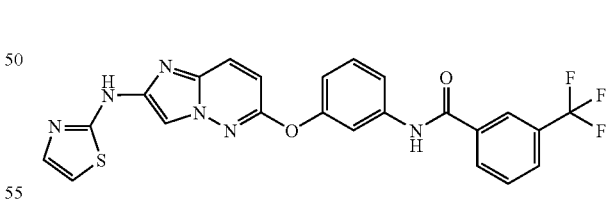

A mixture of N-{3-[(2-aminoimidazo[1,2-b]pyridazin-6-yl)oxy]phenyl}-3-(trifluoromethyl)benzamide (165 mg, 0.4 mmol), tris(dibenzylideneacetone)dipalladium (0) (37 mg, 0.04 mmol), (9,9-dimethyl-9H-xanthene-4,5-diyl)bis(diphenylphosphine) (46 mg, 0.03 mmol), sodium t-butoxide (77 mg, 0.8 mmol), 2-bromothiazole (98 mg, 0.6 mmol) and N,N-dimethylacetamide (2 mL) was heated to 70° C. under nitrogen atmosphere, and the mixture was stirred for 2 hr. After allowing the reaction mixture to cool to room temperature, ethyl acetate was added to the mixture, and the mixture was washed with saturated aqueous sodium hydrogencarbonate solution, dried over anhydrous magnesium sulfate, and filtrated. The residue was purified by silica gel column chromatography (ethyl acetate/hexane=1/19→ethyl acetate alone) to give the title compound (10 mg, 5%) as a light blue solid.

$^1$H-NMR (DMSO-d$_6$, 300 MHz) δ 6.92-7.27 (4H, m), 7.46 (1H, t, J=7.8 Hz), 7.67-8.06 (6H, m), 8.24-8.28 (2H, m), 10.58 (1H, brs), 10.90 (1H, brs).

Example 73

Production of N-(3-{[2-(hydroxymethyl)imidazo[1,2-b]pyridazin-6-yl]oxy}phenyl)-1,3-dimethyl-1H-pyrazole-5-carboxamide

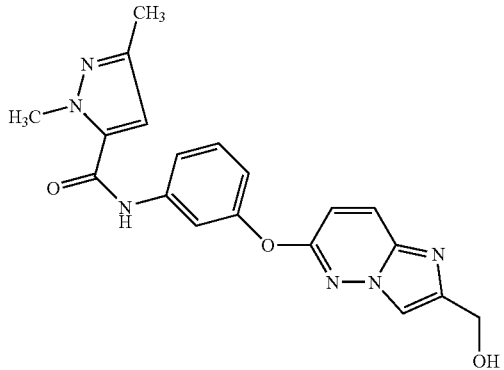

To a solution of (6-iodoimidazo[1,2-b]pyridazin-2-yl)methanol (400 mg, 1.45 mmol) in N,N-dimethylformamide (4.0 mL) were added N-(3-hydroxyphenyl)-1,3-dimethyl-1H-pyrazole-5-carboxamide (504 mg, 2.18 mmol) and potassium carbonate (402 mg, 2.91 mmol), and the mixture was stirred at 150° C. for 16 hr. After cooling the mixture to room temperature, water was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was purified by silica gel column chromatography (ethyl acetate/ethanol=100/0→10/1) to give the title compound (70 mg, 13%) as a white powder.

$^1$H-NMR (DMSO-d$_6$, 300 MHz) δ 2.19 (3H, s), 3.98 (3H, s), 4.55 (1H, d, J=5.4 Hz), 5.19 (1H, d, J=5.4 Hz), 6.82 (1H, s), 6.98-7.03 (1H, m), 7.08 (1H, d, J=9.6 Hz), 7.39-7.46 (1H, m), 7.59-7.63 (1H, m), 7.66-7.68 (1H, m), 7.88 (1H, s), 8.10 (1H, d, J=9.6 Hz), 10.23 (1H, s).

Example 74

Production of N-[4-({2-[(cyclopropylcarbonyl)amino]imidazo[1,2-b]pyridazin-6-yl}oxy)phenyl]-5-methyl-1-phenyl-1H-pyrazole-3-carboxamide

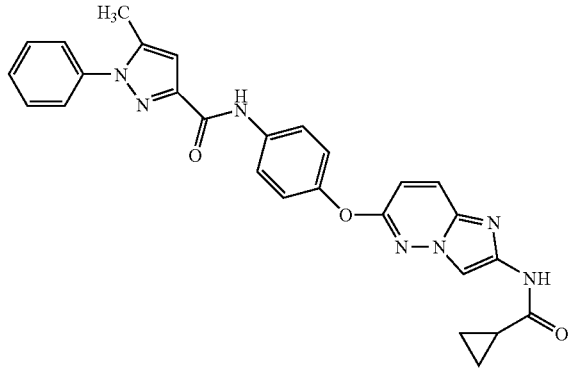

Using 5-methyl-1-phenyl-1H-pyrazole-3-carboxylic acid (196 mg, 0.97 mmol), tetrahydrofuran (2.0 mL), N,N-dimethylformamide (30 μL, 0.39 mmol), oxalyl chloride (85 μL, 0.97 mmol), N-[6-(4-aminophenoxy)imidazo[1,2-b]pyridazin-2-yl]cyclopropanecarboxamide (200 mg, 0.65 mmol) and N,N-dimethylacetamide (4.0 mL), and in the same manner as in Example 255, the title compound (223 mg, 70%) was obtained as a white powder.

$^1$H-NMR (DMSO-d$_6$, 300 MHz) δ 0.76-0.83 (4H, m), 1.86-1.96 (1H, m), 2.31 (3H, s), 6.85 (1H, s), 7.02 (1H, d, J=9.6 Hz), 7.23 (2H, d, J=9.3 Hz), 7.36-7.46 (5H, m), 7.71 (2H, J=9.3 Hz), 7.92 (1H, s), 8.01 (1H, d, J=9.6 Hz), 10.62 (1H, s), 11.05 (1H, s).

Example 75

Production of N-[4-({2-[(cyclopropylcarbonyl)amino]imidazo[1,2-b]pyridazin-6-yl}oxy)phenyl]-3-methyl-1-phenyl-1H-pyrazole-5-carboxamide

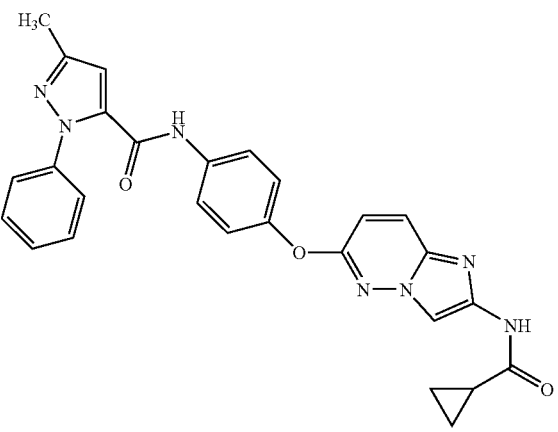

Using 3-methyl-1-phenyl-1H-pyrazole-5-carboxylic acid (196 mg, 0.97 mmol), tetrahydrofuran (2.0 mL), N,N-dimethylformamide (30 μL, 0.39 mmol), oxalyl chloride (85 μL, 0.97 mmol), N-[6-(4-aminophenoxy)imidazo[1,2-b]pyridazin-2-yl]cyclopropanecarboxamide (200 mg, 0.65 mmol) and N,N-dimethylacetamide (4.0 mL), and in the same manner as in Example 255, the title compound (209 mg, 65%) was obtained as a white powder.

$^1$H-NMR (DMSO-d$_6$, 300 MHz) δ 0.77-0.83 (4H, m), 1.86-1.96 (1H, m), 2.36 (3H, s), 6.80 (1H, s), 7.03 (1H, d, J=9.5 Hz), 7.21-7.25 (2H, m), 7.48-7.67 (5H, m), 7.86-7.91 (2H, m), 7.92 (1H, s), 8.01 (1H, d, J=9.5 Hz), 10.18 (1H, s), 11.05 (1H, s).

Example 76

Production of 1-benzyl-N-[5-({2-[(cyclopropylcarbonyl)amino]imidazo[1,2-b]pyridazin-6-yl}oxy)-2-fluorophenyl]-1H-pyrrole-3-carboxamide

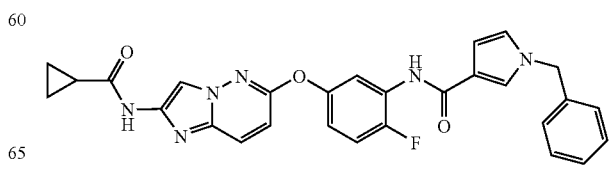

Using 1-benzyl-1H-pyrrole-3-carboxylic acid (276 mg, 1.37 mmol), tetrahydrofuran (3.0 mL), N,N-dimethylformamide (20 μL, 0.26 mmol), oxalyl chloride (120 μL, 1.37 mmol), N-[6-(3-amino-4-fluorophenoxy)imidazo[1,2-b]pyridazin-2-yl]cyclopropanecarboxamide (300 mg, 0.92 mmol) and N,N-dimethylacetamide (6.0 mL), and in the same manner as in Example 249, the title compound (114 mg, 24%) was obtained as a white powder.

$^1$H-NMR (DMSO-d$_6$, 300 MHz) δ 0.77-0.83 (4H, m), 1.85-1.96 (1H, m), 5.15 (2H, s), 6.62-6.64 (1H, m), 6.88-6.92 (1H, m), 7.05 (1H, d, J=9.6 Hz), 7.07-7.12 (1H, m), 7.23-7.62 (6H, m), 7.56-7.62 (2H, m), 7.93 (1H, s), 8.03 (1H, d, J=9.6 Hz), 9.43 (1H, s), 11.07 (1H, s).

Example 77

Production of N-[3-({2-[(cyclopropylcarbonyl)amino]imidazo[1,2-b]pyridazin-6-yl}oxy)phenyl]-3-methyl-1-phenyl-1H-pyrazole-5-carboxamide

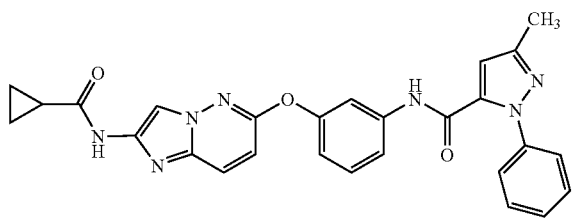

Using 3-methyl-1-phenyl-1H-pyrazole-5-carboxylic acid (294 mg, 1.45 mmol), tetrahydrofuran (3.0 mL), N,N-dimethylformamide (30 μL, 0.39 mmol), oxalyl chloride (127 μL, 1.45 mmol), N-[6-(3-aminophenoxy)imidazo[1,2-b]pyridazin-2-yl]cyclopropanecarboxamide (300 mg, 0.97 mmol) and N,N-dimethylacetamide (6.0 mL), and in the same manner as in Example 255, the title compound (342 mg, 71%) was obtained as a white powder.

$^1$H-NMR (DMSO-d$_6$, 300 MHz) δ 0.75-0.86 (4H, m), 1.85-1.95 (1H, m), 2.34 (3H, s), 6.78 (1H, s), 6.92-6.98 (1H, m), 7.05 (1H, d, J=9.9 Hz), 7.33-7.43 (1H, m), 7.46-7.66 (5H, m), 7.69-7.78 (2H, m), 7.97 (1H, s), 8.04 (1H, d, J=9.9 Hz), 10.21 (1H, s), 11.08 (1H, s).

Example 78

Production of N-[3-({2-[(cyclopropylcarbonyl)amino]imidazo[1,2-b]pyridazin-6-yl}oxy)phenyl]-5-methyl-1-phenyl-1H-pyrazole-3-carboxamide

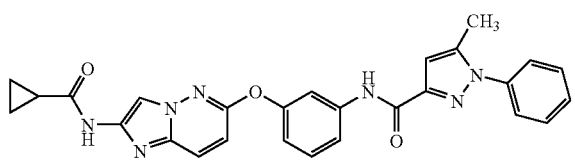

Using 5-methyl-1-phenyl-1H-pyrazole-3-carboxylic acid (294 mg, 1.45 mmol), tetrahydrofuran (3.0 mL), N,N-dimethylformamide (30 μL, 0.39 mmol), oxalyl chloride (127 μL, 1.45 mmol), N-[6-(3-aminophenoxy)imidazo[1,2-b]pyridazin-2-yl]cyclopropanecarboxamide (300 mg, 0.97 mmol) and N,N-dimethylacetamide (6.0 mL), and in the same manner as in Example 255, the title compound (317 mg, 66%) was obtained as a white powder.

$^1$H-NMR (DMSO-d$_6$, 300 MHz) δ 0.76-0.84 (4H, m), 1.84-1.96 (1H, m), 2.29 (3H, s), 6.85 (1H, s), 6.96-7.01 (1H, m), 7.04 (1H, d, J=9.6 Hz), 7.30-7.58 (8H, m), 7.95 (1H, s), 8.03 (1H, d, J=9.6 Hz), 10.64 (1H, s), 11.08 (1H, s).

Example 79

Production of N-[3-({2-[(cyclopropylcarbonyl)amino]imidazo[1,2-b]pyridazin-6-yl}thio)phenyl]-3-methyl-1-phenyl-1H-pyrazole-5-carboxamide

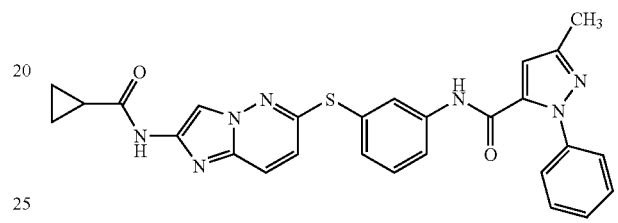

Using 3-methyl-1-phenyl-1H-pyrazole-5-carboxylic acid (186 mg, 0.92 mmol), tetrahydrofuran (2.0 mL), N,N-dimethylformamide (30 μL, 0.39 mmol), oxalyl chloride (80 μL, 0.92 mmol), N-{6-[(3-aminophenyl)thio]imidazo[1,2-b]pyridazin-2-yl}cyclopropanecarboxamide (200 mg, 0.61 mmol) and N,N-dimethylacetamide (4.0 mL), and in the same manner as in Example 255, the title compound (203 mg, 65%) was obtained as a white powder.

$^1$H-NMR (DMSO-d$_6$, 300 MHz) δ 0.78-0.84 (4H, m), 1.86-1.96 (1H, m), 2.35 (3H, s), 6.78 (1H, s), 6.89-6.94 (1H, m), 7.27-7.31 (1H, m), 7.40-7.65 (7H, m), 7.86-7.95 (2H, m), 8.09-8.24 (1H, m), 10.25 (1H, s), 11.17 (1H, s).

Example 80

Production of N-[3-({2-[(cyclopropylcarbonyl)amino]imidazo[1,2-b]pyridazin-6-yl}thio)phenyl]-5-methyl-1-phenyl-1H-pyrazole-3-carboxamide

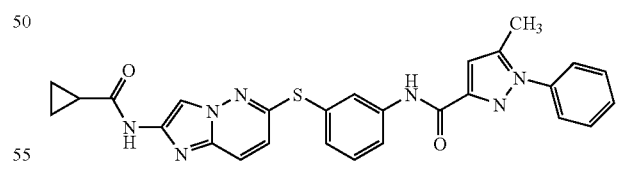

Using 5-methyl-1-phenyl-1H-pyrazole-3-carboxylic acid (196 mg, 0.97 mmol), tetrahydrofuran (2.0 mL), N,N-dimethylformamide (30 μL, 0.39 mmol), oxalyl chloride (80 μL, 0.92 mmol), N-{6-[(3-aminophenyl)thio]imidazo[1,2-b]pyridazin-2-yl}cyclopropanecarboxamide (200 mg, 0.61 mmol) and N,N-dimethylacetamide (4.0 mL), and in the same manner as in Example 255, the title compound (155 mg, 49%) was obtained as a white powder.

$^1$H-NMR (DMSO-d$_6$, 300 MHz) δ 0.78-0.86 (4H, m), 1.85-1.96 (1H, m), 2.29 (3H, s), 6.86 (1H, s), 6.94 (1H, d,

J=9.3 Hz), 7.29-7.46 (7H, m), 7.71-7.76 (1H, m), 7.87 (1H, s), 7.88 (1H, d, J=9.3 Hz), 8.12 (1H, s), 10.63 (1H, s), 11.16 (1H, s).

Example 81

Production of N-[6-(3-amino-4-methylphenoxy)imidazo[1,2-b]pyridazin-2-yl]-2-methylcyclopropanecarboxamide

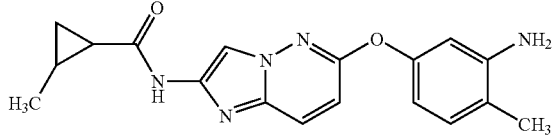

Using 3-amino-4-methylphenol (1.08 g, 8.77 mmol), N,N-dimethylformamide (30.0 mL), potassium tert-butoxide (1.02 g, 9.13 mmol), N-(6-iodoimidazo[1,2-b]pyridazin-2-yl)-2-methylcyclopropanecarboxamide (2.5 g, 7.31 mmol) and potassium carbonate (0.51 g, 3.65 mmol), and in the same manner as in Example 216, the title compound (1.38 g, 56%) was obtained as a brown powder.

$^1$H-NMR (DMSO-$d_6$, 300 MHz) δ 0.61-0.69 (1H, m), 0.96-1.05 (1H, m), 1.06-1.09 (3H, m), 1.19-1.27 (1H, m), 1.63-1.72 (1H, m), 2.04 (3H, s), 5.05 (2H, s), 6.27 (1H, dd, J=8.0, 2.4 Hz), 6.41 (1H, d, J=2.4 Hz), 6.92 (1H, d, J=9.5 Hz), 6.94 (1H, d, J=8.0 Hz), 7.94 (1H, s), 7.96 (1H, d, J=9.5 Hz), 10.96 (1H, s).

Example 82

Production of N-[6-(3-amino-4-fluorophenoxy)imidazo[1,2-b]pyridazin-2-yl]-2-methylcyclopropanecarboxamide

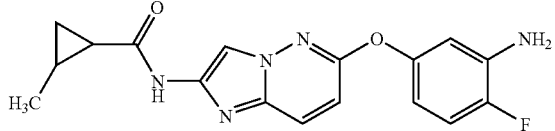

To a solution of 3-amino-4-fluorophenol (0.42 g, 3.29 mmol) in N,N-dimethylformamide (9.0 mL) were added N-(6-iodoimidazo[1,2-b]pyridazin-2-yl)-2-methylcyclopropanecarboxamide (0.75 g, 2.19 mmol) and potassium carbonate (0.61 g, 4.38 mmol), and the mixture was stirred at 140° C. for 16 hr. Saturated brine was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was purified by silica gel column chromatography (ethyl acetate alone), and the obtained residue was washed with hexane/ethyl acetate and filtrated to give the title compound (0.63 g, 88%) as a brown powder.

1H-NMR (DMSO-$d_6$, 300 MHz) δ 0.62-0.74 (1H, m), 0.96-1.04 (1H, m), 1.07-1.09 (3H, m), 1.17-1.28 (1H, m), 1.62-1.72 (1H, m), 5.36 (2H, s), 6.30-6.36 (1H, m), 6.57 (1H, dd, J=7.8, 2.7 Hz), 6.96 (1H, d, J=9.6 Hz), 7.02 (1H, dd, J=11.4, 8.7 Hz), 7.94 (1H, s), 7.96-8.00 (1H, m), 10.97 (1H, s).

Example 83

Production of N-[6-(3-amino-4-chlorophenoxy)imidazo[1,2-b]pyridazin-2-yl]-2-methylcyclopropanecarboxamide

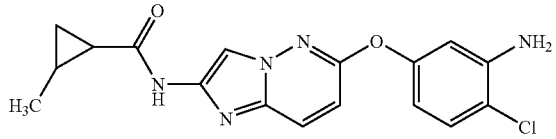

Using 3-amino-4-chlorophenol (1.57 g, 11.0 mmol), N,N-dimethylformamide (25.0 mL), N-(6-iodoimidazo[1,2-b]pyridazin-2-yl)-2-methylcyclopropanecarboxamide (2.50 g, 7.31 mmol) and potassium carbonate (2.02 g, 14.6 mmol), and in the same manner as in Example 82, the title compound (1.92 g, 73%) was obtained as a brown powder.

$^1$H-NMR (DMSO-$d_6$, 300 MHz) δ 0.61-0.72 (1H, m), 0.97-1.04 (1H, m), 1.07-1.12 (3H, m), 1.17-1.28 (1H, m), 1.63-1.73 (1H, m), 5.54 (2H, s), 6.39 (1H, dd, J=8.6, 2.9 Hz), 6.60 (1H, d, J=2.9 Hz), 6.99 (1H, d, J=9.5 Hz), 7.22 (1H, dd, J=8.6 Hz), 7.96 (1H, s), 8.00 (1H, d, J=8.6 Hz), 10.98 (1H, s).

Example 84

Production of N-[5-({2-[(cyclopropylcarbonyl)amino]imidazo[1,2-b]pyridazin-6-yl}oxy)-2-methylphenyl]-4-methyl-2-oxo-2,3-dihydro-1,3-oxazole-5-carboxamide

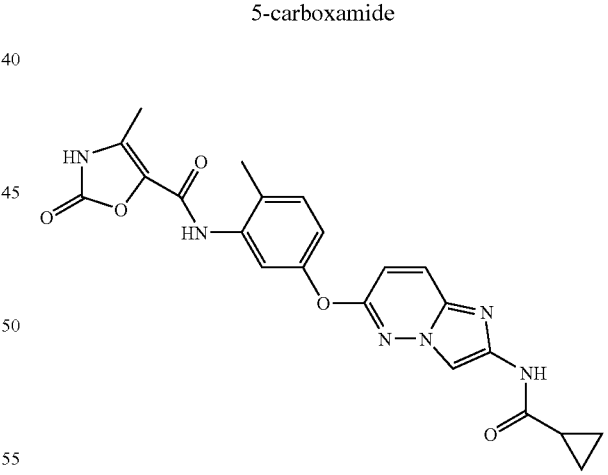

In the same manner as in Example 259 and using 4-methyl-2-oxo-2,3-dihydro-1,3-oxazole-5-carboxylic acid (159 mg, 1.1 mmol), tetrahydrofuran (5 mL), N,N-dimethylformamide (1 drop), oxalyl chloride (382 μL, 4.44 mmol), N-[6-(3-amino-4-methylphenoxy)imidazo[1,2-b]pyridazin-2-yl]cyclopropanecarboxamide (300 mg, 0.93 mmol) and N,N-dimethylacetamide (7 mL) as starting materials, the title compound (145 mg, 35%) was obtained as a white solid.

$^1$H-NMR (DMSO-$d_6$, 300 MHz) δ 0.76-0.84 (4H, m), 1.86-1.97 (1H, m), 2.22 (3H, s), 2.27 (3H, s), 6.98-7.09 (2H, m), 7.24-7.33 (2H, m), 7.94 (1H, s), 8.02 (1H, d, J=9.6 Hz), 9.41 (1H, s), 11.07 (1H, s), 11.46 (1H, brs).

Example 85

Production of N-[5-({2-[(cyclopropylcarbonyl)amino]imidazo[1,2-b]pyridazin-6-yl}oxy)-2-methylphenyl]-1,5-dimethyl-1H-pyrazole-3-carboxamide

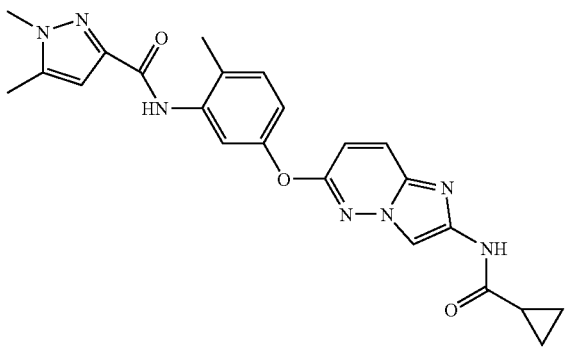

In the same manner as in Example 259 and using 1,5-dimethyl-1H-pyrazole-3-carboxylic acid (145 mg, 1.0 mmol), tetrahydrofuran (5 mL), N,N-dimethylformamide (1 drop), oxalyl chloride (320 µL, 4.44 mmol), N-[6-(3-amino-4-methylphenoxy)imidazo[1,2-b]pyridazin-2-yl]cyclopropanecarboxamide (250 mg, 0.77 mmol) and N,N-dimethylacetamide (7 mL) as starting materials, the title compound (57 mg, 17%) was obtained as a white solid.

$^1$H-NMR (DMSO-$d_6$, 300 MHz) δ 0.76-0.86 (4H, m), 1.87-1.97 (1H, m), 2.27 (3H, s), 2.30 (3H, s), 3.83 (3H, s), 6.53 (1H, s), 6.97-7.06 (2H, m), 7.25-7.34 (1H, m), 7.61 (1H, d, J=2.3 Hz), 7.92-7.97 (1H, m), 8.02 (1H, d, J=9.5 Hz), 9.35 (1H, s), 11.07 (1H, s).

Example 86

Production of N-[5-({2-[(cyclopropylcarbonyl)amino]imidazo[1,2-b]pyridazin-6-yl}oxy)-2-methylphenyl]-1,3-dimethyl-4,5-dihydro-1H-pyrazole-5-carboxamide

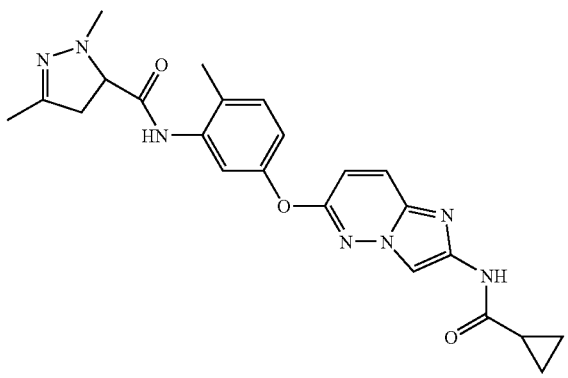

In the same manner as in Example 278 and using 1,3-dimethyl-4,5-dihydro-1H-pyrazole-5-carboxylic acid (120 mg, 0.87 mmol), N-[6-(3-amino-4-methylphenoxy)imidazo[1,2-b]pyridazin-2-yl]cyclopropanecarboxamide (200 mg, 0.62 mmol), O-(7-azabenzotriazol-1-yl)-N,N',N'-tetramethyluronium hexafluorophosphate (330 mg, 0.87 mmol), N,N-diisopropylethylamine (240 mg, 1.8 mmol) and N,N-dimethylformamide (7 mL) as starting materials, the title compound (199 mg, 72%) was obtained as a white solid.

$^1$H-NMR (DMSO-$d_6$, 300 MHz) δ 0.72-0.86 (4H, m), 1.87 (3H, s), 1.89-1.97 (1H, m), 2.23 (3H, s), 2.74 (3H, s), 2.77-2.87 (1H, m), 2.98-3.13 (1H, m), 3.57 (1H, m), 6.95-7.07 (2H, m), 7.30 (1H, d, J=8.3 Hz), 7.51 (1H, d, J=2.3 Hz), 7.92 (1H, s), 8.02 (1H, d, J=9.8 Hz), 9.43 (1H, s), 11.07 (1H, s).

Example 87

Production of N-[5-({2-[(cyclopropylcarbonyl)amino]imidazol[1,2-b]pyridazin-6-yl}oxy)-2-fluorophenyl]-1,3-dimethyl-4,5-dihydro-1H-pyrazole-5-carboxamide

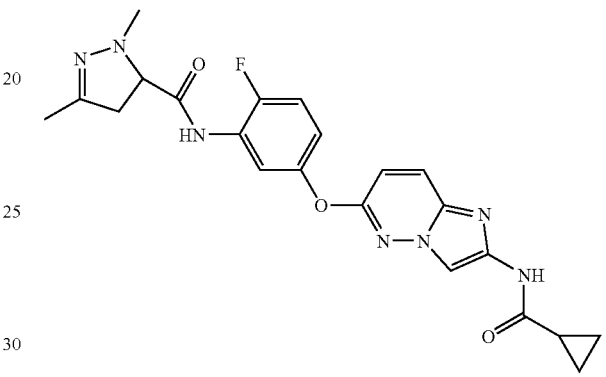

In the same manner as in Example 278 and using 1,3-dimethyl-4,5-dihydro-1H-pyrazole-5-carboxylic acid (170 mg, 1.2 mmol), N-[6-(3-amino-4-fluorophenoxy)imidazo[1,2-b]pyridazin-2-yl]cyclopropanecarboxamide (280 mg, 0.84 mmol), O-(7-azabenzotriazol-1-yl)-N,N,N',N'-tetramethyluronium hexafluorophosphate (450 mg, 1.2 mmol), N,N-diisopropylethylamine (330 mg, 2.5 mmol) and N,N-dimethylformamide (7 mL) as starting materials, the title compound (240 mg, 63%) was obtained as a white solid.

$^1$H-NMR (DMSO-$d_6$, 300 MHz) δ 0.75-0.84 (4H, m), 1.86 (3H, s), 1.89-1.96 (1H, m), 2.71 (3H, s), 2.81 (1H, dd, J=17.4, 12.9 Hz), 2.98-3.11 (1H, m), 3.59-3.71 (1H, m), 7.06 (1H, d, J=9.5 Hz), 7.09-7.14 (1H, m), 7.38 (1H, dd, J=10.4, 8.9 Hz), 7.87 (1H, dd, J=6.4, 3.0 Hz), 7.93 (1H, s), 8.04 (1H, d, J=9.5 Hz), 9.75 (1H, s), 11.08 (1H, s).

Example 88

Production of N-[5-({2-[(cyclopropylcarbonyl)amino]imidazo[1,2-b]pyridazin-6-yl}oxy)-2-methylphenyl]-1,4-dimethyl-4,5-dihydro-1H-pyrazole-3-carboxamide

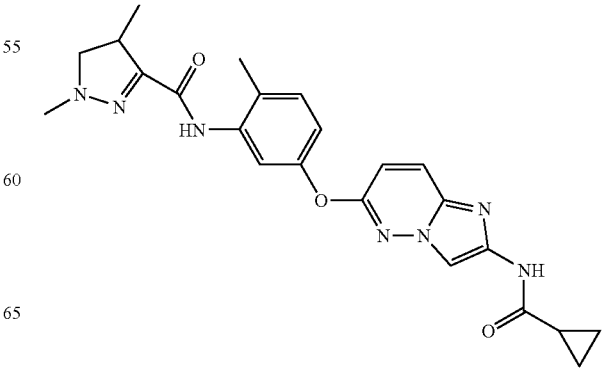

A mixture of N-(6-iodoimidazo[1,2-b]pyridazin-2-yl)cyclopropanecarboxamide (300 mg, 0.91 mmol), N-(5-hydroxy-2-methylphenyl)-1,4-dimethyl-4,5-dihydro-1H-pyrazole-3-carboxamide (290 mg, 1.2 mmol), cesium carbonate (600 mg, 1.8 mmol) and dimethyl sulfoxide (2 mL) was stirred at 100° C. for 6 hr. Ethyl acetate/tetrahydrofuran and water were added to the reaction mixture, and the aqueous layer was extracted with ethyl acetate/tetrahydrofuran (×4). Combined organic layer was washed with saturated brine, dried over anhydrous sodium sulfate, and filtrated. The filtrate was concentrated under reduced pressure, and the residue was purified by silica gel column chromatography (ethyl acetate/hexane=40/60→100/0) to give the title compound (300 mg, 73%) as a white solid.

$^1$H-NMR (DMSO-d$_6$, 300 MHz) δ 0.75-0.85 (4H, m), 1.14 (3H, d, J=6.4 Hz), 1.86-1.97 (1H, m), 2.23 (3H, s), 2.92 (3H, s), 3.05-3.12 (1H, m), 3.22-3.32 (2H, m), 6.98 (1H, dd, J=8.3, 2.7 Hz), 7.03 (1H, d, J=9.8 Hz), 7.28 (1H, d, J=8.3 Hz), 7.53 (1H, d, J=2.7 Hz), 7.94 (1H, s), 8.02 (1H, d, J=9.8 Hz), 9.18 (1H, s), 11.08 (1H, s).

Example 89

Production of 3-({2-[(cyclopropylcarbonyl)amino]imidazo[1,2-b]pyridazin-6-yl}oxy)benzoic acid

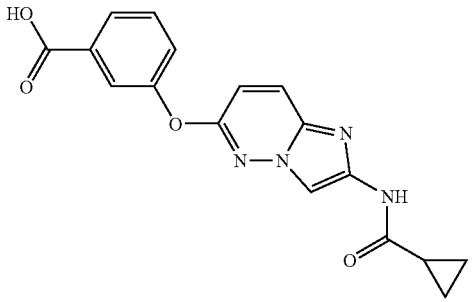

A mixture of N-(6-iodoimidazo[1,2-b]pyridazin-2-yl)cyclopropanecarboxamide (518 mg, 1.58 mmol), methyl 3-hydroxybenzoate (360 mg, 2.37 mmol), potassium carbonate (654 mg, 4.73 mmol) and N,N-dimethylformamide (4.0 mL) was stirred at 110° C. for 2 days. The solvent was evaporated under reduced pressure, ethyl acetate, tetrahydrofuran and water were added to the residue, and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was purified by silica gel column chromatography (ethyl acetate/hexane=20/80→85/15) to give methyl 3-({2-[(cyclopropylcarbonyl)amino]imidazo[1,2-b]pyridazin-6-yl}oxy)benzoate (225 mg, 41%) as a white powder.

To a solution of methyl 3-({2-[(cyclopropylcarbonyl)amino]imidazo[1,2-b]pyridazin-6-yl}oxy)benzoate (225 mg, 0.64 mmol) in tetrahydrofuran (5.0 mL) was added 1N sodium hydroxide (2.5 mL), and the mixture was stirred at room temperature for 24 hr. 1N Hydrochloric acid was added to the mixture (pH=3), and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was filtrated, and washed with ethyl acetate/hexane to give the title compound (150 mg, 69%) as a white powder.

$^1$H-NMR (DMSO-d$_6$, 300 MHz) δ 0.71-0.89 (4H, m), 1.84-2.01 (1H, m), 7.09 (1H, d, J=9.5 Hz), 7.48-7.68 (2H, m), 7.73 (1H, s), 7.84 (1H, d, J=7.2 Hz), 7.94 (1H, s), 8.06 (1H, d, J=9.5 Hz), 11.08 (1H, s), 13.20 (1H, brs).

Example 90

Production of N-[6-(5-amino-2-methylphenoxy)imidazo[1,2-b]pyridazin-2-yl]cyclopropanecarboxamide

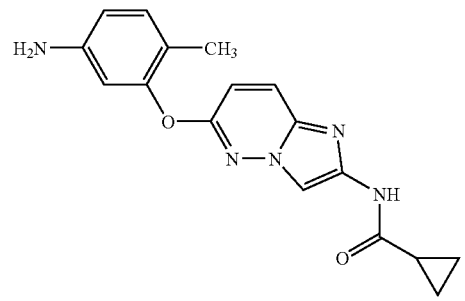

To a suspension of sodium hydride (56 mg, 1.40 mmol) in N,N-dimethylformamide (2.0 mL) was added a solution of 5-amino-2-methylphenol (173 mg, 1.40 mmol) in N,N-dimethylformamide (1.0 mL), and the mixture was stirred at 0° C. for 30 min. To the reaction mixture was added a solution of N-(6-iodoimidazo[1,2-b]pyridazin-2-yl)cyclopropanecarboxamide (306 mg, 0.933 mmol) in N,N-dimethylformamide (1.5 mL), and the mixture was stirred at 110° C. for 24 hr. The solvent was evaporated under reduced pressure, and ethyl acetate and water were added to the residue. The aqueous layer was extracted three times with ethyl acetate. Combined organic layer was washed with saturated brine, dried over anhydrous sodium sulfate, and filtrated. The solvent was evaporated under reduced pressure, and the residue was purified by silica gel column chromatography (ethyl acetate/hexane=17/83→90/10) to give the title compound (94 mg, 31%) as a brown powder.

$^1$H-NMR (DMSO-d$_6$, 300 MHz) δ 0.73-0.89 (4H, m), 1.84-2.01 (1H, m), 1.97 (3H, s), 5.08 (2H, s), 6.30 (1H, d, J=2.3 Hz), 6.40 (1H, dd, J=8.0, 2.3 Hz), 6.94 (1H, d, J=8.0 Hz), 6.95 (1H, d, J=9.5 Hz), 7.93 (1H, s), 7.99 (1H, d, J=9.5 Hz), 11.06 (1H, s).

Example 91

Production of N-[6-(3-amino-4-chlorophenoxy)imidazo[1,2-b]pyridazin-2-yl]cyclopropanecarboxamide

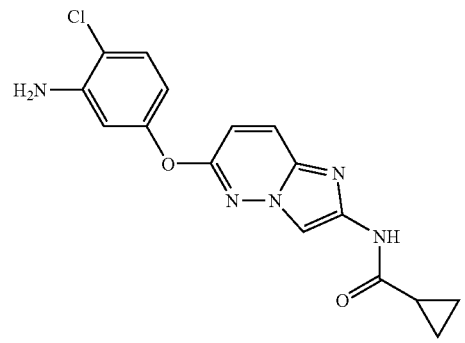

A mixture of N-(6-iodoimidazo[1,2-b]pyridazin-2-yl)cyclopropanecarboxamide (800 mg, 2.44 mmol), 3-amino-4-chlorophenol (422 mg, 2.93 mmol), potassium carbonate (843 mg, 6.10 mmol) and N,N-dimethylformamide (6.0 mL) was stirred using a microwave synthesizer at 180° C. for 30 min. The solvent was evaporated under reduced pressure, ethyl acetate, tetrahydrofuran and water were added to the residue, and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was purified by silica gel column chromatography (ethyl acetate/hexane=17/83→75/25) to give the title compound (610 mg, 73%) as a brown powder.

$^1$H-NMR (DMSO-$d_6$, 300 MHz) δ 0.72-0.87 (4H, m), 1.84-1.98 (1H, m), 5.56 (2H, s), 6.40 (1H, dd, J=8.5, 2.8 Hz), 6.61 (1H, d, J=2.8 Hz), 7.00 (1H, d, J=9.8 Hz), 7.23 (1H, d, J=8.5 Hz), 7.98 (1H, s), 8.02 (1H, d, J=9.8 Hz), 11.09 (1H, s).

Example 92

Production of N-[6-(5-amino-2-chlorophenoxy)imidazo[1,2-b]pyridazin-2-yl]cyclopropanecarboxamide

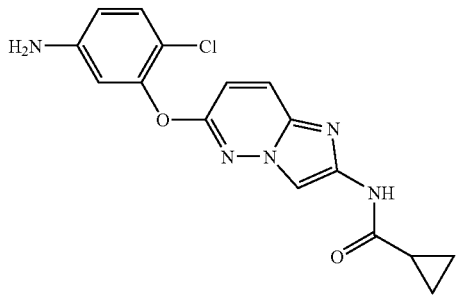

Using N-(6-iodoimidazo[1,2-b]pyridazin-2-yl)cyclopropanecarboxamide (800 mg, 2.44 mmol), 5-amino-2-chlorophenol (422 mg, 2.93 mmol), potassium carbonate (843 mg, 6.1 mmol) and N,N-dimethylformamide (6.0 mL) as starting materials and in the same manner as in Example 91, the title compound (226 mg, 27%) was obtained as a brown solid.

$^1$H-NMR (DMSO-$d_6$, 300 MHz) δ 0.73-0.86 (4H, m), 1.85-1.98 (1H, m), 5.47 (2H, s), 6.47-6.51 (1H, m), 6.51 (1H, s), 7.04 (1H, d, J=9.5 Hz), 7.17 (1H, d, J=9.0 Hz), 7.94 (1H, s), 8.03 (1H, d, J=9.5 Hz), 11.06 (1H, s).

Example 93

Production of N-[6-(5-amino-2-methoxyphenoxy)imidazo[1,2-b]pyridazin-2-yl]cyclopropanecarboxamide

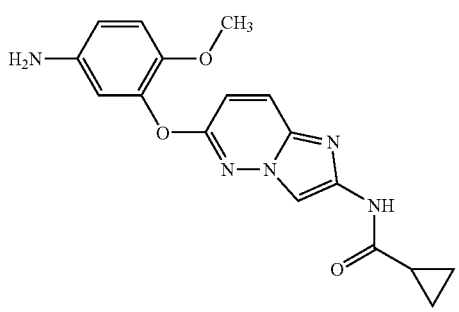

Using N-(6-iodoimidazo[1,2-b]pyridazin-2-yl)cyclopropanecarboxamide (800 mg, 2.44 mmol), 5-amino-2-methoxyphenol (408 mg, 2.93 mmol), potassium carbonate (843 mg, 6.10 mmol) and N,N-dimethylformamide (6.0 mL) as starting materials and in the same manner as in Example 91, the title compound (299 mg, 36%) was obtained as a brown powder.

$^1$H-NMR (DMSO-$d_6$, 300 MHz) δ 0.71-0.85 (4H, m), 1.91 (1H, m), 3.56 (3H, s), 4.87 (2H, s), 6.41-6.49 (2H, m), 6.85-6.91 (1H, m), 6.95 (1H, d, J=9.5 Hz), 7.90 (1H, s), 7.96 (1H, d, J=9.5 Hz), 11.05 (1H, s).

Example 94

Production of N-[6-(3-amino-2-methylphenoxy)imidazo[1,2-b]pyridazin-2-yl]cyclopropanecarboxamide

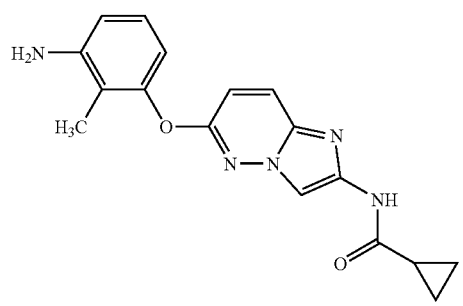

Using N-(6-iodoimidazo[1,2-b]pyridazin-2-yl)cyclopropanecarboxamide (800 mg, 2.44 mmol), 3-amino-2-methylphenol (380 mg, 2.93 mmol), potassium carbonate (843 mg, 6.10 mmol) and N,N-dimethylformamide (6.0 mL) as starting materials and in the same manner as in Example 91, the title compound (454 mg, 58%) was obtained as a blackish brown powder.

$^1$H-NMR (DMSO-$d_6$, 300 MHz) δ 0.71-0.87 (4H, m), 1.83-1.98 (1H, m), 1.89 (3H, s), 5.13 (2H, s), 6.32 (1H, d, J=8.0 Hz), 6.55 (1H, d, J=6.8 Hz), 6.93 (1H, dd, J=8.0, 6.8 Hz), 6.94 (1H, d, J=9.5 Hz), 7.91 (1H, s), 7.98 (1H, d, J=9.5 Hz), 11.05 (1H, s).

Example 95

Production of N-[6-(1H-indol-6-yloxy)imidazo[1,2-b]pyridazin-2-yl]cyclopropanecarboxamide

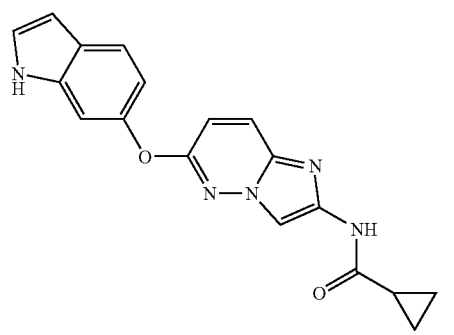

A mixture of N-(6-iodoimidazo[1,2-b]pyridazin-2-yl)cyclopropanecarboxamide (473 mg, 1.44 mmol), 1H-indole-6-ol (250 mg, 1.87 mmol), potassium carbonate (597 mg, 4.32 mmol) and N,N-dimethylformamide (4.0 mL) was stirred at 110° C. for 2 days. The solvent was evaporated under reduced pressure, ethyl acetate, tetrahydrofuran and water were added to the residue, and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was purified by silica gel column chromatography (ethyl acetate/hexane=20/80→85/15), and precipitated from ethyl acetate/hexane to give the title compound (48 mg, 10%) as a white powder.

$^1$H-NMR (DMSO-d$_6$, 300 MHz) δ 0.70-0.89 (4H, m), 1.83-1.97 (1H, m), 6.47 (1H, s), 6.89 (1H, dd, J=8.3, 2.3 Hz), 7.00 (1H, d, J=9.5 Hz), 7.26 (1H, d, J=2.3 Hz), 7.33-7.42 (1H, m), 7.58 (1H, d, J=8.3 Hz), 7.91 (1H, s), 7.99 (1H, d, J=9.5 Hz), 11.06 (1H, s), 11.17 (1H, s).

Example 96

Production of N-[3-({2-[(cyclopropylcarbonyl)amino]imidazo[1,2-b]pyridazin-6-yl}oxy)-4-methylphenyl]-1,3-dimethyl-1H-pyrazole-5-carboxamide

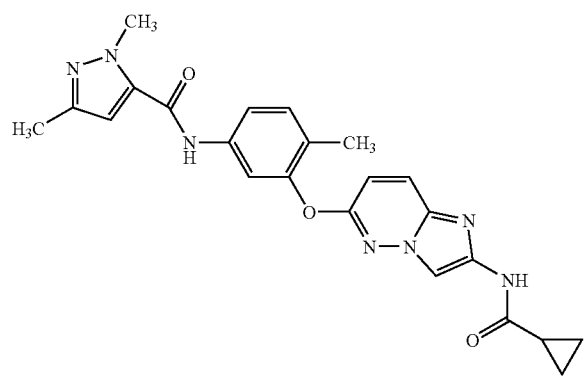

To a solution of N-[6-(5-amino-2-methylphenoxy)imidazo[1,2-b]pyridazin-2-yl]cyclopropanecarboxamide (72.6 mg, 0.224 mmol) in tetrahydrofuran (4.0 mL) were added a solution of 1,3-dimethyl-1H-pyrazole-5-carbonyl chloride (46.3 mg, 0.29 mmol) in tetrahydrofuran (0.5 mL) and triethylamine (68 mg, 0.672 mmol) under ice-cooling, and the mixture was stirred at room temperature for 1 hr. The reaction mixture was diluted with saturated aqueous sodium hydrogencarbonate solution, and extracted three times with ethyl acetate. The organic layer was washed with saturated brine, dried over anhydrous sodium sulfate, and filtrated. The solvent was evaporated under reduced pressure, and the residue was filtrated, washed with ethyl acetate/hexane to give the title compound (64 mg, 64%) as a brown powder.

$^1$H-NMR (DMSO-d$_6$, 300 MHz) δ 0.70-0.88 (4H, m), 1.85-1.97 (1H, m), 2.14 (3H, s), 2.18 (3H, s), 3.97 (3H, s), 6.81 (1H, s), 7.08 (1H, d, J=9.5 Hz), 7.32 (1H, d, J=8.3 Hz), 7.55 (1H, dd, J=8.3, 1.9 Hz), 7.60 (1H, d, J=1.9 Hz), 7.92 (1H, s), 8.05 (1H, d, J=9.5 Hz), 10.18 (1H, s), 11.08 (1H, s).

Example 97

Production of N-[2-chloro-5-({2-[(cyclopropylcarbonyl)amino]imidazo[1,2-b]pyridazin-6-yl}oxy)phenyl]-1,3-dimethyl-1H-pyrazole-5-carboxamide

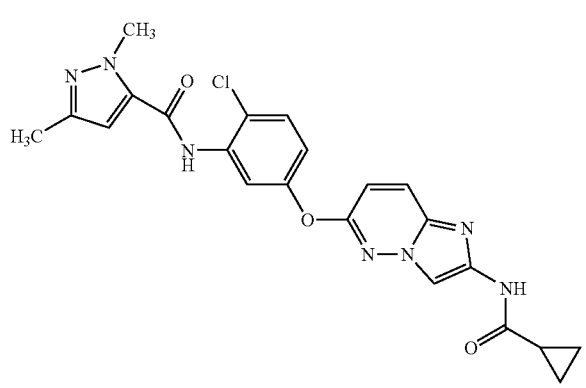

Using N-[6-(3-amino-4-chlorophenoxy)imidazo[1,2-b]pyridazin-2-yl]cyclopropanecarboxamide (128 mg, 0.373 mmol), 1,3-dimethyl-1H-pyrazole-5-carbonyl chloride (77.2 mg, 0.485 mmol), triethylamine (113 mg, 1.12 mmol) and tetrahydrofuran (5.0 mL) as starting materials and in the same manner as in Example 96, the title compound (77 mg, 44%) was obtained as a white powder. melting point 255° C.

$^1$H-NMR (DMSO-d$_6$, 300 MHz) δ 0.72-0.86 (4H, m), 1.85-1.98 (1H, m), 2.20 (3H, s), 3.98 (3H, s), 6.84 (1H, s), 7.10 (1H, d, J=9.6 Hz), 7.26 (1H, dd, J=8.9, 2.8 Hz), 7.54 (1H, d, J=2.8 Hz), 7.64 (1H, d, J=8.9 Hz), 7.96 (1H, s), 8.06 (1H, d, J=9.6 Hz), 9.99 (1H, s), 11.09 (1H, s).

Example 98

Production of N-[4-chloro-3-({2-[(cyclopropylcarbonyl)amino]imidazo[1,2-b]pyridazin-6-yl}oxy)phenyl]-1,3-dimethyl-1H-pyrazole-5-carboxamide

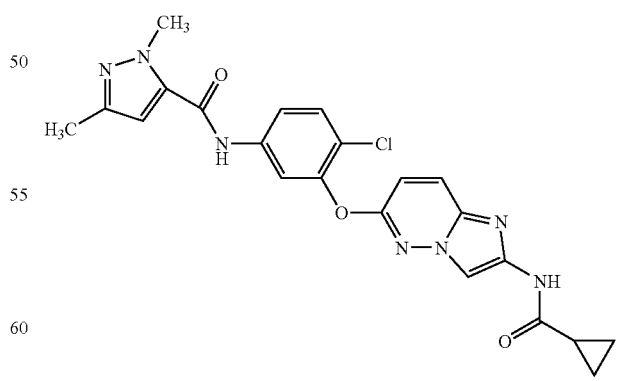

Using N-[6-(5-amino-2-chlorophenoxy)imidazo[1,2-b]pyridazin-2-yl]cyclopropanecarboxamide (131 mg, 0.382 mmol), 1,3-dimethyl-1H-pyrazole-5-carbonyl chloride (91 mg, 0.573 mmol), triethylamine (116 mg, 1.15 mmol) and tetrahydrofuran (5.0 mL) as starting materials and in the same manner as in Example 96, the title compound (163 mg, 92%) was obtained as a white powder.

¹H-NMR (DMSO-d₆, 300 MHz) δ 0.67-0.82 (4H, m), 1.81-1.94 (1H, m), 2.16 (3H, s), 3.96 (3H, s), 6.80 (1H, s), 7.14 (1H, dd, J=9.6, 1.6 Hz), 7.59 (1H, m), 7.66 (1H, m), 7.83 (1H, d, J=1.6 Hz), 7.91 (1H, s), 8.07 (1H, d, J=9.6 Hz), 10.34 (1H, s), 11.08 (1H, s).

Example 99

Production of N-[3-({2-[(cyclopropylcarbonyl) amino]imidazo[1,2-b]pyridazin-6-yl}oxy)-4-methoxyphenyl]-1,3-dimethyl-1H-pyrazole-5-carboxamide

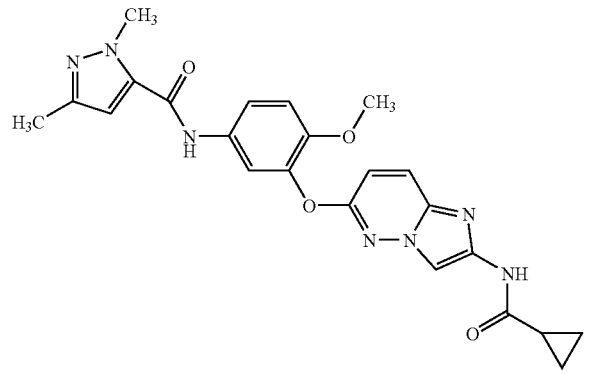

Using N-[6-(5-amino-2-methoxyphenoxy)imidazo[1,2-b]pyridazin-2-yl]cyclopropanecarboxamide (129 mg, 0.379 mmol), 1,3-dimethyl-1H-pyrazole-5-carbonyl chloride (78.3 mg, 0.493 mmol), triethylamine (115 mg, 1.14 mmol) and tetrahydrofuran (5.0 mL) as starting materials and in the same manner as in Example 96, the title compound (124 mg, 71%) was obtained as a white powder.

¹H-NMR (DMSO-d₆, 300 MHz) δ 0.72-0.85 (4H, m), 1.86-1.97 (1H, m), 2.19 (3H, s), 3.71 (3H, s), 3.97 (3H, s), 6.80 (1H, s), 7.06 (1H, d, J=9.5 Hz), 7.20 (1H, d, J=8.9 Hz), 7.59 (1H, dd, J=8.9, 2.5 Hz), 7.68 (1H, d, J=2.5 Hz), 7.89 (1H, s), 8.01 (1H, d, J=9.5 Hz), 10.15 (1H, s), 11.07 (1H, s).

Example 100

Production of N-[3-({2-[(cyclopropylcarbonyl) amino]imidazo[1,2-b]pyridazin-6-yl}oxy)-2-methylphenyl]-1,3-dimethyl-1H-pyrazole-5-carboxamide

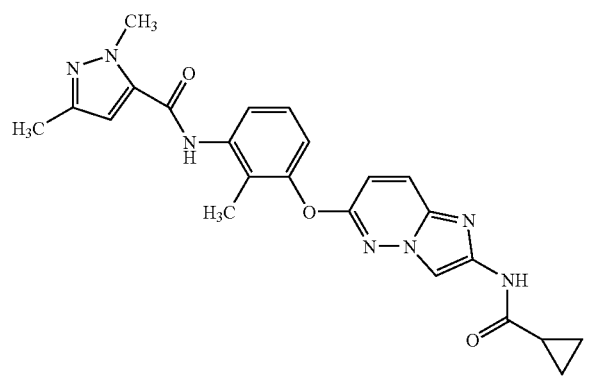

Using N-[6-(3-amino-2-methylphenoxy)imidazo[1,2-b]pyridazin-2-yl]cyclopropanecarboxamide (130 mg, 0.402 mmol), 1,3-dimethyl-1H-pyrazole-5-carbonyl chloride (83 mg, 0.523 mmol), triethylamine (122 mg, 1.21 mmol) and tetrahydrofuran (5.0 mL) as starting materials and in the same manner as in Example 96, the title compound (146 mg, 82%) was obtained as a white powder.

¹H-NMR (DMSO-d₆, 300 MHz) δ 0.72-0.87 (4H, m), 1.86-1.98 (1H, m), 2.06 (3H, s), 2.20 (3H, s), 4.01 (3H, s), 6.84 (1H, s), 7.09 (1H, d, J=9.5 Hz), 7.15 (1H, dd, J=6.8, 2.3 Hz), 7.25-7.36 (2H, m), 7.88 (1H, s), 8.05 (1H, d, J=9.5 Hz), 9.95 (1H, s), 11.07 (1H, s).

Example 101

Production of N-{6-[(2-methyl-1H-indol-5-yl)oxy] imidazo[1,2-b]pyridazin-2-yl}cyclopropanecarboxamide

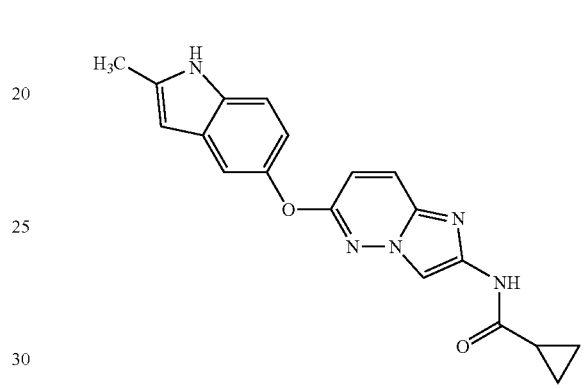

Using N-(6-iodoimidazo[1,2-b]pyridazin-2-yl)cyclopropanecarboxamide (272 mg, 0.830 mmol), 2-methyl-1H-indole-5-ol (244 mg, 1.66 mmol), potassium carbonate (344 mg, 2.49 mmol) and N,N-dimethylformamide (3.0 mL) as starting materials and in the same manner as in Example 95, the title compound (56 mg, 19%) was obtained as a white powder.

¹H-NMR (DMSO-d₆, 300 MHz) δ 0.73-0.85 (4H, m), 1.82-1.97 (1H, m), 2.39 (3H, s), 6.13 (1H, s), 6.86 (1H, dd, J=8.7, 2.3 Hz), 6.95 (1H, d, J=9.5 Hz), 7.23 (1H, d, J=2.3 Hz), 7.30 (1H, d, J=8.7 Hz), 7.88 (1H, s), 7.96 (1H, d, J=9.5 Hz), 11.05 (2H, s).

Example 102

Production of N-{6-[(1,2-dimethyl-1H-benzimidazol-5-yl)oxy]imidazo[1,2-b]pyridazin-2-yl}cyclopropanecarboxamide

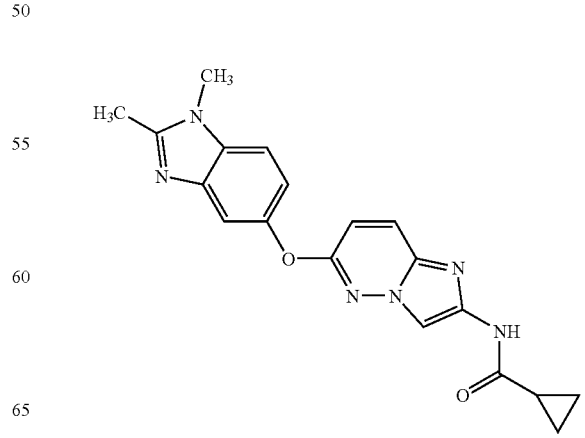

Using N-(6-iodoimidazo[1,2-b]pyridazin-2-yl)cyclopropanecarboxamide (254 mg, 0.774 mmol), 1,2-dimethyl-1H-benzimidazole-5-ol (163 mg, 1.06 mmol), potassium carbonate (267 mg, 1.94 mmol) and N,N-dimethylformamide (3.0 mL) as starting materials and in the same manner as in Example 95, the title compound (79 mg, 28%) was obtained as a white powder.

$^1$H-NMR (DMSO-$d_6$, 300 MHz) δ 0.72-0.84 (4H, m), 1.84-1.96 (1H, m), 2.54 (3H, s), 3.77 (3H, s), 7.00 (1H, d, J=9.8 Hz), 7.09 (1H, dd, J=8.7, 2.3 Hz), 7.39 (1H, d, J=2.3 Hz), 7.53 (1H, d, J=8.7 Hz), 7.86 (1H, s), 7.99 (1H, d, J=9.8 Hz), 11.05 (1H, s).

Example 103

Production of N-[6-(3-{[(ethylamino)carbonyl]amino}phenoxy)imidazo[1,2-b]pyridazin-2-yl]cyclopropanecarboxamide

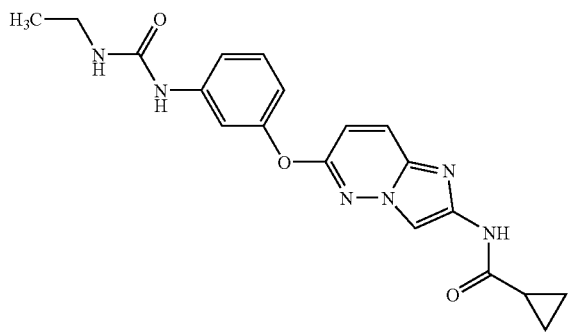

To a solution of N-[6-(3-aminophenoxy)imidazo[1,2-b]pyridazin-2-yl]cyclopropanecarboxamide (160 mg, 0.517 mmol) in pyridine (4.0 mL) was added ethyl isocyanate (409 μL, 5.17 mmol), and the mixture was stirred at room temperature for 24 hr. The solvent was evaporated under reduced pressure, ethyl acetate and saturated aqueous sodium hydrogencarbonate solution were added to the residue, and the aqueous layer was extracted three times with ethyl acetate. Combined organic layer was washed with saturated brine, dried over anhydrous sodium sulfate, and filtrated. The solvent was evaporated under reduced pressure, and the residue was filtrated, and washed with ethyl acetate/hexane to give the title compound (136 mg, 69%) as a white powder.

$^1$H-NMR (DMSO-$d_6$, 300 MHz) δ 0.72-0.86 (4H, m), 1.00 (3H, t, J=7.1 Hz), 1.83-1.95 (1H, m), 2.97-3.12 (2H, m), 6.13 (1H, t, J=5.5 Hz), 6.72 (1H, dd, J=8.0, 2.5 Hz), 6.99 (1H, d, J=9.6 Hz), 7.09 (1H, dd, J=8.2, 1.1 Hz), 7.25 (1H, t, J=8.2 Hz), 7.42 (1H, t, J=1.9 Hz), 7.94 (1H, s), 8.00 (1H, d, J=9.6 Hz), 8.61 (1H, s), 11.08 (1H, s).

Example 104

Production of N-[6-(1H-indol-4-yloxy)imidazo[1,2-b]pyridazin-2-yl]cyclopropanecarboxamide

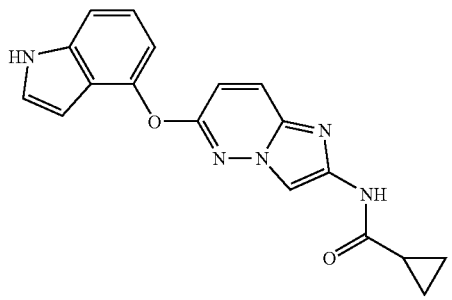

Using N-(6-iodoimidazo[1,2-b]pyridazin-2-yl)cyclopropanecarboxamide (353 mg, 1.08 mmol), 1H-indole-4-ol (241 mg, 1.82 mmol), potassium carbonate (446 mg, 3.23 mmol) and N,N-dimethylformamide (4.0 mL) as starting materials and in the same manner as in Example 95, the title compound (66 mg, 18%) was obtained as a white powder.

$^1$H-NMR (DMSO-$d_6$, 300 MHz) δ 0.70-0.86 (4H, m), 1.83-1.96 (1H, m), 6.16-6.23 (1H, m), 6.85 (1H, dd, J=7.8, 0.8 Hz), 7.01 (1H, d, J=9.6 Hz), 7.12 (1H, t, J=7.8 Hz), 7.26-7.37 (2H, m), 7.89 (1H, s), 8.00 (1H, d, J=9.6 Hz), 11.06 (1H, s), 11.37 (1H, s).

Example 105

Production of N-{6-[(2-methyl-1,3-benzothiazol-5-yl)oxy]imidazo[1,2-b]pyridazin-2-yl}cyclopropanecarboxamide

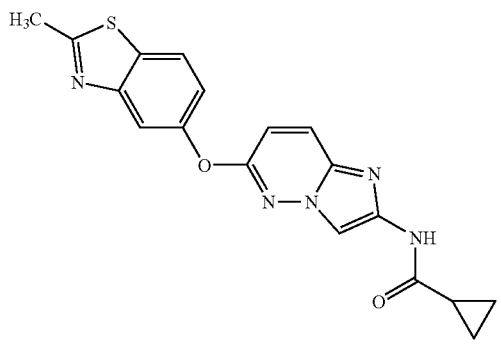

Using N-(6-iodoimidazo[1,2-b]pyridazin-2-yl)cyclopropanecarboxamide (355 mg, 1.08 mmol), 2-methyl-1,3-benzothiazole-5-ol (286 mg, 1.73 mmol), potassium carbonate (448 mg, 3.24 mmol) and N,N-dimethylformamide (4.0 mL) as starting materials and in the same manner as in Example 95, the title compound (275 mg, 70%) was obtained as a pale-yellow powder.

$^1$H-NMR (DMSO-$d_6$, 300 MHz) δ 0.72-0.86 (4H, m), 1.83-1.97 (1H, m), 2.82 (3H, s), 7.09 (1H, d, J=9.6 Hz), 7.35 (1H, dd, J=8.7, 2.3 Hz), 7.82 (1H, d, J=2.3 Hz), 7.92 (1H, s), 8.04 (1H, d, J=9.6 Hz), 8.10 (1H, d, J=8.7 Hz), 11.07 (1H, s).

Example 106

Production of 3-({2-[(cyclopropylcarbonyl)amino]imidazo[1,2-b]pyridazin-6-yl}oxy)-N-(1,3-dimethyl-1H-pyrazol-5-yl)benzamide

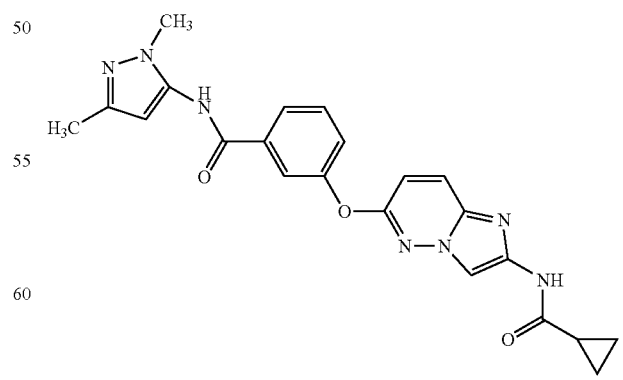

To a solution of 3-({2-[(cyclopropylcarbonyl)amino]imidazo[1,2-b]pyridazin-6-yl}oxy)benzoic acid (121 mg, 0.358 mmol) in N,N-dimethylformamide (5.0 mL) were added 1,3-dimethyl-1H-pyrazol-5-amine (47.8 mg, 0.43 mmol), 1-hydroxybenzotriazole (58 mg, 0.43 mmol), 1-ethyl-3-(3-dimethylaminopropyl)carbodiimide hydrochloride (82.4 mg, 0.43 mmol) and triethylamine (45 mg, 0.43 mmol) and the mixture was stirred at room temperature for 24 hr. The solvent was evaporated under reduced pressure, ethyl acetate, tetrahydrofuran and water were added to the residue, and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was purified by silica gel column chromatography (ethyl acetate/hexane=20/80→90/10, then methanol/ethyl acetate=0/100→15/85), and precipitated from ethyl acetate/hexane to give the title compound (116 mg, 75%) as a white powder.

$^1$H-NMR (DMSO-$d_6$, 300 MHz) δ 0.73-0.85 (4H, m), 1.86-1.96 (1H, m), 2.12 (3H, s), 3.56 (3H, s), 6.02 (1H, s), 7.11 (1H, d, J=9.6 Hz), 7.50-7.57 (1H, m), 7.63 (1H, t, J=7.9 Hz), 7.79-7.92 (2H, m), 7.95 (1H, s), 8.07 (1H, d, J=9.6 Hz), 10.31 (1H, s), 11.09 (1H, s).

Example 107

Production of N-[2-chloro-5-({2-[(cyclopropylcarbonyl)amino]imidazo[1,2-b]pyridazin-6-yl}oxy)phenyl]cyclopropanecarboxamide

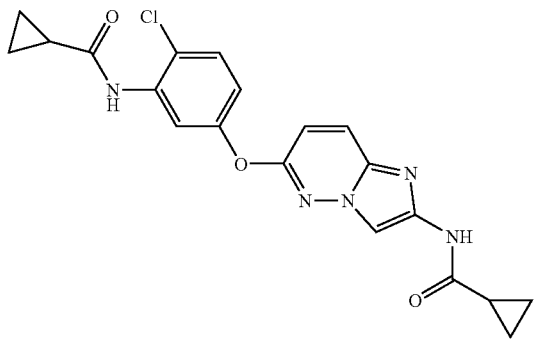

Using N-[6-(3-amino-4-chlorophenoxy)imidazo[1,2-b]pyridazin-2-yl]cyclopropanecarboxamide (150 mg, 0.435 mmol), cyclopropanecarbonyl chloride (71.8 mg, 0.652 mmol), triethylamine (132 mg, 1.30 mmol) and tetrahydrofuran (17 mL) as starting materials and in the same manner as in Example 96, the title compound (156 mg, 87%) was obtained as a white powder.

$^1$H-NMR (DMSO-$d_6$, 300 MHz) δ 0.70-0.89 (8H, m), 1.84-1.98 (1H, m), 2.00-2.11 (1H, m), 7.06 (1H, d, J=9.6 Hz), 7.10 (1H, dd, J=8.7, 2.8 Hz), 7.56 (1H, d, J=8.7 Hz), 7.73 (1H, d, J=2.8 Hz), 7.95 (1H, s), 8.04 (1H, d, J=9.6 Hz), 9.83 (1H, s), 11.09 (1H, s).

Example 108

Production of N-[6-(3-amino-4-methylphenoxy)imidazo[1,2-b]pyridazin-2-yl]cyclopropanecarboxamide

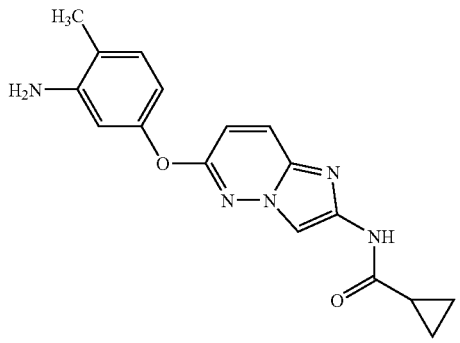

A mixture of N-(6-iodoimidazo[1,2-b]pyridazin-2-yl)cyclopropanecarboxamide (743 mg, 2.26 mmol), 3-amino-4-methylphenol (446 mg, 3.62 mmol), potassium carbonate (782 mg, 5.66 mmol) and N,N-dimethylformamide (5.0 mL) was stirred using a microwave synthesizer at 180° C. for 30 min. The solvent was evaporated under reduced pressure, ethyl acetate, tetrahydrofuran and water were added to the residue, and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was purified by silica gel column chromatography (ethyl acetate/hexane=17/83→75/25) to give the title compound (424 mg, 58%) as a brown powder.

$^1$H-NMR (DMSO-$d_6$, 300 MHz) δ 0.72-0.86 (4H, m), 1.84-1.97 (1H, m), 2.04 (3H, s), 5.06 (2H, s), 6.28 (1H, dd, J=8.1, 2.4 Hz), 6.42 (1H, d, J=2.4 Hz), 6.93 (1H, d, J=9.3 Hz), 6.95 (1H, d, J=8.1 Hz), 7.96 (1H, s), 7.98 (1H, d, J=9.3 Hz), 11.07 (1H, s).

Example 109

Production of N-[3-({2-[(cyclopropylcarbonyl)amino]imidazo[1,2-b]pyridazin-6-yl}oxy)phenyl]-3-methylisoxazole-5-carboxamide

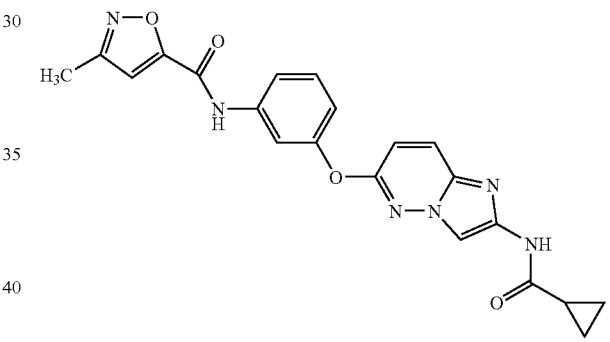

To a solution of 3-methylisoxazole-5-carboxylic acid (87 mg, 0.679 mmol) in tetrahydrofuran (2.0 mL) were added N,N-dimethylformamide (1 drop) and oxalyl chloride (75.8 μL, 0.88 mmol), and the mixture was stirred at room temperature for 30 min. The solvent was evaporated under reduced pressure, and the residue was dissolved in tetrahydrofuran (1 mL), and added to a solution of N-[6-(3-aminophenoxy)imidazo[1,2-b]pyridazin-2-yl]cyclopropanecarboxamide (140 mg, 0.453 mmol) in tetrahydrofuran (12 mL). Then, triethylamine (138 mg, 1.36 mmol) was added to the mixture, and the mixture was stirred at room temperature for 30 min. The reaction mixture was diluted with saturated aqueous sodium hydrogencarbonate solution, and extracted three times with ethyl acetate, and the organic layer was washed with saturated brine, dried over anhydrous sodium sulfate, and filtrated. The solvent was evaporated under reduced pressure, and the residue was purified by silica gel column chromatography (ethyl acetate/hexane=20/80→80/20) and precipitated from ethyl acetate/hexane to give the title compound (42 mg, 22%) as a white powder.

$^1$H-NMR (DMSO-$d_6$, 300 MHz) δ 0.73-0.87 (4H, m), 1.86-1.98 (1H, m), 2.32 (3H, s), 7.01-7.14 (3H, m), 7.45 (1H, t, J=8.2 Hz), 7.62-7.74 (2H, m), 7.98 (1H, s), 8.06 (1H, d, J=9.8 Hz), 10.82 (1H, s), 11.10 (1H, s).

Example 110

Production of N-[3-({2-[(cyclopropylcarbonyl)amino]imidazo[1,2-b]pyridazin-6-yl}oxy)phenyl]-5-methylisoxazole-3-carboxamide

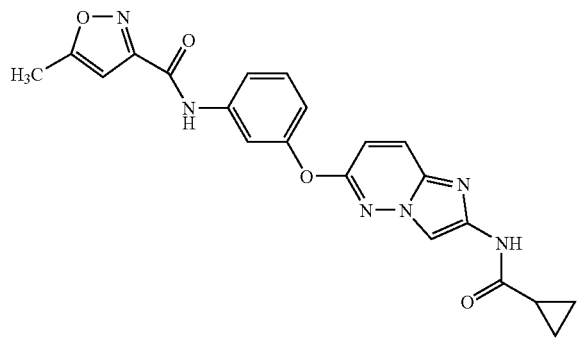

Using 5-methylisoxazole-3-carboxylic acid (87 mg, 0.679 mmol), N,N-dimethylformamide (1 drop), oxalyl chloride (75.8 μL, 0.88 mmol), N-[6-(3-aminophenoxy)imidazo[1,2-b]pyridazin-2-yl]cyclopropanecarboxamide (140 mg, 0.453 mmol), triethylamine (138 mg, 1.36 mmol) and tetrahydrofuran (15 mL) as starting materials and in the same manner as in Example 109, the title compound (109 mg, 58%) was obtained as a white powder.

$^1$H-NMR (DMSO-d$_6$, 300 MHz) δ 0.73-0.86 (4H, m), 1.85-1.96 (1H, m), 2.50 (3H, s), 6.6.6 (1H, d, J=0.9 Hz), 6.97-7.10 (2H, m), 7.43 (1H, t, J=8.2 Hz), 7.63-7.77 (2H, m), 7.98 (1H, s), 8.05 (1H, d, J=9.4 Hz), 10.78 (1H, s), 11.09 (1H, s).

Example 111

Production of N-[5-({2-[(cyclopropylcarbonyl)amino]imidazo[1,2-b]pyridazin-6-yl}oxy)-2-methylphenyl]-1,3-dimethyl-1H-pyrazole-5-carboxamide

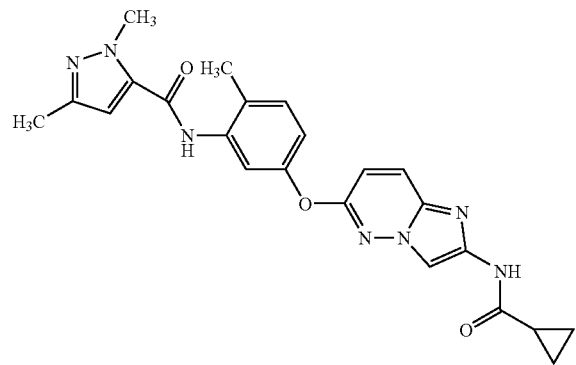

To a solution of N-[6-(3-amino-4-methylphenoxy)imidazo[1,2-b]pyridazin-2-yl]cyclopropanecarboxamide (213 mg, 0.659 mmol) in tetrahydrofuran (10 mL) were added a solution of 1,3-dimethyl-1H-pyrazole-5-carbonyl chloride (136 mg, 0.856 mmol) in tetrahydrofuran (0.5 mL) and triethylamine (200 mg, 1.98 mmol) under ice-cooling, and the mixture was stirred at room temperature for 1 hr. The reaction mixture was diluted with saturated aqueous sodium hydrogencarbonate solution, and extracted three times with ethyl acetate, and the organic layer was washed with saturated brine, dried over anhydrous sodium sulfate, and filtrated. The solvent was evaporated under reduced pressure, and the residue was filtrated and washed with ethyl acetate/hexane to give the title compound (222 mg, 77%) as a white powder. melting point 223° C.

$^1$H-NMR (DMSO-d$_6$, 300 MHz) δ 0.72-0.89 (4H, m), 1.86-1.97 (1H, m), 2.19 (3H, s), 2.25 (3H, s), 3.98 (3H, s), 6.81 (1H, s), 7.04 (1H, d, J=9.6 Hz), 7.10 (1H, dd, J=8.7, 2.4 Hz), 7.28 (1H, d, J=2.4 Hz), 7.35 (1H, d, J=8.7 Hz), 7.93 (1H, s), 8.03 (1H, d, J=9.6 Hz), 9.81 (1H, s), 11.08 (1H, s).

Example 112

Production of N-[3-({2-[(cyclopropylcarbonyl)amino]imidazo[1,2-b]pyridazin-6-yl}oxy)phenyl]-1-methyl-3-(trifluoromethyl)-1H-pyrazole-5-carboxamide

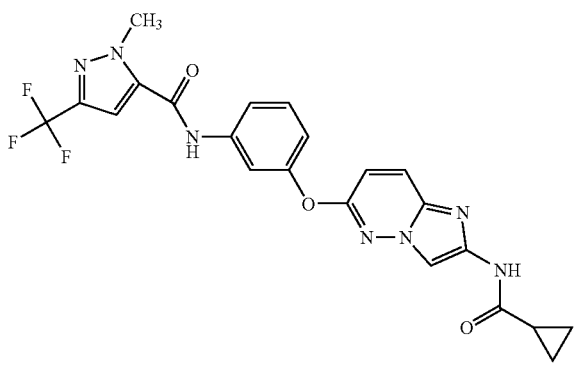

Using 1-methyl-3-(trifluoromethyl)-1H-pyrazole-5-carboxylic acid (100 mg, 0.515 mmol), N,N-dimethylformamide (1 drop), oxalyl chloride (60 μL, 0.7 mmol), N-[6-(3-aminophenoxy)imidazo[1,2-b]pyridazin-2-yl]cyclopropanecarboxamide (122.5 mg, 0.396 mmol), triethylamine (120 mg, 1.19 mmol) and tetrahydrofuran (15 mL) as starting materials and in the same manner as in Example 109, the title compound (149 mg, 78%) was obtained as a white powder.

$^1$H-NMR (DMSO-d$_6$, 300 MHz) δ 0.73-0.85 (4H, m), 1.84-1.97 (1H, m), 4.15 (3H, s), 7.05 (1H, m), 7.08 (1H, d, J=9.6 Hz), 7.46 (1H, t, J=8.2 Hz), 7.50 (1H, s), 7.59-7.64 (1H, m), 7.66 (1H, t, J=2.1 Hz), 7.98 (1H, s), 8.06 (1H, d, J=9.6 Hz), 10.53 (1H, s), 11.10 (1H, s).

Example 113

Production of N-[3-({2-[(cyclopropylcarbonyl)amino]imidazo[1,2-b]pyridazin-6-yl}oxy)phenyl]-5-methyl-2-(trifluoromethyl)-3-furancarboxamide

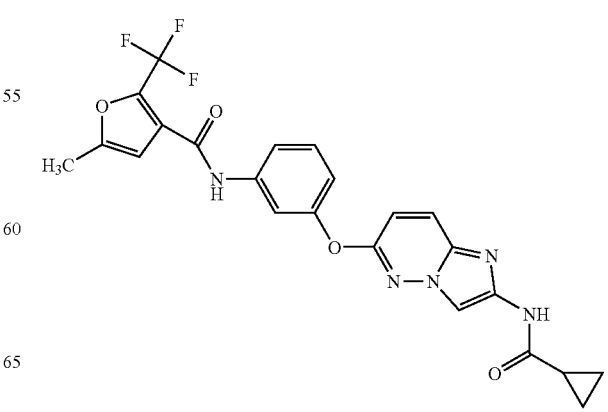

Using 5-methyl-2-(trifluoromethyl)-3-furancarboxylic acid (133.6 mg, 0.668 mmol), N,N-dimethylformamide (1 drop), oxalyl chloride (75 μL, 0.868 mmol), N-[6-(3-aminophenoxy)imidazo[1,2-b]pyridazin-2-yl]cyclopropanecarboxamide (159 mg, 0.514 mmol), triethylamine (156 mg, 1.54 mmol) and tetrahydrofuran (15 mL) as starting materials and in the same manner as in Example 109, the title compound (145 mg, 58%) was obtained as a white powder.

$^1$H-NMR (DMSO-d$_6$, 300 MHz) δ 0.73-0.86 (4H, m), 1.85-1.97 (1H, m), 2.40 (3H, s), 6.80 (1H, s), 7.02 (1H, m), 7.06 (1H, d, J=9.6 Hz), 7.43 (1H, t, J=8.2 Hz), 7.56 (1H, d, J=8.3 Hz), 7.63 (1H, t, J=2.0 Hz), 7.97 (1H, s), 8.05 (1H, d, J=9.6 Hz), 10.50 (1H, s), 11.09 (1H, s).

Example 114

Production of N-[3-({2-[(cyclopropylcarbonyl)amino]imidazo[1,2-b]pyridazin-6-yl}oxy)phenyl]-2,4-dimethyl-1,3-thiazole-5-carboxamide

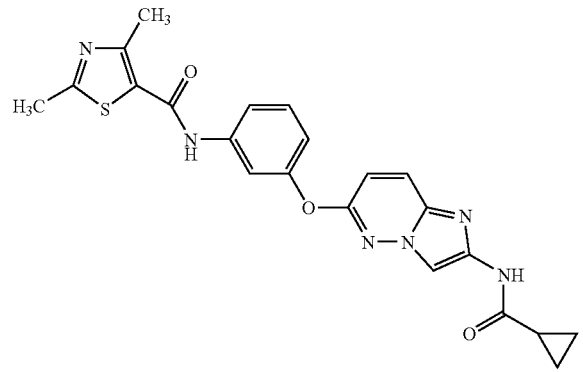

Using 2,4-dimethyl-1,3-thiazole-5-carboxylic acid (78.8 mg, 0.50 mmol), N-[6-(3-aminophenoxy)imidazo[1,2-b]pyridazin-2-yl]cyclopropanecarboxamide (129 mg, 0.417 mmol), 1-hydroxybenzotriazole (68 mg, 0.50 mmol), 1-ethyl-3-(3-dimethylaminopropyl)carbodiimide hydrochloride (96 mg, 0.50 mmol), triethylamine (50 mg, 0.50 mmol) and N,N-dimethylformamide (5.0 mL) as starting materials and in the same manner as in Example 106, the title compound (133 mg, 71%) was obtained as a white powder. melting point 249° C.

$^1$H-NMR (DMSO-d$_6$, 300 MHz) δ 0.74-0.88 (4H, m), 1.85-1.98 (1H, m), 2.53 (3H, s), 2.65 (3H, s), 7.00 (1H, dd, J=7.6, 1.9 Hz), 7.06 (1H, d, J=9.5 Hz), 7.41 (1H, t, J=8.1 Hz), 7.54 (1H, d, J=8.3 Hz), 7.62 (1H, t, J=2.1 Hz), 7.97 (1H, s), 8.05 (1H, d, J=9.5 Hz), 10.22 (1H, s), 11.09 (1H, s).

Example 115

Production of N-{6-[(2-methyl-1,3-benzothiazol-6-yl)oxy]imidazo[1,2-b]pyridazin-2-yl}cyclopropanecarboxamide

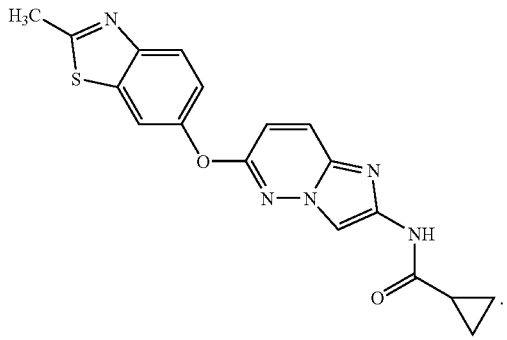

Using N-(6-iodoimidazo[1,2-b]pyridazin-2-yl)cyclopropanecarboxamide (309 mg, 0.942 mmol), 2-methyl-1,3-benzothiazole-6-ol (250 mg, 1.51 mmol), potassium carbonate (390 mg, 2.83 mmol) and N,N-dimethylformamide (4.0 mL) as starting materials and in the same manner as in Example 95, the title compound (151 mg, 44%) was obtained as a pale-yellow powder.

$^1$H-NMR (DMSO-d$_6$, 300 MHz) δ 0.71-0.83 (4H, m), 1.83-1.94 (1H, m), 2.79 (3H, s), 7.07 (1H, d, J=9.6 Hz), 7.37 (1H, dd, J=8.8, 2.5 Hz), 7.90-7.99 (3H, m), 8.02 (1H, d, J=9.6 Hz), 11.06 (1H, s).

Example 116

Production of N-[3-({2-[(cyclopropylcarbonyl)amino]imidazo[1,2-b]pyridazin-6-yl}oxy)phenyl]-3-methyl-1-(2,2,2-trifluoroethyl)-1H-pyrazole-5-carboxamide

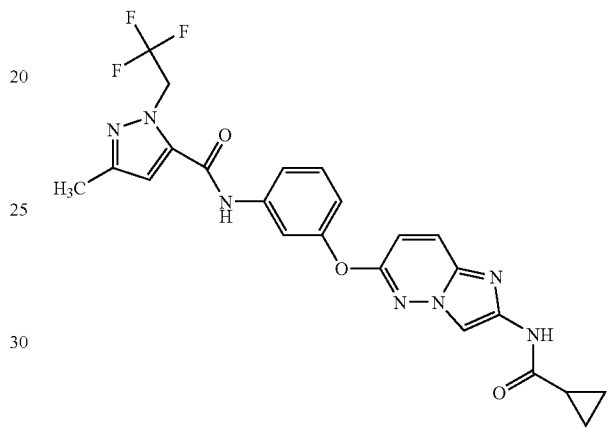

Using 3-methyl-1-(2,2,2-trifluoroethyl)-1H-pyrazole-5-carboxylic acid (175 mg, 0.84 mmol), N,N-dimethylformamide (1 drop), oxalyl chloride (91 μL, 1.01 mmol), N-[6-(3-aminophenoxy)imidazo[1,2-b]pyridazin-2-yl]cyclopropanecarboxamide (200 mg, 0.646 mmol), triethylamine (196 mg, 1.94 mmol) and tetrahydrofuran (15 mL) as starting materials and in the same manner as in Example 109, the title compound (281 mg, 87%) was obtained as a white powder.

$^1$H-NMR (DMSO-d$_6$, 300 MHz) δ 0.73-0.86 (4H, m), 1.87-1.98 (1H, m), 2.25 (3H, s), 5.40 (2H, q, J=8.9 Hz), 7.00 (1H, s), 7.04 (1H, m), 7.07 (1H, d, J=9.4 Hz), 7.45 (1H, t, J=8.2 Hz), 7.58-7.69 (2H, m), 7.97 (1H, s), 8.06 (1H, d, J=9.4 Hz), 10.45 (1H, s), 11.10 (1H, s).

Example 117

Production of N-[3-({2-[(cyclopropylcarbonyl)amino]imidazo[1,2-b]pyridazin-6-yl}oxy)phenyl]-2,5-dimethyl-1,3-oxazole-4-carboxamide

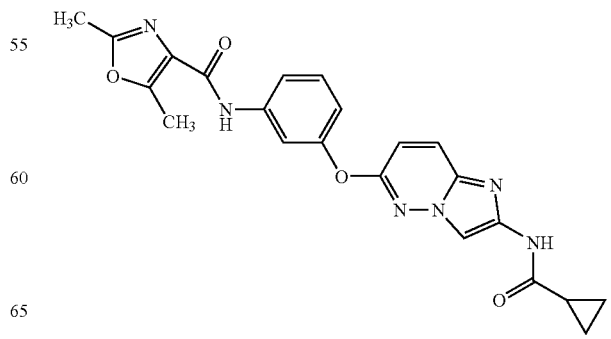

To a solution of N-[6-(3-aminophenoxy)imidazo[1,2-b]pyridazin-2-yl]cyclopropanecarboxamide (202 mg, 0.652 mmol) in N,N-dimethylacetamide (4.0 mL) was added a solution of 2,5-dimethyl-1,3-oxazole-4-carbonyl chloride (135 mg, 0.847 mmol) in N,N-dimethylacetamide (1.0 mL), and the mixture was stirred at 0° C. for 1 hr. Ethyl acetate/tetrahydrofuran and saturated aqueous sodium hydrogencarbonate solution were added to the mixture, and the aqueous layer was extracted three times with ethyl acetate/tetrahydrofuran. Combined organic layer was washed with saturated brine, dried over anhydrous sodium sulfate, and filtrated. The solvent was evaporated under reduced pressure, and the residue was purified by silica gel column chromatography (ethyl acetate/hexane=20/80→490/10), and precipitated from ethyl acetate/hexane to give the title compound (213 mg, 76%) as a white powder. melting point 224° C.

$^1$H-NMR (DMSO-$d_6$, 300 MHz) δ 0.73-0.87 (4H, m), 1.87-1.97 (1H, m), 2.44 (3H, s), 2.56 (3H, s), 6.96 (1H, dd, J=8.3, 2.1 Hz), 7.05 (1H, d, J=9.5 Hz), 7.38 (1H, t, J=8.1 Hz), 7.72 (1H, d, J=8.3 Hz), 7.80 (1H, t, J=2.1 Hz), 7.98 (1H, s), 8.04 (1H, d, J=9.5 Hz), 10.12 (1H, s), 11.09 (1H, s).

Example 118

Production of N-[3-({2-[(cyclopropylcarbonyl)amino]imidazo[1,2-b]pyridazin-6-yl}oxy)phenyl]-1-methyl-1H-pyrazole-5-carboxamide

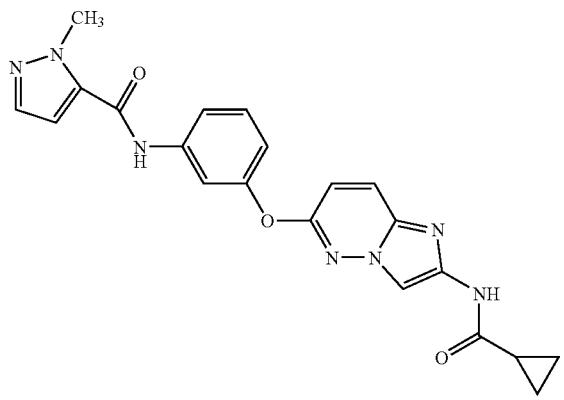

To a solution of 1-methyl-1H-pyrazole-5-carboxylic acid (106 mg, 0.840 mmol) in tetrahydrofuran (2.0 mL) were added N,N-dimethylformamide (1 drop) and oxalyl chloride (91 µL, 1.01 mmol), and the mixture was stirred at room temperature for 30 min. The solvent was evaporated under reduced pressure, and the residue was dissolved in N,N-dimethylacetamide (1 mL) and added to a solution of N-[6-(3-aminophenoxy)imidazo[1,2-b]pyridazin-2-yl]cyclopropanecarboxamide (200 mg, 0.646 mmol) in N,N-dimethylacetamide (5.0 mL). The mixture was stirred at room temperature for 30 min. The reaction mixture was diluted with saturated aqueous sodium hydrogencarbonate solution, and extracted three times with ethyl acetate, and the organic layer was washed with saturated brine, dried over anhydrous sodium sulfate, and filtrated. The solvent was evaporated under reduced pressure, and the residue was purified by silica gel column chromatography (ethyl acetate/hexane=30/70→95/5) and precipitated from ethyl acetate/hexane to give the title compound (241 mg, 89%) as a white powder.

$^1$H-NMR (DMSO-$d_6$, 300 MHz) δ 0.75-0.87 (4H, m), 1.86-1.98 (1H, m), 4.07 (3H, s), 7.00-7.05 (1H, m), 7.04-7.10 (2H, m), 7.44 (1H, t, J=8.2 Hz), 7.53 (1H, d, J=2.1 Hz), 7.59-7.69 (2H, m), 7.98 (1H, s), 8.06 (1H, d, J=9.6 Hz), 10.33 (1H, s), 11.10 (1H, s).

Example 119

Production of N-(3-{[2-(acetylamino)imidazo[1,2-b]pyridazin-6-yl]oxy}phenyl)-1,3-dimethyl-1H-pyrazole-5-carboxamide

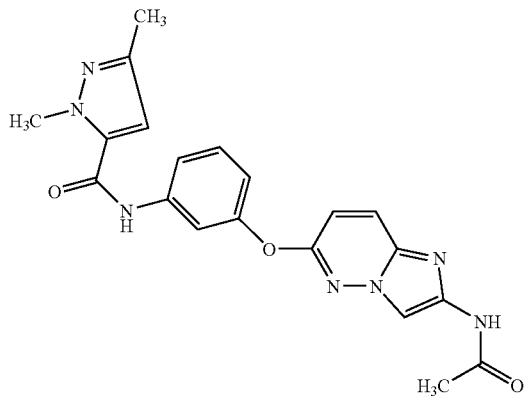

To a solution (4.0 mL) of 1,3-dimethyl-1H-pyrazole-5-carboxylic acid (109 mg, 0.85 mmol) in tetrahydrofuran were added N,N-dimethylformamide (30 µL, 0.39 mmol) and oxalyl chloride (135 µL, 1.55 mmol), and the mixture was stirred at room temperature for 1 hr. The solvent was evaporated under reduced pressure, and a solution of the residue in N,N-dimethylacetamide (2.0 mL) was added dropwise to a solution of N-[6-(3-aminophenoxy)imidazo[1,2-b]pyridazin-2-yl]acetamide (200 mg, 0.71 mmol) in N,N-dimethylacetamide (2.0 mL). After the reaction mixture was stirred at room temperature for 1 hr, water was added to the reaction mixture, and the mixture was extracted with ethyl acetate/tetrahydrofuran, washed with saturated brine, dried over anhydrous magnesium sulfate, and filtrated. The solvent was evaporated under reduced pressure, and the residue was washed with ethyl acetate to give the title compound (182 mg, 67%) as a white powder.

$^1$H-NMR (DMSO-$d_6$, 300 MHz) δ 2.07 (3H, s), 2.19 (3H, s), 3.97 (3H, s), 6.82 (1H, s), 6.98-7.03 (1H, m), 7.06 (1H, d, J=9.6 Hz), 7.42 (1H, t, J=8.1 Hz), 7.59-7.63 (1H, m), 7.66-7.68 (1H, m), 7.98 (1H, s), 8.04 (1H, d, J=9.6 Hz), 10.24 (1H, s), 10.80 (1H, s).

Example 120

Production of N-[3-({2-[(cyclopropylcarbonyl)amino]imidazo[1,2-b]pyridazin-6-yl}oxy)phenyl]-1,3-dimethyl-1H-pyrazole-5-carboxamide

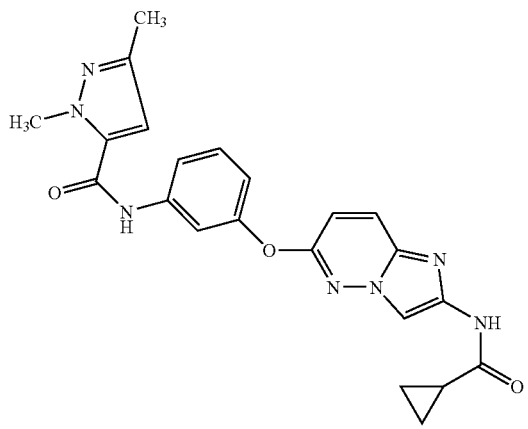

To a solution of N-[6-(3-aminophenoxy)imidazo[1,2-b]pyridazin-2-yl]cyclopropanecarboxamide (200 mg, 0.65 mmol) in N,N-dimethylacetamide (2.0 mL) was added 1,3-dimethyl-1H-pyrazole-5-carbonyl chloride (185 mg, 1.16 mmol). After stirring at room temperature for 1 hr, water was added to the reaction mixture, and the mixture was extracted with ethyl acetate/tetrahydrofuran, washed with saturated brine, dried over anhydrous magnesium sulfate, and filtrated. The solvent was evaporated under reduced pressure, and the residue was purified by silica gel column chromatography (hexane/ethyl acetate=1/2→4-ethyl acetate) and precipitated from hexane/ethyl acetate to give the title compound (70 mg, 25%) as a white powder.

$^1$H-NMR (DMSO-$d_6$, 300 MHz) δ 0.79-0.83 (4H, m), 1.87-1.97 (1H, m), 2.19 (3H, s), 3.98 (3H, s), 6.82 (1H, s), 6.99-7.03 (1H, m), 7.07 (1H, d, J=9.6 Hz), 7.43 (1H, t, J=8.1 Hz), 7.60-7.64 (1H, m), 7.65-7.68 (1H, m), 7.97 (1H, s), 8.06 (1H, d, J=9.6 Hz), 10.24 (1H, s), 11.10 (1H, s).

Example 121

Production of 1,3-dimethyl-N-[3-({2-[(tetrahydro-2H-pyran-4-ylcarbonyl)amino]imidazo[1,2-b]pyridazin-6-yl}oxy)phenyl]-1H-pyrazole-5-carboxamide

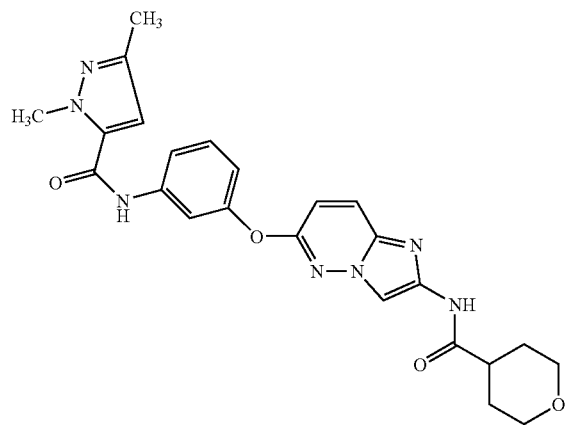

Using N-[6-(3-aminophenoxy)imidazo[1,2-b]pyridazin-2-yl]tetrahydro-2H-pyran-4-carboxamide (200 mg, 0.57 mmol), triethylamine (237 mL, 1.70 mmol), 1,3-dimethyl-1H-pyrazole-5-carbonyl chloride (180 mg, 1.13 mmol) and tetrahydrofuran (6.0 mL) as starting materials and in the same manner as in Example 96, the title compound (73 mg, 27%) was obtained as a white powder.

$^1$H-NMR (DMSO-$d_6$, 300 MHz) δ 1.58-1.72 (4H, m), 2.20 (3H, s), 2.63-2.78 (1H, m), 3.27-3.37 (2H, m), 3.86-3.92 (2H, s), 3.98 (3H, s), 6.83 (1H, s), 6.98-7.03 (1H, m), 7.07 (1H, d, J=9.6 Hz), 7.43 (1H, t, J=8.1 Hz), 7.59-7.63 (1H, m), 7.67-7.70 (1H, m), 8.03 (1H, s), 8.06 (1H, d, J=9.6 Hz), 10.26 (1H, s), 10.82 (1H, s).

Example 122

Production of N-[6-(4-aminophenoxy)imidazo[1,2-b]pyridazin-2-yl]cyclopropanecarboxamide

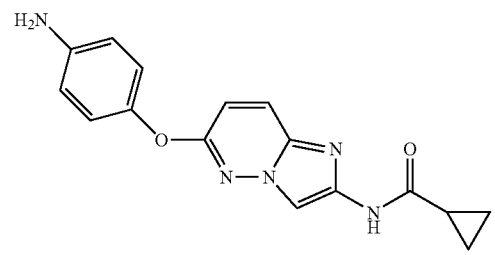

To a solution of 4-aminophenol (0.33 g, 3.05 mmol) in N,N-dimethylformamide (10 mL) was added potassium tert-butoxide (0.36 g, 3.17 mmol), and the mixture was stirred at room temperature for 2 hr. N (6-Iodoimidazo[1,2-b]pyridazin-2-yl)cyclopropanecarboxamide (0.80 g, 2.44 mmol) and potassium carbonate (0.17 g, 1.22 mmol) were added to the reaction mixture, and the mixture was stirred using a microwave synthesizer with heating at 150° C. for 30 min. After cooling the reaction mixture, saturated brine was added to the mixture, and the mixture was extracted with ethyl acetate/tetrahydrofuran, washed with saturated brine, dried over anhydrous magnesium sulfate, and filtrated. The solvent was evaporated under reduced pressure, and the residue was purified by silica gel column chromatography (hexane/ethyl acetate=1/2→ethyl acetate) to give the title compound (376 mg, 50%) as a dark brown powder.

$^1$H-NMR (DMSO-$d_6$, 300 MHz) δ 0.76-0.81 (4H, m), 1.88-1.95 (1H, m), 5.09 (2H, s), 6.57-6.61 (2H, s), 6.88-6.94 (3H, m), 7.89-7.97 (2H, m), 11.05 (1H, s).

Example 123

Production of N-[4-({2-[(cyclopropylcarbonyl)amino]imidazo[1,2-b]pyridazin-6-yl}oxy)phenyl]-1,3-dimethyl-1H-pyrazole-5-carboxamide

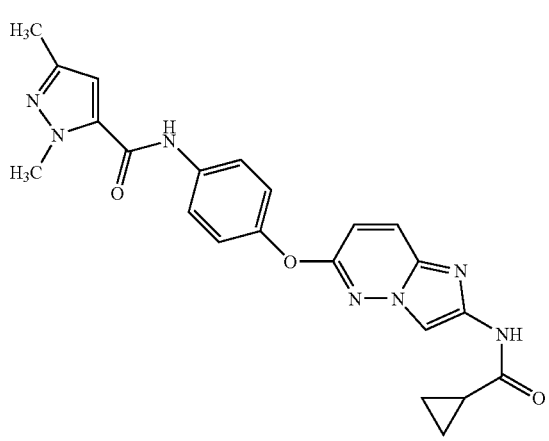

Using N-[6-(4-aminophenoxy)imidazo[1,2-b]pyridazin-2-yl]cyclopropanecarboxamide (220 mg, 0.71 mmol), triethylamine (0.30 mL, 2.13 mmol), 1,3-dimethyl-1H-pyrazole-5-carbonyl chloride (230 mg, 1.42 mmol) and tetrahydrofuran (6.6 mL) as starting materials and in the same manner as in Example 96, the title compound (84 mg, 27%) was obtained as a white powder.

$^1$H-NMR (DMSO-$d_6$, 300 MHz) δ 0.78-0.82 (4H, m), 1.87-1.96 (1H, m), 2.21 (3H, s), 4.00 (3H, s), 6.82 (1H, s), 7.03 (1H, d, J=9.6 Hz), 7.25 (2H, d, J=9.0 Hz), 7.78 (2H, d, J=9.0 Hz), 7.92 (1H, s), 8.02 (1H, d, J=9.6 Hz), 10.22 (1H, s), 11.07 (1H, s).

Example 124

Production of 6-(3-aminophenoxy)-N-methylimidazo[1,2-b]pyridazine-2-carboxamide

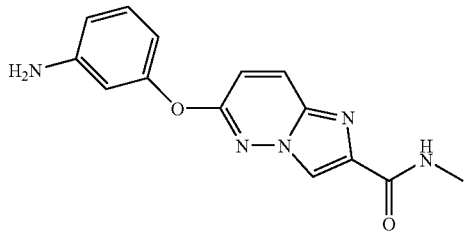

Using 6-iodo-N-methylimidazo[1,2-b]pyridazine-2-carboxamide (0.30 g, 0.99 mmol), N,N-dimethylformamide (3.0 mL), potassium carbonate (275 mg, 1.99 mmol) and 3-aminophenol (163 mg, 1.49 mmol) as starting materials and in the same manner as in Example 91, the title compound (0.10 g, 36%) was obtained as a dark brown powder.

$^1$H-NMR (DMSO-$d_6$, 300 MHz) δ 2.77 (3H, d, J=5.1 Hz), 5.34 (2H, s), 6.32-6.40 (2H, m), 6.43-6.47 (1H, m), 7.06 (1H, t, J=8.1 Hz), 7.13 (1H, d, J=9.6 Hz), 8.15 (1H, d, J=9.6 Hz), 8.34 (1H, s), 8.37 (1H, q, J=5.1 Hz).

Example 125

Production of 6-(3-{[(1,3-dimethyl-1H-pyrazol-5-yl)carbonyl]amino}phenoxy)-N-methylimidazo[1,2-b]pyridazine-2-carboxamide

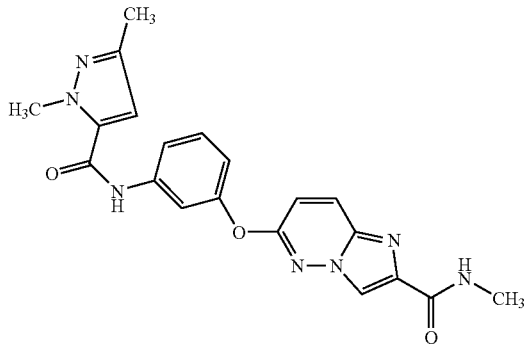

To a solution of 6-(3-aminophenoxy)-N-methylimidazo[1,2-b]pyridazine-2-carboxamide (250 mg, 0.88 mmol) in N,N-dimethylacetamide (2.5 mL) was added 1,3-dimethyl-1H-pyrazole-5-carbonyl chloride (253 mg, 1.59 mmol). After stirring at room temperature for 1 hr, water was added to the reaction mixture, and the precipitate was collected by filtration. The obtained residue was washed with water, acetonitrile and diethyl ether to give the title compound (262 mg, 73%) as a white powder.

$^1$H-NMR (DMSO-$d_6$, 300 MHz) δ 2.20 (3H, s), 2.77 (3H, d, J=5.1 Hz), 3.99 (3H, s), 6.82 (1H, s), 7.04-7.09 (1H, m), 7.24 (1H, d, J=9.9 Hz), 7.44 (1H, t, J=8.1 Hz), 7.57-7.64 (1H, m), 7.71-7.74 (1H, m), 8.20 (1H, d, J=9.6 Hz), 8.34 (1H, s), 8.35-8.41 (1H, m), 10.28 (1H, s).

Example 126

Production of N-[6-(3-aminophenoxy)imidazo[1,2-b]pyridazin-2-yl]-2-methoxyacetamide

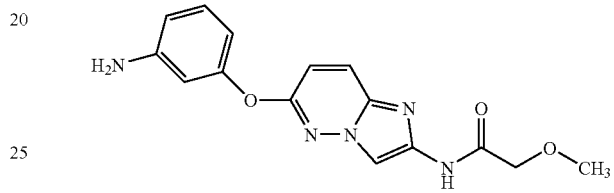

Using N-(6-iodoimidazo[1,2-b]pyridazin-2-yl)-2-methoxyacetamide (0.60 g, 1.81 mmol), N,N-dimethylformamide (6.0 mL), potassium carbonate (499 mg, 3.61 mmol) and 3-aminophenol (296 mg, 2.71 mmol) as starting materials and in the same manner as in Example 91, the title compound (0.29 g, 51%) was obtained as a dark brown powder.

$^1$H-NMR (DMSO-$d_6$, 300 MHz) δ 3.35 (3H, s), 4.06 (2H, s), 5.32 (2H, s), 6.28-6.37 (2H, s), 6.41-6.45 (1H, m), 6.98 (1H, d, J=9.6 Hz), 7.05 (1H, t, J=8.1 Hz), 8.01 (1H, d, J=9.6 Hz), 8.04 (1H, s), 10.57 (1H, s).

Example 127

Production of N-[3-({2-[(methoxyacetyl)amino]imidazo[1,2-b]pyridazin-6-yl}oxy)phenyl]-1,3-dimethyl-1H-pyrazole-5-carboxamide

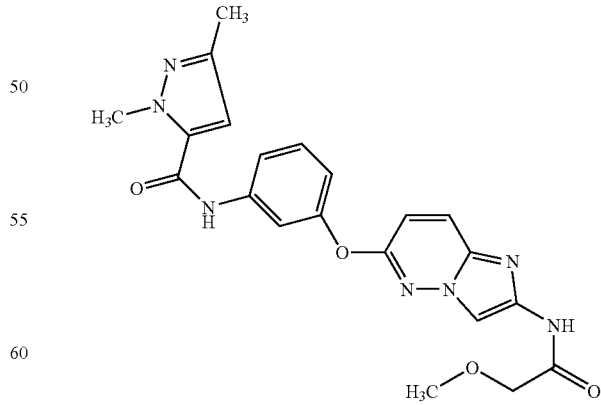

Using N-[6-(3-aminophenoxy)imidazo[1,2-b]pyridazin-2-yl]-2-methoxyacetamide (200 mg, 0.64 mmol), 1,3-dimethyl-1H-pyrazole-5-carbonyl chloride (162 mg, 1.02 mmol) and N,N-dimethylacetamide (4.0 mL) as starting materials and in the same manner as in Example 120, the title compound (176 mg, 64%) was obtained as a white powder.

$^1$H-NMR (DMSO-$d_6$, 300 MHz) δ 2.19 (3H, s), 3.33 (3H, s), 3.98 (3H, s), 4.06 (2H, s), 6.82 (1H, s), 6.97-7.04 (1H, m), 7.09 (1H, d, J=9.3 Hz), 7.43 (1H, t, J=8.1 Hz), 7.58-7.64 (1H, m), 7.66-7.69 (1H, m), 8.03 (1H, s), 8.04 (1H, d, J=9.3 Hz), 10.24 (1H, s), 10.59 (1H, s).

Example 128

Production of N-[3-({2-[(cyclopropylcarbonyl)amino]imidazo[1,2-b]pyridazin-6-yl}oxy)phenyl]-1,5-dimethyl-1H-pyrazole-3-carboxamide

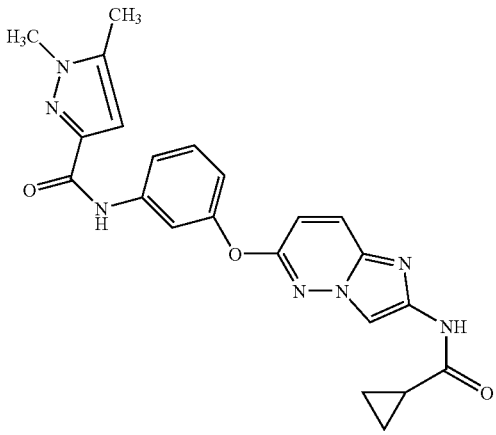

To a solution of 1,5-dimethyl-1H-pyrazole-3-carboxylic acid (109 mg, 0.78 mmol) in tetrahydrofuran (4.0 mL) were added N,N-dimethylformamide (30 μL, 0.39 mmol) and oxalyl chloride (135 μL, 1.55 mmol), and the mixture was stirred at room temperature for 1 hr. The solvent was evaporated under reduced pressure, and a solution of the residue in tetrahydrofuran (2.0 mL) was added dropwise to a solution of N-[6-(3-aminophenoxy)imidazo[1,2-b]pyridazin-2-yl]cyclopropylcarboxamide (200 mg, 0.65 mmol) and triethylamine (360 μL, 2.59 mmol) in tetrahydrofuran (4.0 mL). After stirring at room temperature for 2 hr, water was added to the reaction mixture, and the mixture was extracted with ethyl acetate/tetrahydrofuran, washed with saturated brine, dried over anhydrous magnesium sulfate, and filtrated. The solvent was evaporated under reduced pressure, and the residue was purified by silica gel column chromatography (hexane/ethyl acetate=1/4→ethyl acetate) and precipitated from hexane/ethyl acetate to give the title compound (118 mg, 42%) as a white powder.

$^1$H-NMR (DMSO-$d_6$, 300 MHz) δ 0.78-0.83 (4H, m), 1.88-1.96 (1H, m), 2.30 (3H, s), 3.82 (3H, s), 6.54 (1H, s), 6.91-6.96 (1H, m), 7.05 (1H, d, J=9.6 Hz), 7.37 (1H, t, J=8.1 Hz), 7.69-7.73 (1H, m), 7.76-7.78 (1H, m), 7.97 (1H, s), 8.04 (1H, d, J=9.6 Hz), 10.10 (1H, s), 11.09 (1H, s).

Example 129

Production of N-[6-(3-aminophenoxy)imidazo[1,2-b]pyridazin-2-yl]-2-methylpropanamide

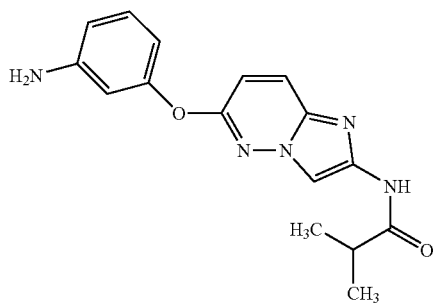

Using N-(6-iodoimidazo[1,2-b]pyridazin-2-yl)-2-methylpropanamide (0.60 g, 1.82 mmol), N,N-dimethylformamide (6.0 mL), potassium carbonate (502 mg, 3.63 mmol) and 3-aminophenol (278 mg, 2.54 mmol) as starting materials and in the same manner as in Example 91, the title compound (0.26 g, 47%) was obtained as a dark brown powder.

$^1$H-NMR (DMSO-$d_6$, 300 MHz) δ 1.09 (6H, d, J=6.9 Hz), 2.66-2.74 (1H, m), 5.32 (2H, s), 6.27-6.36 (2H, m), 6.40-6.44 (1H, m), 6.95 (1H, d, J=9.6 Hz), 7.05 (1H, t, J=8.1 Hz), 7.94-8.02 (2H, m), 10.74 (1H, s).

Example 130

Production of N-(3-{[2-(isobutyrylamino)imidazo[1,2-b]pyridazin-6-yl]oxy}phenyl)-1,3-dimethyl-1H-pyrazole-5-carboxamide

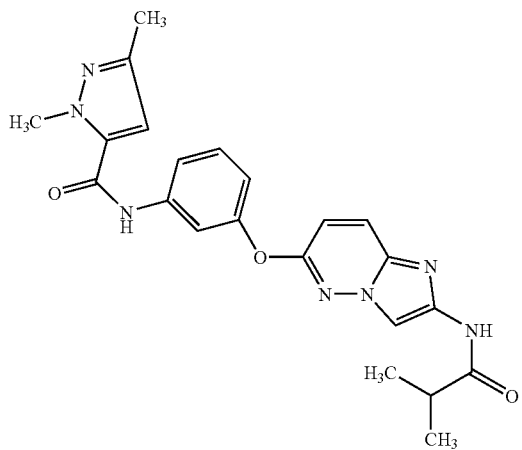

Using 1,3-dimethyl-1H-pyrazole-5-carboxylic acid (108 mg, 0.77 mmol), tetrahydrofuran (3.2 mL), N,N-dimethylformamide (30 μL, 0.39 mmol), oxalyl chloride (134 μL, 1.54 mmol), N-[6-(3-aminophenoxy)imidazo[1,2-b]pyridazin-2-yl]-2-methylpropanamide (200 mg, 0.64 mmol) and N,N-dimethylacetamide (4.0 mL) as starting materials and in the same manner as in Example 119, the title compound (201 mg, 72%) was obtained as a white powder.

$^1$H-NMR (DMSO-d$_6$, 300 MHz) δ 1.08 (6H, d, J=6.9 Hz), 2.19 (3H, s), 2.65-2.74 (1H, m), 3.98 (3H, s), 6.82 (1H, s), 6.98-7.02 (1H, m), 7.06 (1H, d, J=9.6 Hz), 7.42 (1H, t, J=8.1 Hz), 7.59-7.63 (1H, m), 7.66-7.68 (1H, m), 8.01 (1H, s), 8.04 (1H, d, J=9.6 Hz), 10.24 (1H, s), 10.75 (1H, s).

Example 131

Production of N-[3-({2-[(cyclopropylcarbonyl) amino]imidazo[1,2-b]pyridazin-6-yl}oxy)phenyl]-3, 5-dimethylisoxazole-4-carboxamide

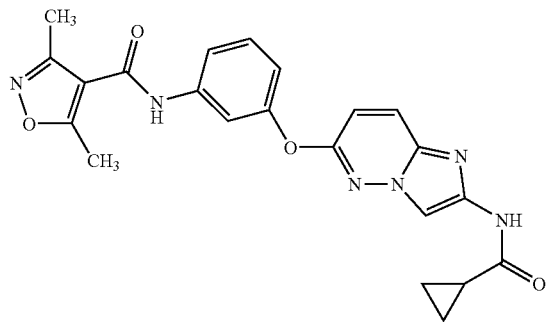

Using N-[6-(3-aminophenoxy)imidazo[1,2-b]pyridazin-2-yl]cyclopropylcarboxamide (160 mg, 0.52 mmol), N,N-dimethylacetamide (3.2 mL) and 3,5-dimethylisoxazole-4-carbonyl chloride (99 mg, 0.62 mmol) and in the same manner as in Example 120, the title compound (163 mg, 73%) was obtained as a white powder.

$^1$H-NMR (DMSO-d$_6$, 300 MHz) δ 0.79-0.82 (4H, m), 1.88-1.95 (1H, m), 2.32 (3H, s), 2.54 (3H, s), 6.98-7.02 (1H, m), 7.06 (1H, d, J=9.6 Hz), 7.42 (1H, t, J=8.1 Hz), 7.48-7.51 (1H, m), 7.61-7.64 (1H, m), 7.96 (1H, s), 8.05 (1H, d, J=9.6 Hz), 10.19 (1H, s), 11.09 (1H, s).

Example 132

Production of N-[3-({2-[(cyclopropylcarbonyl) amino]imidazo[1,2-b]pyridazin-6-yl}oxy)phenyl]-1-methyl-1H-1,2,3-triazole-5-carboxamide

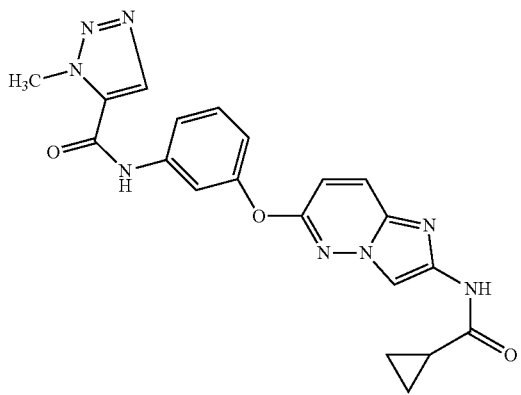

Using 1-methyl-1H-1,2,3-triazole-5-carboxylic acid (99 mg, 0.78 mmol), tetrahydrofuran (4.0 mL), N,N-dimethylformamide (30 μL, 0.39 mmol), oxalyl chloride (135 μL, 1.55 mmol), N-[6-(3-aminophenoxy)imidazo[1,2-b]pyridazin-2-yl]cyclopropylcarboxamide (200 mg, 0.65 mmol) and N,N-dimethylacetamide (4.0 mL) as starting materials and in the same manner as in Example 119, the title compound (182 mg, 67%) was obtained as a white powder.

$^1$H-NMR (DMSO-d$_6$, 300 MHz) δ 0.79-0.82 (4H, m), 1.87-1.96 (1H, m), 4.23 (3H, s), 7.02-7.09 (2H, m), 7.46 (1H, t, J=8.1 Hz), 7.56-7.65 (2H, m), 7.96 (1H, s), 8.05 (1H, d, J=9.6 Hz), 8.37 (1H, s), 10.61 (1H, s), 11.09 (1H, s).

Example 133

Production of N-[3-({2-[(cyclopropylcarbonyl) amino]imidazo[1,2-b]pyridazin-6-yl}oxy)phenyl]-1-methyl-1H-1,2,3-triazole-4-carboxamide

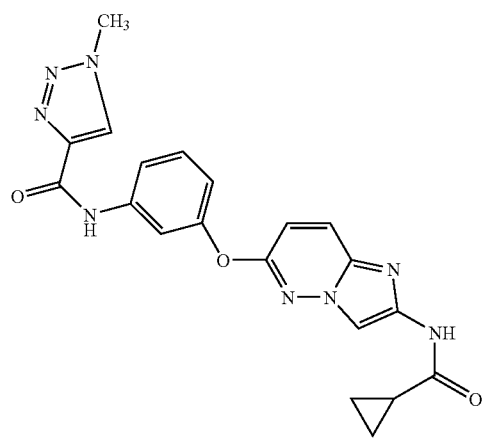

Using 1-methyl-1H-1,2,3-triazole-4-carboxylic acid (99 mg, 0.78 mmol), tetrahydrofuran (4.0 mL), N,N-dimethylformamide (30 mL, 0.39 mmol), oxalyl chloride (135 μL, 1.55 mmol), N-[6-(3-aminophenoxy)imidazo[1,2-b]pyridazin-2-yl]cyclopropylcarboxamide (200 mg, 0.65 mmol) and N,N-dimethylacetamide (4.0 mL) as starting materials and in the same manner as in Example 119, the title compound (189 mg, 70%) was obtained as a white powder.

$^1$H-NMR (DMSO-d$_6$, 300 MHz) δ 0.79-0.82 (4H, m), 1.87-1.96 (1H, m), 4.12 (3H, s), 6.98 (1H, dd, J=11.3, 2.3 Hz), 7.06 (1H, d, J=9.3 Hz), 7.40 (1H, t, J=8.1 Hz), 7.72-7.76 (1H, m), 7.78-7.81 (1H, m), 7.97 (1H, s), 8.04 (1H, d, J=9.3 Hz), 8.66 (1H, s), 10.60 (1H, s), 11.09 (1H, s).

Example 134

Production of N-[6-(3-aminophenoxy)imidazo[1,2-b]pyridazin-2-yl]propaneamide

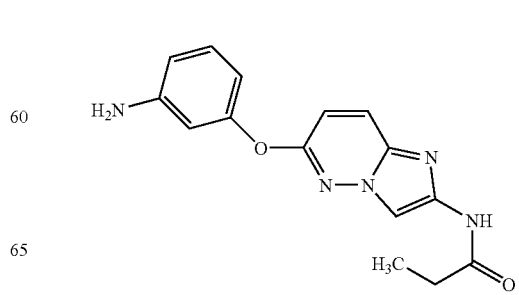

To a solution of 3-aminophenol (331 mg, 3.0 mol) in N,N-dimethylformamide (8.0 mL) was added potassium tert-butoxide (355 mg, 3.16 mmol), and the mixture was stirred at room temperature for 2 hr. To the reaction mixture were added N-(6-iodoimidazo[1,2-b]pyridazin-2-yl)propaneamide (0.80 g, 2.53 mmol) and potassium carbonate (175 mg, 1.27 mmol), and the mixture was stirred at 140° C. for 16 hr. Saturated brine was added to the reaction mixture, and the mixture was extracted with ethyl acetate/tetrahydrofuran, washed with saturated brine, dried over anhydrous magnesium sulfate, and filtrated. The solvent was evaporated under reduced pressure, and the residue was purified by silica gel column chromatography (hexane/ethyl acetate=1/2) and precipitated from hexane/ethyl acetate to give the title compound (420 mg, 56%) as a white powder.

$^1$H-NMR (DMSO-$d_6$, 300 MHz) δ 1.07 (3H, t, J=7.5 Hz), 2.37 (2H, q, J=7.5 Hz), 5.31 (2H, s), 6.27-6.35 (2H, m), 6.40-6.44 (1H, m), 6.95 (1H, d, J=9.3 Hz), 7.04 (1H, d, J=8.0 Hz), 7.98 (1H, d, J=9.3 Hz), 8.00 (1H, d, J=1.5 Hz), 10.73 (1H, s).

Example 135

Production of 1,3-dimethyl-N-(3-{[2-(propionylamino)imidazo[1,2-b]pyridazin-6-yl]oxy}phenyl)-1H-pyrazole-5-carboxamide

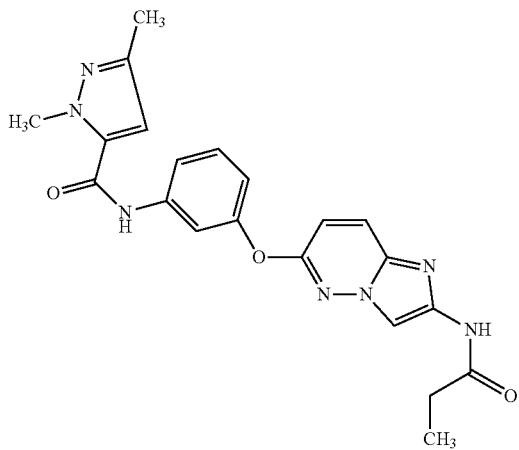

Using 1,3-dimethyl-1H-pyrazole-5-carboxylic acid (113 mg, 0.81 mol), tetrahydrofuran (4.0 mL), N,N-dimethylformamide (30 μL, 0.39 mmol), oxalyl chloride (141 μL, 1.61 mmol), N-[6-(3-aminophenoxy)imidazo[1,2-b]pyridazin-2-yl]propionyl carboxamide (200 mg, 0.67 mmol) and N,N-dimethylacetamide (4.0 mL) as starting materials and in the same manner as in Example 119, the title compound (190 mg, 67%) was obtained as a white powder.

$^1$H-NMR (DMSO-$d_6$, 300 MHz) δ 1.07 (3H, t, J=7.5 Hz), 2.19 (3H, s), 2.37 (2H, q, J=7.5 Hz), 3.98 (3H, s), 6.83 (1H, s), 6.99-7.04 (1H, m), 7.07 (1H, d, J=9.6 Hz), 7.43 (1H, t, J=8.1 Hz), 7.60-7.64 (1H, m), 7.67-7.69 (1H, m), 8.02 (1H, s), 8.05 (1H, d, J=9.6 Hz), 10.25 (1H, s), 10.77 (1H, s).

Example 136

Production of N-[3-({2-[(cyclopropylcarbonyl)amino]imidazo[1,2-b]pyridazin-6-yl}oxy)phenyl]-1-methyl-1H-imidazole-2-carboxamide

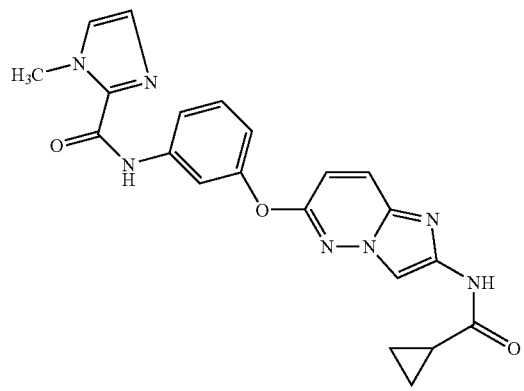

Using 1-methyl-1H-imidazole-2-carboxylic acid (36.7 mg, 0.29 mol), tetrahydrofuran (1.5 mL), N,N-dimethylformamide (30 μL, 0.39 mmol), oxalyl chloride (51 μL, 0.58 mmol), N-[6-(3-aminophenoxy)imidazo[1,2-b]pyridazin-2-yl]cyclopropylcarboxamide (75 mg, 0.24 mmol) and N,N-dimethylacetamide (1.5 mL) as starting materials and in the same manner as in Example 119, the title compound (48 mg, 47%) was obtained as a white powder.

$^1$H-NMR (DMSO-$d_6$, 300 MHz) δ 0.78-0.82 (4H, m), 1.91-1.97 (1H, m), 3.97 (3H, s), 6.97 (1H, dd, J=8.1, 1.5 Hz), 7.05 (1H, d, J=9.6 Hz), 7.07 (1H, s), 7.39 (1H, t, J=8.1 Hz), 7.44-7.45 (1H, m), 7.72 (1H, d, J=8.4 Hz), 7.78-7.80 (1H, m), 7.97 (1H, s), 8.04 (1H, d, J=9.6 Hz), 10.43 (1H, s), 11.08 (1H, s).

Example 137

Production of N-(3-{[2-(acetylamino)imidazo[1,2-b]pyridazin-6-yl]oxy}phenyl)-1-methyl-1H-imidazole-5-carboxamide

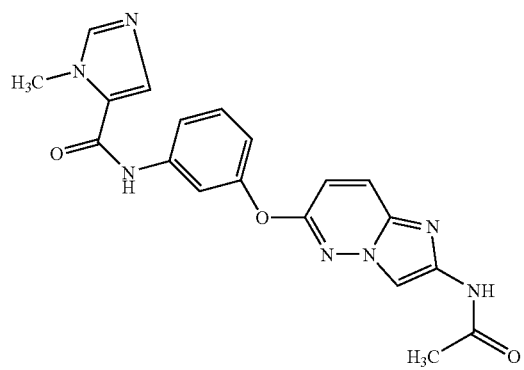

Using 1-methyl-1H-imidazole-5-carboxylic acid (80 mg, 0.64 mol), tetrahydrofuran (3.0 mL), N,N-dimethylformamide (30 μL, 0.39 mmol), oxalyl chloride (111 μL, 1.27=mol), N-[6-(3-aminophenoxy)imidazo[1,2-b]pyridazin-2-yl]acetamide (150 mg, 0.53 mmol) and N,N-dimethylacetamide (3.0 mL) as starting materials and in the same manner as in Example 119, the title compound (98 mg, 47%) was obtained as a white powder.

$^1$H-NMR (DMSO-d$_6$, 300 MHz) δ 2.07 (3H, s), 3.84 (3H, s), 6.96-7.00 (1H, m), 7.06 (1H, d, J=9.3 Hz), 7.42 (1H, t, J=8.1 Hz), 7.57-7.61 (1H, m), 7.64-7.67 (1H, m), 7.79 (1H, s), 7.84 (1H, s), 7.99 (1H, s), 8.05 (1H, d, J=9.3 Hz), 10.16 (1H, s), 10.81 (1H, s).

Example 138

Production of N-[6-(3-amino-4-fluorophenoxy)imidazo[1,2-b]pyridazin-2-yl]cyclopropanecarboxamide

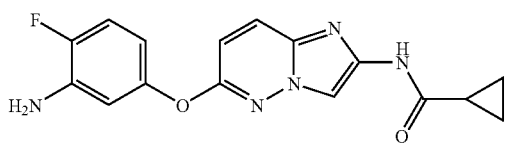

A mixture of N-(6-iodoimidazo[1,2-b]pyridazin-2-yl)cyclopropanecarboxamide (2.62 g, 8.0 mmol), 3-amino-4-fluorophenol (2.03 g, 16.0 mmol), potassium carbonate (1.66 g, 12.0 mmol) and N,N-dimethylformamide (20 mL) was stirred at 150° C. for 15 hr. Tetrahydrofuran/ethyl acetate and saturated brine were added to the reaction mixture, and insoluble material was filtered off. The filtrate was extracted with ethyl acetate, dried over anhydrous magnesium sulfate, and filtrated. The solvent was evaporated under reduced pressure, and the residue was purified by silica gel column chromatography (hexane/ethyl acetate=20/80→0/100) and recrystallized from ethyl acetate to give the title compound (1.91 g, 73%) as pale-yellow crystals.

$^1$H-NMR (DMSO-d$_6$, 300 MHz) δ 0.75-0.90 (4H, m), 1.85-2.00 (1H, m), 5.36 (2H, s), 6.30-6.40 (1H, m), 6.50-6.60 (1H, m), 6.96 (1H, d, J=9.8 Hz), 7.00-7.10 (1H, m), 7.95 (1H, s), 7.99 (1H, d, J=9.8 Hz), 11.06 (1H, s).

Example 139

Production of 4-(imidazo[1,2-b]pyridazin-6-yloxy)aniline

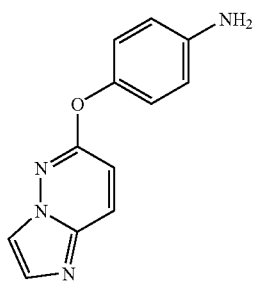

A mixture of 6-chloroimidazo[1,2-b]pyridazine (768 mg, 5.0 mmol), 4-aminophenol (818 mg, 7.5 mmol), potassium carbonate (2073 mg, 15.0 mmol) and N-methylpyrrolidone (5.0 mL) was stirred at 120° C. for 18 hr. The reaction mixture was diluted with 1N aqueous sodium hydroxide solution, and extracted with ethyl acetate. The organic layer was washed with 1N aqueous sodium hydroxide solution and saturated brine, and concentrated under reduced pressure. The residue was purified by NH silica gel column chromatography (hexane/ethyl acetate=70/30→0/100) and precipitated from diisopropyl ether to give the title compound (759 mg, 67%) as a gray powder.

$^1$H-NMR (DMSO-d$_6$, 300 MHz) δ 5.07 (2H, s), 6.60 (2H, d, J=8.9 Hz), 6.92 (2H, d, J=8.9 Hz), 7.00 (1H, d, J=9.8 Hz), 7.61 (1H, s), 8.01 (1H, s), 8.09 (1H, d, J=9.8 Hz).

Example 140

3-(imidazo[1,2-b]pyridazin-6-yloxy)aniline

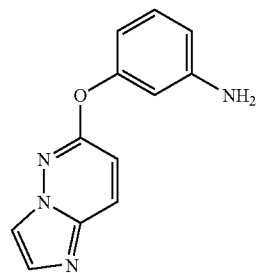

A mixture of 6-chloroimidazo[1,2-b]pyridazine (1536 mg, 10.0 mmol), 3-aminophenol (1419 mg, 13.0 mmol), potassium carbonate (4146 mg, 30.0 mmol) and N-methylpyrrolidone (10 mL) was stirred at 120° C. for 48 hr. The reaction mixture was diluted with 1N aqueous sodium hydroxide solution, and extracted with ethyl acetate. The organic layer was washed with 1N aqueous sodium hydroxide solution and saturated brine, and concentrated under reduced pressure. The residue was purified by NH silica gel column chromatography (hexane/ethyl acetate=70/30→0/100), and precipitated from diisopropyl ether to give the title compound (932 mg, 41%) as a white powder.

$^1$H-NMR (DMSO-d$_6$, 300 MHz) δ 5.29 (2H, s), 6.31-6.35 (1H, m), 6.37 (1H, t, J=2.2 Hz), 6.42-6.47 (1H, m), 7.02 (1H, d, J=9.8 Hz), 7.06 (1H, t, J=7.9 Hz), 7.65 (1H, d, J=1.2 Hz), 8.08 (1H, s), 8.13 (1H, d, J=9.8 Hz).

Example 141

Production of N-[4-(imidazo[1,2-b]pyridazin-6-yloxy)phenyl]-N'-phenylurea

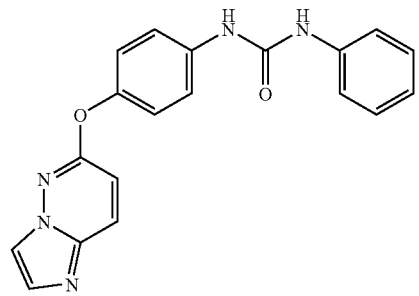

To a solution of 4-(imidazo[1,2-b]pyridazin-6-yloxy) aniline (181 mg, 0.80 mmol) and triethylamine (0.011 mL, 0.08 mmol) in tetrahydrofuran (10 mL) was added phenyl isocyanate (0.104 mL, 0.96 mmol), and the mixture was stirred at room temperature for 18 hr. The reaction mixture was concentrated under reduced pressure, and the residue was purified by NH silica gel column chromatography (ethyl acetate/methanol=100/0→90/10) and precipitated from ethyl acetate to give the title compound (223 mg, 81%) as a white powder.

$^1$H-NMR (DMSO-$d_6$, 300 MHz) δ 6.97 (1H, t, J=7.6 Hz), 7.09 (1H, d, J=9.8 Hz), 7.22 (2H, d, J=8.7 Hz), 7.28 (2H, t, J=7.6 Hz), 7.46 (2H, d, J=7.6 Hz), 7.52 (2H, d, J=8.7 Hz), 7.64 (1H, s), 8.05 (1H, s), 8.15 (1H, d, J=9.8 Hz), 8.70 (1H, s), 8.76 (1H, s).

Example 142

Production of N-[3-(imidazo[1,2-b]pyridazin-6-yloxy)phenyl]-N'-phenylurea

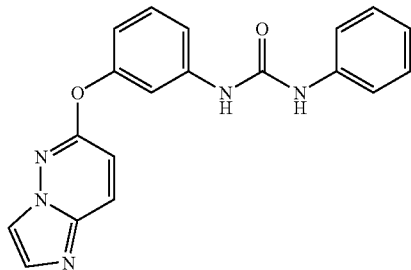

To a solution of 3-(imidazo[1,2-b]pyridazin-6-yloxy) aniline (181 mg, 0.80 mmol) and triethylamine (0.011 mL, 0.08 mmol) in tetrahydrofuran (10 mL) was added phenyl isocyanate (0.104 mL, 0.96 mmol), and the mixture was stirred at room temperature for 18 hr. The reaction mixture was concentrated under reduced pressure, and the residue was purified by NH silica gel column chromatography (ethyl acetate/methanol=100/0→90/10) and precipitated from ethyl acetate to give the title compound (196 mg, 71%) as a white powder.

$^1$H-NMR (DMSO-$d_6$, 300 MHz) δ 6.85-6.90 (1H, m), 6.97 (1H, t, J=7.5 Hz), 7.11 (1H, d, J=9.6 Hz), 7.22-7.31 (3H, m), 7.36 (1H, t, J=7.9 Hz), 7.43 (2H, d, J=7.5 Hz), 7.51 (1H, t, J=2.1 Hz), 7.66 (1H, d, J=0.9 Hz), 8.08 (1H, s), 8.18 (1H, d, J=9.6 Hz), 8.72 (1H, s), 8.87 (1H, s).

Example 143

Production of N-[3-(imidazo[1,2-b]pyridazin-6-yloxy)phenyl]-N'-[3-(trifluoromethyl)phenyl]urea

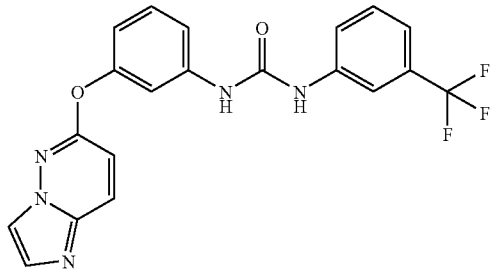

To a solution of 3-(imidazo[1,2-b]pyridazin-6-yloxy) aniline (181 mg, 0.80 mmol) and triethylamine (0.040 mL, 0.29 mmol) in tetrahydrofuran (10 mL) was added 3-(trifluoromethyl)phenyl isocyanate (0.154 mL, 1.12 mmol), and the mixture was stirred at room temperature for 18 hr. The reaction mixture was concentrated under reduced pressure, and the residue was purified by silica gel column chromatography (ethyl acetate/methanol=100/0→90/10) and precipitated from methanol to give the title compound (205 mg, 62%) as a white powder.

$^1$H-NMR (DMSO-$d_6$, 300 MHz) δ 6.89-6.94 (1H, m), 7.12 (1H, d, J=9.8 Hz), 7.26-7.34 (2H, m), 7.38 (1H, t, J=8.1 Hz), 7.47-7.60 (3H, m), 7.66 (1H, d, J=0.9 Hz), 7.99 (1H, s), 8.08 (1H, s), 8.18 (1H, d, J=9.8 Hz), 9.01 (1H, s), 9.11 (1H, s).

Example 144

Production of N-[3-(imidazo[1,2-b]pyridazin-6-yloxy)phenyl]-N'-[4-(trifluoromethyl)phenyl]urea

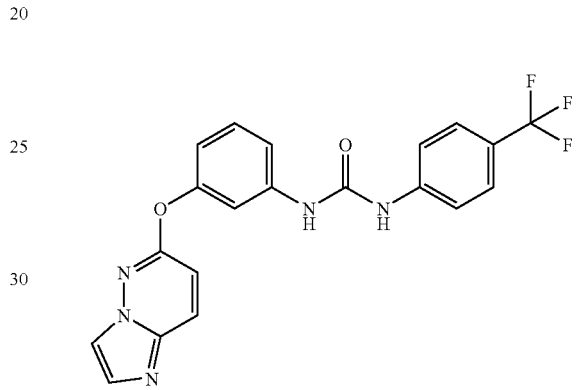

To a solution of 3-(imidazo[1,2-b]pyridazin-6-yloxy) aniline (113 mg, 0.50 mmol) and triethylamine (0.040 mL, 0.29 mmol) in tetrahydrofuran (10 mL) was added 4-(trifluoromethyl)phenyl isocyanate (0.100 mL, 0.70 mmol), and the mixture was stirred at room temperature for 18 hr. The reaction mixture was concentrated under reduced pressure, and the residue was precipitated from methanol to give the title compound (103 mg, 50%) as a white powder.

$^1$H-NMR (DMSO-$d_6$, 300 MHz) δ 6.86-6.94 (1H, m), 7.11 (1H, d, J=9.8 Hz), 7.24-7.31 (1H, m), 7.38 (1H, t, J=8.2 Hz), 7.51 (1H, t, J=1.8 Hz), 7.58-7.68 (5H, m), 8.08 (1H, s), 8.18 (1H, d, J=9.8 Hz), 9.00 (1H, s), 9.16 (1H, s).

Example 145

Production of N-[3-(imidazo[1,2-b]pyridazin-6-yloxy)phenyl]benzamide

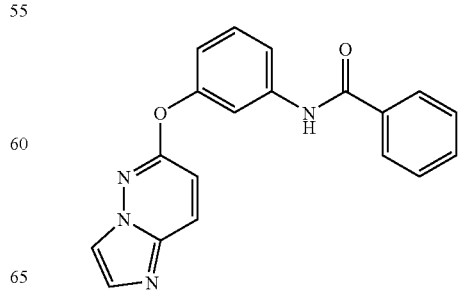

To a solution of 3-(imidazo[1,2-b]pyridazin-6-yloxy) aniline (113 mg, 0.50 mmol) in N-methylpyrrolidone (1.0 mL) was added benzoyl chloride (0.116 mL, 1.00 mmol), and the mixture was stirred at room temperature for 18 hr. The reaction mixture was diluted with 1N aqueous sodium hydroxide solution, and extracted with ethyl acetate. The organic layer was washed with 1N aqueous sodium hydroxide solution and saturated brine, and concentrated under reduced pressure. The residue was purified by silica gel column chromatography (ethyl acetate/methanol=100/0→75/25) and precipitated from ethyl acetate to give the title compound (122 mg, 74%) as a white powder.

$^1$H-NMR (DMSO-d$_6$, 300 MHz) δ 7.01-7.06 (1H, m), 7.14 (1H, d, J=9.8 Hz), 7.45 (1H, t, J=8.2 Hz), 7.50-7.64 (3H, m), 7.66-7.71 (2H, m), 7.77 (1H, t, J=2.1 Hz), 7.92-7.97 (2H, m), 8.09 (1H, s), 8.19 (1H, d, J=9.8 Hz), 10.39 (1H, s).

Example 146

Production of N-[3-(imidazo[1,2-b]pyridazin-6-yloxy)phenyl]-3-(trifluoromethyl)benzamide

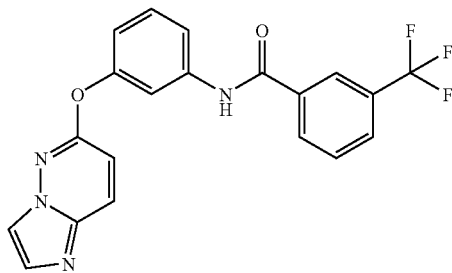

To a solution of 3-(imidazo[1,2-b]pyridazin-6-yloxy) aniline (113 mg, 0.50 mmol) in N-methylpyrrolidone (1.0 mL) was added 3-(trifluoromethyl)benzoyl chloride (0.151 mL, 1.00 mmol), and the mixture was stirred at room temperature for 18 hr. The reaction mixture was diluted with 1N aqueous sodium hydroxide solution, and extracted with ethyl acetate. The organic layer was washed with 1N aqueous sodium hydroxide solution and saturated brine, and concentrated under reduced pressure. The residue was purified by silica gel column chromatography (ethyl acetate/methanol=100/0→75/25), and precipitated from diisopropyl ether to give the title compound (195 mg, 98%) as a white powder.

$^1$H-NMR (DMSO-d$_6$, 300 MHz) δ 7.05-7.10 (1H, m), 7.15 (1H, d, J=9.6 Hz), 7.47 (1H, t, J=7.9 Hz), 7.67-7.71 (1H, m), 7.67 (1H, d, J=1.2 Hz), 7.75 (1H, t, J=2.1 Hz), 7.79 (1H, t, J=7.8 Hz), 7.98 (1H, d, J=7.8 Hz), 8.09 (1H, s), 8.20 (1H, d, J=9.6 Hz), 8.26 (1H, d, J=8.4 Hz), 8.29 (1H, s), 10.61 (1H, s).

Example 147

Production of N-{6-[(3-aminophenyl)sulfanyl]imidazo[1,2-b]pyridazin-2-yl}cyclopropanecarboxamide

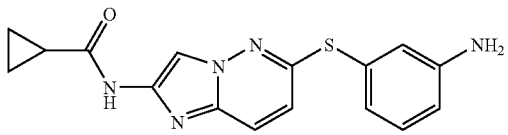

A mixture of N-(6-iodoimidazo[1,2-b]pyridazin-2-yl)cyclopropanecarboxamide (500 mg, 1.52 mmol), 3-aminobenzenethiol (381 mg, 3.04 mmol), potassium carbonate (630 mg, 4.56 mmol) and N,N-dimethylformamide (5.0 mL) was stirred at 80° C. for 3 hr. The reaction mixture was diluted with water, and extracted with ethyl acetate. The organic layer was concentrated under reduced pressure, and the residue was purified by silica gel column chromatography (ethyl acetate/methanol=100/0→80/20) and precipitated from ethyl acetate to give the title compound (396 mg, 80%).

$^1$H-NMR (DMSO-d$_6$, 300 MHz) δ 0.79-0.86 (4H, m), 1.89-1.99 (1H, m), 5.38 (2H, s), 6.61-6.66 (1H, m), 6.66-6.70 (1H, m), 6.74 (1H, t, J=1.9 Hz), 6.83 (1H, d, J=9.6 Hz), 7.11 (1H, t, J=7.8 Hz), 7.86 (1H, d, J=9.6 Hz), 8.14 (1H, s), 11.16 (1H, s).

Example 148

Production of N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide

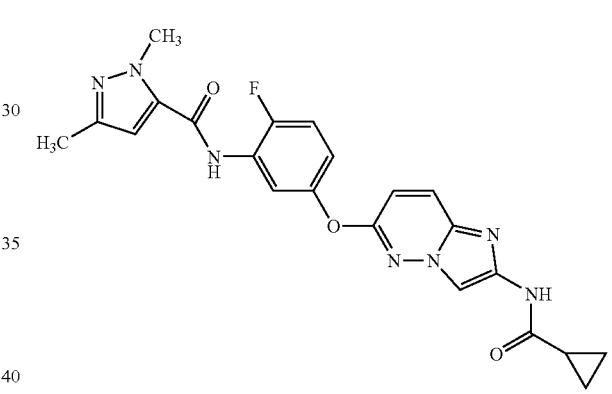

To a solution of N-[6-(3-amino-4-fluorophenoxy)imidazo[1,2-b]pyridazin-2-yl]cyclopropanecarboxamide (100 mg, 0.306 mmol) in N,N-dimethylacetamide (4.0 mL) was added a solution of 1,3-dimethyl-1H-pyrazole-5-carbonyl chloride (51 mg, 0.321 mmol) in N,N-dimethylacetamide (1.0 mL) under ice-cooling, and the mixture was stirred at room temperature for 30 min. Under ice-cooling, aqueous sodium hydrogencarbonate solution was added to the reaction mixture, and the mixture was extracted with ethyl acetate, washed with saturated brine, dried over anhydrous magnesium sulfate, and filtrated. The solvent was evaporated under reduced pressure, and the residue was purified by silica gel column chromatography (methanol/ethyl acetate=0/100→5/95) and recrystallized from methanol/ethyl acetate to give the title compound (88.8 mg, 65%) as pale-yellow crystals. melting point 237° C.

$^1$H-NMR (DMSO-d$_6$, 300 MHz) δ 0.75-0.90 (4H, m), 1.85-2.00 (1H, m), 2.19 (3H, s), 3.97 (3H, s), 6.84 (1H, s), 7.07 (1H, d, J=9.3 Hz), 7.15-7.25 (1H, m), 7.40 (1H, t, J=9.6 Hz), 7.50-7.60 (1H, m), 7.93 (1H, s), 8.04 (1H, d, J=9.6 Hz), 10.10 (1H, s), 11.07 (1H, s).

Example 149

Production of N-[3-({2-[(N,N-dimethylglycyl)amino]imidazo[1,2-b]pyridazin-6-yl}oxy)phenyl]-1,3-dimethyl-1H-pyrazole-5-carboxamide

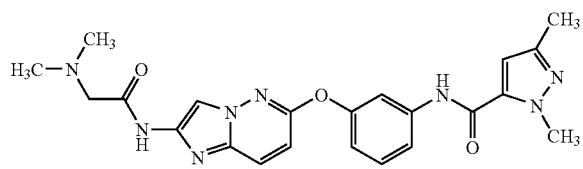

To a solution of N-[6-(3-aminophenoxy)imidazo[1,2-b]pyridazin-2-yl]-$N^2,N^2$-dimethylglycinamide (196 mg, 0.6 mmol) in N-methylpyrrolidone (5.0 mL) was added 1,3-dimethylpyrazole-5-carbonyl chloride (270 mg, 1.7 mmol), and the mixture was stirred at room temperature for 5 hr. The reaction mixture was diluted with 1N aqueous sodium hydroxide solution, and extracted with ethyl acetate. The organic layer was concentrated under reduced pressure, and the residue was purified by silica gel column chromatography (ethyl acetate/methanol=100/0→460/40) and precipitated from ethyl acetate to give the title compound (131 mg, 49%) as a white powder. melting point 210° C.

$^1$H-NMR (DMSO-$d_6$, 300 MHz) δ 2.19 (3H, s), 2.27 (6H, s), 3.13 (2H, s), 3.98 (3H, s), 6.83 (1H, s), 6.99-7.04 (1H, m), 7.09 (1H, d, J=9.6 Hz), 7.43 (1H, t, J=8.1 Hz), 7.59-7.64 (1H, m), 7.68 (1H, t, J=2.1 Hz), 8.04 (1H, s), 8.07 (1H, d, J=9.6 Hz), 10.25 (1H, s), 10.37 (1H, s).

Example 150

Production of N-[3-({2-[(cyclopropylcarbonyl)amino]imidazo[1,2-b]pyridazin-6-yl}sulfanyl)phenyl]-1,3-dimethyl-1H-pyrazole-5-carboxamide

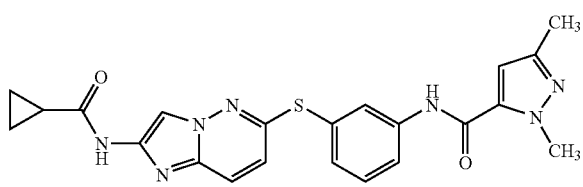

To a solution of N-{6-[(3-aminophenyl)sulfanyl]imidazo[1,2-b]pyridazin-2-yl}cyclopropanecarboxamide (195 mg, 0.6 mmol) in N-methylpyrrolidone (3.0 mL) was added 1,3-dimethylpyrazole-5-carbonyl chloride (159 mg, 1.0 mmol), and the mixture was stirred at room temperature for 18 hr. The reaction mixture was diluted with water, and extracted with ethyl acetate. The organic layer was concentrated under reduced pressure, and the residue was purified by silica gel column chromatography (ethyl acetate/methanol=100/0→70/30) and precipitated from methanol to give the title compound (245 mg, 91%) as a white powder.

$^1$H-NMR (DMSO-$d_6$, 300 MHz) δ 0.78-0.87 (4H, m), 1.89-1.99 (1H, m), 2.19 (3H, s), 3.98 (3H, s), 6.82 (1H, s), 6.94 (1H, d, J=9.4 Hz), 7.31-7.36 (1H, m), 7.47 (1H, t, J=7.8 Hz), 7.81-7.86 (1H, m), 7.90 (1H, dd, J=9.4, 0.5 Hz), 7.99 (1H, t, J=1.9 Hz), 8.15 (1H, s), 10.25 (1H, s), 11.16 (1H, s). melting point 251° C.

Example 151

Production of N-[6-(3-aminophenoxy)imidazo[1,2-b]pyridazin-2-yl]-$N^2,N^2$-dimethylglycinamide

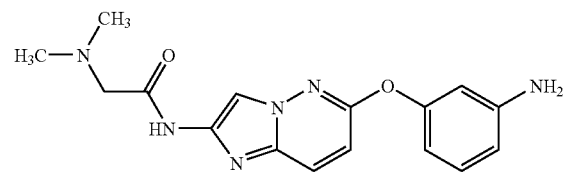

A mixture of N-(6-iodoimidazo[1,2-b]pyridazin-2-yl)-$N^2,N^2$-dimethylglycinamide (517 mg, 1.5 mmol), 3-aminophenol (491 mg, 4.5 mmol), potassium carbonate (415 mg, 3.0 mmol) and N,N-dimethylformamide (3.0 mL) was stirred using a microwave synthesizer at 180° C. for 40 min. The reaction mixture was diluted with water, and the precipitate was collected by filtration, washed with water, and dried under reduced pressure. The obtained solid was washed with ethyl acetate to give the title compound (410 mg, 84%) as a brown powder.

$^1$H-NMR (DMSO-$d_6$, 300 MHz) δ 2.27 (6H, s), 3.13 (2H, s), 5.31 (2H, s), 6.28-6.33 (1H, m), 6.36 (1H, t, J=2.1 Hz), 6.41-6.46 (1H, m), 6.98 (1H, d, J=9.6 Hz), 7.05 (1H, t, J=8.1 Hz), 8.01 (1H, d, J=9.6 Hz), 8.04 (1H, s), 10.35 (1H, s).

Example 152

Production of N-[5-({2-[(cyclopropylcarbonyl)amino]imidazo[1,2-b]pyridazin-6-yl}oxy)-2-methylphenyl]-1,3-dimethyl-1H-pyrazole-5-carboxamide p-toluenesulfonate

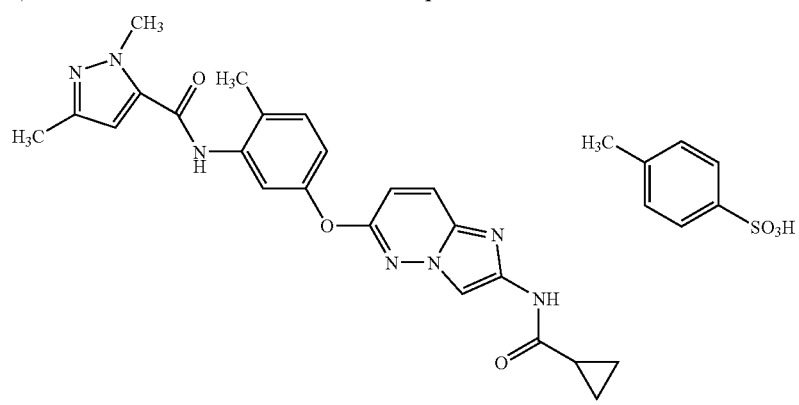

To N-[5-({2-[(cyclopropylcarbonyl)amino]imidazo[1,2-b]pyridazin-6-yl}oxy)-2-methylphenyl]-1,3-dimethyl-1H-pyrazole-5-carboxamide (2.00 g, 4.49 mmol) was added ethanol (80 mL), and the mixture was heated to 70° C. to give a uniform solution. p-Toluenesulfonic acid monohydrate (0.90 g, 4.71 mmol) was added to the mixture, and the mixture was naturally cooled to room temperature. The solvent was evaporated under reduced pressure. To the obtained residue was added hexane/ethanol (3/1, 40 mL), and the mixture was stirred at room temperature for 2 hr. The precipitated crystals were collected by filtration, and washed with hexane/ethanol (3:1). The obtained crystals were dissolved in ethanol (40 mL) by heating and the mixture was naturally cooled to room temperature. The precipitated crystals were collected by filtration and washed with ethanol. The crystals were dried at 70° C. for 3 hr under reduced pressure to give the title compound (2.34 g, 84%) as white crystals.

$^1$H-NMR (DMSO-$d_6$, 300 MHz) δ 0.76-0.85 (4H, m), 1.87-1.97 (1H, m), 2.19 (3H, s), 2.25 (3H, s), 2.29 (3H, s), 3.98 (3H, s), 6.82 (1H, s), 7.09-7.15 (4H, m), 7.29 (1H, d, J=2.7 Hz), 7.35 (1H, d, J=8.4 Hz), 7.47-7.51 (2H, m), 7.96 (1H, s), 8.08 (1H, d, J=9.6 Hz), 9.81 (1H, s), 11.17 (1H, s).

Example 153

Production of N-[5-({2-[(cyclopropylcarbonyl)amino]imidazo[1,2-b]pyridazin-6-yl}oxy)-2-methylphenyl]-1,3-dimethyl-1H-pyrazole-5-carboxamide benzenesulfonate Example 154

Production of N-[5-({2-[(cyclopropylcarbonyl)amino]imidazo[1,2-b]pyridazin-6-yl}oxy)-2-methylphenyl]-1,3-dimethyl-1H-pyrazole-5-carboxamide methanesulfonate

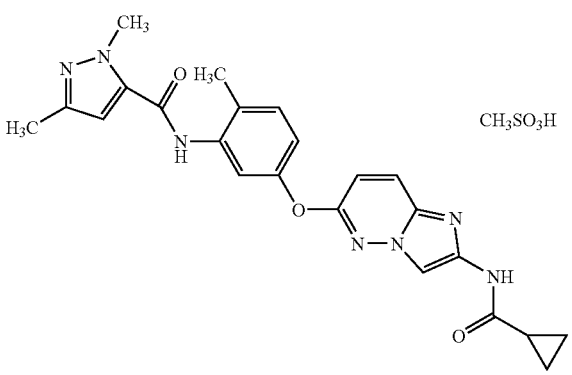

Using N-[5-({2-[(cyclopropylcarbonyl)amino]imidazo[1,2-b]pyridazin-6-yl}oxy)-2-methylphenyl]-1,3-dimethyl-1H-pyrazole-5-carboxamide (2.00 g, 4.49 mmol), ethanol (80 mL) and methanesulfonic acid (0.34 mL, 4.71 mmol), and in

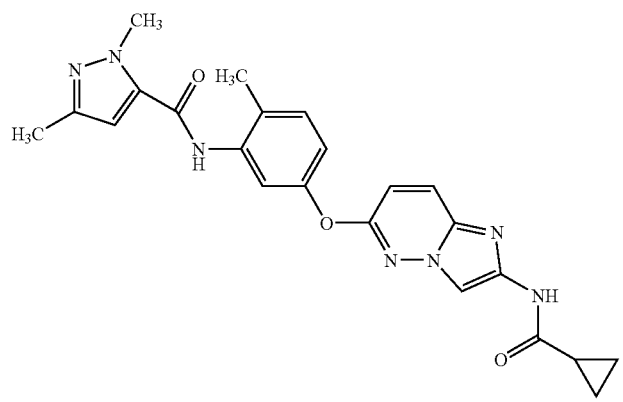

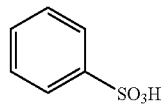

Using N-[5-({2-[(cyclopropylcarbonyl)amino]imidazo[1,2-b]pyridazin-6-yl}oxy)-2-methylphenyl]-1,3-dimethyl-1H-pyrazole-5-carboxamide (2.00 g, 4.49 mmol), ethanol (100 mL) and benzenesulfonic acid monohydrate (0.83 g, 4.71 mmol), and in the same manner as in Example 152, the title compound (2.02 g, 75%) was obtained as white crystals.

$^1$H-NMR (DMSO-$d_6$, 300 MHz) δ 0.78-0.84 (4H, m), 1.87-1.97 (1H, m), 2.19 (3H, s), 2.25 (3H, s), 3.97 (3H, s), 6.80 (1H, s), 7.06-7.12 (2H, m), 7.26-7.36 (5H, m), 7.57-7.61 (2H, m), 7.94 (1H, s), 8.05 (1H, d, J=9.6 Hz), 9.79 (1H, s), 11.13 (1H, s).

elemental analysis ($C_{23}H_{23}N_7O_3 \cdot C_6H_6O_3S$)
Calculated: C, 57.70; H, 4.84; N, 16.24.
Found: C, 57.73; H, 4.80; N, 16.30.

the same manner as in Example 152, the title compound (1.63 g, 67%) was obtained as white crystals.

$^1$H-NMR (DMSO-$d_6$, 300 MHz) δ 0.79-0.84 (4H, m), 1.87-1.97 (1H, m), 2.19 (3H, s), 2.25 (3H, s), 2.40 (3H, s), 3.97 (3H, s), 6.81 (1H, s), 7.07-7.12 (2H, m), 7.28 (1H, d, J=2.4 Hz), 7.34 (1H, d, J=8.7 Hz), 7.94 (1H, s), 8.05 (1H, d, J=9.6 Hz), 9.80 (1H, s), 11.13 (1H, s).

elemental analysis ($C_{23}H_{23}N_7O_3 \cdot CH_4O_3S$)
Calculated: C, 53.23; H, 5.03; N, 18.10.
Found: C, 53.14; H, 5.05; N, 18.15.

Example 155

Production of N-[5-({2-[(cyclopropylcarbonyl)amino]imidazo[1,2-b]pyridazin-6-yl}oxy)-2-methylphenyl]-1,3-dimethyl-1H-pyrazole-5-carboxamide 0.5 fumarate

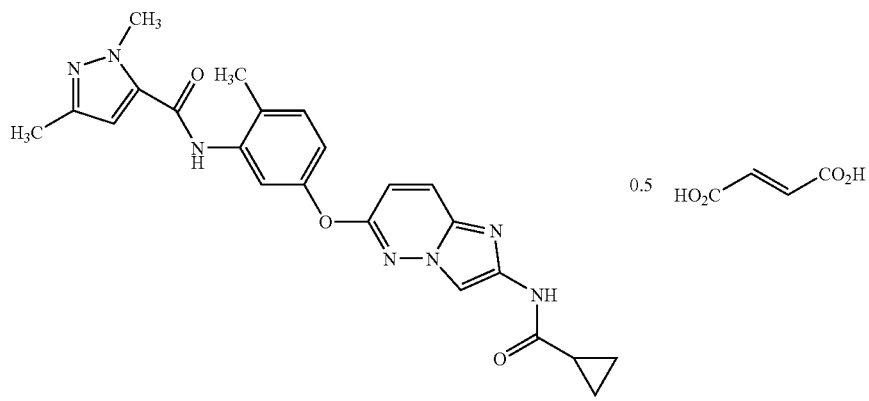

To N-[5-({2-[(cyclopropylcarbonyl)amino]imidazo[1,2-b]pyridazin-6-yl}oxy)-2-methylphenyl]-1,3-dimethyl-1H-pyrazole-5-carboxamide (2.00 g, 4.49 mmol) was added ethanol (100 mL) and the mixture was heated to 75° C. to give a uniform solution. Fumaric acid (0.55 g, 4.71 mmol) was added to the mixture, and the mixture was naturally cooled to room temperature and stirred for 3 hr. The precipitated crystals were collected by filtration, and washed with ethanol. The obtained mother liquor was concentrated under reduced pressure, and ethanol (30 mL) was added to the obtained residue. The mixture was stirred at 60° C. for 30 min. The mixture was cooled to room temperature and stood for 2 hr, and the precipitated crystals were collected by filtration, and washed with ethanol. The crystals were dried under reduced pressure at 70° C. for 3 hr to give the title compound (1.73 g, 77%) as white crystals.

$^1$H-NMR (DMSO-$d_6$, 300 MHz) δ 0.78-0.83 (4H, m), 1.87-1.97 (1H, m), 2.20 (3H, s), 2.25 (3H, s), 3.98 (3H, s), 6.63 (1H, s), 6.81 (1H, s), 7.05 (1H, d, J=9.5 Hz), 7.10 (1H, dd, J=8.6, 2.6 Hz), 7.28 (1H, d, J=2.6 Hz), 7.35 (1H, d, J=8.6 Hz), 7.94 (1H, s), 8.03 (1H, d, J=9.5 Hz), 9.80 (1H, s), 11.08 (1H, s).

elemental analysis ($C_{23}H_{23}N_7O_3$ 0.5$C_4H_4O_4$)
Calculated: C, 59.63; H, 5.00; N, 19.47.
Found: C, 59.58; H, 4.98; N, 19.47.

Example 156

Production of N-[5-({2-[(cyclopropylcarbonyl)amino]imidazo[1,2-b]pyridazin-6-yl}oxy)-2-methylphenyl]-1,3-dimethyl-1H-pyrazole-5-carboxamide 0.5 succinate

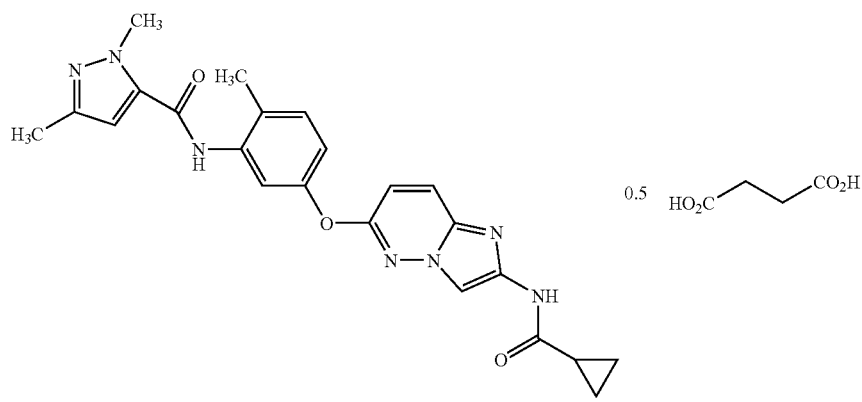

Using N-[5-({2-[(cyclopropylcarbonyl)amino]imidazo[1,2-b]pyridazin-6-yl}oxy)-2-methylphenyl]-1,3-dimethyl-1H-pyrazole-5-carboxamide (2.00 g, 4.49 mmol), ethanol (100 mL) and succinic acid (0.56 g, 4.71 mmol), and in the same manner as in Example 155, the title compound (1.04 g, 46%) was obtained as white crystals.

$^1$H-NMR (DMSO-$d_6$, 300 MHz) δ 0.78-0.83 (4H, m), 1.87-1.96 (1H, m), 2.19 (3H, s), 2.24 (3H, s), 2.49 (2H, s), 3.97 (3H, s), 6.80 (1H, s), 7.04 (1H, d, J=9.6 Hz), 7.09 (1H, dd, J=8.3, 2.6 Hz), 7.27 (1H, d, J=2.6 Hz), 7.34 (1H, d, J=8.3 Hz), 7.92 (1H, s), 8.02 (1H, d, J=9.6 Hz), 9.79 (1H, s), 11.06 (1H, s).

elemental analysis ($C_{23}H_{23}N_7O_3 \cdot 0.5C_4H_6O_4$)

Calculated: C, 59.52; H, 5.19; N, 19.43.

Found: C, 59.36; H, 5.19; N, 19.37.

Example 157

Production of N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide p-toluenesulfonate

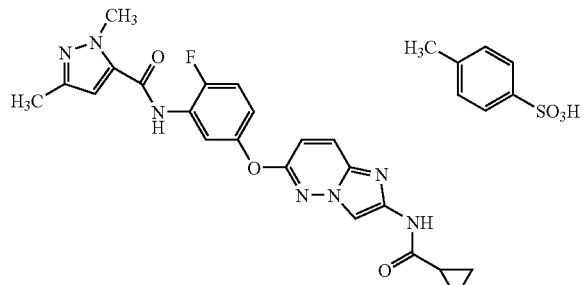

To N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide (225 mg, 0.5 mmol) were added tetrahydrofuran (5.0 mL) and ethanol (5.0 mL), dissolved at 70° C., and p-toluenesulfonic acid monohydrate (95 mg, 0.5 mmol) was added thereto. Ethanol (15.0 mL) was further added to the mixture and insoluble material was filtered off. The filtrate was concentrated, ethyl acetate (10 mL) and ethanol (10 mL) were added thereto, and the mixture was concentrated again. Ethyl acetate (10 mL) and ethanol (1.0 mL) were added thereto, and the mixture was stood at room temperature for 6 hr. The precipitated crystals were collected by filtration, washed successively with a small amount of ethanol and diethyl ether, and dried under reduced pressure at 80° C. for 6 hr to give the title compound (285 mg, 92%) as white crystals.

$^1$H-NMR (DMSO-$d_6$, 300 MHz) δ 0.75-0.85 (4H, m), 1.85-1.95 (1H, m), 2.19 (3H, s), 2.29 (3H, s), 3.98 (3H, s), 6.85 (1H, s), 7.08 (1H, d, J=9.6 Hz), 7.11 (2H, d, J=7.7 Hz), 7.15-7.25 (1H, m), 7.40 (1H, t, J=9.6 Hz), 7.47 (2H, d, J=7.7 Hz), 7.50-7.55 (1H, m), 7.94 (1H, s), 8.05 (1H, d, J=9.6 Hz), 10.10 (1H, s), 11.09 (1H, s).

Example 158

Production of N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide benzenesulfonate

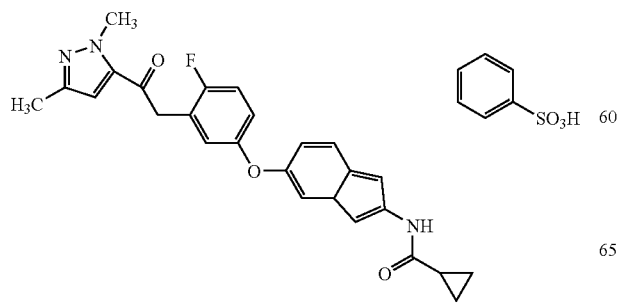

To N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide (1.00 g, 2.23 mmol) was added ethanol (50 mL), and the mixture was stirred at 80° C. for 20 min. Benzenesulfonic acid monohydrate (0.41 g, 2.33 mmol) was added to the mixture, and the mixture was further stirred for 10 min. Insoluble material was removed by filtration, and the mixture was naturally cooled to room temperature. The mixture was stood at room temperature for 16 hr, and the precipitated crystals were collected by filtration and washed with ethanol. The precipitated crystals were dried under reduced pressure at 80° C. for 6 hr to give the title compound (1.17 g, 86%) as white crystals.

$^1$H-NMR (DMSO-$d_6$, 300 MHz) δ 0.78-0.84 (4H, m), 1.88-1.97 (1H, m), 2.19 (3H, s), 3.98 (3H, s), 6.85 (1H, s), 7.10 (1H, d, J=9.6 Hz), 7.18-7.24 (1H, m), 7.30-7.34 (3H, m), 7.41 (1H, t, J=9.5 Hz), 7.52-7.56 (1H, m), 7.58-7.62 (2H, m), 7.95 (1H, s), 8.06 (1H, d, J=9.6 Hz), 10.10 (1H, s), 11.11 (1H, s).

elemental analysis ($C_{22}H_{20}FN_7O_3 \cdot C_6H_6O_3S$)

Calculated: C, 55.35; H, 4.31; N, 16.14.

Found: C, 55.25; H, 4.33; N, 16.14.

Example 159

Production of N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide methanesulfonate

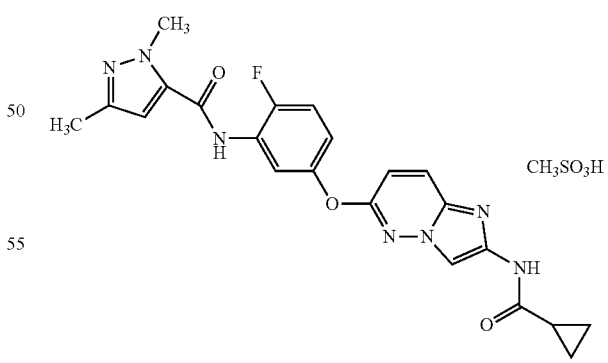

A solution of N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide (1.00 g, 2.23 mmol) in ethanol (50 ml) was stirred at 70° C. for 20 min. Methane sulfonic acid (0.17 mL, 2.33 mmol) was added to the mixture, and the mixture was further stirred for 10 min. The mixture was naturally cooled to room temperature, and the solvent was evaporated under reduced pressure. To the obtained residue was added hexane/ethanol (3:1, 40 mL), and the mixture was stirred at room temperature for 2 hr. The precipitated precipitate was collected by filtration, and washed with hexane/ethanol (3:1). The obtained precipitate was dissolved in ethanol (40 mL) by heating, and the mixture was naturally cooled to room temperature. The precipitated crystals were collected by filtration, ethyl acetate (20 mL) was added to the mixture, and the mixture was stirred at 80° C. by heating. After cooling the mixture to room temperature, the precipitate was collected by filtration, washed with ethyl acetate and dried under reduced pressure at 100° C. for 3 hr to give the title compound (0.32 g, 26%) as white crystals.

$^1$H-NMR (DMSO-$d_6$, 300 MHz) δ 0.77-0.83 (4H, m), 1.86-1.96 (1H, m), 2.19 (3H, s), 2.33 (3H, s), 3.97 (3H, s), 6.84 (1H, s), 7.08 (1H, d, J=9.6 Hz), 7.18-7.23 (1H, m), 7.39 (1H, t, J=9.6 Hz), 7.51-7.55 (1H, m), 7.93 (1H, s), 8.04 (1H, d, J=9.6 Hz), 10.09 (1H, s), 11.08 (1H, s).

elemental analysis ($C_{22}H_{20}FN_7O_3 \cdot CH_4O_3S$)
Calculated: C, 50.64; H, 4.43; N, 17.97.
Found: C, 50.63; H, 4.38; N, 18.11.

Example 160

Production of N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide 0.5 fumarate acetate and dried under reduced pressure at 80° C. for 3 hr to give the title compound (1.88 g, 83%) as white crystals.

$^1$H-NMR (DMSO-$d_6$, 300 MHz) δ 0.77-0.82 (4H, m), 1.87-1.96 (1H, m), 2.19 (3H, s), 3.97 (3H, s), 6.61 (1H, s), 6.84 (1H, s), 7.07 (1H, d, J=9.6 Hz), 7.18-7.23 (1H, m), 7.39 (1H, t, J=9.6 Hz), 7.51-7.54 (1H, m), 7.93 (1H, s), 8.04 (1H, d, J=9.6 Hz), 10.09 (1H, s), 11.06 (1H, s).

elemental analysis ($C_{22}H_{20}FN_7O_3 \cdot 0.5C_4H_4O_4$)
Calculated: C, 56.80; H, 4.37; N, 19.32.
Found: C, 56.73; H, 4.33; N, 19.24.

Example 161

Production of N-[5-({2-[(cyclopropylcarbonyl)amino]imidazo[1,2-b]pyridazin-6-yl}oxy)-2-fluorophenyl]-1-ethyl-3-methyl-1H-pyrazole-4-carboxamide

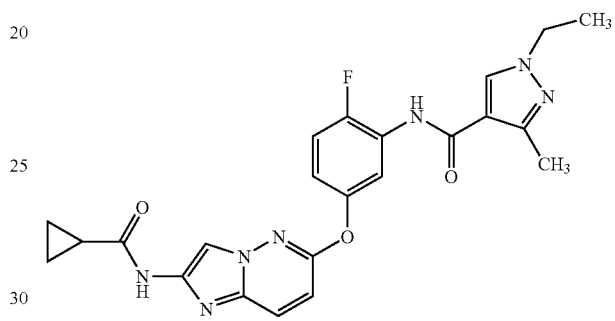

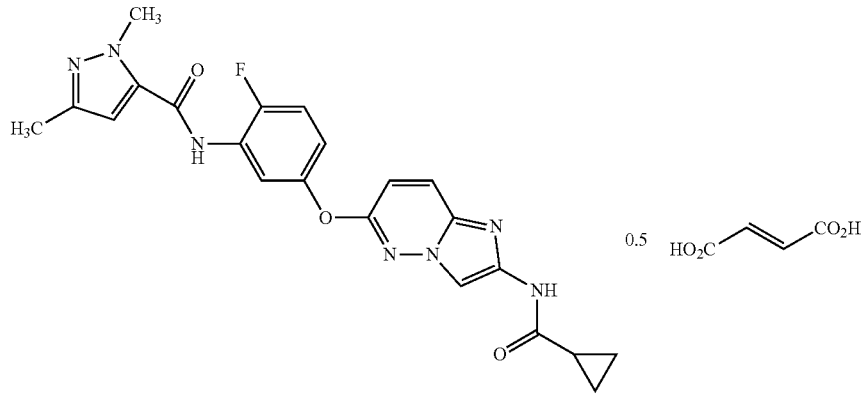

To N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide (2.00 g, 4.45 mmol) was added tetrahydrofuran (100 mL), and the mixture was heated to 60° C. to give a uniform solution. Fumaric acid (0.54 g, 4.67 mmol) was added to the mixture and the mixture was allowed to cool to room temperature. Insoluble material was filtrated, ethyl acetate (50 mL) was added to the filtrate, and the solvent was evaporated to ¼ under reduced pressure. The precipitated crystals were collected by filtration, washed with ethyl To a solution of 1-ethyl-3-methyl-1H-pyrazole-4-carboxylic acid (2.00 g, 13.0 mmol) and N,N-dimethylformamide (3 drops) in tetrahydrofuran (30 mL) was added oxalyl chloride (2.23 mL, 26.0 mmol) with stirring under ice-cooling, and the mixture was stirred at room temperature for 3 hr. The reaction mixture was concentrated under reduced pressure. The residue was dissolved in N,N-dimethylacetamide (20 mL) with stirring under ice-cooling, N-[6-(3-amino-4-fluorophenoxy)

imidazo[1,2-b]pyridazin-2-yl]cyclopropanecarboxamide (3.27 g, 10.0 mmol) was added thereto, and the mixture was stirred at room temperature for 18 hr. The reaction mixture was diluted with 1N aqueous sodium hydroxide solution (50 ml) and extracted with a mixed solvent of ethyl acetate/tetrahydrofuran (1:1, 80 mL, 40 mL×2). The organic layer was washed with water (10 mL×3), and concentrated under reduced pressure. The residue was purified by silica gel column chromatography (ethyl acetate/methanol=100/0→70/30) and crystallized from ethyl acetate to give the title compound (2.39 g, yield 52%) as a white solid. melting point 199° C.

$^1$H-NMR (DMSO-d$_6$, 300 MHz) δ 0.75-0.85 (4H, m), 1.38 (3H, t, J=7.3 Hz), 1.86-1.98 (1H, m), 2.33 (3H, s), 4.09 (2H, q, J=7.3 Hz), 7.06 (1H, d, J=9.6 Hz), 7.07-7.15 (1H, m), 7.36 (1H, dd, J=10.2, 9.0 Hz), 7.66 (1H, dd, J=6.3, 3.0 Hz), 7.94 (1H, s), 8.04 (1H, dd, J=9.6, 0.6 Hz), 8.39 (1H, s), 9.54 (1H, s), 11.07 (1H, s).

Example 162

Production of N-[3-({2-[(cyclopropylcarbonyl)amino]imidazo[1,2-b]pyridazin-6-yl}oxy)phenyl]pyridine-2-carboxamide

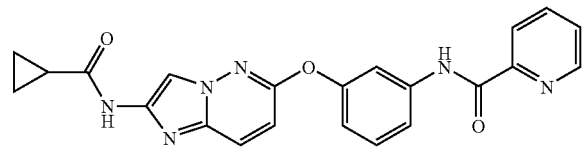

To a solution of N-[6-(3-aminophenoxy)imidazo[1,2-b]pyridazin-2-yl]cyclopropanecarboxamide (155 mg, 0.50 mmol) in N-methylpyrrolidone (3 mL) was added pyridine-2-carbonylchloride hydrochloride (107 mg, 0.60 mmol), and the mixture was stirred at room temperature for 18 hr. A 5% aqueous sodium hydrogencarbonate solution was added to the reaction mixture, and the mixture was extracted with ethyl acetate. The organic layer was concentrated under reduced pressure, and the residue was purified by silica gel column chromatography (ethyl acetate/methanol=100/0→80/20) and crystallized from ethyl acetate to give the title compound (131 mg, yield 63%) as a white solid.

$^1$H-NMR (DMSO-d$_6$, 300 MHz) δ 0.73-0.87 (4H, m), 1.86-1.99 (1H, m), 7.02 (1H, ddd, J=8.1, 2.5, 0.7 Hz), 7.07 (1H, d, J=9.3 Hz), 7.44 (1H, t, J=8.2 Hz), 7.68 (1H, ddd, J=7.3, 4.7, 1.3 Hz), 7.80-7.85 (1H, m), 7.90 (1H, t, J=2.3 Hz), 7.99 (1H, s), 8.03-8.10 (2H, m), 8.12-8.18 (1H, m), 8.72-8.76 (1H, m), 10.81 (1H, s), 11.09 (1H, s).

Example 163

Production of N-[3-({2-[(cyclopropylcarbonyl)amino]imidazo[1,2-b]pyridazin-6-yl}oxy)phenyl]isonicotinamide

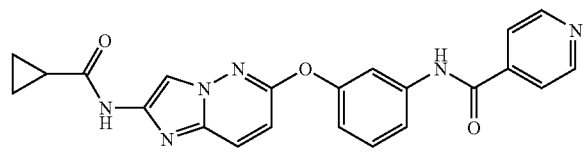

Using N-[6-(3-aminophenoxy)imidazo[1,2-b]pyridazin-2-yl]cyclopropanecarboxamide (155 mg, 0.50 mmol), N-methylpyrrolidone (3 mL) and pyridine-4-carbonylchloride hydrochloride (107 mg, 0.60 mmol), and in the same manner as in Example 162, the title compound (163 mg, yield 78%) was obtained.

$^1$H-NMR (DMSO-d$_6$, 300 MHz) δ 0.75-0.85 (4H, m), 1.84-2.00 (1H, m), 7.01-7.07 (1H, m), 7.08 (1H, d, J=9.6 Hz), 7.46 (1H, t, J=8.1 Hz), 7.63-7.69 (1H, m), 7.73 (1H, t, J=2.1 Hz), 7.82-7.87 (2H, m), 7.98 (1H, s), 8.06 (1H, d, J=9.6 Hz), 8.76-8.81 (2H, m), 10.62 (1H, s), 11.09 (1H, s).

Example 164

Production of N-[3-({2-[(cyclopropylcarbonyl)amino]imidazo[1,2-b]pyridazin-6-yl}oxy)phenyl]nicotinamide

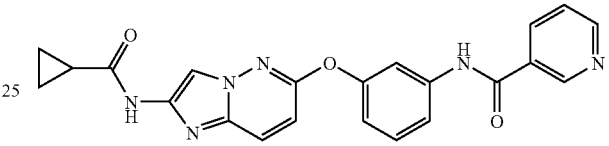

Using N-[6-(3-aminophenoxy)imidazo[1,2-b]pyridazin-2-yl]cyclopropanecarboxamide (155 mg, 0.50 mmol), N-methylpyrrolidone (3 mL) and pyridine-3-carbonylchloride hydrochloride (107 mg, 0.60 mmol), and in the same manner as in Example 162, the title compound (89 mg, yield 43%) was obtained.

$^1$H-NMR (DMSO-d$_6$, 300 MHz) δ 0.74-0.87 (4H, m), 1.86-1.99 (1H, m), 7.03 (1H, dd, J=7.8, 1.8 Hz), 7.08 (1H, d, J=9.6 Hz), 7.45 (1H, t, J=8.4 Hz), 7.57 (1H, dd, J=7.8, 4.8 Hz), 7.66 (1H, d, J=8.1 Hz), 7.73 (1H, t, J=1.9 Hz), 7.98 (1H, s), 8.06 (1H, d, J=9.6 Hz), 8.28 (1H, dt, J=7.9, 1.9 Hz), 8.76 (1H, d, J=3.9 Hz), 9.09 (1H, s), 10.57 (1H, s), 11.09 (1H, s).

Example 165

Production of N-[3-({2-[(cyclopropylcarbonyl)amino]imidazo[1,2-b]pyridazin-6-yl}oxy)phenyl]benzamide

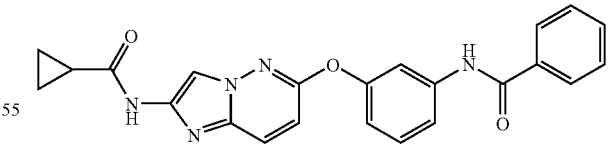

Using N-[6-(3-aminophenoxy)imidazo[1,2-b]pyridazin-2-yl]cyclopropanecarboxamide (155 mg, 0.50 mmol), N-methylpyrrolidone (3 mL) and benzoyl chloride (0.070 mL, 0.60 mmol), and in the same manner as in Example 162, the title compound (176 mg, yield 85%) was obtained. melting point 265° C.

$^1$H-NMR (DMSO-d$_6$, 300 MHz) δ 0.74-0.86 (4H, m), 1.87-1.99 (1H, m), 7.00 (1H, ddd, J=8.1, 2.4, 0.8 Hz), 7.07 (1H, d, J=9.5 Hz), 7.43 (1H, t, J=8.1 Hz), 7.49-7.64 (3H, m), 7.68 (1H, d, J=8.4 Hz), 7.74 (1H, t, J=2.1 Hz), 7.90-7.97 (2H, m), 7.98 (1H, s), 8.05 (1H, d, J=9.5 Hz), 10.38 (1H, s), 11.09 (1H, s).

Example 166

Production of N-[3-({2-[(cyclopropylcarbonyl)amino]imidazo[1,2-b]pyridazin-6-yl}oxy)phenyl]-1,3-thiazole-2-carboxamide

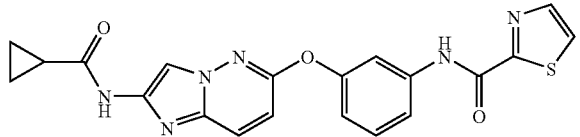

Using N-[6-(3-aminophenoxy)imidazo[1,2-b]pyridazin-2-yl]cyclopropanecarboxamide (155 mg, 0.50 mmol), N-methylpyrrolidone (3 mL) and 1,3-thiazole-2-carbonyl chloride (89 mg, 0.60 mmol), and in the same manner as in Example 162, the title compound (136 mg, yield 65%) was obtained.

$^1$H-NMR (DMSO-d$_6$, 300 MHz) δ 0.76-0.85 (4H, m), 1.86-1.99 (1H, m), 7.03 (1H, ddd, J=8.2, 2.4, 1.0 Hz), 7.07 (1H, d, J=9.6 Hz), 7.44 (1H, t, J=8.1 Hz), 7.75-7.83 (2H, m), 7.98 (1H, s), 8.06 (1H, dd, J=9.6, 0.6 Hz), 8.11 (1H, d, J=3.0 Hz), 8.15 (1H, d, J=3.0 Hz), 10.94 (1H, s), 11.09 (1H, s).

Example 167

Production of N-[3-({2-[(cyclopropylcarbonyl)amino]imidazo[1,2-b]pyridazin-6-yl}oxy)phenyl]-1,3-dimethyl-1H-pyrazole-4-carboxamide

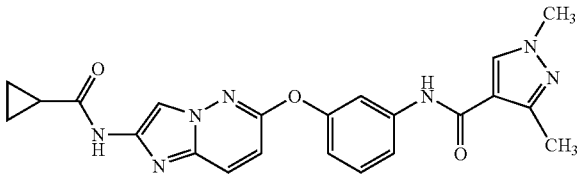

To a suspension of 1,3-dimethyl-1H-pyrazole-4-carboxylic acid (140 mg, 1.0 mmol) in dichloromethane (10 mL) were added N,N-dimethylformamide (2 drops) then oxalyl chloride (0.171 mL, 2.0 mmol), and the mixture was stirred at room temperature for 2 hr. The reaction mixture was concentrated under reduced pressure. The residue was diluted with N-methylpyrrolidone (5 mL), N-[6-(3-aminophenoxy)imidazo[1,2-b]pyridazin-2-yl]cyclopropanecarboxamide (155 mg, 0.50 mmol) was added thereto, and the mixture was stirred at room temperature for 6 hr. To the reaction mixture was added 0.5N aqueous sodium hydroxide solution, and the mixture was extracted with ethyl acetate. The organic layer was concentrated under reduced pressure, and the residue was purified by silica gel column chromatography (ethyl acetate/methanol=100/0→70/30). The objective fraction was concentrated under reduced pressure, and the residue was washed with diisopropyl ether to give the title compound (126 mg, yield 58%) as a white solid.

$^1$H-NMR (DMSO-d$_6$, 300 MHz) δ 0.74-0.87 (4H, m), 1.86-1.99 (1H, m), 2.33 (3H, s), 3.81 (3H, s), 6.93 (1H, dd, J=8.1, 1.8 Hz), 7.05 (1H, d, J=9.6 Hz), 7.38 (1H, t, J=8.1 Hz), 7.55 (1H, d, J=8.1 Hz), 7.64 (1H, t, J=2.1 Hz), 7.97 (1H, s), 8.05 (1H, d, J=9.6 Hz), 8.27 (1H, s), 9.78 (1H, s), 11.09 (1H, s).

Example 168

Production of N-[6-(3-amino-4-ethylphenoxy)imidazo[1,2-b]pyridazin-2-yl]cyclopropanecarboxamide

A mixture of N-(6-iodoimidazo[1,2-b]pyridazin-2-yl)cyclopropanecarboxamide (984 mg, 3.0 mmol), 3-amino-4-ethylphenol (617 mg, 4.5 mmol), potassium carbonate (829 mg, 6.0 mmol) and N,N-dimethylformamide (9 mL) was stirred at 150° C. for 24 hr. The reaction mixture was diluted with water and extracted with a mixed solvent of ethyl acetate/tetrahydrofuran (3:1). The organic layer was concentrated under reduced pressure, and the residue was purified by silica gel column chromatography (hexane/ethyl acetate=50/50→0/100) and recrystallized from a mixed solvent of ethyl acetate/diisopropyl ether to give the title compound (706 mg, yield 70%) as a khaki solid.

$^1$H-NMR (DMSO-d$_6$, 300 MHz) δ 0.73-0.88 (4H, m), 1.14 (3H, t, J=7.4 Hz), 1.85-2.00 (1H, m), 2.43 (2H, q, J=7.4 Hz), 5.07 (2H, s), 6.31 (1H, dd, J=8.1, 2.7 Hz), 6.42 (1H, d, J=2.7 Hz), 6.93 (1H, d, J=9.6 Hz), 6.95 (1H, d, J=7.8 Hz), 7.97 (1H, s), 7.98 (1H, d, J=9.0 Hz), 11.05 (1H, s).

Example 169

Production of N-[5-({2-[(cyclopropylcarbonyl)amino]imidazo[1,2-b]pyridazin-6-yl}oxy)-2-ethylphenyl]-1,3-dimethyl-1H-pyrazole-5-carboxamide

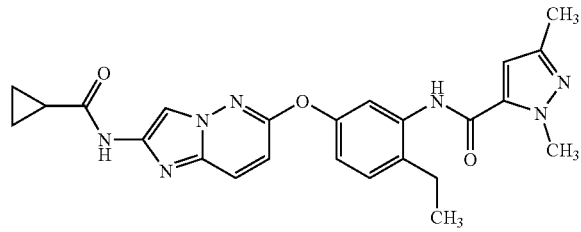

To a solution of N-[6-(3-amino-4-ethylphenoxy)imidazo[1,2-b]pyridazin-2-yl]cyclopropanecarboxamide (202 mg, 0.60 mmol) in N-methylpyrrolidone (3 mL) was added 1,3-dimethyl-1H-pyrazole-5-carbonyl chloride (143 mg, 0.90 mmol), and the mixture was stirred at room temperature for 8 hr. A 1N aqueous sodium hydroxide solution was added to the reaction mixture, and the mixture was extracted with ethyl acetate. The organic layer was concentrated under reduced pressure, and the residue was purified by silica gel column chromatography (ethyl acetate/methanol=100/0→80/20) and recrystallized from a mixed solvent of ethyl acetate/diisopropyl ether to give the title compound (167 mg, yield 61%) as a white solid.

$^1$H-NMR (DMSO-d$_6$, 300 MHz) δ 0.76-0.84 (4H, m), 1.15 (3H, t, J=7.6 Hz), 1.84-2.00 (1H, m), 2.19 (3H, s), 2.63 (2H, q, J=7.6 Hz), 3.97 (3H, s), 6.80 (1H, s), 7.04 (1H, d, J=9.6 Hz), 7.15 (1H, dd, J=8.6, 2.6 Hz), 7.23 (1H, d, J=2.6 Hz), 7.37 (1H, d, J=8.6 Hz), 7.94 (1H, s), 8.03 (1H, dd, J=9.6, 0.6 Hz), 9.82 (1H, s), 11.07 (1H, s).

Example 170

Production of N-[3-({2-[(cyclopropylcarbonyl) amino]imidazo[1,2-b]pyridazin-6-yl}oxy)phenyl]-1H-pyrazole-5-carboxamide

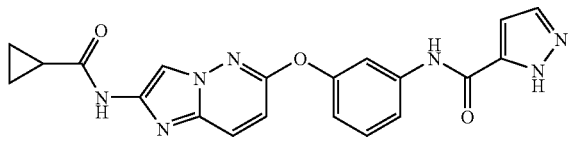

To a mixture of N-[6-(3-aminophenoxy)imidazo[1,2-b]pyridazin-2-yl]cyclopropanecarboxamide (155 mg, 0.50 mmol), 1H-pyrazole-5-carboxylic acid (84 mg, 0.75 mmol), 1-hydroxybenzotriazole (101 mg, 0.75 mmol) and N,N-dimethylformamide (5 mL) were added 1-[3-(dimethylamino)propyl]-3-ethylcarbodiimide hydrochloride (192 mg, 1.0 mmol), triethylamine (0.279 mL, 2.0 mmol), and the mixture was stirred at room temperature for 18 hr. Water was added to the reaction mixture, and the mixture was extracted with a mixed solvent of ethyl acetate/tetrahydrofuran. The organic layer was concentrated under reduced pressure, and the residue was purified by silica gel column chromatography (ethyl acetate/methanol=100/0→70/30) and crystallized from ethyl acetate to give the title compound (43 mg, yield 21%) as a white solid.

$^1$H-NMR (DMSO-d$_6$, 300 MHz) δ 0.73-0.88 (4H, m), 1.87-1.99 (1H, m), 6.76 (1H, s), 6.95 (1H, dd, J=8.1, 1.8 Hz), 7.05 (1H, d, J=9.6 Hz), 7.39 (1H, t, J=8.4 Hz), 7.73 (1H, d, J=8.4 Hz), 7.79 (1H, s), 7.89 (1H, s), 7.98 (1H, s), 8.04 (1H, d, J=9.6 Hz), 10.20 (1H, s), 11.07 (1H, s), 13.42 (1H, s).

Example 171

Production of N-{6-[(4-aminophenyl)thio]imidazo[1,2-b]pyridazin-2-yl}cyclopropanecarboxamide

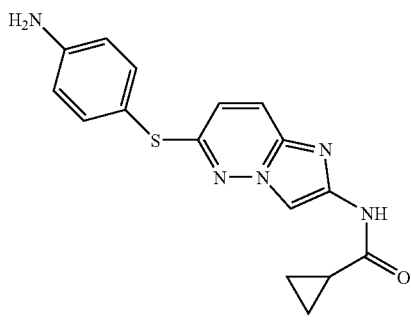

To a solution of N-(6-iodoimidazo[1,2-b]pyridazin-2-yl)-2-methylcyclopropanecarboxamide (2.0 g, 6.10 mmol) in N,N-dimethylformamide (20.0 mL) were added potassium carbonate (1.27 g, 9.14 mmol) and 4-aminothiophenol (0.92 g, 7.31 mmol), and the mixture was stirred at 80° C. for 4 hr. After cooling the mixture to room temperature, water was added to the reaction mixture, and the mixture was extracted with ethyl acetate/tetrahydrofuran, washed with saturated brine, and dried over anhydrous magnesium sulfate. The solvent was evaporated under reduced pressure, and the residue was collected by filtration and washed with ethyl acetate to give the title compound (1.53 g, 77%) as brown crystals.

$^1$H-NMR (DMSO-d$_6$, 300 MHz) δ 0.78-0.85 (4H, m), 1.87-1.97 (1H, m), 5.68 (2H, s), 6.60-6.67 (3H, m), 7.24-7.29 (2H, m), 7.78 (1H, d, J=9.5 Hz), 8.06 (1H, s), 11.09 (1H, s).

Example 172

Production of N-{6-[3-({[(phenylacetyl)amino]thiocarbonyl}amino)phenoxy]imidazo[1,2-b]pyridazin-2-yl}cyclopropanecarboxamide

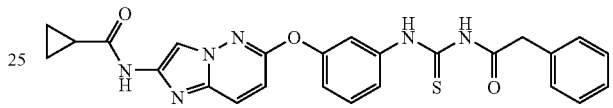

To a solution of phenylacetyl chloride (155 mg, 1.0 mmol) in acetonitrile (20 mL) was added potassium thiocyanate (292 mg, 3.0 mmol), and the mixture was stirred at 60° C. for 3 hr and concentrated under reduced pressure. The residue was diluted with tetrahydrofuran (20 mL). N-[6-(3-Aminophenoxy)imidazo[1,2-b]pyridazin-2-yl]cyclopropanecarboxamide (155 mg, 0.50 mmol) was added to the mixture, and the mixture was stirred at room temperature for 18 hr. The reaction mixture was concentrated under reduced pressure, water was added to the residue and the mixture was extracted with ethyl acetate. The organic layer was concentrated under reduced pressure, and the residue was purified by silica gel column chromatography (ethyl acetate/methanol=100/0→70/30) and precipitated from diisopropyl ether to give the title compound (142 mg, yield 58%) as a white solid.

$^1$H-NMR (DMSO-d$_6$, 300 MHz) δ 0.75-0.86 (4H, m), 1.86-1.98 (1H, m), 3.81 (2H, s), 7.04 (1H, d, J=9.6 Hz), 7.10-7.19 (1H, m), 7.23-7.38 (5H, m), 7.45 (2H, d, J=5.1 Hz), 7.74 (1H, s), 7.96 (1H, s), 8.03 (1H, d, J=9.6 Hz), 11.07 (1H, s), 11.72 (1H, s), 12.46 (1H, s).

Example 173

Production of N-[5-({2-[(cyclopropylcarbonyl)amino]imidazo[1,2-b]pyridazin-6-yl}oxy)-2-fluorophenyl]-1,3-dimethyl-1H-pyrazole-4-carboxamide

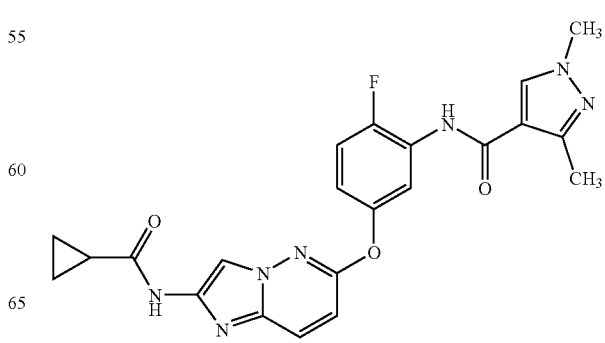

To a solution of 1,3-dimethyl-1H-pyrazole-4-carboxylic acid (140 mg, 1.0 mmol) and N,N-dimethylformamide (2 drops) in tetrahydrofuran (10 mL) was added oxalyl chloride (0.171 mL, 2.0 mmol) with stirring under ice-cooling, and the mixture was stirred at room temperature for 2 hr. The reaction mixture was concentrated under reduced pressure. The residue was dissolved in N-methylpyrrolidone (5 mL) with stirring under ice-cooling, N-[6-(3-amino-4-fluorophenoxy) imidazo[1,2-b]pyridazin-2-yl]cyclopropanecarboxamide (164 mg, 0.50 mmol) was added, and the mixture was stirred at room temperature for 18 hr. The reaction mixture was diluted with ethyl acetate (80 mL), and washed with 1N aqueous sodium hydroxide solution (10 mL) and water (10 mL×3). The organic layer was concentrated under reduced pressure, and the residue was purified by silica gel column chromatography (ethyl acetate/methanol=100/0→70/30) and recrystallized from ethyl acetate to give the title compound (88 mg, yield 39%) as a white solid. melting point 205° C.

$^1$H-NMR (DMSO-$d_6$, 300 MHz) δ 0.73-0.88 (4H, m), 1.86-1.99 (1H, m), 2.32 (3H, s), 3.81 (3H, s), 7.06 (1H, d, J=9.5 Hz), 7.06-7.14 (1H, m), 7.36 (1H, dd, J=10.2, 9.0 Hz), 7.66 (1H, dd, J=6.4, 3.2 Hz), 7.94 (1H, s), 8.03 (1H, d, J=9.5 Hz), 8.32 (1H, s), 9.53 (1H, s), 11.06 (1H, s).

Example 174

Production of N-[5-({2-[(cyclopropylcarbonyl)amino]imidazo[1,2-b]pyridazin-6-yl}oxy)-2-fluorophenyl]-1-ethyl-1H-pyrazole-5-carboxamide

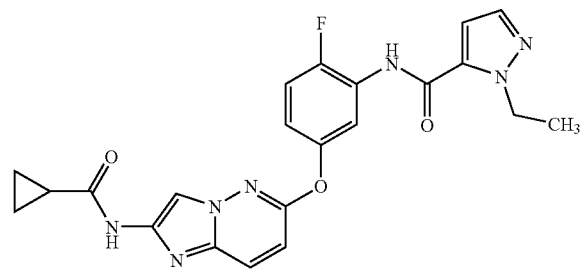

Using 1-ethyl-1H-pyrazole-5-carboxylic acid (140 mg, 1.0 mmol), N,N-dimethylformamide (2 drops), tetrahydrofuran (10 mL), oxalyl chloride (0.172 mL, 2.0 mmol), N-methylpyrrolidone (5 mL) and N-[6-(3-amino-4-fluorophenoxy)imidazo[1,2-b]pyridazin-2-yl]cyclopropanecarboxamide (164 mg, 0.50 mmol), and in the same manner as in Example 173, the title compound (119 mg, yield 53%) was obtained. melting point 209° C.

$^1$H-NMR (DMSO-$d_6$, 300 MHz) δ 0.75-0.86 (4H, m), 1.31 (3H, t, J=7.2 Hz), 1.86-1.98 (1H, m), 4.50 (2H, q, J=7.2 Hz), 7.07 (1H, d, J=2.0 Hz), 7.08 (1H, d, J=9.5 Hz), 7.22 (1H, ddd, J=9.0, 3.9, 3.0 Hz), 7.41 (1H, dd, J=10.2, 9.0 Hz), 7.52-7.57 (1H, m), 7.55 (1H, d, J=2.0 Hz), 7.94 (1H, s), 8.04 (1H, d, J=9.5 Hz), 10.19 (1H, s), 11.06 (1H, s).

Example 175

Production of N-[5-({2-[(cyclopropylcarbonyl)amino]imidazo[1,2-b]pyridazin-6-yl}oxy)-2-fluorophenyl]-3-methylisoxazole-4-carboxamide

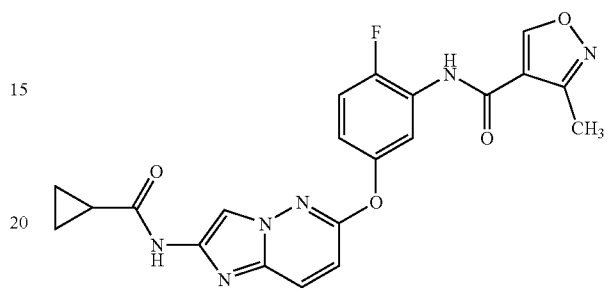

Using 3-methylisoxazole-4-carboxylic acid (127 mg, 1.0 mmol), N,N-dimethylformamide (2 drops), tetrahydrofuran (10 mL), oxalyl chloride (0.172 mL, 2.0 mmol), N-methylpyrrolidone (5 mL) and N-[6-(3-amino-4-fluorophenoxy)imidazo[1,2-b]pyridazin-2-yl]cyclopropanecarboxamide (164 mg, 0.50 mmol), and in the same manner as in Example 173, the title compound (143 mg, yield 65%) was obtained.

$^1$H-NMR (DMSO-$d_6$, 300 MHz) δ 0.75-0.86 (4H, m), 1.86-1.99 (1H, m), 2.40 (3H, s), 7.07 (1H, d, J=9.3 Hz), 7.14-7.21 (1H, m), 7.40 (1H, dd, J=10.2, 9.0 Hz), 7.66 (1H, dd, J=6.3, 2.7 Hz), 7.94 (1H, s), 8.04 (1H, d, J=9.3 Hz), 9.48 (1H, s), 10.19 (1H, s), 11.06 (1H, s).

Example 176

Production of N-[5-({2-[(cyclopropylcarbonyl)amino]imidazo[1,2-b]pyridazin-6-yl}oxy)-2-fluorophenyl]-5-methylisoxazole-4-carboxamide

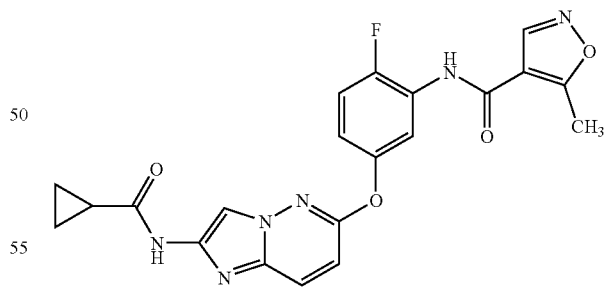

Using N-[6-(3-amino-4-fluorophenoxy)imidazo[1,2-b]pyridazin-2-yl]cyclopropanecarboxamide (164 mg, 0.50 mmol), N-methylpyrrolidone (5 mL) and 5-methylisoxazole-4-carbonyl chloride (146 mg, 1.00 mmol), and in the same manner as in Example 162, the title compound (112 mg, yield 51%) was obtained.

$^1$H-NMR (DMSO-$d_6$, 300 MHz) δ 0.75-0.85 (4H, m), 1.86-1.98 (1H, m), 2.66 (3H, s), 7.08 (1H, d, J=9.6 Hz), 7.19 (1H, ddd, J=9.0, 3.9, 3.0 Hz), 7.41 (1H, dd, J=9.9, 9.0 Hz), 7.62 (1H, dd, J=6.3, 3.0 Hz), 7.94 (1H, s), 8.05 (1H, dd, J=9.6, 0.6 Hz), 9.06 (1H, s), 10.09 (1H, s), 11.08 (1H, s).

Example 177

Production of N-[5-({2-[(cyclopropylcarbonyl)amino]imidazo[1,2-b]pyridazin-6-yl}oxy)-2-fluorophenyl]-1,5-dimethyl-1H-pyrazole-4-carboxamide

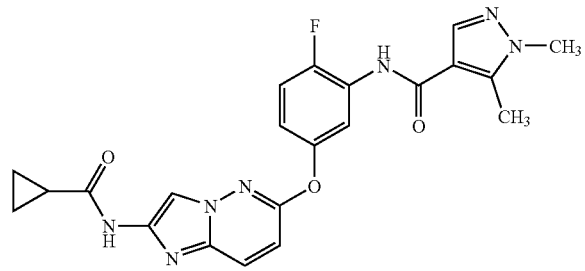

Using 1,5-dimethyl-1H-pyrazole-4-carboxylic acid (140 mg, 1.0 mmol), N,N-dimethylformamide (2 drops), tetrahydrofuran (10 mL), oxalyl chloride (0.172 mL, 2.0 mmol), N-methylpyrrolidone (5 mL) and N-[6-(3-amino-4-fluorophenoxy)imidazo[1,2-b]pyridazin-2-yl]cyclopropanecarboxamide (164 mg, 0.50 mmol), and in the same manner as in Example 173, the title compound (106 mg, yield 47%) was obtained.

$^1$H-NMR (DMSO-$d_6$, 300 MHz) δ 0.75-0.86 (4H, m), 1.85-1.98 (1H, m), 2.48 (3H, s), 3.75 (3H, s), 7.06 (1H, d, J=9.6 Hz), 7.13 (1H, ddd, J=8.9, 3.8, 3.1 Hz), 7.36 (1H, dd, J=10.2, 9.0 Hz), 7.58 (1H, dd, J=6.3, 3.0 Hz), 7.94 (1H, s), 8.04 (1H, s), 8.04 (1H, dd, J=9.6, 0.6 Hz), 9.63 (1H, s), 11.07 (1H, s).

Example 178

Production of N-[5-({2-[(cyclopropylcarbonyl)amino]imidazo[1,2-b]pyridazin-6-yl}oxy)-2-fluorophenyl]-4-methyl-1,3-thiazole-5-carboxamide

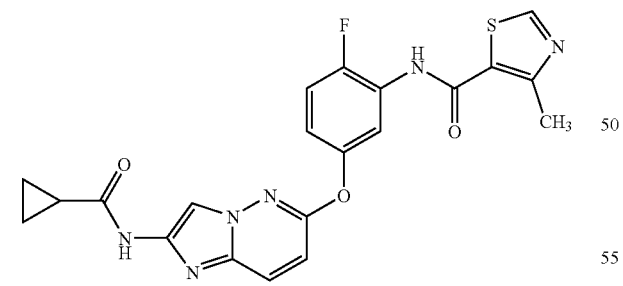

Using 4-methyl-1,3-thiazole-5-carboxylic acid (143 mg, 1.0 mmol), N,N-dimethylformamide (2 drops), tetrahydrofuran (10 mL), oxalyl chloride (0.172 mL, 2.0 mmol), N-methylpyrrolidone (5 mL) and N-[6-(3-amino-4-fluorophenoxy)imidazo[1,2-b]pyridazin-2-yl]cyclopropanecarboxamide (164 mg, 0.50 mmol), and in the same manner as in Example 173, the title compound (179 mg, yield 79%) was obtained.

$^1$H-NMR (DMSO-$d_6$, 300 MHz) δ 0.73-0.86 (4H, m), 1.85-1.98 (1H, m), 2.63 (3H, s), 7.08 (1H, d, J=9.5 Hz), 7.20 (1H, ddd, J=8.8, 3.7, 3.2 Hz), 7.40 (1H, dd, J=9.9, 9.3 Hz), 7.59 (1H, dd, J=6.6, 3.0 Hz), 7.94 (1H, s), 8.04 (1H, d, J=9.5 Hz), 9.14 (1H, s), 10.13 (1H, s), 11.07 (1H, s).

Example 179

Production of N-[5-({2-[(cyclopropylcarbonyl)amino]imidazo[1,2-b]pyridazin-6-yl}oxy)-2-fluorophenyl]-5-methyl-1,3-thiazole-4-carboxamide

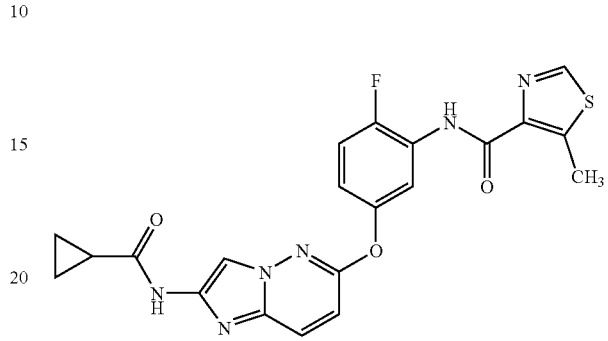

Using 5-methyl-1,3-thiazole-4-carboxylic acid (143 mg, 1.0 mmol), N,N-dimethylformamide (2 drops), tetrahydrofuran (10 mL), oxalyl chloride (0.172 mL, 2.0 mmol), N-methylpyrrolidone (5 mL) and N-[6-(3-amino-4-fluorophenoxy)imidazo[1,2-b]pyridazin-2-yl]cyclopropanecarboxamide (164 mg, 0.50 mmol), and in the same manner as in Example 173, the title compound (107 mg, yield 47%) was obtained.

$^1$H-NMR (DMSO-$d_6$, 300 MHz) δ 0.75-0.85 (4H, m), 1.86-1.98 (1H, m), 2.78 (3H, s), 7.08 (1H, d, J=9.6 Hz), 7.08-7.16 (1H, m), 7.42 (1H, dd, J=10.5, 9.0 Hz), 7.95 (1H, s), 8.00 (1H, dd, J=6.6, 3.0 Hz), 8.05 (1H, d, J=9.6 Hz), 9.02 (1H, s), 9.94 (1H, s), 11.08 (1H, s).

Example 180

Production of N-[5-({2-[(cyclopropylcarbonyl)amino]imidazo[1,2-b]pyridazin-6-yl}oxy)-2-fluorophenyl]-3-methoxy-1-methyl-1H-pyrazole-5-carboxamide

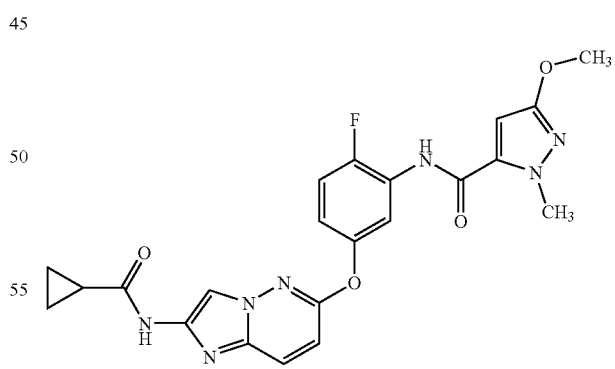

Using 3-methoxy-1-methyl-1H-pyrazole-5-carboxylic acid (156 mg, 1.0 mmol), N,N-dimethylformamide (2 drops), tetrahydrofuran (15 mL), oxalyl chloride (0.172 mL, 2.0 mmol), N-methylpyrrolidone (5 mL) and N-[6-(3-amino-4-fluorophenoxy)imidazo[1,2-b]pyridazin-2-yl]cyclopropanecarboxamide (164 mg, 0.50 mmol), and in the same manner as in Example 173, the title compound (85 mg, yield 36%) was obtained.

¹H-NMR (DMSO-d₆, 300 MHz) δ 0.76-0.84 (4H, m), 1.86-1.98 (1H, m), 3.80 (3H, s), 3.92 (3H, s), 6.50 (1H, s), 7.08 (1H, d, J=9.6 Hz), 7.21 (1H, ddd, J=9.1, 4.0, 3.1 Hz), 7.40 (1H, dd, J=10.0, 9.1 Hz), 7.53 (1H, dd, J=6.3, 3.0 Hz), 7.94 (1H, s), 8.05 (1H, dd, J=9.6, 0.6 Hz), 10.14 (1H, s), 11.07 (1H, s).

Example 181

Production of N-[5-({2-[(cyclopropylcarbonyl)amino]imidazo[1,2-b]pyridazin-6-yl}oxy)-2-fluorophenyl]-3-ethoxy-1-methyl-1H-pyrazole-5-carboxamide

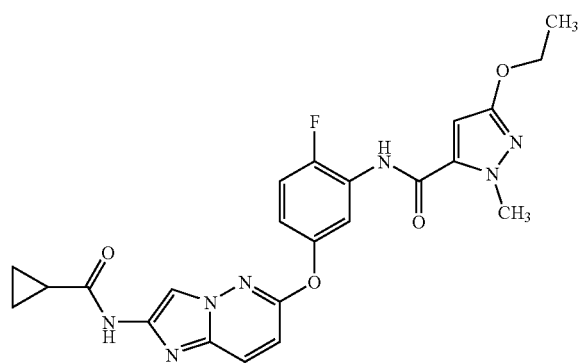

Using 3-ethoxy-1-methyl-1H-pyrazole-5-carboxylic acid (170 mg, 1.0 mmol), N,N-dimethylformamide (2 drops), tetrahydrofuran (15 mL), oxalyl chloride (0.172 mL, 2.0 mmol), N-methylpyrrolidone (5 mL) and N-[6-(3-amino-4-fluorophenoxy)imidazo[1,2-b]pyridazin-2-yl]cyclopropanecarboxamide (164 mg, 0.50 mmol), and in the same manner as in Example 173, the title compound (92 mg, yield 38%) was obtained.

¹H-NMR (DMSO-d₆, 300 MHz) δ 0.76-0.85 (4H, m), 1.30 (3H, t, J 7.0 Hz), 1.85-1.99 (1H, m), 3.91 (3H, s), 4.12 (2H, q, J=7.0 Hz), 6.48 (1H, s), 7.08 (1H, d, J=9.6 Hz), 7.18-7.25 (1H, m), 7.36-7.45 (1H, m), 7.53 (1H, dd, J=6.5, 3.1 Hz), 7.94 (1H, s), 8.05 (1H, dd, J=9.6, 0.4 Hz), 10.12 (1H, s), 11.07 (1H, s).

Example 182

Production of N-[5-({2-[(cyclopropylcarbonyl)amino]imidazo[1,2-b]pyridazin-6-yl}oxy)-2-fluorophenyl]-3-(2-methoxyethoxy)-1-methyl-1H-pyrazole-5-carboxamide

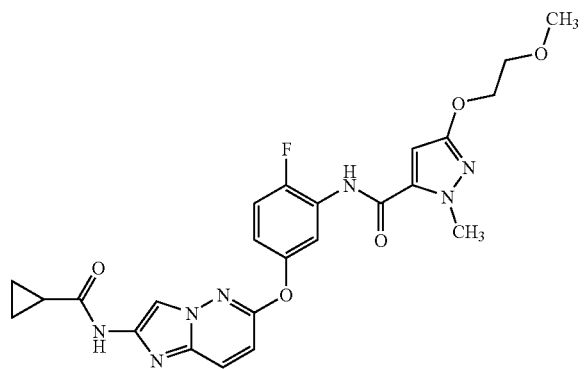

Using 3-(2-methoxyethoxy)-1-methyl-1H-pyrazole-5-carboxylic acid (200 mg, 1.0 mmol), N,N-dimethylformamide (2 drops), tetrahydrofuran (15 mL), oxalyl chloride (0.172 mL, 2.0 mmol), N-methylpyrrolidone (5 mL) and N-[6-(3-amino-4-fluorophenoxy)imidazo[1,2-b]pyridazin-2-yl]cyclopropanecarboxamide (164 mg, 0.50 mmol), and in the same manner as in Example 173, the title compound (128 mg, yield 50%) was obtained.

¹H-NMR (DMSO-d₆, 300 MHz) δ 0.76-0.85 (4H, m), 1.85-1.99 (1H, m), 3.29 (3H, s), 3.59-3.67 (2H, m), 3.91 (3H, s), 4.15-4.23 (2H, m), 6.49 (1H, s), 7.08 (1H, d, J=9.5 Hz), 7.18-7.25 (1H, m), 7.41 (1H, dd, J=10.1, 9.1 Hz), 7.53 (1H, dd, J=6.4, 2.9 Hz), 7.94 (1H, s), 8.05 (1H, dd, J=9.5, 0.7 Hz), 10.14 (1H, s), 11.07 (1H, s).

Example 183

Production of 6-(3-aminophenoxy)imidazo[1,2-b]pyridazin-2-amine

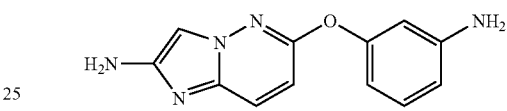

A mixture of 6-iodoimidazo[1,2-b]pyridazin-2-amine (390 mg, 1.5 mmol), 3-aminophenol (491 mg, 4.5 mmol), potassium carbonate (415 mg, 3.0 mmol) and N,N-dimethylformamide (3 mL) was stirred using a microwave synthesizer at 180° C. for 40 min. The reaction mixture was diluted with water and extracted with a mixed solvent of ethyl acetate/tetrahydrofuran (1:1). The organic layer was concentrated under reduced pressure, and the residue was purified by silica gel column chromatography (ethyl acetate/methanol=100/0→60/40). The objective fraction was concentrated under reduced pressure, and the residue was purified by NH silica gel column chromatography (ethyl acetate/methanol=100/0→80/20) and precipitated from ethyl acetate to give the title compound (133 mg, yield 37%) as a purple solid.

¹H-NMR (DMSO-d₆, 300 MHz) δ 5.27 (2H, s), 5.31 (2H, s), 6.23 (1H, ddd, J=7.8, 2.4, 0.9 Hz), 6.27 (1H, t, J=2.1 Hz), 6.38 (1H, ddd, J=8.1, 2.1, 0.9 Hz), 6.69 (1H, d, J=9.3 Hz), 7.02 (1H, t, J=7.9 Hz), 7.14 (1H, s), 7.68 (1H, dd, J=9.3, 0.6 Hz).

Example 184

Production of N-[5-({2-[(cyclopropylcarbonyl)amino]imidazo[1,2-b]pyridazin-6-yl}oxy)-2-methylphenyl]-5-methylisoxazole-4-carboxamide

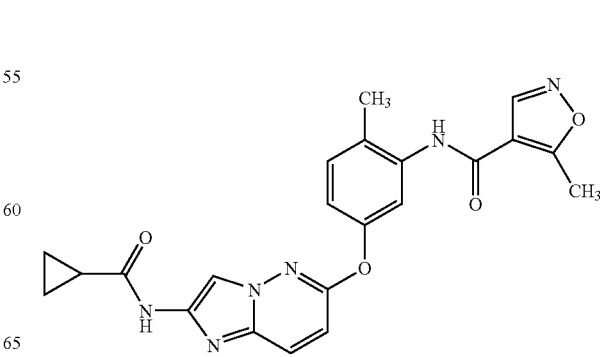

Using N-[6-(3-amino-4-methylphenoxy)imidazo[1,2-b]pyridazin-2-yl]cyclopropanecarboxamide (162 mg, 0.50 mmol), N-methylpyrrolidone (5 mL) and 5-methylisoxazole-4-carbonyl chloride (146 mg, 1.0 mmol), and in the same manner as in Example 162, the title compound (174 mg, yield 80%) was obtained.

¹H-NMR (DMSO-d₆, 300 MHz) δ 0.73-0.88 (4H, m), 1.86-1.99 (1H, m), 2.26 (3H, s), 2.66 (3H, s), 7.04 (1H, d, J=9.6 Hz), 7.09 (1H, dd, J=8.6, 2.6 Hz), 7.29 (1H, d, J=2.6 Hz), 7.35 (1H, d, J=8.6 Hz), 7.93 (1H, s), 8.03 (1H, dd, J=9.6, 0.4 Hz), 9.02 (1H, s), 9.75 (1H, s), 11.07 (1H, s).

Example 185

Production of N-[6-(3-amino-4-bromophenoxy)imidazo[1,2-b]pyridazin-2-yl]cyclopropanecarboxamide

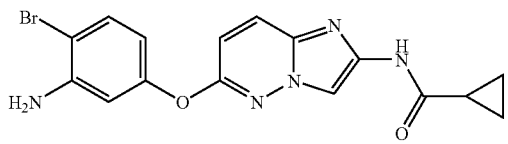

A mixture of N-(6-iodoimidazo[1,2-b]pyridazin-2-yl)cyclopropanecarboxamide (3.28 g, 10 mmol), 3-amino-4-bromophenol (2.82 g, 15 mmol), potassium carbonate (2.76 g, 20 mmol) and N,N-dimethylformamide (20 mL) was stirred at 110° C. for 24 hr, then at 150° C. for 24 hr. The reaction mixture was diluted with water and extracted with a mixed solvent of ethyl acetate/tetrahydrofuran (1:1). The organic layer was concentrated under reduced pressure, and the residue was purified by silica gel column chromatography (hexane/ethyl acetate=50/50→40/100) and recrystallized from ethyl acetate to give the title compound (1.85 g, yield 48%) as a pale-yellow solid.

¹H-NMR (DMSO-d₆, 300 MHz) δ 0.74-0.88 (4H, m), 1.86-1.98 (1H, m), 5.51 (2H, s), 6.35 (1H, dd, J=8.6, 2.8 Hz), 6.62 (1H, d, J=2.8 Hz), 7.01 (1H, d, J=9.6 Hz), 7.37 (1H, d, J=8.6 Hz), 7.99 (1H, s), 8.02 (1H, d, J=9.6 Hz), 11.08 (1H, s).

Example 186

Production of N-[2-bromo-5-({2-[(cyclopropylcarbonyl)amino]imidazo[1,2-b]pyridazin-6-yl}oxy)phenyl]-1,3-dimethyl-1H-pyrazole-5-carboxamide

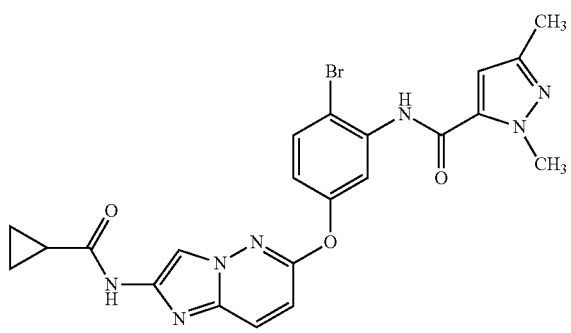

To a solution of N-[6-(3-amino-4-bromophenoxy)imidazo[1,2-b]pyridazin-2-yl]cyclopropanecarboxamide (582 mg, 1.50 mmol) in N-methylpyrrolidone (5 mL) was added 1,3-dimethyl-1H-pyrazole-5-carbonyl chloride (310 mg, 1.95 mmol), and the mixture was stirred at room temperature for 18 hr. A 5% aqueous sodium hydrogencarbonate solution was added to the reaction mixture, and the mixture was extracted with a mixed solvent of ethyl acetate/tetrahydrofuran (1:1). The organic layer was washed with water, dried over anhydrous sodium sulfate, filtrated, and concentrated under reduced pressure. The residue was suspended in ethyl acetate, and the mixture was stirred with heating under reflux for 15 min. After allowing the reaction mixture to cool to room temperature, the precipitate was collected by filtration, washed with ethyl acetate, and dried under reduced pressure to give the title compound (658 mg, yield 86%) as a cream solid.

¹H-NMR (DMSO-d₆, 300 MHz) δ 0.73-0.88 (4H, m), 1.86-1.98 (1H, m), 2.20 (3H, s), 3.98 (3H, s), 6.83 (1H, s), 7.10 (1H, d, J=9.6 Hz), 7.20 (1H, dd, J=8.9, 2.9 Hz), 7.51 (1H, dd, J=2.9 Hz), 7.79 (1H, d, J=8.9 Hz), 7.95 (1H, s), 8.06 (1H, dd, J=9.6, 0.6 Hz), 9.97 (1H, s), 11.09 (1H, s).

Example 187

Production of N-[3-({2-[(cyclopropylcarbonyl)amino]imidazo[1,2-b]pyridazin-6-yl}oxy)phenyl]-3-methylpyridine-2-carboxamide

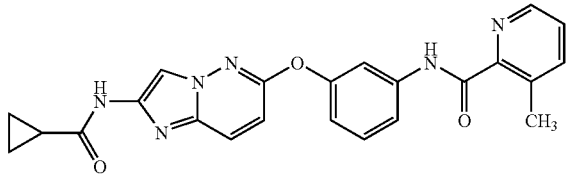

To a solution of N-[6-(3-aminophenoxy)imidazo[1,2-b]pyridazin-2-yl]cyclopropanecarboxamide (100 mg, 0.323 mmol), 3-methylpyridine-2-carboxylic acid (66 mg, 0.485 mmol) and 1-hydroxybenzotriazole (71 mg, 0.522 mmol) in N,N-dimethylformamide (4.0 mL) were added triethylamine (0.08 mL, 0.549 mmol) and 1-[3-(dimethylamino)propyl]-3-ethylcarbodiimide hydrochloride (99 mg, 0.517 mmol) under ice-cooling, and the mixture was stirred at room temperature for 20 hr. Under ice-cooling, aqueous sodium hydrogencarbonate solution was added to the reaction mixture, and the mixture was extracted with ethyl acetate. The extract was washed with saturated brine, dried over anhydrous magnesium sulfate, and filtered. The solvent was evaporated under reduced pressure, and the residue was purified by silica gel column chromatography (ethyl acetate/hexane=80/20→100/0) and recrystallized from ethyl acetate/methanol to give the title compound (98 mg, 71%) as colorless crystals.

¹H-NMR (DMSO-d₆, 300 MHz) δ 0.70-0.90 (4H, m), 1.85-2.00 (1H, m), 2.55 (3H, s), 6.95-7.05 (1H, m), 7.05 (1H, d, J=9.6 Hz), 7.41 (1H, t, J=7.8 Hz), 7.45-7.55 (1H, m), 7.71

(1H, d, J=8.4 Hz), 7.75-7.85 (2H, m), 8.04 (1H, d, J=8.7 Hz), 8.50-8.55 (1H, m), 10.68 (1H, s), 11.07 (1H, s).

Example 188

Production of N-[3-({2-[(cyclopropylcarbonyl)amino]imidazo[1,2-b]pyridazin-6-yl}oxy)phenyl]-6-methylpyridine-2-carboxamide

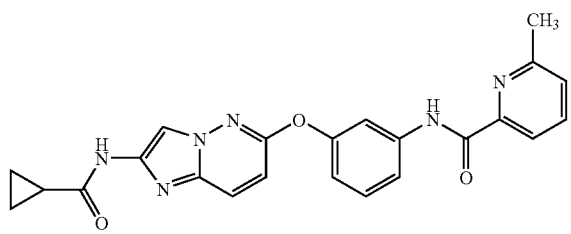

Using N-[6-(3-aminophenoxy)imidazo[1,2-b]pyridazin-2-yl]cyclopropanecarboxamide (100 mg, 0.323 mmol), 6-methylpyridine-2-carboxylic acid (66 mg, 0.485 mmol), 1-[3-(dimethylamino)propyl]-3-ethylcarbodiimide hydrochloride (99 mg, 0.517 mmol), 1-hydroxybenzotriazole (71 mg, 0.522 mmol), triethylamine (0.08 mL, 0.549 mmol) and N,N-dimethylformamide (4.0 mL), and by a reaction in the same manner as in Example 187, the title compound (100 mg, 72%) was obtained as colorless crystals.

$^1$H-NMR (DMSO-d$_6$, 300 MHz) δ 0.75-0.85 (4H, m), 1.85-1.95 (1H, m), 2.62 (3H, s), 7.00-7.05 (1H, m), 7.07 (1H, d, J=9.6 Hz), 7.44 (1H, t, J=7.8 Hz), 7.50-7.55 (1H, m), 7.79 (1H, d, J=7.8 Hz), 7.85-7.95 (3H, m), 8.05 (1H, d, J=9.6 Hz), 7.97 (1H, s), 10.56 (1H, s), 11.08 (1H, s).

Example 189

Production of N-[6-(3{[(methylsulfonyl)acetyl]amino}phenoxy)imidazo[1,2-b]pyridazin-2-yl]cyclopropanecarboxamide

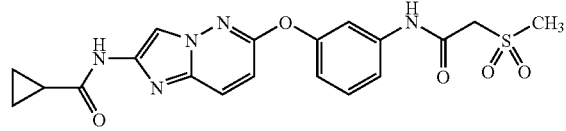

Using N-[6-(3-aminophenoxy)imidazo[1,2-b]pyridazin-2-yl]cyclopropanecarboxamide (100 mg, 0.323 mmol), (methylsulfonyl)acetic acid (67 mg, 0.485 mmol), 1-[3-(dimethylamino)propyl]-3-ethylcarbodiimide hydrochloride (99 mg, 0.517 mmol), 1-hydroxybenzotriazole (71 mg, 0.522 mmol), triethylamine (0.08 mL, 0.549 mmol) and N,N-dimethylformamide (4.0 mL), and by a reaction in the same manner as in Example 187, the title compound (87 mg, 63%) was obtained as pale-yellow crystals.

$^1$H-NMR (DMSO-d$_6$, 300 MHz) δ 0.75-0.85 (4H, m), 1.90-2.00 (1H, m), 3.15 (3H, s), 4.27 (2H, s), 6.95-7.05 (1H, m), 7.05 (1H, d, J=9.3 Hz), 7.35-7.45 (2H, m), 7.57 (1H, s), 7.95 (1H, s), 8.04 (1H, d, J=9.3 Hz), 10.58 (1H, s), 11.08 (1H, s).

Example 190

Production of N-(6-{3-[(3-hydroxy-3-methylbutanoyl)amino]phenoxy}imidazo[1,2-b]pyridazin-2-yl)cyclopropanecarboxamide

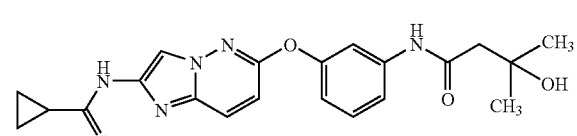

Using N-[6-(3-aminophenoxy)imidazo[1,2-b]pyridazin-2-yl]cyclopropanecarboxamide (100 mg, 0.323 mmol), 3-hydroxy-3-methylbutanoic acid (57 mg, 0.485 mmol), 1-[3-(dimethylamino)propyl]-3-ethylcarbodiimide hydrochloride (99 mg, 0.517 mmol), 1-hydroxybenzotriazole (71 mg, 0.522 mmol), triethylamine (0.08 mL, 0.549 mmol) and N,N-dimethylformamide (4.0 mL), and by a reaction in the same manner as in Example 187, the title compound (22 mg, 16%) was obtained as pale-yellow crystals.

$^1$H-NMR (DMSO-d$_6$, 300 MHz) δ 0.75-0.85 (4H, m), 1.21 (6H, s), 1.90-2.00 (1H, m), 2.41 (2H, s), 4.69 (1H, s), 6.90-6.95 (1H, m), 7.03 (1H, d, J=9.4 Hz), 7.30-7.45 (2H, m), 7.55-7.60 (1H, m), 7.96 (1H, s), 8.04 (1H, d, J=9.4 Hz), 9.97 (1H, s), 11.09 (1H, s).

Example 191

Production of N-[6-(3-aminophenoxy)imidazo[1,2-b]pyridazin-2-yl]-2-cyclopropylacetamide

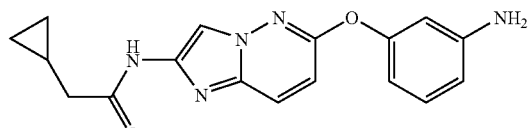

A mixture of 2-cyclopropyl-N-(6-iodoimidazo[1,2-b]pyridazin-2-yl)acetamide (501 mg, 1.46 mmol), 3-aminophenol (479 mg, 4.39 mmol), potassium carbonate (807 mg, 5.84 mmol) and N,N-dimethylformamide (5 mL) was stirred at 120° C. for 12 hr. Tetrahydrofuran/ethyl acetate and saturated brine were added to the reaction mixture, and insoluble material was filtered off. The filtrate was extracted with ethyl acetate, dried over anhydrous magnesium sulfate, and filtrated. The solvent was evaporated under reduced pressure, and the residue was purified by silica gel column chromatography (hexane/ethyl acetate=20/80→0/100) to give the title compound (156 mg, 33%) as a pale-yellow powder.

¹H-NMR (DMSO-d₆, 300 MHz) δ 0.10-0.25 (2H, m), 0.45-0.55 (2H, m), 1.00-1.10 (1H, m), 2.25 (2H, d, J=7.2 Hz), 5.31 (2H, s), 6.30 (1H, d, J=8.1 Hz), 6.35 (1H, s), 6.43 (1H, d, J=8.1 Hz), 6.95 (1H, d, J=9.6 Hz), 7.05 (1H, t, J=8.1 Hz), 7.99 (1H, d, J=9.6 Hz), 8.03 (1H, s), 10.70 (1H, s).

Example 192

Production of N-[5-({2-[(cyclopropylacetyl)amino]imidazo[1,2-b]pyridazin-6-yl}oxy)-2-fluorophenyl]-1,3-dimethyl-1H-pyrazole-5-carboxamide

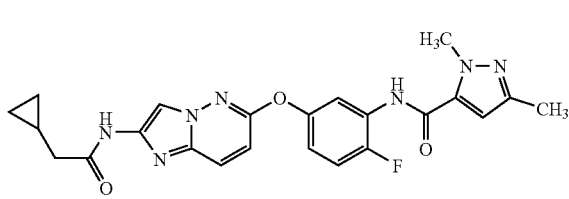

Using 2-cyclopropyl-N-(6-iodoimidazo[1,2-b]pyridazin-2-yl)acetamide (171 mg, 0.5 mmol), N-(2-fluoro-5-hydroxyphenyl)-1,3-dimethyl-1H-pyrazole-5-carboxamide (150 mg, 0.6 mmol), potassium carbonate (104 mg, 0.75 mmol) and N,N-dimethylformamide (4 mL), and by a reaction in the same manner as in Example 191, the title compound (53 mg, 23%) was obtained as pale-pink crystals.

¹H-NMR (DMSO-d₆, 300 MHz) δ 0.10-0.20 (2H, m), 0.40-0.50 (2H, m), 1.00-1.15 (1H, m), 2.19 (3H, s), 2.24 (2H, d, J=7.2 Hz), 3.97 (3H, s), 6.84 (1H, s), 7.07 (1H, d, J=9.6 Hz), 7.15-7.25 (1H, m), 7.40 (1H, t, J=9.6 Hz), 7.50-7.60 (1H, m), 7.98 (1H, s), 8.03 (1H, d, J=9.6 Hz), 10.09 (1H, s), 10.68 (1H, s).

Example 193

Production of N-[3-({2-[(cyclopropylacetyl)amino]imidazo[1,2-b]pyridazin-6-yl}oxy)phenyl]-1,3-dimethyl-1H-pyrazole-5-carboxamide

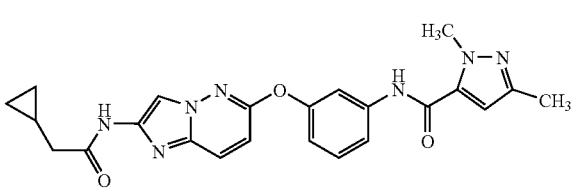

Using N-[6-(3-aminophenoxy)imidazo[1,2-b]pyridazin-2-yl]-2-cyclopropylacetamide (100 mg, 0.309 mmol), 1,3-dimethyl-1H-pyrazole-5-carbonyl chloride (64 mg, 0.404 mmol) and N,N-dimethylacetamide (5.0 mL), and by a reaction in the same manner as in Example 148, the title compound (85 mg, 62%) was obtained as colorless crystals.

¹H-NMR (DMSO-d₆, 300 MHz) δ 0.15-0.25 (2H, m), 0.40-0.50 (2H, m), 1.00-1.15 (1H, m), 2.19 (3H, s), 2.25 (2H, d, J=6.9 Hz), 3.97 (3H, s), 6.82 (1H, s), 7.00 (1H, d, J=8.1 Hz), 7.05 (1H, d, J=9.6 Hz), 7.42 (1H, t, J=8.1 Hz), 7.60 (1H, d, J=8.1 Hz), 7.67 (1H, s), 8.02 (1H, s), 8.05-8.10 (1H, m), 10.23 (1H, s), 10.70 (1H, s).

Example 194

Production of N-[5-({2-[(cyclopropylcarbonyl)amino]imidazo[1,2-b]pyridazin-6-yl}oxy)-2-methylphenyl]-4-methylpyridine-2-carboxamide

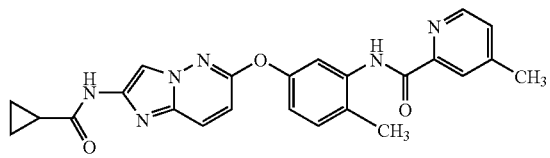

Using N-[6-(3-amino-4-methylphenoxy)imidazo[1,2-b]pyridazin-2-yl]cyclopropanecarboxamide (120 mg, 0.371 mmol), 4-methylpyridine-2-carboxylic acid (76 mg, 0.557 mmol), 1-[3-(dimethylamino)propyl]-3-ethylcarbodiimide hydrochloride (114 mg, 0.594 mmol), 1-hydroxybenzotriazole (81 mg, 0.600 mmol), triethylamine (0.09 mL, 0.631 mmol) and N,N-dimethylformamide (6.0 mL), and by a reaction in the same manner as in Example 187, the title compound (40 mg, 24%) was obtained as pale-yellow crystals.

¹H-NMR (DMSO-d₆, 300 MHz) δ 0.75-0.85 (4H, m), 1.85-2.00 (1H, m), 2.35 (3H, s), 2.44 (3H, s), 7.00-7.10 (2H, m), 7.34 (1H, d, J=8.7 Hz), 7.50-7.55 (1H, m), 7.85-8.00 (3H, m), 8.02 (1H, d, J=9.3 Hz), 8.58 (1H, d, J=4.8 Hz), 10.31 (1H, s), 11.07 (1H, s).

Example 195

Production of N-[5-({2-[(cyclopropylcarbonyl)amino]imidazo[1,2-b]pyridazin-6-yl}oxy)-2-methylphenyl]-2-methylnicotinamide

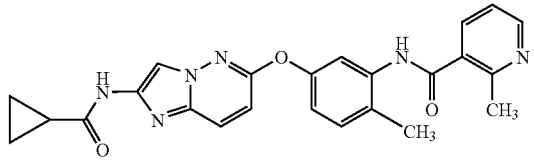

Using N-[6-(3-amino-4-methylphenoxy)imidazo[1,2-b]pyridazin-2-yl]cyclopropanecarboxamide (120 mg, 0.371 mmol), 2-methylpyridine-3-carboxylic acid (76 mg, 0.557 mmol), 1-[3-(dimethylamino)propyl]-3-ethylcarbodiimide hydrochloride (114 mg, 0.594 mmol), 1-hydroxybenzotriazole (81 mg, 0.600 mmol), triethylamine (0.09 mL, 0.631 mmol) and N,N-dimethylformamide (6.0 mL), and by a reaction in the same manner as in Example 187, the title compound (52 mg, 31%) was obtained as pale-pink crystals.

¹H-NMR (DMSO-d₆, 300 MHz) δ 0.75-0.85 (4H, m), 1.85-1.95 (1H, m), 2.30 (3H, s), 2.59 (3H, s), 7.00-7.10 (2H, m), 7.30-7.35 (2H, m), 7.40-7.45 (1H, m), 7.85-7.90 (1H, m), 7.93 (1H, s), 8.02 (1H, d, J=9.6 Hz), 8.54 (1H, d, J=3.0 Hz), 9.98 (1H, s), 11.06 (1H, s).

Example 196

Production of N-(6-{4-methyl-3-[(pyridin-2-ylacetyl)amino]phenoxy}imidazo[1,2-b]pyridazin-2-yl)cyclopropanecarboxamide

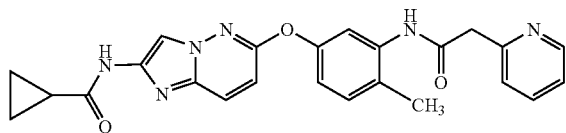

To a solution of N-[6-(3-amino-4-methylphenoxy)imidazo[1,2-b]pyridazin-2-yl]cyclopropanecarboxamide (120 mg, 0.371 mmol) and pyridin-2-ylacetic acid hydrochloride (129 mg, 0.742 mmol) in N,N-dimethylformamide (4.0 mL) were added dropwise triethylamine (0.21 mL, 1.484 mmol) and diethyl cyanophosphate (0.12 mL, 0.816 mmol) under ice-cooling, and the mixture was stirred at room temperature for 3 hr. Under ice-cooling, aqueous sodium hydrogencarbonate solution was added to the reaction mixture, and the mixture was extracted with ethyl acetate. The extract was washed with saturated brine, dried over anhydrous magnesium sulfate, and filtered. The solvent was evaporated under reduced pressure, and the residue was purified by silica gel column chromatography (ethyl acetate/methanol=100/0→95/5) and recrystallized from ethyl acetate to give the title compound (67 mg, 41%) as pale-yellow crystals.

$^1$H-NMR (DMSO-d$_6$, 300 MHz) δ 0.75-0.85 (4H, m), 1.90-2.00 (1H, m), 2.25 (3H, s), 3.90 (2H, s), 6.90-7.00 (1H, m), 7.00 (1H, d, J=9.6 Hz), 7.20-7.30 (2H, m), 7.40 (1H, t, J=7.8 Hz), 7.50-7.55 (1H, m), 7.70-7.80 (1H, m), 7.91 (1H, s), 7.99 (1H, d, J=9.6 Hz), 8.50-8.55 (1H, m), 9.79 (1H, s), 11.05 (1H, s).

Example 197

Production of N-[5-({2-[(cyclopropylcarbonyl)amino]imidazo[1,2-b]pyridazin-6-yl}oxy)-2-fluorophenyl]-3-methylpyridine-2-carboxamide

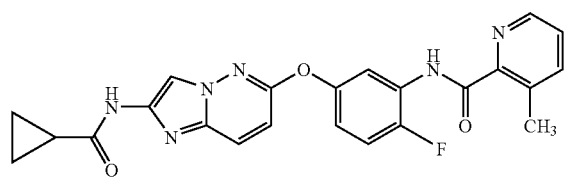

Using N-[6-(3-amino-4-fluorophenoxy)imidazo[1,2-b]pyridazin-2-yl]cyclopropanecarboxamide (200 mg, 0.611 mmol), 3-methylpyridine-2-carboxylic acid (126 mg, 0.917 mmol), 1-[3-(dimethylamino)propyl]-3-ethylcarbodiimide hydrochloride (187 mg, 0.978 mmol), 1-hydroxybenzotriazole (133 mg, 0.988 mmol), triethylamine (0.14 mL, 1.039 mmol) and N,N-dimethylformamide (6.0 mL), and by a reaction in the same manner as in Example 187, the title compound (128 mg, 47%) was obtained as colorless crystals.

$^1$H-NMR (DMSO-d$_6$, 300 MHz) δ 0.75-0.90 (4H, m), 1.85-2.00 (1H, m), 2.63 (3H, s), 7.05-7.20 (2H, m), 7.35-7.50 (1H, m), 7.50-7.60 (1H, m), 7.84 (1H, d, J=7.5 Hz), 7.94 (1H, s), 8.04 (1H, d, J=9.9 Hz), 8.10-8.15 (1H, m), 8.55-8.60 (1H, m), 10.57 (1H, s), 11.07 (1H, s).

Example 198

Production of N-[6-(3-amino-4-methylphenoxy)imidazo[1,2-b]pyridazin-2-yl]-2-cyclopropylacetamide

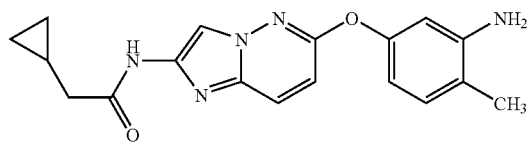

Using 2-cyclopropyl-N-(6-iodoimidazo[1,2-b]pyridazin-2-yl)acetamide (300 mg, 0.877 mmol), 3-amino-4-methylphenol (216 mg, 1.754 mmol), potassium carbonate (182 mg, 1.316 mmol) and N,N-dimethylformamide (3 mL), and by a reaction in the same manner as in Example 191, the title compound (138 mg, 47%) was obtained as a orange powder.

$^1$H-NMR (DMSO-d$_6$, 300 MHz) δ 0.15-0.25 (2H, m), 0.40-0.50 (2H, m), 1.00-1.10 (1H, m), 2.05 (3H, s), 2.25 (2H, d, J=6.9 Hz), 5.07 (2H, s), 6.28 (1H, d, J=7.5 Hz), 6.42 (1H, s), 6.90-7.00 (2H, m), 7.97 (1H, d, J=9.6 Hz), 8.01 (1H, s), 10.68 (1H, s).

Example 199

Production of N-[5-({2-[(cyclopropylacetyl)amino]imidazo[1,2-b]pyridazin-6-yl}oxy)-2-methylphenyl]-1,3-dimethyl-1H-pyrazole-5-carboxamide

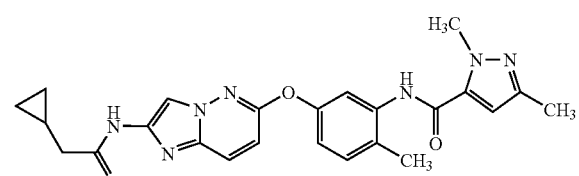

Using N-[6-(4-methyl-3-aminophenoxy)imidazo[1,2-b]pyridazin-2-yl]-2-cyclopropylacetamide (120 mg, 0.356 mmol), 1,3-dimethyl-1H-pyrazole-5-carbonyl chloride (59 mg, 0.374 mmol) and N,N-dimethylacetamide (4.0 mL), and by a reaction in the same manner as in Example 148, the title compound (99 mg, 61%) was obtained as a pale-yellow powder.

$^1$H-NMR (DMSO-d$_6$, 300 MHz) δ 0.15-0.25 (2H, m), 0.40-0.50 (2H, m), 1.00-1.15 (1H, m), 2.19 (3H, s), 2.25-2.30 (5H, m), 3.97 (3H, s), 6.80 (1H, s), 7.04 (1H, d, J=9.8 Hz), 7.05-7.15 (1H, m), 7.25-7.30 (1H, m), 7.34 (1H, d, J=8.1 Hz), 7.98 (1H, s), 8.02 (1H, d, J=9.8 Hz), 9.80 (1H, s), 10.68 (1H, s).

Example 200

Production of N-[6-(4-fluoro-3-{[(methoxyamino) carbonyl]amino}phenoxy)imidazo[1,2-b]pyridazin-2-yl]cyclopropanecarboxamide

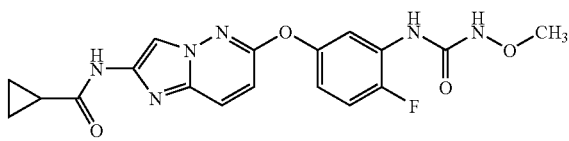

A solution of 1,1'-carbonyldiimidazole (297 mg, 1.833 mmol), O-methylhydroxyammonium chloride (153 mg, 1.833 mmol) and triethylamine (0.25 mL, 1.833 mmol) in N,N-dimethylformamide (4.0 mL) was stirred at room temperature for 30 min. A solution of N-[6-(3-amino-4-fluorophenoxy)imidazo[1,2-b]pyridazin-2-yl]cyloprcpanecarboxamide (200 mg, 0.611 mmol) in N,N-dimethylformamide (2.0 mL) was further added to the mixture, and the mixture was stirred at room temperature for 2 days. Under ice-cooling, aqueous sodium hydrogencarbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was recrystallized from tetrahydrofuran/ethanol to give the title compound (67 mg, 27%) as colorless crystals.

$^1$H-NMR (DMSO-d$_6$, 300 MHz) δ 0.75-0.85 (4H, m), 1.85-2.00 (1H, m), 3.63 (3H, s), 6.95-7.05 (1H, m), 7.05 (1H, d, J=9.3 Hz), 7.25-7.40 (1H, m), 7.70-7.75 (1H, m), 7.93 (1H, s), 8.03 (1H, d, J=9.3 Hz), 8.55 (1H, s), 9.76 (1H, s), 11.07 (1H, s).

Example 201

Production of N-[6-(4-fluoro-3-{[(isobutoxyamino) carbonyl]amino}phenoxy)imidazo[1,2-b]pyridazin-2-yl]cyclopropanecarboxamide

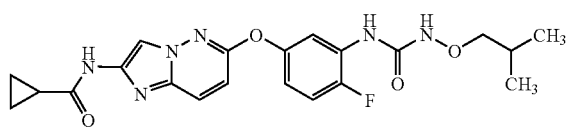

Using N-[6-(3-amino-4-fluorophenoxy)imidazo[1,2-b]pyridazin-2-yl]cyclopropanecarboxamide (200 mg, 0.611 mmol), 1,1'-carbonyldiimidazole (297 mg, 1.833 mmol), 1-(aminooxy)-2-methylpropane hydrochloride (230 mg, 1.833 mmol), triethylamine (0.25 mL, 1.833 mmol) and N,N-dimethylformamide (6.0 mL), and by a reaction in the same manner as in Example 200, the title compound (170 mg, 63%) was obtained as colorless crystals.

$^1$H-NMR (DMSO-d$_6$, 300 MHz) δ 0.75-0.85 (4H, m), 0.92 (6H, d, J=6.9 Hz), 1.85-2.00 (1H, m), 3.58 (2H, d, J=6.9 Hz), 6.95-7.05 (1H, m), 7.04 (1H, d, J=9.9 Hz), 7.33 (1H, t, J=9.9 Hz), 7.80-7.90 (1H, m), 7.92 (1H, s), 8.02 (1H, d, J=9.9 Hz), 8.31 (1H, s), 9.80 (1H, s), 11.06 (1H, s).

Example 202

Production of N-{6-[4-fluoro-3-({[(5-methylisoxazol-3-yl)amino]carbonyl}amino)phenoxy]imidazo[1,2-b]pyridazin-2-yl}cyclopropanecarboxamide

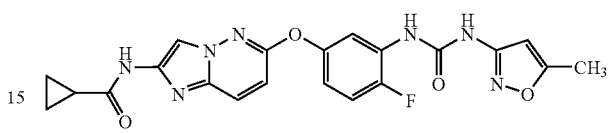

To a solution of pyridine (475 mg, 6 mmol) and 3-amino-5-methylisoxazole (147 mg, 1.5 mmol) in N,N-dimethylformamide (2.0 mL) was added dropwise a solution of phenyl chlorocarbonate (235 mg, 1.5 mmol) in N,N-dimethylformamide (2.0 mL) under ice-cooling. After the mixture was stirred at room temperature for 2 hr, N-[6-(3-amino-4-fluorophenoxy)imidazo[1,2-b]pyridazin-2-yl]cyclopropanecarboxamide (327 mg, 1.0 mmol) was added to the mixture, and the mixture was stirred at 80° C. for 15 hr and at 100° C. for 2 hr. Under ice-cooling, aqueous sodium hydrogencarbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was purified by basic silica gel column chromatography (ethyl acetate/hexane=80/20→100/0) and recrystallized from tetrahydrofuran/ethanol to give the title compound (101 mg, 22%) as colorless crystals.

$^1$H-NMR (DMSO-d$_6$, 300 MHz) δ 0.75-0.90 (4H, m), 1.85-2.00 (1H, m), 2.34 (3H, s), 6.48 (1H, s), 6.90-7.00 (1H, m), 7.04 (1H, d, J=9.3 Hz), 7.35 (1H, t, J=9.9 Hz), 7.90 (1H, s), 8.03 (1H, d, J=9.3 Hz), 9.00 (1H, br s), 9.85 (1H, br s), 11.06 (1H, s).

Example 203

Production of N-[5-({2-[(cyclopropylcarbonyl) amino]imidazo[1,2-b]pyridazin-6-yl}oxy)-2-fluorophenyl]-1,4-dimethyl-1H-pyrazole-3-carboxamide

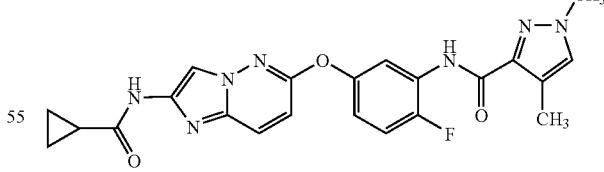

To a suspension of 1,4-dimethyl-1H-pyrazole-3-carboxylic acid (151 mg, 1.08 mmol) in tetrahydrofuran (2.0 mL) were added N,N-dimethylformamide (1 drop) and thionyl chloride (0.08 mL, 1.1 mmol), and the mixture was stirred at room temperature for 50 min. The reaction mixture was concentrated under reduced pressure and dissolved in N,N-dimethylacetamide (2.0 mL). On the other hand, to a solution of N-[6-(3-amino-4-fluorophenoxy)imidazo[1,2-b]pyridazin-2-yl]cyclopropanecarboxamide (327 mg, 1.0 mmol) in N,N- dimethylacetamide (6.0 mL) was added dropwise the above-mentioned solution under ice-cooling, and the mixture was stirred at room temperature for 2 hr. Under ice-cooling, aqueous sodium hydrogencarbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was purified by basic silica gel column chromatography (ethyl acetate/hexane=80/20→100/0) and recrystallized from tetrahydrofuran/ethanol to give the title compound (283 mg, 63%) as pale-yellow crystals.

$^1$H-NMR (DMSO-$d_6$, 300 MHz) δ 0.75-0.85 (4H, m), 1.85-2.00 (1H, m), 2.21 (3H, s), 3.89 (3H, s), 7.05-7.15 (2H, m), 7.38 (1H, t, J=9.6 Hz), 7.65 (1H, s), 7.90-8.00 (2H, m), 8.03 (1H, d, J=9.6 Hz), 9.40 (1H, s), 11.06 (1H, s).

Example 204

Production of N-[5-({2-[(cyclopropylcarbonyl)amino]imidazo[1,2-b]pyridazin-6-yl}oxy)-2-fluorophenyl]-1,4-dimethyl-1H-pyrazole-5-carboxamide

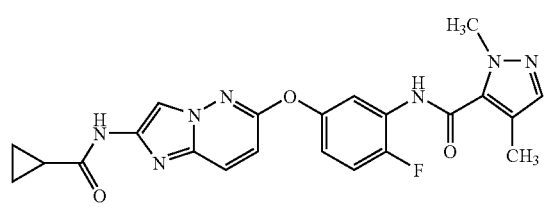

Using N-[6-(3-amino-4-fluorophenoxy)imidazo[1,2-b]pyridazin-2-yl]cyclopropanecarboxamide (327 mg, 1.0 mmol), 1,4-dimethyl-1H-pyrazole-5-carboxylic acid (154 mg, 1.1 mmol), tetrahydrofuran (2.0 mL), N,N-dimethylformamide (1 drop), thionyl chloride (0.08 mL, 1.1 mmol) and N,N-dimethylacetamide (6.0 mL), and by a reaction in the same manner as in Example 203, the title compound (300 mg, 67%) was obtained as pale-yellow crystals.

$^1$H-NMR (DMSO-$d_6$, 300 MHz) δ 0.75-0.85 (4H, m), 1.85-2.00 (1H, m), 2.19 (3H, s), 3.90 (3H, s), 7.07 (1H, d, J=9.6 Hz), 7.15-7.25 (1H, m), 7.33 (1H, s), 7.40 (1H, t, J=9.6 Hz), 7.75-7.80 (1H, m), 7.93 (1H, s), 8.04 (1H, d, J=9.6 Hz), 10.06 (1H, s), 11.06 (1H, s).

Example 205

Production of N-(2-fluoro-5-{[2-(isobutyrylamino)imidazo[1,2-b]pyridazin-6-yl]oxy}phenyl)-1,3-dimethyl-1H-pyrazole-5-carboxamide

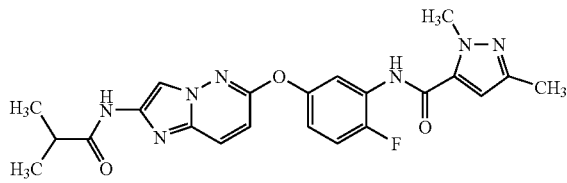

Using N-{5-[(2-aminoimidazo[1,2-b]pyridazin-6-yl)oxy]-2-fluorophenyl}-1,3-dimethyl-1H-pyrazole-5-carboxamide hydrochloride (200 mg, 0.48 mmol), 2-methylpropanoyl chloride (53 mg, 0.50 mmol) and N,N-dimethylacetamide (5.0 mL), and by a reaction in the same manner as in Example 148, the title compound (98 mg, 45%) was obtained as pale-blue crystals.

$^1$H-NMR (DMSO-$d_6$, 300 MHz) δ 1.08 (6H, d, J=6.9 Hz), 2.19 (3H, s), 2.65-2.75 (1H, m), 3.97 (3H, s), 6.84 (1H, s), 7.06 (1H, d, J=9.6 Hz), 7.15-7.25 (1H, m), 7.40 (1H, t, J=9.6 Hz), 7.50-7.60 (1H, m), 7.98 (1H, s), 8.03 (1H, d, J=9.6 Hz), 10.09 (1H, s), 10.72 (1H, s).

Example 206

Production of N-[5-({2-[(cyclopropylcarbonyl)amino]imidazo[1,2-b]pyridazin-6-yl}oxy)-2-fluorophenyl]pyrazine-2-carboxamide

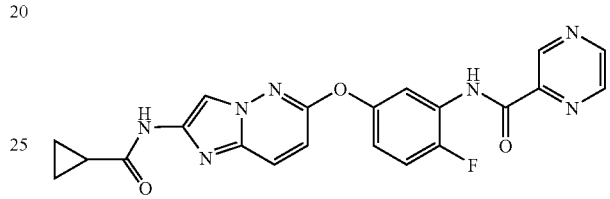

Using a solution of N-[6-(3-amino-4-fluorophenoxy)imidazo[1,2-b]pyridazin-2-yl]cyclopropanecarboxamide (327 mg, 1.0 mmol) and 2-pyrazinecarbonylchloride (171 mg, 1.2 mmol) in N,N-dimethylacetamide (6.0 mL), and by a reaction in the same manner as in Example 148, the title compound (113 mg, 26%) was obtained as colorless crystals.

$^1$H-NMR (DMSO-$d_6$, 300 MHz) δ 0.70-0.85 (4H, m), 1.85-2.00 (1H, m), 7.09 (1H, d, J=9.6 Hz), 7.15-7.25 (1H, m), 7.44 (1H, t, J=9.6 Hz), 7.90-8.00 (2H, m), 8.05 (1H, d, J=9.6 Hz), 8.83 (1H, s), 8.96 (1H, s), 9.28 (1H, s), 10.44 (1H, s), 11.07 (1H, s).

Example 207

Production of N-[5-({2-[(cyclopropylcarbonyl)amino]imidazo[1,2-b]pyridazin-6-yl}oxy)-2-fluorophenyl]-1-methyl-1H-pyrrole-2-carboxamide

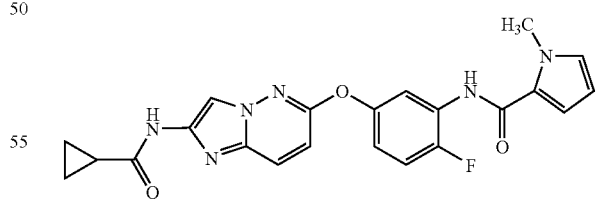

Using N-[6-(3-amino-4-fluorophenoxy)imidazo[1,2-b]pyridazin-2-yl]cyclopropanecarboxamide (327 mg, 1.0 mmol), 1-methyl-1H-pyrrole-2-carbonyl chloride (151 mg, 1.05 mmol) and N,N-dimethylacetamide (6.0 mL), and by a reaction in the same manner as in Example 148, the title compound (268 mg, 62%) was obtained as colorless crystals.

$^1$H-NMR (DMSO-$d_6$, 300 MHz) δ 0.75-0.85 (4H, m), 1.90-2.00 (1H, m), 3.84 (3H, s), 6.05-6.10 (1H, m), 7.00-7.20

(4H, m), 7.35 (1H, t, J=9.6 Hz), 7.50-7.60 (1H, m), 7.93 (1H, s), 8.03 (1H, d, J=9.6 Hz), 9.63 (1H, s), 11.06 (1H, s).

Example 208

Production of N-[5-({2-[(cyclopropylcarbonyl)amino]imidazo[1,2-b]pyridazin-6-yl}oxy)-2-fluorophenyl]-3-ethyl-1-methyl-1H-pyrazole-5-carboxamide

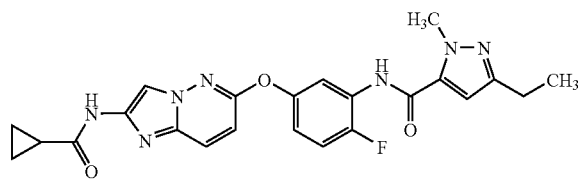

Using N-[6-(3-amino-4-fluorophenoxy)imidazo[1,2-b]pyridazin-2-yl]cyclopropanecarboxamide (327 mg, 1.0 mmol), 3-ethyl-1-methyl-1H-pyrazole-5-carboxylic acid (170 mg, 1.1 mmol) tetrahydrofuran (2.0 mL), N,N-dimethylformamide (1 drop), thionyl chloride (0.08 mL, 1.1 mmol) and N,N-dimethylacetamide (6.0 mL), and by a reaction in the same manner as in Example 203, the title compound (256 mg, 55%) was obtained as colorless crystals. melting point 236° C.

$^1$H-NMR (DMSO-d$_6$, 300 MHz) δ 0.75-0.85 (4H, m), 1.19 (3H, t, J=7.5 Hz), 1.90-2.00 (1H, m), 2.56 (2H, q, J=7.5 Hz), 3.98 (3H, s), 6.89 (1H, s), 7.06 (1H, d, J=9.6 Hz), 7.15-7.25 (1H, m), 7.39 (1H, t, J=9.6 Hz), 7.50-7.55 (1H, m), 7.93 (1H, s), 8.04 (1H, d, J=9.6 Hz), 10.10 (1H, s), 11.07 (1H, s).

Example 209

Production of N-[5-({2-[(cyclopropylcarbonyl)amino]imidazo[1,2-b]pyridazin-6-yl}oxy)-2-methylphenyl]-1,4-dimethyl-1H-pyrazole-3-carboxamide

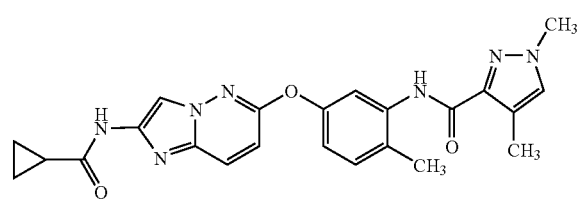

Using N-[6-(3-amino-4-methylphenoxy)imidazo[1,2-b]pyridazin-2-yl]cyclopropanecarboxamide (323 mg, 1.0 mmol), 1,4-dimethyl-1H-pyrazole-3-carboxylic acid (154 mg, 1.1 mmol) tetrahydrofuran (2.0 mL), N,N-dimethylformamide (1 drop), thionyl chloride (0.08 mL, 1.1 mmol) and N,N-dimethylacetamide (6.0 mL), and by a reaction in the same manner as in Example 203, the title compound (208 mg, 47%) was obtained as pale-yellow crystals.

$^1$H-NMR (DMSO-d$_6$, 300 MHz) δ 0.75-0.85 (4H, m), 1.85-2.00 (1H, m), 2.20 (3H, s), 2.28 (3H, s), 3.88 (3H, s), 6.95-7.05 (1H, m), 7.02 (1H, d, J=9.6 Hz), 7.30 (1H, d, J=8.7 Hz), 7.63 (1H, s), 7.65-7.70 (1H, m), 7.93 (1H, s), 8.02 (1H, d, J=9.6 Hz), 9.28 (1H, s), 11.06 (1H, s).

Example 210

Production of N-{2-fluoro-5-[(2-{[(methoxyamino)carbonyl]amino}imidazo[1,2-b]pyridazin-6-yl)oxy]phenyl}-1,3-dimethyl-1H-pyrazole-5-carboxamide

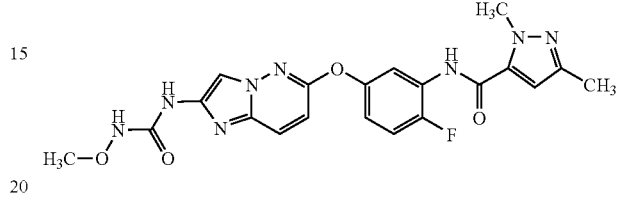

Using N-{5-[(2-aminoimidazo[1,2-b]pyridazin-6-yl)oxy]-2-fluorophenyl}-1,3-dimethyl-1H-pyrazole-5-carboxamide hydrochloride (200 mg, 0.48 mmol), 1,1'-carbonyldiimidazole (233 mg, 1.44 mmol), O-methylhydroxyammonium chloride (120 mg, 1.44 mmol), triethylamine (0.27 mL, 1.92 mmol) and N,N-dimethylformamide (6.0 mL), and by a reaction in the same manner as in Example 200, the title compound (117 mg, 54%) was obtained as pale-yellow crystals.

$^1$H-NMR (DMSO-d$_6$, 300 MHz) δ 2.19 (3H, s), 3.60 (3H, s), 3.97 (3H, s), 6.84 (1H, s), 7.05 (1H, d, J=9.6 Hz), 7.15-7.25 (1H, m), 7.39 (1H, t, J=9.0 Hz), 7.50-7.55 (1H, m), 7.83 (1H, s), 8.01 (1H, d, J=9.6 Hz), 9.46 (1H, s), 9.67 (1H, s), 10.09 (1H, s).

Example 211

Production of N-(2-fluoro-5-{[2-(glycoloylamino)imidazo[1,2-b]pyridazin-6-yl]oxy}phenyl)-1,3-dimethyl-1H-pyrazole-5-carboxamide

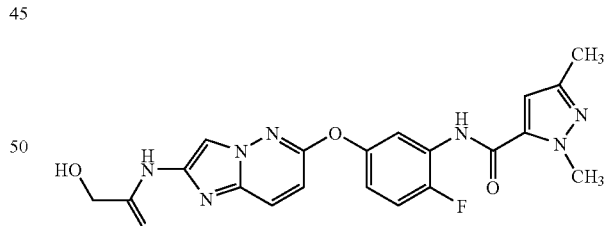

To N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide (507 mg, 1.13 mmol) was added 10% hydrogen chloride methanol solution (30 mL), and the mixture was stirred at 50° C. for 23 hr. The solvent was evaporated under reduced pressure. To the residue were added acetoxyacetic acid (242 mg, 2.05 mmol), 1-(3-dimethylaminopropyl)-3-ethylcarbodiimide hydrochloride (336 mg, 1.75 mmol), 1-hydroxybenzotriazole (167 mg, 1.24 mmol), N-ethyldiisopropylamine (0.60 mL, 3.51 mmol) and N,N-dimethylformamide (10 mL), and the mixture was stirred at room temperature for 62 hr. Methanol (10 mL), water (10 mL) and saturated aqueous sodium carbonate solution (2 mL) were added to the mixture, and the mixture was stirred at room temperature for 2 hr and concentrated under reduced pressure. A saturated aqueous sodium hydrogencarbonate solution was added to the residue, and the mixture was extracted with ethyl acetate. The organic layer was washed with saturated brine, dried over anhydrous magnesium sulfate, and concentrated under reduced pressure. The residue was separated and purified by NH silica gel column chromatography (ethyl acetate/hexane=0/100→100/0-methanol/ethyl acetate=2/98) and crystallized from ethanol to give the title compound (94 mg, 19%) as a white powder.

$^1$H-NMR (DMSO-d$_6$, 300 MHz) δ 2.19 (3H, s), 3.98 (3H, s), 4.05 (2H, d, J=6.0 Hz), 5.51 (1H, t, J=6.0 Hz), 6.85 (1H, s), 7.11 (1H, d, J=9.8 Hz), 7.18-7.27 (1H, m), 7.41 (1H, m), 7.55 (1H, dd, J=6.4, 3.0 Hz), 8.01 (1H, s), 8.07 (1H, d, J=9.0 Hz), 10.11 (1H, s), 10.23 (1H, s).

Example 212

Production of N-{2-fluoro-5-[(2-{[(4-methylpiperazin-1-yl)acetyl]amino}imidazo[1,2-b]pyridazin-6-yl)oxy]phenyl}-1,3-dimethyl-1H-pyrazole-5-carboxamide dihydrochloride

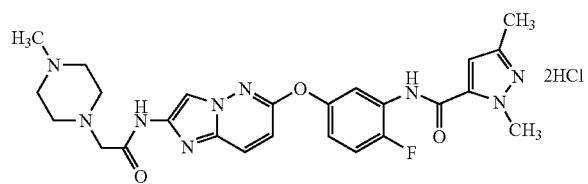

To N-[5-({2-[(cyclopropylcarbonyl)amino]imidazo[1,2-b]pyridazin-6-yl}oxy)-2-fluorophenyl]-1,3-dimethyl-1H-pyrazole-5-carboxamide (1.05 mg, 2.33 mmol) was added 10% hydrogen chloride methanol solution (120 mL), and the mixture was stirred at 50° C. for 44 hr. The solvent was evaporated under reduced pressure. To a half of the residue were added (4-methylpiperazin-1-yl)acetic acid (205 mg, 1.30 mmol), 1-(3-dimethylaminopropyl)-3-ethylcarbodiimide hydrochloride (284 mg, 1.48 mmol), 1-hydroxybenzotriazole (167 mg, 1.24 mmol), N-ethyldiisopropylamine (0.60 mL, 3.51 mmol) and N,N-dimethylformamide (10 mL), and the mixture was stirred at room temperature for 11 hr. A saturated aqueous sodium hydrogencarbonate solution was added to the reaction mixture, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane=0/100→70/30) and the objective fraction was concentrated under reduced pressure. The residue was dissolved in methanol and treated with a 4N hydrogen chloride ethyl acetate solution to give the title compound (43 mg, 6%) as a white powder.

$^1$H-NMR (DMSO-d$_6$, 300 MHz) δ 2.19 (3H, s), 2.78 (3H, s), 3.21 (1H, brs), 3.34 (1H, brs), 3.67 (1H, br), 3.98 (3H, s), 6.87 (1H, s), 7.13 (1H, d, J=9.5 Hz), 7.18-7.27 (1H, m), 7.41 (1H, t, J=9.7 Hz), 7.51-7.60 (1H, m), 8.02 (1H, s), 8.09 (1H, d, J=9.5 Hz), 10.13 (1H, s), 11.03 (1H, s).

Example 213

Production of N-[3-({2-[(cyclopropylcarbonyl)amino]imidazo[1,2-b]pyridazin-6-yl}oxy)phenyl]-1-methyl-1H-pyrrole-2-carboxamide

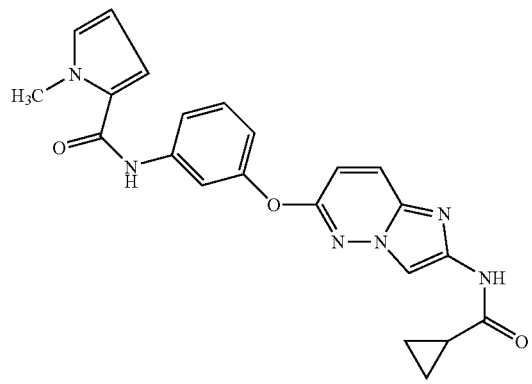

Using 1-methyl-1H-pyrrole-2-carboxylic acid (97 mg, 0.78 mmol), tetrahydrofuran (4.0 mL), N,N-dimethylformamide (30 μL, 0.39 mmol), oxalyl chloride (135 μL, 1.55 mmol), N-[6-(3-aminophenoxy)imidazo[1,2-b]pyridazin-2-yl]cyclopropylcarboxamide (200 mg, 0.65 mmol) and N,N-dimethylacetamide (4.0 mL), and in the same manner as in Example 119, the title compound (133 mg, 49%) was obtained as a white powder.

$^1$H-NMR (DMSO-d$_6$, 300 MHz) δ 0.78-0.82 (4H, m), 1.88-1.96 (1H, m), 3.85 (3H, s), 6.09 (1H, dd, J=3.9, 2.7 Hz), 6.91-6.95 (1H, m), 7.01-7.07 (3H, m), 7.35-7.41 (1H, m), 7.58-7.62 (1H, m), 7.66-7.68 (1H, m), 7.98 (1H, s), 8.05 (1H, d, J=9.6 Hz), 9.87 (1H, s), 11.09 (1H, s).

Example 214

Production of N-[5-({2-[(cyclopropylcarbonyl)amino]imidazo[1,2-b]pyridazin-6-yl}oxy)-2-methylphenyl]cyclopentanecarboxamide

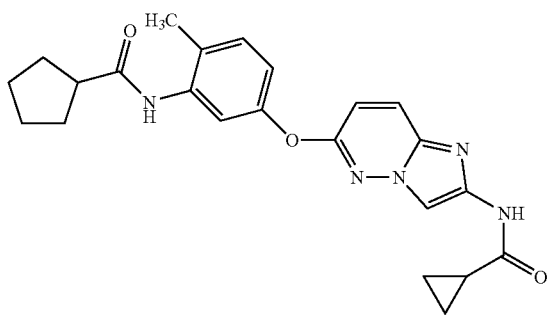

Using N-[6-(3-amino-4-methylphenoxy)imidazo[1,2-b]pyridazin-2-yl]cyclopropanecarboxamide (200 mg, 0.62 mmol), N,N-dimethylacetamide (3.0 mL) and cyclopentanecarbonyl chloride (90 μL, 0.74 mmol), and in the same manner as in Example 120, the title compound (119 mg, 46%) was obtained as a white powder.

¹H-NMR (DMSO-d₆, 300 MHz) δ 0.75-0.83 (4H, m), 1.48-1.96 (9H, m), 2.22 (3H, s), 2.82-2.93 (1H, m), 6.97 (1H, dd, J=8.4, 2.6 Hz), 7.01 (1H, d, J=9.6 Hz), 7.26 (1H, d, J=8.4 Hz), 7.37 (1H, d, J=2.6 Hz), 7.93 (1H, s), 8.01 (1H, d, J=9.6 Hz), 9.24 (1H, s), 11.07 (1H, s).

Example 215

Production of N-[6-(3-{[(ethylamino)carbonyl]amino}-4-methylphenoxy)imidazo[1,2-b]pyridazin-2-yl]cyclopropanecarboxamide

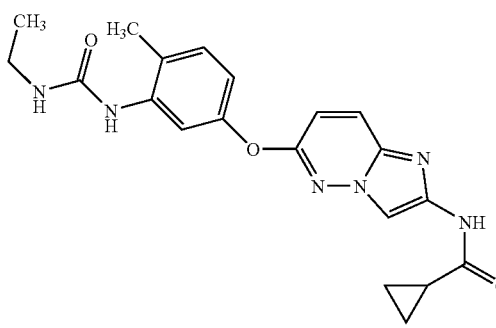

To a solution of N-[6-(3-amino-4-methylphenoxy)imidazo[1,2-b]pyridazin-2-yl]cyclopropanecarboxamide (200 mg, 0.62 mmol) in pyridine (4.0 mL) was added ethyl isocyanate (490 μL, 6.19 mmol), and the mixture was stirred at room temperature for 16 hr. The solvent was evaporated under reduced pressure and water was added to the residue. The mixture was extracted with ethyl acetate/tetrahydrofuran, washed with saturated brine, dried over anhydrous sodium sulfate, and filtrated. The solvent was evaporated under reduced pressure, and the residue was washed with ethyl acetate/ethanol and filtrated to give the title compound (142 mg, 58%) as a white powder.
¹H-NMR (DMSO-d₆, 300 MHz) δ 0.76-0.83 (4H, m), 1.04 (3H, t, J=7.1 Hz), 1.86-1.95 (1H, m), 2.19 (3H, s), 3.02-3.14 (2H, m), 6.64-6.75 (2H, m), 6.98 (1H, d, J=9.6 Hz), 7.16 (1H, d, J=8.1 Hz), 7.71 (1H, s), 7.86 (1H, d, J=2.7 Hz), 7.93 (1H, s), 8.00 (1H, d, J=9.6 Hz), 11.07 (1H, s).

Example 216

Production of N-[6-(3-amino-4-methylphenoxy)imidazo[1,2-b]pyridazin-2-yl]acetamide

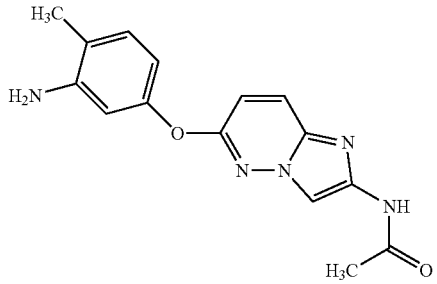

To a solution of 3-amino-4-methylphenol (1.22 g, 9.93 mmol) in N,N-dimethylformamide (25.0 mL) was added potassium tert-butoxide (1.16 g, 10.3 mmol), and the mixture was stirred at room temperature for 2 hr. To the reaction mixture were added N-(6-iodoimidazo[1,2-b]pyridazin-2-yl)acetamide (2.5 g, 8.28 mmol) and potassium carbonate (0.57 g, 4.14 mmol), and the mixture was stirred at 140° C. for 16 hr. Saturated brine was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was purified by silica gel column chromatography (ethyl acetate alone) and the obtained residue was washed with hexane/ethyl acetate, and filtrated to give the title compound (1.04 g, 42%) as a brown powder.
¹H-NMR (DMSO-d₆, 300 MHz) δ 2.05 (3H, s), 2.07 (3H, s), 5.06 (2H, s), 6.28 (1H, d, J=8.1, 2.4 Hz), 6.42 (1H, d, J=2.4 Hz), 6.94 (1H, d, J=9.6 Hz), 6.95 (1H, d, J=8.1 Hz), 7.97 (1H, d, J=8.1 Hz), 7.98 (1H, s), 10.78 (1H, s).

Example 217

Production of N-(6-phenoxyimidazo[1,2-b]pyridazin-2-yl)cyclopropanecarboxamide

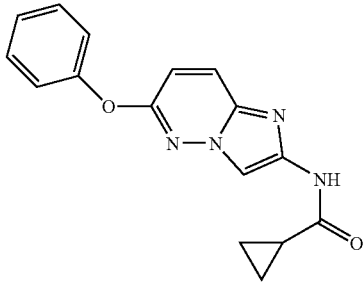

Using phenol (69 mg, 0.73 mmol), N,N-dimethylformamide (25.0 mL), potassium tert-butoxide (1.16 g, 10.3 mmol), N-(6-iodoimidazo[1,2-b]pyridazin-2-yl)cyclopropanecarboxamide (200 mg, 0.61 mmol) and potassium carbonate (42 mg, 0.31 mmol), and in the same manner as in Example 216, the title compound (98 mg, 54%) was obtained as a white powder.
¹H-NMR (DMSO-d₆, 300 MHz) δ 0.76-0.83 (4H, m), 1.86-1.96 (1H, m), 7.03 (1H, d, J=9.6 Hz), 7.23-7.29 (3H, m), 7.42-7.49 (2H, m), 7.92 (1H, s), 8.02 (1H, d, J=9.6 Hz), 11.06 (1H, s).

Example 218

Production of N-[5-({2-[(cyclopropylcarbonyl)amino]imidazo[1,2-b]pyridazin-6-yl}oxy)-2-methylphenyl]-1-methyl-1H-pyrrole-2-carboxamide

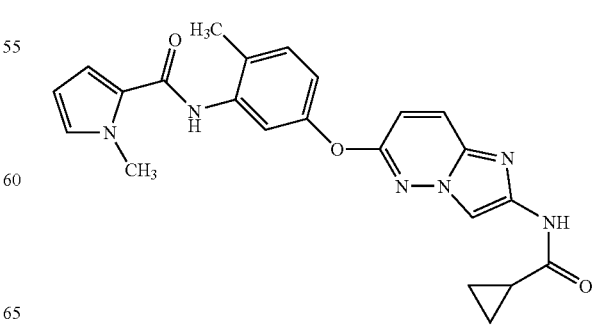

Using 1-methyl-1H-pyrrole-2-carboxylic acid (93 mg, 0.74 mmol), tetrahydrofuran (4.0 mL), N,N-dimethylformamide (30 μL, 0.39 mmol), oxalyl chloride (135 μL, 1.48 mmol), N-[6-(3-amino-4-methylphenoxy)imidazo[1,2-b]pyridazin-2-yl]cyclopropanecarboxamide (200 mg, 0.62 mmol) and N,N-dimethylacetamide (4.0 mL), and in the same manner as in Example 119, the title compound (15 mg, 6%) was obtained as a white powder.

$^1$H-NMR (DMSO-$d_6$, 300 MHz) δ 0.76-0.83 (4H, m), 1.87-1.95 (1H, m), 2.25 (3H, s), 3.84 (3H, s), 6.06-6.09 (1H, m), 6.96-7.03 (3H, m), 7.03 (1H, d, J=9.6 Hz), 7.26-7.32 (2H, m), 7.92 (1H, s), 8.02 (1H, d, J=9.6 Hz), 9.35 (1H, s), 11.07 (1H, s).

Example 219

Production of N-[3-({2-[(cyclopropylcarbonyl)amino]imidazo[1,2-b]pyridazin-6-yl}oxy)phenyl]-1-methyl-L-prolinamide

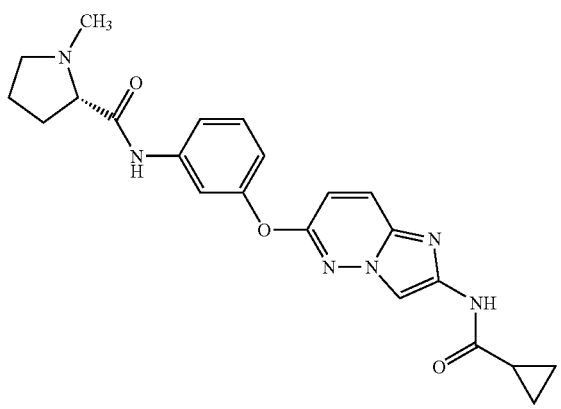

To a solution of N-[6-(3-aminophenoxy)imidazo[1,2-b]pyridazin-2-yl]cyclopropylcarboxamide (200 mg, 0.65 mmol) in N,N-dimethylformamide (4.0 mL) were added 1-methyl-L-proline (167 mg, 1.29 mmol), O-(benzotriazol-1-yl)-N,N,N',N'-tetramethyluronium hexafluorophosphate (736 mg, 1.94 mmol), hydroxybenzotriazole (262 mg, 1.94 mmol) and N,N-diisopropylethylamine (338 μL, 1.94 mmol), and the mixture was stirred at room temperature for 3 hr. Saturated aqueous sodium hydrogencarbonate solution was added to the reaction mixture, and the mixture was extracted with ethyl acetate, washed with saturated brine, dried over anhydrous sodium sulfate, and filtrated. The solvent was evaporated under reduced pressure, and the residue was purified by silica gel column chromatography (ethyl acetate/ethanol=8/1), and the obtained residue was recrystallized from ethyl acetate to give the title compound (86 mg, 32%) as a white powder.

$^1$H-NMR (DMSO-$d_6$, 300 MHz) δ 0.76-0.83 (4H, m), 1.68-1.84 (3H, m), 1.87-1.95 (1H, m), 2.06-2.18 (1H, m), 2.25-2.36 (1H, m), 2.32 (3H, s), 2.85-2.92 (1H, m), 3.05-3.13 (1H, m), 6.91-6.95 (1H, m), 7.03 (1H, d, J=9.8 Hz), 7.32-7.39 (1H, m), 7.54-7.58 (1H, m), 7.65-7.68 (1H, m), 7.95 (1H, s), 8.03 (1H, d, J=9.8 Hz), 9.81 (1H, s), 11.08 (1H, s).

Example 220

Production of N-(5-{[2-(acetylamino)imidazo[1,2-b]pyridazin-6-yl]oxy}-2-methylphenyl)-1-methyl-1H-imidazole-2-carboxamide

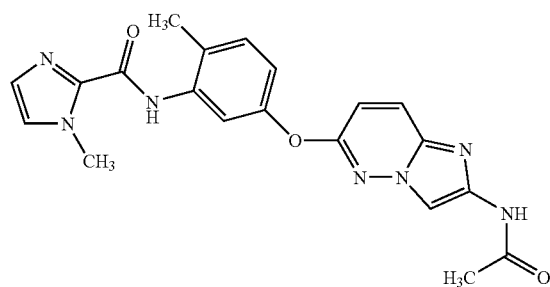

To a solution of N-[6-(3-amino-4-methylphenoxy)imidazo[1,2-b]pyridazin-2-yl]acetamide (150 mg, 0.50 mmol) in N,N-dimethylformamide (3.0 mL) were added 1-methyl-1H-imidazole-2-carboxylic acid (127 mg, 1.01 mmol), 1-ethyl-3-(3-dimethylaminopropyl)carbodiimide hydrochloride (290 mg, 1.51 mmol) and 1-hydroxybenzotriazole (205 mg, 1.51 mmol), and the mixture was stirred at room temperature for 16 hr. Saturated aqueous sodium hydrogencarbonate solution was added to the reaction mixture, and the mixture was extracted with ethyl acetate/tetrahydrofuran, washed with saturated brine, dried over anhydrous sodium sulfate, and filtrated. The solvent was evaporated under reduced pressure, and the obtained residue was recrystallized from ethyl acetate/ethanol to give the title compound (115 mg, 56%) as a white powder.

$^1$H-NMR (DMSO-$d_6$, 300 MHz) δ 2.05 (3H, s), 2.30 (3H, s), 3.97 (3H, s), 6.96-7.09 (3H, m), 7.33 (1H, d, J=8.4 Hz), 7.45 (1H, s), 7.68 (1H, d, J=2.4 Hz), 7.95 (1H, s), 8.02 (1H, d, J=9.9 Hz), 9.77 (1H, s), 10.78 (1H, s).

Example 221

Production of N-[5-({2-[(cyclopropylcarbonyl)amino]imidazo[1,2-b]pyridazin-6-yl}oxy)-2-methylphenyl]-1-methyl-1H-imidazole-2-carboxamide

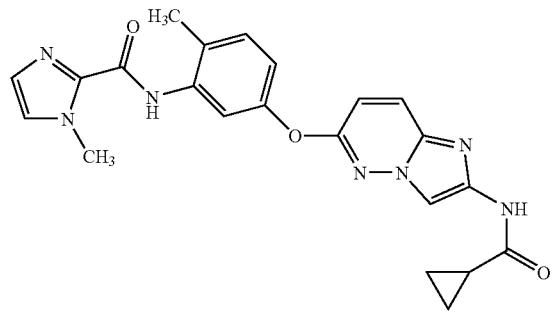

To a solution of N-[6-(3-amino-4-methylphenoxy)imidazo[1,2-b]pyridazin-2-yl]cyclopropanecarboxamide (150 mg, 0.46 mmol) in N,N-dimethylformamide (3.0 mL) were added 1-methyl-1H-imidazole-2-carboxylic acid (117 mg, 0.93 mmol), 1-ethyl-3-(3-dimethylaminopropyl)carbodiimide hydrochloride (267 mg, 1.39 mmol) and 1-hydroxybenzotriazole (188 mg, 1.39 mmol), and the mixture was stirred at room temperature for 16 hr. Saturated aqueous sodium hydrogencarbonate solution was added to the reaction mixture, and the mixture was extracted with ethyl acetate/tetrahydrofuran, washed with saturated brine, dried over anhydrous sodium sulfate, and filtrated. The solvent was evaporated under reduced pressure, and the obtained residue was washed with ethyl acetate/hexane to give the title compound (66 mg, 32%) as a white powder.

$^1$H-NMR (DMSO-$d_6$, 300 MHz) δ 0.76-0.83 (4H, m), 1.85-1.96 (1H, m), 2.30 (3H, s), 3.96 (3H, s), 6.98-7.03 (2H, m), 7.07 (1H, d, J=9.5 Hz), 7.32 (1H, d, J=8.4 Hz), 7.42 (1H, s), 7.68 (1H, d, J=2.7 Hz), 7.93 (1H, s), 8.02 (1H, d, J=9.5 Hz), 9.76 (1H, s), 11.06 (1H, s).

Example 222

Production of N-(6-{4-methyl-3-[(3-methylbut-2-enoyl)amino]phenoxy}imidazo[1,2-b]pyridazin-2-yl)cyclopropanecarboxamide

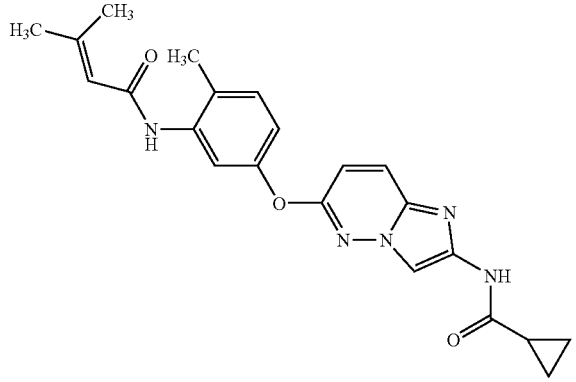

Using N-[6-(3-amino-4-methylphenoxy)imidazo[1,2-b]pyridazin-2-yl]cyclopropanecarboxamide (200 mg, 0.62 mmol), N,N-dimethylacetamide (2.0 mL) and 3,3-dimethylacryloyl chloride (83 µL, 0.74 mmol), and in the same manner as in Example 120, the title compound (142 mg, 57%) was obtained as a white powder.

$^1$H-NMR (DMSO-$d_6$, 300 MHz) δ 0.75-0.84 (4H, m), 1.86 (3H, s), 1.87-1.93 (1H, m), 2.11 (3H, s), 2.22 (3H, s), 5.99 (1H, s), 6.94 (1H, dd, J=8.3, 2.6 Hz), 7.01 (1H, d, J=9.6 Hz), 7.25 (1H, d, J=8.3 Hz), 7.49 (1H, d, J=2.6 Hz), 7.92 (1H, s), 8.02 (1H, d, J=9.6 Hz), 9.14 (1H, s), 11.05 (1H, s).

Example 223

Production of 3-tert-butyl-N-[5-({2[(cyclopropylcarbonyl)amino]imidazo[1,2-b]pyridazin-6-yl}oxy)-2-methylphenyl]-1-methyl-1H-pyrazole-5-carboxamide

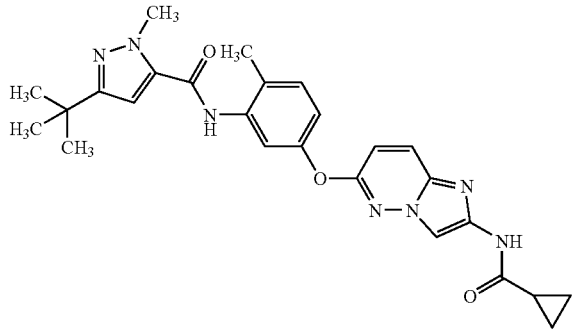

Using 3-tert-butyl-1-methyl-1H-pyrazole-5-carboxylic acid (61 mg, 0.33 mmol), tetrahydrofuran (1.8 mL), N,N-dimethylformamide (30 µL, 0.39 mmol), oxalyl chloride (44 µL, mmol), N-[6-(3-amino-4-methylphenoxy)imidazo[1,2-b]pyridazin-2-yl]cyclopropanecarboxamide (90 mg, 0.28 mmol) and N,N-dimethylacetamide (1.8 mL), and in the same manner as in Example 119, the title compound (55 mg, 41%) was obtained as a white powder.

$^1$H-NMR (DMSO-$d_6$, 300 MHz) δ 0.75-0.83 (4H, m), 1.27 (9H, s), 1.86-1.94 (1H, m), 2.25 (3H, s), 3.99 (3H, s), 6.92 (1H, s), 7.04 (1H, d, J=9.5 Hz), 7.09 (1H, dd, J=8.4, 2.4 Hz), 7.25 (1H, d, J=2.4 Hz), 7.34 (1H, d, J=8.4 Hz), 7.94 (1H, s), (1H, d, J=9.5 Hz), 9.84 (1H, s), 11.07 (1H, s).

Example 224

Production of N-[5-({2-[(cyclopropylcarbonyl)amino]imidazo[1,2-b]pyridazin-6-yl}oxy)-2-methylphenyl]cyclopent-1-ene-1-carboxamide

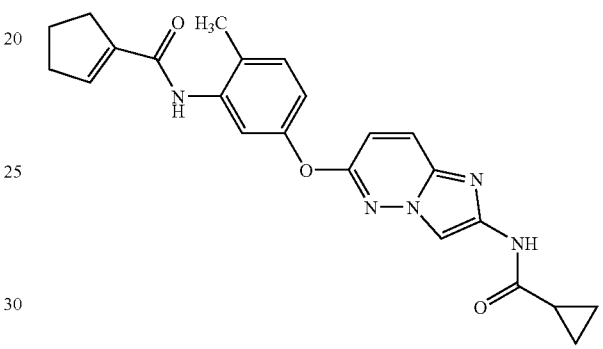

Using N-[6-(3-amino-4-methylphenoxy)imidazo[1,2-b]pyridazin-2-yl]cyclopropanecarboxamide (200 mg, 0.62 mmol), N,N-dimethylacetamide (4.0 mL), 1-cyclopentenecarboxylic acid (139 mg, 1.24 mmol), O-(benzotriazol-1-yl)-N,N,N',N'-tetramethyluronium hexafluorophosphate (704 mg, 1.86 mmol), 1-hydroxybenzotriazole (251 mg, 1.86 mmol) and N,N-diisopropylethylamine (323 µL, 1.86 mmol), and in the same manner as in Example 219, the title compound (69 mg, 21%) was obtained as a white powder.

$^1$H-NMR (DMSO-$d_6$, 300 MHz) δ 0.76-0.83 (4H, m), 1.84-1.95 (3H, m), 2.21 (3H, s), 2.40-2.61 (4H, m), 6.67-6.70 (1H, m), 7.00-7.04 (2H, m), 7.23-7.30 (2H, m), 7.91 (1H, s), 8.01 (1H, d, J=9.3 Hz), 9.18 (1H, s), 11.06 (1H, s).

Example 225

Production of N-[5-({2-[(cyclopropylcarbonyl)amino]imidazo[1,2-b]pyridazin-6-yl}oxy)-2-methylphenyl]-1,2,5-trimethyl-1H-pyrrole-3-carboxamide

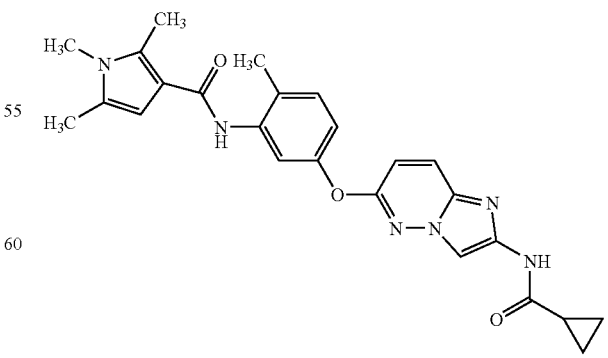

To a solution of 1,2,5-trimethylpyrrole-3-carboxylic acid (142 mg, 0.93 mmol) in tetrahydrofuran (4.0 mL) were added N,N-dimethylformamide (20 µL, 0.26 mmol) and oxalyl chloride (108 μL, 1.24 mmol), and the mixture was stirred at room temperature for 30 min. The reaction mixture was added to a solution of N-[6-(3-amino-4-methylphenoxy)imidazo[1,2-b]pyridazin-2-yl]cyclopropanecarboxamide (200 mg, 0.62 mmol) and triethylamine (259 μL, 1.86 mmol) in N,N-dimethylacetamide (4.0 mL), and the mixture was stirred at 50° C. for 16 hr. Water was added to the reaction mixture, and the mixture was extracted with ethyl acetate, washed with saturated brine, dried over anhydrous sodium sulfate, and filtrated. The solvent was evaporated under reduced pressure, and the residue was purified by silica gel column chromatography (hexane/ethyl acetate=1/3→ethyl acetate alone), washed with hexane/ethyl acetate and filtrated to give the title compound (68 mg, 24%) as a white powder.

¹H-NMR (DMSO-d₆, 300 MHz) δ 0.75-0.83 (4H, m), 1.86-1.94 (1H, m), 2.17 (3H, s), 2.23 (3H, s), 2.44 (3H, s), 3.37 (3H, s), 6.35 (1H, s), 6.96 (1H, dd, J=8.1, 2.4 Hz), 7.01 (1H, d, J=9.6 Hz), 7.26 (1H, d, J=8.1 Hz), 7.36 (1H, d, J=2.4 Hz), 7.92 (1H, s), 8.01 (1H, d, J=9.6 Hz), 8.73 (1H, s), 11.05 (1H, s).

Example 226

Production of N-[6-(3-amino-4-methoxyphenoxy)imidazo[1,2-b]pyridazin-2-yl]cyclopropanecarboxamide

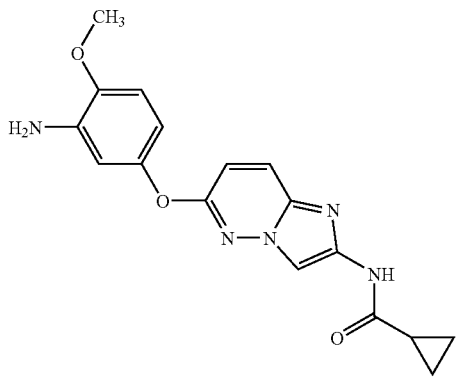

Using 3-amino-4-methoxyphenol (408 mg, 2.93 mmol), N,N-dimethylformamide (16 mL), potassium tert-butoxide (343 mg, 3.05 mmol), N-(6-iodoimidazo[1,2-b]pyridazin-2-yl)acetamide (800 mg, 2.44 mmol) and potassium carbonate (169 mg, 1.22 mmol), and in the same manner as in Example 216, the title compound (1.04 g, 42%) was obtained as a brown powder.

¹H-NMR (DMSO-d₆, 300 MHz) δ 0.76-0.83 (4H, m), 1.86-1.94 (1H, m), 3.77 (3H, s), 4.95 (2H, s), 6.33 (1H, dd, J=8.7, 2.9 Hz), 6.46 (1H, d, J=2.9 Hz), 6.79 (1H, d, J=8.7 Hz), 6.91 (1H, d, J=9.6 Hz), 7.93 (1H, s), 7.96 (1H, d, J=9.6 Hz), 11.04 (1H, s).

Example 227

Production of N-[5-({2-[(cyclopropylcarbonyl)amino]imidazo[1,2-b]pyridazin-6-yl}oxy)-2-methoxyphenyl]-1,3-dimethyl-1H-pyrazole-5-carboxamide

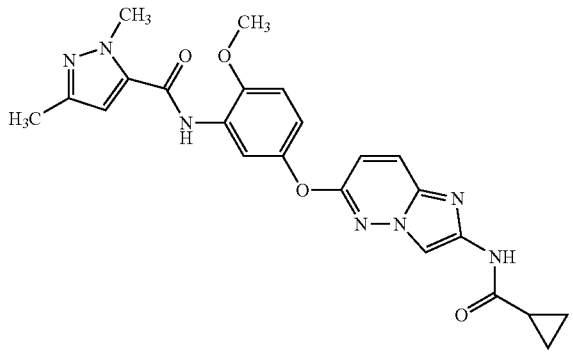

Using N-[6-(3-amino-4-methoxyphenoxy)imidazo[1,2-b]pyridazin-2-yl]cyclopropanecarboxamide (200 mg, 0.59 mmol), N,N-dimethylacetamide (4.0 mL) and 1,3-dimethyl-1H-pyrazole-5-carbonyl chloride (113 mg, 0.71 mmol), and in the same manner as in Example 120, the title compound (146 mg, 54%) was obtained as a white powder.

¹H-NMR (DMSO-d₆, 300 MHz) δ 0.76-0.83 (4H, m), 1.87-1.96 (1H, m), 2.19 (3H, s), 3.88 (3H, s), 3.97 (3H, s), 6.82 (1H, s), 7.03 (1H, d, J=9.6 Hz), 7.07-7.19 (2H, m), 7.70 (1H, d, J=3.0 Hz), 7.92 (1H, s), 8.02 (1H, d, J=9.6 Hz), 9.35 (1H, s), 11.06 (1H, s).

Example 228

Production of N-[5-({2-[(cyclopropylcarbonyl)amino]imidazo[1,2-b]pyridazin-6-yl}oxy)-2-fluorophenyl]-1-methyl-1H-imidazole-2-carboxamide

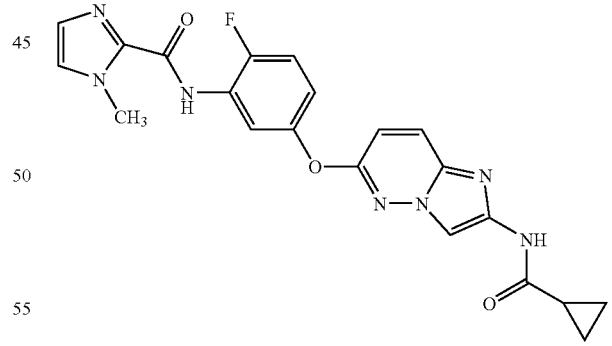

To a solution of N-[6-(3-amino-4-fluorophenoxy)imidazo[1,2-b]pyridazin-2-yl]cyclopropanecarboxamide (200 mg, 0.61 mmol) in N,N-dimethylformamide (4.0 mL) were added 1-methyl-1H-imidazole-2-carboxylic acid (154 mg, 1.22 mmol), 1-ethyl-3-(3-dimethylaminopropyl)carbodiimide hydrochloride (351 mg, 1.83 mmol) and 1-hydroxybenzotriazole (248 mg, 1.83 mmol), and the mixture was stirred at room temperature for 16 hr. Saturated aqueous sodium hydrogencarbonate solution was added to the reaction mixture, and the mixture was extracted with ethyl acetate/tetrahydrofuran, washed with saturated brine, dried over anhydrous sodium sulfate, and filtrated. The solvent was evaporated under reduced pressure, and the obtained residue was purified by silica gel column chromatography (ethyl acetate alone) to give the title compound (31 mg, 12%) as a white powder.

$^1$H-NMR (DMSO-d$_6$, 300 MHz) δ 0.76-0.83 (4H, m), 1.86-1.96 (1H, m), 3.97 (3H, s), 7.03-7.17 (3H, m), 7.37-7.48 (2H, m), 7.88 (1H, dd, J=6.5, 2.9 Hz), 7.94 (1H, s), 8.04 (1H, d, J=9.9 Hz), 9.91 (1H, s), 11.07 (1H, s).

Example 229
Production of N-[5-({2-[(cyclopropylcarbonyl) amino]imidazo[1,2-b]pyridazin-6-yl}oxy)-2-fluorophenyl]-1,5-dimethyl-1H-pyrazole-3-carboxamide

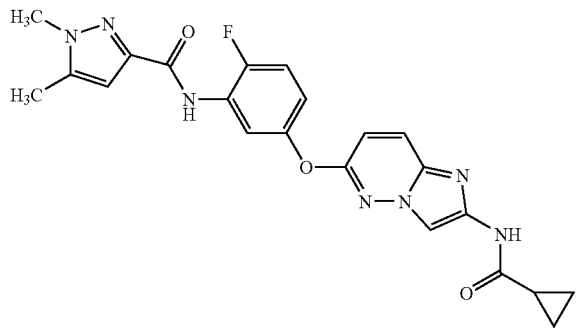

To a solution of N-[6-(3-amino-4-fluorophenoxy)imidazo[1,2-b]pyridazin-2-yl]cyclopropanecarboxamide (200 mg, 0.61 mmol) in N,N-dimethylformamide (4.0 mL) were added 1,5-dimethyl-1H-pyrazole-3-carboxylic acid (171 mg, 1.22 mmol), 1-ethyl-3-(3-dimethylaminopropyl)carbodiimide hydrochloride (351 mg, 1.83 mmol), 1-hydroxybenzotriazole (248 mg, 1.83 mmol) and triethylamine (256 μL, 1.83 mmol), and the mixture was stirred at 60° C. for 36 hr. Water was added to the reaction mixture, and the mixture was extracted with ethyl acetate/tetrahydrofuran, washed with saturated brine, dried over anhydrous sodium sulfate, and filtrated. The solvent was evaporated under reduced pressure, and the obtained residue was purified by silica gel column chromatography (ethyl acetate/hexane=3/1→ethyl acetate alone) to give the title compound (72 mg, 26%) as a white powder.

$^1$H-NMR (DMSO-d$_6$, 300 MHz) δ 0.76-0.82 (4H, m), 1.87-1.96 (1H, m), 2.30 (3H, s), 3.84 (3H, s), 6.57 (1H, s), 7.07 (1H, d, J=9.6 Hz), 7.07-7.14 (1H, m), 7.35-7.43 (1H, m), 7.89 (1H, dd, J=6.3, 3.0 Hz), 7.95 (1H, s), 8.04 (1H, d, J=9.6 Hz), 9.46 (1H, s), 11.08 (1H, s).

Example 230
Production of N-{6-[3-({[(1,3-dimethyl-1H-pyrazol-5-yl)amino]carbonyl}amino)-4-methylphenoxy]imidazo[1,2-b]pyridazin-2-yl}cyclopropanecarboxamide

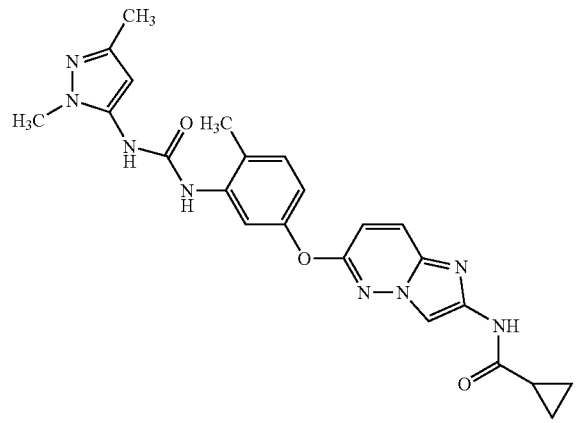

To a solution of 1,3-dimethyl-1H-pyrazol-5-amine (104 mg, 0.93 mmol) in N,N-dimethylformamide (4.0 mL) was added N,N-carbonyldiimidazole (150 mg, 0.93 mmol), and the mixture was stirred at room temperature for 30 min. To the reaction mixture was added N-[6-(3-amino-4-methylphenoxy)imidazo[1,2-b]pyridazin-2-yl]cyclopropanecarboxamide (200 mg, 0.62 mmol), and the mixture was stirred at room temperature for 16 hr. Water was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was purified by silica gel column chromatography (ethanol/ethyl acetate=1/20→1/10) to give the title compound (58 mg, 20%) as a white powder.

$^1$H-NMR (DMSO-d$_6$, 300 MHz) δ 0.76-0.82 (4H, m), 1.87-1.95 (1H, m), 2.05 (3H, s), 2.27 (3H, s), 3.59 (3H, s), 5.94 (1H, s), 6.83 (1H, dd, J=8.0, 2.6 Hz), 7.00 (1H, d, J=9.5 Hz), 7.24 (1H, d, J=8.4 Hz), 7.80 (1H, d, J=2.6 Hz), 7.92 (1H, s), 8.00 (1H, d, J=9.5 Hz), 8.25 (1H, s), 8.99 (1H, s), 11.05 (1H, s).

Example 231

Production of N-[6-(3-{[(2,4-dimethyl-1,3-thiazol-5-yl)sulfonyl]amino}-4-methylphenoxy)imidazo[1,2-b]pyridazin-2-yl]cyclopropanecarboxamide

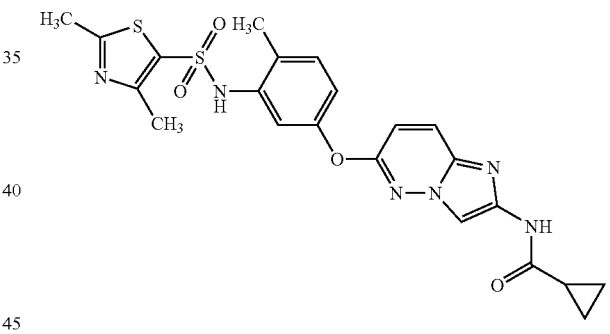

To a solution of N-[6-(3-amino-4-methylphenoxy)imidazo[1,2-b]pyridazin-2-yl]cyclopropanecarboxamide (200 mg, 0.62 mmol) in pyridine (4.0 mL) was added 2,4-dimethyl-1,3-thiazole-5-sulfonyl chloride (157 mg, 0.74 mmol), and the mixture was stirred at room temperature for 16 hr. Water was added to the reaction mixture, and the mixture was extracted with ethyl acetate, washed with saturated brine, dried over anhydrous sodium sulfate, and filtrated. The solvent was evaporated under reduced pressure, and the residue was purified by silica gel column chromatography (ethyl acetate/hexane=3/1→ethyl acetate alone) and washed with hexane/ethyl acetate to give the title compound (196 mg, 64%) as a white powder.

$^1$H-NMR (DMSO-d$_6$, 300 MHz) δ 0.76-0.86 (4H, m), 1.88-1.95 (1H, m), 2.07 (3H, s), 2.20 (3H, s), 2.55 (3H, s), 6.92 (1H, d, J=2.7 Hz), 7.01 (1H, d, J=9.8 Hz), 7.07-7.12 (1H, dd, J=8.4, 2.7 Hz), 7.27 (1H, d, J=8.4 Hz), 7.93 (1H, s), 8.02 (1H, d, J=9.8 Hz), 10.10 (1H, s), 11.08 (1H, s).

Example 232

Production of N-[6-(3-amino-4-fluorophenoxy)imidazo[1,2-b]pyridazin-2-yl]acetamide

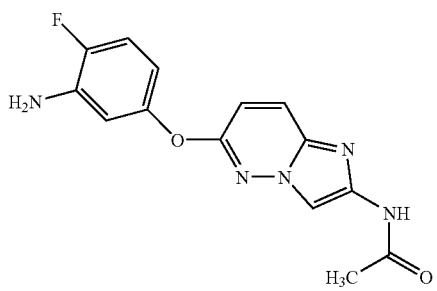

To a solution of N-(6-iodoimidazo[1,2-b]pyridazin-2-yl)acetamide (12 g, 39.7 mmol) in N,N-dimethylformamide (120 mL) were added 3-amino-4-fluorophenol (7.6 g, 59.6 mmol) and potassium carbonate (11.0 g, 79.5 mmol), and the mixture was stirred at 140° C. for 12 hr. After cooling the mixture to room temperature, water was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was purified by silica gel column chromatography (ethyl acetate/hexane=3/1→ethyl acetate alone) to give the title compound (9.5 g, 79%) as a brown powder.

$^1$H-NMR (DMSO-d$_6$, 300 MHz) δ 2.07 (3H, s), 5.36 (2H, s), 6.30-6.37 (1H, m), 6.58 (1H, dd, J=7.8, 2.7 Hz), 6.97 (1H, d, J=9.6 Hz), 6.98-7.06 (1H, m), 7.99 (1H, d, J=9.6 Hz), 8.00 (1H, s), 10.78 (1H, s).

Example 233

Production of N-(5-{[2-(acetylamino)imidazo[1,2-b]pyridazin-6-yl]oxy}-2-fluorophenyl)-1,3-dimethyl-1H-pyrazole-5-carboxamide

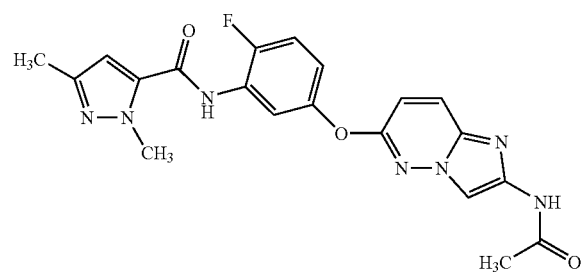

To a solution of N-[6-(3-amino-4-fluorophenoxy)imidazo[1,2-b]pyridazin-2-yl]acetamide (5.6 g, 18.6 mmol) in N,N-dimethylacetamide (44.8 mL) was added 1,3-dimethyl-1H-pyrazole-5-carbonyl chloride (3.25 g, 20.4 mmol). After stirring at room temperature for 2 hr, water was added to the reaction mixture, and the mixture was extracted with ethyl acetate/tetrahydrofuran, washed with saturated brine, dried over anhydrous magnesium sulfate, and filtrated. The solvent was evaporated under reduced pressure, and the residue was washed with ethyl acetate/ethanol to give the title compound (6.1 g, 78%) as a white powder.

$^1$H-NMR (DMSO-d$_6$, 300 MHz) δ 2.06 (3H, s), 2.19 (3H, s), 3.97 (3H, s), 6.85 (1H, s), 7.07 (1H, d, J=9.6 Hz), 7.17-7.25 (1H, m), 7.34-7.44 (1H, m), 7.50-7.58 (1H, m), 7.96 (1H, s), 8.04 (1H, d), 10.10 (1H, s), 10.79 (1H, s).

Example 234

Production of N-[6-(5-amino-2-chloro-4-fluorophenoxy)imidazo[1,2-b]pyridazin-2-yl]cyclopropanecarboxamide

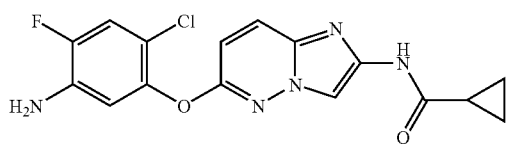

To a solution of N-(6-iodoimidazo[1,2-b]pyridazin-2-yl)cyclopropanecarboxamide (600 mg, 1.83 mmol) in N,N-dimethylformamide (12 mL) were added 3-amino-6-chloro-4-fluorophenol (443 mg, 2.74 mmol) and potassium carbonate (505 mg, 3.66 mmol). In the same manner as in Example 232, the title compound (372 mg, 56%) was obtained as a brown powder.

$^1$H-NMR (DMSO-d$_6$, 300 MHz) δ 0.76-0.83 (4H, m), 1.87-1.95 (1H, m), 5.56 (2H, s), 6.74 (1H, d, J=8.4 Hz), 7.07 (1H, d, J=9.5 Hz), 7.34 (1H, d, J=10.5 Hz), 7.94 (1H, s), 8.04 (1H, d, J=9.5 Hz), 11.07 (1H, s).

Example 235

Production of N-[4-chloro-5-({2-[(cyclopropylcarbonyl)amino]imidazo[1,2-b]pyridazin-6-yl}oxy)-2-fluorophenyl]-1,3-dimethyl-1H-pyrazole-5-carboxamide

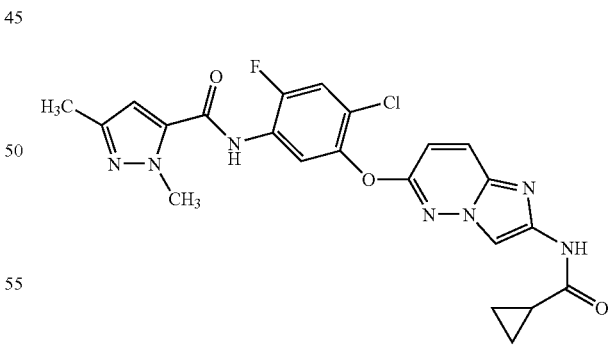

Using N-[6-(5-amino-2-chloro-4-fluorophenoxy)imidazo[1,2-b]pyridazin-2-yl]cyclopropanecarboxamide (200 mg, 0.55 mmol), N,N-dimethylacetamide (4.0 mL) and 1,3-dimethyl-1H-pyrazole-5-carbonyl chloride (105 mg, 0.66 mmol), and in the same manner as in Example 120, the title compound (108 mg, 40%) was obtained as a white powder.

$^1$H-NMR (DMSO-d$_6$, 300 MHz) δ 0.78-0.84 (4H, m), 1.85-1.96 (1H, m), 2.19 (3H, s), 3.97 (3H, s), 6.84 (1H, s), 7.16 (1H, d, J=9.6 Hz), 7.74-7.81 (2H, m), 7.90 (1H, s), 8.08 (1H, d, J=9.6 Hz), 10.19 (1H, s), 11.07 (1H, s).

Example 236

Production of N-{5-[(2-aminoimidazo[1,2-b]pyridazin-6-yl)oxy]-2-fluorophenyl}-1,3-dimethyl-1H-pyrazole-5-carboxamide.hydrochloride

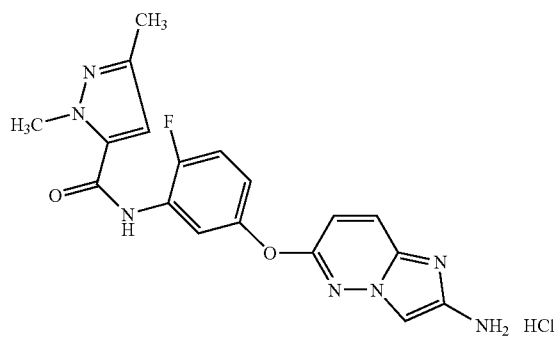

To a suspension of N-[4-chloro-5-({2-[(cyclopropylcarbonyl)amino]imidazo[1,2-b]pyridazin-6-yl}oxy)-2-fluorophenyl]-1,3-dimethyl-1H-pyrazole-5-carboxamide (2.0 g, 4.72 mmol) in methanol (20 mL) was added 4N hydrochloric acid/ethyl acetate (16 mL) solution. After stirring at room temperature for 4 hr, the mixture was stirred at 50° C. for 12 hr. The solvent was evaporated under reduced pressure, and diisopropyl ether/ethanol (8 mL/2 mL) was added to the residue. The mixture was stirred at room temperature for 2 hr. The precipitate was collected by filtration and washed with diisopropyl ether to give the title compound (2.0 g, quant.) as a brown powder.

$^1$H-NMR (DMSO-$d_6$, 300 MHz) δ 2.19 (3H, s), 3.98 (3H, s), 6.91 (1H, s), 7.18-7.26 (1H, m), 7.37 (1H, d, J=9.6 Hz), 7.39-7.48 (2H, m), 7.54-7.60 (1H, m), 8.20 (1H, d, J=9.6 Hz), 10.24 (1H, s).

Example 237

Production of N-(2-fluoro-5-{[2-(propionylamino)imidazo[1,2-b]pyridazin-6-yl]oxy}phenyl)-1,3-dimethyl-1H-pyrazole-5-carboxamide

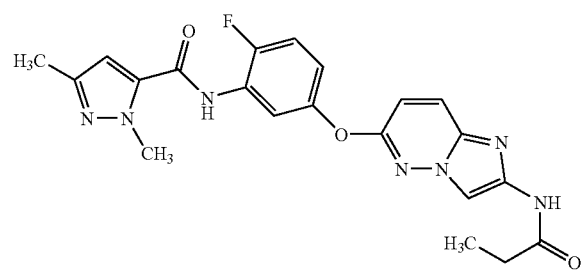

To a solution of N-{5-[(2-aminoimidazo[1,2-b]pyridazin-6-yl)oxy]-2-fluorophenyl}-1,3-dimethyl-1H-pyrazole-5-carboxamide.hydrochloride (200 mg, 0.48 mmol) in N,N-dimethylacetamide (2.0 mL) was added propionyl chloride (49.9 µL, 0.57 mmol), and the mixture was stirred at room temperature for 2 hr. Water was added to the reaction mixture, and the mixture was extracted with ethyl acetate, washed with saturated brine, dried over anhydrous sodium sulfate, and filtrated. The solvent was evaporated under reduced pressure, and the residue was purified by silica gel column chromatography (ethyl acetate/hexane=3/1→ethyl acetate alone) and washed with ethyl acetate to give the title compound (78 mg, 37%) as a white powder.

$^1$H-NMR (DMSO-$d_6$, 300 MHz) δ 1.06 (3H, t, J=7.5 Hz), 2.19 (3H, s), 2.37 (2H, q, J=7.5 Hz), 3.98 (3H, s), 6.85 (1H, s), 7.07 (1H, d, J=9.6 Hz), 7.18-7.24 (1H, m), 7.37-7.44 (1H, m), 7.55 (1H, dd, J=6.3, 3.3 Hz), 7.98 (1H, s), 8.08 (1H, d, J=9.6 Hz), 10.11 (1H, s), 10.74 (1H, s).

Example 238

Production of N-[5-({2-[(cyclopropylcarbonyl)amino]imidazo[1,2-b]pyridazin-6-yl}oxy)-2-fluorophenyl]-1-methyl-1H-pyrazole-3-carboxamide

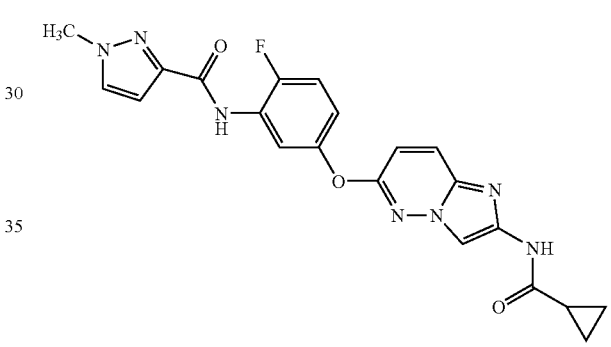

To a solution of 1-methyl-1H-pyrazole-3-carboxylic acid (115 mg, 0.92 mmol) in tetrahydrofuran (4.0 mL) were added N,N-dimethylformamide (20 µL, 0.26 mmol) and oxalyl chloride (80 µL, 0.92 mmol), and the mixture was stirred at room temperature for 30 min. The reaction mixture was added to a solution of N-[6-(3-amino-4-fluorophenoxy)imidazo[1,2-b]pyridazin-2-yl]cyclopropanecarboxamide (200 mg, 0.62 mmol) in N,N-dimethylacetamide (4.0 mL), and the mixture was stirred at room temperature for 2 hr. Saturated aqueous sodium hydrogencarbonate solution was added to the reaction mixture, and the mixture was extracted with ethyl acetate/tetrahydrofuran, washed with saturated brine, dried over anhydrous sodium sulfate, and filtrated. The solvent was evaporated under reduced pressure and ethanol (10 mL) was added to the residue. The mixture was stirred with heating at 75° C. and cooled to room temperature, and the precipitate was collected by filtration to give the title compound (144 mg, 54%) as a white powder.

$^1$H-NMR (DMSO-$d_6$, 300 MHz) δ 0.77-0.83 (4H, m), 1.87-1.97 (1H, m), 3.97 (3H, s), 6.77 (1H, d, J=2.4 Hz), 7.06-7.16 (2H, m), 7.36-7.43 (1H, m), 7.82-7.89 (2H, m), 7.95 (1H, s), 8.05 (1H, d, J=9.6 Hz), 9.59 (1H, s), 11.08 (1H, s).

Example 239

Production of N-{2-fluoro-5-[(2-{[(2,2,3,3-tetramethylcyclopropyl)carbonyl]amino}imidazo[1,2-b]pyridazin-6-yl)oxy]phenyl}-1,3-dimethyl-1H-pyrazole-5-carboxamide

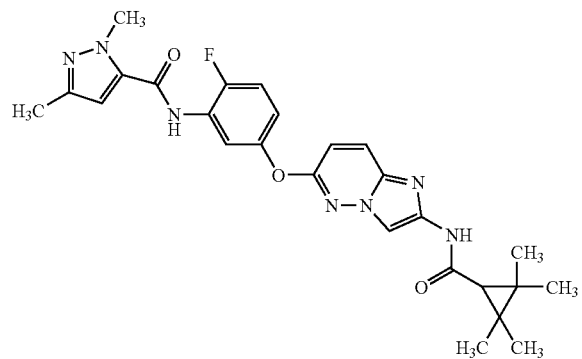

To a solution of 2,2,3,3-tetramethylcyclopropanecarboxylic acid (102 mg, 0.72 mmol) in tetrahydrofuran (4.0 mL) were added N,N-dimethylformamide (20 μL, 0.26 mmol) and oxalyl chloride (63 mL, 0.72 mmol), and the mixture was stirred at room temperature for 30 min. The reaction mixture was added to a solution of N-{5-[(2-aminoimidazo[1,2-b]pyridazin-6-yl)oxy]-2-fluorophenyl}-1,3-dimethyl-1H-pyrazole-5-carboxamide.hydrochloride (200 mg, 0.48 mmol) in N,N-dimethylacetamide (4.0 mL), and the mixture was stirred at room temperature for 3 hr. Saturated aqueous sodium hydrogencarbonate solution was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was purified by silica gel column chromatography (ethyl acetate/hexane=3/1) and precipitated from hexane/ethyl acetate to give the title compound (46 mg, 19%) as a white powder.

$^1$H-NMR (DMSO-$d_6$, 300 MHz) δ 1.16 (6H, s), 1.22 (6H, s), 1.47 (1H, s), 2.19 (3H, s), 3.97 (3H, s), 6.83 (1H, s), 7.04 (1H, d, J=9.5 Hz), 7.17-7.22 (1H, m), 7.34-7.42 (1H, m), 7.51-7.55 (1H, m), 7.95 (1H, s), 8.01 (1H, d, J=9.5 Hz), 10.09 (1H, s), 11.70 (1H, s).

Example 240

Production of N-[5-({2-[(cyclopropylsulfonyl)amino]imidazo[1,2-b]pyridazin-6-yl}oxy)-2-fluorophenyl]-1,3-dimethyl-1H-pyrazole-5-carboxamide

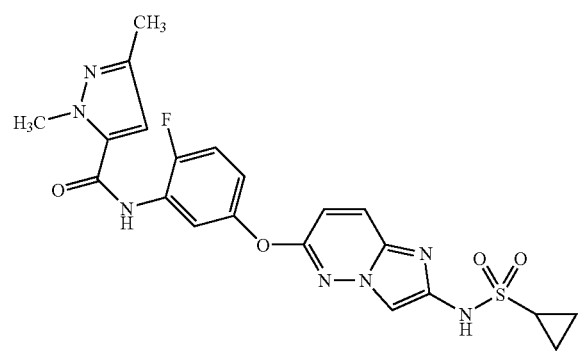

To a solution of N-{5-[(2-aminoimidazo[1,2-b]pyridazin-6-yl)oxy]-2-fluorophenyl}-1,3-dimethyl-1H-pyrazole-5-carboxamide.hydrochloride (400 mg, 0.97 mmol) in 1-methyl-2-pyrrolidone (4.0 mL) were added triethylamine (404 μL, 2.90 mmol) and cyclopropanesulfonyl chloride (204 mg, 1.45 mmol), and the mixture was stirred at 70° C. for 16 hr. After cooling the mixture to room temperature, water was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was purified by silica gel column chromatography (ethyl acetate alone) and precipitated from hexane/ethyl acetate to give the title compound (74 mg, 16%) as a white powder.

$^1$H-NMR (DMSO-$d_6$, 300 MHz) δ 0.92-1.03 (4H, m), 2.19 (3H, s), 2.75-2.86 (1H, m), 3.97 (3H, s), 6.84 (1H, s), 7.10 (1H, d, J=9.6 Hz), 7.18-7.25 (1H, m), 7.36-7.43 (1H, m), 7.52-7.56 (1H, m), 7.63 (1H, s), 8.06 (1H, d, J=9.6 Hz), 10.09 (1H, s), 10.30 (1H, s).

Example 241

Production of N-{6-[3-(but-2-ynoylamino)-4-methylphenoxy]imidazo[1,2-b]pyridazin-2-yl}cyclopropanecarboxamide

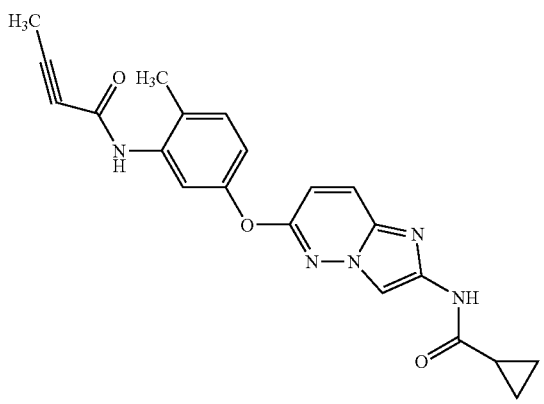

Using 2-butynoic acid (78 mg, 0.93 mmol), tetrahydrofuran (4.0 mL), N,N-dimethylformamide (20 μL, 0.26 mmol), oxalyl chloride (81 μL, 0.93 mmol), N-[6-(3-amino-4-fluorophenoxy)imidazo[1,2-b]pyridazin-2-yl]cyclopropanecarboxamide (200 mg, 0.62 mmol) and N,N-dimethylacetamide (4.0 mL), and in the same manner as in Example 238, the title compound (47 mg, 20%) was obtained as a white powder.

$^1$H-NMR (DMSO-$d_6$, 300 MHz) δ 0.76-0.86 (4H, m), 1.85-1.95 (1H, m), 2.03 (3H, s), 2.21 (3H, s), 6.96-7.04 (2H, m), 7.25-7.29 (2H, m), 7.92 (1H, s), 8.10 (1H, d, J=9.3 Hz), 10.05 (1H, s), 11.05 (1H, s).

Example 242

Production of N-[5-({2-[(cyclopropylcarbonyl)amino]imidazo[1,2-b]pyridazin-6-yl}oxy)-2-fluorophenyl]-1-ethyl-1H-pyrazole-3-carboxamide

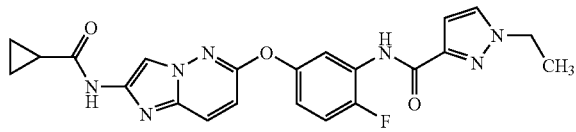

Using 1-ethyl-1H-pyrazole-3-carboxylic acid (128 mg, 0.92 mmol), tetrahydrofuran (2.0 mL), N,N-dimethylformamide (20 μL, 0.26 mmol), oxalyl chloride (80 μL, 0.92 mmol), N-[6-(3-amino-4-fluorophenoxy)imidazo[1,2-b]pyridazin-2-yl]cyclopropanecarboxamide (200 mg, 0.61 mmol) and N,N-dimethylacetamide (4.0 mL), and in the same manner as in Example 238, the title compound (111 mg, 40%) was obtained as a white powder.

$^1$H-NMR (DMSO-$d_6$, 300 MHz) δ 0.76-0.85 (4H, m), 1.44 (3H, t, J=7.2 Hz), 1.87-1.97 (1H, m), 4.26 (2H, q, J=7.2 Hz), 6.77 (1H, d, J=2.1 Hz), 7.07 (1H, d, J=9.6 Hz), 7.09-7.16 (1H, m), 7.39 (1H, dd, J=11.4, 8.7 Hz), 7.84 (1H, dd, J=6.5, 2.9 Hz), 7.91-7.96 (2H, m), 8.04 (1H, d, J=9.6 Hz), 9.57 (1H, s), 11.07 (1H, s).

Example 243

Production of N-{2-fluoro-5-[(2-{[(2-methylcyclopropyl)carbonyl]amino}imidazo[1,2-b]pyridazin-6-yl)oxy]phenyl}-1,3-dimethyl-1H-pyrazole-5-carboxamide

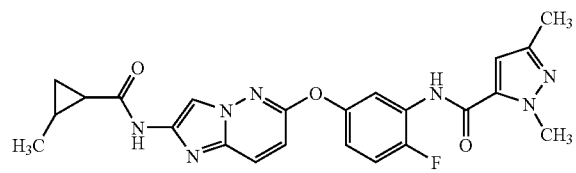

Using 2-methylcyclopropanecarboxylic acid (72 mg, 0.72 mmol), tetrahydrofuran (2.0 mL), N,N-dimethylformamide (20 μL, 0.26 mmol), oxalyl chloride (63 μL, 0.72 mmol), N-{5-[(2-aminoimidazo[1,2-b]pyridazin-6-yl)oxy]-2-fluorophenyl}-1,3-dimethyl-1H-pyrazole-5-carboxamide.hydrochloride (200 mg, 0.48 mmol) and N,N-dimethylacetamide (4.0 mL), and in the same manner as in Example 239, the title compound (55 mg, 25%) was obtained as a white powder.

$^1$H-NMR (DMSO-$d_6$, 300 MHz) δ 0.61-0.72 (1H, m), 0.95-1.05 (1H, m), 1.06-1.09 (3H, m), 1.18-1.27 (1H, m), 1.64-1.73 (1H, m), 2.19 (3H, s), 3.98 (3H, s), 6.84 (1H, s), 7.07 (1H, d, J=9.6 Hz), 7.09-7.24 (1H, m), 7.36-7.43 (1H, m), 7.52-7.56 (1H, m), 7.93 (1H, s), 8.04 (1H, d, J=9.6 Hz), 10.10 (1H, s), 10.99 (1H, s).

Example 244

Production of N-{5-[(2-{[(2,2-dimethylcyclopropyl)carbonyl]amino}imidazo[1,2-b]pyridazin-6-yl)oxy]-2-fluorophenyl}-1,3-dimethyl-1H-pyrazole-5-carboxamide

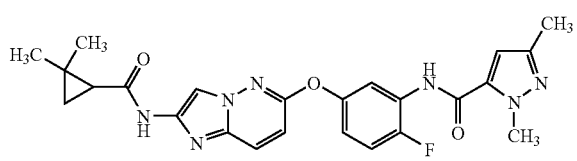

Using 2,2-dimethylcyclopropanecarboxylic acid (82 mg, 0.72 mmol), tetrahydrofuran (3.0 mL), N,N-dimethylformamide (20 μL, 0.26 mmol), oxalyl chloride (63 μL, 0.72 mmol), N-{5-[(2-aminoimidazo[1,2-b]pyridazin-6-yl)oxy]-2-fluorophenyl}-1,3-dimethyl-1H-pyrazole-5-carboxamide.hydrochloride (200 mg, 0.48 mmol) and N,N-dimethylacetamide (4.0 mL), and in the same manner as in Example 239, the title compound (37 mg, 16%) was obtained as a white powder.

$^1$H-NMR (DMSO-$d_6$, 300 MHz) δ 0.76-1.27 (2H, m), 1.12 (3H, s), 1.14 (3H, s), 1.75-1.84 (1H, m), 2.19 (3H, s), 3.97 (3H, s), 6.83 (1H, s), 7.05 (1H, d, J=8.7 Hz), 7.16-7.24 (1H, m), 7.35-7.42 (1H, m), 7.50-7.55 (1H, m), 7.95 (1H, s), 8.03 (1H, d, J=8.7 Hz), 10.09 (1H, s), 10.90 (1H, s).

Example 245

Production of N-(5-{[2-(acetylamino)imidazo[1,2-b]pyridazin-6-yl]oxy}-2-fluorophenyl)-3-ethyl-1-methyl-1H-pyrazole-5-carboxamide

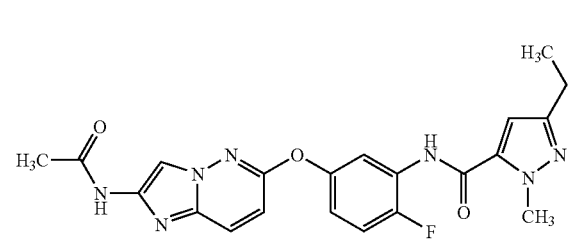

Using 3-ethyl-1-methyl-1H-pyrazole-5-carboxylic acid (215 mg, 1.39 mmol), tetrahydrofuran (4.5 mL), N,N-dimethylformamide (30 μL, 0.39 mmol), oxalyl chloride (122 μL, 1.39 mmol), N-[6-(3-amino-4-fluorophenoxy)imidazo[1,2-b]pyridazin-2-yl]acetamide (300 mg, 1.00 mmol) and N,N-dimethylacetamide (6.0 mL), and in the same manner as in Example 238, the title compound (219 mg, 50%) was obtained as a white powder.

$^1$H-NMR (DMSO-$d_6$, 300 MHz) δ 1.19 (3H, t, J=7.5 Hz), 2.06 (3H, s), 2.55 (2H, q, J=7.5 Hz), 3.99 (3H, s), 6.89 (1H, s), 7.07 (1H, d, J=9.6 Hz), 7.18-7.25 (1H, m), 7.36-7.43 (1H, m), 7.52-7.56 (1H, m), 7.95 (1H, s), 8.03 (1H, d, J=9.6 Hz), 10.10 (1H, s), 10.78 (1H, s).

Example 246

Production of N-[2-chloro-5-({2-[(cyclopropylcarbonyl)amino]imidazo[1,2-b]pyridazin-6-yl}oxy)phenyl]-3-methoxy-1-methyl-1H-pyrazole-5-carboxamide

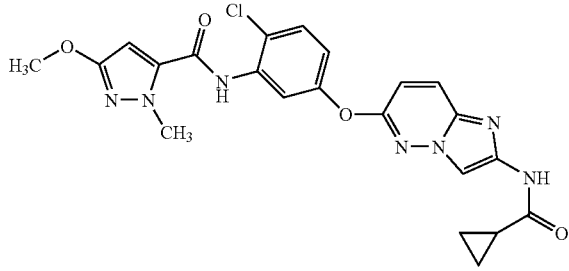

Using 3-methoxy-1-methyl-1H-pyrazole-5-carboxylic acid (191 mg, 1.22 mmol), tetrahydrofuran (4.5 mL), N,N-dimethylformamide (30 µL, 0.39 mmol), oxalyl chloride (107 µL, 1.22 mmol), N-[6-(3-amino-4-chlorophenoxy)imidazo[1,2-b]pyridazin-2-yl]cyclopropanecarboxamide (300 mg, 0.87 mmol) and N,N-dimethylacetamide (6.0 mL), and in the same manner as in Example 238, the title compound (259 mg, 62%) was obtained as a white powder.

$^1$H-NMR (DMSO-$d_6$, 300 MHz) δ 0.76-0.87 (4H, m), 1.86-1.99 (1H, m), 3.79 (3H, s), 3.91 (3H, s), 6.47 (1H, s), 7.09 (1H, d, J=9.9 Hz), 7.23-7.28 (1H, m), 7.49-7.53 (1H, m), 7.62 (1H, d, J=8.7 Hz), 7.94 (1H, s), 8.05 (1H, d, J=9.9 Hz), 10.05 (1H, s), 11.07 (1H, s).

Example 247

Production of N-[2-chloro-5-({2-[(cyclopropylcarbonyl)amino]imidazo[1,2-b]pyridazin-6-yl}oxy)phenyl]-3-ethyl-1-methyl-1H-pyrazole-5-carboxamide

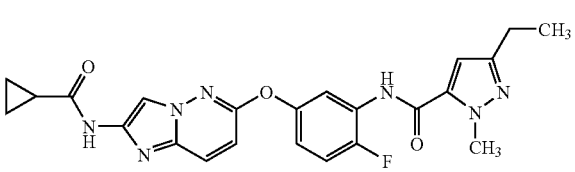

Using 3-ethyl-1-methyl-1H-pyrazole-5-carboxylic acid (188 mg, 1.22 mmol), tetrahydrofuran (4.5 mL), N,N-dimethylformamide (30 µL, 0.39 mmol), oxalyl chloride (107 µL, 1.22 mmol), N-[6-(3-amino-4-chlorophenoxy)imidazo[1,2-b]pyridazin-2-yl]cyclopropanecarboxamide (300 mg, 0.87 mmol) and N,N-dimethylacetamide (6.0 mL), and in the same manner as in Example 238, the title compound (268 mg, 64%) was obtained as a white powder.

$^1$H-NMR (DMSO-$d_6$, 300 MHz) δ 0.76-0.86 (4H, m), 1.19 (3H, t, J=7.7 Hz), 1.84-1.97 (1H, m), 2.55 (2H, q, J=7.7 Hz), 3.99 (3H, s), 6.88 (1H, s), 7.09 (1H, d, J=9.6 Hz), 7.25 (1H, dd, J=8.7, 2.9 Hz), 7.53 (1H, d, J=2.9 Hz), 7.62 (1H, d, J=8.7 Hz), 7.95 (1H, s), 8.05 (1H, d, J=9.6 Hz), 10.00 (1H, s), 11.07 (1H, s).

Example 248

Production of N-[5-({2-[(cyclopropylcarbonyl)amino]imidazo[1,2-b]pyridazin-6-yl}oxy)-2-fluorophenyl]-2,5-dimethyl-1,3-oxazole-4-carboxamide

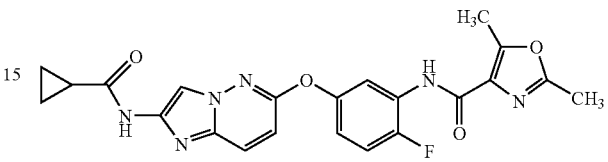

To a solution of N-[6-(3-amino-4-fluorophenoxy)imidazo[1,2-b]pyridazin-2-yl]cyclopropanecarboxamide (200 mg, 0.61 mmol) in N,N-dimethylacetamide (4.0 mL) was added 2,5-dimethyl-1,3-oxazole-4-carbonyl chloride (127 mg, 0.79 mmol), and the mixture was stirred at room temperature for 2 hr. Water was added to the reaction mixture, and the mixture was extracted with ethyl acetate, washed with saturated brine, dried over anhydrous sodium sulfate, and filtrated. The solvent was evaporated under reduced pressure, and the residue was washed with ethanol to give the title compound (198 mg, 72%) as a white powder.

$^1$H-NMR (DMSO-$d_6$, 300 MHz) δ 0.77-0.83 (4H, m), 1.86-1.97 (1H, m), 2.45 (3H, s), 2.55 (3H, s), 7.06 (1H, d, J=9.6 Hz), 7.08-7.15 (1H, m), 7.35-7.42 (1H, m), 7.87 (1H, dd, J=6.5, 2.9 Hz), 7.93 (1H, s), 8.03 (1H, d, J=9.6 Hz), 9.48 (1H, s), 11.06 (1H, s).

Example 249

Production of 3-ethyl-N-{2-fluoro-5-[(2-{[(2-methylcyclopropyl)carbonyl]amino}imidazo[1,2-b]pyridazin-6-yl)oxy]phenyl}-1-methyl-1H-pyrazole-5-carboxamide

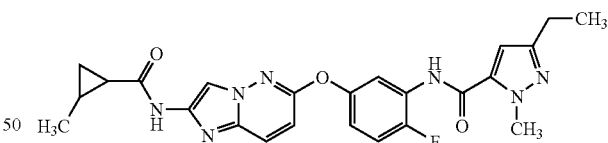

To a solution of 3-ethyl-1-methyl-1H-pyrazole-5-carboxylic acid (158 mg, 1.03 mmol) in tetrahydrofuran (3.8 mL) were added N,N-dimethylformamide (20 µL, 0.26 mmol) and oxalyl chloride (90 µL, 1.03 mmol), and the mixture was stirred at room temperature for 30 min. The reaction mixture was added to a solution of N-[6-(3-amino-4-fluorophenoxy)imidazo[1,2-b]pyridazin-2-yl]-2-methylcyclopropanecarboxamide (250 mg, 0.73 mmol) in N,N-dimethylacetamide (5.0 mL), and the mixture was stirred at room temperature for 2 hr. Saturated aqueous sodium hydrogencarbonate solution was added to the reaction mixture, and the mixture was extracted with ethyl acetate/tetrahydrofuran, washed with saturated brine, dried over anhydrous sodium sulfate, and filtrated. The solvent was evaporated under reduced pressure, the residue was purified by silica gel column chromatography (ethyl acetate alone) and recrystallized from hexane/ethyl acetate to give the title compound (201 mg, 57%) as a white powder.

1H-NMR (DMSO-d$_6$, 300 MHz) δ 0.61-0.71 (1H, m), 0.95-1.04 (1H, m), 1.06-1.10 (3H, m), 1.19 (3H, t, J=7.7 Hz), 1.17-1.29 (1H, m), 1.61-1.72 (1H, m), 2.57 (2H, q, J=7.7 Hz), 3.98 (3H, s), 6.89 (1H, s), 7.06 (1H, d, J=9.3 Hz), 7.18-7.22 (1H, m), 7.35-7.42 (1H, m), 7.50-7.53 (1H, m), 7.92 (1H, s), 8.03 (1H, d, J=9.3 Hz), 10.10 (1H, s), 10.98 (1H, s).

Example 250

Production of 3-methoxy-1-methyl-N-{2-methyl-5-[(2-{[(2-methylcyclopropyl)carbonyl]amino}imidazo[1,2-b]pyridazin-6-yl)oxy]phenyl}-1H-pyrazole-5-carboxamide

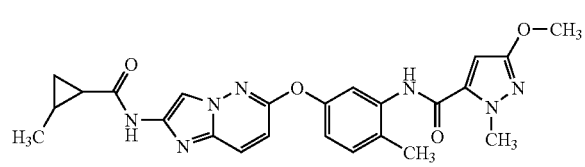

Using 3-methoxy-1-methyl-1H-pyrazole-5-carboxylic acid (194 mg, 1.24 mmol), tetrahydrofuran (4.5 mL), N,N-dimethylformamide (30 μL, 0.39 mmol), oxalyl chloride (109 μL, 1.22 mmol), N-[6-(3-amino-4-methylphenoxy)imidazo[1,2-b]pyridazin-2-yl]-2-methylcyclopropanecarboxamide (300 mg, 0.89 mmol) and N,N-dimethylacetamide (6.0 mL), and in the same manner as in Example 249, the title compound (291 mg, 69%) was obtained as a white powder.

1H-NMR (DMSO-d$_6$, 300 MHz) δ 0.61-0.71 (1H, m), 0.95-1.04 (1H, m), 1.06-1.09 (3H, m), 1.19-1.26 (1H, m), 1.62-1.72 (1H, m), 2.24 (3H, s), 3.79 (3H, s), 3.91 (3H, s), 6.45 (1H, s), 7.03 (1H, d, J=9.3 Hz), 7.09 (1H, dd, J=8.3, 2.6 Hz), 7.25 (1H, d, J=2.6 Hz), 7.34 (1H, d, J=8.3 Hz), 7.91 (1H, s), 8.02 (1H, d, J=9.6 Hz), 9.84 (1H, s), 10.97 (1H, s).

Example 251

Production of N-[2-chloro-5-({2-[(cyclopropylcarbonyl)amino]imidazo[1,2-b]pyridazin-6-yl}oxy)phenyl]-2,4-dimethyl-1,3-thiazole-5-carboxamide

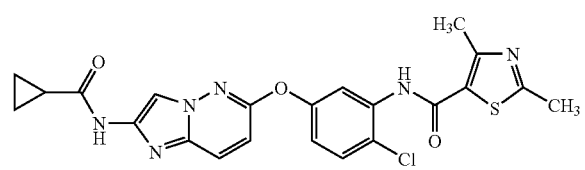

Using 2,4-dimethyl-1,3-thiazole-5-carboxylic acid (192 mg, 1.22 mmol), tetrahydrofuran (4.5 mL), N,N-dimethylformamide (30 μL, 0.39 mmol), oxalyl chloride (107 μL, 1.22 mmol), N-[6-(3-amino-4-chlorophenoxy)imidazo[1,2-b]pyridazin-2-yl]cyclopropanecarboxamide (300 mg, 0.87 mmol) and N,N-dimethylacetamide (6.0 mL), and in the same manner as in Example 249, the title compound (206 mg, 49%) was obtained as a white powder.

1H-NMR (DMSO-d$_6$, 300 MHz) δ 0.77-0.82 (4H, m), 1.83-1.97 (1H, m), 2.59 (3H, s), 2.64 (3H, s), 7.08 (1H, d, J=9.5 Hz), 7.20-7.24 (1H, m), 7.59-7.63 (2H, m), 7.94 (1H, s), 8.05 (1H, d, J=9.5 Hz), 9.78 (1H, s), 11.07 (1H, s).

Example 252

Production of N-{2-chloro-5-[(2-{[(2-methylcyclopropyl)carbonyl]amino}imidazo[1,2-b]pyridazin-6-yl)oxy]phenyl}-3-ethyl-1-methyl-1H-pyrazole-5-carboxamide

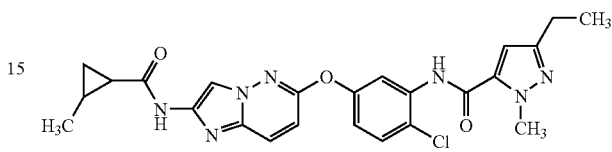

Using 3-ethyl-1-methyl-1H-pyrazole-5-carboxylic acid (181 mg, 1.17 mmol), tetrahydrofuran (4.5 mL), N,N-dimethylformamide (30 μL, 0.39 mmol), oxalyl chloride (102 μL, 1.17 mmol), N-[6-(3-amino-4-chlorophenoxy)imidazo[1,2-b]pyridazin-2-yl]-2-methylcyclopropanecarboxamide (300 mg, 0.84 mmol) and N,N-dimethylacetamide (6.0 mL), and in the same manner as in Example 249, the title compound (207 mg, 50%) was obtained as a white powder.

1H-NMR (DMSO-d$_6$, 300 MHz) δ 0.61-0.73 (1H, m), 0.97-1.04 (1H, m), 1.05-1.09 (3H, m), 1.16-1.25 (1H, m), 1.19 (3H, t, J=7.5 Hz), 1.62-1.73 (1H, m), 2.55 (2H, q, J=7.5 Hz), 3.99 (3H, s), 6.88 (1H, s), 7.08 (1H, d, J=9.5 Hz), 7.21-7.27 (1H, m), 7.53 (1H, d, J=3.0 Hz), 7.62 (1H, d, J=8.7 Hz), 7.94 (1H, s), 8.05 (1H, d, J=9.5 Hz), 10.00 (1H, s), 10.99 (1H, s).

Example 253

Production of N-[5-({2-[(cyclopropylsulfonyl)amino]imidazo[1,2-b]pyridazin-6-yl}oxy)-2-methylphenyl]-1,3-dimethyl-1H-pyrazole-5-carboxamide

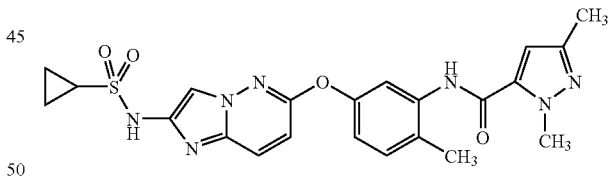

To a solution of N-{5-[(2-aminoimidazo[1,2-b]pyridazin-6-yl)oxy]-2-methylphenyl}-1,3-dimethyl-1H-pyrazole-5-carboxamide.hydrochloride (400 mg, 0.97 mmol) in 1-methyl-2-pyrrolidone (4.0 mL) were added triethylamine (404 μL, 2.90 mmol) and cyclopropanesulfonyl chloride (204 mg, 1.45 mmol), and the mixture was stirred at 70° C. for 16 hr. After cooling to room temperature, water was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was purified by silica gel column chromatography (ethyl acetate alone) and recrystallized from hexane/ethyl acetate to give the title compound (74 mg, 16%) as a white powder.

1H-NMR (DMSO-d$_6$, 300 MHz) δ 0.84-1.03 (4H, m), 2.19 (3H, s), 2.25 (3H, s), 2.72-2.86 (1H, m), 3.97 (3H, s), 6.80

(1H, s), 7.05-7.12 (2H, m), 7.26-7.29 (1H, m), 7.34 (1H, d, J=8.4 Hz), 7.61 (1H, s), 8.04 (1H, d, J=9.6 Hz), 9.79 (1H, s), 10.29 (1H, s).

Example 254

Production of N-[2-chloro-5-({2-[(cyclopropylcarbonyl)amino]imidazo[1,2-b]pyridazin-6-yl}oxy)phenyl]-1-ethyl-3-methyl-1H-pyrazole-4-carboxamide

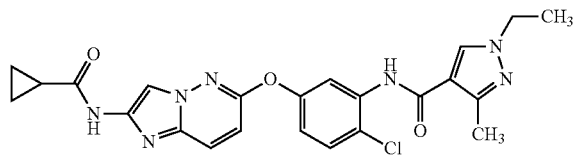

Using 1-ethyl-3-methyl-1H-pyrazole-4-carboxylic acid (188 mg, 1.22 mmol), tetrahydrofuran (4.5 mL), N,N-dimethylformamide (30 μL, 0.39 mmol), oxalyl chloride (107 μL, 1.22 mmol), N-[6-(3-amino-4-chlorophenoxy)imidazo[1,2-b]pyridazin-2-yl]cyclopropanecarboxamide (300 mg, 0.87 mmol) and N,N-dimethylacetamide (6.0 mL), and in the same manner as in Example 249, the title compound (135 mg, 33%) was obtained as a white powder. melting point 200° C.

$^1$H-NMR (DMSO-d$_6$, 300 MHz) δ 0.78-0.83 (4H, m), 1.38 (3H, t, J=7.2 Hz), 1.78-1.96 (1H, m), 2.35 (3H, s), 4.09 (2H, q, J=7.2 Hz), 7.08 (1H, d, J=9.6 Hz), 7.15 (1H, dd, J=8.9, 3.0 Hz), 7.62 (1H, d, J=8.9 Hz), 7.65 (1H, d, J=3.0 Hz), 7.95 (1H, s), 8.04 (1H, d, J=9.6 Hz), 8.36 (1H, s), 9.30 (1H, s), 11.06 (1H, s).

Example 255

Production of N-[5-({2-[(cyclopropylcarbonyl)amino]imidazo[1,2-b]pyridazin-6-yl}oxy)-2-fluorophenyl]-3-isopropyl-1-methyl-1H-pyrazole-5-carboxamide

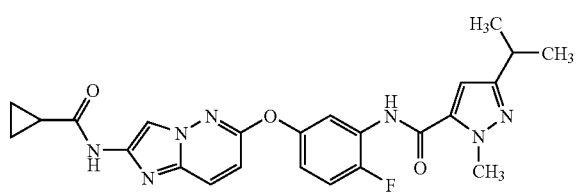

To a solution of 3-isopropyl-1-methyl-1H-pyrazole-5-carboxylic acid (144 mg, 0.86 mmol) in tetrahydrofuran (3.0 mL) were added N,N-dimethylformamide (30 μL, 0.39 mmol) and oxalyl chloride (75 μL, 0.86 mmol), and the mixture was stirred at room temperature for 30 min. The reaction mixture was added to a solution of N-[6-(3-amino-4-fluorophenoxy)imidazo[1,2-b]pyridazin-2-yl]cyclopropanecarboxamide (200 mg, 0.62 mmol) in N,N-dimethylacetamide (4.0 mL), and the mixture was stirred at room temperature for 2 hr. Saturated aqueous sodium hydrogencarbonate solution was added to the reaction mixture, and the mixture was extracted with ethyl acetate/tetrahydrofuran, washed with saturated brine, dried over anhydrous sodium sulfate, and filtrated. The solvent was evaporated under reduced pressure, and the residue was washed with ethyl acetate to give the title compound (216 mg, 74%) as a white powder.

$^1$H-NMR (DMSO-d$_6$, 300 MHz) δ 0.78-0.82 (4H, m), 1.21 (6H, d, J=6.6 Hz), 1.85-1.96 (1H, m), 2.83-2.96 (1H, m), 3.98 (3H, s), 6.91 (1H, s), 7.06 (1H, d, J=9.3 Hz), 7.17-7.22 (1H, m), 7.35-7.42 (1H, m), 7.50-7.54 (1H, m), 7.93 (1H, s), 8.03 (1H, d, J=9.3 Hz), 10.10 (1H, s), 11.06 (1H, s).

Example 256

Production of N-{2-chloro-5-[(2-{[(2-methylcyclopropyl)carbonyl]amino}imidazo[1,2-b]pyridazin-6-yl)oxy]phenyl}-1-ethyl-3-methyl-1H-pyrazole-4-carboxamide

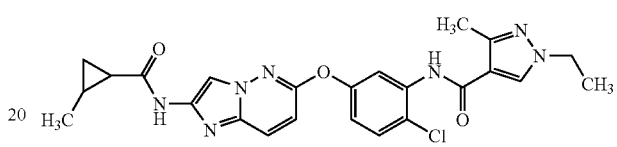

Using 1-ethyl-3-methyl-1H-pyrazole-4-carboxylic acid (181 mg, 1.17 mmol), tetrahydrofuran (4.5 mL), N,N-dimethylformamide (30 μL, 0.39 mmol), oxalyl chloride (102 μL, 1.17 mmol), N-[6-(3-amino-4-chlorophenoxy)imidazo[1,2-b]pyridazin-2-yl]-2-methylcyclopropanecarboxamide (300 mg, 0.84 mmol) and N,N-dimethylacetamide (6.0 mL), and in the same manner as in Example 249, the title compound (118 mg, 28%) was obtained as a white powder.

$^1$H-NMR (DMSO-d$_6$, 300 MHz) δ 0.61-0.69 (1H, m), 0.96-1.04 (1H, m), 1.06-1.10 (3H, m), 1.18-1.29 (1H, m), 1.38 (3H, t, J=7.2 Hz), 1.62-1.71 (1H, m), 2.35 (3H, s), 4.09 (2H, q, J=7.2 Hz), 7.07 (1H, d, J=9.6 Hz), 7.15 (1H, dd, J=8.9, 3.2 Hz), 7.58 (1H, d, J=8.9 Hz), 7.64 (1H, d, J=3.2 Hz), 7.93 (1H, s), 8.04 (1H, d, J=9.6 Hz), 8.36 (1H, s), 9.30 (1H, s), 10.99 (1H, s).

Example 257

Production of N-[6-(3-{[(1,3-dimethyl-1H-pyrazol-5-yl)methyl]amino}-4-methylphenoxy)imidazo[1,2-b]pyridazin-2-yl]cyclopropanecarboxamide

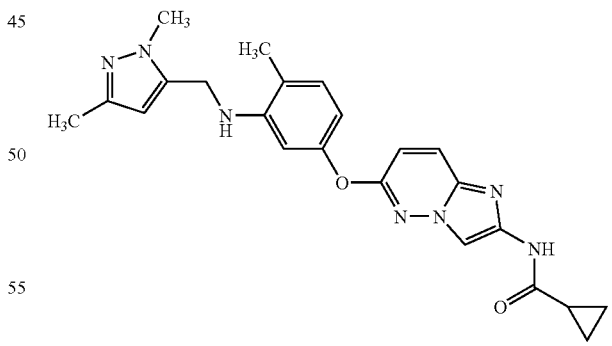

A mixture of N-(6-iodoimidazo[1,2-b]pyridazin-2-yl)cyclopropanecarboxamide (210 mg, 0.64 mmol), 3-{[(1,3-dimethyl-1H-pyrazol-5-yl)methyl]amino}-4-methylphenol (220 mg, 0.96 mmol), potassium carbonate (220 mg, 1.6 mmol) and N,N-dimethylformamide (1.5 mL) was stirred under microwave irradiation at 150° C. for 40 min. The solvent was evaporated under reduced pressure, ethyl acetate/tetrahydrofuran and water were added to the residue, the aqueous layer was extracted with ethyl acetate/tetrahydrofuran (×4). Combined organic layer was washed with saturated brine, dried over anhydrous sodium sulfate, and filtrated. The filtrate was concentrated under reduced pressure, and the residue was purified by silica gel column chromatography (methanol/ethyl acetate=0/100→5/95) to give the title compound (200 mg, 72%) as a brown solid.

¹H-NMR (DMSO-d₆, 300 MHz) δ 0.74-0.84 (4H, m), 1.87-1.96 (1H, m), 2.00 (3H, s), 2.11 (3H, s), 3.68 (3H, s), 4.26 (2H, d, J=5.7 Hz), 5.64 (1H, t, J=5.7 Hz), 5.80 (1H, s), 6.34 (1H, dd, J=7.9, 2.3 Hz), 6.40 (1H, d, J=2.3 Hz), 6.89 (1H, d, J=9.8 Hz), 7.01 (1H, d, J=8.5 Hz), 7.91-8.01 (2H, m), 11.07 (1H, s).

Example 258
Production of N-{6-[(2-methyl-1H-indol-6-yl)oxy]imidazo[1,2-b]pyridazin-2-yl}cyclopropanecarboxamide

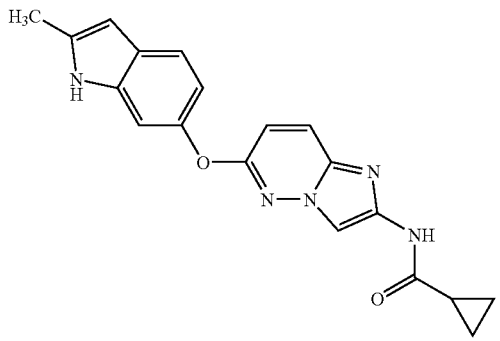

A mixture of N-(6-iodoimidazo[1,2-b]pyridazin-2-yl)cyclopropanecarboxamide (360 mg, 1.1 mmol), 2-methyl-1H-indole-6-ol (320 mg, 2.2 mmol), potassium carbonate (450 mg, 3.3 mmol) and N,N-dimethylformamide (4 mL) was stirred at 120° C. for 24 hr. The solvent was evaporated under reduced pressure, ethyl acetate/tetrahydrofuran and water were added to the residue, and the aqueous layer was extracted with ethyl acetate/tetrahydrofuran (×4). Combined organic layer was washed with saturated brine, dried over anhydrous sodium sulfate, and filtrated. The filtrate was concentrated under reduced pressure, and the residue was purified by silica gel column chromatography (ethyl acetate/hexane=20/80→90/10) to give the title compound (140 mg, 36%) as a brown solid.

¹H-NMR (DMSO-d₆, 300 MHz) δ 0.72-0.86 (4H, m), 1.84-1.97 (1H, m), 2.39 (3H, s), 6.15 (1H, s), 6.81 (1H, dd, J=8.5, 2.1 Hz), 6.96 (1H, d, J=9.8 Hz), 7.13 (1H, d, J=2.1 Hz), 7.42 (1H, d, J=8.5 Hz), 7.90 (1H, s), 7.97 (1H, d, J=9.8 Hz), 11.00 (1H, s), 11.04 (1H, s).

Example 259
Production of N-[5-({2-[(cyclopropylcarbonyl)amino]imidazo[1,2-b]pyridazin-6-yl}oxy)-2-methylphenyl]-1-methyl-1H-pyrazole-5-carboxamide

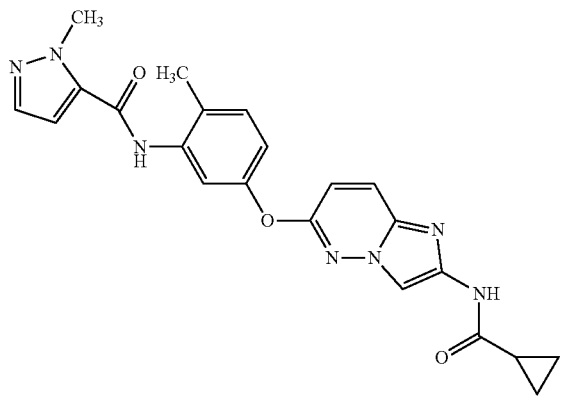

To a solution of 1-methyl-1H-pyrazole-5-carboxylic acid (106 mg, 0.84 mmol) in tetrahydrofuran (5 mL) were added N,N-dimethylformamide (1 drop), oxalyl chloride (91 µL, 1.0 mmol), and the mixture was stirred at room temperature for 30 min. The solvent was evaporated under reduced pressure, and the obtained 1-methyl-1H-pyrazole-5-carbonylchloride was dissolved in N,N-dimethylacetamide (2 mL). This was added to a solution of N-[6-(3-amino-4-methylphenoxy)imidazo[1,2-b]pyridazin-2-yl]cyclopropanecarboxamide (210 mg, 0.65 mmol) in N,N-dimethylacetamide (5 mL), and the mixture was stirred at room temperature for 30 min. To the mixture were added ethyl acetate/tetrahydrofuran and saturated aqueous sodium hydrogencarbonate solution, and the aqueous layer was extracted with ethyl acetate/tetrahydrofuran (×4). Combined organic layer was washed with water and saturated brine, dried over anhydrous sodium sulfate, and filtrated. The filtrate was concentrated under reduced pressure, and the residue was purified by silica gel column chromatography (ethyl acetate/hexane=30/70→90/10) to give the title compound (230 mg, 83%) as a white solid.

¹H-NMR (DMSO-d₆, 300 MHz) δ 0.73-0.85 (4H, m), 1.87-1.97 (1H, m), 2.25 (3H, s), 4.05 (3H, s), 7.00-7.07 (2H, m), 7.11 (1H, dd, J=8.3, 2.3 Hz), 7.28 (1H, d, J=2.7 Hz), 7.36 (1H, d, J=8.3 Hz), 7.53 (1H, d, J=2.3 Hz), 7.93 (1H, s), 8.03 (1H, d, J=9.5 Hz), 9.91 (1H, s), 11.07 (1H, s).

Example 260
Production of N-[5-({2-[(cyclopropylcarbonyl)amino]imidazo[1,2-b]pyridazin-6-yl}oxy)-2-methylphenyl]-1-ethyl-3-methyl-1H-pyrazole-5-carboxamide

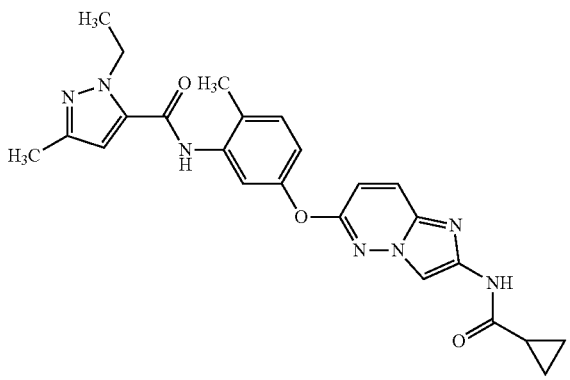

In the same manner as in Example 259 and using 1-ethyl-3-methyl-1H-pyrazole-5-carboxylic acid (130 mg, 0.84=mol), tetrahydrofuran (5 mL), N,N-dimethylformamide (1 drop), oxalyl chloride (91 µL, 1.0 mmol), N-[6-(3-amino-4-methylphenoxy)imidazo[1,2-b]pyridazin-2-yl]cyclopropanecarboxamide (210 mg, 0.65 mmol) and N,N-dimethylacetamide (7 mL) as starting materials, the title compound (220 mg, 75%) was obtained as a white solid.

¹H-NMR (DMSO-d₆, 300 MHz) δ 0.71-0.83 (4H, m), 1.26 (3H, t, J=7.1 Hz), 1.84-1.95 (1H, m), 2.18 (3H, s), 2.23 (3H, s), 4.39 (2H, q, J=7.1 Hz), 6.78 (1H, s), 7.02 (1H, d, J=9.6 Hz), 7.08 (1H, dd, J=8.2, 2.7 Hz), 7.26 (1H, d, J=2.7 Hz), 7.32 (1H, d, J=8.2 Hz), 7.91 (1H, s), 8.01 (1H, d, J=9.6 Hz), 9.79 (1H, s), 11.05 (1H, s).

Example 261

Production of N-[5-({2-[(cyclopropylcarbonyl)amino]imidazo[1,2-b]pyridazin-6-yl}oxy)-2-methylphenyl]-2-methyl-1,3-thiazole-4-carboxamide

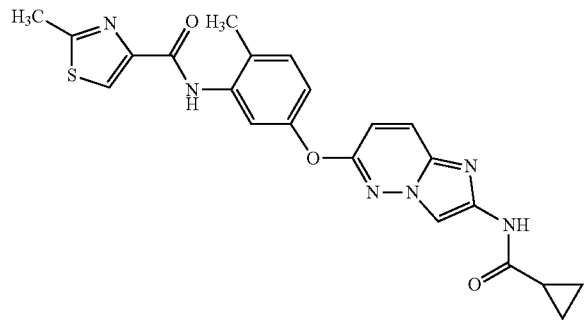

A mixture of 2-methyl-1,3-thiazole-4-carboxylic acid (120 mg, 0.84 mmol), N-[6-(3-amino-4-methylphenoxy)imidazo[1,2-b]pyridazin-2-yl]cyclopropanecarboxamide (210 mg, 0.65 mmol), 1-hydroxybenzotriazole (110 mg, 0.84 mmol), 1-ethyl-3-(3-dimethylaminopropyl)carbodiimide hydrochloride (160 mg, 0.84 mmol), triethylamine (85 mg, 0.84 mmol) and N,N-dimethylformamide (5 mL) was stirred at room temperature for 16 hr. The solvent was evaporated under reduced pressure, ethyl acetate/tetrahydrofuran and water were added to the residue, and the aqueous layer was extracted with ethyl acetate/tetrahydrofuran (×4). Combined organic layer was washed with saturated brine, dried over anhydrous sodium sulfate, and filtrated. The filtrate was concentrated under reduced pressure, and the residue was purified by silica gel column chromatography (ethyl acetate/hexane=40/60→100/0) to give the title compound (180 mg, 62%) as a white solid.

$^1$H-NMR (DMSO-$d_6$, 300 MHz) δ 0.71-0.82 (4H, m), 1.82-1.94 (1H, m), 2.27 (3H, s), 2.72 (3H, s), 6.95-7.07 (2H, m), 7.32 (1H, d, J=8.8 Hz), 7.65 (1H, d, J=2.7 Hz), 7.93 (1H, s), 8.01 (1H, d, J=9.6 Hz), 8.25 (1H, s), 9.73 (1H, s), 11.06 (1H, s).

Example 262

Production of N-[5-({2-[(cyclopropylcarbonyl)amino]imidazo[1,2-b]pyridazin-6-yl}oxy)-2-methylphenyl]-1-methyl-L-prolinamide

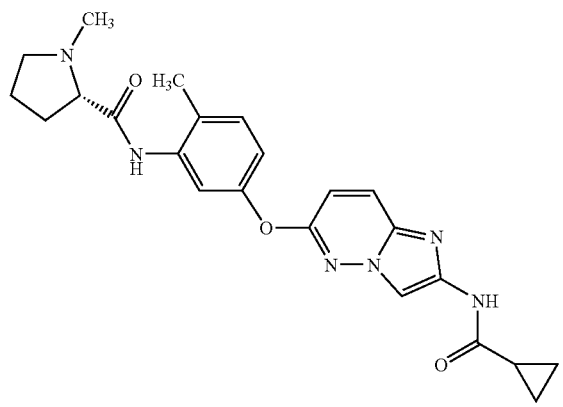

A mixture of 1-methyl-L-proline (170 mg, 1.3 mmol), N-[6-(3-amino-4-methylphenoxy)imidazo[1,2-b]pyridazin-2-yl]cyclopropanecarboxamide (210 mg, 0.65 mmol), 1-hydroxybenzotriazole (175 mg, 1.3 mmol), O-(benzotriazol-1-yl)-N,N,N',N'-tetramethyluronium hexafluorophosphate (490 mg, 1.3 mmol), N,N-diisopropylethylamine (330 mg, 2.6 mmol) and N,N-dimethylformamide (15 mL) was stirred at room temperature for 18 hr, and then at 40° C. for 4 hr. The solvent was evaporated under reduced pressure, ethyl acetate/tetrahydrofuran and water were added to the residue, the aqueous layer was extracted with ethyl acetate/tetrahydrofuran (×4). Combined organic layer was washed with saturated brine, dried over anhydrous sodium sulfate, and filtrated. The filtrate was concentrated under reduced pressure, and the residue was purified by silica gel column chromatography (methanol/ethyl acetate=0/100→10/90) to give the title compound (15 mg, 5%) as a white solid.

$^1$H-NMR (DMSO-$d_6$, 300 MHz) δ 0.76-0.84 (4H, m), 1.69-1.86 (3H, m), 1.87-1.99 (1H, m), 2.11-2.22 (1H, m), 2.23 (3H, s), 2.38 (1H, d, J=8.0 Hz), 2.43 (3H, s), 2.95 (1H, dd, J=10.0, 4.7 Hz), 3.16 (1H, dd, J=7.4, 4.7 Hz), 6.95 (1H, dd, J=8.3, 2.7 Hz), 7.02 (1H, d, J=9.5 Hz), 7.29 (1H, d, J=8.3 Hz), 7.77 (1H, d, J=2.7 Hz), 7.92 (1H, s), 8.02 (1H, d, J=9.5 Hz), 9.61 (1H, s), 11.07 (1H, s).

Example 263

Production of N-[6-(4-chloro-3-{[(1,3-dimethyl-1H-pyrazol-5-yl)methyl]amino}phenoxy)imidazo[1,2-b]pyridazin-2-yl]cyclopropanecarboxamide

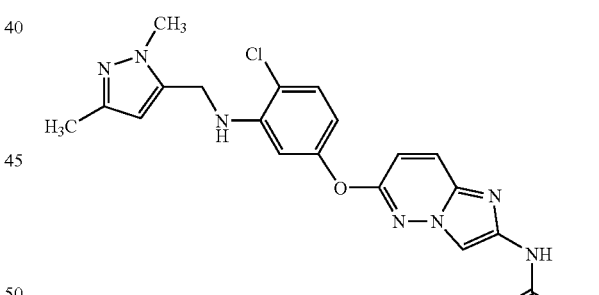

In the same manner as in Example 257 and using N-(6-iodoimidazo[1,2-b]pyridazin-2-yl)cyclopropanecarboxamide (210 mg, 0.65 mmol), 4-chloro-3-{[(1,3-dimethyl-1H-pyrazol-5-yl)methyl]amino}phenol (240 mg, 0.97 mmol), potassium carbonate (220 mg, 1.6 mmol) and N,N-dimethylformamide (1.5 mL) as starting materials, the title compound (180 mg, 61%) was obtained as a brown solid.

$^1$H-NMR (DMSO-$d_6$, 300 MHz) δ 0.72-0.86 (4H, m), 1.86-1.91 (1H, m), 1.98 (3H, s), 3.68 (3H, s), 4.35 (2H, d, J=6.1 Hz), 5.78 (1H, s), 6.11 (1H, t, J=6.1 Hz), 6.46 (1H, dd,

J=8.7, 2.7 Hz), 6.61 (1H, d, J=2.7 Hz), 6.96 (1H, d, J=9.5 Hz), 7.30 (1H, d, J=8.7 Hz), 7.93-8.03 (2H, m), 11.06 (1H, s).

Example 264

Production of 1-tert-butyl-N-[5-({2-[(cyclopropyl-carbonyl)amino]imidazo[1,2-b]pyridazin-6-yl}oxy)-2-methylphenyl]-3-methyl-1H-pyrazole-5-carboxamide

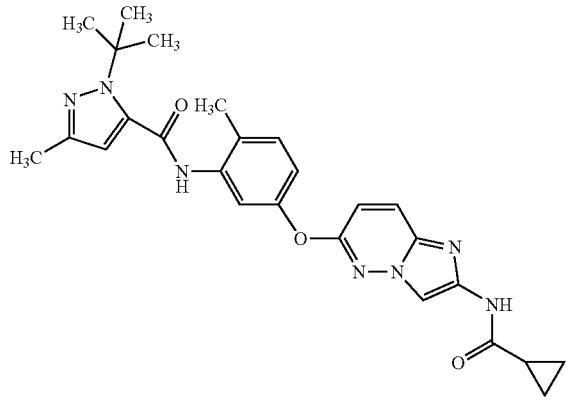

To a solution of N-[6-(3-amino-4-methylphenoxy)imidazo[1,2-b]pyridazin-2-yl]cyclopropanecarboxamide (210 mg, 0.65 mmol) in N,N-dimethylacetamide (5 mL) was added a solution of 1-tert-butyl-3-methyl-1H-pyrazole-5-carbonylchloride (160 mg, 0.78 mmol) in N,N-dimethylacetamide (1 mL), and the mixture was stirred at room temperature for 30 min. Ethyl acetate/tetrahydrofuran and saturated aqueous sodium hydrogencarbonate solution were added to the mixture, the aqueous layer was extracted with ethyl acetate/tetrahydrofuran (×4). Combined organic layer was washed with water and saturated brine, dried over anhydrous sodium sulfate, and filtrated. The filtrate was concentrated under reduced pressure, and the residue was purified by silica gel column chromatography (ethyl acetate/hexane=40/60→90/10) to give the title compound (14 mg, 4%) as a white solid.

$^1$H-NMR (DMSO-d$_6$, 300 MHz) δ 0.74-0.88 (4H, m), 1.60 (9H, s), 1.86-1.98 (1H, m), 2.19 (3H, s), 2.27 (3H, s), 6.45 (1H, s), 6.99-7.15 (2H, m), 7.27-7.41 (2H, m), 7.91-7.97 (1H, m), 8.02 (1H, d, J=9.8 Hz), 10.05 (1H, s), 11.05 (1H, s).

Example 265

Production of N-[5-({2-[(cyclopropylcarbonyl)amino]imidazo[1,2-b]pyridazin-6-yl}oxy)-2-methylphenyl]-1-(2-methoxyethyl)-3-methyl-1H-pyrazole-5-carboxamide

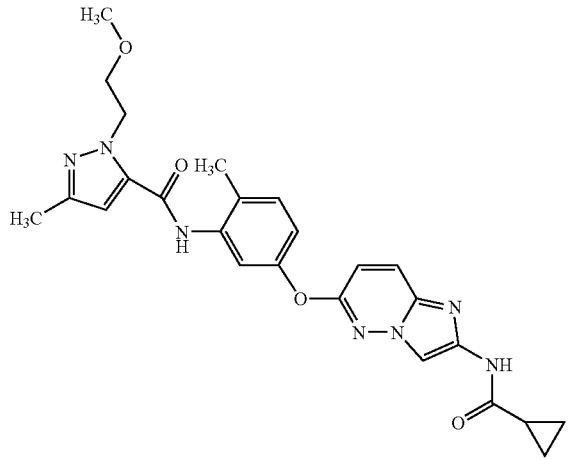

In the same manner as in Example 259 and using 1-(2-methoxyethyl)-3-methyl-1H-pyrazole-5-carboxylic acid (150 mg, 0.80 mmol), tetrahydrofuran (5 mL), N,N-dimethylformamide (1 drop), oxalyl chloride (83 μL, 0.97 mmol), N-[6-(3-amino-4-methylphenoxy)imidazo[1,2-b]pyridazin-2-yl]cyclopropanecarboxamide (200 mg, 0.62 mmol) and N,N-dimethylacetamide (7 mL) as starting materials, the title compound (230 mg, 77%) was obtained as a pale-green solid.

$^1$H-NMR (DMSO-d$_6$, 300 MHz) δ 0.74-0.85 (4H, m), 1.85-1.98 (1H, m), 2.20 (3H, s), 2.25 (3H, s), 3.17 (3H, s), 3.62 (2H, t, J=5.5 Hz), 4.56 (2H, t, J=5.5 Hz), 6.76 (1H, s), 7.04 (1H, d, J=9.5 Hz), 7.10 (1H, dd, J=8.3, 2.3 Hz), 7.26 (1H, d, J=2.3 Hz), 7.34 (1H, d, J=8.3 Hz), 7.93 (1H, s), 8.02 (1H, d, J=9.5 Hz), 9.82 (1H, s), 11.05 (1H, s).

Example 266

Production of N-[5-({2-[(cyclopropylcarbonyl)amino]imidazo[1,2-b]pyridazin-6-yl}oxy)-2-methylphenyl]-2,4-dimethyl-1,3-thiazole-5-carboxamide

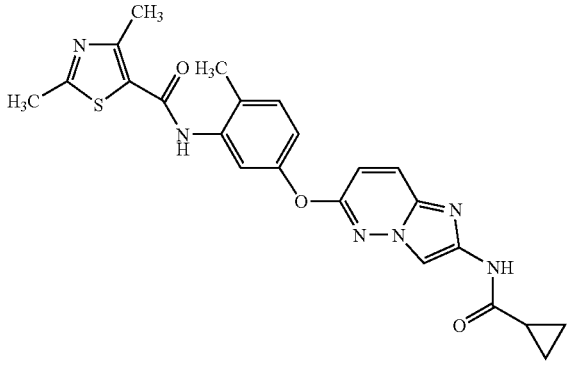

In the same manner as in Example 261 and using 2,4-dimethyl-1,3-thiazole-5-carboxylic acid (130 mg, 0.80 mmol), N-[6-(3-amino-4-methylphenoxy)imidazo[1,2-b]pyridazin-2-yl]cyclopropanecarboxamide (200 mg, 0.62 mmol), 1-hydroxybenzotriazole (110 mg, 0.80 mmol), 1-ethyl-3-(3-dimethylaminopropyl)carbodiimide hydrochloride (150 mg, 0.80 mmol), triethylamine (94 mg, 0.93 mmol) and N,N-dimethylformamide (5 mL) as starting materials, the title compound (120 mg, 41%) was obtained as a pale-yellow solid.

$^1$H-NMR (DMSO-d$_6$, 300 MHz) δ 0.75-0.84 (4H, m), 1.86-1.97 (1H, m), 2.26 (3H, s), 2.57 (3H, s), 2.64 (3H, s), 7.03 (1H, d, J=9.5 Hz), 7.08 (1H, dd, J=8.3, 2.3 Hz), 7.30-7.37 (2H, m), 7.93 (1H, s), 8.02 (1H, d, J=9.5 Hz), 9.62 (1H, s), 11.06 (1H, s).

Example 267

Production of N-[5-({2-[(cyclopropylcarbonyl)amino]imidazo[1,2-b]pyridazin-6-yl}oxy)-2-fluorophenyl]-2,4-dimethyl-1,3-thiazole-5-carboxamide

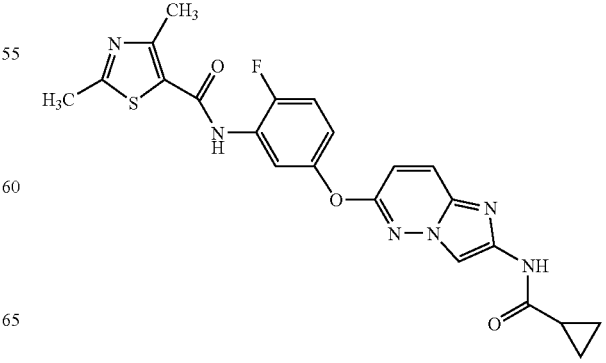

In the same manner as in Example 261 and using 2,4-dimethyl-1,3-thiazole-5-carboxylic acid (190 mg, 1.2 mmol), N-[6-(3-amino-4-fluorophenoxy)imidazo[1,2-b]pyridazin-2-yl]cyclopropanecarboxamide (200 mg, 0.62 mmol), 1-hydroxybenzotriazole (170 mg, 1.2 mmol), 1-ethyl-3-(3-dimethylaminopropyl)carbodiimide hydrochloride (240 mg, 1.2 mmol), N,N-diisopropylethylamine (240 mg, 1.9 mmol) and N,N-dimethylformamide (5 mL) as starting materials, the title compound (93 mg, 32%) was obtained as a pale-yellow solid.

$^1$H-NMR (DMSO-$d_6$, 300 MHz) δ 0.76-0.85 (4H, m), 1.86-1.97 (1H, m), 2.56 (3H, s), 2.65 (3H, s), 7.07 (1H, d, J=9.8 Hz), 7.14-7.23 (1H, m), 7.33-7.44 (1H, m), 7.58 (1H, dd, J=6.2, 2.8 Hz), 7.94 (1H, s), 8.04 (1H, d, J=9.8 Hz), 9.94 (1H, s), 11.06 (1H, s).

Example 268

Production of N-[5-({2-[(cyclopropylcarbonyl)amino]imidazo[1,2-b]pyridazin-6-yl}oxy)-2-fluorophenyl]-1-(2-methoxyethyl)-3-methyl-1H-pyrazole-5-carboxamide

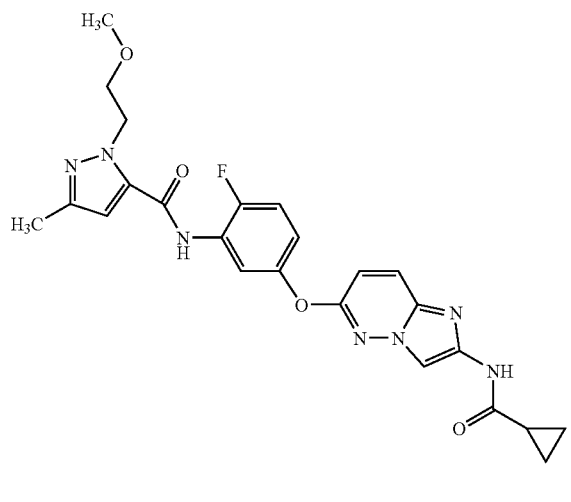

In the same manner as in Example 259 and using 1-(2-methoxyethyl)-3-methyl-1H-pyrazole-5-carboxylic acid (150 mg, 0.80 mmol), tetrahydrofuran (5 mL), N,N-dimethylformamide (1 drop), oxalyl chloride (83 µL, 0.97 mmol), N-[6-(3-amino-4-fluorophenoxy)imidazo[1,2-b]pyridazin-2-yl]cyclopropanecarboxamide (200 mg, 0.62 mmol) and N,N-dimethylacetamide (7 mL) as starting materials, the title compound (230 mg, 77%) was obtained as a white solid.

$^1$H-NMR (DMSO-$d_6$, 300 MHz) δ 0.73-0.82 (4H, m), 1.85-1.97 (1H, m), 2.19 (3H, s), 3.30 (3H, s), 3.63 (2H, t, J=5.7 Hz), 4.56 (2H, t, J=5.7 Hz), 6.81 (1H, s), 7.07 (1H, d, J=9.5 Hz), 7.17-7.25 (1H, m), 7.35-7.44 (1H, m), 7.54 (1H, dd, J=6.2, 2.8 Hz), 7.94 (1H, s), 8.04 (1H, d, J=9.5 Hz), 10.12 (1H, s), 11.06 (1H, s).

Example 269

Production of N-(5-{[2-(acetylamino)imidazo[1,2-b]pyridazin-6-yl]oxy}-2-methylphenyl)-1,3-dimethyl-1H-pyrazole-5-carboxamide

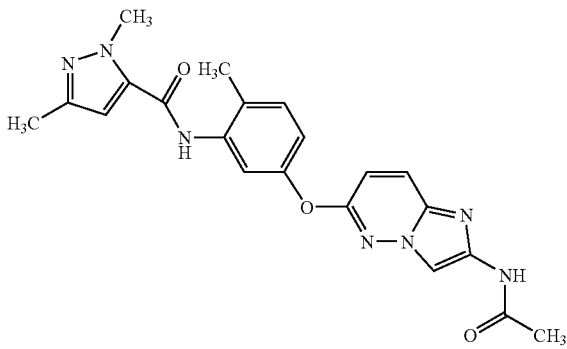

In the same manner as in Example 264 and using N-[6-(3-amino-4-methylphenoxy)imidazo[1,2-b]pyridazin-2-yl]acetamide (840 mg, 2.8 mmol), 1,3-dimethyl-1H-pyrazole-5-carbonylchloride (540 mg, 3.4 mmol) and N,N-dimethylacetamide (35 mL), the title compound (910 mg, 77%) was obtained as a white solid.

$^1$H-NMR (DMSO-$d_6$, 300 MHz) δ 2.05 (3H, s), 2.18 (3H, s), 2.25 (3H, s), 3.98 (3H, s), 6.81 (1H, s), 7.04 (1H, d, J=9.8 Hz), 7.10 (1H, dd, J=8.3, 2.7 Hz), 7.28 (1H, d, J=2.7 Hz), 7.35 (1H, d, J=8.3 Hz), 7.95 (1H, s), 8.02 (1H, d, J=9.8 Hz), 9.79 (1H, s), 10.78 (1H, s).

Example 270

Production of N-[5-({2-[(cyclopropylcarbonyl)amino]imidazo[1,2-b]pyridazin-6-yl}oxy)-2-methylphenyl]-4-methyl-1,3-oxazole-5-carboxamide

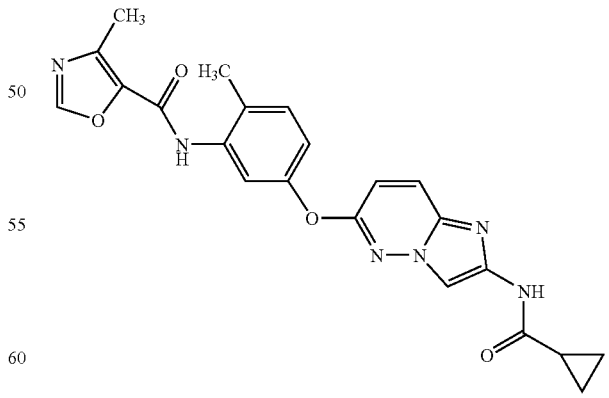

In the same manner as in Example 259 and using 4-methyl-1,3-oxazole-5-carboxylic acid (77 mg, 0.60 mmol), tetrahydrofuran (10 mL), N,N-dimethylformamide (1 drop), oxalyl chloride (62 µL, 0.72 mmol), N-[6-(3-amino-4-methylphenoxy)imidazo[1,2-b]pyridazin-2-yl]cyclopropanecarboxamide (150 mg, 0.46 mmol) and N,N-dimethylacetamide (7 mL) as starting materials, the title compound (170 mg, 83%) was obtained as a white solid.

¹H-NMR (DMSO-d₆, 300 MHz) δ 0.73-0.87 (4H, m), 1.86-1.98 (1H, m), 2.25 (3H, s), 2.41 (3H, s), 7.04 (1H, d, J=9.5 Hz), 7.09 (1H, dd, J=8.1, 2.5 Hz), 7.29-7.39 (2H, m), 7.94 (1H, s), 8.03 (1H, d, J=9.5 Hz), 8.51 (1H, s), 9.82 (1H, s), 11.06 (1H, s).

Example 271

Production of N-[5-({2-[(cyclopropylcarbonyl)amino]imidazo[1,2-b]pyridazin-6-yl}oxy)-2-methylphenyl]-2-methyl-1,3-oxazole-4-carboxamide

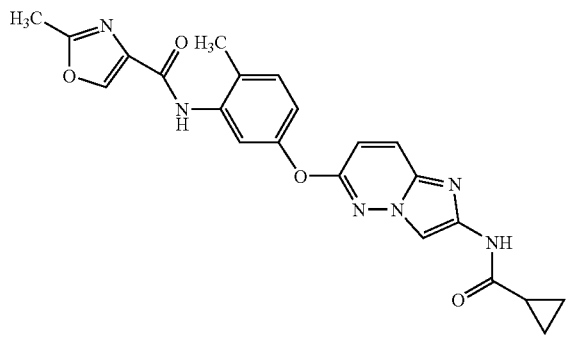

In the same manner as in Example 259 and using 2-methyl-1,3-oxazole-4-carboxylic acid (77 mg, 0.60 mmol), tetrahydrofuran (10 mL), N,N-dimethylformamide (1 drop), oxalyl chloride (62 μL, 0.72 mmol), N-[6-(3-amino-4-methylphenoxy)imidazo[1,2-b]pyridazin-2-yl]cyclopropanecarboxamide (150 mg, 0.46 mmol) and N,N-dimethylacetamide (7 mL) as starting materials, the title compound (150 mg, 74%) was obtained as a white solid.

¹H-NMR (DMSO-d₆, 300 MHz) δ 0.73-0.85 (4H, m), 1.87-1.96 (1H, m), 2.27 (3H, s), 2.51 (3H, s), 6.99-7.07 (2H, m), 7.32 (1H, d, J=8.7 Hz), 7.54 (1H, d, J=2.7 Hz), 7.94 (1H, s), 8.02 (1H, d, J=9.8 Hz), 8.62 (1H, s), 9.54 (1H, s), 11.06 (1H, s).

Example 272

Production of N-[5-({2-[(cyclopropylcarbonyl)amino]imidazo[1,2-b]pyridazin-6-yl}oxy)-2-methylphenyl]-2,4-dimethyl-1,3-oxazole-5-carboxamide

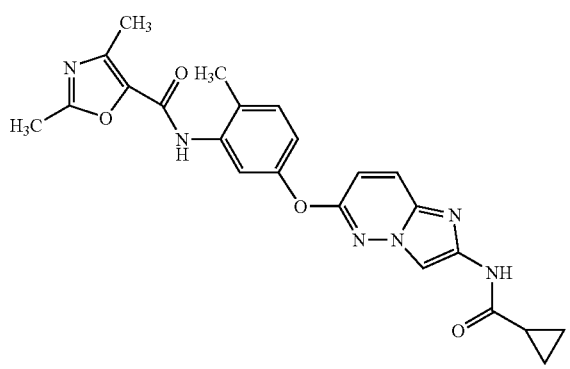

In the same manner as in Example 259 and using 2,4-dimethyl-1,3-oxazole-5-carboxylic acid (85 mg, 0.60 mmol), tetrahydrofuran (5 mL), N,N-dimethylformamide (1 drop), oxalyl chloride (62 μL, 0.72 mmol), N-[6-(3-amino-4-methylphenoxy)imidazo[1,2-b]pyridazin-2-yl]cyclopropanecarboxamide (150 mg, 0.46 mmol) and N,N-dimethylacetamide (7 mL) as starting materials, the title compound (170 mg, 81%) was obtained as a white solid.

¹H-NMR (DMSO-d₆, 300 MHz) δ 0.76-0.84 (4H, m), 1.86-1.98 (1H, m), 2.24 (3H, s), 2.34 (3H, s), 2.48 (3H, s), 7.03 (1H, d, J=9.5 Hz), 7.08 (1H, dd, J=8.3, 2.7 Hz), 7.29 (1H, d, J=2.7 Hz), 7.33 (1H, d, J=8.3 Hz), 7.94 (1H, s), 8.02 (1H, d, J=9.5 Hz), 9.70 (1H, s), 11.06 (1H, s).

Example 273

Production of N-[5-({2-[(cyclopropylcarbonyl)amino]imidazo[1,2-b]pyridazin-6-yl}oxy)-2-methylphenyl]-3-methyl-1H-pyrazole-5-carboxamide

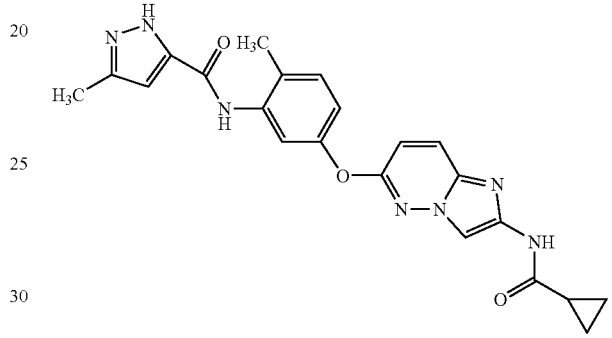

In the same manner as in Example 261 and using 3-methyl-1H-pyrazole-5-carboxylic acid (160 mg, 1.2 mmol), N-[6-(3-amino-4-methylphenoxy)imidazo[1,2-b]pyridazin-2-yl]cyclopropanecarboxamide (200 mg, 0.62 mmol), 1-hydroxybenzotriazole (170 mg, 1.2 mmol), 1-ethyl-3-(3-dimethylaminopropyl)carbodiimide hydrochloride (240 mg, 1.2 mmol), triethylamine (190 mg, 1.9 mmol) and N,N-dimethylformamide (3 mL) as starting materials, the title compound (190 mg, 70%) was obtained as a white solid.

¹H-NMR (DMSO-d₆, 300 MHz) δ 0.74-0.84 (4H, m), 1.87-1.97 (1H, m), 2.29 (6H, s), 6.49 (1H, s), 6.99 (1H, dd, J=8.3, 2.7 Hz), 7.03 (1H, d, J=9.5 Hz), 7.31 (1H, d, J=8.3 Hz), 7.68 (1H, d, J=2.7 Hz), 7.94 (1H, s), 8.02 (1H, d, J=9.5 Hz), 9.36 (1H, s), 11.06 (1H, s), 13.09 (1H, s).

Example 274

Production of N-{5-[(2-{[(2,2-difluorocyclopropyl)carbonyl]amino}imidazo[1,2-b]pyridazin-6-yl)oxy]-2-methylphenyl}-1,3-dimethyl-1H-pyrazole-5-carboxamide

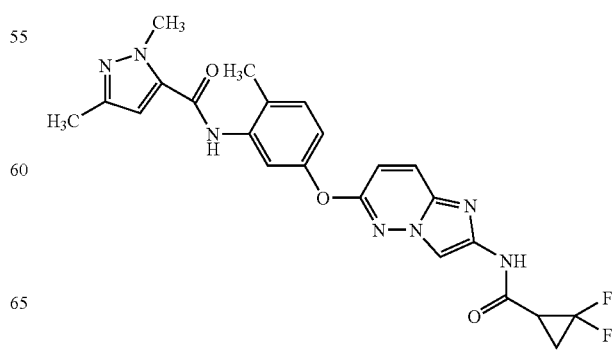

In the same manner as in Example 259 and using 2,2-difluorocyclopropanecarboxylic acid (88 mg, 0.60 mmol), tetrahydrofuran (5 mL), N,N-dimethylformamide (1 drop), oxalyl chloride (74 μL, 0.86 mmol), N-{5-[(2-aminoimidazo [1,2-b]pyridazin-6-yl)oxy]-2-methylphenyl}-1,3-dimethyl-1H-pyrazole-5-carboxamide hydrochloride (250 mg, 0.60 mmol) and N,N-dimethylacetamide (7 mL) as starting materials, the title compound (210 mg, 73%) was obtained as a white solid.

$^1$H-NMR (DMSO-d$_6$, 300 MHz) δ 1.95-2.09 (2H, m), 2.19 (3H, s), 2.25 (3H, s), 2.86-2.96 (1H, m), 3.98 (3H, s), 6.81 (1H, s), 7.05-7.13 (2H, m), 7.29 (1H, d, J=2.3 Hz), 7.35 (1H, d, J=8.3 Hz), 7.96 (1H, s), 8.06 (1H, d, J=9.8 Hz), 9.79 (1H, s), 11.29 (1H, s).

Example 275

Production of N-{5-[(2-aminoimidazo[1,2-b]pyridazin-6-yl)oxy]-2-methylphenyl}-1,3-dimethyl-1H-pyrazole-5-carboxamide hydrochloride

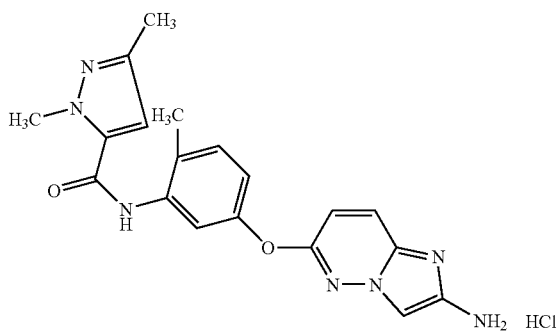

To a suspension of N-(5-{[2-(acetylamino)imidazo[1,2-b]pyridazin-6-yl]oxy}-2-methylphenyl)-1,3-dimethyl-1H-pyrazole-5-carboxamide (310 mg, 0.73 mmol) in methanol (10 mL) was added 4N hydrochloric acid/ethyl acetate (10 mL, 40 mmol), and the mixture was stirred at room temperature for 16 hr. The solvent was evaporated under reduced pressure, and the residue was washed with ethyl acetate/tetrahydrofuran, and then with diethyl ether to give the title compound (240 mg, 78%) as a pale-yellow solid.

$^1$H-NMR (DMSO-d$_6$, 300 MHz) δ 2.18 (3H, s), 2.27 (3H, s), 3.97 (3H, s), 6.90 (1H, s), 7.12 (1H, dd, J=8.3, 2.3 Hz), 7.29-7.41 (3H, m), 7.45 (1H, s), 8.20 (1H, d, J=9.5 Hz), 9.94 (1H, s).

Example 276

Production of 2-({2-[(cyclopropylcarbonyl)amino]imidazo[1,2-b]pyridazin-6-yl}oxy)benzoic acid

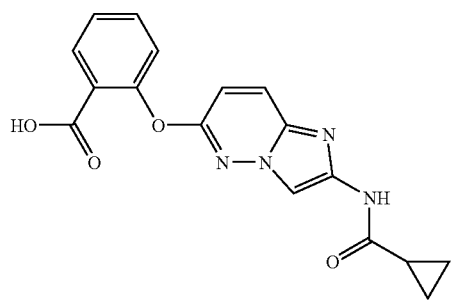

To a solution of ethyl salicylate (1010 mg, 6.1 mmol) in N,N-dimethylformamide (8 mL) was added potassium tert-butoxide (840 mg, 6.4 mmol) at 0° C., and the mixture was stirred at 0° C. for 5 min and at room temperature for 25 min. To the reaction mixture were added N-(6-iodoimidazo[1,2-b]pyridazin-2-yl)cyclopropanecarboxamide (1.0 g, 3.1 mmol) and potassium carbonate (420 mg, 3.1 mmol), and the mixture was stirred at 100° C. for 24 hr. The solvent was evaporated under reduced pressure, ethyl acetate/tetrahydrofuran and water were added to the residue. The aqueous layer was extracted with ethyl acetate/tetrahydrofuran (×3). Combined organic layer was washed with saturated brine, dried over anhydrous sodium sulfate, and filtrated. The filtrate was concentrated under reduced pressure, and the residue was purified by silica gel column chromatography (ethyl acetate/hexane=40/60→90/10) to give ethyl 2-({2-[(cyclopropylcarbonyl)amino]imidazo[1,2-b]pyridazin-6-yl}oxy)benzoate (200 mg, 18%) as a white solid.

$^1$H-NMR (DMSO-d$_6$, 300 MHz) δ 0.74-0.83 (4H, m), 1.00 (3H, t, J=7.2 Hz), 1.83-1.97 (1H, m), 4.08 (2H, q, J=7.2 Hz), 7.09 (1H, d, J=9.5 Hz), 7.39-7.51 (2H, m), 7.69-7.76 (1H, m), 7.80 (1H, s), 7.95 (1H, dd, J=7.8, 1.7 Hz), 8.03 (1H, d, J=9.5 Hz), 11.02 (1H, s).

To a solution of ethyl 2-({2-[(cyclopropylcarbonyl)amino]imidazo[1,2-b]pyridazin-6-yl}oxy)benzoate (200 mg, 0.54 mmol) in tetrahydrofuran (10 mL) was added 4N aqueous sodium hydroxide solution (1.5 mL), and the mixture was stirred at room temperature for 3 hr. 6N Hydrochloric acid (1.5 mL) and ethyl acetate were added to the reaction mixture, and the aqueous layer was extracted with ethyl acetate (×4). Combined organic layer was washed with saturated brine, dried over anhydrous sodium sulfate, and filtrated. The filtrate was concentrated under reduced pressure, and the residue was washed with ethyl acetate/hexane to give the title compound (130 mg, 73%) as a white solid.

$^1$H-NMR (DMSO-d$_6$, 300 MHz) δ 0.72-0.83 (4H, m), 1.84-1.96 (1H, m), 7.07 (1H, d, J=9.6 Hz), 7.35-7.46 (2H, m), 7.66-7.73 (1H, m), 7.81 (1H, s), 7.94 (1H, dd, J=7.7, 1.7 Hz), 8.00 (1H, d, J=9.6 Hz), 11.02 (1H, s).

Example 277

Production of 2-({2-[(cyclopropylcarbonyl)amino]imidazo[1,2-b]pyridazin-6-yl}thio)benzoic acid

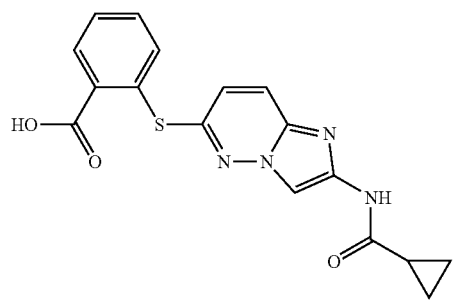

A mixture of methyl 2-mercaptobenzoate (1030 mg, 6.1 mmol), N-(6-iodoimidazo[1,2-b]pyridazin-2-yl)cyclopropanecarboxamide (1.0 g, 3.1 mmol), potassium carbonate (1050 mg, 7.6 mmol) and N,N-dimethylformamide (10 mL) was stirred at 80° C. for 7 hr. The mixture was evaporated under reduced pressure, and ethyl acetate/tetrahydrofuran and water were added to the residue. The aqueous layer was extracted with ethyl acetate/tetrahydrofuran (×3). Combined organic layer was washed with saturated brine, dried over anhydrous sodium sulfate, and filtrated. The filtrate was concentrated under reduced pressure, and the residue was purified by silica gel column chromatography (ethyl acetate/hexane=40/60→90/10) to give methyl 2-({2-[(cyclopropylcarbonyl)amino]imidazo[1,2-b]pyridazin-6-yl}thio)benzoate (200 mg, 18%) as a brown solid.

¹H-NMR (DMSO-d₆, 300 MHz) δ 0.78-0.89 (4H, m), 1.90-2.00 (1H, m), 3.85 (3H, s), 7.16 (1H, d, J=9.5 Hz), 7.28 (1H, d, J=8.0 Hz), 7.39-7.46 (1H, m), 7.48-7.55 (1H, m), 7.90-8.00 (2H, m), 8.21 (1H, s), 11.21 (1H, s).

In the same manner as in Example 276 and using methyl 2-({2-[(cyclopropylcarbonyl)amino]imidazo[1,2-b]pyridazin-6-yl}thio)benzoate (390 mg, 1.1 mmol) and 4N aqueous sodium hydroxide solution (2 mL) as starting materials, the title compound (340 mg, 92%) was obtained as a pale-yellow solid.

¹H-NMR (DMSO-d₆, 300 MHz) δ 0.77-0.91 (4H, m), 1.88-2.02 (1H, m), 7.15-7.21 (2H, m), 7.38 (1H, t, J=6.8 Hz), 7.43-7.50 (1H, m), 7.89-8.01 (2H, m), 8.22 (1H, s), 11.21 (1H, s).

Example 278

Production of 2-({2-[(cyclopropylcarbonyl)amino]imidazo[1,2-b]pyridazin-6-yl}thio)-N-methylbenzamide

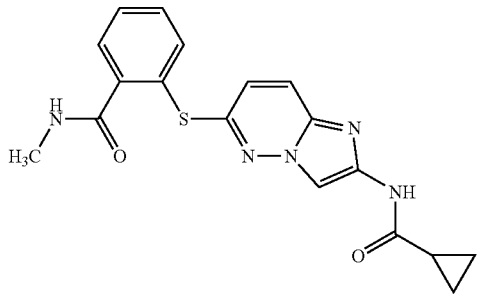

A mixture of 2-({2-[(cyclopropylcarbonyl)amino]imidazo[1,2-b]pyridazin-6-yl}thio)benzoic acid (120 mg, 0.35 mmol), a solution of methylamine in tetrahydrofuran (2M, 1 mL, 2.0 mmol), O-(7-azabenzotriazol-1-yl)-N,N,N',N'-tetramethyluronium hexafluorophosphate (200 mg, 0.53 mmol) and N,N-dimethylformamide (4 mL) was stirred at room temperature for 5 hr. The mixture was evaporated under reduced pressure, ethyl acetate/tetrahydrofuran and water were added to the residue, and the aqueous layer was extracted with ethyl acetate/tetrahydrofuran (×4). Combined organic layer was washed with saturated brine, dried over anhydrous sodium sulfate, and filtrated. The filtrate was concentrated under reduced pressure, and the residue was purified by silica gel column chromatography (ethyl acetate/hexane=40/60→90/10) to give the title compound (45 mg, 41%) as a pale-yellow solid.

¹H-NMR (DMSO-d₆, 300 MHz) δ 0.77-0.88 (4H, m), 1.89-1.97 (1H, m), 2.71 (3H, d, J=4.5 Hz), 6.97 (1H, d, J=9.5 Hz), 7.38-7.46 (3H, m), 7.49-7.56 (1H, m), 7.88 (1H, d, J=9.5 Hz), 8.15 (1H, s), 8.40 (1H, t, J=4.5 Hz), 11.15 (1H, s).

Example 279

Production of 1,3-dimethyl-N-{2-methyl-5-[(2-{[(1-methylcyclopropyl)carbonyl]amino}imidazo[1,2-b]pyridazin-6-yl)oxy]phenyl}-1H-pyrazole-5-carboxamide

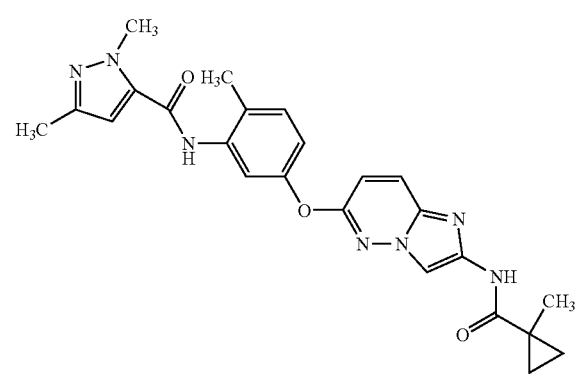

To a solution of 1-methylcyclopropanecarboxylic acid (97 mg, 0.97 mmol) in tetrahydrofuran (1.5 mL) were added N,N-dimethylformamide (1 drop) and oxalyl chloride (83 μL, 0.97 mmol), and the mixture was stirred at room temperature for 30 min. The reaction mixture was added to a solution of N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol) in N,N-dimethylacetamide (5 mL), and the mixture was stirred at room temperature for 1 hr. Ethyl acetate/tetrahydrofuran and saturated aqueous sodium hydrogencarbonate solution were added to the mixture, and the aqueous layer was extracted with ethyl acetate/tetrahydrofuran (×4). Combined organic layer was washed with water and saturated brine, dried over anhydrous sodium sulfate, and filtrated. The filtrate was concentrated under reduced pressure, and the residue was purified by silica gel column chromatography (ethyl acetate/hexane=30/70→100/0) to give the title compound (105 mg, 74%) as a white solid.

¹H-NMR (DMSO-d₆, 300 MHz) δ 0.60-0.68 (2H, m), 1.09-1.15 (2H, m), 1.40 (3H, s), 2.19 (3H, s), 2.25 (3H, s), 3.98 (3H, s), 6.81 (1H, s), 7.05 (1H, d, J=9.6 Hz), 7.10 (1H, dd, J=8.7, 2.4 Hz), 7.28 (1H, d, J=2.4 Hz), 7.35 (1H, d, J=8.7 Hz), 7.98 (1H, s), 8.02 (1H, d, J=9.6 Hz), 9.80 (1H, s), 10.15 (1H, s).

Example 280

Production of 1,3-dimethyl-N-{2-methyl-5-[(2-{[(2-methylcyclopropyl)carbonyl]amino}imidazo[1,2-b]pyridazin-6-yl)oxy]phenyl}-1H-pyrazole-5-carboxamide

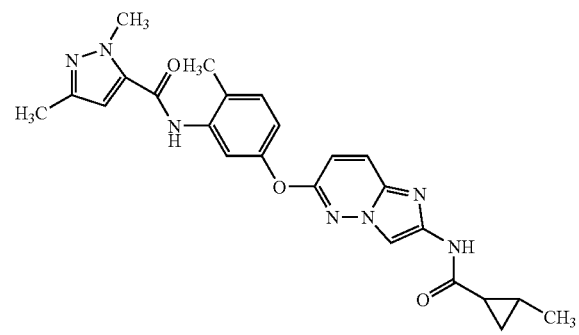

In the same manner as in Example 279 and using 2-methylcyclopropanecarboxylic acid (97 mg, 0.97 mmol), tetrahydrofuran (1.5 mL), N,N-dimethylformamide (1 drop), oxalyl chloride (83 μL, 0.97 mmol), N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol) and N,N-dimethylacetamide (5 mL) as starting materials, the title compound (155 mg, 70%) was obtained as a white solid.

$^1$H-NMR (DMSO-$d_6$, 300 MHz) δ 0.58-0.69 (1H, m), 0.93-1.04 (1H, m), 1.04-1.12 (3H, m), 1.17-1.28 (1H, m), 1.61-1.71 (1H, m), 2.20 (3H, s), 2.25 (3H, s), 3.98 (3H, s), 6.81 (1H, s), 7.03 (1H, d, J=9.5 Hz), 7.09 (1H, dd, J=8.3, 2.7 Hz), 7.27 (1H, d, J=2.7 Hz), 7.34 (1H, d, J=8.3 Hz), 7.92 (1H, s), 8.02 (1H, d, J=9.5 Hz), 9.79 (1H, s), 10.97 (1H, s).

Example 281

Production of N-[5-({2-[(cyclobutylcarbonyl)amino]imidazo[1,2-b]pyridazin-6-yl}oxy)-2-methylphenyl]-1,3-dimethyl-1H-pyrazole-5-carboxamide

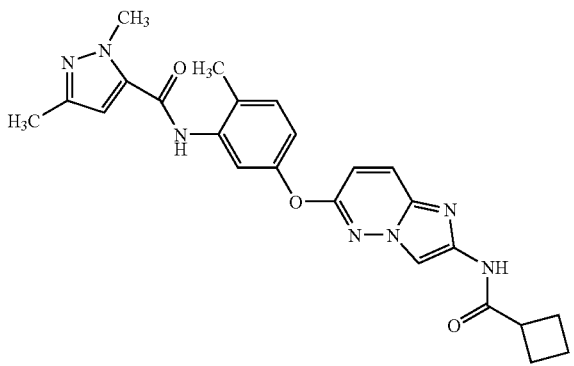

In the same manner as in Example 264 and using N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol), cyclobutanecarbonyl chloride (86 mg, 0.73 mmol) and N,N-dimethylacetamide (5 mL) as starting materials, the title compound (170 mg, 76%) was obtained as a white solid.

$^1$H-NMR (DMSO-$d_6$, 300 MHz) δ 1.73-1.98 (3H, m), 2.01-2.22 (4H, m), 2.19 (3H, s), 2.25 (3H, s), 3.99 (3H, s), 6.81 (1H, s), 7.04 (1H, d, J=9.8 Hz), 7.10 (1H, dd, J=8.7, 2.4 Hz), 7.28 (1H, d, J=2.4 Hz), 7.35 (1H, d, J=8.7 Hz), 7.96-8.06 (2H, m), 9.81 (1H, s), 10.64 (1H, s).

Example 282

Production of 1,3-dimethyl-N-[2-methyl-5-({2-[(3-methylbut-2-enoyl)amino]imidazo[1,2-b]pyridazin-6-yl}oxy)phenyl]-1H-pyrazole-5-carboxamide

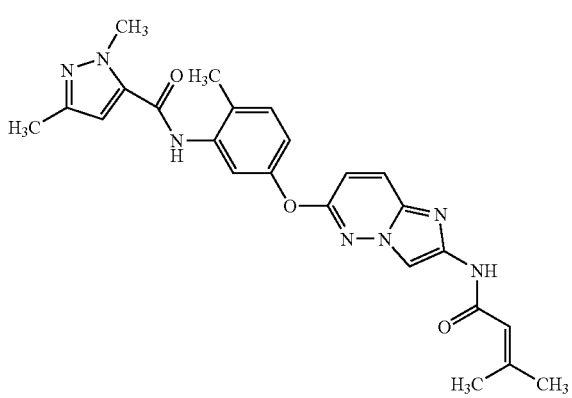

In the same manner as in Example 264 and using N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol), 3-methylbut-2-enoylchloride (81 μL, 0.73 mmol) and N,N-dimethylacetamide (5 mL) as starting materials, the title compound (150 mg, 68%) was obtained as a pale-yellow solid.

$^1$H-NMR (DMSO-$d_6$, 300 MHz) δ 1.85 (3H, s), 2.17 (3H, d, J=0.8 Hz), 2.19 (3H, s), 2.25 (3H, s), 3.98 (3H, s), 5.98 (1H, s), 6.81 (1H, s), 7.03 (1H, d, J=9.6 Hz), 7.10 (1H, dd, J=8.5, 2.4 Hz), 7.28 (1H, d, J=2.4 Hz), 7.35 (1H, d, J=8.5 Hz), 7.96-8.05 (2H, m), 9.81 (1H, s), 10.69 (1H, s).

Example 283

Production of N-{5-[(2-{[(2E)-3-methoxyprop-2-enoyl]amino}imidazo[1,2-b]pyridazin-6-yl)oxy]-2-methylphenyl}-1,3-dimethyl-1H-pyrazole-5-carboxamide

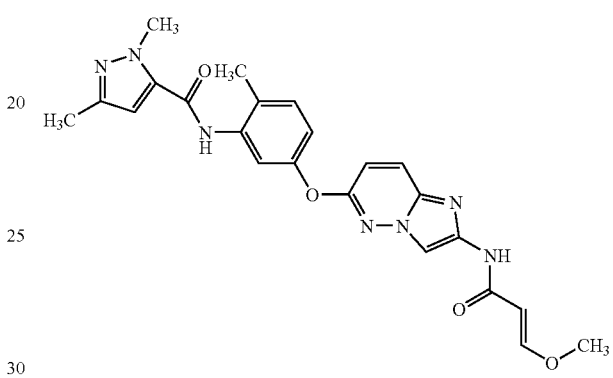

In the same manner as in Example 279 and using (2E)-3-methoxyacrylic acid (99 mg, 0.97 mmol), tetrahydrofuran (1.5 mL), N,N-dimethylformamide (1 drop), oxalyl chloride (83 μL, 0.97 mmol), N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol) and N,N-dimethylacetamide (5 mL) as starting materials, the title compound (63 mg, 28%) was obtained as a white solid.

$^1$H-NMR (DMSO-$d_6$, 300 MHz) δ 2.19 (3H, s), 2.25 (3H, s), 3.68 (3H, s), 3.98 (3H, s), 5.68 (1H, d, J=12.2 Hz), 6.83 (1H, s), 7.04 (1H, d, J=9.6 Hz), 7.10 (1H, dd, J=8.7, 2.6 Hz), 7.27 (1H, d, J=2.6 Hz), 7.35 (1H, d, J=8.7 Hz), 7.54 (1H, d, J=12.2 Hz), 7.96-8.07 (2H, m), 9.84 (1H, s), 10.61 (1H, s).

Example 284

Production of N-{5-[(2-{[(ethylamino)carbonyl]amino}imidazo[1,2-b]pyridazin-6-yl)oxy]-2-methylphenyl}-1,3-dimethyl-1H-pyrazole-5-carboxamide

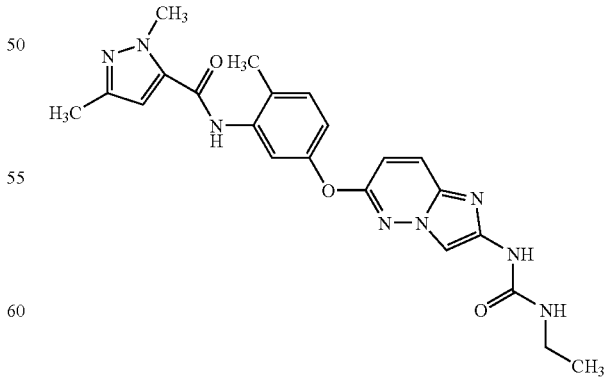

To a solution of N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol) in pyridine (3 mL) was added ethyl isocyanate (380 μL, 4.8 mmol), and the mixture was stirred at room temperature for 2 hr. Ethyl acetate/tetrahydrofuran and water were added to the reaction mixture, and the aqueous layer was extracted with ethyl acetate/tetrahydrofuran (×3). Combined organic layer was washed with saturated brine, dried over anhydrous sodium sulfate, and filtrated. The filtrate was concentrated under reduced pressure, and the residue was purified by silica gel column chromatography (ethyl acetate/hexane=30/70→100/0) to give the title compound (160 mg, 72%) as a pale-yellow solid.

$^1$H-NMR (DMSO-$d_6$, 300 MHz) δ 1.05 (3H, t, J=7.2 Hz), 2.20 (3H, s), 2.24 (3H, s), 3.06-3.18 (2H, m), 3.98 (3H, s), 6.47-6.55 (1H, m), 6.81 (1H, s), 6.97 (1H, d, J=9.6 Hz), 7.08 (1H, dd, J=8.7, 2.6 Hz), 7.26 (1H, d, J=2.6 Hz), 7.34 (1H, d, J=8.7 Hz), 7.70 (1H, s), 7.95 (1H, d, J=9.6 Hz), 8.99 (1H, s), 9.80 (1H, s).

Example 285
Production of 1,3-dimethyl-N-{2-methyl-5-[(2-{[(methylsulfonyl)acetyl]amino}imidazo[1,2-b]pyridazin-6-yl)oxy]phenyl}-1H-pyrazole-5-carboxamide

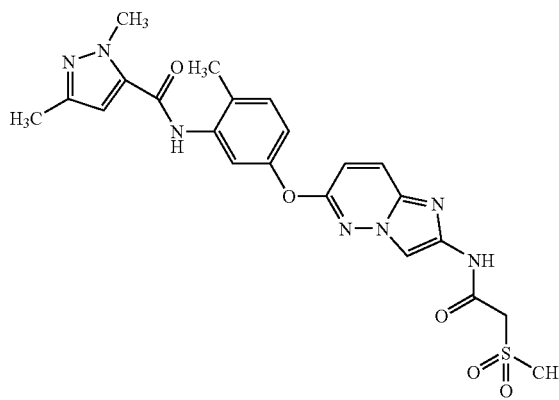

In the same manner as in Example 279 and using (methylsulfonyl)acetic acid (100 mg, 0.73 mmol), tetrahydrofuran (1.5 mL), N,N-dimethylformamide (1 drop), oxalyl chloride (63 μL, 0.73 mmol), N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol) and N,N-dimethylacetamide (5 mL) as starting materials, the title compound (91 mg, 38%) was obtained as a pale-yellow solid.

$^1$H-NMR (DMSO-$d_6$, 300 MHz) δ 2.20 (3H, s), 2.25 (3H, s), 3.17 (3H, s), 3.99 (3H, s), 4.37 (2H, s), 6.81 (1H, s), 7.07-7.14 (2H, m), 7.29 (1H, d, J=2.7 Hz), 7.35 (1H, d, J=8.7 Hz), 8.01 (1H, s), 8.08 (1H, d, J=9.5 Hz), 9.79 (1H, s), 11.26 (1H, s).

Example 286
Production of N-[5-({2-[(cyclopropylcarbonyl)amino]imidazo[1,2-b]pyridazin-6-yl}oxy)-2-fluorophenyl]-1-ethyl-3-methyl-1H-pyrazole-5-carboxamide

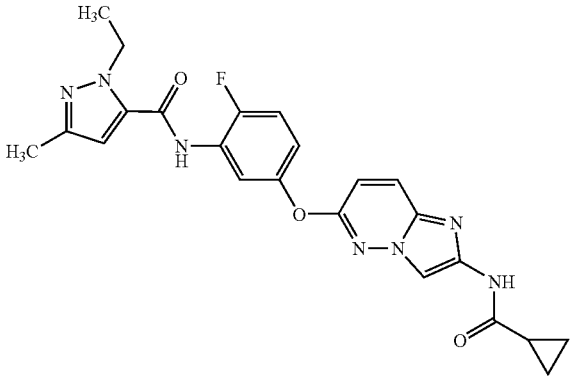

In the same manner as in Example 259 and using 1-ethyl-3-methyl-1H-pyrazole-5-carboxylic acid (120 mg, 0.79 mmol), tetrahydrofuran (5 mL), N,N-dimethylformamide (1 drop), oxalyl chloride (89 μL, 1.0 mmol), N-[6-(3-amino-4-fluorophenoxy)imidazo[1,2-b]pyridazin-2-yl]cyclopropanecarboxamide (200 mg, 0.61 mmol) and N,N-dimethylacetamide (7 mL) as starting materials, the title compound (150 mg, 53%) was obtained as a white solid.

$^1$H-NMR (DMSO-$d_6$, 300 MHz) δ 0.75-0.85 (4H, m), 1.29 (3H, t, J=7.0 Hz), 1.86-1.97 (1H, m), 2.21 (3H, s), 4.40 (2H, q, J=7.0 Hz), 6.83 (1H, s), 7.07 (1H, d, J=9.5 Hz), 7.16-7.25 (1H, m), 7.34-7.45 (1H, m), 7.54 (1H, dd, J=6.4, 3.0 Hz), 7.94 (1H, s), 8.04 (1H, d, J=9.5 Hz), 10.08 (1H, s), 11.06 (1H, s).

Example 287

Production of N-[5-({2-[(cyclopropylcarbonyl)amino]imidazo[1,2-b]pyridazin-6-yl}oxy)-2-fluorophenyl]-1-methyl-1H-pyrazole-5-carboxamide

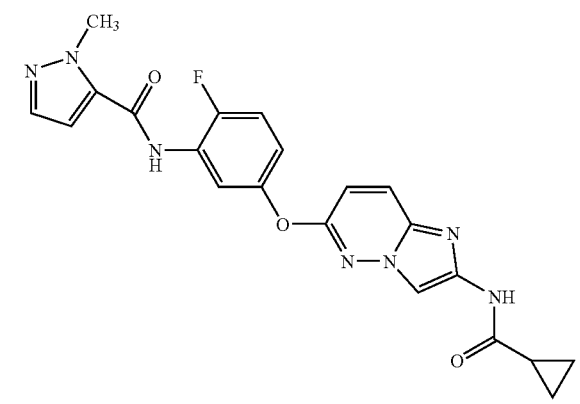

In the same manner as in Example 259 and using 1-methyl-1H-pyrazole-5-carboxylic acid (100 mg, 0.79 mmol), tetrahydrofuran (5 mL), N,N-dimethylformamide (1 drop), oxalyl chloride (89 μL, 1.0 mmol), N-[6-(3-amino-4-fluorophenoxy)imidazo[1,2-b]pyridazin-2-yl]cyclopropanecarboxamide (200 mg, 0.61 mmol) and N,N-dimethylacetamide (7 mL) as starting materials, the title compound (180 mg, 68%) was obtained as a white solid. melting point 253° C.

$^1$H-NMR (DMSO-$d_6$, 300 MHz) δ 0.75-0.85 (4H, m), 1.87-1.98 (1H, m), 4.06 (3H, s), 7.07 (1H, d, J=7.2 Hz), 7.09 (1H, s), 7.17-7.26 (1H, m), 7.34-7.46 (1H, m), 7.50-7.56 (2H, m), 7.94 (1H, s), 8.04 (1H, d, J=9.8 Hz), 10.19 (1H, s), 11.06 (1H, s).

Example 288

Production of N-[5-({2-[(3-hydroxy-3-methylbutanoyl)amino]imidazo[1,2-b]pyridazin-6-yl}oxy)-2-methylphenyl]-1,3-dimethyl-1H-pyrazole-5-carboxamide

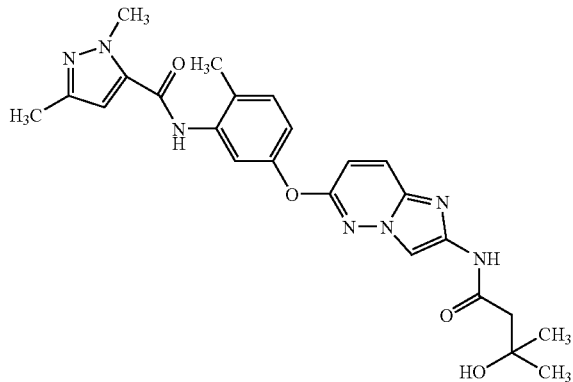

In the same manner as in Example 278 and using 3-hydroxy-3-methylbutanoic acid (74 mg, 0.63 mmol), N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol), O-(7-azabenzotriazol-1-yl)-N,N,N',N'-tetramethyluronium hexafluorophosphate (240 mg, 0.63 mmol), N,N-diisopropylethylamine (190 mg, 1.5 mmol) and N,N-dimethylformamide (7 mL) as starting materials, the title compound (150 mg, 66%) was obtained as a pale-yellow solid.

$^1$H-NMR (DMSO-d$_6$, 300 MHz) δ 1.19 (6H, s), 2.19 (3H, s), 2.25 (3H, s), 2.48 (2H, s), 3.98 (3H, s), 4.76 (1H, s), 6.81 (1H, s), 6.99-7.14 (2H, m), 7.28 (1H, d, J=2.3 Hz), 7.35 (1H, d, J=8.3 Hz), 7.94-8.06 (2H, m), 9.79 (1H, s), 10.58 (1H, s).

Example 289

Production of N-[5-({2-[(cyclopropylcarbonyl)amino]imidazo[1,2-b]pyridazin-6-yl}oxy)-2-fluorophenyl]-2,4-dimethyl-1,3-oxazole-5-carboxamide

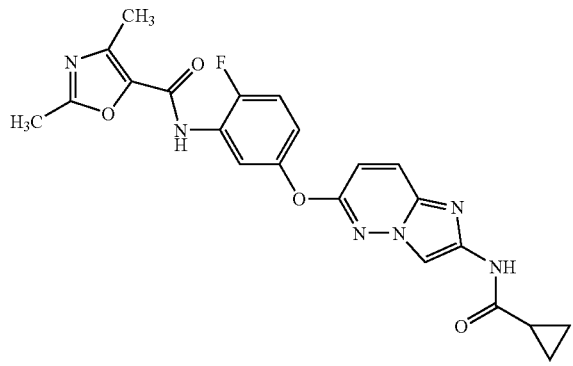

In the same manner as in Example 259 and using 2,4-dimethyl-1,3-oxazole-5-carboxylic acid (84 mg, 0.59 mmol), tetrahydrofuran (5 mL), N,N-dimethylformamide (1 drop), oxalyl chloride (61 μL, 0.71 mmol), N-[6-(3-amino-4-fluorophenoxy)imidazo[1,2-b]pyridazin-2-yl]cyclopropanecarboxamide (150 mg, 0.46 mmol) and N,N-dimethylacetamide (7 mL) as starting materials, the title compound (140 mg, 67%) was obtained as a white solid. melting point 202° C.

$^1$H-NMR (DMSO-d$_6$, 300 MHz) δ 0.73-0.86 (4H, m), 1.84-1.98 (1H, m), 2.3.5 (3H, s), 2.48 (3H, s), 7.07 (1H, d, J=9.6 Hz), 7.14-7.23 (1H, m), 7.39 (1H, dd, J=10.0, 9.0 Hz), 7.56 (1H, dd, J=6.4, 3.0 Hz), 7.95 (1H, s), 8.04 (1H, d, J=9.6 Hz), 9.95 (1H, s), 11.07 (1H, s).

Example 290

Production of N-[5-({2-[(cyclopropylcarbonyl)amino]imidazo[1,2-b]pyridazin-6-yl}oxy)-2-fluorophenyl]-4-methyl-1,3-oxazole-5-carboxamide

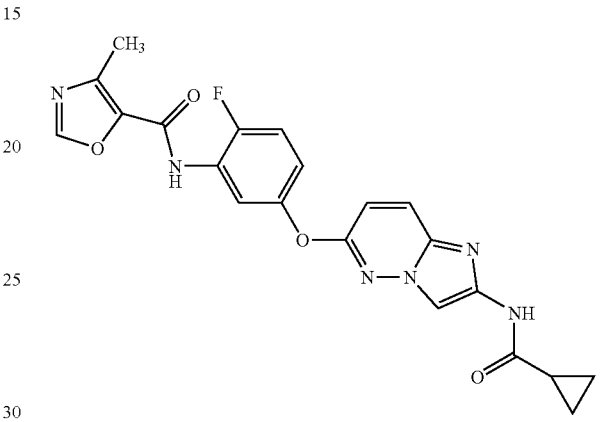

In the same manner as in Example 259 and using 4-methyl-1,3-oxazole-5-carboxylic acid (76 mg, 0.59 mmol), tetrahydrofuran (10 mL), N,N-dimethylformamide (1 drop), oxalyl chloride (61 μL, 0.71 mmol), N-[6-(3-amino-4-fluorophenoxy)imidazo[1,2-b]pyridazin-2-yl]cyclopropanecarboxamide (150 mg, 0.46 mmol) and N,N-dimethylacetamide (7 mL) as starting material, the title compound (170 mg, 84%) was obtained as a white solid.

$^1$H-NMR (DMSO-d$_6$, 300 MHz) δ 0.74-0.86 (4H, m), 1.85-1.97 (1H, m), 2.41 (3H, s), 7.07 (1H, d, J=9.4 Hz), 7.16-7.25 (1H, m), 7.40 (1H, dd, J=10.0, 9.0 Hz), 7.57 (1H, dd, J=6.4, 3.0 Hz), 7.94 (1H, s), 8.04 (1H, d, J=9.4 Hz), 8.54 (1H, s), 10.10 (1H, s), 11.07 (1H, s).

Example 291

Production of N-[5-({2-[(cyclopropylcarbonyl)amino]imidazo[1,2-b]pyridazin-6-yl}oxy)-2-methylphenyl]-1-ethyl-1H-pyrazole-5-carboxamide

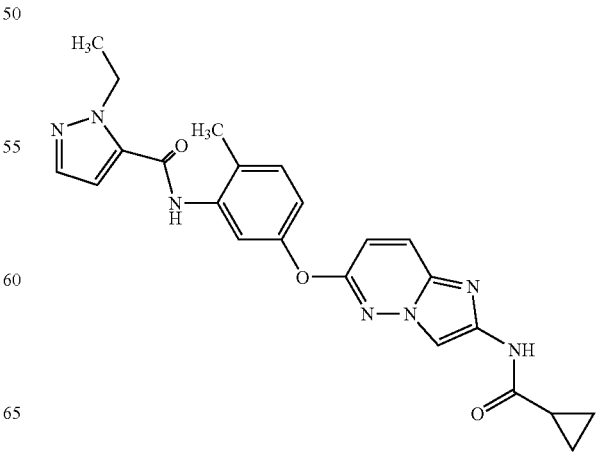

In the same manner as in Example 259 and using 1-ethyl-1H-pyrazole-5-carboxylic acid (110 mg, 0.80 mmol), tetrahydrofuran (5 mL), N,N-dimethylformamide (1 drop), oxalyl chloride (83 µL, 0.97 mmol), N-[6-(3-amino-4-methylphenoxy)imidazo[1,2-b]pyridazin-2-yl]cyclopropanecarboxamide (200 mg, 0.62 mmol) and N,N-dimethylacetamide (7 mL) as starting materials, the title compound (210 mg, 75%) was obtained as a white solid.

$^1$H-NMR (DMSO-$d_6$, 300 MHz) δ 0.73-0.85 (4H, m), 1.32 (3H, t, J=7.2 Hz), 1.86-1.96 (1H, m), 2.25 (3H, s), 4.50 (2H, q, J=7.2 Hz), 7.02-7.07 (2H, m), 7.11 (1H, dd, J=8.3, 2.4 Hz), 7.28 (1H, d, J=2.4 Hz), 7.36 (1H, d, J=8.3 Hz), 7.54 (1H, d, J=2.1 Hz), 7.93 (1H, s), 8.03 (1H, d, J=10.0 Hz), 9.92 (1H, s), 11.10 (1H, s).

Example 292

Production of N-{5-[(2-{[(2-methoxycyclopropyl)carbonyl]amino}imidazo[1,2-b]pyridazin-6-yl)oxy]-2-methylphenyl}-1,3-dimethyl-1H-pyrazole-5-carboxamide

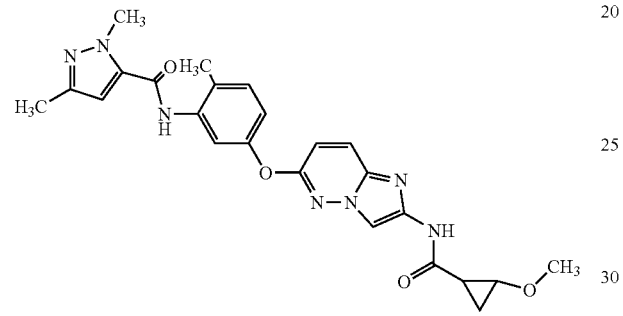

In the same manner as in Example 278 and using 2-methoxycyclopropanecarboxylic acid (86 mg, 0.74 mmol), N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.49 mmol), O-(7-azabenzotriazol-1-yl)-N,N,N',N'-tetramethyluronium hexafluorophosphate (280 mg, 0.74 mmol), N,N-diisopropylethylamine (190 mg, 1.5 mmol) and N,N-dimethylformamide (7 mL) as starting materials, the title compound (83 mg, 35%) was obtained as a pale-yellow solid.

$^1$H-NMR (DMSO-$d_6$, 300 MHz) δ 1.09-1.20 (2H, m), 2.03-2.13 (1H, m), 2.19 (3H, s), 2.25 (3H, s), 3.30 (3H, s), 3.40-3.49 (1H, m), 3.97 (3H, s), 6.81 (1H, s), 7.04 (1H, d, J=9.8 Hz), 7.09 (1H, dd, J=8.3, 2.7 Hz), 7.28 (1H, d, J=2.7 Hz), 7.34 (1H, d, J=8.3 Hz), 7.91 (1H, s), 8.03 (1H, d, J=9.8 Hz), 9.79 (1H, s), 11.09 (1H, s).

Example 293

Production of N-[5-({2-[(cyclopropylcarbonyl)amino]imidazo[1,2-b]pyridazin-6-yl}oxy)-2-methylphenyl]-4-methoxy-2-methyl-1,3-thiazole-5-carboxamide

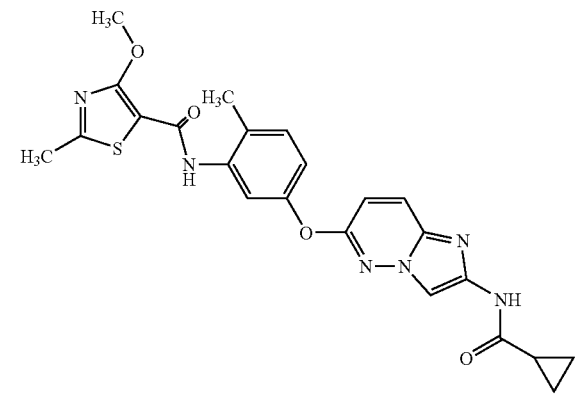

In the same manner as in Example 259 and using 4-methoxy-2-methyl-1,3-thiazole-5-carboxylic acid (120 mg, 0.70 mmol), tetrahydrofuran (5 mL), N,N-dimethylformamide (1 drop), oxalyl chloride (120 µL, 1.4 mmol), N-[6-(3-amino-4-methylphenoxy)imidazo[1,2-b]pyridazin-2-yl]cyclopropanecarboxamide (150 mg, 0.46 mmol) and N,N-dimethylacetamide (7 mL) as starting materials, the title compound (120 mg, 53%) was obtained as a white solid.

$^1$H-NMR (DMSO-$d_6$, 300 MHz) δ 0.74-0.85 (4H, m), 1.88-1.98 (1H, m), 2.32 (3H, s), 2.65 (3H, s), 4.18 (3H, s), 6.96 (1H, dd, J=8.3, 2.7 Hz), 7.03 (1H, d, J=9.8 Hz), 7.33 (1H, d, J=8.3 Hz), 7.93 (1H, s), 7.97 (1H, d, J=2.7 Hz), 8.02 (1H, d, J=9.8 Hz), 9.05 (1H, s), 11.06 (1H, s).

Example 294

Production of N-[5-({2-[(cyclopropylcarbonyl)amino]imidazo[1,2-b]pyridazin-6-yl}oxy)-2-fluorophenyl]-3-methoxy-1-methyl-1H-pyrazole-4-carboxamide

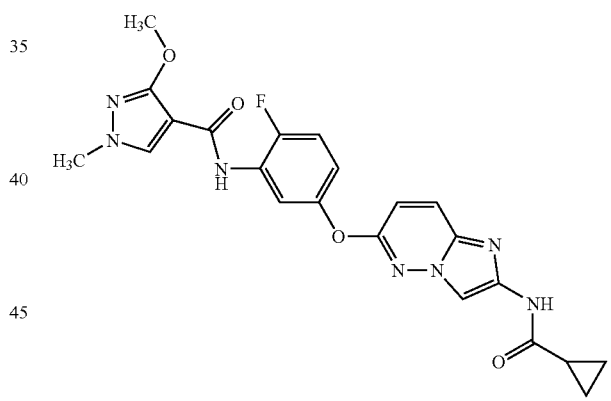

In the same manner as in Example 259 and using 3-methoxy-1-methyl-1H-pyrazole-4-carboxylic acid (93 mg, 0.60 mmol), tetrahydrofuran (5 mL), N,N-dimethylformamide (1 drop), oxalyl chloride (61 µL, 0.72 mmol), N-[6-(3-amino-4-fluorophenoxy)imidazo[1,2-b]pyridazin-2-yl]cyclopropanecarboxamide (150 mg, 0.46 mmol) and N,N-dimethylacetamide (7 mL) as starting materials, the title compound (59 mg, 28%) was obtained as a white solid.

$^1$H-NMR (DMSO-$d_6$, 300 MHz) δ 0.74-0.85 (4H, m), 1.86-1.97 (1H, m), 3.75 (3H, s), 4.01 (3H, s), 6.97-7.09 (2H, m), 7.33-7.44 (1H, m), 7.94 (1H, s), 8.04 (1H, d, J=9.8 Hz), 8.11-8.19 (2H, m), 8.94 (1H, d, J=2.7 Hz), 11.07 (1H, s).

Example 295

Production of N-[5-({2-[(cyclopropylcarbonyl)amino]imidazo[1,2-b]pyridazin-6-yl}oxy)-2-fluorophenyl]-4-methoxy-2-methyl-1,3-thiazole-5-carboxamide

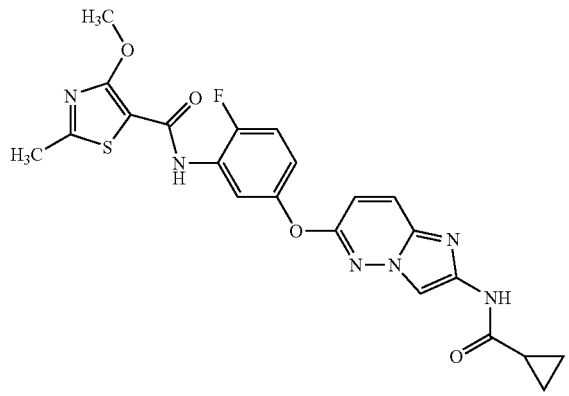

In the same manner as in Example 259 and using 4-methoxy-2-methyl-1,3-thiazole-5-carboxylic acid (100 mg, 0.60 mmol), tetrahydrofuran (5 mL), N,N-dimethylformamide (1 drop), oxalyl chloride (61 μL, 0.72 mmol), N-[6-(3-amino-4-fluorophenoxy)imidazo[1,2-b]pyridazin-2-yl]cyclopropanecarboxamide (150 mg, 0.46 mmol) and N,N-dimethylacetamide (7 mL) as starting materials, the title compound (89 mg, 40%) was obtained as a white solid.

$^1$H-NMR (DMSO-$d_6$, 300 MHz) δ 0.74-0.84 (4H, m), 1.88-1.96 (1H, m), 2.64-2.68 (3H, m), 4.18 (3H, s), 7.03-7.12 (2H, m), 7.42 (1H, dd, J=10.6, 9.1 Hz), 7.93 (1H, s), 8.01-8.09 (2H, m), 9.27 (1H, s), 11.06 (1H, s).

Example 296

Production of 1,3-dimethyl-N-[2-methyl-5-({2-[(oxirane-2-ylcarbonyl)amino]imidazo[1,2-b]pyridazin-6-yl}oxy)phenyl]-1H-pyrazole-5-carboxamide

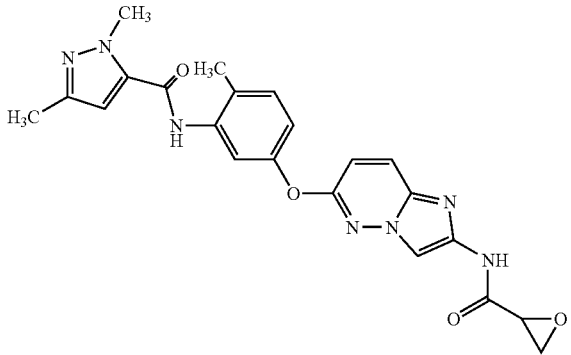

In the same manner as in Example 279 and using oxirane-2-carboxylic acid (54 mg, 0.62 mmol), tetrahydrofuran (1.5 mL), N,N-dimethylformamide (1 drop), oxalyl chloride (53 μL, 0.62 mmol), N-{5-[(2-aminoimidazo[1,2-b]pyridazin-6-yl)oxy]-2-methylphenyl}-1,3-dimethyl-1H-pyrazole-5-carboxamide hydrochloride (170 mg, 0.41 mmol) and N,N-dimethylacetamide (5 mL) as starting materials, the title compound (96 mg, 52%) was obtained as a white solid.

$^1$H-NMR (DMSO-$d_6$, 300 MHz) δ 2.19 (3H, s), 2.25 (3H, s), 2.88-2.99 (2H, m), 3.64-3.70 (1H, m), 3.97 (3H, s), 6.81 (1H, s), 7.04-7.16 (2H, m), 7.29 (1H, d, J=2.7 Hz), 7.35 (1H, d, J=8.3 Hz), 7.99 (1H, s), 8.07 (1H, d, J=9.8 Hz), 9.79 (1H, br. s), 11.30 (1H, br. s).

Example 297

Production of methyl 2-({[6-(3-{[(1,3-dimethyl-1H-pyrazol-5-yl)carbonyl]amino}-4-methylphenoxy)imidazo[1,2-b]pyridazin-2-yl]amino}carbonyl)cyclopropanecarboxylate

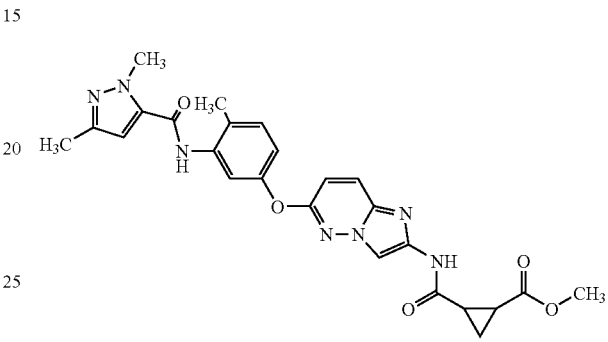

In the same manner as in Example 279 and using 2-(methoxycarbonyl)cyclopropanecarboxylic acid (140 mg, 0.78 mmol), tetrahydrofuran (1.5 mL), N,N-dimethylformamide (1 drop), oxalyl chloride (69 μL, 0.8 mmol), N-{5-[(2-aminoimidazo[1,2-b]pyridazin-6-yl)oxy]-2-methylphenyl}-1,3-dimethyl-1H-pyrazole-5-carboxamide hydrochloride (250 mg, 0.6 mmol) and N,N-dimethylacetamide (5 mL) as starting materials, the title compound (75 mg, 25%) was obtained as a white solid.

$^1$H-NMR (DMSO-$d_6$, 300 MHz) δ 1.19-1.29 (2H, m), 1.39-1.47 (1H, m), 2.19 (3H, s), 2.24 (3H, s), 2.25-2.33 (1H, m), 3.51 (3H, s), 3.97 (3H, s), 6.80 (1H, s), 7.04 (1H, d, J=9.8 Hz), 7.09 (1H, dd, J=8.3, 2.7 Hz), 7.27 (1H, d, J=2.7 Hz), 7.34 (1H, d, J=8.3 Hz), 7.90 (1H, s), 8.03 (1H, d, J=9.8 Hz), 9.79 (1H, s), 11.10 (1H, s).

Example 298

Production of N-[5-({2-[(cyclopropylcarbonyl)amino]imidazo[1,2-b]pyridazin-6-yl}oxy)-2-methylphenyl]-4-methyl-1,3-thiazole-5-carboxamide

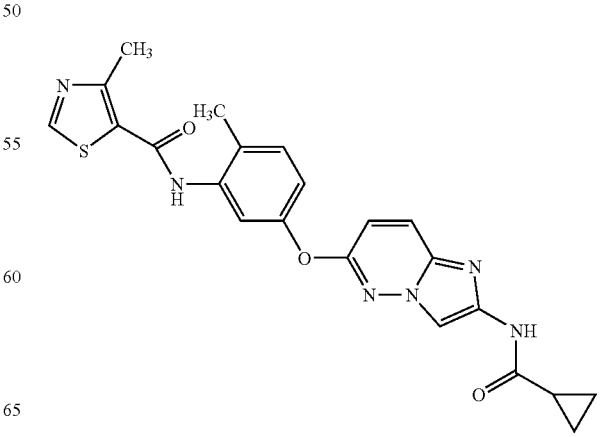

In the same manner as in Example 259 and using 4-methyl-1,3-thiazole-5-carboxylic acid (86 mg, 0.60 mmol), tetrahydrofuran (5 mL), N,N-dimethylformamide (1 drop), oxalyl chloride (100 μL, 1.2 mmol), N-[6-(3-amino-4-methylphenoxy)imidazo[1,2-b]pyridazin-2-yl]cyclopropanecarboxamide (150 mg, 0.46 mmol) and N,N-dimethylacetamide (7 mL) as starting materials, the title compound (170 mg, 80%) was obtained as a white solid.

¹H-NMR (DMSO-d₆, 300 MHz) δ 0.74-0.85 (4H, m), 1.85-1.97 (1H, m), 2.26 (3H, s), 2.65 (3H, s), 7.04 (1H, d, J=9.8 Hz), 7.09 (1H, dd, J=8.3, 2.7 Hz), 7.30-7.39 (2H, m), 7.94 (1H, s), 8.03 (1H, d, J=9.8 Hz), 9.12 (1H, s), 9.80 (1H, s), 11.06 (1H, s).

Example 299

Production of 1-({[6-(3-{[(1,3-dimethyl-1H-pyrazol-5-yl)carbonyl]amino}-4-methylphenoxy)imidazo[1,2-b]pyridazin-2-yl]amino}carbonyl)cyclopropyl acetate

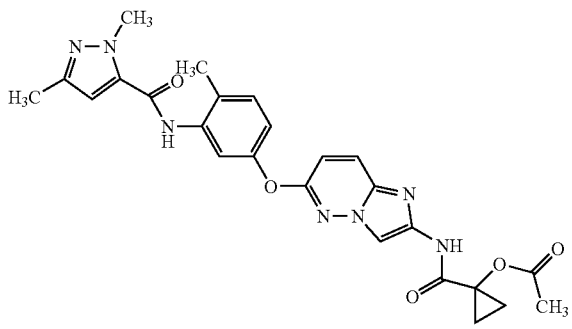

In the same manner as in Example 279 and using 1-acetoxycyclopropanecarboxylic acid (90 mg, 0.63 mmol), tetrahydrofuran (1.5 mL), N,N-dimethylformamide (1 drop), oxalyl chloride (54 μL, 0.63 mmol), N-{5-[(2-aminoimidazo[1,2-b]pyridazin-6-yl)oxy]-2-methylphenyl}-1,3-dimethyl-1H-pyrazole-5-carboxamide hydrochloride (200 mg, 0.48 mmol) and N,N-dimethylacetamide (5 mL) as starting materials, the title compound (180 mg, 74%) was obtained as a white solid.

¹H-NMR (DMSO-d₆, 300 MHz) δ 1.11-1.19 (2H, m), 1.42-1.48 (2H, m), 2.10 (3H, s), 2.19 (3H, s), 2.25 (3H, s), 3.98 (3H, s), 6.81 (1H, s), 7.06 (1H, d, J=9.8 Hz), 7.10 (1H, dd, J=8.3, 2.7 Hz), 7.28 (1H, d, J=2.7 Hz), 7.35 (1H, d, J=8.3 Hz), 7.99 (1H, s), 8.03 (1H, d, J=9.8 Hz), 9.79 (1H, br. s), 10.87 (1H, br. s).

Example 300

Production of N-{5-[(2-{[(1-hydroxycyclopropyl)carbonyl]amino}imidazo[1,2-b]pyridazin-6-yl)oxy]-2-methylphenyl}-1,3-dimethyl-1H-pyrazole-5-carboxamide

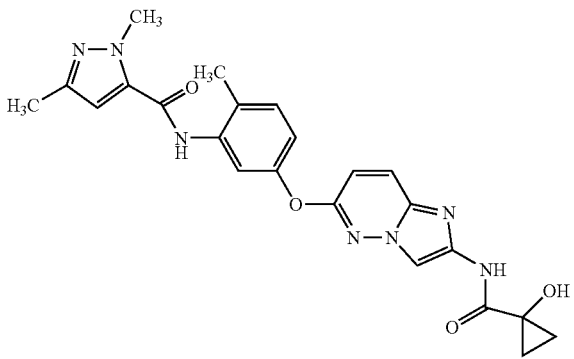

To a solution of 1-({[6-(3-{[(1,3-dimethyl-1H-pyrazol-5-yl)carbonyl]amino}-4-methylphenoxy)imidazo[1,2-b]pyridazin-2-yl]amino}carbonyl)cyclopropyl acetate (130 mg, 0.25 mmol) in tetrahydrofuran (2 mL) was added 1N aqueous sodium hydroxide solution (2 mL), and the mixture was stirred at room temperature for 2 hr. 1N Hydrochloric acid (2.5 mL) and ethyl acetate were added to the reaction mixture, and the aqueous layer was extracted with ethyl acetate (×3). Combined organic layer was washed with saturated brine, dried over anhydrous sodium sulfate, and filtrated. The filtrate was concentrated under reduced pressure, and the residue was washed with ethyl acetate/hexane to give the title compound (99 mg, 86%) as a pale-yellow solid.

¹H-NMR (DMSO-d₆, 300 MHz) δ 0.96-1.03 (2H, m), 1.13-1.22 (2H, m), 2.19 (3H, s), 2.26 (3H, s), 3.97 (3H, s), 6.63 (1H, br. s), 6.81 (1H, s), 7.03-7.14 (2H, m), 7.29 (1H, d, J=2.7 Hz), 7.35 (1H, d, J=8.3 Hz), 7.98 (1H, s), 8.06 (1H, d, J=9.8 Hz), 9.79 (2H, br. s).

Example 301

Production of N-[5-({2-[(cyclopropylcarbonyl)amino]imidazo[1,2-b]pyridazin-6-yl}oxy)-2-methylphenyl]-5-methyl-1,3-thiazole-4-carboxamide

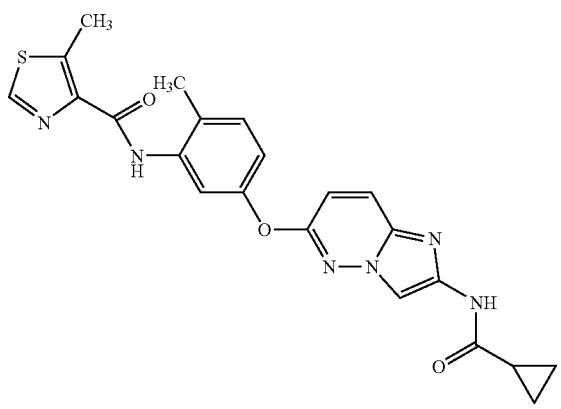

In the same manner as in Example 259 and using 5-methyl-1,3-thiazole-4-carboxylic acid (74 mg, 0.52 mmol), tetrahydrofuran (5 mL), N,N-dimethylformamide (1 drop), oxalyl chloride (170 μL, 2.0 mmol), N-[6-(3-amino-4-methylphenoxy)imidazo[1,2-b]pyridazin-2-yl]cyclopropanecarboxamide (130 mg, 0.40 mmol) and N,N-dimethylacetamide (7 mL) as starting materials, the title compound (110 mg, 60%) was obtained as a white solid.

¹H-NMR (DMSO-d₆, 300 MHz) δ 0.76-0.84 (4H, m), 1.85-1.96 (1H, m), 2.31 (3H, s), 2.78 (3H, s), 6.96-7.09 (2H, m), 7.34 (1H, d, J=8.7 Hz), 7.79 (1H, d, J=2.4 Hz), 7.94 (1H, s), 8.03 (1H, d, J=10.2 Hz), 9.02 (1H, s), 9.79 (1H, s), 11.07 (1H, s).

Example 302

Production of N-[5-({2-[(cyclopropylcarbonyl)amino]imidazo[1,2-b]pyridazin-6-yl}oxy)-2-methylphenyl]-3-methoxy-1-methyl-1H-pyrazole-5-carboxamide

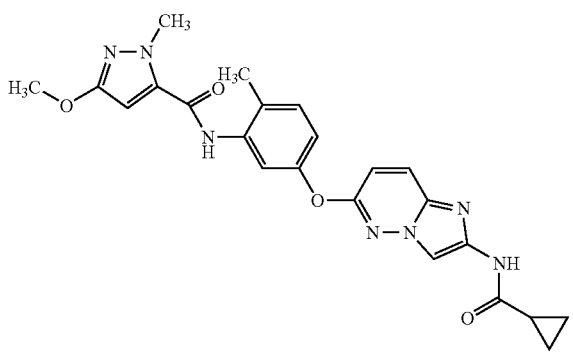

In the same manner as in Example 259 and using 3-methoxy-1-methyl-1H-pyrazole-5-carboxylic acid (80 mg, 0.52 mmol), tetrahydrofuran (5 mL), N,N-dimethylformamide (1 drop), oxalyl chloride (170 μL, 2.0 mmol), N-[6-(3-amino-4-methylphenoxy)imidazo[1,2-b]pyridazin-2-yl]cyclopropanecarboxamide (130 mg, 0.40 mmol) and N,N-dimethylacetamide (7 mL) as starting materials, the title compound (160 mg, 85%) was obtained as a white solid. melting point 224° C.

$^1$H-NMR (DMSO-$d_6$, 300 MHz) δ 0.72-0.86 (4H, m), 1.86-1.97 (1H, m), 2.24 (3H, s), 3.80 (3H, s), 3.90 (3H, s), 6.46 (1H, s), 7.04 (1H, d, J=9.6 Hz), 7.10 (1H, dd, J=8.7, 2.6 Hz), 7.26 (1H, d, J=2.6 Hz), 7.35 (1H, d, J=8.7 Hz), 7.93 (1H, s), 8.03 (1H, d, J=9.6 Hz), 9.86 (1H, s), 11.07 (1H, s).

Example 303

Production of N-(5-{[2-(but-2-ynoylamino)imidazo[1,2-b]pyridazin-6-yl]oxy}-2-methylphenyl)-1,3-dimethyl-1H-pyrazole-5-carboxamide

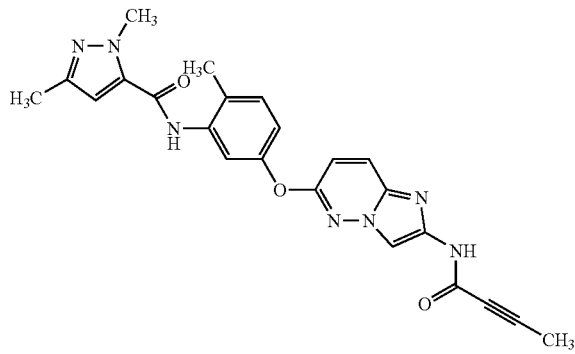

In the same manner as in Example 279 and using but-2-ynoic acid (46 mg, 0.54 mmol), tetrahydrofuran (1.5 mL), N,N-dimethylformamide (1 drop), oxalyl chloride (47 μL, 0.54 mmol), N-{5-[(2-aminoimidazo[1,2-b]pyridazin-6-yl)oxy]-2-methylphenyl}-1,3-dimethyl-1H-pyrazole-5-carboxamide hydrochloride (150 mg, 0.36 mmol) and N,N-dimethylacetamide (5 mL) as starting materials, the title compound (60 mg, 37%) was obtained as a white solid.

$^1$H-NMR (DMSO-$d_6$, 300 MHz) δ 2.03 (3H, s), 2.19 (3H, s), 2.25 (3H, s), 3.98 (3H, s), 6.81 (1H, s), 7.03-7.14 (2H, m), 7.28 (1H, d, J=2.4 Hz), 7.35 (1H, d, J=8.5 Hz), 7.94 (1H, s), 8.06 (1H, d, J=9.6 Hz), 9.81 (1H, br. s), 11.48 (1H, br. s).

Example 304

Production of N-(5-{[2-({[2-(hydroxymethyl)cyclopropyl]carbonyl}amino)imidazo[1,2-b]pyridazin-6-yl]oxy}-2-methylphenyl)-1,3-dimethyl-1H-pyrazole-5-carboxamide

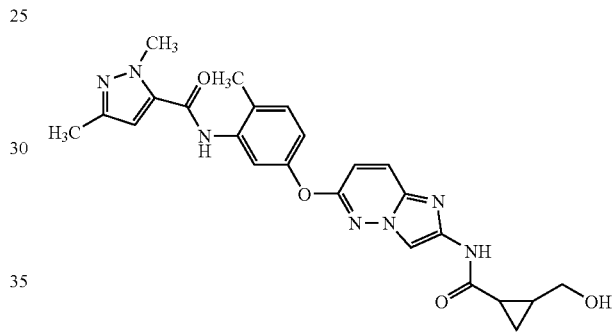

To a suspension of calcium chloride (135 mg, 1.1 mmol) in tetrahydrofuran/ethanol (2/1, 1 mL) was added a solution of sodium borohydride (92 mg, 2.2 mmol) and methyl 2-({[6-(3-{[(1,3-dimethyl-1H-pyrazol-5-yl)carbonyl]amino}-4-methylphenoxy)imidazo[1,2-b]pyridazin-2-yl]amino}carbonyl)cyclopropanecarboxylate (180 mg, 0.37 mmol) in tetrahydrofuran/ethanol (2/1, 1 mL), and the mixture was stirred at room temperature for 18 hr. Saturated aqueous ammonium chloride solution and ethyl acetate were added to the reaction mixture, and the aqueous layer was extracted with ethyl acetate (×3). Combined organic layer was washed with saturated brine, dried over anhydrous sodium sulfate, and filtrated. The filtrate was concentrated under reduced pressure, and the residue was purified by silica gel column chromatography (ethyl acetate/hexane=40/60→100/0, and then methanol/ethyl acetate=0/100→5/95) to give the title compound (35 mg, 20%) as a white solid.

$^1$H-NMR (DMSO-$d_6$, 300 MHz) δ 0.83-1.04 (2H, m), 1.37-1.49 (1H, m), 1.94-2.05 (1H, m), 2.19 (3H, s), 2.25 (3H, s), 3.41-3.53 (1H, m), 3.56-3.66 (1H, m), 3.97 (3H, s), 4.44 (1H, t, J=5.2 Hz), 6.81 (1H, s), 7.03 (1H, d, J=9.6 Hz), 7.09

(1H, dd, J=8.5, 2.6 Hz), 7.27 (1H, d, J=2.6 Hz), 7.34 (1H, d, J=8.5 Hz), 7.95 (1H, s), 8.03 (1H, d, J=9.6 Hz), 9.80 (1H, s), 10.99 (1H, s).

Example 305

Production of N-(5-{[2-({[2-(1-hydroxy-1-methylethyl)cyclopropyl]carbonyl}amino)imidazo[1,2-b]pyridazin-6-yl]oxy}-2-methylphenyl)-1,3-dimethyl-1H-pyrazole-5-carboxamide

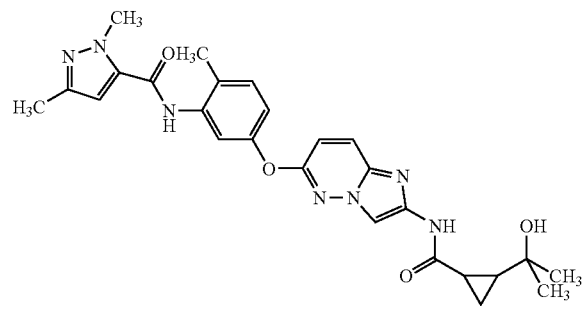

To a solution of methyl 2-({[6-(3-{[(1,3-dimethyl-1H-pyrazol-5-yl)carbonyl]amino}-4-methylphenoxy)imidazo[1,2-b]pyridazin-2-yl]amino}carbonyl)cyclopropanecarboxylate (250 mg, 0.49 mmol) in tetrahydrofuran (5 mL) was added a solution of iodo(methyl)magnesium in diethyl ether (2M, 540 μL, 1.1 mmol) at 0° C., and the mixture was stirred at room temperature for 1 hr. 0.5N Hydrochloric acid (3 mL) and ethyl acetate were added to the reaction mixture, and the aqueous layer was extracted with ethyl acetate (×3). Combined organic layer was washed with saturated brine, dried over anhydrous sodium sulfate, and filtrated. The filtrate was concentrated under reduced pressure, and the residue was washed with ethyl acetate/hexane to give the title compound (190 mg, 78%) as a pale-green solid.
$^1$H-NMR (CDCl$_3$, 300 MHz) δ 1.35-1.46 (1H, m), 1.67 (3H, s), 1.69-1.78 (1H, m), 2.06-2.23 (2H, m), 2.30 (3H, s), 2.34 (3H, s), 3.70 (3H, s), 4.12 (3H, s), 6.43 (1H, s), 6.85 (1H, d, J=9.6 Hz), 6.97 (1H, dd, J=8.3, 2.4 Hz), 7.24-7.28 (1H, m), 7.58 (1H, s), 7.73 (1H, d, J=9.6 Hz), 7.94 (1H, m), 8.13 (1H, s), 8.97 (1H, s).

Example 306

Production of N-[5-({2-[(cyclopropylcarbonyl)amino]imidazo[1,2-b]pyridazin-6-yl}oxy)-2-methylphenyl]-3-ethyl-1-methyl-1H-pyrazole-5-carboxamide

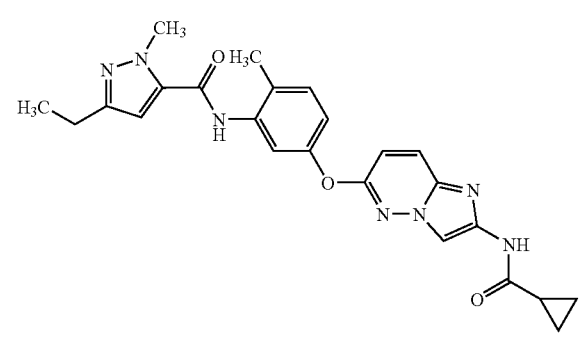

In the same manner as in Example 259 and using 3-ethyl-1-methyl-1H-pyrazole-5-carboxylic acid (120 mg, 0.80 mmol), tetrahydrofuran (5 mL), N,N-dimethylformamide (1 drop), oxalyl chloride (170 μL, 2.0 mmol), N-[6-(3-amino-4-methylphenoxy)imidazo[1,2-b]pyridazin-2-yl]cyclopropanecarboxamide (200 mg, 0.62 mmol) and N,N-dimethylacetamide (7 mL) as starting materials, the title compound (190 mg, 68%) was obtained as a white solid.
$^1$H-NMR (DMSO-d$_6$, 300 MHz) δ 0.73-0.86 (4H, m), 1.19 (3H, t, J=7.8 Hz), 1.87-1.97 (1H, m), 2.25 (3H, s), 2.57 (2H, q, J=7.8 Hz), 3.99 (3H, s), 6.85 (1H, s), 7.04 (1H, d, J=9.5 Hz), 7.10 (1H, d, J=8.3 Hz), 7.27 (1H, s), 7.35 (1H, d, J=8.3 Hz), 7.94 (1H, s), 8.03 (1H, d, J=9.5 Hz), 9.81 (1H, s), 11.06 (1H, s).

Example 307

Production of 2-chloro-N-[5-({2-[(cyclopropylcarbonyl)amino]imidazo[1,2-b]pyridazin-6-yl}oxy)-2-methylphenyl]-4-methyl-1,3-thiazole-5-carboxamide

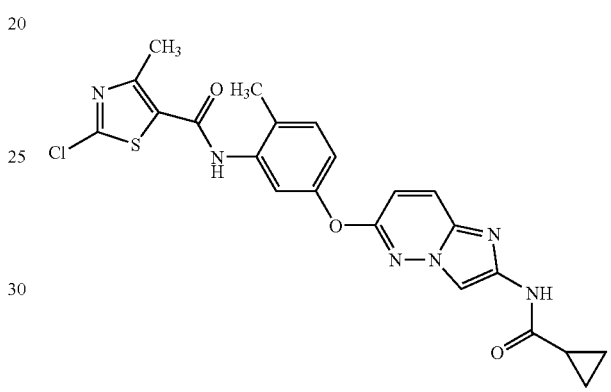

In the same manner as in Example 259 and using 2-chloro-4-methyl-1,3-thiazole-5-carboxylic acid (140 mg, 0.80 mmol), tetrahydrofuran (5 mL), N,N-dimethylformamide (1 drop), oxalyl chloride (170 μL, 2.0 mmol), N-[6-(3-amino-4-methylphenoxy)imidazo[1,2-b]pyridazin-2-yl]cyclopropanecarboxamide (200 mg, 0.62 mmol) and N,N-dimethylacetamide (7 mL) as starting materials, the title compound (270 mg, 91%) was obtained as a pale-green solid.
$^1$H-NMR (DMSO-d$_6$, 300 MHz) δ 0.74-0.85 (4H, m), 1.86-1.96 (1H, m), 2.25 (3H, s), 2.58 (3H, s), 7.04 (1H, d, J=9.5 Hz), 7.10 (1H, dd, J=8.3, 2.3 Hz), 7.31-7.38 (2H, m), 7.93 (1H, s), 8.03 (1H, d, J=9.5 Hz), 9.86 (1H, s), 11.06 (1H, s).

Example 308

Production of 2-chloro-N-[5-({2-[(cyclopropylcarbonyl)amino]imidazo[1,2-b]pyridazin-6-yl}oxy)-2-fluorophenyl]-4-methyl-1,3-thiazole-5-carboxamide

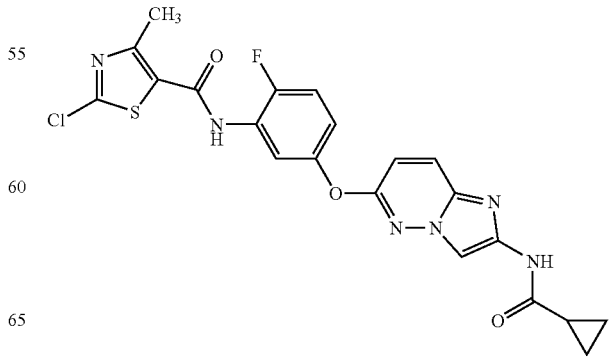

In the same manner as in Example 259 and using 2-chloro-4-methyl-1,3-thiazole-5-carboxylic acid (140 mg, 0.80 mmol), tetrahydrofuran (5 mL), N,N-dimethylformamide (1 drop), oxalyl chloride (140 μL, 1.6 mmol), N-[6-(3-amino-4-fluorophenoxy)imidazo[1,2-b]pyridazin-2-yl]cyclopropanecarboxamide (200 mg, 0.61 mmol) and N,N-dimethylacetamide (7 mL) as starting materials, the title compound (230 mg, 78%) was obtained as a pale-green solid.

$^1$H-NMR (DMSO-d$_6$, 300 MHz) δ 0.75-0.86 (4H, m), 1.85-1.97 (1H, m), 2.58 (3H, s), 7.08 (1H, d, J=9.4 Hz), 7.17-7.26 (1H, m), 7.41 (1H, dd, J=10.0, 9.0 Hz), 7.59 (1H, dd, J=6.3, 2.9 Hz), 7.94 (1H, s), 8.05 (1H, d, J=9.4 Hz), 10.23 (1H, s), 11.08 (1H, s).

Example 309

Production of N-[5-({2-[(cyclopropylcarbonyl)amino]imidazo[1,2-b]pyridazin-6-yl}oxy)-2-methylphenyl]-1-methyl-3-(trifluoromethyl)-1H-pyrazole-5-carboxamide

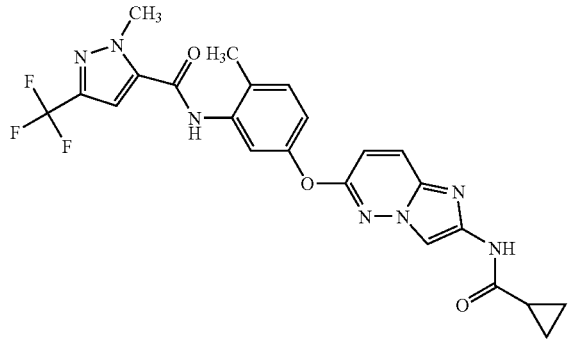

In the same manner as in Example 259 and using 1-methyl-3-(trifluoromethyl)-1H-pyrazole-5-carboxylic acid (160 mg, 0.80 mmol), tetrahydrofuran (5 mL), N,N-dimethylformamide (1 drop), oxalyl chloride (170 μL, 2.0 mmol), N-[6-(3-amino-4-methylphenoxy)imidazo[1,2-b]pyridazin-2-yl]cyclopropanecarboxamide (200 mg, 0.62 mmol) and N,N-dimethylacetamide (7 mL) as starting materials, the title compound (240 mg, 76%) was obtained as a white solid.

$^1$H-NMR (DMSO-d$_6$, 300 MHz) δ 0.74-0.86 (4H, m), 1.86-1.97 (1H, m), 2.27 (3H, s), 4.15 (3H, s), 7.05 (1H, d, J=9.6 Hz), 7.13 (1H, dd, J=8.3, 2.6 Hz), 7.30 (1H, d, J=2.6 Hz), 7.37 (1H, d, J=8.3 Hz), 7.49 (1H, s), 7.94 (1H, s), 8.04 (1H, d, J=9.6 Hz), 10.13 (1H, s), 11.08 (1H, s).

Example 310

Production of N-[5-({2-[(cyclopropylcarbonyl)amino]imidazo[1,2-b]pyridazin-6-yl}oxy)-2-fluorophenyl]-1-methyl-3-(trifluoromethyl)-1H-pyrazole-5-carboxamide

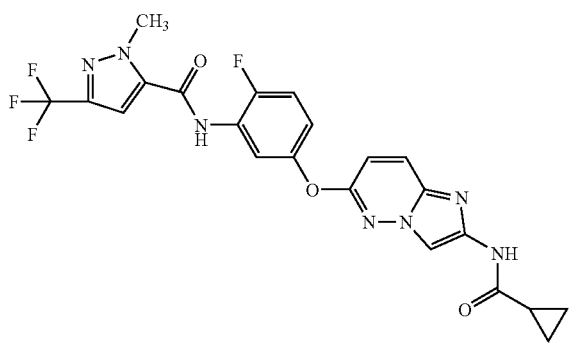

In the same manner as in Example 259 and using 1-methyl-3-(trifluoromethyl)-1H-pyrazole-5-carboxylic acid (150 mg, 0.79 mmol), tetrahydrofuran (5 mL), N,N-dimethylformamide (1 drop), oxalyl chloride (140 μL, 1.6 mmol), N-[6-(3-amino-4-fluorophenoxy)imidazo[1,2-b]pyridazin-2-yl]cyclopropanecarboxamide (200 mg, 0.61 mmol) and N,N-dimethylacetamide (7 mL) as starting materials, the title compound (240 mg, 77%) was obtained as a white solid.

$^1$H-NMR (DMSO-d$_6$, 300 MHz) δ 0.71-0.85 (4H, m), 1.85-1.97 (1H, m), 4.15 (3H, s), 7.09 (1H, d, J=9.4 Hz), 7.21-7.28 (1H, m), 7.39-7.47 (1H, m), 7.54 (1H, s), 7.58 (1H, dd, J=6.3, 2.9 Hz), 7.95 (1H, s), 8.05 (1H, d, J=9.4 Hz), 10.45 (1H, s), 11.08 (1H, s).

Example 311

Production of 4-chloro-N-[5-({2-[(cyclopropylcarbonyl)amino]imidazo[1,2-b]pyridazin-6-yl}oxy)-2-methylphenyl]-1-methyl-1H-pyrazole-3-carboxamide

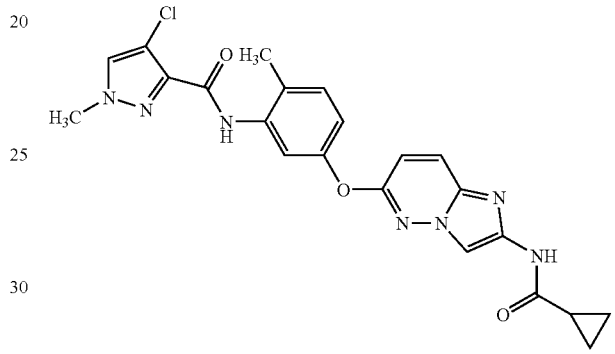

In the same manner as in Example 259 and using 4-chloro-1-methyl-1H-pyrazole-3-carboxylic acid (130 mg, 0.80 mmol), tetrahydrofuran (5 mL), N,N-dimethylformamide (1 drop), oxalyl chloride (170 μL, 2.0 mmol), N-[6-(3-amino-4-methylphenoxy)imidazo[1,2-b]pyridazin-2-yl]cyclopropanecarboxamide (200 mg, 0.62 mmol) and N,N-dimethylacetamide (7 mL) as starting materials, the title compound (235 mg, 82%) was obtained as a white solid.

$^1$H-NMR (DMSO-d$_6$, 300 MHz) δ 0.74-0.84 (4H, m), 1.87-1.96 (1H, m), 2.27 (3H, s), 3.93 (3H, s), 6.99-7.08 (2H, m), 7.32 (1H, d, J=8.7 Hz), 7.52 (1H, d, J=2.6 Hz), 7.95 (1H, s), 8.03 (1H, d, J=10.2 Hz), 8.12 (1H, s), 9.54 (1H, s), 11.07 (1H, s).

Example 312

Production of 4-chloro-N-[5-({2-[(cyclopropylcarbonyl)amino]imidazo[1,2-b]pyridazin-6-yl}oxy)-2-fluorophenyl]-1-methyl-1H-pyrazole-3-carboxamide

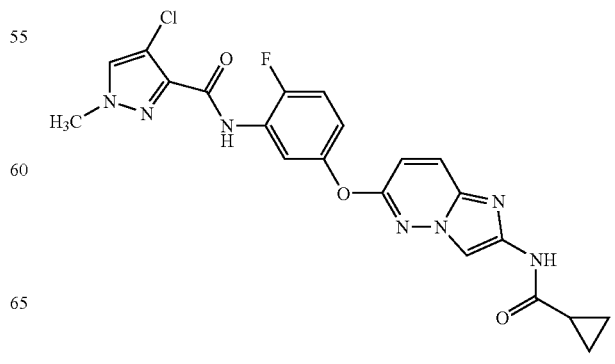

In the same manner as in Example 259 and using 4-chloro-1-methyl-1H-pyrazole-3-carboxylic acid (130 mg, 0.79 mmol), tetrahydrofuran (5 mL), N,N-dimethylformamide (1 drop), oxalyl chloride (170 μL, 2.0 mmol), N-[6-(3-amino-4-fluorophenoxy)imidazo[1,2-b]pyridazin-2-yl]cyclopropanecarboxamide (200 mg, 0.61 mmol) and N,N-dimethylacetamide (7 mL) as starting materials, the title compound (230 mg, 80%) was obtained as a white solid.

$^1$H-NMR (DMSO-$d_6$, 300 MHz) δ 0.76-0.84 (4H, m), 1.86-1.97 (1H, m), 3.94 (3H, s), 7.08 (1H, d, J=9.6 Hz), 7.10-7.18 (1H, m), 7.39 (1H, dd, J=10.4, 9.0 Hz), 7.80 (1H, dd, J=6.5, 2.9 Hz), 7.95 (1H, s), 8.05 (1H, d, J=9.6 Hz), 8.14 (1H, s), 9.68 (1H, s), 11.08 (1H, s).

Example 313

Production of N-[5-({2-[(cyclopropylcarbonyl)amino]imidazo[1,2-b]pyridazin-6-yl}oxy)-2-methylphenyl]-2-ethyl-4-methyl-1,3-oxazole-5-carboxamide

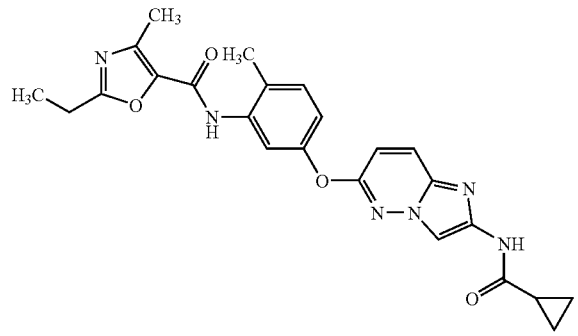

In the same manner as in Example 259 and using 2-ethyl-4-methyl-1,3-oxazole-5-carboxylic acid (230 mg, 1.5 mmol), tetrahydrofuran (6 mL), N,N-dimethylformamide (1 drop), oxalyl chloride (520 μL, 6.0 mmol), N-[6-(3-amino-4-methylphenoxy)imidazo[1,2-b]pyridazin-2-yl]cyclopropanecarboxamide (400 mg, 1.2 mmol) and N,N-dimethylacetamide (10 mL) as starting materials, the title compound (390 mg, 69%) was obtained as a white solid.

$^1$H-NMR (DMSO-$d_6$, 300 MHz) δ 0.74-0.85 (4H, m), 1.29 (3H, t, J=7.6 Hz), 1.92 (1H, m), 2.24 (3H, s), 2.36 (3H, s), 2.81 (2H, q, J=7.6 Hz), 7.04 (1H, d, J=9.5 Hz), 7.08 (1H, dd, J=8.3, 2.7 Hz), 7.26-7.37 (2H, m), 7.94 (1H, s), 8.03 (1H, d, J=9.5 Hz), 9.71 (1H, s), 11.07 (1H, s).

Example 314

Production of N-[5-({2-[(cyclopropylcarbonyl)amino]imidazo[1,2-b]pyridazin-6-yl}oxy)-2-fluorophenyl]-2-ethyl-4-methyl-1,3-oxazole-5-carboxamide

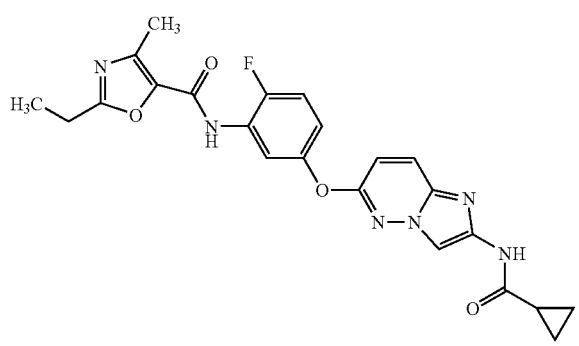

In the same manner as in Example 259 and using 2-ethyl-4-methyl-1,3-oxazole-5-carboxylic acid (230 mg, 1.5 mmol), tetrahydrofuran (6 mL), N,N-dimethylformamide (1 drop), oxalyl chloride (520 μL, 6.0 mmol), N-[6-(3-amino-4-fluorophenoxy)imidazo[1,2-b]pyridazin-2-yl]cyclopropanecarboxamide (400 mg, 1.2 mmol) and N,N-dimethylacetamide (10 mL) as starting materials, the title compound (400 mg, 70%) was obtained as a white solid. melting point 228° C.

$^1$H-NMR (DMSO-$d_6$, 300 MHz) δ 0.74-0.85 (4H, m), 1.29 (3H, t, J=7.6 Hz), 1.83-1.95 (1H, m), 2.36 (3H, s), 2.82 (2H, q, J=7.6 Hz), 7.07 (1H, d, J=9.8 Hz), 7.16-7.25 (1H, m), 7.33-7.44 (1H, m), 7.56 (1H, dd, J=6.2, 2.8 Hz), 7.94 (1H, s), 8.04 (1H, d, J=9.8 Hz), 9.95 (1H, s), 11.07 (1H, s).

Example 315

Production of 3-chloro-N-[5-({2-[(cyclopropylcarbonyl)amino]imidazo[1,2-b]pyridazin-6-yl}oxy)-2-methylphenyl]-1-methyl-1H-pyrazole-5-carboxamide

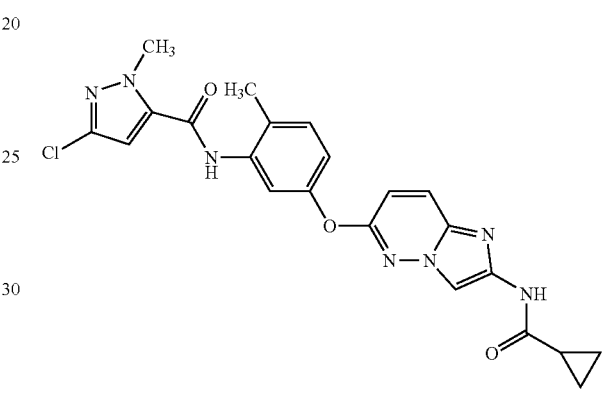

In the same manner as in Example 259 and using 3-chloro-1-methyl-1H-pyrazole-5-carboxylic acid (60 mg, 0.37 mmol), tetrahydrofuran (5 mL), N,N-dimethylformamide (1 drop), oxalyl chloride (130 μL, 1.5 mmol), N-[6-(3-amino-4-methylphenoxy)imidazo[1,2-b]pyridazin-2-yl]cyclopropanecarboxamide (100 mg, 0.31 mmol) and N,N-dimethylacetamide (5 mL) as starting materials, the title compound (110 mg, 74%) was obtained as a white solid.

$^1$H-NMR (DMSO-$d_6$, 300 MHz) δ 0.01-0.15 (4H, m), 1.14-1.27 (1H, m), 1.54 (3H, s), 1.80 (3H, s), 6.27-6.46 (3H, m), 6.58 (1H, d, J=2.4 Hz), 6.65 (1H, d, J=8.5 Hz), 7.22 (1H, s), 7.33 (1H, d, J=9.6 Hz), 9.30 (1H, br. s), 10.37 (1H, s).

Example 316

Production of 3-chloro-N-[5-({2-[(cyclopropylcarbonyl)amino]imidazo[1,2-b]pyridazin-6-yl}oxy)-2-fluorophenyl]-1-methyl-1H-pyrazole-5-carboxamide

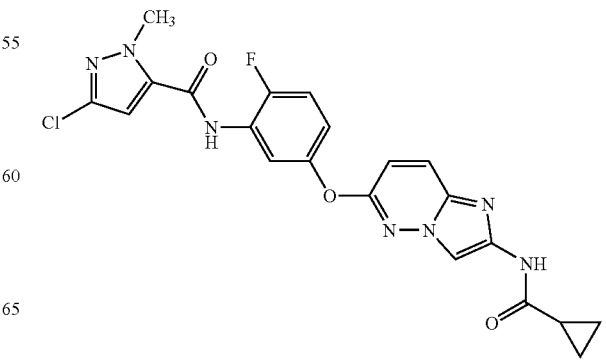

In the same manner as in Example 259 and using 3-chloro-1-methyl-1H-pyrazole-5-carboxylic acid (59 mg, 0.37 mmol), tetrahydrofuran (5 mL), N,N-dimethylformamide (1 drop), oxalyl chloride (130 µL, 1.5 mmol), N-[6-(3-amino-4-fluorophenoxy)imidazo[1,2-b]pyridazin-2-yl]cyclopropanecarboxamide (100 mg, 0.31 mmol) and N,N-dimethylacetamide (5 mL) as starting materials, the title compound (100 mg, 71%) was obtained as a white solid.

$^1$H-NMR (DMSO-$d_6$, 300 MHz) δ 0.72-0.85 (4H, m), 1.84-1.97 (1H, m), 4.03 (3H, s), 7.02-7.14 (2H, m), 7.19-7.28 (1H, m), 7.37-7.47 (1H, m), 7.56 (1H, dd, J=6.3, 2.9 Hz), 7.94 (1H, s), 8.05 (1H, d, J=9.6 Hz), 10.33 (1H, br. s), 11.08 (1H, s).

Example 317

Production of N-[3-({2-[(cyclopropylcarbonyl)amino]imidazo[1,2-b]pyridazin-6-yl}amino)phenyl]-1,3-dimethyl-1H-pyrazole-5-carboxamide

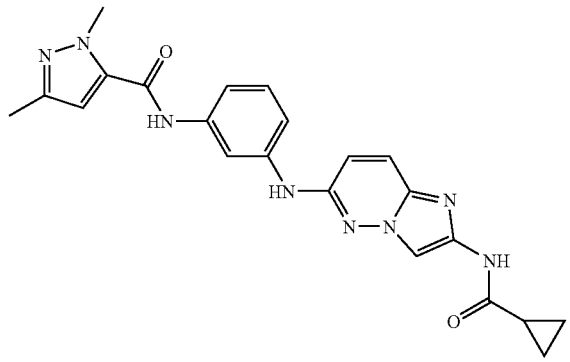

A mixture of N-(6-iodoimidazo[1,2-b]pyridazin-2-yl)cyclopropanecarboxamide (330 mg, 1.0 mmol), N-(3-aminophenyl)-1,3-dimethyl-1H-pyrazole-5-carboxamide (280 mg, 1.2 mmol), tris(dibenzylideneacetone)dipalladium (0) (46 mg, 0.050 mmol), 2-dicyclohexylphosphino-2',4',6'-triisopropyl-1,1'-biphenyl (48 mg, 0.10 mmol), potassium tert-butoxide (170 mg, 1.5 mmol) and tert-butanol was heated under reflux for 2 days. Ethyl acetate/tetrahydrofuran and saturated aqueous sodium hydrogencarbonate solution were added to the mixture, the aqueous layer was extracted with ethyl acetate/tetrahydrofuran (×4). Combined organic layer was washed with saturated brine, dried over anhydrous sodium sulfate, and filtrated. The filtrate was concentrated under reduced pressure, and the residue was purified by silica gel column chromatography (ethyl acetate/hexane=30/70→100/0) to give the title compound (37 mg, 9%) as a brown solid.

$^1$H-NMR (DMSO-$d_6$, 300 MHz) δ 0.74-0.88 (4H, m), 1.86-1.98 (1H, m), 2.22 (3H, s), 4.01 (3H, s), 6.85 (1H, s), 6.89 (1H, d, J=9.6 Hz), 7.24-7.36 (2H, m), 7.45-7.53 (1H, m), 7.75 (1H, d, J=9.6 Hz), 8.00 (1H, s), 8.21 (1H, s), 9.37 (1H, s), 10.15 (1H, s), 10.93 (1H, s).

Example 318

Production of 4-chloro-N-[3-({2-[(cyclopropylcarbonyl)amino]imidazo[1,2-b]pyridazin-6-yl}oxy)phenyl]-3-(trifluoromethyl)benzamide

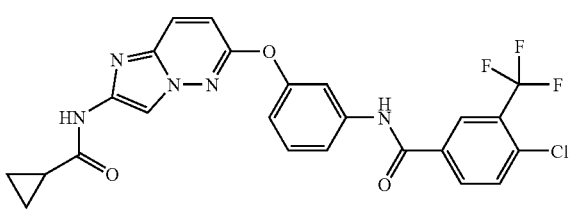

To a solution of N-[6-(3-aminophenoxy)imidazo[1,2-b]pyridazin-2-yl]cyclopropanecarboxamide (100 mg, 0.32 mmol) in N,N-dimethylformamide (6.0 mL) were added 4-chloro-3-(trifluoromethyl)benzoic acid (73 mg, 0.32 mmol), N-[3-(dimethylamino)propyl]-N'-ethylcarbodiimide hydrochloride (65 mg, 0.34 mmol) and 1-hydroxybenzotriazole (46 mg, 0.34 mmol), and the mixture was stirred at room temperature overnight. The reaction mixture was diluted with water and extracted with ethyl acetate. The organic layer was washed with saturated brine, dried over anhydrous sodium sulfate, and filtrated. The solvent was evaporated under reduced pressure, and the residue was purified by silica gel column chromatography (ethyl acetate/hexane=30/70→80/20) and precipitated from ethyl acetate/diisopropyl ether to give the title compound (130 mg, 77%) as a white powder.

$^1$H-NMR (DMSO-$d_6$, 300 MHz) δ 0.64-0.93 (4H, m), 1.79-2.04 (1H, m), 6.99-7.13 (2H, m), 7.46 (1H, t, J=8.1 Hz), 7.59-7.69 (1H, m), 7.71 (1H, t, J=2.1 Hz), 7.93 (1H, d, J=8.4 Hz), 7.98 (1H, s), 8.06 (1H, d, J=9.6 Hz), 8.24 (1H, dd, J=8.4, 2.1 Hz), 8.37 (1H, d, J=2.1 Hz), 10.64 (1H, s), 11.09 (1H, s).

Example 319

Production of N-[3-({2-[(cyclopropylcarbonyl)amino]imidazo[1,2-b]pyridazin-6-yl}oxy)phenyl]-3-(trifluoromethyl)benzamide

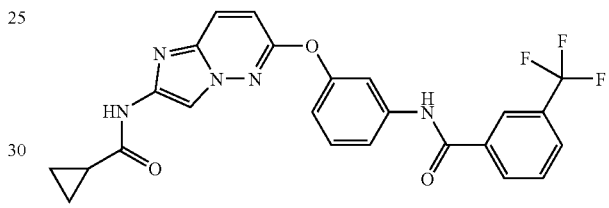

Using N-[6-(3-aminophenoxy)imidazo[1,2-b]pyridazin-2-yl]cyclopropanecarboxamide (80 mg, 0.26 mmol), 3-(trifluoromethyl)benzoic acid (54 mg, 0.29 mmol), N-[3-(dimethylamino)propyl]-N'-ethylcarbodiimide hydrochloride (55 mg, 0.29 mmol), 1-hydroxybenzotriazole (39 mg, 0.29 mmol) and N,N-dimethylformamide (5.0 mL) as starting materials and in the same manner as in Example 318, the title compound (86 mg, 69%) was obtained as a white powder.

$^1$H-NMR (DMSO-$d_6$, 300 MHz) δ 0.72-0.89 (4H, m), 1.84-2.03 (1H, m), 6.98-7.15 (2H, m), 7.46 (1H, t, J=8.1 Hz), 7.60-7.70 (1H, m), 7.73 (1H, t, J=2.1 Hz), 7.79 (1H, t, J=7.8 Hz), 7.91-8.02 (2H, m), 8.06 (1H, d, J=9.6 Hz), 8.19-8.34 (2H, m), 10.59 (1H, s), 11.09 (1H, s).

Example 320

Production of 3-(1-cyano-1-methylethyl)-N-[3-({2-[(cyclopropylcarbonyl)amino]imidazo[1,2-b]pyridazin-6-yl}oxy)phenyl]benzamide

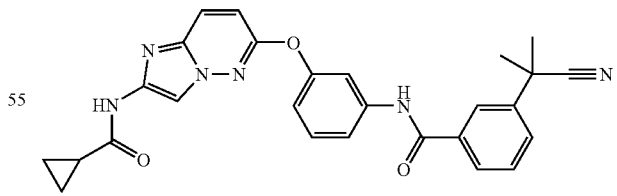

Using N-[6-(3-aminophenoxy)imidazo[1,2-b]pyridazin-2-yl]cyclopropanecarboxamide (100 mg, 0.32 mmol), 3-(1-cyano-1-methylethyl)benzoic acid (62 mg, 0.33 mmol), N-[3-(dimethylamino)propyl]-N'-ethylcarbodiimide hydrochloride (65 mg, 0.34 mmol), 1-hydroxybenzotriazole (46 mg, 0.34 mmol) and N,N-dimethylformamide (5.0 mL) as starting materials and in the same manner as in Example 318, the title compound (120 mg, 77%) was obtained as a white powder.

¹H-NMR (DMSO-d₆, 300 MHz) δ 0.73-0.86 (4H, m), 1.74 (6H, s), 1.83-1.98 (1H, m), 6.99-7.04 (1H, m), 7.08 (1H, d, J=9.6 Hz), 7.45 (1H, t, J=8.1 Hz), 7.54-7.69 (2H, m), 7.69-7.80 (2H, m), 7.92 (1H, dt, J=7.8, 1.2 Hz), 7.98 (1H, s), 8.00-8.10 (2H, m), 10.45 (1H, s), 11.09 (1H, s).

Example 321

Production of N-[3-({2-[(cyclopropylcarbonyl)amino]imidazo[1,2-b]pyridazin-6-yl}oxy)phenyl]-4-(trifluoromethyl)benzamide

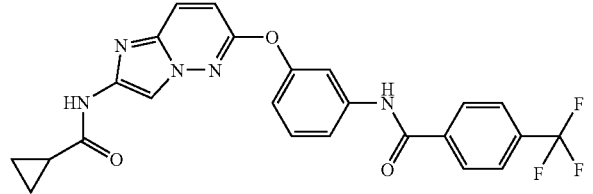

Using N-[6-(3-aminophenoxy)imidazo[1,2-b]pyridazin-2-yl]cyclopropanecarboxamide (100 mg, 0.32 mmol), 4-(trifluoromethyl)benzoic acid (63 mg, 0.33 mmol), N-[3-(dimethylamino)propyl]-N'-ethylcarbodiimide hydrochloride (65 mg, 0.34 mmol), 1-hydroxybenzotriazole (46 mg, 0.34 mmol) and N,N-dimethylformamide (5.0 mL) as starting materials and in the same manner as in Example 318, the title compound (110 mg, 68%) was obtained as a white powder.

¹H-NMR (DMSO-d₆, 300 MHz) δ 0.62-0.94 (4H, m), 1.76-2.06 (1H, m), 6.99-7.05 (1H, m), 7.08 (1H, d, J=9.6 Hz), 7.45 (1H, t, J=8.1 Hz), 7.63-7.71 (1H, m), 7.74 (1H, t, J=2.1 Hz), 7.92 (2H, d, J=8.2 Hz), 7.98 (1H, s), 8.06 (1H, d, J=9.6 Hz), 8.13 (2H, d, J=8.2 Hz), 10.60 (1H, s), 11.09 (1H, s).

Example 322

Production of 4-chloro-N-[5-({2-[(cyclopropylcarbonyl)amino]imidazo[1,2-b]pyridazin-6-yl}oxy)-2-methylphenyl]-3-(trifluoromethyl)benzamide

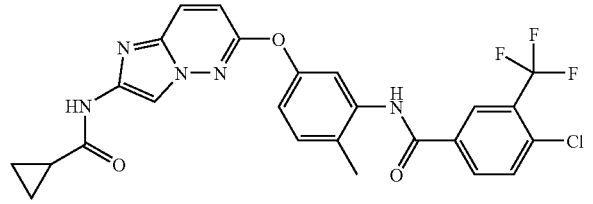

Using N-[6-(3-amino-4-methylphenoxy)imidazo[1,2-b]pyridazin-2-yl]cyclopropanecarboxamide (80 mg, 0.25 mmol), 4-chloro-3-(trifluoromethyl)benzoic acid (57 mg, 0.25 mmol), N-[3-(dimethylamino)propyl]-N'-ethylcarbodiimide hydrochloride (50 mg, 0.26 mmol), 1-hydroxybenzotriazole (35 mg, 0.26 mmol) and N,N-dimethylformamide (4.0 mL) as starting materials and in the same manner as in Example 318, the title compound (83 mg, 63%) was obtained as a white powder.

¹H-NMR (DMSO-d₆, 300 MHz) δ 0.73-0.85 (4H, m), 1.84-1.97 (1H, m), 2.26 (3H, s), 7.05 (1H, d, J=9.6 Hz), 7.12 (1H, dd, J=8.4, 2.7 Hz), 7.30 (1H, d, J=2.7 Hz), 7.36 (1H, d, J=8.4 Hz), 7.86-7.97 (2H, m), 8.03 (1H, d, J=9.6 Hz), 8.25 (1H, dd, J=8.4, 1.8 Hz), 8.39 (1H, d, J=1.8 Hz), 10.26 (1H, s), 11.07 (1H, s).

Example 323

Production of N-[5-({2-[(cyclopropylcarbonyl)amino]imidazo[1,2-b]pyridazin-6-yl}oxy)-2-methylphenyl]-3-(trifluoromethyl)benzamide

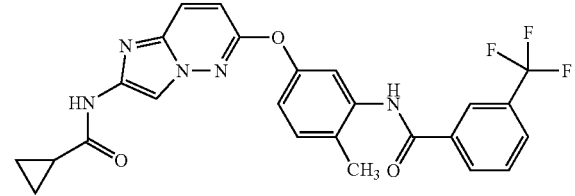

Using N-[6-(3-amino-4-methylphenoxy)imidazo[1,2-b]pyridazin-2-yl]cyclopropanecarboxamide (80 mg, 0.25 mmol), 3-(trifluoromethyl)benzoic acid (57 mg, 0.25 mmol), N-[3-(dimethylamino)propyl]-N'-ethylcarbodiimide hydrochloride (50 mg, 0.26 mmol), 1-hydroxybenzotriazole (35 mg, 0.26 mmol) and N,N-dimethylformamide (4.0 mL) as starting materials and in the same manner as in Example 318, the title compound (83 mg, 63%) was obtained as a white powder.

¹H-NMR (DMSO-d₆, 300 MHz) δ 0.72-0.86 (4H, m), 1.85-1.99 (1H, m), 2.27 (3H, s), 7.05 (1H, d, J=9.6 Hz), 7.11 (1H, dd, J=8.4, 2.4 Hz), 7.31 (1H, d, J=2.4 Hz), 7.36 (1H, d, J=8.6 Hz), 7.78 (1H, t, J=7.8 Hz), 7.90-8.00 (2H, m), 8.03 (1H, d, J=9.6 Hz), 8.20-8.36 (2H, m), 10.21 (1H, s), 11.07 (1H, s).

Example 324

Production of N-[3-({2-[(cyclopropylcarbonyl)amino]imidazo[1,2-b]pyridazin-6-yl}oxy)phenyl]-5-(methylsulfonyl)thiophene-2-carboxamide

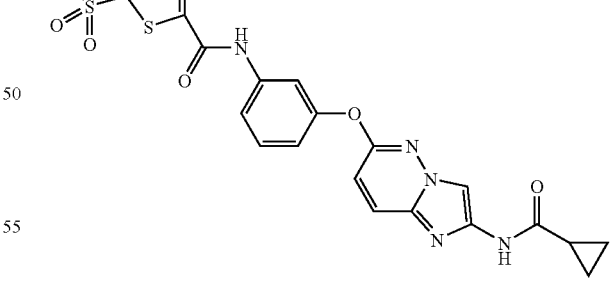

Using N-[6-(3-aminophenoxy)imidazo[1,2-b]pyridazin-2-yl]cyclopropanecarboxamide (100 mg, 0.32 mmol), 5-(methylsulfonyl)thiophene-2-carboxylic acid (47 mg, 0.33 mmol), N-[3-(dimethylamino)propyl]-N'-ethylcarbodiimide hydrochloride (65 mg, 0.34 mmol), 1-hydroxybenzotriazole (46 mg, 0.34 mmol) and N,N-dimethylformamide (5.0 mL) as starting materials and in the same manner as in Example 318, the title compound (41 mg, 26%) was obtained as a white powder.

¹H-NMR (DMSO-d₆, 300 MHz) δ 0.73-0.88 (4H, m), 1.82-1.98 (1H, m), 3.41 (3H, s), 6.99-7.14 (2H, m), 7.46 (1H, t, J=8.1 Hz), 7.58-7.65 (1H, m), 7.66 (1H, t, J=2.1 Hz), 7.88 (1H, d, J=4.2 Hz), 7.97 (1H, s), 8.03-8.09 (2H, m), 10.66 (1H, s), 11.09 (1H, s).

Example 325

Production of N-[3-({2-[(cyclopropylcarbonyl)amino]imidazo[1,2-b]pyridazin-6-yl}oxy)phenyl]-2-(1-hydroxy-1-methylethyl)-1,3-thiazole-5-carboxamide

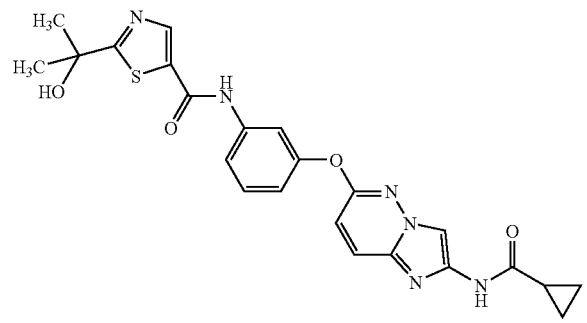

Using N-[6-(3-aminophenoxy)imidazo[1,2-b]pyridazin-2-yl]cyclopropanecarboxamide (150 mg, 0.49 mmol), 2-(1-hydroxy-1-methylethyl)-1,3-thiazole-5-carboxylic acid (96 mg, 0.51 mmol), N-[3-(dimethylamino)propyl]-N'-ethylcarbodiimide hydrochloride (95 mg, 0.50 mmol), 1-hydroxybenzotriazole (67 mg, 0.50 mmol) and N,N-dimethylformamide (8.0 mL) as starting materials and in the same manner as in Example 318, the title compound (99 mg, 43%) was obtained as a white powder.
¹H-NMR (DMSO-d₆, 300 MHz) δ 0.73-0.85 (4H, m), 1.51 (6H, s), 1.85-1.98 (1H, m), 6.17 (1H, s), 6.98-7.04 (1H, m), 7.07 (1H, d, J=9.6 Hz), 7.44 (1H, t, J=8.1 Hz), 7.54-7.68 (2H, m), 7.98 (1H, s), 8.06 (1H, d, J=9.6 Hz), 8.43 (1H, s), 10.42 (1H, s), 11.09 (1H, s).

Example 326

Production of 3-(4-cyanotetrahydro-2H-pyran-4-yl)-N-[3-({2-[(cyclopropylcarbonyl)amino]imidazo[1,2-b]pyridazin-6-yl}oxy)phenyl]benzamide

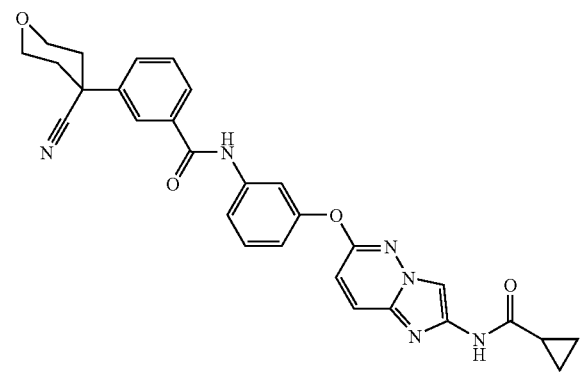

Using N-[6-(3-aminophenoxy)imidazo[1,2-b]pyridazin-2-yl]cyclopropanecarboxamide (150 mg, 0.49 mmol), 3-(4-cyanotetrahydro-2H-pyran-4-yl)benzoic acid (120 mg, 0.51 mmol), N-[3-(dimethylamino)propyl]-N'-ethylcarbodiimide hydrochloride (95 mg, 0.50 mmol), 1-hydroxybenzotriazole (67 mg, 0.50 mmol), triethylamine (130 μL, 0.97 mmol) and N,N-dimethylformamide (8.0 mL) as starting materials and in the same manner as in Example 318, the title compound (150 mg, 58%) was obtained as a white powder.
¹H-NMR (DMSO-d₆, 300 MHz) δ 0.67-0.92 (4H, m), 1.85-1.98 (1H, m), 2.10-2.23 (4H, m), 3.58-3.79 (2H, m), 3.86-4.15 (2H, m), 6.95-7.05 (1H, m), 7.08 (1H, d, J=9.6 Hz), 7.45 (1H, t, J=8.1 Hz), 7.52-7.70 (2H, m), 7.71 (1H, t, J=2.1 Hz), 7.76-7.85 (1H, m), 7.92-8.00 (2H, m), 8.02-8.12 (2H, m), 10.44 (1H, s), 11.09 (1H, s).

Example 327

Production of N-[3-({2-[(cyclopropylcarbonyl)amino]imidazo[1,2-b]pyridazin-6-yl}oxy)phenyl]-2-(trifluoromethyl)pyrimidine-4-carboxamide

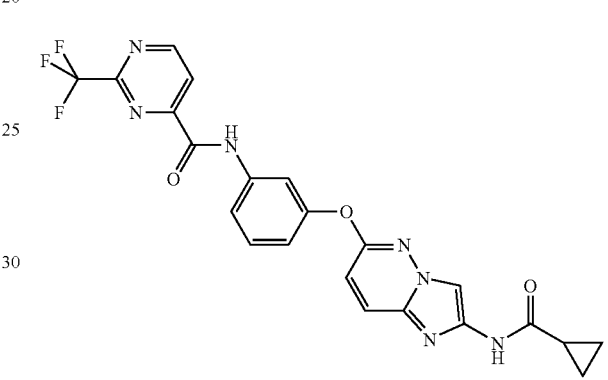

Using N-[6-(3-aminophenoxy)imidazo[1,2-b]pyridazin-2-yl]cyclopropanecarboxamide (150 mg, 0.49 mmol), 2-(trifluoromethyl)pyrimidine-4-carboxylic acid (150 mg, 0.83 mmol), N-[3-(dimethylamino)propyl]-N'-ethylcarbodiimide hydrochloride (100 mg, 0.53 mmol), 1-hydroxybenzotriazole (72 mg, 0.53=mol) and N,N-dimethylformamide (6.0 mL) as starting materials and in the same manner as in Example 318, the title compound (130 mg, 54%) was obtained as a white powder.
¹H-NMR (DMSO-d₆, 300 MHz) δ 0.73-0.88 (4H, m), 1.84-1.98 (1H, m), 7.04-7.15 (2H, m), 7.49 (1H, t, J=8.1 Hz), 7.72-7.86 (2H, m), 7.98 (1H, s), 8.06 (1H, d, J=9.6 Hz), 8.36 (1H, d, J=4.8 Hz), 9.35 (1H, d, J=4.8 Hz), 10.82 (1H, s), 11.09 (1H, s).

Example 328

Production of N-[3-({2-[(cyclopropylcarbonyl)amino]imidazo[1,2-b]pyridazin-6-yl}oxy)phenyl]-5-(ethylsulfonyl)thiophene-2-carboxamide

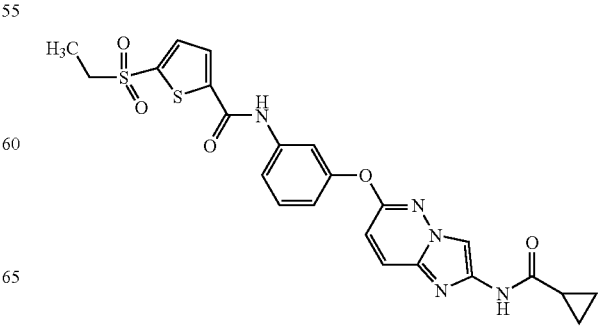

Using N-[6-(3-aminophenoxy)imidazo[1,2-b]pyridazin-2-yl]cyclopropanecarboxamide (150 mg, 0.49 mmol), 5-(ethylsulfonyl)thiophene-2-carboxylic acid (110 mg, 0.50 mmol), N-[3-(dimethylamino)propyl]-N'-ethylcarbodiimide hydrochloride (98 mg, 0.51 mmol), 1-hydroxybenzotriazole (69 mg, 0.51 mmol) and N,N-dimethylformamide (6.0 mL) as starting materials and in the same manner as in Example 318, the title compound (180 mg, 71%) was obtained as a white powder.

$^1$H-NMR (DMSO-d$_6$, 300 MHz) δ 0.76-0.86 (4H, m), 1.19 (3H, t, J=7.2 Hz), 1.86-1.98 (1H, m), 3.47 (2H, q, J=7.2 Hz), 7.01-7.12 (2H, m), 7.46 (1H, t, J=8.1 Hz), 7.58-7.64 (1H, m), 7.66 (1H, t, J=2.1 Hz), 7.86 (1H, d, J=3.9 Hz), 7.97 (1H, s), 8.06 (1H, d, J=9.6 Hz), 8.09 (1H, d, J=3.9 Hz), 10.66 (1H, s), 11.09 (1H, s).

Example 329

Production of 5-acetyl-N-[3-({2-[(cyclopropylcarbonyl)amino]imidazo[1,2-b]pyridazin-6-yl}oxy)phenyl]thiophene-2-carboxamide

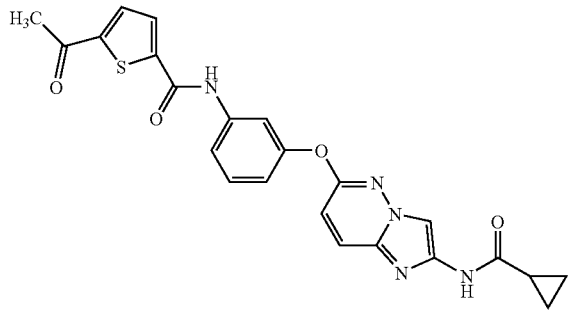

Using N-[6-(3-aminophenoxy)imidazo[1,2-b]pyridazin-2-yl]cyclopropanecarboxamide (150 mg, 0.49 mmol), 5-acetylthiophene-2-carboxylic acid (85 mg, 0.50 mmol), N-[3-(dimethylamino)propyl]-N'-ethylcarbodiimide hydrochloride (98 mg, 0.51 mmol), 1-hydroxybenzotriazole (69 mg, 0.51 mmol) and N,N-dimethylformamide (6.0 mL) as starting materials and in the same manner as in Example 318, the title compound (110 mg, 48%) was obtained as a white powder.

$^1$H-NMR (DMSO-d$_6$, 300 MHz) δ 0.75-0.85 (4H, m), 1.86-1.98 (1H, m), 2.58 (3H, s), 7.00-7.13 (2H, m), 7.45 (1H, t, J=8.1 Hz), 7.59-7.66 (1H, m), 7.67 (1H, t, J=2.1 Hz), 7.96-8.01 (2H, m), 8.02-8.11 (2H, m), 10.55 (1H, s), 11.09 (1H, s).

Example 330

Production of 3-(1-cyano-1-methylethyl)-N-[5-({2-[(cyclopropylcarbonyl)amino]imidazo[1,2-b]pyridazin-6-yl}oxy)-2-methylphenyl]benzamide

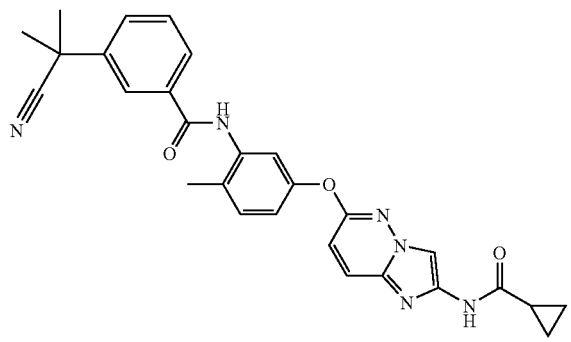

To a solution of 3-(1-cyano-1-methylethyl)benzoic acid (560 mg, 2.97 mmol) in tetrahydrofuran (15 mL) were added oxalyl chloride (320 μL, 3.71 mmol) and N,N-dimethylformamide (2 drops), and the mixture was stirred at room temperature for 1 hr. The solvent was evaporated under reduced pressure, and the residue was dissolved in N-methylpyrrolidone (15 mL). N-[6-(3-Amino-4-methylphenoxy)imidazo[1,2-b]pyridazin-2-yl]cyclopropanecarboxamide (800 mg, 2.47 mmol) was added to the mixture, and the mixture was stirred at room temperature for 12 hr. The reaction mixture was diluted with 1N hydrochloric acid, and the mixture was extracted with ethyl acetate. The organic layer was washed with 5% aqueous sodium hydrogencarbonate solution and saturated brine, dried over anhydrous sodium sulfate, and filtrated. The solvent was evaporated under reduced pressure, and the residue was purified by NH silica gel column chromatography (ethyl acetate/hexane=50/50→100/0) to give a colorless oil. The oil was dissolved ethyl acetate, and diisopropyl ether was added to allow precipitation to give the title compound (220 mg, 18%) as a white solid.

$^1$H-NMR (DMSO-d$_6$, 300 MHz) δ 0.71-0.86 (4H, m), 1.74 (6H, s), 1.84-1.98 (1H, m), 2.27 (3H, s), 7.05 (1H, d, J=9.6 Hz), 7.10 (1H, dd, J=8.4, 2.7 Hz), 7.31 (1H, d, J=2.7 Hz), 7.36 (1H, d, J=8.4 Hz), 7.59 (1H, t, J=7.8 Hz), 7.70-7.80 (1H, m), 7.91-7.99 (2H, m), 8.00-8.11 (2H, m), 10.04 (1H, s), 11.07 (1H, s).

Example 331

Production of N-{6-[(5-bromopyridin-3-yl)oxy]imidazo[1,2-b]pyridazin-2-yl}cyclopropanecarboxamide

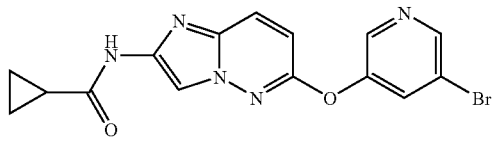

To a solution of N-(6-iodoimidazo[1,2-b]pyridazin-2-yl)cyclopropanecarboxamide (1.7 g, 5.0 mmol) in N,N-dimethylformamide (20 mL) were added 5-bromopyridine-3-ol (1.7 g, 10 mmol) and potassium carbonate (1.7 g, 13 mmol), and the mixture was stirred at 140° C. for 8 hr. After cooling the mixture to room temperature, the mixture was diluted with water, and extracted with ethyl acetate. The organic layer was washed with 5% aqueous sodium hydrogencarbonate solution and saturated brine, dried over anhydrous sodium sulfate, and filtrated. The solvent was evaporated under reduced pressure, and the residue was purified by silica gel column chromatography (ethyl acetate/hexane=50/50→100/0), and precipitated from ethyl acetate/diisopropyl ether to give the title compound (1.6 g, 85%) as a yellow powder.

$^1$H-NMR (DMSO-d$_6$, 300 MHz) δ 0.67-0.90 (4H, m), 1.85-1.98 (1H, m), 7.16 (1H, m), 7.98 (1H, s), 8.08 (1H, d, J=9.6 Hz), 8.19-8.25 (1H, m), 8.61-8.67 (2H, m), 11.09 (1H, s).

Example 332

Production of N-[5-({2-[(cyclopropylcarbonyl)amino]imidazo[1,2-b]pyridazin-6-yl}oxy)pyridin-3-yl]-3-(trifluoromethyl)benzamide

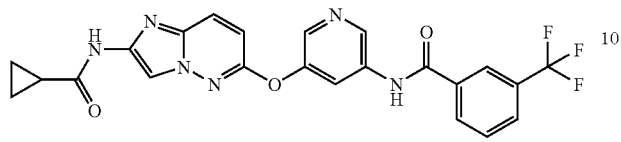

To a solution of N-{6-[(5-bromopyridin-3-yl)oxy]imidazo[1,2-b]pyridazin-2-yl}cyclopropanecarboxamide (200 mg, 0.53 mmol), 3-(trifluoromethyl)benzamide (160 mg, 0.91 mmol), trans-1,2-diaminocyclohexane (15 mg, 0.13 mmol) and potassium carbonate (220 mg, 1.6 mmol) in 1,4-dioxane (3.0 mL) was added copper (I) iodide (25 mg, 0.13 mmol) under argon atmosphere, and the mixture was stirred at 110° C. for 60 hr. The reaction mixture was cooled, and diluted with 20% tetrahydrofuran/ethyl acetate. The mixture was washed with water, 5% aqueous sodium hydrogencarbonate solution and saturated brine, dried over anhydrous magnesium sulfate, and filtrated. The solvent was evaporated under reduced pressure, and the residue was purified by NH silica gel column chromatography (ethyl acetate/hexane=60/40→100/0) and precipitated from ethyl acetate/hexane to give the title compound (110 mg, 42%) as a white powder.

$^1$H-NMR (DMSO-d$_6$, 300 MHz) δ 0.72-0.86 (4H, m), 1.84-1.98 (1H, m), 7.17 (1H, d, J=9.6 Hz), 7.81 (1H, t, J=7.8 Hz), 7.96-8.04 (2H, m), 8.10 (1H, d, J=9.6 Hz), 8.20 (1H, t, J=2.4 Hz), 8.23-8.35 (2H, m), 8.38 (1H, d, J=2.4 Hz), 8.85 (1H, d, J=2.4 Hz), 10.83 (1H, s), 11.10 (1H, s).

Example 333

Production of methyl 3-({[3-({2-[(cyclopropylcarbonyl)amino]imidazo[1,2-b]pyridazin-6-yl}oxy)phenyl]amino}carbonyl)benzoate

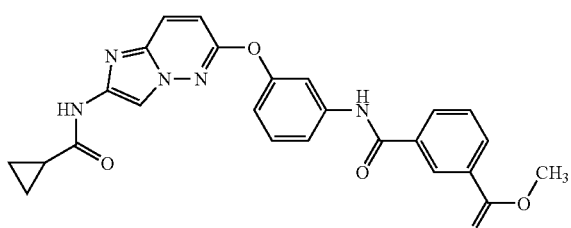

Using N-[6-(3-aminophenoxy)imidazo[1,2-b]pyridazin-2-yl]cyclopropanecarboxamide (250 mg, 0.81 mmol), 3-(methoxycarbonyl)benzoic acid (150 mg, 0.83 mmol), N-[3-(dimethylamino)propyl]-N'-ethylcarbodiimide hydrochloride (160 mg, 0.84 mmol), 1-hydroxybenzotriazole (110 mg, 0.81 mmol) and N,N-dimethylformamide (8.0 mL) as starting materials and in the same manner as in Example 318, the title compound (270 mg, 72%) was obtained as a white powder.

$^1$H-NMR (DMSO-d$_6$, 300 MHz) δ 0.74-0.85 (4H, m), 1.84-1.98 (1H, m), 3.91 (3H, s), 6.97-7.05 (1H, m), 7.08 (1H, d, J=9.6 Hz), 7.45 (1H, t, J=8.1 Hz), 7.63-7.79 (3H, m), 7.98 (1H, s), 8.06 (1H, d, J=9.6 Hz), 8.12-8.19 (1H, m), 8.19-8.26 (1H, m), 8.52 (1H, t, J=1.5 Hz), 10.59 (1H, s), 11.09 (1H, s).

Example 334

Production of N-[3-({2-[(cyclopropylcarbonyl)amino]imidazo[1,2-b]pyridazin-6-yl}oxy)phenyl]-3-(1-hydroxy-1-methylethyl)benzamide

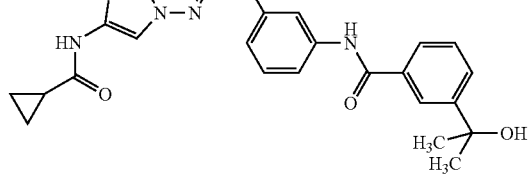

To a solution of methyl 3-({[3-({2-[(cyclopropylcarbonyl)amino]imidazo[1,2-b]pyridazin-6-yl}oxy)phenyl]amino}carbonyl)benzoate in tetrahydrofuran (5.0 mL) was added dropwise a solution of 1.4M methyl magnesium bromide in tetrahydrofuran/toluene (0.76 mL, 1.1 mmol) under ice-cooling. After dropwise addition, the reaction mixture was stirred at room temperature for 12 hr, and water (10 mL) was added. 1N Hydrochloric acid (5.0 mL) was added to the mixture, and the mixture was extracted with ethyl acetate. The organic layer was washed with saturated brine, dried over anhydrous sodium sulfate, and filtrated. The solvent was evaporated under reduced pressure, and the residue was purified by silica gel column chromatography (ethyl acetate/hexane=40/60→100/0) and precipitated from diisopropyl ether/hexane to give the title compound (19 mg, 19%) as a white powder.

$^1$H-NMR (DMSO-d$_6$, 300 MHz) δ 0.75-0.85 (4H, m), 1.46 (6H, s), 1.85-1.97 (1H, m), 5.14 (1H, s), 6.96-7.03 (1H, m), 7.07 (1H, d, J=9.6 Hz), 7.37-7.50 (2H, m), 7.67 (2H, m), 7.73 (1H, t, J=2.1 Hz), 7.75-7.81 (1H, m), 7.98 (1H, s), 8.01 (1H, t, J=1.5 Hz), 8.05 (1H, d, J=9.6 Hz), 10.35 (1H, s), 11.09 (1H, s).

Example 335

Production of 3-(1-cyano-1-methylethyl)-N-[5-({2-[(cyclopropylcarbonyl)amino]imidazo[1,2-b]pyridazin-6-yl}oxy)-2-fluorophenyl]benzamide

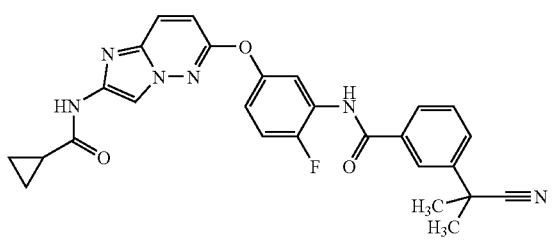

To a solution of 3-(1-cyano-1-methylethyl)benzoic acid (100 mg, 0.55 mmol) in tetrahydrofuran (2.0 mL) were added oxalyl chloride (59 μL, 0.69 mmol) and N,N-dimethylformamide (1 drop), and the mixture was stirred at room temperature for 2 hr. The solvent was evaporated under reduced pressure, and the residue was dissolved in N-methylpyrrolidone (2 mL). N-[6-(3-Amino-4-fluorophenoxy)imidazo[1,2-b]pyridazin-2-yl]cyclopropanecarboxamide (150 mg, 0.46 mmol) was added to the mixture, and the mixture was stirred at room temperature for 10 hr. The reaction mixture was diluted with 1N aqueous sodium hydroxide solution. The mixture was extracted with ethyl acetate, and the organic layer was washed with 5% aqueous sodium hydrogencarbonate solution and saturated brine, dried over anhydrous sodium sulfate, and filtrated. The solvent was evaporated under reduced pressure, and the residue was purified by NH silica gel column chromatography (ethyl acetate/hexane=40/60→100/0), and precipitated from ethyl acetate/diisopropyl ether to give the title compound (140 mg, 62%) as a white powder.

$^1$H-NMR (DMSO-d$_6$, 300 MHz) δ 0.74-0.85 (4H, m), 1.74 (6H, s), 1.85-1.98 (1H, m), 7.08 (1H, d, J=9.6 Hz), 7.15-7.26 (1H, m), 7.34-7.48 (1H, m), 7.52-7.65 (2H, m), 7.71-7.82 (1H, m), 7.89-7.98 (2H, m), 8.01-8.12 (2H, m), 10.32 (1H, s), 11.07 (1H, s).

Example 336

Production of N-[4-chloro-5-({2-[(cyclopropylcarbonyl)amino]imidazo[1,2-b]pyridazin-6-yl}oxy)-2-fluorophenyl]-3-(1-cyano-1-methylethyl)benzamide

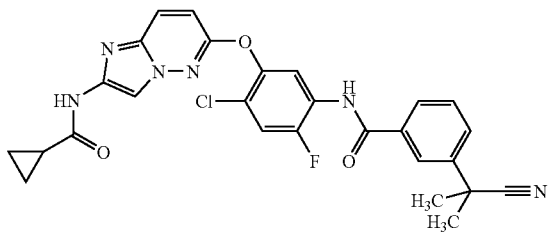

Using 3-(1-cyano-1-methylethyl)benzoic acid (100 mg, 0.55 mmol), oxalyl chloride (59 μL, 0.69 mmol), N,N-dimethylformamide (1 drop), tetrahydrofuran (2.0 mL), N-[6-(5-amino-2-chloro-4-fluorophenoxy)imidazo[1,2-b]pyridazin-2-yl]cyclopropanecarboxamide (170 mg, 0.46 mmol) and N-methylpyrrolidone (2.0 mL) as starting materials and in the same manner as in Example 335, the title compound (170 mg, 70%) was obtained as a white powder.

$^1$H-NMR (DMSO-d$_6$, 300 MHz) δ 0.66-0.91 (4H, m), 1.74 (6H, s), 1.86-1.98 (1H, m), 7.18 (1H, d, J=9.6 Hz), 7.60 (1H, t, J=7.8 Hz), 7.71-7.86 (3H, m), 7.89-7.99 (2H, m), 8.04-8.16 (2H, m), 10.42 (1H, s), 11.08 (1H, s).

Example 337

Production of 3-(1-cyano-1-methylethyl)-N-[3-({2-[(cyclopropylcarbonyl)amino]imidazo[1,2-b]pyridazin-6-yl}oxy)-4-methylphenyl]benzamide

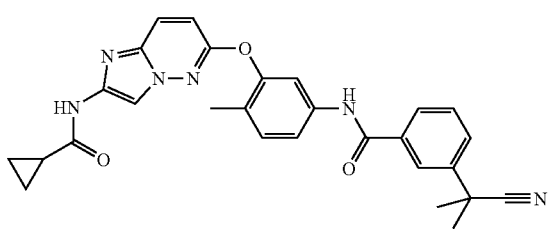

Using N-[6-(5-amino-2-methylphenoxy)imidazo[1,2-b]pyridazin-2-yl]cyclopropanecarboxamide (150 mg, 0.46 mmol), 3-(1-cyano-1-methylethyl)benzoic acid (92 mg, 0.49 mmol), N-[3-(dimethylamino)propyl]-N'-ethylcarbodiimide hydrochloride (94 mg, 0.49 mmol), 1-hydroxybenzotriazole (66 mg, 0.49 mmol) and N,N-dimethylformamide (7.0 mL) as starting materials and in the same manner as in Example 318, the title compound (160 mg, 70%) was obtained as a white powder.

$^1$H-NMR (DMSO-d$_6$, 300 MHz) δ 0.75-0.84 (4H, m), 1.73 (6H, s), 1.85-1.98 (1H, m), 2.15 (3H, s), 7.08 (1H, d, J=9.6 Hz), 7.34 (1H, d, J=8.4 Hz), 7.54-7.66 (3H, m), 7.70-7.78 (1H, m), 7.86-7.96 (2H, m), 8.01 (1H, t, J=1.8 Hz), 8.05 (1H, d, J=9.6 Hz), 10.37 (1H, s), 11.07 (1H, s).

Example 338

Production of N-[3-({2-[(cyclopropylcarbonyl)amino]imidazo[1,2-b]pyridazin-6-yl}oxy)-4-methylphenyl]-3-(trifluoromethyl)benzamide

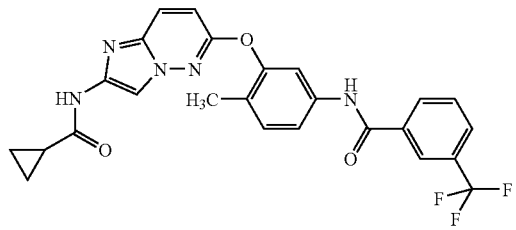

Using N-[6-(5-amino-2-methylphenoxy)imidazo[1,2-b]pyridazin-2-yl]cyclopropanecarboxamide (150 mg, 0.46 mmol), 3-(trifluoromethyl)benzoic acid (93 mg, 0.49 mmol), N-[3-(dimethylamino)propyl]-N'-ethylcarbodiimide hydrochloride (94 mg, 0.49 mmol), 1-hydroxybenzotriazole (66 mg, 0.49 mmol) and N,N-dimethylformamide (7.0 mL) as starting materials and in the same manner as in Example 318, the title compound (166 mg, 72%) was obtained as a white powder.

$^1$H-NMR (DMSO-d$_6$, 300 MHz) δ 0.73-0.89 (4H, m), 1.82-2.02 (1H, m), 2.16 (3H, s), 7.08 (1H, d, J=9.6 Hz), 7.35 (1H, d, J=8.4 Hz), 7.55-7.69 (2H, m), 7.77 (1H, t, J=7.8 Hz), 7.91-8.00 (2H, m), 8.06 (1H, d, J=9.6 Hz), 8.19-8.31 (2H, m), 10.51 (1H, s), 11.07 (1H, s).

Example 339

Production of 3-(1-cyanocyclopropyl)-N-[3-({2-[(cyclopropylcarbonyl)amino]imidazo[1,2-b]pyridazin-6-yl}oxy)phenyl]benzamide

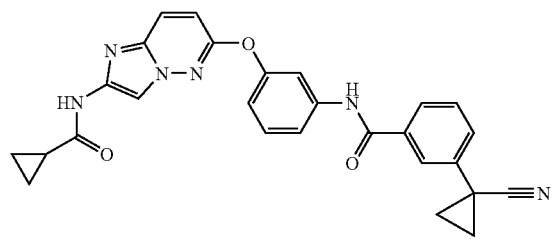

Using N-[6-(3-aminophenoxy)imidazo[1,2-b]pyridazin-2-yl]cyclopropanecarboxamide (170 mg, 0.55 mmol), 3-(1-cyanocyclopropyl)benzoic acid (100 mg, 0.55 mmol), N-[3-(dimethylamino)propyl]-N'-ethylcarbodiimide hydrochloride (110 mg, 0.55 mmol), 1-hydroxybenzotriazole (74 mg, 0.55 mmol) and N,N-dimethylformamide (10 mL) as starting materials and in the same manner as in Example 318, the title compound (122 mg, 47%) was obtained as a white powder.

$^1$H-NMR (DMSO-d$_6$, 300 MHz) δ 0.58-0.92 (4H, m), 1.55-1.68 (2H, m), 1.77-1.86 (2H, m), 1.86-1.99 (1H, m), 7.00 (1H, m), 7.07 (1H, d, J=9.6 Hz), 7.44 (1H, t, J=8.1 Hz), 7.50-7.61 (2H, m), 7.61-7.68 (1H, m), 7.71 (1H, t, J=2.1 Hz), 7.81 (1H, s), 7.84-7.91 (1H, m), 7.98 (1H, s), 8.06 (1H, d, J=9.6 Hz), 10.42 (1H, s), 11.09 (1H, s).

Example 340

Production of N-[3-({2-[(cyclopropylcarbonyl) amino]imidazo[1,2-b]pyridazin-6-yl}oxy)phenyl]-3,5-bis(trifluoromethyl)benzamide

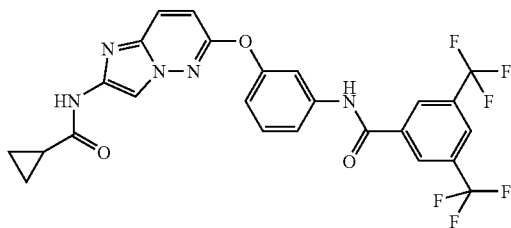

Using 3,5-bis(trifluoromethyl)benzoic acid (120 mg, 0.45 mmol), oxalyl chloride (48 μL, 0.56 mmol), N,N-dimethylformamide (1 drop), tetrahydrofuran (2.0 mL), N-[6-(3-aminophenoxy)imidazo[1,2-b]pyridazin-2-yl]cyclopropanecarboxamide (120 mg, 0.37 mmol) and N-methylpyrrolidone (2.0 mL) as starting materials and in the same manner as in Example 335, the title compound (63 mg, 31%) was obtained as a white powder.

$^1$H-NMR (DMSO-d$_6$, 300 MHz) δ 0.73-0.86 (4H, m), 1.85-1.98 (1H, m), 7.01-7.15 (2H, m), 7.48 (1H, t, J=8.1 Hz), 7.63-7.69 (1H, m), 7.71 (1H, t, J=2.1 Hz), 7.98 (1H, s), 8.06 (1H, d, J=9.6 Hz), 8.38 (1H, s), 8.59 (2H, s), 10.77 (1H, s), 11.09 (1H, s).

Example 341

Production of N-(3-{[2-(acetylamino)imidazo[1,2-b]pyridazin-6-yl]oxy}phenyl)-3-(1-cyano-1-methylethyl)benzamide

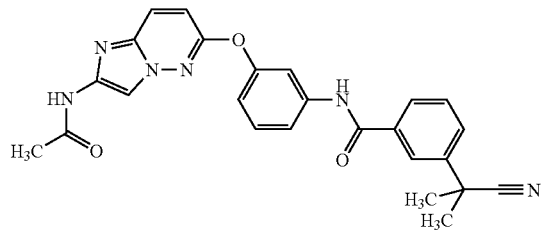

Using 3-(1-cyano-1-methylethyl)benzoic acid (160 mg, 0.85 mmol), oxalyl chloride (90 μL, 1.1 mmol), N,N-dimethylformamide (1 drop), tetrahydrofuran (4.0 mL), N-[6-(3-aminophenoxy)imidazo[1,2-b]pyridazin-2-yl]acetamide (200 mg, 0.71 mmol) and N-methylpyrrolidone (5.0 mL) as starting materials and in the same manner as in Example 335, the title compound (220 mg, 69%) was obtained as a white powder.

$^1$H-NMR (DMSO-d$_6$, 300 MHz) δ 1.74 (6H, s), 2.07 (3H, s), 6.97-7.05 (1H, m), 7.08 (1H, d, J=9.6 Hz), 7.45 (1H, t, J=8.1 Hz), 7.60 (1H, t, J=7.8 Hz), 7.63-7.69 (1H, m), 7.70-7.80 (2H, m), 7.88-7.96 (1H, m), 8.00 (1H, s), 8.02 (1H, t, J=1.8 Hz), 8.05 (1H, d, J=9.6 Hz), 10.45 (1H, s), 10.80 (1H, s).

Example 342

Production of 3-(1-cyanocyclohexyl)-N-[3-({2-[(cyclopropylcarbonyl)amino]imidazo[1,2-b]pyridazin-6-yl}oxy)phenyl]benzamide

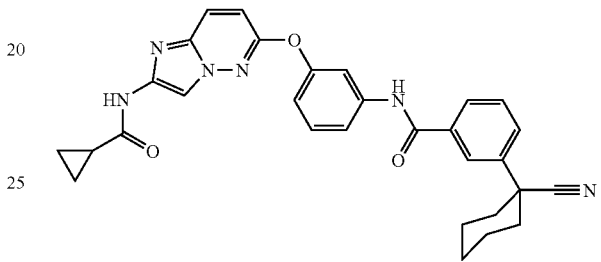

Using 3-(1-cyanocyclohexyl)benzoic acid (100 mg, 0.45 mmol), oxalyl chloride (48 μL, 0.56 mmol), N,N-dimethylformamide (1 drop), tetrahydrofuran (3.0 mL), N-[6-(3-aminophenoxy)imidazo[1,2-b]pyridazin-2-yl]cyclopropanecarboxamide (120 mg, 0.37 mmol) and N-methylpyrrolidone (2.0 mL) as starting materials and in the same manner as in Example 335, the title compound (150 mg, 78%) was obtained as a white powder.

$^1$H-NMR (DMSO-d$_6$, 300 MHz) δ 0.74-0.85 (4H, m), 1.22-1.41 (1H, m), 1.54-1.98 (8H, m), 2.05-2.20 (2H, m), 6.97-7.05 (1H, m), 7.08 (1H, d, J=9.6 Hz), 7.45 (1H, t, J=8.1 Hz), 7.60 (1H, t, J=7.8 Hz), 7.63-7.69 (1H, m), 7.72 (1H, t, J=2.1 Hz), 7.74-7.80 (1H, m), 7.89-7.96 (1H, m), 7.98 (1H, s), 8.01-8.10 (2H, m), 10.44 (1H, s), 11.09 (1H, s).

Example 343

Production of 3-(1-cyano-1-methylethyl)-N-[3-({2-[(cyclopropylcarbonyl)amino]imidazo[1,2-b]pyridazin-6-yl}oxy)-4-methoxyphenyl]benzamide

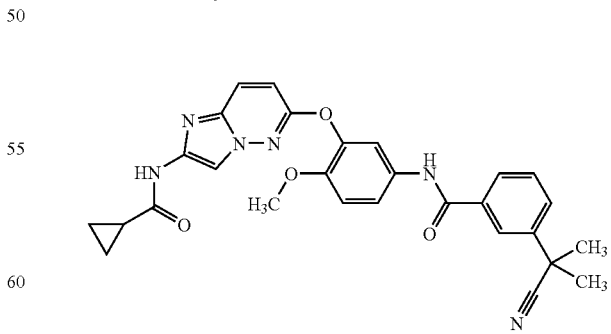

Using N-[6-(5-amino-2-methoxyphenoxy)imidazo[1,2-b]pyridazin-2-yl]cyclopropanecarboxamide (150 mg, 0.44 mmol), 3-(1-cyano-1-methylethyl)benzoic acid (88 mg, 0.46 mmol), N-[3-(dimethylamino)propyl]-N'-ethylcarbodiimide hydrochloride (87 mg, 0.46 mmol), 1-hydroxybenzotriazole (62 mg, 0.46 mmol) and N,N-dimethylformamide (10 mL) as starting materials and in the same manner as in Example 318, the title compound (160 mg, 71%) was obtained as a white powder.

$^1$H-NMR (DMSO-d$_6$, 300 MHz) δ 0.75-0.84 (4H, m), 1.74 (6H, s), 1.85-1.97 (1H, m), 3.72 (3H, s), 7.06 (1H, d, J=9.6 Hz), 7.22 (1H, d, J=9.0 Hz), 7.59 (1H, t, J=7.8 Hz), 7.65 (1H, dd, J=9.0, 2.4 Hz), 7.71 (1H, d, J=2.4 Hz), 7.72-7.78 (1H, m), 7.89 (1H, s), 7.90-7.95 (1H, m), 7.97-8.07 (2H, m), 10.32 (1H, s), 11.05 (1H, s).

Example 344

Production of N-[3-({2-[(cyclopropylcarbonyl)amino]imidazo[1,2-b]pyridazin-6-yl}oxy)-4-methoxyphenyl]-3-(trifluoromethyl)benzamide

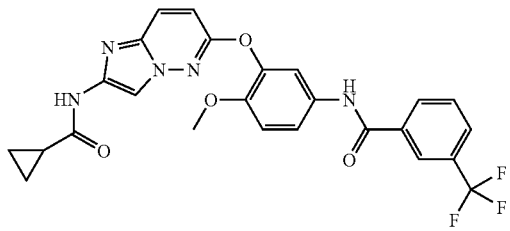

To a solution of N-[6-(5-amino-2-methoxyphenoxy)imidazo[1,2-b]pyridazin-2-yl]cyclopropanecarboxamide (150 mg, 0.44 mmol) in N-methylpyrrolidone (6.0 mL) was added 3-(trifluoromethyl)benzoyl chloride (92 mg, 0.44 mmol) under ice-cooling, and the mixture was stirred at room temperature for 12 hr. The reaction mixture was diluted with 1N hydrochloric acid and extracted with ethyl acetate, and the organic layer was washed with 5% aqueous sodium hydrogencarbonate solution and saturated brine, dried over anhydrous sodium sulfate, and filtrated. The solvent was evaporated under reduced pressure, and the residue was purified by NH silica gel column chromatography (ethyl acetate/hexane=50/50→100/0), and precipitated from ethyl acetate/diisopropyl ether to give the title compound (180 mg, 80%) as a white powder.

$^1$H-NMR (DMSO-d$_6$, 300 MHz) δ 0.74-0.83 (4H, m), 1.82-1.97 (1H, m), 3.73 (3H, s), 7.06 (1H, d, J=9.6 Hz), 7.23 (1H, d, J=9.0 Hz), 7.66 (1H, dd, J=9.0, 2.4 Hz), 7.73 (1H, d, J=2.4 Hz), 7.78 (1H, t, J=7.8 Hz), 7.89 (1H, s), 7.96 (1H, d, J=7.8 Hz), 8.01 (1H, d, J=10.2 Hz), 8.18-8.36 (2H, m), 10.48 (1H, s), 11.05 (1H, s).

Example 345

Production of 3-(1-cyanocyclopropyl)-N-[3-({2-[(cyclopropylcarbonyl)amino]imidazo[1,2-b]pyridazin-6-yl}oxy)-4-methylphenyl]benzamide

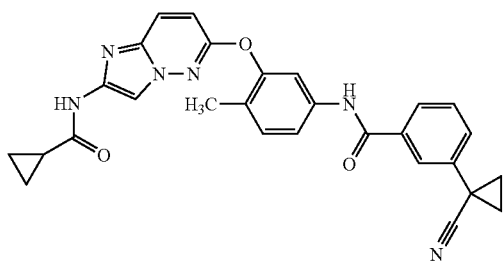

Using N-[6-(5-amino-2-methylphenoxy)imidazo[1,2-b]pyridazin-2-yl]cyclopropanecarboxamide (150 mg, 0.46 mmol), 3-(1-cyanocyclopropyl)benzoic acid (91 mg, 0.49 mmol), N-[3-(dimethylamino)propyl]-N'-ethylcarbodiimide hydrochloride (94 mg, 0.49 mmol), 1-hydroxybenzotriazole (66 mg, 0.49 mmol) and N,N-dimethylformamide (7.0 mL) as starting materials and in the same manner as in Example 318, the title compound (178 mg, 75%) was obtained as a white powder.

$^1$H-NMR (DMSO-d$_6$, 300 MHz) δ 0.69-0.88 (4H, m), 1.55-1.65 (2H, m), 1.76-1.84 (2H, m), 1.85-2.00 (1H, m), 2.15 (3H, s), 7.08 (1H, d, J=9.6 Hz), 7.34 (1H, d, J=8.1 Hz), 7.48-7.69 (4H, m), 7.80 (1H, s), 7.82-7.89 (1H, m), 7.92 (1H, s), 8.05 (1H, d, J=9.6 Hz), 10.34 (1H, s), 11.06 (1H, s).

Example 346

Production of 3-(1-cyanocyclobutyl)-N-[3-({2-[(cyclopropylcarbonyl)amino]imidazo[1,2-b]pyridazin-6-yl}oxy)phenyl]benzamide

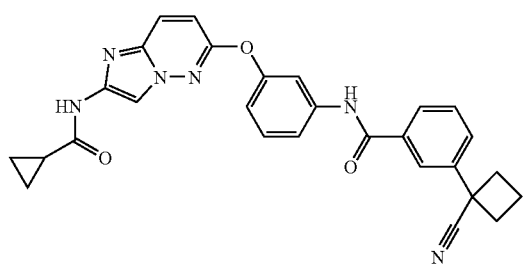

Using 3-(1-cyanocyclobutyl)benzoic acid (110 mg, 0.56 mmol), oxalyl chloride (60 μL, 0.70 mmol), N,N-dimethylformamide (1 drop), tetrahydrofuran (3.0 mL), N-[6-(3-aminophenoxy)imidazo[1,2-b]pyridazin-2-yl]cyclopropanecarboxamide (150 mg, 0.47 mmol) and N-methylpyrrolidone (3.0 mL) as starting materials and in the same manner as in Example 335, the title compound (140 mg, 60%) was obtained as a white powder.

$^1$H-NMR (DMSO-d$_6$, 300 MHz) δ 0.72-0.86 (4H, m), 1.81-2.12 (2H, m), 2.20-2.41 (1H, m), 2.60-2.86 (4H, m), 6.97-7.05 (1H, m), 7.07 (1H, d, J=9.6 Hz), 7.45 (1H, t, J=8.1 Hz), 7.60 (1H, t, J=7.8 Hz), 7.64-7.76 (3H, m), 7.89-8.01 (3H, m), 8.06 (1H, d, J=9.6 Hz), 10.46 (1H, s), 11.09 (1H, s).

Example 347

Production of 3-(1-cyanocyclobutyl)-N-[3-({2-[(cyclopropylcarbonyl)amino]imidazo[1,2-b]pyridazin-6-yl}oxy)-4-methylphenyl]benzamide

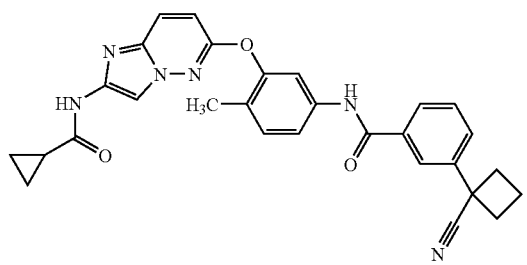

Using 3-(1-cyanocyclobutyl)benzoic acid (110 mg, 0.56 mmol), oxalyl chloride (60 μL, 0.70 mmol), N,N-dimethylformamide (1 drop), tetrahydrofuran (3.0 mL), N-[6-(5-amino-2-methylphenoxy)imidazo[1,2-b]pyridazin-2-yl]cyclopropanecarboxamide (150 mg, 0.46 mmol) and N-methylpyrrolidone (3.0 mL) as starting materials and in the same manner as in Example 335, the title compound (150 mg, 64%) was obtained as a white powder.

¹H-NMR (DMSO-d₆, 300 MHz) δ 0.66-0.92 (4H, m), 1.72-2.11 (2H, m), 2.15 (3H, s), 2.20-2.42 (1H, m), 2.60-2.94 (4H, m), 7.08 (1H, d, J=9.6 Hz), 7.34 (1H, d, J=8.4 Hz), 7.53-7.75 (4H, m), 7.81-7.99 (3H, m), 8.05 (1H, d, J=9.6 Hz), 10.38 (1H, s), 11.07 (1H, s).

Example 348

Production of N-[4-chloro-5-({2-[(cyclopropylcarbonyl)amino]imidazo[1,2-b]pyridazin-6-yl}oxy)-2-fluorophenyl]-3-(1-cyanocyclobutyl)benzamide

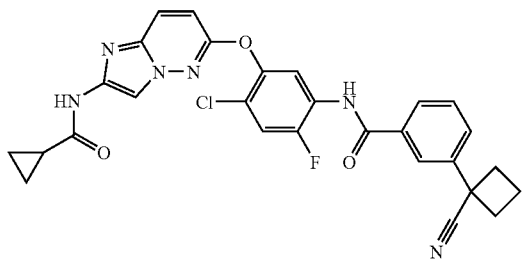

Using 3-(1-cyanocyclobutyl)benzoic acid (110 mg, 0.56 mmol), oxalyl chloride (60 μL, 0.70 mmol), N,N-dimethylformamide (1 drop), tetrahydrofuran (3.0 mL), N-[6-(5-amino-2-chloro-4-fluorophenoxy)imidazo[1,2-b]pyridazin-2-yl]cyclopropanecarboxamide (170 mg, 0.46 mmol) and N-methylpyrrolidone (3.0 mL) as starting materials and in the same manner as in Example 335, the title compound (170 mg, 68%) was obtained as a white powder.

¹H-NMR (DMSO-d₆, 300 MHz) δ 0.80 (4H, s), 1.85-1.96 (1H, m), 1.97-2.12 (1H, m), 2.20-2.41 (1H, m), 2.60-2.88 (4H, m), 7.18 (1H, d, J=9.6 Hz), 7.61 (1H, t, J=7.8 Hz), 7.67-7.75 (1H, m), 7.79 (1H, d, J=2.7 Hz), 7.82 (1H, s), 7.88-7.97 (2H, m), 8.02 (1H, t, J=1.5 Hz), 8.09 (1H, d, J=9.6 Hz), 10.44 (1H, s), 11.08 (1H, s).

Example 349

Production of 2-chloro-N-[3-({2-[(cyclopropylcarbonyl)amino]imidazo[1,2-b]pyridazin-6-yl}oxy)phenyl]-5-(trifluoromethyl)benzamide

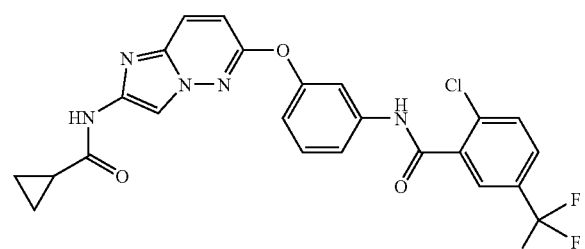

Using N-[6-(3-aminophenoxy)imidazo[1,2-b]pyridazin-2-yl]cyclopropanecarboxamide (100 mg, 0.32 mmol), 2-chloro-5-(trifluoromethyl)benzoyl acid chloride (87 mg, 0.36 mmol) and N-methylpyrrolidone (3.0 mL) as starting materials and in the same manner as in Example 344, the title compound (130 mg, 75%) was obtained as a white powder.

¹H-NMR (DMSO-d₆, 300 MHz) δ 0.74-0.86 (4H, m), 1.86-1.98 (1H, m), 6.95-7.18 (2H, m), 7.45 (1H, t, J=8.1 Hz), 7.50-7.58 (1H, m), 7.67 (1H, t, J=2.1 Hz), 7.77-7.93 (2H, m), 7.97 (1H, s), 8.02-8.08 (2H, m), 10.80 (1H, s), 11.09 (1H, s).

Example 350

Production of 2-chloro-N-[3-({2-[(cyclopropylcarbonyl)amino]imidazo[1,2-b]pyridazin-6-yl}oxy)phenyl]-3-(trifluoromethyl)benzamide

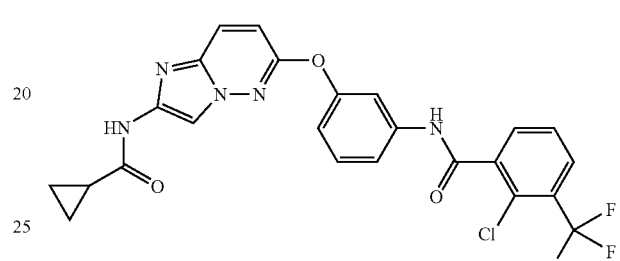

Using 2-chloro-3-(trifluoromethyl)benzoic acid (88 mg, 0.39 mmol), oxalyl chloride (42 μL, 0.49 mmol), N,N-dimethylformamide (1 drop), tetrahydrofuran (3.0 mL), N-[6-(3-aminophenoxy)imidazo[1,2-b]pyridazin-2-yl]cyclopropanecarboxamide (100 mg, 0.32 mmol) and N-methylpyrrolidone (4.0 mL) as starting materials and in the same manner as in Example 335, the title compound (110 mg, 68%) was obtained as a white powder.

¹H-NMR (DMSO-d₆, 300 MHz) δ 0.75-0.86 (4H, m), 1.86-1.97 (1H, m), 6.99-7.15 (2H, m), 7.45 (1H, t, J=8.1 Hz), 7.49-7.58 (1H, m), 7.61-7.76 (2H, m), 7.88-7.95 (1H, m), 7.96-8.02 (2H, m), 8.05 (1H, d, J=9.6 Hz), 10.83 (1H, s), 11.09 (1H, s).

Example 351

Production of N-[4-chloro-5-({2-[(cyclopropylcarbonyl)amino]imidazo[1,2-b]pyridazin-6-yl}oxy)-2-fluorophenyl]-3-(1-cyanocyclopropyl)benzamide

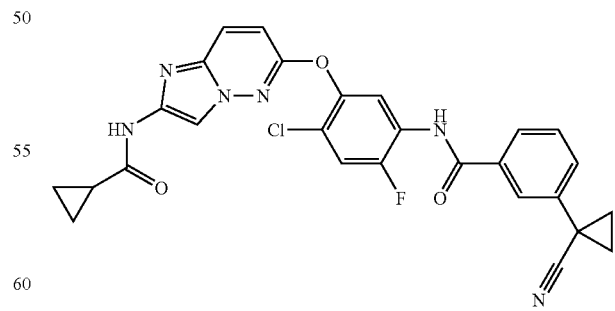

Using 3-(1-cyanocyclopropyl)benzoic acid (100 mg, 0.50 mmol), oxalyl chloride (55 μL, 0.62 mmol), N,N-dimethylformamide (1 drop), tetrahydrofuran (3.0 mL), N-[6-(5-amino-2-chloro-4-fluorophenoxy)imidazo[1,2-b]pyridazin-2-yl]cyclopropanecarboxamide (150 mg, 0.42 mmol) and N-methylpyrrolidone (3.0 mL) as starting materials and in the same manner as in Example 335, the title compound (160 mg, 73%) was obtained as a white powder.

$^1$H-NMR (DMSO-d$_6$, 300 MHz) δ 0.73-0.83 (4H, m), 1.55-1.66 (2H, m), 1.76-1.85 (2H, m), 1.86-1.97 (1H, m), 7.18 (1H, d, J=9.6 Hz), 7.46-7.65 (2H, m), 7.79 (1H, d, J=2.7 Hz), 7.82 (1H, s), 7.83-7.91 (2H, m), 7.92 (1H, s), 8.09 (1H, d, J=9.6 Hz), 10.40 (1H, s), 11.08 (1H, s).

Example 352

Production of N-[6-(3-amino-2-chloro-6-methylphenoxy)imidazo[1,2-b]pyridazin-2-yl]cyclopropanecarboxamide

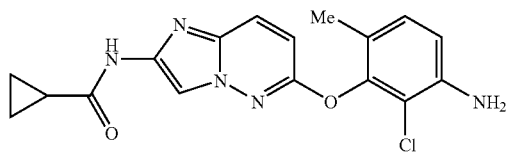

To a solution of N-(6-iodoimidazo[1,2-b]pyridazin-2-yl) cyclopropanecarboxamide (2.0 g, 6.1 mmol) in N,N-dimethylformamide (20 mL) were added 3-amino-2-chloro-6-methylphenol (1.9 g, 12 mmol) and potassium carbonate (2.1 g, 15 mmol), and the mixture was stirred at 140° C. for 12 hr. After cooling the mixture to room temperature, the mixture was diluted with water and extracted with ethyl acetate. The organic layer was washed with 5% aqueous sodium hydrogencarbonate solution and saturated brine, dried over anhydrous sodium sulfate, and filtrated. The solvent was evaporated under reduced pressure, and the residue was purified by NH silica gel column chromatography (ethyl acetate/hexane=50/50→80/20) and precipitated from methanol/diisopropyl ether to give the title compound (1.4 g, 64%) as a pale-yellow powder.

$^1$H-NMR (DMSO-d$_6$, 300 MHz) δ 0.74-0.83 (4H, m), 1.85-1.97 (1H, m), 2.00 (3H, s), 5.37 (2H, s), 6.69 (1H, d, J=8.4 Hz), 6.99 (1H, d, J=9.0 Hz), 7.07 (1H, d, J=9.6 Hz), 7.87 (1H, s), 8.03 (1H, d, J=9.6 Hz), 11.04 (1H, s).

Example 353

Production of N-[2-chloro-3-({2-[(cyclopropylcarbonyl)amino]imidazo[1,2-b]pyridazin-6-yl}oxy)-4-methylphenyl]-3-(1-cyano-1-methylethyl)benzamide

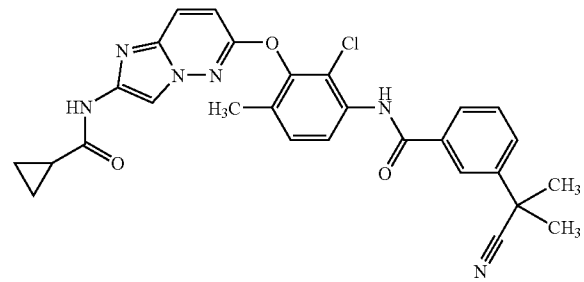

Using 3-(1 cyano-1 -methylethyl) benzoic acid (95 mg, 0.50 mmol), oxalyl chloride (55 µL, 0.63 mmol), N,N-dimethylformamide (1 drop), tetrahydrofuran (3.0 mL), N-[6-(3-amino-2-chloro-6-methylphenoxy)imidazo[1,2-b]pyridazin-2-yl]cyclopropanecarboxamide (150 mg, 0.42 mmol) and N-methylpyrrolidone (3.0 mL) as starting materials and in the same manner as in Example 335, the title compound (110 mg, 51%) was obtained as a white powder.

$^1$H-NMR (DMSO-d$_6$, 300 MHz) δ 0.63-0.95 (4H, m), 1.74 (6H, s), 1.82-1.97 (1H, m), 2.22 (3H, s), 7.20 (1H, d, J=9.6 Hz), 7.34-7.53 (2H, m), 7.59 (1H, t, J=7.8 Hz), 7.76 (1H, dq, J=7.8, 1.2 Hz), 7.85 (1H, s), 7.97 (1H, dt, J=7.8, 1.2 Hz), 8.06-8.15 (2H, m), 10.25 (1H, s), 11.06 (1H, s).

Example 354

Production of N-[2-chloro-3-({2-[(cyclopropylcarbonyl)amino]imidazo[1,2-b]pyridazin-6-yl}oxy)-4-methylphenyl]-3-(trifluoromethyl)benzamide

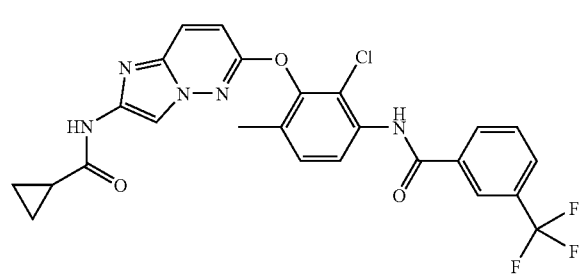

Using N-[6-(3-amino-2-chloro-6-methylphenoxy)imidazo[1,2-b]pyridazin-2-yl]cyclopropanecarboxamide (150 mg, 0.42 mmol), 3-(trifluoromethyl)benzoyl chloride (92 mg, 0.44 mmol) and N-methylpyrrolidone (5.0 mL) as starting materials and in the same manner as in Example 344, the title compound (130 mg, 60%) was obtained as a white powder.

$^1$H-NMR (DMSO-d$_6$, 300 MHz) δ 0.70-0.87 (4H, m), 1.81-1.98 (1H, m), 2.22 (3H, s), 7.20 (1H, d, J=9.6 Hz), 7.33-7.58 (2H, m), 7.79 (1H, t, J=7.8 Hz), 7.85 (1H, s), 7.98 (1H, d, J=7.8 Hz), 8.09 (1H, d, J=9.6 Hz), 8.29 (1H, d, J=7.8 Hz), 8.34 (1H, s), 10.45 (1H, s), 11.06 (1H, s).

Example 355

Production of 3-(1-cyanocyclopropyl)-N-[3-({2-[(cyclopropylcarbonyl)amino]imidazo[1,2-b]pyridazin-6-yl}oxy)-4-methoxyphenyl]benzamide

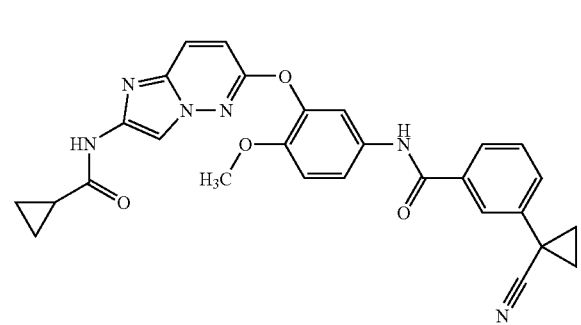

Using 3-(1-cyanocyclopropyl)benzoic acid (40 mg, 0.21 mmol), oxalyl chloride (23 µL, 0.27 mmol), N,N-dimethylformamide (1 drop), tetrahydrofuran (2.0 mL), N-[6-(5-amino-2-methoxyphenoxy)imidazo[1,2-b]pyridazin-2-yl]

cyclopropanecarboxamide (60 mg, 0.18 mmol) and N-methylpyrrolidone (2.0 mL) as starting materials and in the same manner as in Example 335, the title compound (67 mg, 74%) was obtained as a white powder.

¹H-NMR (DMSO-d₆, 300 MHz) δ 0.70-0.83 (4H, m), 1.54-1.65 (2H, m), 1.75-1.86 (2H, m), 1.86-1.98 (1H, m), 3.72 (3H, s), 7.06 (1H, d, J=9.6 Hz), 7.22 (1H, d, J=9.0 Hz), 7.48-7.60 (2H, m), 7.64 (1H, dd, J=9.0, 2.4 Hz), 7.71 (1H, d, J=2.4 Hz), 7.82 (1H, s), 7.84-7.92 (2H, m), 8.01 (1H, d, J=9.6 Hz), 10.31 (1H, s), 11.06 (1H, s).

Example 356

Production of 3-(1-cyanocyclobutyl)-N-[3-({2-[(cyclopropylcarbonyl)amino]imidazo[1,2-b]pyridazin-6-yl}oxy)-4-methoxyphenyl]benzamide

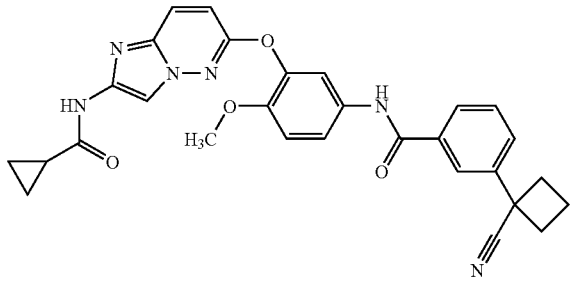

Using 3-(1-cyanocyclobutyl)benzoic acid (43 mg, 0.21 mmol), oxalyl chloride (23 μL, 0.27 mmol), N,N-dimethylformamide (1 drop), tetrahydrofuran (2.0 mL), N-[6-(5-amino-2-methoxyphenoxy)imidazo[1,2-b]pyridazin-2-yl]cyclopropanecarboxamide (60 mg, 0.18 mmol) and N-methylpyrrolidone (2.0 mL) as starting materials and in the same manner as in Example 335, the title compound (68 mg, 74%) was obtained as a white powder.

¹H-NMR (DMSO-d₆, 300 MHz) δ 0.72-0.86 (4H, m), 1.86-1.96 (1H, m), 2.21-2.38 (2H, m), 2.64-2.87 (4H, m), 3.72 (3H, s), 7.06 (1H, d, J=9.6 Hz), 7.22 (1H, d, J=9.0 Hz), 7.53-7.75 (4H, m), 7.89 (1H, s), 7.90-8.07 (3H, m), 10.35 (1H, s), 11.06 (1H, s).

Example 357

Production of N-[3-({2-[(cyclopropylcarbonyl)amino]imidazo[1,2-b]pyridazin-6-yl}oxy)phenyl]-3-(2-oxopyrrolidin-1-yl)benzamide

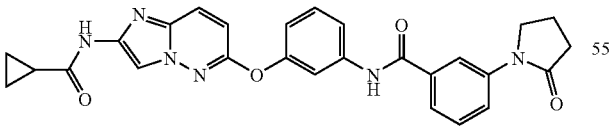

Using 3-(2-oxopyrrolidin-1-yl)benzoic acid (120 mg, 0.58 mmol), oxalyl chloride (60 μL, 0.68 mmol), N,N-dimethylformamide (1 drop), tetrahydrofuran (3.0 mL), N-[6-(3-aminophenoxy)imidazo[1,2-b]pyridazin-2-yl]cyclopropanecarboxamide (150 mg, 0.49 mmol) and N-methylpyrrolidone (2.0 mL) as starting materials and in the same manner as in Example 335, the title compound (170 mg, 70%) was obtained as a white powder.

¹H-NMR (DMSO-d₆, 300 MHz) δ 0.75-0.86 (4H, m), 1.85-1.97 (1H, m), 2.01-2.16 (2H, m), 2.52-2.56 (2H, m), 3.90 (2H, t, J=6.6 Hz), 6.97-7.03 (1H, m), 7.07 (1H, d, J=9.6 Hz), 7.44 (1H, t, J=8.1 Hz), 7.52 (1H, t, J=8.1 Hz), 7.61-7.75 (3H, m), 7.89-7.95 (1H, m), 7.98 (1H, s), 8.02-8.11 (2H, m), 10.40 (1H, s), 11.09 (1H, s).

Example 358

Production of N-[3-({2-[(cyclopropylcarbonyl)amino]imidazo[1,2-b]pyridazin-6-yl}oxy)phenyl]-3-(trifluoromethoxy)benzamide

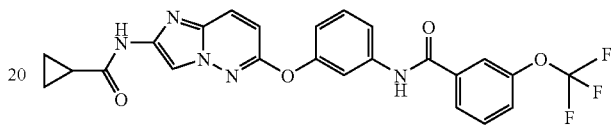

Using 3-(trifluoromethoxy)benzoic acid (120 mg, 0.58 mmol), oxalyl chloride (60 μL, 0.68 mmol), N,N-dimethylformamide (1 drop), tetrahydrofuran (3.0 mL), N-[6-(3-aminophenoxy)imidazo[1,2-b]pyridazin-2-yl]cyclopropanecarboxamide (150 mg, 0.49 mmol) and N-methylpyrrolidone (2.0 mL) as starting materials and in the same manner as in Example 335, the title compound (130 mg, 54%) was obtained as a white powder.

¹H-NMR (DMSO-d₆, 300 MHz) δ 0.73-0.87 (4H, m), 1.83-1.98 (1H, m), 6.99-7.05 (1H, m), 7.08 (1H, d, J=9.6 Hz), 7.45 (1H, t, J=8.1 Hz), 7.58-7.70 (3H, m), 7.72 (1H, t, J=2.1 Hz), 7.89 (1H, s), 7.95-8.03 (2H, m), 8.06 (1H, d, J=9.6 Hz), 10.51 (1H, s) 11.09 (1H, s).

Example 359

Production of N-[3-({2-[(cyclopropylcarbonyl)amino]imidazo[1,2-b]pyridazin-6-yl}oxy)-4-methoxyphenyl]-3-(trifluoromethoxy)benzamide

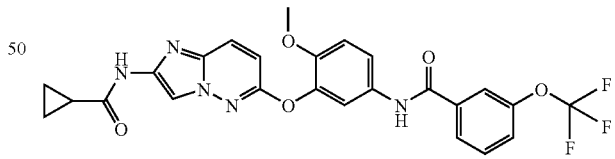

Using 3-(trifluoromethoxy)benzoic acid (120 mg, 0.58 mmol), oxalyl chloride (60 μL, 0.68 mmol), N,N-dimethylformamide (1 drop), tetrahydrofuran (3.0 mL), N-[6-(5-amino-2-methoxyphenoxy)imidazo[1,2-b]pyridazin-2-yl]cyclopropanecarboxamide (150 mg, 0.49 mmol) and N-methylpyrrolidone (2.0 mL) as starting materials and in the same manner as in Example 335, the title compound (130 mg, 54%) was obtained as a white powder.

¹H-NMR (DMSO-d₆, 300 MHz) δ 0.72-0.86 (4H, m), 1.83-1.98 (1H, m), 3.72 (3H, s), 7.06 (1H, d, J=9.6 Hz), 7.22

(1H, d, J=9.1 Hz), 7.54-7.78 (4H, m), 7.84-7.93 (2H, m), 7.96-8.08 (2H, m), 10.40 (1H, s), 11.05 (1H, s).

Example 360

Production of 3-(1-cyanoethyl)-N-[3-({2-[(cyclopropylcarbonyl)amino]imidazo[1,2-b]pyridazin-6-yl}oxy)-4-methoxyphenyl]benzamide

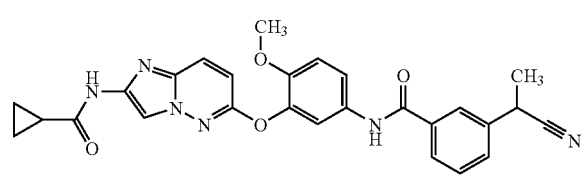

Using 3-(1-cyanoethyl)benzoic acid (62 mg, 0.35 mmol), oxalyl chloride (38 μL, 0.44 mmol), N,N-dimethylformamide (1 drop), tetrahydrofuran (3.0 mL), N-[6-(5-amino-2-methoxyphenoxy)imidazo[1,2-b]pyridazin-2-yl]cyclopropanecarboxamide (100 mg, 0.30 mmol) and N-methylpyrrolidone (2.0 mL) as starting materials and in the same manner as in Example 335, the title compound (84 mg, 58%) was obtained as a white powder.

$^1$H-NMR (DMSO-$d_6$, 300 MHz) δ 0.70-0.88 (4H, m), 1.60 (3H, d, J=7.2 Hz), 1.81-1.99 (1H, m), 3.72 (3H, s), 4.42 (1H, q, J=7.2 Hz), 7.06 (1H, d, J=9.6 Hz), 7.22 (1H, d, J=9.0 Hz), 7.47-7.70 (3H, m), 7.72 (1H, d, J=2.4 Hz), 7.84-7.97 (3H, m), 8.01 (1H, d, J=9.9 Hz), 10.32 (1H, s), 11.05 (1H, s).

Example 361

Production of N-[3-({2-[(cyclopropylcarbonyl)amino]imidazo[1,2-b]pyridazin-6-yl}oxy)phenyl]-3-methoxybenzamide

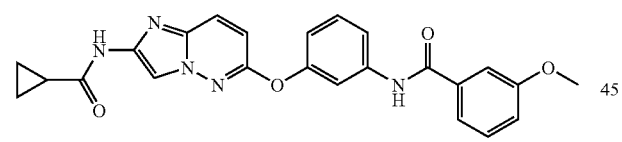

Using 3-methoxybenzoic acid (48 mg, 0.32 mmol), oxalyl chloride (32 μL, 0.37 mmol), N,N-dimethylformamide (1 drop), tetrahydrofuran (2.0 mL), N-[6-(3-aminophenoxy)imidazo[1,2-b]pyridazin-2-yl]cyclopropanecarboxamide (80 mg, 0.26 mmol) and N-methylpyrrolidone (2.0 mL) as starting materials and in the same manner as in Example 335, the title compound (49 mg, 43%) was obtained as a white powder.

$^1$H-NMR (DMSO-$d_6$, 300 MHz) δ 0.77-0.85 (4H, m), 1.85-1.99 (1H, m), 3.83 (3H, s), 6.95-7.03 (1H, m), 7.07 (1H, d, J=9.6 Hz), 7.12-7.21 (1H, m), 7.37-7.49 (3H, m), 7.48-7.56 (1H, m), 7.61-7.70 (1H, m), 7.73 (1H, t, J=2.1 Hz), 7.98 (1H, s), 8.05 (1H, d, J=9.6 Hz), 10.34 (1H, s), 11.09 (1H, s).

Example 362

Production of N-[3-({2-[(cyclopropylcarbonyl)amino]imidazo[1,2-b]pyridazin-6-yl}oxy)phenyl]-3-isopropoxybenzamide

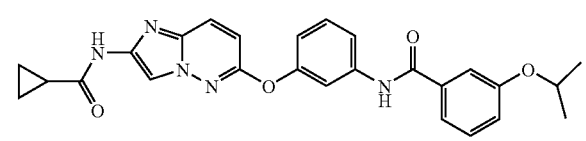

Using 3-(isopropoxy)benzoic acid (56 mg, 0.31 mmol), oxalyl chloride (33 μL, 0.39 mmol), N,N-dimethylformamide (1 drop), tetrahydrofuran (3.0 mL), N-[6-(3-aminophenoxy)imidazo[1,2-b]pyridazin-2-yl]cyclopropanecarboxamide (80 mg, 0.26 mmol) and N,N-dimethylacetamide (2.0 mL) as starting materials and in the same manner as in Example 335, the title compound (82 mg, 67%) was obtained as a white powder.

$^1$H-NMR (DMSO-$d_6$, 300 MHz) δ 0.77-0.85 (4H, m), 1.29 (6H, d, J=6.0 Hz), 1.85-1.98 (1H, m), 4.60-4.78 (1H, m), 6.96-7.02 (1H, m), 7.07 (1H, d, J=9.6 Hz), 7.11-7.17 (1H, m), 7.33-7.55 (4H, m), 7.63-7.71 (1H, m), 7.74 (1H, t, J=2.1 Hz), 7.98 (1H, s), 8.05 (1H, d, J=9.6 Hz), 10.31 (1H, s), 11.09 (1H, s).

Example 363

Production of N-[3-({2-[(cyclopropylcarbonyl)amino]imidazo[1,2-b]pyridazin-6-yl}oxy)phenyl]-3-(1,1,2,2-tetrafluoroethoxy)benzamide

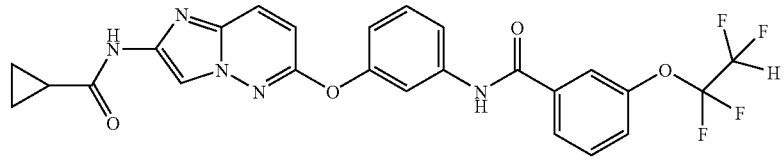

Using 3-(1,1,2,2-tetrafluoroethoxy)benzoic acid (74 mg, 0.31 mmol), oxalyl chloride (33 μL, 0.39 mmol), N,N-dimethylformamide (1 drop), tetrahydrofuran (3.0 mL), N-[6-(3-aminophenoxy)imidazo[1,2-b]pyridazin-2-yl]cyclopropanecarboxamide (80 mg, 0.26 mmol) and N-methylpyrrolidone (2.0 mL) as starting materials and in the same manner as in Example 335, the title compound (46 mg, 34%) was obtained as a white powder.

¹H-NMR (DMSO-d₆, 300 MHz) δ 0.73-0.87 (4H, m), 1.85-1.99 (1H, m), 6.62-7.05 (2H, m), 7.07 (1H, d, J=9.6 Hz), 7.45 (1H, t, J=8.1 Hz), 7.49-7.58 (1H, m), 7.61-7.69 (2H, m), 7.72 (1H, t, J=2.1 Hz), 7.82 (1H, br. s.), 7.93-8.00 (2H, m), 8.06 (1H, d, J=9.6 Hz), 10.50 (1H, s), 11.09 (1H, s).

Example 364

Production of N-[3-({2-[(cyclopropylcarbonyl)amino]imidazo[1,2-b]pyridazin-6-yl}oxy)-4-methoxyphenyl]-3-(1,1,2,2-tetrafluoroethoxy)benzamide

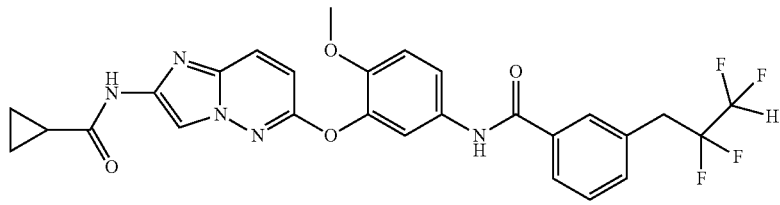

Using 3-(1,1,2,2-tetrafluoroethoxy)benzoic acid (85 mg, 0.35 mmol), oxalyl chloride (38 μL, 0.44=mol), N,N-dimethylformamide (1 drop), tetrahydrofuran (3.0 mL), N-[6-(5-amino-2-methoxyphenoxy)imidazo[1,2-b]pyridazin-2-yl]cyclopropanecarboxamide (100 mg, 0.30 mmol) and N-methylpyrrolidone (2.0 mL) as starting materials and in the same manner as in Example 335, the title compound (110 mg, 64%) was obtained as a white powder.

¹H-NMR (DMSO-d₆, 300 MHz) δ 0.76-0.86 (4H, m), 1.84-1.98 (1H, m), 3.83 (3H, s), 6.96-7.03 (1H, m), 7.07 (1H, d, J=9.6 Hz), 7.12-7.20 (1H, m), 7.36-7.49 (3H, m), 7.49-7.55 (1H, m), 7.62-7.70 (1H, m), 7.73 (1H, t, J=2.1 Hz), 7.98 (1H, s), 8.05 (1H, d, J=9.6 Hz), 10.34 (1H, s), 11.09 (1H, s).

Example 365

Production of 3-({2-[(cyclopropylcarbonyl)amino]imidazo[1,2-b]pyridazin-6-yl}oxy)-N-[3-(trifluoromethyl)phenyl]benzamide

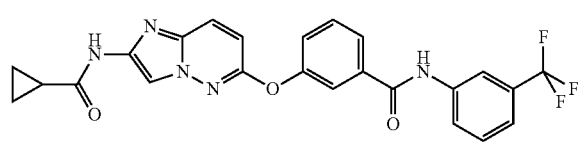

Using 3-({2-[(cyclopropylcarbonyl)amino]imidazo[1,2-b]pyridazin-6-yl}oxy)benzoic acid (100 mg, 0.30 mmol), oxalyl chloride (100 μL, 1.2 mmol), N,N-dimethylformamide (1 drop), tetrahydrofuran (2.0 mL), 3-(trifluoromethyl)aniline (80 mg, 0.48 mmol) and N-methylpyrrolidone (1.0 mL) as starting materials and in the same manner as in Example 335, the title compound (13 mg, 8.9%) was obtained as a pale-yellow powder.

¹H-NMR (DMSO-d₆, 300 MHz) δ 0.74-0.83 (4H, m), 1.86-1.97 (1H, m), 7.12 (1H, d, J=9.6 Hz), 7.46 (1H, d, J=7.8 Hz), 7.51-7.70 (3H, m), 7.83-7.99 (3H, m), 8.01-8.11 (2H, m), 8.23 (1H, s), 10.59 (1H, s), 11.08 (1H, s).

Example 366

Production of 3-({2-[(cyclopropylcarbonyl)amino]imidazo[1,2-b]pyridazin-6-yl}oxy)-N-[4-(trifluoromethyl)phenyl]benzamide

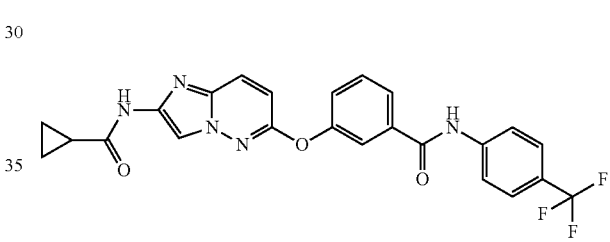

Using 3-({2-[(cyclopropylcarbonyl)amino]imidazo[1,2-b]pyridazin-6-yl}oxy)benzoic acid (30 mg, 0.089 mmol), 4-(trifluoromethyl)aniline (44 mg, 0.27 mmol), N-[3-(dimethylamino)propyl]-N'-ethylcarbodiimide hydrochloride (26 mg, 0.14 mmol), 4-(dimethylamino)pyridine (17 mg, 0.14 mmol) and pyridine (1.0 mL) as starting materials and in the same manner as in Example 318, the title compound (18 mg, 42%) was obtained as a white powder.

¹H-NMR (DMSO-d₆, 300 MHz) δ 0.71-0.86 (4H, m), 1.84-1.98 (1H, m), 7.11 (1H, d, J=9.6 Hz), 7.50-7.59 (1H, m), 7.65 (1H, t, J=7.9 Hz), 7.73 (2H, d, J=8.7 Hz), 7.81-7.93 (2H, m), 7.95 (1H, s), 8.00 (2H, d, J=8.7 Hz), 8.07 (1H, d, J=9.6 Hz), 10.63 (1H, s), 11.08 (1H, s).

Example 367

Production of 3-tert-butoxy-N-[3-({2-[(cyclopropylcarbonyl)amino]imidazo[1,2-b]pyridazin-6-yl}oxy)phenyl]benzamide

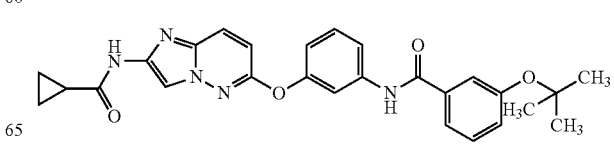

Using 3-tert-butoxybenzoic acid (110 mg, 0.58 mmol), oxalyl chloride (63 μL, 0.73 mmol), N,N-dimethylformamide (1 drop), tetrahydrofuran (4.0 mL), N-[6-(3-aminophenoxy)imidazo[1,2-b]pyridazin-2-yl]cyclopropanecarboxamide (150 mg, 0.49 mmol) and N-methylpyrrolidone (4.0 mL) as starting materials and in the same manner as in Example 335, the title compound (160 mg, 57%) was obtained as a white powder.

$^1$H-NMR (DMSO-$d_6$, 300 MHz) δ 0.74-0.87 (4H, m), 1.33 (9H, s), 1.85-1.98 (1H, m), 6.90-7.03 (1H, m), 7.07 (1H, d, J=9.6 Hz), 7.16-7.27 (1H, m), 7.36-7.48 (2H, m), 7.48-7.53 (1H, m), 7.61-7.70 (2H, m), 7.73 (1H, t, J=2.1 Hz), 7.98 (1H, s), 8.05 (1H, d, J=9.6 Hz), 10.34 (1H, s), 11.09 (1H, s).

Example 368

Production of N-(4-tert-butylphenyl)-3-({2-[(cyclopropylcarbonyl)amino]imidazo[1,2-b]pyridazin-6-yl}oxy)benzamide

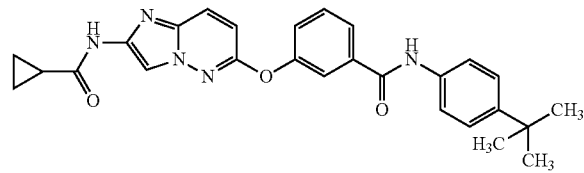

Using 3-({2-[(cyclopropylcarbonyl)amino]imidazo[1,2-b]pyridazin-6-yl}oxy)benzoic acid (100 mg, 0.30 mmol), 4-tert-butylaniline (57 mg, 0.36 mmol), N-[3-(dimethylamino)propyl]-N'-ethylcarbodiimide hydrochloride (68 mg, 0.36 mmol), 4-(dimethylamino)pyridine (43 mg, 0.36 mmol) and pyridine (5.0 mL) as starting materials and in the same manner as in Example 318, the title compound (70 mg, 50%) was obtained as a white powder.

$^1$H-NMR (DMSO-$d_6$, 300 MHz) δ 0.68-0.88 (4H, m), 1.28 (9H, s), 1.85-1.98 (1H, m), 7.11 (1H, d, J=9.6 Hz), 7.37 (2H, d, J=8.7 Hz), 7.47-7.55 (1H, m), 7.56-7.72 (3H, m), 7.77-7.92 (2H, m), 7.96 (1H, s), 8.07 (1H, d, J=9.6 Hz), 10.23 (1H, s), 11.08 (1H, s).

Example 369

Production of N-[3-(1-cyano-1-methylethyl)phenyl]-3-({2-[(cyclopropylcarbonyl)amino]imidazo[1,2-b]pyridazin-6-yl}oxy)benzamide

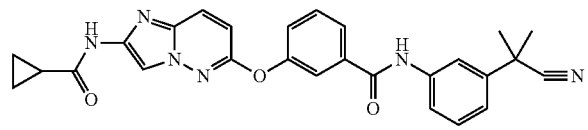

Using 3-({2-[(cyclopropylcarbonyl)amino]imidazo[1,2-b]pyridazin-6-yl}oxy)benzoic acid (100 mg, 0.30 mmol), 2-(3-aminophenyl)-2-methylpropanenitrile (57 mg, 0.36 mmol), N-[3-(dimethylamino)propyl]-N'-ethylcarbodiimide hydrochloride (68 mg, 0.36 mmol), 4-(dimethylamino)pyridine (43 mg, 0.36 mmol) and pyridine (5.0 mL) as starting materials and in the same manner as in Example 318, the title compound (64 mg, 45%) was obtained as a white powder.

$^1$H-NMR (DMSO-$d_6$, 300 MHz) δ 0.68-0.89 (4H, m), 1.69 (6H, s), 1.85-1.98 (1H, m), 7.11 (1H, d, J=9.6 Hz), 7.20-7.30 (1H, m), 7.41 (1H, t, J=8.0 Hz), 7.48-7.57 (1H, m), 7.64 (1H, t, J=7.9 Hz), 7.74-8.00 (5H, m), 8.07 (1H, d, J=9.6 Hz), 10.42 (1H, s), 11.08 (1H, s).

Example 370

Production of N-[4-(1-cyano-1-methylethyl)phenyl]-3-({2-[(cyclopropylcarbonyl)amino]imidazo[1,2-b]pyridazin-6-yl}oxy)benzamide

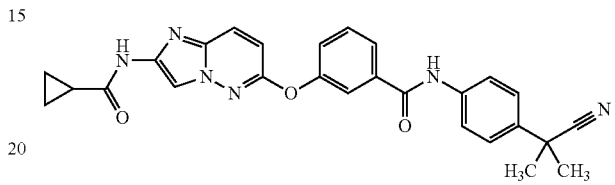

Using 3-({2-[(cyclopropylcarbonyl)amino]imidazo[1,2-b]pyridazin-6-yl}oxy)benzoic acid (100 mg, 0.30 mmol), 2-(4-aminophenyl)-2-methylpropanenitrile (57 mg, 0.36 mmol), N-[3-(dimethylamino)propyl]-N'-ethylcarbodiimide hydrochloride (63 mg, 0.33=mol), 4-(dimethylamino)pyridine (54 mg, 0.44 mmol) and pyridine (3.0 mL) as starting materials and in the same manner as in Example 318, the title compound (81 mg, 57%) was obtained as a white powder.

$^1$H-NMR (DMSO-$d_6$, 300 MHz) δ 0.71-0.87 (4H, m), 1.68 (6H, s), 1.85-1.98 (1H, m), 7.11 (1H, d, J=9.6 Hz), 7.45-7.56 (3H, m), 7.63 (1H, t, J=7.9 Hz), 7.77-7.86 (3H, m), 7.86-7.92 (1H, m), 7.95 (1H, s), 8.07 (1H, d, J=9.4 Hz), 10.38 (1H, s), 11.08 (1H, s).

Example 371

Production of 3-(1-cyano-2-cyclopropyl-1-methylethyl)-N-[3-({2-[(cyclopropylcarbonyl)amino]imidazo[1,2-b]pyridazin-6-yl}oxy)-4-methoxyphenyl]benzamide

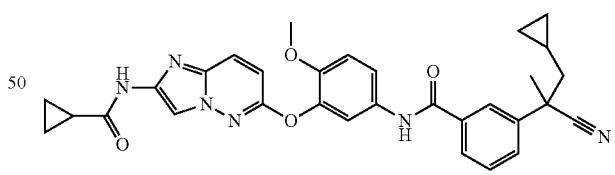

Using 3-(1-cyano-2-cyclopropyl-1-methylethyl)benzoic acid (70 mg, 0.31 mmol), oxalyl chloride (33 μL, 0.38 mmol), N,N-dimethylformamide (1 drop), tetrahydrofuran (2.0 mL), N-[6-(5-amino-2-methoxyphenoxy)imidazo[1,2-b]pyridazin-2-yl]cyclopropanecarboxamide (86 mg, 0.25 mmol) and N-methylpyrrolidone (2.0 mL) as starting materials and in the same manner as in Example 335, the title compound (67 mg, 48%) was obtained as a white powder.

$^1$H-NMR (DMSO-$d_6$, 300 MHz) δ −0.03-0.08 (1H, m), 0.16-0.27 (1H, m), 0.30-0.52 (2H, m), 0.55-0.69 (1H, m), 0.73-0.86 (4H, m, J=4.5 Hz), 1.69-2.12 (6H, m), 3.72 (3H, s), 7.06 (1H, d, J=9.3 Hz), 7.22 (1H, d, J=9.3 Hz), 7.59 (1H, t,

J=7.8 Hz), 7.65 (1H, dd, J=8.7, 2.4 Hz), 7.69-7.80 (2H, m), 7.86-7.97 (2H, m), 7.96-8.07 (2H, m), 10.31 (1H, s), 11.05 (1H, s).

Example 372

Production of 2-(1-cyano-1-methylethyl)-N-[3-({2-[(cyclopropylcarbonyl)amino]imidazo[1,2-b]pyridazin-6-yl}oxy)-4-methoxyphenyl]-1,3-thiazole-4-carboxamide

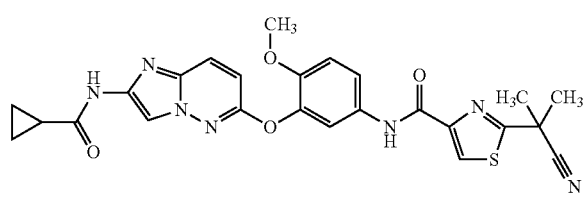

Using 2-(1-cyano-1-methylethyl)-1,3-thiazole-4-carboxylic acid (104 mg, 0.53 mmol), oxalyl chloride (57 µL, 0.66 mmol), N,N-dimethylformamide (1 drop), tetrahydrofuran (5.0 mL), N-[6-(5-amino-2-methoxyphenoxy)imidazo[1,2-b]pyridazin-2-yl]cyclopropanecarboxamide (150 mg, 0.44 mmol) and N,N-dimethylacetamide (4.0 mL) as starting materials and in the same manner as in Example 335, the title compound (179 mg, 78%) was obtained as a white powder.

$^1$H-NMR (DMSO-$d_6$, 300 MHz) δ 0.70-0.89 (4H, m), 1.82-1.98 (7H, m), 3.73 (3H, s), 7.06 (1H, d, J=9.6 Hz), 7.22 (1H, d, J=9.4 Hz), 7.64-7.80 (2H, m), 7.89 (1H, s), 8.01 (1H, d, J=10.2 Hz), 8.47 (1H, s), 10.13 (1H, s), 11.05 (1H, s).

Example 373

N-{3-[(2-aminoimidazo[1,2-b]pyridazin-6-yl)oxy]phenyl}cyclopropanecarboxamide

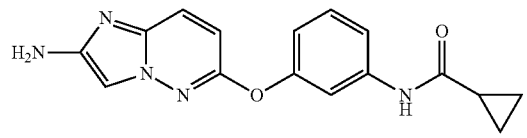

A mixture of N-{3-[(2-acetamidoimidazo[1,2-b]pyridazin-6-yl)oxy]phenyl}cyclopropanecarboxamide (465 mg, 1.32 mmol), 4N hydrochloric acid-ethyl acetate solution (10 mL) and methanol (10 mL) was stirred at room temperature for 14 hr. The reaction mixture was neutralized by the addition of 8N aqueous sodium hydroxide solution, and the mixture was extracted with ethyl acetate. The extract was washed with saturated brine, dried over anhydrous magnesium sulfate, and filtrated. The solvent was evaporated under reduced pressure, and the residue was washed with ethyl acetate/diisopropyl ether to give the title compound (376 mg, 92%) as a pale-green powder.

$^1$H-NMR (DMSO-$d_6$, 300 MHz) δ 0.75-0.81 (4H, m), 1.69-1.79 (1H, m), 5.33 (2H, s), 6.76 (1H, d, J=9.3 Hz), 6.80-6.86 (1H, m), 7.14 (1H, s), 7.28-7.39 (2H, m), 7.47 (1H, t, J=1.9 Hz), 7.71 (1H, d, J=9.3 Hz), 10.30 (1H, s).

Example 374

Production of N-[6-(5-amino-2-bromophenoxy)imidazo[1,2-b]pyridazin-2-yl]cyclopropanecarboxamide

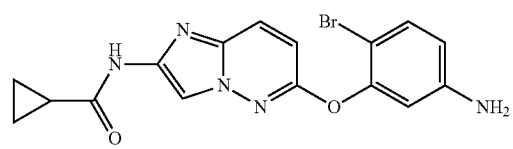

To a solution of N-(6-iodoimidazo[1,2-b]pyridazin-2-yl)cyclopropanecarboxamide (2.2 g, 6.7 mmol) in N,N-dimethylformamide (60 mL) were added 5-amino-2-bromophenol (1.9 g, 10 mmol) and potassium carbonate (1.8 g, 13 mmol), and the mixture was stirred at 140° C. for 12 hr. After cooling the mixture to room temperature, the mixture was diluted with water, and extracted with ethyl acetate. The organic layer was washed with 5% aqueous sodium hydrogencarbonate solution and saturated brine, dried over anhydrous sodium sulfate, and filtrated. The solvent was evaporated under reduced pressure, and the residue was purified by NH silica gel column chromatography (ethyl acetate/hexane=50/50→100/0). The solvent was evaporated under reduced pressure and the obtained solid was washed with diisopropyl ether to give the title compound (0.79 g, 31%) as a yellow powder.

$^1$H-NMR (DMSO-$d_6$, 300 MHz) δ 0.69-0.88 (4H, m), 1.84-1.97 (1H, m), 5.52 (2H, s), 6.45 (1H, dd, J=8.7, 2.7 Hz), 6.50 (1H, d, J=2.7 Hz), 7.03 (1H, d, J=9.0 Hz), 7.29 (1H, d, J=8.7 Hz), 7.94 (1H, s), 8.03 (1H, d, J=9.0 Hz), 11.07 (1H, s).

Example 375

Production of N-[4-bromo-3-({2-[(cyclopropylcarbonyl)amino]imidazo[1,2-b]pyridazin-6-yl}oxy)phenyl]-3-(1-cyano-1-methylethyl)benzamide

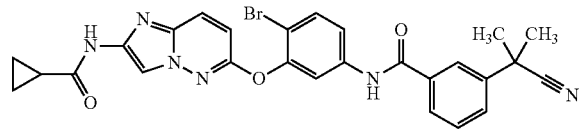

Using 3-(1-cyano-1-methylethyl)benzoic acid (330 mg, 1.8 mmol), oxalyl chloride (170 µL, 2.0 mmol), N,N-dimethylformamide (1 drop), tetrahydrofuran (15 mL), N-[6-(5-amino-2-bromophenoxy)imidazo[1,2-b]pyridazin-2-yl]cyclopropanecarboxamide (650 mg, 1.7 mmol) and N,N-dimethylacetamide (5.0 mL) as starting materials and in the same manner as in Example 335, the title compound (800 mg, 85%) was obtained as a white powder.

$^1$H-NMR (DMSO-$d_6$, 300 MHz) δ 0.71-0.88 (4H, m), 1.74 (6H, s), 1.85-1.96 (1H, m), 7.16 (1H, d, J=9.6 Hz), 7.60 (1H, t, J=7.8 Hz), 7.64-7.71 (1H, m), 7.73-7.81 (2H, m), 7.83-7.97 (3H, m), 8.02 (1H, s), 8.10 (1H, d, J=9.6 Hz), 10.56 (1H, s), 11.10 (1H, s).

Example 376

Production of N-{6-[3-({[(3-tert-butyl-1-phenyl-1H-pyrazol-5-yl)amino]carbonyl}amino)phenoxy]imidazo[1,2-b]pyridazin-2-yl}cyclopropanecarboxamide

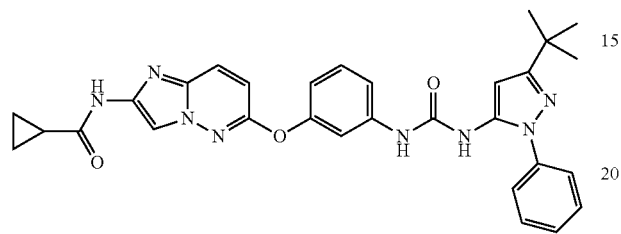

To a solution of N-[6-(3-aminophenoxy)imidazo[1,2-b]pyridazin-2-yl]cyclopropanecarboxamide (160 mg, 0.52 mmol) and 2,2,2-trichloroethyl (3-tert-butyl-1-phenyl-1H-pyrazol-5-yl)carbamate (200 mg, 0.52 mmol) in dimethylsulfoxide/water (2.0 mL/1.5 mL) was added triethylamine (53 mg, 0.52 mmol), and the mixture was stirred at 85° C. for 8 hr. The reaction mixture was diluted with ethyl acetate, washed with 1N hydrochloric acid, 5% aqueous sodium hydrogencarbonate solution and saturated brine, dried over anhydrous sodium sulfate, and filtrated. The solvent was evaporated under reduced pressure, and the residue was purified by NH silica gel column chromatography (ethyl acetate/hexane=50/50→100/0) and precipitated from ethyl acetate/diisopropyl ether/hexane to give the title compound (285 mg, 99%) as a white powder.

$^1$H-NMR (DMSO-d$_6$, 300 MHz) δ 0.75-0.86 (4H, m), 1.85-2.02 (1H, m), 3.32 (9H, s), 6.35 (1H, s), 6.84 (1H, dd, J=7.8, 1.8 Hz), 7.03 (1H, d, J=9.6 Hz), 7.16 (1H, dd, J=8.1, 1.2 Hz), 7.28-7.46 (3H, m), 7.48-7.58 (4H, m), 7.96 (1H, s), 8.03 (1H, d, J=9.6 Hz), 8.46 (1H, s), 9.22 (1H, s), 11.08 (1H, s).

Example 377

Production of N-[3-({2-[(cyclopropylcarbonyl)amino]imidazo[1,2-b]pyridazin-6-yl}oxy)phenyl]-6-(trifluoromethyl)pyridine-2-carboxamide

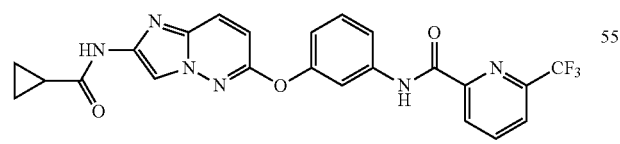

To a solution of N-[6-(3-aminophenoxy)imidazo[1,2-b]pyridazin-2-yl]cyclopropanecarboxamide (95 mg, 0.307 mmol) in N,N-dimethylformamide (5 mL) were added 6-(trifluoromethyl)pyridine-2-carboxylic acid (65 mg, 0.337 mmol), N-[3-(dimethylamino)propyl]-N'-ethylcarbodiimide hydrochloride (65 mg, 0.337 mmol) and 1-hydroxybenzotriazole (46 mg, 0.337 mmol), and the mixture was stirred at room temperature for 2 hr. Saturated aqueous ammonium chloride solution was added to the reaction mixture. The mixture was extracted with ethyl acetate, and the organic layer was washed with saturated brine, dried over anhydrous magnesium sulfate, and filtrated. The solvent was evaporated under reduced pressure, and the residue was washed with ethyl acetate/diisopropyl ether to give the title compound (126 mg, 85%) as a white powder.

$^1$H-NMR (DMSO-d$_6$, 300 MHz) δ 0.76-0.84 (4H, m), 1.87-1.98 (1H, m), 7.03-7.11 (2H, m), 7.47 (1H, t, J=8.2 Hz), 7.75-7.81 (1H, m), 7.83 (1H, t, J=2.2 Hz), 7.98 (1H, s), 8.06 (1H, d, J=9.2 Hz), 8.18 (1H, dd, J=6.9, 2.0 Hz), 8.31-8.41 (2H, m), 10.56 (1H, s), 11.09 (1H, s).

Example 378

Production of N-[3-({2-[(cyclopropylcarbonyl)amino]imidazo[1,2-b]pyridazin-6-yl}oxy)phenyl]-2-(trifluoromethyl)nicotinamide

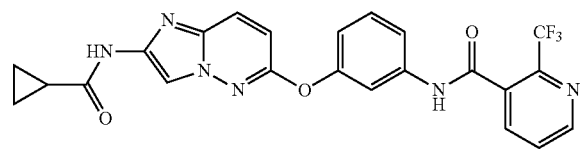

To a solution of N-[6-(3-aminophenoxy)imidazo[1,2-b]pyridazin-2-yl]cyclopropanecarboxamide (95 mg, 0.307 mmol) in N,N-dimethylformamide (5 mL) were added 2-(trifluoromethyl)nicotinic acid (65 mg, 0.337 mmol), N-[3-(dimethylamino)propyl]-N'-ethylcarbodiimide hydrochloride (65 mg, 0.337 mmol) and 1-hydroxybenzotriazole (46 mg, 0.337 mmol), and the mixture was stirred at room temperature for 2 hr, heated to 50° C. and stirred for 2 hr. Saturated aqueous ammonium chloride solution was added to the reaction mixture, and the mixture was extracted with ethyl acetate. The organic layer was washed with saturated brine, dried over anhydrous magnesium sulfate, and filtrated. The solvent was evaporated under reduced pressure, and the residue was purified by silica gel column chromatography (ethyl acetate/hexane=20/80→100/0), and precipitated from ethyl acetate/diisopropyl ether to give the title compound (79.6 mg, 54%) as a pale-green powder.

$^1$H-NMR (DMSO-d$_6$, 300 MHz) δ 0.76-0.85 (4H, m), 1.87-1.98 (1H, m), 7.01-7.11 (2H, m), 7.41-7.53 (2H, m), 7.62 (1H, t, J=2.0 Hz), 7.82-7.89 (1H, m), 7.94-7.99 (1H, m), 8.05 (1H, d, J=9.6 Hz), 8.25 (1H, d, J=7.5 Hz), 8.86 (1H, d, J=4.7 Hz), 10.85 (1H, s), 11.09 (1H, s).

Example 379

Production of 2,6-dichloro-N-[3-({2-[(cyclopropylcarbonyl)amino]imidazo[1,2-b]pyridazin-6-yl}oxy)phenyl]isonicotinamide

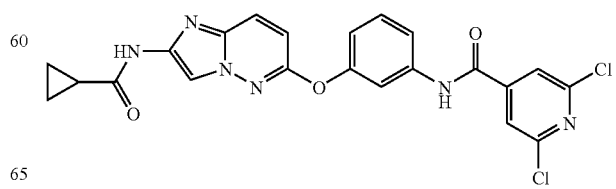

Using N-[6-(3-aminophenoxy)imidazo[1,2-b]pyridazin-2-yl]cyclopropanecarboxamide (95 mg, 0.307 mmol), 2,6-dichloropyridine-4-carboxylic acid (65 mg, 0.337 mmol), N-[3-(dimethylamino)propyl]-N'-ethylcarbodiimide hydrochloride (65 mg, 0.337 mmol), 1-hydroxybenzotriazole (46 mg, 0.337 mmol) and N,N-dimethylformamide (5 mL) as starting materials and in the same manner as in Example 377, the title compound (124 mg, 84%) was obtained as a pale-green powder.

$^1$H-NMR (DMSO-$d_6$, 300 MHz) δ 0.77-0.84 (4H, m), 1.87-1.98 (1H, m), 7.04-7.11 (2H, m), 7.47 (1H, t, J=8.2 Hz), 7.60-7.65 (1H, m), 7.68 (1H, t, J=2.1 Hz), 7.96-8.02 (3H, m), 8.06 (1H, d, J=9.2 Hz), 10.73 (1H, s), 11.09 (1H, s).

Example 380

Production of 2-chloro-N-[3-({2-[(cyclopropylcarbonyl)amino]imidazo[1,2-b]pyridazin-6-yl}oxy)phenyl]-6-methylisonicotinamide

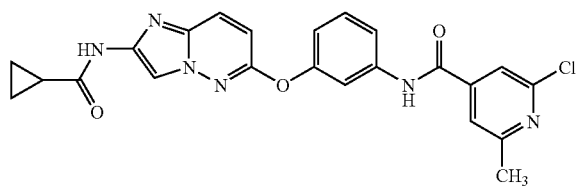

To a solution of N-[6-(3-aminophenoxy)imidazo[1,2-b]pyridazin-2-yl]cyclopropanecarboxamide (95 mg, 0.307 mmol) in N,N-dimethylformamide (5 mL) were added 2-chloro-6-methylpyridine-4-carboxylic acid (58 mg, 0.337 mmol), N-[3-(dimethylamino)propyl]-N'-ethylcarbodiimide hydrochloride (65 mg, 0.337 mmol) and 1-hydroxybenzotriazole (46 mg, 0.337 mmol), and the mixture was stirred at room temperature for 2 hr. Saturated aqueous ammonium chloride solution was added to the reaction mixture, and the mixture was extracted with ethyl acetate. The organic layer was washed with saturated brine, dried over anhydrous magnesium sulfate, and filtrated. The solvent was evaporated under reduced pressure, and the residue was purified by silica gel column chromatography (ethyl acetate/hexane=3/97→100/0) and precipitated from ethyl acetate/hexane to give the title compound (115 mg, 82%) as a white powder.

$^1$H-NMR (DMSO-$d_6$, 300 MHz) δ 0.77-0.83 (4H, m), 1.86-1.98 (1H, m), 2.55 (3H, s), 7.01-7.11 (2H, m), 7.46 (1H, t, J=8.2 Hz), 7.60-7.79 (4H, m), 7.98 (1H, s), 8.06 (1H, d, J=9.6 Hz), 10.64 (1H, s), 11.09 (1H, s).

Example 381

Production of N-(3-{[2-(propionylamino)imidazo[1,2-b]pyridazin-6-yl]oxy}phenyl)-3-(trifluoromethyl)benzamide

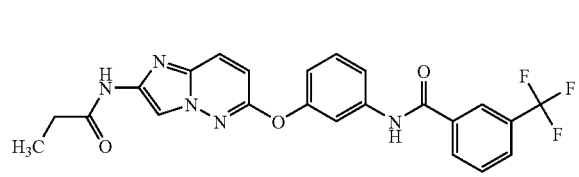

Using N-{3-[(2-aminoimidazo[1,2-b]pyridazin-6-yl)oxy]phenyl}-3-(trifluoromethyl)benzamide (150 mg, 0.363 mmol), propionic acid (40 μL, 0.544 mmol), N-[3-(dimethylamino)propyl]-N'-ethylcarbodiimide hydrochloride (104 mg, 0.544 mmol), 1-hydroxybenzotriazole (73 mg, 0.544 mmol), triethylamine (76 μL, 0.544 mmol) and N,N-dimethylformamide (5 mL) as starting materials and in the same manner as in Example 380, the title compound (116 mg, 68%) was obtained as a white powder.

$^1$H-NMR (DMSO-$d_6$, 300 MHz) δ 1.07 (3H, t, J=7.5 Hz), 2.37 (2H, q, J=7.5 Hz), 7.01-7.11 (2H, m), 7.46 (1H, t, J=8.2 Hz), 7.65-7.83 (3H, m), 7.94-8.00 (1H, m), 8.02 (1H, s), 8.05 (1H, d, J=9.6 Hz), 8.22-8.30 (2H, m), 10.59 (1H, s), 10.75 (1H, s).

Example 382

Production of N-(3-{[2-(isobutyrylamino)imidazo[1,2-b]pyridazin-6-yl]oxy}phenyl)-3-(trifluoromethyl)benzamide

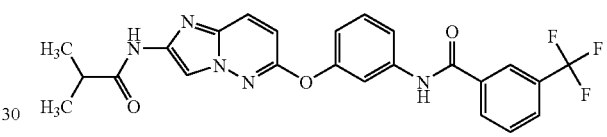

Using N-{3-[(2-aminoimidazo[1,2-b]pyridazin-6-yl)oxy]phenyl}-3-(trifluoromethyl)benzamide (150 mg, 0.363 mmol), 2-methylpropanoic acid (50 μL, 0.544 mmol), N-[3-(dimethylamino)propyl]-N'-ethylcarbodiimide hydrochloride (104 mg, 0.544 mmol), 1-hydroxybenzotriazole (73 mg, 0.544 mmol), triethylamine (76 μL, 0.544 mmol) and N,N-dimethylformamide (5 ml) as starting materials and in the same manner as in Example 380, the title compound (74 mg, 42%) was obtained as a pale-green powder.

$^1$H-NMR (DMSO-$d_6$, 300 MHz) δ 1.08 (6H, d, J=7.0 Hz), 2.65-2.77 (1H, m), 7.00-7.11 (2H, m), 7.46 (1H, t, J=8.1 Hz), 7.63-7.83 (3H, m), 7.94-8.09 (3H, m), 8.22-8.30 (2H, m), 10.59 (1H, s), 10.75 (1H, s).

Example 383

Production of N-{3-[(2-{[(methylsulfonyl)acetyl]amino}imidazo[1,2-b]pyridazin-6-yl)oxy]phenyl}-3-(trifluoromethyl)benzamide

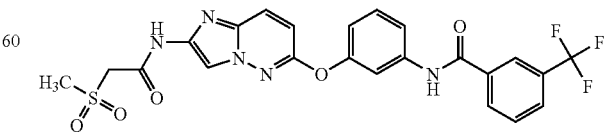

Using N-{3-[(2-aminoimidazo[1,2-b]pyridazin-6-yl)oxy]phenyl}-3-(trifluoromethyl)benzamide (150 mg, 0.363 mmol), (methylsulfonyl)acetic acid (75 mg, 0.544 mmol), N-[3-(dimethylamino)propyl]-N'-ethylcarbodiimide hydrochloride (104 mg, 0.544 mmol), 1-hydroxybenzotriazole (73 mg, 0.544 mmol), triethylamine (76 μL, 0.544 mmol) and N,N-dimethylformamide (5 mL) as starting materials and in the same manner as in Example 377, the title compound (171 mg, 88%) was obtained as a white powder.

$^1$H-NMR (DMSO-d$_6$, 300 MHz) δ 3.16 (3H, s), 4.37 (2H, m), 7.05 (1H, dd, J=8.1, 2.0 Hz), 7.14 (1H, d, J=9.6 Hz), 7.47 (1H, t, J=8.1 Hz), 7.65-7.83 (3H, m), 7.94-8.01 (1H, m), 8.06 (1H, s), 8.12 (1H, d, J=9.6 Hz), 8.22-8.30 (2H, m), 10.60 (1H, s), 11.29 (1H, s).

Example 384

Production of N-[3-({2-[(2,2-dimethylpropanoyl)amino]imidazo[1,2-b]pyridazin-6-yl}oxy)phenyl]-3-(trifluoromethyl)benzamide

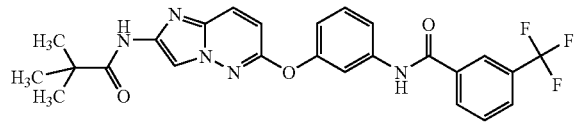

To a solution of N-{3-[(2-aminoimidazo[1,2-b]pyridazin-6-yl)oxy]phenyl}-3-(trifluoromethyl)benzamide (150 mg, 0.363 mmol) in pyridine (5 mL) was added dropwise 2,2-dimethylpropanoyl chloride (49 μL, 0.399 mmol), and the mixture was stirred at room temperature for 16 hr. Saturated aqueous sodium hydrogencarbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was purified by silica gel column chromatography (ethyl acetate/hexane=0/100→50/50), and precipitated from ethyl acetate/hexane to give the title compound (90 mg, 50%) as a white powder.

$^1$H-NMR (DMSO-d$_6$, 300 MHz) δ 1.22 (9H, s), 6.99-7.12 (2H, m), 7.46 (1H, t, J=8.2 Hz), 7.63-7.84 (3H, m), 7.98 (1H, d, J=7.9 Hz), 8.05 (2H, m), 8.22-8.30 (2H, m), 10.36 (1H, s), 10.60 (1H, s)

Example 385

Production of 2,2,2-trichloroethyl [6-(3-{[3-(trifluoromethyl)benzoyl]amino}phenoxy)imidazo[1,2-b]pyridazin-2-yl]carbamate

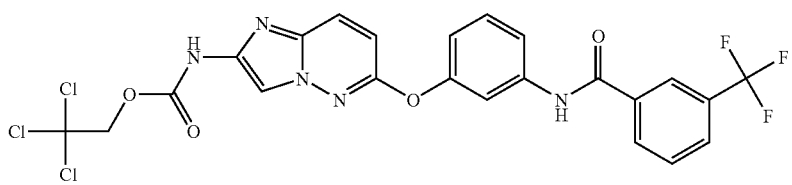

To a solution of N-{3-[(2-aminoimidazo[1,2-b]pyridazin-6-yl)oxy]phenyl}-3-(trifluoromethyl)benzamide (400 mg, 0.967 mmol) in tetrahydrofuran (10 mL) were added dropwise 2,2,2-trichloroethyl chlorocarbonate (159 μL, 1.16 mmol) and triethylamine (202 μL, 1.45 mmol), and the mixture was stirred at room temperature for 16 hr. The solvent was evaporated under reduced pressure, and the residue was washed with diisopropyl ether and water to give the title compound (436 mg, 76%) as a pale-yellow powder.

$^1$H-NMR (DMSO-d$_6$, 300 MHz) δ 4.97 (2H, s), 7.01-7.14 (2H, m), 7.46 (1H, t, J=8.0 Hz), 7.64-7.88 (4H, m), 7.98 (1H, d, J=8.0 Hz), 8.08 (1H, d, J=9.6 Hz), 8.22-8.30 (2H, m), 10.59 (1H, s), 10.97 (1H, s).

Example 386

Production of N-[6-(3-{[3-(trifluoromethyl)benzoyl]amino}phenoxy)imidazo[1,2-b]pyridazin-2-yl]morpholine-4-carboxamide A mixture of 2,2,2-trichloroethyl [6-(3-{[3-(trifluoromethyl)benzoyl]amino}phenoxy)imidazo[1,2-b]pyridazin-2-yl]carbamate (140 mg, 0.237 mmol), morpholine (31 mL, 0.356 mmol), N,N-diisopropylpropan-2-amine (123 μL, 0.713 mmol) and dimethyl sulfoxide (10 mL) was heated to 80° C. and the mixture was stirred for 24 hr. After the reaction mixture was allowed to cool to room temperature, saturated aqueous sodium hydrogencarbonate solution was added to the reaction mixture, and the mixture was extracted with ethyl acetate. The extract was washed with water and saturated brine, dried over anhydrous magnesium sulfate, and filtrated. The solvent was evaporated under reduced pressure, and the residue was purified by silica gel column chromatography (ethyl acetate/hexane=50/50→100/0) and precipitated from diisopropyl ether to give the title compound (92 mg, 73%) as a pale-green powder.

$^1$H-NMR (DMSO-d$_6$, 300 MHz) δ 3.41-3.49 (4H, m), 3.58 (4H, m), 6.98-7.06 (2H, m), 7.46 (1H, t, J=8.1 Hz), 7.64-7.83 (3H, m), 7.89 (1H, s), 7.93-8.03 (2H, m), 8.20-8.32 (2H, m), 9.56 (1H, s), 10.59 (1H, s).

Example 387

Production of 4-methyl-N-[6-(3-{[3-(trifluoromethyl)benzoyl]amino}phenoxy)imidazo[1,2-b]pyridazin-2-yl]piperazine-1-carboxamide

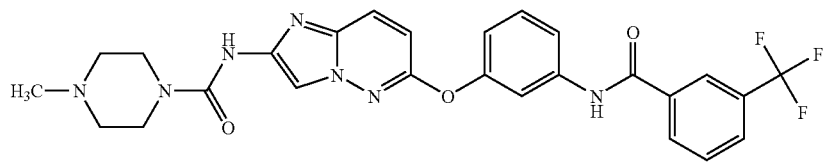

Using 2,2,2-trichloroethyl [6-(3-{[3-(trifluoromethyl)benzoyl]amino}phenoxy)imidazo[1,2-b]pyridazin-2-yl]carbamate (140 mg, 0.237 mmol), 1-methylpiperazine (40 μL, 0.356 mmol), N,N-diisopropylpropan-2-amine (123 μL, 0.713 mmol) and dimethyl sulfoxide (10 mL) as starting materials and in the same manner as in Example 386, the title compound (65 mg, 50%) was obtained as a pale-yellow powder.

$^1$H-NMR (DMSO-$d_6$, 300 MHz) δ 2.18 (3H, s), 2.25-2.32 (4H, m), 3.41-3.49 (4H, m), 6.98-7.06 (2H, m), 7.46 (1H, t, J=8.1 Hz), 7.63-7.83 (3H, m), 7.88 (1H, s), 7.94-8.03 (2H, m), 8.22-8.30 (2H, m), 9.51 (1H, s), 10.59 (1H, s).

Example, 388

Production of N-[3-({2-[(cyclobutylcarbonyl)amino]imidazo[1,2-b]pyridazin-6-yl}oxy)phenyl]-3-(trifluoromethyl)benzamide

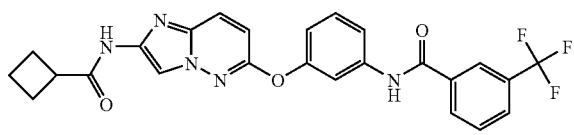

To a solution of N-{3-[(2-aminoimidazo[1,2-b]pyridazin-6-yl)oxy]phenyl}-3-(trifluoromethyl)benzamide (150 mg, 0.362 mmol) in tetrahydrofuran (5 mL) were added dropwise triethylamine (75 μL, 0.544 mmol) and cyclobutanecarbonyl chloride (50 μL, 0.435 mmol), and the mixture was stirred at room temperature for 16 hr. Saturated aqueous ammonium chloride solution was added to the reaction mixture, and the mixture was extracted with ethyl acetate. The extract was dried over anhydrous magnesium sulfate, and filtrated. The solvent was evaporated under reduced pressure, and the residue was purified by silica gel column chromatography (ethyl acetate/hexane=50/50→100/0) to give the title compound (98 mg, 54%) as a white powder.

$^1$H-NMR (CDCl$_3$, 300 MHz) δ 1.83-2.11 (2H, m), 2.15-2.46 (4H, m), 3.14-3.28 (1H, m), 6.88 (1H, d, J=9.4 Hz), 7.00-7.06 (1H, m), 7.42-7.48 (2H, m), 7.60-7.68 (1H, m), 7.69-7.85 (4H, m), 7.91-7.98 (1H, m), 8.04-8.09 (1H, m), 8.13 (1H, s), 8.19 (1H, s).

Example 389

Production of N-[3-({2-[(methylsulfonyl)amino]imidazo[1,2-b]pyridazin-6-yl}oxy)phenyl]-3-(trifluoromethyl)benzamide

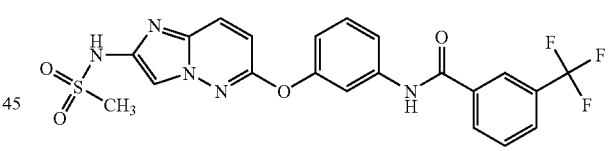

Using N-{3-[(2-aminoimidazo[1,2-b]pyridazin-6-yl)oxy]phenyl}-3-(trifluoromethyl)benzamide (150 mg, 0.362 mmol), triethylamine (76 μL, 0.544 mmol), methanesulfonyl chloride (34 μL, 0.435 mmol) and tetrahydrofuran (5 mL) as starting materials and in the same manner as in Example 388, the title compound (108 mg, 61%) was obtained as a pale-green-powder.

$^1$H-NMR (DMSO-$d_6$, 300 MHz) δ 3.13 (3H, s), 7.05 (1H, dd, J=8.0, 1.6 Hz), 7.14 (1H, d, J=9.6 Hz), 7.46 (1H, t, J=8.0 Hz), 7.63-7.84 (4H, m), 7.98 (1H, d, J=8.0 Hz), 8.10 (1H, d, J=9.6 Hz), 8.22-8.30 (2H, m), 10.29 (1H, s), 10.60 (1H, s).

Example 390

Production of 6-chloro-N-[6-(3-{[3-(trifluoromethyl)benzoyl]amino}phenoxy)imidazo[1,2-b]pyridazin-2-yl]nicotinamide

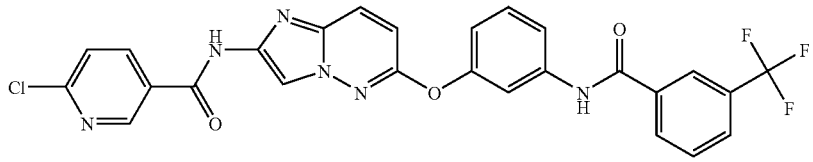

Using N-{3-[(2-aminoimidazo[1,2-b]pyridazin-6-yl)oxy]phenyl}-3-(trifluoromethyl)benzamide (150 mg, 0.362 mmol), triethylamine (76 μL, 0.544 mmol), 6-chloronicotinoyl chloride (76 mg, 0.435 mmol) and tetrahydrofuran (5 mL) as starting materials and in the same manner as in Example 388, the title compound (155 mg, 77%) was obtained as a pale-yellow powder.

$^1$H-NMR (DMSO-$d_6$, 300 MHz) δ 7.07 (1H, dd, J=8.2, 1.8 Hz), 7.15 (1H, d, J=9.7 Hz), 7.48 (1H, t, J=8.2 Hz), 7.69 (2H, d, J=8.5 Hz), 7.74-7.84 (2H, m), 7.98 (1H, d, J=7.7 Hz), 8.14 (1H, d, J=9.7 Hz), 8.20-8.33 (3H, m), 8.43 (1H, dd, J=8.5, 2.4 Hz), 9.03 (1H, d, J=2.4 Hz), 10.61 (1H, s), 11.66 (1H, s).

Example 391

Production of N-(3-{[2-({[2-(2-hydroxyethoxy)ethyl]carbamoyl}amino)imidazo[1,2-b]pyridazin-6-yl]oxy}phenyl)-3-(trifluoromethyl)benzamide

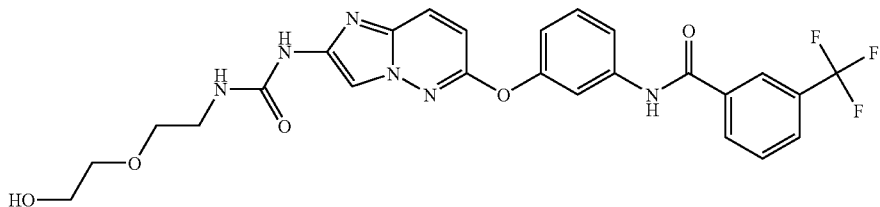

Using 2,2,2-trichloroethyl [6-(3-{[3-(trifluoromethyl)benzoyl]amino}phenoxy)imidazo[1,2-b]pyridazin-2-yl]carbamate (140 mg, 0.237 mmol), 2-(2-aminoethoxy)ethanol (43 μL, 0.435 mmol), N,N-diisopropylpropane-2-amine (76 μL, 0.435 mmol) and dimethyl sulfoxide (5 mL) as starting materials and in the same manner as in Example 386, the title compound (86 mg, 62%) was obtained as a pale-yellow powder.

$^1$H-NMR (DMSO-$d_6$, 300 MHz) δ 3.40-3.67 (8H, m), 4.58 (1H, t, J=5.4 Hz), 6.67 (1H, brs), 7.01 (2H, d, J=9.4 Hz), 7.45 (1H, t, J=8.0 Hz), 7.63-7.83 (4H, m), 7.93-8.02 (2H, m), 8.21-8.30 (2H, m), 9.11 (1H, s), 10.58 (1H, s).

Example 392

Production of N-{3-[(2-acetamidoimidazo[1,2-b]pyridazin-6-yl)oxy]phenyl}-3-(trifluoromethyl)benzamide

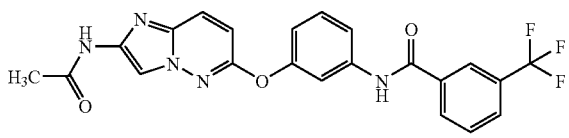

Using N-{3-[(2-aminoimidazo[1,2-b]pyridazin-6-yl)oxy]phenyl}-3-(trifluoromethyl)benzamide (150 mg, 0.362 mmol), acetyl chloride (31 μL, 0.435 mmol) and pyridine (3 mL) as starting materials and in the same manner as in Example 384, the title compound (99 mg, 60%) was obtained as a pale-yellow powder.

$^1$H-NMR (DMSO-$d_6$, 300 MHz) δ 2.07 (3H, s), 7.01-7.11 (2H, m), 7.46 (1H, t, J=8.1 Hz), 7.63-7.83 (3H, m), 7.95-8.01 (2H, m), 8.06 (1H, d, J=9.6 Hz), 8.22-8.30 (2H, m), 10.59 (1H, s), 10.80 (1H, s).

Example 393

Production of N-[3-({2-[(cyclopentylcarbonyl)amino]imidazo[1,2-b]pyridazin-6-yl}oxy)phenyl]-3-(trifluoromethyl)benzamide

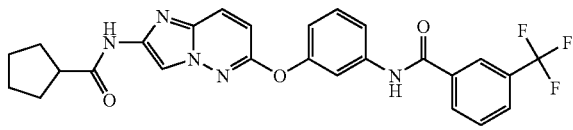

Using N-{3-[(2-aminoimidazo[1,2-b]pyridazin-6-yl)oxy]phenyl}-3-(trifluoromethyl)benzamide (150 mg, 0.362 mmol), cyclopentanecarbonyl chloride (53 µL, 0.435 mmol), triethylamine (75 µL, 0.544 mmol) and tetrahydrofuran (5 mL) as starting materials and in the same manner as in Example 388, the title compound (105 mg, 57%) was obtained as a white powder.

$^1$H-NMR (DMSO-$d_6$, 300 MHz) δ 1.47-1.90 (8H, m), 2.81-2.95 (1H, m), 7.00-7.10 (2H, m), 7.46 (1H, t, J=8.2 Hz), 7.63-7.83 (3H, m), 7.94-8.09 (3H, m), 8.21-8.30 (2H, m), 10.59 (1H, s), 10.77 (1H, s).

Example 394

Production of N-[3-({2-[(3-hydroxypropanoyl)amino]imidazo[1,2-b]pyridazin-6-yl}oxy)phenyl]-3-(trifluoromethyl)benzamide

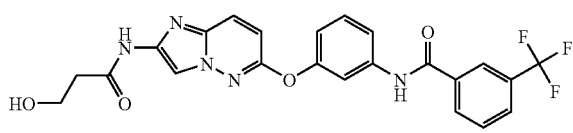

To a solution of N-{3-[(2-aminoimidazo[1,2-b]pyridazin-6-yl)oxy]phenyl}-3-(trifluoromethyl)benzamide (150 mg, 0.362 mmol) and 3-hydroxypropanoic acid (131 mg, 0.435 mmol) in N,N-dimethylformamide (5 mL) was added 4-(4,6-dimethoxy-1,3,5-triazin-2-yl)-4-methylmorpholin-4-ium chloride (160 mg, 0.544 mmol), and the mixture was stirred at room temperature for 16 hr. Saturated aqueous ammonium chloride solution was added to the reaction mixture, and the mixture was extracted with ethyl acetate. The extract was washed with saturated brine, dried over anhydrous magnesium sulfate, and filtrated. The solvent was evaporated under reduced pressure, and the residue was purified by silica gel column chromatography (ethyl acetate/hexane=30/70→100/0) and precipitated from ethanol to give the title compound (30 mg, 17%) as a pale-green powder.

$^1$H-NMR (CDCl$_3$, 300 MHz) δ 2.63-2.70 (2H, m), 3.73 (1H, brs), 3.96-4.03 (2H, m), 6.89 (1H, d, J=9.4 Hz), 7.01-7.07 (1H, m), 7.42-7.48 (2H, m), 7.59-7.86 (4H, m), 7.95 (1H, s), 8.07 (1H, d, J=7.9 Hz), 8.11-8.17 (2H, m), 8.54 (1H, s).

Example 395

Production of 2-oxo-2-{[6-(3-{[3-(trifluoromethyl)benzoyl]amino}phenoxy)imidazo[1,2-b]pyridazin-2-yl]amino}ethyl acetate

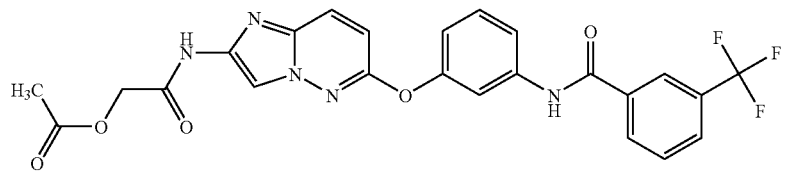

Using N-{3-[(2-aminoimidazo[1,2-b]pyridazin-6-yl)oxy]phenyl}-3-(trifluoromethyl)benzamide (300 mg, 0.725 mmol), triethylamine (152 µL, 1.08 mmol), 2-chloro-2-oxo-ethyl acetate (94 µL, 0.870 mmol) and tetrahydrofuran (7 mL) as starting materials and in the same manner as in Example 388, the title compound (299 mg, 80%) was obtained as a white powder.

$^1$H-NMR (DMSO-$d_6$, 300 MHz) δ 2.11 (3H, s), 4.70 (2H, s), 7.04 (1H, dd, J=8.6, 2.0 Hz), 7.11 (1H, d, J=9.8 Hz), 7.46 (1H, t, J=8.0 Hz), 7.64-7.83 (3H, m), 7.94-8.02 (2H, m), 8.09 (1H, d, J=9.8 Hz), 8.22-8.30 (2H, m), 10.59 (1H, s), 11.03 (1H, s).

Example 396

Production of N-(3-{[2-(glycoloylamino)imidazo[1,2-b]pyridazin-6-yl]oxy}phenyl)-3-(trifluoromethyl)benzamide A mixture of 2-oxo-2-{[6-(3-{[3-(trifluoromethyl)benzoyl]amino}phenoxy)imidazo[1,2-b]pyridazin-2-yl]amino}ethyl acetate (250 mg, 0.486 mmol), 1N aqueous sodium hydroxide solution (3 mL) and methanol (5 mL) was stirred at room temperature for 3 hr. The reaction mixture was neutralized by the addition of 1N hydrochloric acid, and extracted with ethyl acetate. The extract was washed with saturated brine, dried over anhydrous magnesium sulfate, and filtrated. The solvent was evaporated under reduced pressure, and the residue was washed with ethanol to give the title compound (185 mg, 81%) as a white powder.

$^1$H-NMR (DMSO-$d_6$, 300 MHz) δ 4.02-4.08 (2H, m), 5.46-5.55 (1H, m), 7.05 (1H, dd, J=7.6, 2.2 Hz), 7.11 (1H, d,

J=9.6 Hz), 7.47 (1H, t, J=8.0 Hz), 7.64-7.83 (3H, m), 7.98 (1H, d, J=8.0 Hz), 8.03-8.12 (2H, m), 8.22-8.30 (2H, m), 10.23 (1H, s), 10.60 (1H, s).

Example 397

Production of N-[3-({2-[(chloroacetyl)amino]imidazo[1,2-b]pyridazin-6-yl}oxy)phenyl]-3-(trifluoromethyl)benzamide

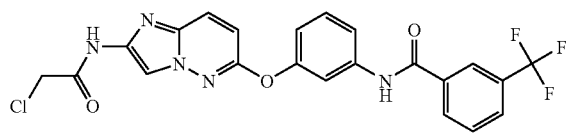

To a solution of N-{3-[(2-aminoimidazo[1,2-b]pyridazin-6-yl)oxy]phenyl}-3-(trifluoromethyl)benzamide (500 mg, 1.20 mmol) in tetrahydrofuran (10 mL) were added chloroacetyl chloride (168 μL, 1.45 mmol) and triethylamine (253 μL, 1.81 mmol), and the mixture was stirred at room temperature for 16 hr. Saturated aqueous ammonium chloride solution was added to the reaction mixture, and the mixture was extracted with ethyl acetate. The extract was washed with saturated brine, dried over anhydrous magnesium sulfate, and filtrated. The solvent was evaporated under reduced pressure, and the residue was washed with ethanol to give the title compound (418 mg, 71%) as a pale-yellow powder.

$^1$H-NMR (DMSO-$d_6$, 300 MHz) δ 4.31 (2H, s), 7.05 (1H, dd, J=8.2, 2.4 Hz), 7.12 (1H, d, J=9.4 Hz), 7.47 (1H, t, J=8.2 Hz), 7.64-7.84 (3H, m), 7.93-8.13 (3H, m), 8.21-8.30 (2H, m), 10.59 (1H, s), 11.20 (1H, s).

Example 398

Production of N-[3-({2-[(N,N-dimethylglycyl)amino]imidazo[1,2-b]pyridazin-6-yl}oxy)phenyl]-3-(trifluoromethyl)benzamide

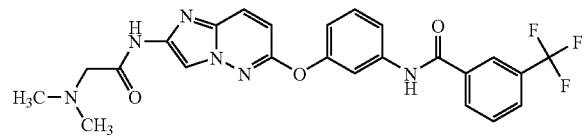

A mixture of N-[3-({2-[(chloroacetyl)amino]imidazo[1,2-b]pyridazin-6-yl}oxy)phenyl]-3-(trifluoromethyl)benzamide (120 mg, 0.244 mmol), aqueous dimethylamine (3 mL) solution and acetonitrile (3 mL) was heated to 80° C. and stirred for 3 hr. After the reaction mixture was allowed to cool to room temperature, saturated aqueous sodium hydrogencarbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was washed with ethanol to give the title compound (85 mg, 70%) as a pale-yellow powder.

$^1$H-NMR (CDCl$_3$, 300 MHz) δ 2.37 (6H, s), 3.11 (2H, s), 6.88 (1H, d, J=9.6 Hz), 6.99-7.06 (1H, m), 7.39-7.50 (2H, m), 7.63 (1H, t, J=7.9 Hz), 7.69-7.72 (1H, m), 7.75 (1H, d, J=9.6 Hz), 7.81 (1H, d, J=7.9 Hz), 8.00 (1H, s), 8.06 (1H, d, J=7.5 Hz), 8.13 (1H, s), 8.21 (1H, s), 9.65 (1H, brs).

Example 399

Production of N-[3-({2-[(morpholin 4-ylacetyl)amino]imidazo[1,2-b]pyridazin-6-yl}oxy)phenyl]-3-(trifluoromethyl)benzamide

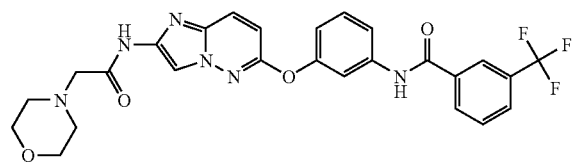

Using N-[3-({2-[(chloroacetyl)amino]imidazo[1,2-b]pyridazin-6-yl}oxy)phenyl]-3-(trifluoromethyl)benzamide (120 mg, 0.244 mmol), morpholine (1 mL) and acetonitrile (3 mL) as starting materials and in the same manner as in Example 398, the title compound (116 mg, 87%) was obtained as a white powder.

$^1$H-NMR (CDCl$_3$, 300 MHz) δ 2.59-2.65 (4H, m), 3.18 (2H, s), 3.75-3.82 (4H, m), 6.90 (1H, d, J=9.6 Hz), 7.01-7.07 (1H, m), 7.42-7.46 (2H, m), 7.59-7.68 (1H, m), 7.71-7.85 (3H, m), 7.92-7.98 (1H, m), 8.06 (1H, d, J=7.9 Hz), 8.13 (1H, s), 8.21 (1H, s), 9.50 (1H, s).

Example 400

Production of N-{3-[(2-{[(4-methylpiperazin-1-yl)acetyl]amino}imidazo[1,2-b]pyridazin-6-yl)oxy]phenyl}-3-(trifluoromethyl)benzamide

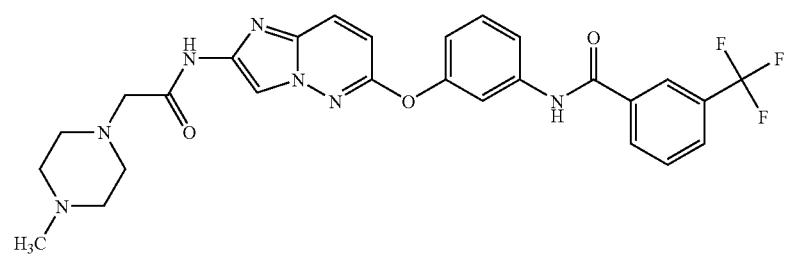

Using N-[3-({2-[(chloroacetyl)amino]imidazo[1,2-b]pyridazin-6-yl}oxy)phenyl]-3-(trifluoromethyl)benzamide (120 mg, 0.244 mmol), 1-methylpiperazine (1 mL) and acetonitrile (2 mL) as starting materials and in the same manner as in Example 398, the title compound (67 mg, 50%) was obtained as a white powder.

$^1$H-NMR (CDCl$_3$, 300 MHz) δ 2.32 (3H, s), 2.43-2.74 (8H, m), 3.18 (2H, s), 6.89 (1H, d, J=9.6 Hz), 7.00-7.07 (1H, m), 7.41-7.48 (2H, m), 7.64 (1H, t, J=7.8 Hz), 7.71-7.85 (3H, m), 7.96-8.01 (1H, m), 8.06 (1H, d, J=7.8 Hz), 8.13 (1H, s), 8.21 (1H, s), 9.55 (1H, s).

Example 401

Production of N-[3-({2-[(N-methylglycyl)amino]imidazo[1,2-b]pyridazin-6-yl}oxy)phenyl]-3-(trifluoromethyl)benzamide

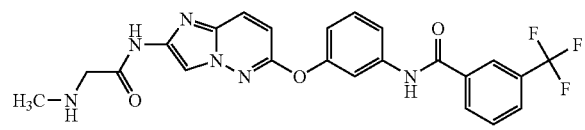

Using N-[3-({2-[(chloroacetyl)amino]imidazo[1,2-b]pyridazin-6-yl}oxy)phenyl]-3-(trifluoromethyl)benzamide (92 mg, 0.187 mmol), methylamine/methanol (2 mL) solution and acetonitrile (1 mL) as starting materials and in the same manner as in Example 398, the title compound (22 mg, 25%) was obtained as a white powder.

$^1$H-NMR (CDCl$_3$, 300 MHz) δ 2.50 (3H, s), 3.39 (2H, s), 6.88 (1H, d, J=9.4 Hz), 7.03 (1H, dd, J=6.7, 2.0 Hz), 7.39-7.51 (2H, m), 7.59-7.85 (4H, m), 7.93-8.10 (2H, m), 8.13 (1H, s), 8.20-8.25 (1H, m), 9.72 (1H, s).

Example 402

Production of N-{3-[(2-acetamidoimidazo[1,2-b]pyridazin-6-yl)oxy]phenyl}-3-(1-cyanocyclopropyl)benzamide

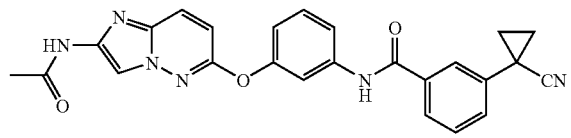

To a solution of 3-(1-cyanocyclopropyl)benzoic acid (1.50 g, 8.01 mmol) in tetrahydrofuran (30 mL) were added N,N-dimethylformamide (2 drops) and oxalyl chloride (1.16 mL, 13.3 mmol), and the mixture was stirred at room temperature for 1.5 hr. The solvent was evaporated under reduced pressure, and the residue and N-[6-(3-aminophenoxy)imidazo[1,2-b]pyridazin-2-yl]acetamide (1.89 g, 6.67 mmol) were dissolved in N-methylpyrrolidone (30 mL), and the mixture was stirred at room temperature for 3 hr. Saturated aqueous sodium hydrogencarbonate solution was added to the reaction mixture, and the mixture was extracted with ethyl acetate. The extract was washed with saturated brine, dried over anhydrous magnesium sulfate and filtrated, and the residue was purified by silica gel column chromatography (ethyl acetate/hexane=0/100→100/0) to give the title compound (2.25 g, 75%) as a pale-brown powder.

$^1$H-NMR (DMSO-d$_6$, 300 MHz) δ 1.58-1.65 (2H, m), 1.77-1.84 (2H, m), 2.07 (3H, s), 6.99-7.11 (2H, m), 7.45 (1H, t, J=8.2 Hz), 7.51-7.60 (2H, m), 7.62-7.68 (1H, m), 7.72 (1H, t, J=2.1 Hz), 7.82 (1H, s), 7.84-7.90 (1H, m), 8.00 (1H, s), 8.05 (1H, d, J=9.6 Hz), 10.42 (1H, s), 10.80 (1H, s).

Example 403

Production of N-{3-[(2-aminoimidazo[1,2-b]pyridazin-6-yl)oxy]phenyl}-3-(1-cyanocyclopropyl)benzamide

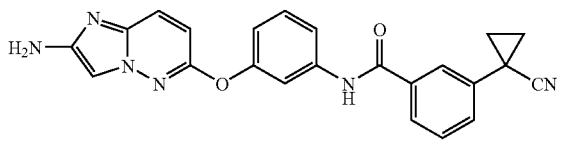

A mixture of N-{3-[(2-acetamidoimidazo[1,2-b]pyridazin-6-yl)oxy]phenyl}-3-(1-cyanocyclopropyl)benzamide (2.20 g, 4.86 mmol), 4N hydrochloric acid-ethyl acetate solution (35 mL) and methanol (35 mL) was stirred at room temperature for 14 hr. The reaction mixture was neutralized by the addition of 8N aqueous sodium hydroxide solution and extracted with ethyl acetate. The extract was washed with saturated brine, dried over anhydrous magnesium sulfate, and filtrated. The solvent was evaporated under reduced pressure, and the residue was washed with diisopropyl ether to give the title compound (1.63 g, 82%) as a yellow powder.

$^1$H-NMR (DMSO-d$_6$, 300 MHz) δ 1.58-1.64 (2H, m), 1.77-1.84 (2H, m), 5.34 (2H, brs), 6.80 (1H, d, J=9.3 Hz), 6.91-6.97 (1H, m), 7.15 (1H, s), 7.41 (1H, t, J=8.3 Hz), 7.51-7.67 (4H, m), 7.73 (1H, d, J=9.3 Hz), 7.81 (1H, s), 7.84-7.89 (1H, m), 10.38 (1H, s).

Example 404

Production of 6-chloro-N-[6-(3-{[3-(1-cyanocyclopropyl)benzoyl]amino}phenoxy)imidazo[1,2-b]pyridazin-2-yl]nicotinamide

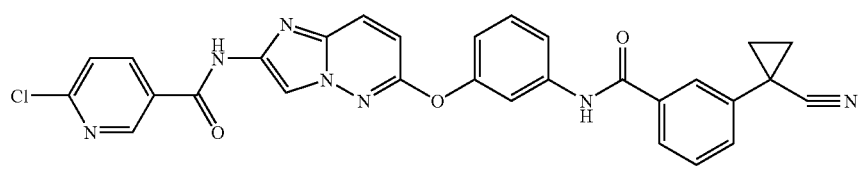

Using N-{3-[(2-aminoimidazo[1,2-b]pyridazin-6-yl)oxy]phenyl}-3-(1-cyanocyclopropyl)benzamide (120 mg, 0.292 mmol), 6-chloronicotinoyl chloride (61 mg, 0.350 mmol), triethylamine (62 μL, 0.438 mmol) and tetrahydrofuran (5 mL) as starting materials and in the same manner as in Example 385, the title compound (121 mg, 75%) was obtained as a white powder.

$^1$H-NMR (DMSO-$d_6$, 300 MHz) δ 1.58-1.65 (2H, m), 1.78-1.84 (2H, m), 7.05 (1H, dd, J=8.2, 1.8 Hz), 7.14 (1H, d, J=9.6 Hz), 7.47 (1H, t, J=8.2 Hz), 7.52-7.60 (2H, m), 7.64-7.72 (2H, m), 7.73-7.77 (1H, m), 7.82 (1H, s), 7.85-7.91 (1H, m), 8.13 (1H, d, J=9.6 Hz), 8.22 (1H, s), 8.43 (1H, dd, J=8.2, 2.4 Hz), 9.02 (1H, d, J=2.4 Hz), 10.44 (1H, s), 11.65 (1H, s).

Example 405

Production of 2-{[6-(3-{[3-(1-cyanocyclopropyl)benzoyl]amino}phenoxy)imidazo[1,2-b]pyridazin-2-yl]amino}-2-oxoethyl acetate Using 2-{[6-(3-{[3-(1-cyanocyclopropyl)benzoyl]amino}phenoxy)imidazo[1,2-b]pyridazin-2-yl]amino}-2-oxoethyl acetate (130 mg, 0.254 mmol), 1N aqueous sodium hydroxide solution (1.5 mL) and methanol (3 mL) as starting materials and in the same manner as in Example 396, the title compound (59 mg, 50%) was obtained as a pale-yellow powder.

$^1$H-NMR (DMSO-$d_6$, 300 MHz) δ 1.58-1.64 (2H, m), 1.78-1.84 (2H, m), 4.02-4.08 (2H, m), 5.47-5.54 (1H, m), 7.03 (1H, dd, J=8.0, 2.0 Hz), 7.10 (1H, d, J=9.6 Hz), 7.45 (1H, t, J=8.0 Hz), 7.53-7.59 (2H, m), 7.63-7.69 (1H, m), 7.73 (1H,

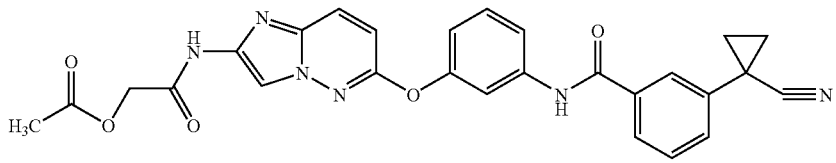

Using N-{3-[(2-aminoimidazo[1,2-b]pyridazin-6-yl)oxy]phenyl}-3-(1-cyanocyclopropyl)benzamide (200 mg, 0.487 mmol), triethylamine (101 μL, 0.730 mmol), 2-chloro-2-oxoethyl acetate (63 μL, 0.584 mmol) and tetrahydrofuran (5 mL) as starting materials and in the same manner as in Example 385, the title compound (183 mg, 74%) was obtained as a gray powder.

$^1$H-NMR (DMSO-$d_6$, 300 MHz) δ 1.58-1.65 (2H, m), 1.77-1.85 (2H, m), 2.11 (3H, s), 4.70 (2H, s), 7.02 (1H, dd, J=7.9, 2.0 Hz), 7.10 (1H, d, J=9.6 Hz), 7.45 (1H, t, J=7.9 Hz), 7.51-7.61 (2H, m), 7.66 (1H, d, J=7.9 Hz), 7.72 (1H, t, J=2.0 Hz), 7.82 (1H, s), 7.84-7.90 (1H, m), 8.00 (1H, s), 8.08 (1H, d, J=9.6 Hz), 10.42 (1H, s), 11.03 (1H, s).

Example 406

Production of 3-(1-cyanocyclopropyl)-N-(3-{[2-(glycoloylamino)imidazo[1,2-b]pyridazin-6-yl]oxy}phenyl)benzamide

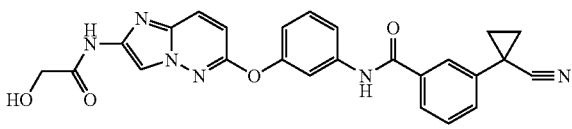

t, J=2.0), 7.81 (1H, d, J=2.0), 7.84-7.90 (1H, m), 8.03-8.11 (2H, m), 10.22 (1H, s), 10.42 (1H, s).

Example 407

Production of N-[3-({2-[(chloroacetyl)amino]imidazo[1,2-b]pyridazin-6-yl}oxy)phenyl]-3-(1-cyanocyclopropyl)benzamide

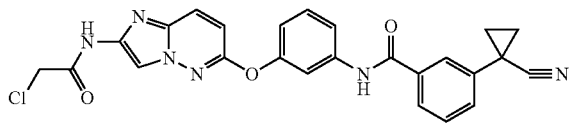

Using N-{3-[(2-aminoimidazo[1,2-b]pyridazin-6-yl)oxy]phenyl}-3-(1-cyanocyclopropyl)benzamide (600 mg, 1.46 mmol), triethylamine (305 μL, 2.19 mmol), chloroacetyl chloride (202 μL, 1.75 mmol) and tetrahydrofuran (10 mL) as starting materials and in the same manner as in Example 385, the title compound (636 mg, 89%) was obtained as a gray powder.

$^1$H-NMR (DMSO-$d_6$, 300 MHz) δ 1.57-1.65 (2H, m), 1.77-1.85 (2H, m), 4.31 (2H, s), 7.03 (1H, dd, J=8.0, 2.2 Hz), 7.12 (1H, d, J=9.6 Hz), 7.45 (1H, t, J=8.0 Hz), 7.52-7.60 (2H, m), 7.66 (1H, d, J=8.0 Hz), 7.73 (1H, t, J=2.2 Hz), 7.82 (1H, s), 7.85-7.91 (1H, m), 8.04 (1H, s), 8.09 (1H, d, J=9.6 Hz), 10.43 (1H, s), 11.20 (1H, s).

Example 408

Production of 3-(1-cyanocyclopropyl)-N-{3-[(2-{[(4-methylpiperazin-1-yl)acetyl]amino}imidazo[1,2-b]pyridazin-6-yl)oxy]phenyl}benzamide

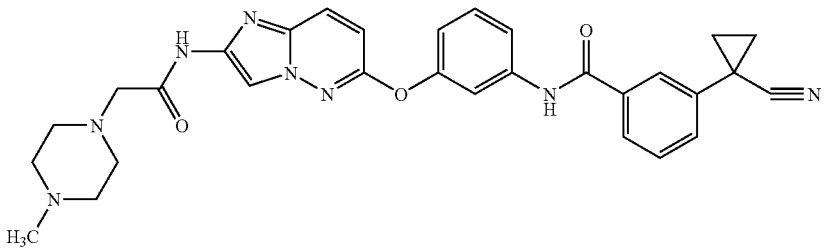

A mixture of N-[3-({2-[(chloroacetyl)amino]imidazo[1,2-b]pyridazin-6-yl}oxy)phenyl]-3-(1-cyanocyclopropyl)benzamide (140 mg, 0.287 mmol), 1-methylpiperazine (1 mL) and acetonitrile (2 mL) was stirred with heating at 80° C. for 4 hr. After the reaction mixture was allowed to cool to room temperature, saturated aqueous sodium hydrogencarbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was purified by NH silica gel column chromatography (ethyl acetate/hexane=0/100→100/0) to give the title compound (65 mg, 41%) as a white powder.

$^1$H-NMR (CDCl$_3$, 300 MHz) δ 1.43-1.53 (2H, m), 1.75-1.83 (2H, m), 2.32 (3H, s), 2.40-2.72 (8H, m), 3.18 (2H, s), 6.89 (1H, d, J=9.6 Hz), 6.98-7.05 (1H, m), 7.38-7.59 (4H, m), 7.69-7.80 (4H, m), 8.01 (1H, s), 8.21 (1H, s), 9.55 (1H, s).

Example 409

Production of 3-(1-cyanocyclopropyl)-N-[3-({2-[(morpholin-4-ylacetyl)amino]imidazo[1,2-b]pyridazin-6-yl}oxy)phenyl]benzamide

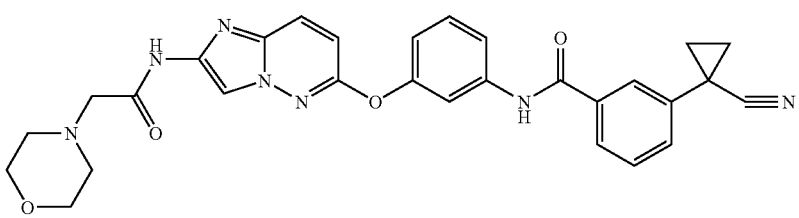

Using N-[3-({2-[(chloroacetyl)amino]imidazo[1,2-b]pyridazin-6-yl}oxy)phenyl]-3-(1-cyanocyclopropyl)benzamide (140 mg, 0.287 mmol), morpholine (1 mL) and acetonitrile (2 mL) as starting materials and in the same manner as in Example 408, the title compound (123 mg, 79%) was obtained as a white powder.

$^1$H-NMR (CDCl$_3$, 300 MHz) δ 1.45-1.52 (2H, m), 1.75-1.82 (2H, m), 2.59-2.66 (4H, m), 3.18 (2H, s), 3.75-3.82 (4H, m), 6.90 (1H, d, J=9.4 Hz), 6.98-7.05 (1H, m), 7.37-7.59 (4H, m), 7.70-7.79 (4H, m), 8.02 (1H, s), 8.20 (1H, s), 9.50 (1H, s).

Example 410

Production of methyl [6-(3-{[3-(trifluoromethyl)benzoyl]amino}phenoxy)imidazo[1,2-b]pyridazin-2-yl]carbamate

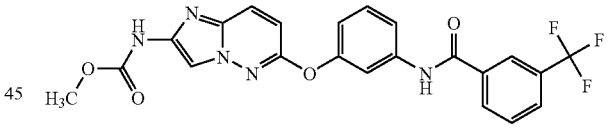

Using N-{3-[(2-aminoimidazo[1,2-b]pyridazin-6-yl)oxy]phenyl}-3-(trifluoromethyl)benzamide (150 mg, 0.362 mmol), methyl chlorocarbonate (33 μL, 0.435 mmol), triethylamine (75 μL, 0.544 mmol) and tetrahydrofuran (3 mL) as starting materials and in the same manner as in Example 388, the title compound (104 mg, 61%) was obtained as a white powder.

¹H-NMR (DMSO-d₆, 300 MHz) δ 3.68 (3H, s), 7.01-7.09 (2H, m), 7.46 (1H, t, J=8.1 Hz), 7.64-7.84 (4H, m), 7.94-8.06 (2H, m), 8.22-8.30 (2H, m), 10.40 (1H, brs), 10.58 (1H, s).

Example 411

Production of ethyl [6-(3-{[3-(trifluoromethyl)benzoyl]amino}phenoxy)imidazo[1,2-b]pyridazin-2-yl] carbamate

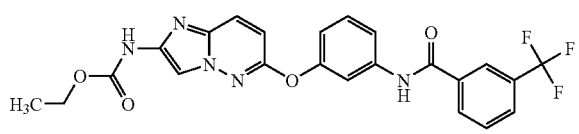

Using N-{3-[(2-aminoimidazo[1,2-b]pyridazin-6-yl)oxy]phenyl}-3-(trifluoromethyl)benzamide (150 mg, 0.362 mmol), ethyl chlorocarbonate (41 μL, 0.435 mmol), triethylamine (75 μL, 0.544 mmol) and tetrahydrofuran (3 mL) as starting materials and in the same manner as in Example 388, the title compound (109 mg, 62%) was obtained as a white powder.

¹H-NMR (DMSO-d₆, 300 MHz) δ 1.23 (3H, t, J=7.1 Hz), 4.14 (2H, q, J=7.1 Hz), 7.00-7.09 (2H, m), 7.46 (1H, t, J=8.1 Hz), 7.63-7.84 (4H, m), 7.94-8.06 (2H, m), 8.22-8.30 (2H, m), 10.33 (1H, brs), 10.58 (1H, s).

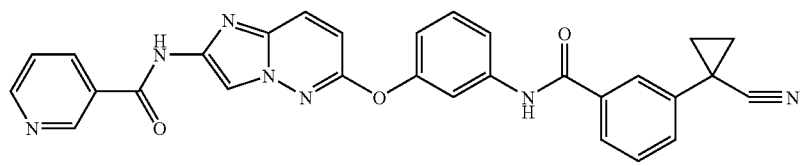

To a solution of nicotinic acid (54 mg, 0.438 mmol) in tetrahydrofuran (3 mL) were added N,N-dimethylformamide (1 drop) and oxalyl chloride (64 μL, 0.734 mmol), and the mixture was stirred at room temperature for 1 hr. The solvent was evaporated under reduced pressure, and the residue and N-{3-[(2-aminoimidazo[1,2-b]pyridazin-6-yl)oxy]phenyl}-3-(1-cyanocyclopropyl)benzamide (150 mg, 0.365 mmol) were dissolved in N-methylpyrrolidone (3 mL), and the mixture was stirred at room temperature for 14 hr. Saturated aqueous sodium hydrogencarbonate solution was added to the reaction mixture, and the mixture was extracted with ethyl acetate. The extract was washed with saturated brine, dried over anhydrous magnesium sulfate, and filtrated. The solvent was evaporated under reduced pressure, and the residue was purified by silica gel column chromatography (ethyl acetate/hexane=20/80→100/0) to give the title compound (100 mg, 53%) as a pale-green powder.

¹H-NMR (DMSO-d₆, 300 MHz) δ 1.57-1.65 (2H, m), 1.76-1.85 (2H, m), 7.05 (1H, d, J=8.5 Hz), 7.14 (1H, d, J=9.6 Hz), 7.47 (1H, t, J=8.1 Hz), 7.51-7.61 (3H, m), 7.63-7.93 (4H, m), 8.13 (1H, d, J=9.6 Hz), 8.24 (1H, s), 8.39 (1H, d, J=7.7 Hz), 8.75 (1H, d, J=4.9 Hz), 9.18 (1H, d, J=1.1 Hz), 10.44 (1H, s), 11.57 (1H, s).

Example 412

Production of N-[6-(3-{[3-(1-cyanocyclopropyl)benzoyl]amino}phenoxy)imidazo[1,2-b]pyridazin-2-yl]nicotinamide

Example 413

Production of N-[6-(3-{[3-(1-cyanocyclopropyl)benzoyl]amino}phenoxy)imidazo[1,2-b]pyridazin-2-yl]-6-methylnicotinamide

Example 414

Production of N-[3-({2-[(cyclopropylcarbonyl)amino]imidazo[1,2-b]pyridazin-6-yl}oxy)phenyl]-2-(trifluoromethyl)benzamide

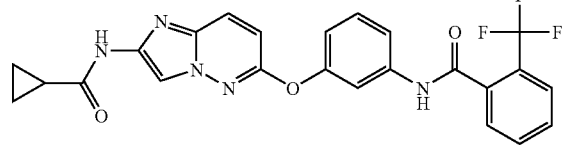

Using N-[6-(3-aminophenoxy)imidazo[1,2-b]pyridazin-2-yl]cyclopropanecarboxamide (150 mg, 0.484 mmol),

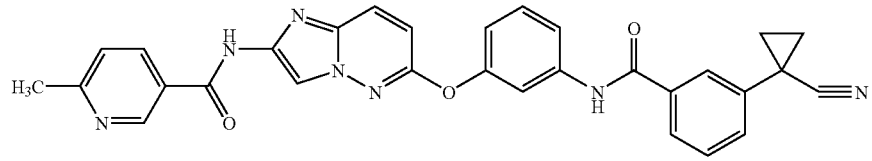

Using N-{3-[(2-aminoimidazo[1,2-b]pyridazin-6-yl)oxy]phenyl}-3-(1-cyanocyclopropyl)benzamide (150 mg, 0.365 mmol), 6-methylnicotinoyl chloride (75 mg, 0.548 mmol), N-[3-(dimethylamino)propyl]-N'-ethylcarbodiimide hydrochloride (105 mg, 0.548 mmol), 1-hydroxybenzotriazole (74 mg, 0.548 mmol) and N,N-dimethylformamide (5 mL) as starting materials and in the same manner as in Example 380, the title compound (44 mg, 23%) was obtained as a pale-green powder.

$^1$H-NMR (DMSO-$d_6$, 300 MHz) δ 1.59-1.65 (2H, m), 1.78-1.84 (2H, m), 2.55 (3H, s), 7.03-7.07 (1H, m), 7.14 (1H, d, J=9.6 Hz), 7.40 (1H, d, J=8.2 Hz), 7.47 (1H, t, J=8.2 Hz), 7.54-7.60 (2H, m), 7.65-7.69 (1H, m), 7.75 (1H, t, J=2.2 Hz), 7.81-7.83 (1H, m), 7.86-7.90 (1H, m), 8.12 (1H, dd, J=9.6, 0.5 Hz), 8.22 (1H, s), 8.29 (1H, dd, J=8.2, 2.2 Hz), 9.08 (1H, d, J=2.2 Hz), 10.45 (1H, s), 11.50 (1H, s). 2-(trifluoromethyl)benzoic acid (110 mg, 0.581 mmol), oxalyl chloride (84 mL, 0.969 mmol), N,N-dimethylformamide (1 drop), tetrahydrofuran (5 mL) and N-methylpyrrolidone (5 mL) as starting materials and in the same manner as in Example 412, the title compound (175 mg, 75%) was obtained as a white powder.

$^1$H-NMR (DMSO-$d_6$, 300 MHz) δ 0.77-0.84 (4H, m), 1.86-1.98 (1H, m), 6.98-7.04 (1H, m), 7.07 (1H, d, J=9.6 Hz), 7.43 (1H, t, J=8.1 Hz), 7.51-7.57 (1H, m), 7.64 (1H, t, J=2.1 Hz), 7.67-7.76 (2H, m), 7.76-7.88 (2H, m), 7.98 (1H, s), 8.05 (1H, d, J=9.6 Hz), 10.71 (1H, s), 11.07 (1H, s).

Example 415

Production of N-[4-({2-[(cyclopropylcarbonyl)amino]imidazo[1,2-b]pyridazin-6-yl}oxy)phenyl]-3-(trifluoromethyl)benzamide

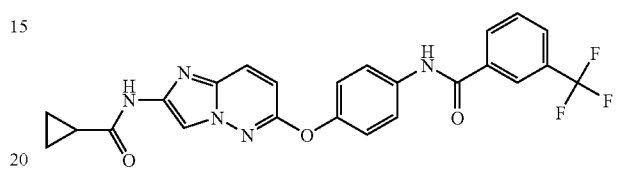

Using N-[6-(4-aminophenoxy)imidazo[1,2-b]pyridazin-2-yl]cyclopropanecarboxamide (150 mg, 0.484 mmol), 3-(trifluoromethyl)benzoic acid (110 mg, 0.581 mmol), oxalyl chloride (84 μL, 0.969 mmol), N,N-dimethylformamide (1 drop), tetrahydrofuran (5 mL) and N-methylpyrrolidone (5 mL) as starting materials and in the same manner as in Example 412, the title compound (57 mg, 24%) was obtained as a white powder.

$^1$H-NMR (DMSO-$d_6$, 300 MHz) δ 0.76-0.84 (4H, m), 1.86-1.97 (1H, m), 7.05 (1H, d, J=9.6 Hz), 7.29 (2H, d, J=8.9 Hz), 7.77-7.88 (3H, m), 7.94 (1H, s), 7.96-8.06 (2H, m), 8.25-8.32 (2H, m), 10.57 (1H, s), 11.06 (1H, s).

Example 416

Production of N-[3-({2-[(cyclopropylcarbonyl)amino]imidazo[1,2-b]pyridazin-6-yl}oxy)phenyl]-1H-indazole-3-carboxamide

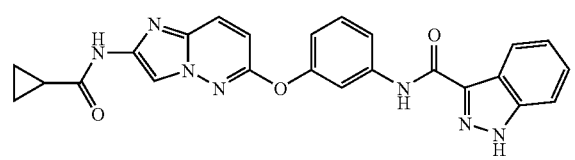

Using N-[6-(3-aminophenoxy)imidazo[1,2-b]pyridazin-2-yl]cyclopropanecarboxamide (150 mg, 0.484 mmol), 1H-indazole-3-carboxylic acid (94 mg, 0.581 mmol), oxalyl chloride (84 μL, 0.969 mmol), N,N-dimethylformamide (1 drop), tetrahydrofuran (5 mL) and N-methylpyrrolidone (5 mL) as starting materials and in the same manner as in Example 412, the title compound (149 mg, 68%) was obtained as a white powder.

¹H-NMR (DMSO-d₆, 300 MHz) δ 0.76-0.84 (4H, m), 1.84-1.98 (1H, m), 6.98 (1H, dd, J=7.6, 2.0 Hz), 7.07 (1H, d, J=9.6 Hz), 7.28 (1H, t, J=7.6 Hz), 7.38-7.49 (2H, m), 7.66 (1H, d, J=8.3 Hz), 7.78-7.83 (1H, m), 7.88 (1H, t, J=2.0 Hz), 7.99 (1H, s), 8.05 (1H, d, J=9.6 Hz), 8.20 (1H, d, J=8.3 Hz), 10.51 (1H, s), 11.08 (1H, s), 13.79 (1H, brs).

Example 417

Production of N-[6-(3-{[3-(1-cyanocyclopropyl)benzoyl]amino}phenoxy)imidazo[1,2-b]pyridazin-2-yl]pyridine-2-carboxamide

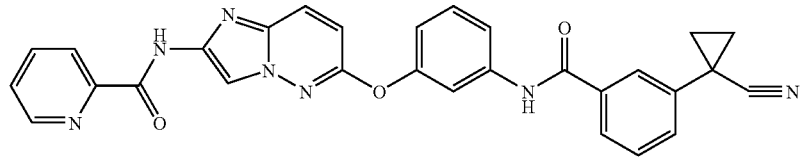

Using N-{3-[(2-aminoimidazo[1,2-b]pyridazin-6-yl)oxy]phenyl}-3-(1-cyanocyclopropyl)benzamide (150 mg, 0.365 mmol), pyridine-2-carboxylic acid (54 mg, 0.438 mmol), oxalyl chloride (63 μL), N,N-dimethylformamide (1 drop), tetrahydrofuran (3 mL) and N-methylpyrrolidone (5 mL) as starting materials and in the same manner as in Example 412, the title compound (125 mg, 67%) was obtained as a white powder.

¹H-NMR (DMSO-d₆, 300 MHz) δ 1.58-1.65 (2H, m), 1.78-1.85 (2H, m), 7.05 (1H, dd, J=8.0, 1.8 Hz), 7.16 (1H, d, J=9.6 Hz), 7.47 (1H, t, J=8.0 Hz), 7.52-7.61 (2H, m), 7.65-7.77 (3H, m), 7.83 (1H, s), 7.85-7.91 (1H, m), 8.05-8.20 (3H, m), 8.24 (1H, s), 8.73-8.78 (1H, m), 10.44 (1H, s), 10.69 (1H, s).

Example 418

Production of N-[6-(3-{[3-(1-cyanocyclopropyl)benzoyl]amino}phenoxy)imidazo[1,2-b]pyridazin-2-yl]isonicotinamide

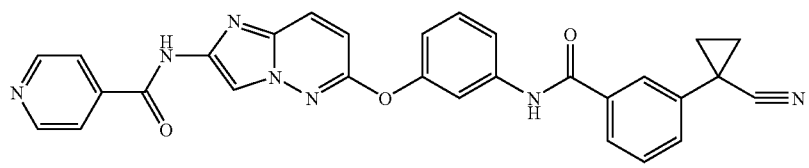

Using N-{3-[(2-aminoimidazo[1,2-b]pyridazin-6-yl)oxy]phenyl}-3-(1-cyanocyclopropyl)benzamide (150 mg, 0.365 mmol), pyridine-4-carboxylic acid (54 mg, 0.438 mmol), oxalyl chloride (63 μL, 0.734 mmol), N,N-dimethylformamide (1 drop), tetrahydrofuran (3 mL) and N-methylpyrrolidone (3 mL) as starting materials and in the same manner as in Example 412, the title compound (111 mg, 59%) was obtained as a pale-green powder.

¹H-NMR (DMSO-d₆, 300 MHz) δ 1.57-1.65 (2H, m), 1.77-1.85 (2H, m), 7.01-7.09 (1H, m), 7.15 (1H, d, J=9.6 Hz), 7.47 (1H, t, J=8.2 Hz), 7.51-7.61 (2H, m), 7.64-7.70 (1H, m), 7.75 (1H, t, J=2.1 Hz), 7.79-7.84 (1H, m), 7.85-7.91 (1H, m), 7.93-7.98 (2H, m), 8.13 (1H, d, J=9.6 Hz), 8.24 (1H, s), 8.73-8.81 (2H, m), 10.44 (1H, s), 11.67 (1H, s).

Example 419

Production of N-[3-({2-[(cyclopropylcarbonyl)amino]imidazo[1,2-b]pyridazin-6-yl}oxy)phenyl]-1H-indole-2-carboxamide

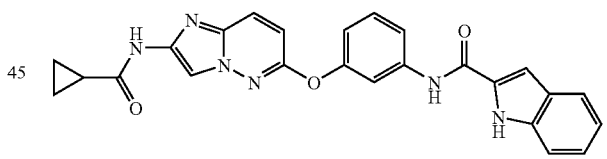

Using N-[6-(3-aminophenoxy)imidazo[1,2-b]pyridazin-2-yl]cyclopropanecarboxamide (150 mg, 0.484 mmol), 1H-indole-2-carboxylic acid (93 mg, 0.581 mmol), oxalyl chloride (84 μL, 0.969 mmol), N,N-dimethylformamide (1 drop), tetrahydrofuran (5 mL) and N-methylpyrrolidone (3 mL) as starting materials and in the same manner as in Example 412, the title compound (153 mg, 70%) was obtained as a white powder.

$^1$H-NMR (DMSO-$d_6$, 300 MHz) δ 0.76-0.85 (4H, m), 1.83-2.01 (1H, m), 6.96-7.12 (3H, m), 7.18-7.26 (1H, m), 7.39-7.49 (3H, m), 7.69 (2H, t, J=8.1 Hz), 7.76 (1H, t, J=2.1 Hz), 8.00 (1H, s), 8.06 (1H, d, J=9.4 Hz), 10.33 (1H, s), 11.09 (1H, s), 11.75 (1H, s).

Example 420

Production of 6-cyano-N-[6-(3-{[3-(1-cyanocyclopropyl)benzoyl]amino}phenoxy)imidazo[1,2-b]pyridazin-2-yl]nicotinamide

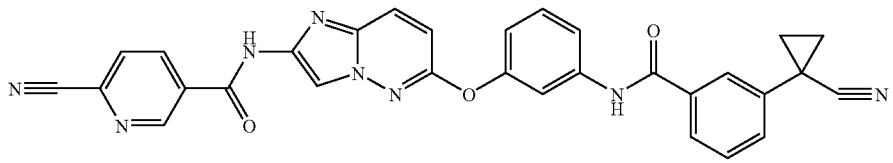

A mixture of 6-chloro-N-[6-(3-{[3-(1-cyanocyclopropyl)benzoyl]amino}phenoxy)imidazo[1,2-b]pyridazin-2-yl]nicotinamide (120 mg, 0.201 mmol), tetrakis(triphenylphosphine)palladium (0) (58 mg, 50.4 mol), zinc cyanide (26 mg, 0.225 mmol) and N,N-dimethylformamide (2.5 mL) was stirred with heating under an argon atmosphere at 100° C. for 6.5 hr. After the reaction mixture was allowed to cool to room temperature, saturated aqueous sodium hydrogencarbonate solution was added to the mixture, and the mixture was extracted with ethyl acetate. The extract was washed with saturated brine, dried over anhydrous magnesium sulfate, and filtrated. The solvent was evaporated under reduced pressure, and the residue was purified by silica gel column chromatography (ethyl acetate/hexane=50/50→100/0) to give the title compound (51 mg, 47%) as a yellow powder.

$^1$H-NMR (DMSO-$d_6$, 300 MHz) δ 1.58-1.65 (2H, m), 1.78-1.85 (2H, m), 7.05 (1H, dd, J=8.2, 1.4 Hz), 7.16 (1H, d, J=9.6 Hz), 7.47 (1H, t, J=8.2 Hz), 7.51-7.60 (2H, m), 7.67 (1H, d, J=8.5 Hz), 7.74-7.91 (3H, m), 8.14 (1H, d, J=9.6 Hz), 8.19-8.27 (2H, m), 8.60 (1H, dd, J=8.0, 2.0 Hz), 9.29 (1H, s), 10.45 (1H, s), 11.84 (1H, s).

Example 421

Production of N-{6-[3-(but-2-ynoylamino)phenoxy]imidazo[1,2-b]pyridazin-2-yl}cyclopropanecarboxamide

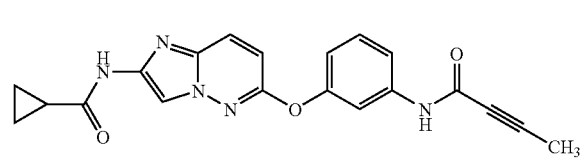

To a solution of but-2-ynoic acid (61 mg, 0.581 mmol) in tetrahydrofuran (3 mL) were added isobutyl chlorocarbonate (76 μL, 0.581 mmol) and 4-methylmorpholine (80 μL, 0.727 mmol), a solution of N-[6-(3-aminophenoxy)imidazo[1,2-b]pyridazin-2-yl]cyclopropanecarboxamide (150 mg, 0.484 mmol) in pyridine (1.5 mL)/N,N-dimethylformamide (2 mL) was further added under ice-cooling, and the mixture was stirred at room temperature for 3 hr. Saturated aqueous sodium hydrogencarbonate solution was added to the reaction mixture, and the mixture was extracted with ethyl acetate/tetrahydrofuran. The extract was washed with saturated brine, dried over anhydrous sodium sulfate, and filtrated. The solvent was evaporated under reduced pressure, and the residue was washed with ethyl acetate to give the title compound (132 mg, 73%) as a pale-orange powder.

$^1$H-NMR (DMSO-$d_6$, 300 MHz) δ 0.76-0.85 (4H, m), 1.86-1.97 (1H, m), 2.04 (3H, s), 6.92-6.99 (1H, m), 7.04 (1H, d, J=9.6 Hz), 7.32-7.47 (2H, m), 7.54 (1H, t, J=1.9 Hz), 7.93-7.99 (1H, m), 8.04 (1H, d, J=9.6 Hz), 10.75 (1H, s), 11.08 (1H, s).

Example 422

Production of N-{6-[3-(propioloylamino)phenoxy]imidazo[1,2-b]pyridazin-2-yl}cyclopropanecarboxamide

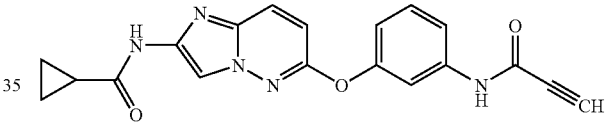

To a solution of propiolic acid (27 mg, 0.387 mmol) in tetrahydrofuran (2 mL) and N,N-dimethylformamide (2 mL) was added N,N'-dicyclohexylcarbodiimide (100 mg, 0.484 mmol) under ice-cooling, and the mixture was stirred for 30 min. To the reaction mixture was added N-[6-(3-aminophenoxy)imidazo[1,2-b]pyridazin-2-yl]cyclopropanecarboxamide (100 mg, 0.323 mmol), and the mixture was stirred under ice-cooling for 4 hr. The solvent was evaporated under reduced pressure, and the residue was purified by silica gel column chromatography (ethyl acetate/hexane=0/100→100/0) to give the title compound (24 mg, 21%) as a pale-orange powder.

$^1$H-NMR (DMSO-$d_6$, 300 MHz) δ 0.75-0.85 (4H, m), 1.87-1.98 (1H, m), 4.45 (1H, s), 6.97-7.08 (2H, m), 7.35-7.48 (2H, m), 7.51-7.57 (1H, m), 7.96 (1H, s), 8.04 (1H, d, J=9.8 Hz), 10.95 (1H, s), 11.08 (1H, s).

Example 423

Production of N-(6-{3-[(3-phenylprop-2-ynoyl)amino]phenoxy}imidazo[1,2-b]pyridazin-2-yl)cyclopropanecarboxamide

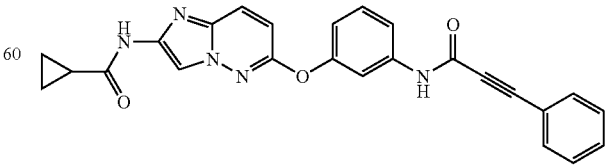

To a solution of 3-phenylprop-2-ynoic acid (85 mg, 0.581 mmol) in tetrahydrofuran (3 mL) were added isobutyl chlorocarbonate (76 μL, 0.581 mmol) and 4-methylmorpholine (80 μL, 0.727 mmol) under ice-cooling, a solution of N-[6-(3-aminophenoxy)imidazo[1,2-b]pyridazin-2-yl]cyclopropanecarboxamide (150 mg, 0.484 mmol) in N,N-dimethylformamide (3 mL) was further added thereto, and the mixture was stirred at room temperature for 16 hr. Water was added to the reaction mixture, and the precipitated solid was filtrated and washed with water to give the title compound (188 mg, 89%) as a white powder.

$^1$H-NMR (DMSO-$d_6$, 300 MHz) δ 0.77-0.84 (4H, m), 1.88-1.98 (1H, m), 6.98-7.04 (1H, m), 7.06 (1H, d, J=9.5 Hz), 7.38-7.56 (5H, m), 7.59 (1H, t, J=2.0 Hz), 7.62-7.68 (2H, m), 7.98 (1H, s), 8.05 (1H, d, J=9.5 Hz), 11.01 (1H, s), 11.08 (1H, s).

Example 424

Production of N-[6-(3-{[3-(1-cyanocyclopropyl)benzoyl]amino}phenoxy)imidazo[1,2-b]pyridazin-2-yl]-6-fluoronicotinamide

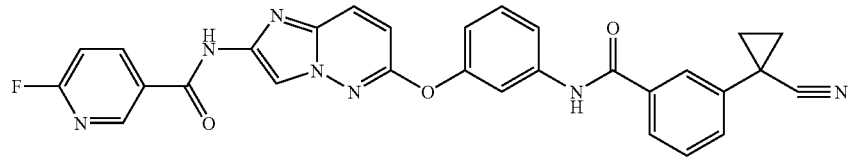

Using N-{3-[(2-aminoimidazo[1,2-b]pyridazin-6-yl)oxy]phenyl}-3-(1-cyanocyclopropyl)benzamide (150 mg, 0.365 mmol), 6-fluoronicotinic acid (61 mg, 0.438 mmol), oxalyl chloride (64 μL, 0.730 mmol), N,N-dimethylformamide (1 drop), tetrahydrofuran (3 mL) and N,N-dimethylacetamide (3 mL) as starting materials and in the same manner as in Example 412, the title compound (38 mg, 20%) was obtained as a pale-green powder.

$^1$H-NMR (DMSO-$d_6$, 300 MHz) δ 1.57-1.65 (2H, m), 1.78-1.85 (2H, m), 7.05 (1H, dd, J=8.2, 2.2 Hz), 7.15 (1H, d, J=9.5 Hz), 7.35 (1H, dd, J=8.2, 2.8 Hz), 7.47 (1H, t, J=8.2 Hz), 7.52-7.60 (2H, m), 7.64-7.69 (1H, m), 7.75 (1H, t, J=2.2 Hz), 7.80-7.84 (1H, m), 7.85-7.91 (1H, m), 8.13 (1H, d, J=9.5 Hz), 8.22 (1H, s), 8.55-8.63 (1H, m), 8.90 (1H, d, J=2.2 Hz), 10.45 (1H, s), 11.61 (1H, s).

Example 425

Production of N-[6-(3-{[3-(1-cyanocyclopropyl)benzoyl]amino}phenoxy)imidazo[1,2-b]pyridazin-2-yl]-6-(trifluoromethyl)nicotinamide

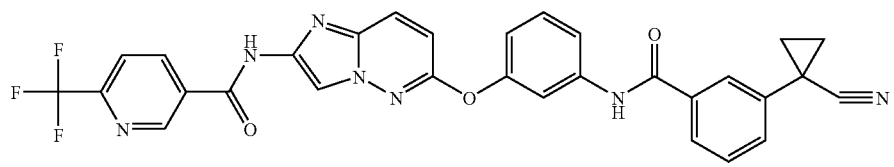

Using N-{3-[(2-aminoimidazo[1,2-b]pyridazin-6-yl)oxy]phenyl}-3-(1-cyanocyclopropyl)benzamide (150 mg, 0.365 mmol), 6-(trifluoromethyl)nicotinic acid (83 mg, 0.438 mmol), oxalyl chloride (64 μL, 0.730 mmol), N,N-dimethylformamide (1 drop), tetrahydrofuran (3 mL) and N,N-dimethylacetamide (3 mL) as starting materials and in the same manner as in Example 412, the title compound (57 mg, 27%) was obtained as a pale-yellow powder.

$^1$H-NMR (DMSO-d$_6$, 300 MHz) δ 1.58-1.65 (2H, m), 1.78-1.85 (2H, m), 7.03-7.09 (1H, m), 7.16 (1H, d, J=9.6 Hz), 7.47 (1H, t, J=8.1 Hz), 7.52-7.61 (2H, m), 7.64-7.70 (1H, m), 7.74-7.85 (2H, m), 7.86-7.91 (1H, m), 8.06-8.18 (2H, m), 8.25 (1H, s), 8.62-8.69 (1H, m), 9.31-9.35 (1H, m), 10.45 (1H, s), 11.83 (1H, s).

Example 426

Production of N-[6-(3-{[3-(1-cyanocyclopropyl)benzoyl]amino}phenoxy)imidazo[1,2-b]pyridazin-2-yl]pyrimidine-5-carboxamide

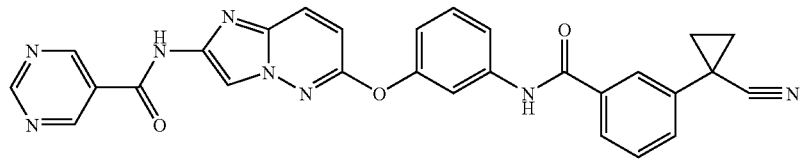

Using N-{3-[(2-aminoimidazo[1,2-b]pyridazin-6-yl)oxy]phenyl}-3-(1-cyanocyclopropyl)benzamide (140 mg, 0.313 mmol), pyrimidine-5-carboxylic acid (58 mg, 0.471 mmol), N-[3-(dimethylamino)propyl]-N'-ethylcarbodiimide hydrochloride (90 mg, 0.471 mmol), 1-hydroxybenzotriazole (63 mg, 0.471 mmol), triethylamine (60 μL, 0.471 mmol) and N,N-dimethylformamide (5 mL) as starting materials and in the same manner as in Example 380, the title compound (42 mg, 26%) was obtained as a pale-yellow powder.

$^1$H-NMR (DMSO-d$_6$, 300 MHz) δ 1.59-1.65 (2H, m), 1.79-1.85 (2H, m), 7.03-7.08 (1H, m), 7.16 (1H, d, J=9.6 Hz), 7.47 (1H, t, J=8.2 Hz), 7.54-7.60 (2H, m), 7.65-7.70 (1H, m), 7.76 (1H, t, J=2.1 Hz), 7.81-7.84 (1H, m), 7.86-7.91 (1H, m), 8.15 (1H, dd, J=9.6, 0.7 Hz), 8.23 (1H, s), 9.32-9.37 (3H, m), 10.46 (1H, s), 11.79 (1H, s).

Example 427

Production of N-[3-({2-[(cyclopropylcarbonyl)amino]imidazo[1,2-b]pyridazin-6-yl}thio)phenyl]-3-(trifluoromethyl)benzamide

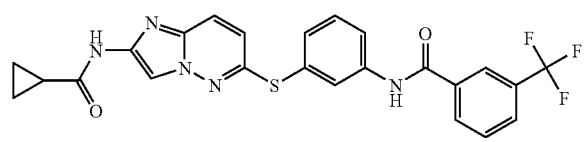

Using N-{6-[(3-aminophenyl)sulfanyl]imidazo[1,2-b]pyridazin-2-yl}cyclopropanecarboxamide (140 mg, 0.430 mmol), 3-(trifluoromethyl)benzoic acid (98 mg, 0.516 mmol), oxalyl chloride (75 μL, 0.860 mmol), N,N-dimethylformamide (1 drop), tetrahydrofuran (3 mL) and N,N-dimethylacetamide (3 mL) as starting materials and in the same manner as in Example 412, the title compound (148 mg, 75%) was obtained as a white powder.

$^1$H-NMR (DMSO-d$_6$, 300 MHz) δ 0.79-0.86 (4H, m), 1.89-2.00 (1H, m), 6.96 (1H, d, J=9.4 Hz), 7.34-7.39 (1H, m), 7.50 (1H, t, J=8.0 Hz), 7.79 (1H, t, J=8.0 Hz), 7.88-7.94 (2H, m), 7.98 (1H, d, J=8.0 Hz), 8.03 (1H, t, J=1.8 Hz), 8.15 (1H, s), 8.25 (1H, d, J=8.0 Hz), 8.28 (1H, s), 10.60 (1H, s), 11.18 (1H, s).

Example 428

Production of 3-(1-cyano-1-methylethyl)-N-[3-({2-[(cyclopropylcarbonyl)amino]imidazo[1,2-b]pyridazin-6-yl}thio)phenyl]benzamide

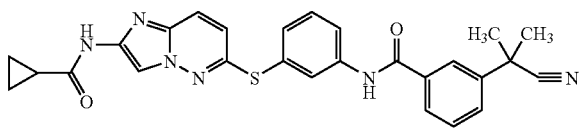

Using N-{6-[(3-aminophenyl)sulfanyl]imidazo[1,2-b]pyridazin-2-yl}cyclopropanecarboxamide (140 mg, 0.430 mmol), 3-(1-cyano-1-methylethyl)benzoic acid (97 mg, 0.516 mmol), oxalyl chloride (75 μL, 0.860 mmol), N,N-dimethylformamide (1 drop), tetrahydrofuran (3 mL) and N,N-dimethylacetamide (3 mL) as starting materials and in the same manner as in Example 412, the title compound (108 mg, 51%) was obtained as a white powder.

$^1$H-NMR (DMSO-d$_6$, 300 MHz) δ 0.78-0.87 (4H, m), 1.74 (6H, s), 1.89-1.99 (1H, m), 6.95 (1H, d, J=9.4 Hz), 7.32-7.38 (1H, m), 7.49 (1H, t, J=8.0 Hz), 7.60 (1H, t, J=7.8 Hz), 7.72-7.79 (1H, m), 7.86-7.96 (3H, m), 8.00-8.05 (2H, m), 8.15 (1H, s), 10.45 (1H, s), 11.18 (1H, s).

Example 429

Production of 3-(1-cyanocyclopropyl)-N-[3-({2-[(cyclopropylcarbonyl)amino]imidazo[1,2-b]pyridazin-6-yl}thio)phenyl]benzamide

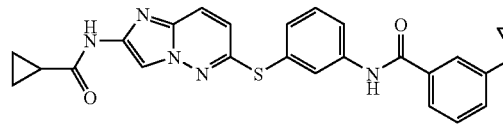

Using N-{6-[(3-aminophenyl)sulfanyl]imidazo[1,2-b]pyridazin-2-yl}cyclopropanecarboxamide (130 mg, 0.399 mmol), 3-(1-cyanocyclopropyl)benzoic acid (89 mg, 0.479 mmol), oxalyl chloride (70 μL, 0.799 mmol), N,N-dimethylformamide (1 drop), tetrahydrofuran (3 mL) and N,N-dimethylacetamide (3 mL) as starting materials and in the same manner as in Example 412, the title compound (158 mg, 80%) was obtained as a pale-brown powder.

$^1$H-NMR (DMSO-$d_6$, 300 MHz) δ 0.78-0.88 (4H, m), 1.58-1.65 (2H, m), 1.77-1.85 (2H, m), 1.89-2.00 (1H, m), 6.95 (1H, d, J=9.4 Hz), 7.32-7.38 (1H, m), 7.45-7.53 (1H, m), 7.54-7.61 (2H, m), 7.82 (1H, s), 7.84-7.94 (3H, m), 8.02 (1H, t, J=1.7 Hz), 8.15 (1H, s), 10.44 (1H, s), 11.18 (1H, s).

Example 430

Production of N-{3-[(2-anilinoimidazo[1,2-b]pyridazin-6-yl)oxy]phenyl}-3-(trifluoromethyl)benzamide

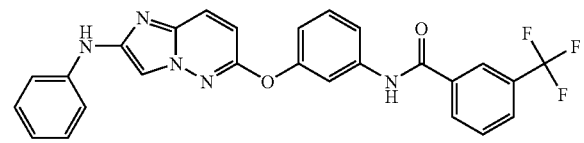

A mixture of N-{3-[(2-aminoimidazo[1,2-b]pyridazin-6-yl)oxy]phenyl}-3-(trifluoromethyl)benzamide (100 mg, 0.242 mmol), iodobenzene (32 μl, 0.290 mmol), tris(dibenzylideneacetone)dipalladium (0) (11 mg, 24.2 μmol), dicyclohexyl(2',4',6'-triisopropylbiphenyl-2-yl)phosphine (23 mg, 48.4 μmol), sodium tert-butoxide (34 mg, 0.362 mmol) and toluene (2 mL) was stirred under an argon atmosphere with heating at 80° C. for 5 hr. After the reaction mixture was allowed to cool to room temperature, saturated aqueous sodium hydrogencarbonate solution was added to the mixture, and the mixture was extracted with ethyl acetate. The extract was washed with saturated brine, dried over anhydrous magnesium sulfate, and filtrated. The solvent was evaporated under reduced pressure, and the residue was purified by silica gel column chromatography (ethyl acetate/hexane=0/100→50/50) to give the title compound (19 mg, 16%) as a pale-green powder.

$^1$H-NMR (DMSO-$d_6$, 300 MHz) δ 6.78 (1H, t, J=7.3 Hz), 6.96-7.07 (2H, m), 7.18-7.25 (2H, m), 7.36-7.50 (3H, m), 7.65-7.72 (3H, m), 7.79 (1H, t, J=7.6 Hz), 7.98 (2H, d, J=9.2 Hz), 8.18-8.32 (2H, m), 8.91 (1H, s), 10.58 (1H, s).

Example 431

Production of N-{6-[3-({[3-(trifluoromethyl)phenyl]carbamoyl}amino)phenoxy]imidazo[1,2-b]pyridazin-2-yl}cyclopropanecarboxamide

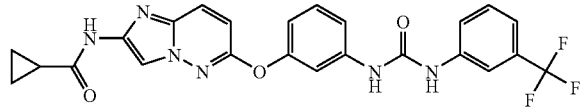

A mixture of N-[6-(3-aminophenoxy)imidazo[1,2-b]pyridazin-2-yl]cyclopropanecarboxamide (300 mg, 0.969 mmol), 3-(trifluoromethyl)phenyl isocyanate (667 μL, 4.84 mmol), toluene (4 mL) and tetrahydrofuran (1 mL) was stirred with heating under reflux for 3 hr. After the reaction mixture was allowed to cool to room temperature, the precipitate was collected by filtration and washed with ethyl acetate/diisopropyl ether to give the title compound (268 mg, 56%) as a white powder.

$^1$H-NMR (DMSO-$d_6$, 300 MHz) δ 0.76-0.84 (4H, m), 1.87-1.98 (1H, m), 6.83-6.89 (1H, m), 7.04 (1H, d, J=9.5 Hz), 7.23-7.40 (3H, m), 7.46-7.53 (2H, m), 7.56-7.64 (1H, m), 7.95-8.00 (2H, m), 8.03 (1H, d, J=9.5 Hz), 9.12-9.35 (2H, m), 11.08 (1H, s).

Example 432

Production of 2-({2-[(cyclopropylcarbonyl)amino]imidazo[1,2-b]pyridazin-6-yl}thio)-N-phenylbenzamide

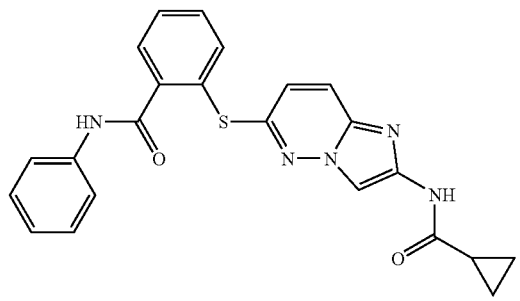

In the same manner as in Example 278 and using 2-({2-[(cyclopropylcarbonyl)amino]imidazo[1,2-b]pyridazin-6-yl}thio)benzoic acid (250 mg, 0.71 mmol), aniline (184 mg, 2.0 mmol), O-(7-azabenzotriazol-1-yl)-N,N,N',N'-tetramethyluronium hexafluorophosphate (380 mg, 1.0 mmol), N,N-diisopropylethylamine (270 mg, 2.0 mmol) and N,N-dimethylformamide (7 mL) as starting materials, the title compound (280 mg, 93%) was obtained as a white solid.

$^1$H-NMR (DMSO-$d_6$, 300 MHz) δ 0.76-0.88 (4H, m), 1.88-1.97 (1H, m), 6.98 (1H, d, J=9.5 Hz), 7.08 (1H, t, J=7.4

Hz), 7.31 (2H, t, J=8.0 Hz), 7.49-7.60 (3H, m), 7.61-7.76 (3H, m), 7.88 (1H, d, J=9.1 Hz), 8.14 (1H, s), 10.51 (1H, s), 11.16 (1H, s).

Example 433

Production of N-benzyl-2-({2-[(cyclopropylcarbonyl)amino]imidazo[1,2-b]pyridazin-6-yl}thio)benzamide

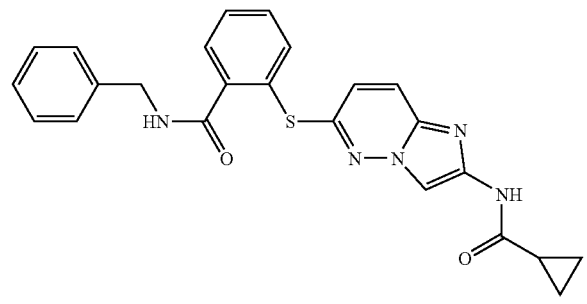

In the same manner as in Example 278 and using 2-({2-[(cyclopropylcarbonyl)amino]imidazo[1,2-b]pyridazin-6-yl}thio)benzoic acid (250 mg, 0.71 mmol), benzylamine (212 mg, 2.0 mmol), O-(7-azabenzotriazol-1-yl)-N,N,N',N'-tetramethyluronium hexafluorophosphate (380 mg, 1.0 mmol), N,N-diisopropylethylamine (270 mg, 2.0 mmol) and N,N-dimethylformamide (7 mL) as starting materials, the title compound (280 mg, 89%) was obtained as a white solid.

$^1$H-NMR (DMSO-d$_6$, 300 MHz) δ 0.74-0.90 (4H, m), 1.90-2.01 (1H, m), 4.42 (2H, d, J=6.1 Hz), 6.96 (1H, d, J=9.5 Hz), 7.17-7.35 (4H, m), 7.43-7.52 (4H, m), 7.61 (1H, dd, J=7.0, 2.5 Hz), 7.88 (1H, d, J=9.5 Hz), 8.16 (1H, s), 9.04 (1H, t, J=5.9 Hz), 11.17 (1H, s).

Example 434

Production of 2-({2-[(cyclopropylcarbonyl)amino]imidazo[1,2-b]pyridazin-6-yl}thio)-N-[3-(trifluoromethyl)phenyl]benzamide

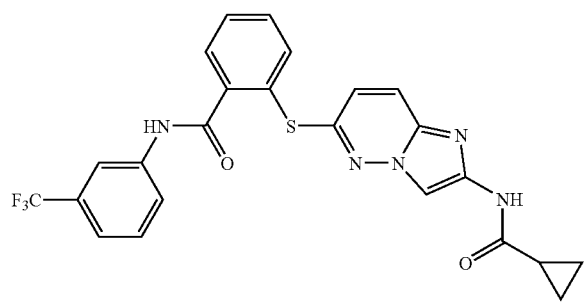

In the same manner as in Example 278 and using 2-({2-[(cyclopropylcarbonyl)amino]imidazo[1,2-b]pyridazin-6-yl}thio)benzoic acid (150 mg, 0.42 mmol), 3-(trifluoromethyl)aniline (191 mg, 1.2 mmol), O-(7-azabenzotriazol-1-yl)-N,N,N',N'-tetramethyluronium hexafluorophosphate (230 mg, 0.6 mmol), N,N-diisopropylethylamine (160 mg, 1.3 mmol) and N,N-dimethylformamide (5 mL) as starting materials, the title compound (208 mg, 99%) was obtained as a white solid.

$^1$H-NMR (DMSO-d$_6$, 300 MHz) δ 0.75-0.88 (4H, m), 1.87-1.97 (1H, m), 6.99 (1H, d, J=9.4 Hz), 7.40-7.46 (1H, m), 7.49-7.63 (4H, m), 7.72-7.78 (1H, m), 7.83-7.90 (2H, m), 8.09-8.16 (2H, m), 10.85 (1H, s), 11.14 (1H, s).

Example 435

Production of 2-({2-[(cyclopropylcarbonyl)amino]imidazo[1,2-b]pyridazin-6-yl}thio)-N-[4-(trifluoromethyl)phenyl]benzamide

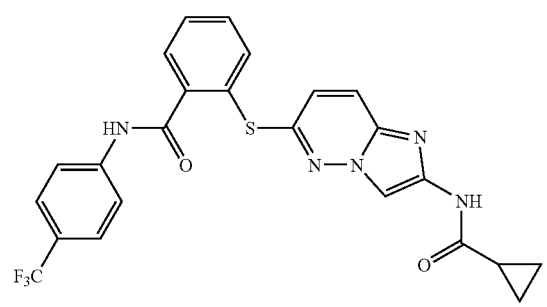

In the same manner as in Example 278 and using 2-({2-[(cyclopropylcarbonyl)amino]imidazo[1,2-b]pyridazin-6-yl}thio)benzoic acid (150 mg, 0.42 mmol), 4-(trifluoromethyl)aniline (191 mg, 1.2 mmol), O-(7-azabenzotriazol-1-yl)-N,N,N',N'-tetramethyluronium hexafluorophosphate (230 mg, 0.6 mmol), N,N-diisopropylethylamine (160 mg, 1.3 mmol) and N,N-dimethylformamide (5 mL) as starting materials, the title compound (155 mg, 74%) was obtained as a white solid.

$^1$H-NMR (DMSO-d$_6$, 300 MHz) δ 0.74-0.89 (4H, m), 1.86-1.98 (1H, m), 6.99 (1H, d, J=9.3 Hz), 7.49-7.62 (3H, m), 7.67 (2H, d, J=8.7 Hz), 7.72-7.77 (1H, m), 7.83-7.90 (3H, m), 8.13 (1H, s), 10.87 (1H, s), 11.14 (1H, s).

Example 436

Production of 2-({2-[(cyclopropylcarbonyl)amino]imidazo[1,2-b]pyridazin-6-yl}thio)-N-(1,3-dimethyl-1H-pyrazol-5-yl)benzamide

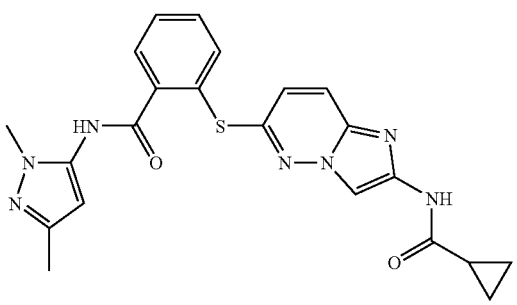

In the same manner as in Example 278 and using 2-({2-[(cyclopropylcarbonyl)amino]imidazo[1,2-b]pyridazin-6-yl}thio)benzoic acid (150 mg, 0.42 mmol), 1,3-dimethyl-1H-pyrazol-5-amine (130 mg, 1.2 mmol), O-(7-azabenzotriazol-1-yl)-N,N,N',N'-tetramethyluronium hexafluorophosphate (230 mg, 0.6 mmol), N,N-diisopropylethylamine (160 mg, 1.3 mmol) and N,N-dimethylformamide (5 mL) as starting materials, the title compound (130 mg, 70%) was obtained as a white solid.

¹H-NMR (DMSO-d₆, 300 MHz) δ 0.75-0.86 (4H, m), 1.89-1.99 (1H, m), 2.08 (3H, s), 3.59 (3H, s), 5.97 (1H, s), 7.00 (1H, d, J=9.8 Hz), 7.46-7.63 (3H, m), 7.71-7.79 (1H, m), 7.90 (1H, d, J=9.8 Hz), 8.15 (1H, s), 10.49 (1H, s), 11.17 (1H, s).

Example 437

Production of N-[4-({2-[(cyclopropylcarbonyl)amino]imidazo[1,2-b]pyridazin-6-yl}thio)phenyl]-5-methyl-1-phenyl-1H-pyrazole-3-carboxamide

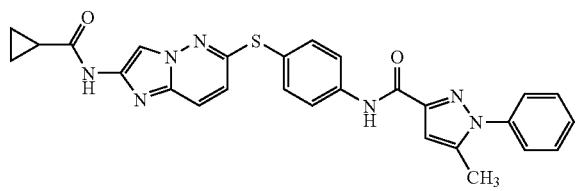

Using 5-methyl-1-phenyl-1H-pyrazole-3-carboxylic acid (186 mg, 0.92 mmol), tetrahydrofuran (3.0 mL), N,N-dimethylformamide (20 µL, 0.26 mmol), oxalyl chloride (80 µL, 0.92 mmol), N-{6-[(4-aminophenyl)thio]imidazo[1,2-b]pyridazin-2-yl}cyclopropanecarboxamide (200 mg, 0.62 mmol) and N,N-dimethylacetamide (4.0 mL), and in the same manner as in Example 249, the title compound (201 mg, 64%) was obtained as a white powder.

¹H-NMR (DMSO-d₆, 300 MHz) δ 0.79-0.85 (4H, m), 1.89-1.97 (1H, m), 2.31 (3H, s), 6.81 (1H, d, J=9.3 Hz), 6.89 (1H, s), 7.35-7.49 (5H, m), 7.57-7.61 (2H, m), 7.76-7.86 (3H, m), 8.09 (1H, s), 10.74 (1H, s), 11.14 (1H, s).

Example 438

Production of N-{6-[4-({[(phenylacetyl)amino]thiocarbonyl}amino)phenoxy]imidazo[1,2-b]pyridazin-2-yl}cyclopropanecarboxamide

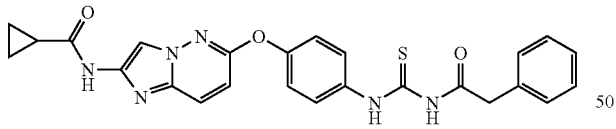

To a solution of phenylacetyl chloride (342 µL, 2.59 mmol) in acetonitrile (8.0 mL) was added potassium thiocyanate (0.31 g, 3.23 mmol), and the mixture was stirred at 50° C. for 1 hr. After cooling the mixture to room temperature, the solvent was evaporated under reduced pressure. Saturated brine was added to the residue, and the mixture was extracted with ethyl acetate, and dried over anhydrous magnesium sulfate. The solvent was evaporated under reduced pressure. Toluene/ethanol (2.0 mL/2.0 mL) was added to the residue, N-[6-(4-aminophenoxy)imidazo[1,2-b]pyridazin-2-yl]cyclopropanecarboxamide (200 mg, 0.65 mmol) was added to the mixture, and the mixture was stirred at room temperature for 1 hr. Saturated brine was added to the reaction mixture, and the mixture was extracted with ethyl acetate, washed with saturated brine, and dried over anhydrous magnesium sulfate.

The solvent was evaporated under reduced pressure, and the residue was purified by silica gel column chromatography (hexane/ethyl acetate=1/3) to give the title compound (164 mg, 51%) as white crystals.

¹H-NMR (DMSO-d₆, 300 MHz) δ 0.78-0.82 (4H, m), 1.87-1.95 (1H, m), 3.82 (2H, s), 7.05 (1H, d, J=9.6 Hz), 7.24-7.36 (7H, m), 7.66 (2H, d, J=9.0 Hz), 7.93 (1H, s), 8.02 (1H, d, J=9.6 Hz), 11.06 (1H, s), 11.71 (1H, s), 12.36 (1H, s).

Example 439

Production of N-[6-(4-{[(2E)-3-phenylprop-2-enoyl]amino}phenoxy)imidazo[1,2-b]pyridazin-2-yl]cyclopropanecarboxamide

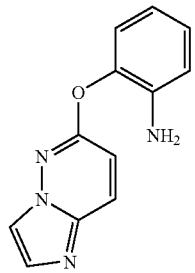

Using (2E)-3-phenylacrylic acid (135 mg, 0.91 mmol), tetrahydrofuran (3.0 mL), N,N-dimethylformamide (20 µL, 0.26 mmol), oxalyl chloride (80 µL, 0.91 mmol), N-[6-(4-aminophenoxy)imidazo[1,2-b]pyridazin-2-yl]cyclopropanecarboxamide (200 mg, 0.65 mmol) and N,N-dimethylacetamide (4.0 mL), and in the same manner as in Example 255, the title compound (133 mg, 47%) was obtained as a white powder.

¹H-NMR (DMSO-d₆, 300 MHz) δ 0.77-0.82 (4H, m), 1.86-1.96 (1H, m), 6.84 (1H, d, J=15.9 Hz), 7.04 (1H, d, J=9.8 Hz), 7.25 (2H, d, J=9.0 Hz), 7.38-7.50 (3H, m), 7.58-7.66 (3H, m), 7.77 (2H, d, J=9.0 Hz), 7.93 (1H, s), 8.02 (1H, d, J=9.8 Hz), 10.33 (1H, s), 11.07 (1H, s).

Example 440

Production of 2-(imidazo[1,2-b]pyridazin-6-yloxy)aniline

A mixture of 6-chloroimidazo[1,2-b]pyridazine (1536 mg, 10.0 mmol), 2-aminophenol (1419 mg, 13.0 mmol), potassium carbonate (4146 mg, 30.0 mmol) and N-methylpyrrolidone (10 mL) was stirred at 120° C. for 3 days. The reaction mixture was diluted with 1N aqueous sodium hydroxide solution and extracted with ethyl acetate. The organic layer was concentrated under reduced pressure, and the residue was purified by NH silica gel column chromatography (hexane/ethyl acetate=70/30→0/100). The objective fraction was concentrated under reduced pressure, and the residue was purified by silica gel column chromatography (ethyl acetate/methanol=100/0→75/25), and precipitated from diisopropyl ether to give the title compound (307 mg, 1.4 mmol, yield 14%) as a pale-brown solid.

$^1$H-NMR (DMSO-$d_6$, 300 MHz) δ 5.08 (2H, s), 6.57 (1H, td, J=7.6, 1.6 Hz), 6.81 (1H, dd, J=7.9, 1.7 Hz), 6.95-7.04 (2H, m), 7.04 (1H, d, J=9.9 Hz), 7.61 (1H, d, J=0.9 Hz), 8.02 (1H, s), 8.11 (1H, d, J=9.9 Hz).

Example 441

Production of methyl 2-(imidazo[1,2-b]pyridazin-6-ylthio)benzoate

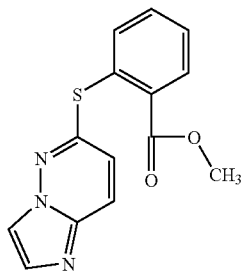

A mixture of 6-chloroimidazo[1,2-b]pyridazine (1536 mg, 10.0 mmol), methyl 2-mercaptobenzoate (1.788 mL, 13.0 mmol), potassium carbonate (4146 mg, 30.0 mmol) and N,N-dimethylformamide (20 mL) was stirred at 70° C. for 18 hr. To the reaction mixture was added methyl 2-mercaptobenzoate (0.963 mL, 7.0 mmol), and the mixture was stirred at 70° C. for 6 hr. The reaction mixture was concentrated under reduced pressure, the residue was diluted with water, and extracted with ethyl acetate. The organic layer was washed with water and concentrated under reduced pressure. The residue was purified by NH silica gel column chromatography (hexane/ethyl acetate=90/10→20/80) and precipitated from diisopropyl ether to give the title compound (663 mg, 2.3 mmol, yield 23%) as a white solid.

$^1$H-NMR (DMSO-$d_6$, 300 MHz) δ 3.83 (3H, s), 7.14 (1H, d, J=9.5 Hz), 7.37 (1H, dd, J=7.7, 1.0 Hz), 7.47 (1H, td, J=7.4, 1.4 Hz), 7.55 (1H, td, J=7.7, 1.5 Hz), 7.80 (1H, d, J=1.2 Hz), 7.95 (1H, dd, J=7.7, 1.4 Hz), 8.10 (1H, dd, J=9.5, 0.6 Hz), 8.29 (1H, t, J=0.9 Hz).

Example 442

Production of N-[2-(imidazo[1,2-b]pyridazin-6-yloxy)phenyl]-N'-phenylurea

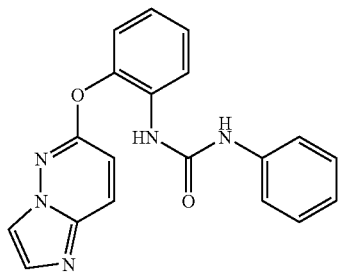

To a solution of 2-(imidazo[1,2-b]pyridazin-6-yloxy) aniline (90 mg, 0.40 mmol) and triethylamine (0.011 mL, 0.08 mmol) in tetrahydrofuran (20 mL) was added phenyl isocyanate (0.061 mL, 0.56 mmol), and the mixture was stirred at room temperature for 18 hr. The reaction mixture was concentrated under reduced pressure, and the residue was recrystallized from methanol to give the title compound (99 mg, 0.29 mmol, yield 72%) as a white powder.

$^1$H-NMR (DMSO-$d_6$, 300 MHz) δ 6.92-7.00 (1H, m), 7.02-7.09 (1H, m), 7.17-7.30 (5H, m), 7.38-7.44 (2H, m), 7.66 (1H, d, J=6.9 Hz), 8.09 (1H, s), 8.20-8.28 (2H, m), 8.33 (1H, s), 9.04 (1H, s).

Example 443

Production of 2-(imidazo[1,2-b]pyridazin-6-ylthio)benzoic acid

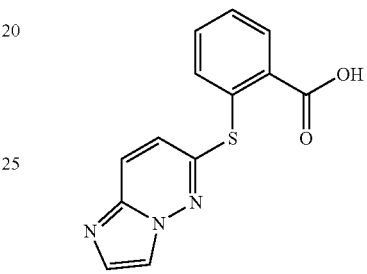

To a solution of methyl 2-(imidazo[1,2-b]pyridazin-6-ylthio)benzoate (619 mg, 2.17 mmol) in methanol (20 mL) was added 8N aqueous sodium hydroxide solution (1.00 mL), and the mixture was stirred at 70° C. for 18 hr. After the reaction mixture was allowed to cool to room temperature, 6N hydrochloric acid (1.33 mL) was added to the reaction mixture, and the precipitated precipitate was collected by filtration, and washed with water. The precipitate was suspended in methanol (10 mL), and the suspension was stirred with heating under reflux for 10 min. After the suspension was allowed to cool to room temperature, the precipitate was collected by filtration, washed with methanol, and dried under reduced pressure to give the title compound (496 mg, 1.83 mmol, yield 84%) as a white solid.

$^1$H-NMR (DMSO-$d_6$, 300 MHz) δ 7.15 (1H, d, J=9.5 Hz), 7.29 (1H, dd, J=7.9, 1.1 Hz), 7.42 (1H, td, J=7.5, 1.2 Hz), 7.50 (1H, td, J=7.6, 1.6 Hz), 7.80 (1H, d, J=1.2 Hz), 7.95 (1H, dd, J=7.5, 1.5 Hz), 8.10 (1H, d, J=9.5 Hz), 8.30 (1H, t, J=0.9 Hz), 13.39 (1H, br s).

Example 444

Production of 2-(imidazo[1,2-b]pyridazin-6-ylthio)-N-phenylbenzamide

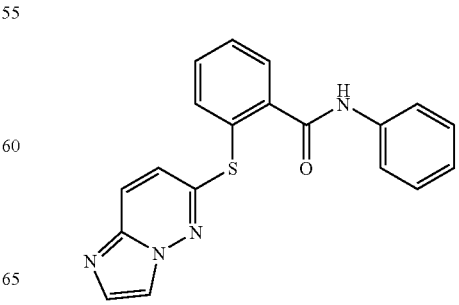

To a mixture of 2-(imidazo[1,2-b]pyridazin-6-ylthio)benzoic acid (109 mg, 0.40 mmol), aniline (75 mg, 0.81 mmol), 1-hydroxybenzotriazole hydrate (61 mg, 0.40 mmol) and N,N-dimethylformamide (5 mL) were added 1-[3-(dimethylamino)propyl]-3-ethylcarbodiimide hydrochloride (153 mg, 0.80 mmol) and triethylamine (0.167 mL, 1.20 mmol), and the mixture was stirred at room temperature for 18 hr. A 1N aqueous sodium hydroxide solution was added to the mixture and the mixture was extracted with ethyl acetate. The organic layer was concentrated under reduced pressure, and the residue was purified by silica gel column chromatography (ethyl acetate/methanol=100/0→80/20) and precipitated from ethyl acetate/diisopropyl ether to give the title compound (110 mg, 0.32 mmol, yield 79%) as a white solid.

$^1$H-NMR (DMSO-$d_6$, 300 MHz) δ 6.97 (1H, d, J=9.5 Hz), 7.08 (1H, t, J=7.4 Hz), 7.31 (2H, t, J=7.8 Hz), 7.51-7.76 (7H, m), 8.02 (1H, dd, J=9.5, 0.5 Hz), 8.18 (1H, s), 10.51 (1H, s).

Example 445

Production of N-[4-(imidazo[1,2-b]pyridazin-6-yloxy)phenyl]benzamide

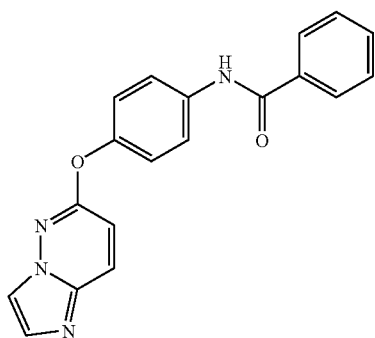

Using 4-(imidazo[1,2-b]pyridazin-6-yloxy)aniline (113 mg, 0.50 mmol), N-methylpyrrolidone (1 mL) and benzoyl chloride (0.116 mL, 1.00 mmol), and in the same manner as in Example 145, the title compound (144 mg, 0.44 mmol, yield 87%) was obtained.

$^1$H-NMR (DMSO-$d_6$, 300 MHz) δ 7.12 (1H, d, J=9.6 Hz), 7.29 (2H, d, J=8.9 Hz), 7.51-7.66 (3H, m), 7.65 (1H, d, J=1.2 Hz), 7.85 (2H, d, J=8.9 Hz), 7.94-8.01 (2H, m), 8.06 (1H, s), 8.17 (1H, dd, J=9.6, 0.3 Hz), 10.35 (1H, s).

Example 446

Production of methyl 3-(imidazo[1,2-b]pyridazin-6-yloxy)benzoate

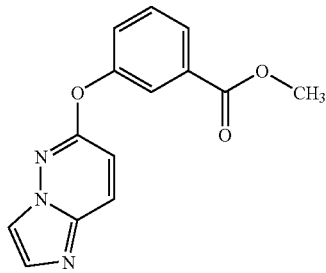

A mixture of 6-chloroimidazo[1,2-b]pyridazine (1536 mg, 10.0 mmol), methyl 3-hydroxybenzoate (1978 mg, 13.0 mmol), potassium carbonate (4146 mg, 30.0 mmol) and N-methylpyrrolidone (10 mL) was stirred at 120° C. for 18 hr. The reaction mixture was diluted with water and extracted with ethyl acetate. The organic layer was washed with water and concentrated under reduced pressure. The residue was purified by NH silica gel column chromatography (hexane/ethyl acetate=90/10→20/80). The objective fraction was concentrated under reduced pressure, and the residue was purified by silica gel column chromatography (hexane/ethyl acetate=60/40→0/100) and precipitated from diisopropyl ether to give the title compound (1722 mg, 6.4 mmol, yield 64%) as a white solid.

$^1$H-NMR (DMSO-$d_6$, 300 MHz) δ 3.87 (3H, s), 7.16 (1H, d, J=9.5 Hz), 7.60-7.68 (3H, m), 7.79-7.83 (1H, m), 7.84-7.93 (1H, m), 8.05 (1H, s), 8.19 (1H, d, J=9.5 Hz).

Example 447

Production of 3-(imidazo[1,2-b]pyridazin-6-yloxy)benzoic acid

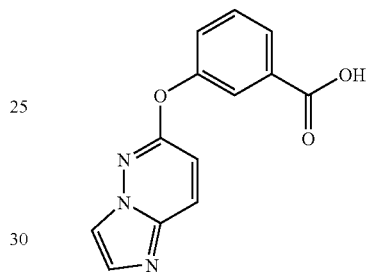

To a solution of methyl 3-(imidazo[1,2-b]pyridazin-6-yloxy)benzoate (1665 mg, 6.18 mmol) in methanol (30 mL) was added 8N aqueous sodium hydroxide solution (3.00 mL), and the mixture was stirred at room temperature for 18 hr and at 80° C. for 8 hr. After the reaction mixture was allowed to cool to room temperature, 6N hydrochloric acid (4.00 mL) was added to the mixture, and the mixture was concentrated under reduced pressure. Water (30 mL) was added to the residue, and the precipitate was collected by filtration and washed with water. The precipitate was suspended in methanol (10 mL) and the suspension was stirred with heating under reflux for 10 min. After the suspension was allowed to cool to room temperature, the precipitate was collected by filtration washed with methanol and dried under reduced pressure to give the title compound (1045 mg, 4.09 mmol, yield 66%) as a white solid.

$^1$H-NMR (DMSO-$d_6$, 300 MHz) δ 7.15 (1H, d, J=9.9 Hz), 7.54-7.68 (3H, m), 7.74-7.80 (1H, m), 7.82-7.91 (1H, m), 8.06 (1H, s), 8.19 (1H, d, J=9.9 Hz), 13.17 (1H, br s).

Example 448

Production of 3-(imidazo[1,2-b]pyridazin-6-yloxy)-N-phenylbenzamide

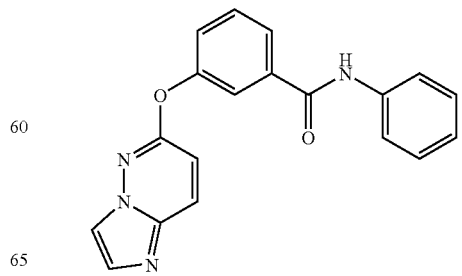

To a mixture of 3-(imidazo[1,2-b]pyridazin-6-yloxy)benzoic acid (128 mg, 0.50 mmol), aniline (56 mg, 0.60 mmol), 1-hydroxybenzotriazole hydrate (92 mg, 0.60 mmol) and N,N-dimethylformamide (5 mL) were added 1-[3-(dimethylamino)propyl]-3-ethylcarbodiimide hydrochloride (192 mg, 1.00 mmol) and triethylamine (0.209 mL, 1.50 mmol), and the mixture was stirred at room temperature for 18 hr. 1N Aqueous sodium hydroxide solution was added to the reaction mixture, and the mixture was extracted with ethyl acetate. The organic layer was washed with water and saturated brine and concentrated under reduced pressure. The residue was purified by silica gel column chromatography (ethyl acetate/methanol=100/0→75/25) and precipitated from ethyl acetate to give the title compound (122 mg, 0.37 mmol, yield 74%) as a white solid.

$^1$H-NMR (DMSO-$d_6$, 300 MHz) δ 7.11 (1H, t, J=7.4 Hz), 7.18 (1H, d, J=9.6 Hz), 7.35 (2H, t, J=7.9 Hz), 7.52-7.58 (1H, m), 7.63 (1H, d, J=8.1 Hz), 7.66 (1H, d, J=0.9 Hz), 7.73-7.80 (2H, m), 7.86-7.93 (2H, m), 8.07 (1H, s), 8.21 (1H, d, J=9.6 Hz), 10.28 (1H, s).

Example 449

Production of 3-(imidazo[1,2-b]pyridazin-6-yloxy)-N-[3-(trifluoromethyl)phenyl]benzamide

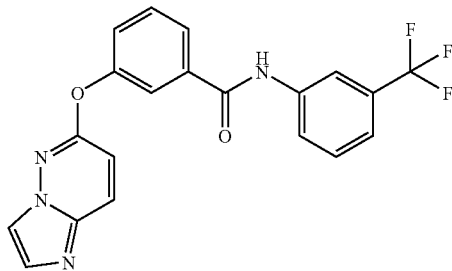

Using 3-(imidazo[1,2-b]pyridazin-6-yloxy)benzoic acid (128 mg, 0.50 mmol), 3-(trifluoromethyl)aniline (97 mg, 0.60 mmol), 1-hydroxybenzotriazole hydrate (92 mg, 0.60 mmol), N,N-dimethylformamide (5 mL), 1-[3-(dimethylamino)propyl]-3-ethylcarbodiimide hydrochloride (192 mg, 1.00 mmol) and triethylamine (0.209 mL, 1.50 mmol), and in the same manner as in Example 448, the title compound (114 mg, 0.29 mmol, yield 57%) was obtained.

$^1$H-NMR (DMSO-$d_6$, 300 MHz) δ 7.18 (1H, d, J=9.9 Hz), 7.47 (1H, d, J=7.8 Hz), 7.55-7.71 (4H, m), 7.89-7.95 (2H, m), 8.02-8.08 (2H, m), 8.19-8.25 (2H, m), 10.59 (1H, s).

Formulation Example 1

A pharmaceutical agent containing the compound of the present invention as an active ingredient can be produced, for example, according to the following formulation.

| 1. capsule | |
|---|---|
| (1) compound obtained in Example 1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended, granulated and the rest of (4) is added thereto. The whole mixture is sealed in a gelatin capsule.

| 2. tablet | |
|---|---|
| (1) compound obtained in Example 1 | 40 mg |
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4), and ½ of (5) are blended and granulated. The rest of (4) and (5) are added to the granules. The mixture is compression-formed into a tablet.

Formulation Example 2

The compound (50 mg) obtained Example 1 is dissolved in Japanese Pharmacopoeia distilled water for injection (50 mL), and the Japanese Pharmacopoeia distilled water for injection is added to 100 mL. This solution is filtrated under sterile conditions. The solution (1 mL) is taken, filled in a vial for injection under sterile conditions, freeze-dried and sealed.

Experimental Example 1

Cloning of Human Vascular Endothelial Growth Factor Receptor 2 (VEGFR2) Gene and Preparation of Recombinant Baculovirus Human vascular endothelial growth factor receptor 2 (hereinafter to be referred to as VEGFR2) gene was cloned by PCR using cDNA Libraries Human Placenta (Clontech) as a template. The primer used for PCR was prepared from base sequence (Genbank Accession AF035121) information of VEGFR2 gene by adding a base sequence encoding flag peptide and a recognition sequence of the restriction enzyme to a base sequence (2671-4374 of Genbank Accession AF035121) encoding the VEGFR2 intracellular domain region, so that the protein contains an N-terminal Flag tag. The primer base sequence is shown below.

VEGFR2-U:
(SEQ ID NO: 1)
5'-AATTAAGTCGACATGGACTACAAGGATGACGATGACAAGAAGCGGGC

CAATGGAGGGGAACTGAAGACA-3'
and

VEGFR2-L:
(SEQ ID NO: 2)
5'-AATTAAGCATGCTTAAACAGGAGGAGAGCTCAGTGTGGTCCC-3'

The base sequence of primer VEGFR2-U is shown in SEQUENCE LISTING SEQ ID NO: 1, and the base sequence of primer VEGFR2-L is shown in SEQUENCE LISTING SEQ ID NO: 2.

The PCR reaction was conducted using a KOD-plus kit (TOYOBO). The obtained PCR product was electrophoresed on agarose gel (1%), the DNA fragment amplified by PCR was recovered from the gel, and then digested with restriction enzymes Sal I and Sph I. The DNA treated with the restriction enzymes was electrophoresed on agarose gel (1%), and the obtained DNA fragment was recovered and ligated to plasmid pFASTBAC1 (Invitrogen) digested with restriction enzymes Sal I and Sph I to give expression plasmid pFB-VEGFR2. The base sequence of the insert fragment was confirmed and found to be identical with the base sequence (2671-4374 of Genbank Accession AF035121) of VEGFR2 intracellular domain. Furthermore, using BAC-TO-BAC Baculovirus Expression System (Invitrogen), virus stock BAC-VEGFR2 of recombinant baculovirus was prepared.

Experimental Example 2

Preparation of Vascular Endothelial Growth Factor Receptor 2 (VEGFR2) Intracellular Domain Protein SF-21 cells were sown at $1 \times 10^6$ cells/mL to Sf-900II SFM medium (1 L, Invitrogen) containing 10% fetal bovine serum (trace), 50 mg/L Gentamicin (Invitrogen) and 0.1% Pluronic F-68 (Invitrogen), and shaking culture was performed using a 2 L volume Erlenmeyer flask at 27° C., 100 rpm. After culturing for 24 hrs, recombinant baculovirus BAC-VEGFR2 (13.4 mL) was added to the mixture, and the mixture was further cultured for 3 days. The culture medium was centrifuged at 2,000 rpm for 5 min to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The ruptured medium was clarified by centrifugation at 40,000 rpm for 30 min and filtered with a 0.45 μm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 μg/mL of FLAG peptide. The eluate was concentrated with Vivaspin 20 (Vivascience) having a molecular weight cut off of 30K. The buffer of this concentrate was exchanged using NAP™ 25 column (Amersham Bioscience) equilibrated with buffer A. The fractions containing intracellular domain protein of VEGFR2 were collected, glycerol was added to the final concentration of 50% and cryopreserved at −80° C.

Experimental Example 3

Cloning of Human BRAF (B-Raf) Gene and Preparation of Recombinant Baculovirus

Human BRAF gene was cloned by PCR using human Testis cDNA library (Clontech) as a template. The primer used for PCR was prepared from base sequence (Genbank Accession NM_004333) information of BRAF gene by adding a base sequence encoding flag peptide and a recognition sequence of the restriction enzyme to area encoding the BRAF kinase domain region, so that the protein contains an N-terminal Flag. The primer base sequence is shown below.

BRAF-U:
(SEQ ID NO: 3)
5'-AAAGAATTCACCATGGACTACAAGGACGACGATGACAAGACCCCCC
CTGCCTCATTACCTGGCT-3'
and

BRAF-L:
(SEQ ID NO: 4)
5'-AAAAGTCGACTCAGTGGACAGGAAACGCACCATAT-3'

The PCR reaction was conducted using Pyrobest (Takara Shuzo Co., Ltd). The obtained PCR product was electrophoresed on agarose gel (1%), the DNA fragment amplified by PCR was recovered from the gel, and then digested with restriction enzymes EcoRI and SalI. The DNA treated with the restriction enzymes was electrophoresed on agarose gel (1%), and the obtained DNA fragment was recovered and ligated to plasmid pFASTBAC1 (Invitrogen) digested with restriction enzymes EcoRI and SalI to give expression plasmid pFB-BRAF, and the base sequence of the insert fragment was confirmed. In addition, mutation was introduced into V600E using a Quick change Site Directed Mutagenesis kit (Stratagene). The nucleotide sequences of the primers used are shown in the following.

V600E-U:
5'-GGTCTAGCTACAGAGAAATCTCGATGGAG-3'  (SEQ ID NO: 5)
and

V600E-L:
5'-CTCCATCGAGATTTCTCTGTAGCTAGACC-3'  (SEQ ID NO: 6)

The obtained plasmid was sequenced to confirm the introduction of mutation into V600E. The plasmid was digested with restriction enzymes EcoRI and SalI, DNA was electrophoresed on agarose gel (1%), and the obtained DNA fragment was recovered and ligated to plasmid pFASTBAC1 (Invitrogen) digested with restriction enzymes EcoRI and SalI to give expression plasmid pFB-V600E.

Using BAC-TO-BAC Baculovirus Expression System (Invitrogen), virus stock BAC-V600E of recombinant baculovirus was prepared.

Experimental Example 4

Preparation of BRAF (V600E) Protein

SF-21 cells were sown at $1 \times 10^6$ cells/mL to Sf-900II SFM medium (1 L, Invitrogen) containing 10% fetal bovine serum (Trace), 50 mg/L Gentamicin (Invitrogen) and 0.1% Pluronic F-68 (Invitrogen), and shaking culture was performed using a 2 L volume Erlenmeyer flask at 27° C., 100 rpm. After culturing for 24 hrs, recombinant baculovirus BAC-V600E (13.4 mL) was added to the mixture, and the mixture was further cultured for 3 days. The culture medium was centrifuged at 2,000 rpm for 5 min to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The ruptured medium was clarified by centrifugation at 40,000 rpm for 30 min and filtered with a 0.45 μm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 μg/mL of FLAG peptide. The buffer of this concentrate was exchanged using NAP25 column (Amersham Bioscience) equilibrated with buffer A and the fractions were cryopreserved at −80° C.

Test Example 1

Determination of Vascular Endothelial Growth Factor Receptor 2 (VEGFR2) Kinase Inhibitory Activity A test compound dissolved in dimethyl sulfoxide (DMSO) was diluted with a buffer (50 mM Tris-HCl (pH 7.5), 5 mM $MgCl_2$, 5 mM $MnCl_2$, 2 mM dithiothreitol, 0.01% Tween-20). To this compound solution (5 μL) was added a buffer (10 μL) containing 50 ng/mL of VEGFR2 intracellular domain protein and 250 ng/mL of biotin labeled polypeptide biotinyl-poly-Glu:Tyr (4:1) (CIS bio International). To the obtained mixture was added a buffer (10 μL) containing ATP (25 μM), the mixture was allowed to react at 25° C. for 5 min and the reaction was quenched with 25 μL of a stop solution (100 mM EDTA disodium salt, 62.5 mM HEPES buffer (pH 7.4), 250 mM NaCl, 0.1% bovine serum albumin, 10 μg/mL AlphaScreen assay streptavidin donor beads (Streptavidin Donor beads: PerkinElmer), 10 μg/mL AlphaScreen assay anti-phosphotyrosine recognition antibody PY-100 binding acceptor beads (Anti-phosphotyrosine (P-Tyr-100) Acceptor beads: PerkinElmer)). The reaction solution was allowed to stand at 25° C. for 16 hrs, and the wells were counted using a plate reader Fusion™ (PerkinElmer). The kinase inhibitory rate (%) of the test compound was calculated by the following formula:

Inhibitory rate(%)=(1−(count of test compound−blank)÷(control−blank))×100

The count of the solution reacted without addition of the compound was used as a "control", and the count of the solution without the compound and ATP was used as a "blank". The inhibitory rate of the compounds of Examples 95, 97, 103, 108, 111, 114, 117, 127, 148, 149, 150, 161, 165, 173, 174, 180, 187, 208, 241, 243, 247, 254, 267, 287, 289, 298, 302, 314 and 317 at 1 μM was not less than 90%.

Test Example 2

Vascular Endothelial Cell Growth Inhibitory Test

Human umbilical vein-derived vascular endothelial cells (HUVEC purchased from KURABO INDUSTRIES LTD.) were cultured in an incubator at 37° C., 5% carbon dioxide in a vascular endothelial cell medium (Invitrogen) containing 5% bovine fetal serum and 2.5 ng/mL basic fibroblast growth factor. To be specific, HUVEC was suspended in a vascular endothelial cell medium containing the aforementioned 5% bovine fetal serum and plated on a 96 well flat bottom plate by 50 μL (3000 cells) each well. After culture overnight, various concentrations of the test substance and 120 ng/mL of vascular endothelial growth factor (VEGF) were dissolved in a vascular endothelial cell medium containing 5% bovine fetal serum and added to each well by 50 μL. After 5 days of culture, a XTT reagent (Wako Pure Chemical Industries, Ltd.) was added to each well by 10 μL, and the mixture was reacted in an incubator at 37° C., 5% carbon dioxide for 2-3 hr. The absorbance at 450 nm was measured by a microtiter plate reader and the cell growth inhibitory activity was determined. Using the absorbance with addition of a test substance at each concentration and based on the nonlinear least-squares analysis using a logistic curve of SAS system NLIN procedure, the concentration of the test substance ($IC_{50}$ value) necessary for showing 50% of the value obtained without addition of the test substance was calculated.

As a result, $IC_{50}$ value of the compounds of Examples 95, 97, 103, 108, 111, 114, 117, 127, 148, 149, 150, 161, 165, 173, 174, 180, 187, 208, 241, 243, 247, 254, 267, 287, 289, 298, 302, 314 and 317 was not more than 500 nM.

Test Example 3

Antitumor Test

Cancer cells are cultivated in an incubator at 37° C., 5% carbon dioxide in a culture medium containing 10% bovine fetal serum. The cells are isolated by a trypsin treatment, washed with HBSS (HANK's Balanced Saline Solution) and adjusted to cell density of $5\times10^7$ cells/mL with HBSS. The cell suspension (0.1 mL, $5\times10^6$ cells) is transplanted by subcutaneously injecting into the abdomen of 6-week-old female nude mice (BALB/c nu/nu, CLEA Japan, Inc.). When the tumor volume reached 100-200 $mm^3$, the mice are grouped, and orally administered with various doses of test substance for 14 consecutive days starting from the next day. The major axis length and minor axis length of the tumor are measured over time and the tumor volume is calculated from tumor volume=major axis length×minor axis length×minor axis length×0.5.

Test Example 4

Determination of Platelet-Derived Growth Factor Receptor α (PDGFRα) Kinase Inhibitory Activity A test compound dissolved in dimethyl sulfoxide (DMSO) was diluted with a buffer (50 mM Tris-HCl (pH 7.5), 5 mM $MgCl_2$, 5 mM $MnCl_2$, 2 mM dithiothreitol, 0.01% Tween-20). To this compound solution (5 μL) was added a buffer (10 μL) containing 125 ng/ml of PDGFRα intracellular domain protein (UPSTATE) and 250 ng/mL of biotin labeled polypeptide biotinyl-poly-Glu:Tyr (4:1) (CIS bio International). At 5 min after mixing kinase enzyme and the compound and biotin labeled polypeptide, to the obtained mixture was added a buffer (10 μL) containing ATP (25 μM), the mixture was allowed to react at 25° C. for 30 min and the reaction was quenched with 25 μL of a stop solution (100 mM EDTA disodium salt, 62.5 mM HEPES buffer (pH 7.4), 250 mM NaCl, 0.1% bovine serum albumin, 10 μg/mL AlphaScreen assay streptavidin donor beads (Streptavidin Donor beads: PerkinElmer), 10 μg/mL AlphaScreen assay anti-phosphotyrosine recognition antibody PT-66 binding acceptor beads (Anti-phosphotyrosine (P-Tyr-66) Acceptor beads: PerkinElmer)). The reaction solution was allowed to stand at 25° C. for 16 hrs, and the wells were counted using a plate reader Fusion™ (PerkinElmer). The kinase inhibitory rate (%) of the test compound was calculated by the following formula:

Inhibitory rate(%)=(1−(count of test compound−blank)÷(control−blank))×100

The count of the solution reacted without addition of the compound was used as a "control", and the count of the solution without the compound and ATP was used as a "blank".

The $IC_{50}$ value of the compounds of Examples 95, 97, 111, 148, 161, 165, 173, 174, 180, 187, 208, 241, 243, 247, 267, 287, 289, 298, 302, 314 and 317 was not more than 500 nM.

Test Example 5

Determination of Platelet-Derived Growth Factor Receptor β (PDGFRβ) Kinase Inhibitory Activity A test compound dissolved in dimethyl sulfoxide (DMSO) was diluted with a buffer (50 mM Tris-HCl (pH 7.5), 5 mM MgCl$_2$, 5 mM MnCl$_2$, 2 mM dithiothreitol, 0.01% Tween-20). To this compound solution (5 μL) was added a buffer (10 μL) containing 125 ng/ml of PDGFRβ intracellular domain protein (UPSTATE) and 250 ng/mL of biotin labeled polypeptide biotinyl-poly-Glu:Tyr (4:1) (CIS bio International). At 5 min after mixing kinase enzyme and the compound and biotin labeled polypeptide, to the obtained mixture was added a buffer (10 μL) containing ATP (25 μM), the mixture was allowed to react at 25° C. for 30 min and the reaction was quenched with 25 μL of a stop solution (100 mM EDTA disodium salt, 62.5 mM HEPES buffer (pH 7.4), 250 mM NaCl, 0.1% bovine serum albumin, 10 μg/mL AlphaScreen assay streptavidin donor beads (Streptavidin Donor Beads: PerkinElmer), 10 μg/mL AlphaScreen assay anti-phosphotyrosine recognition antibody PT-66 binding acceptor beads (Anti-phosphotyrosine (P-Tyr-66) Acceptor beads: PerkinElmer)). The reaction solution was allowed to stand at 25° C. for 16 hrs, and the wells were counted using a plate reader Fusion™ (PerkinElmer). The kinase inhibitory rate (%) of the test compound was calculated by the following formula:

Inhibitory rate(%)=(1−(count of test compound=blank)÷(control−blank))×100

The count of the solution reacted without addition of the compound was used as a "control", and the count of the solution without the compound and ATP was used as a "blank".

The IC$_{50}$ value of the compounds of Examples 97, 103, 111, 114, 117, 127, 148, 149, 150, 161, 165, 173, 174, 180, 187, 208, 241, 243, 247, 254, 267, 287, 289, 298, 302, 314 and 317 was not more than 500 nM.

Test Example 6

Determination of BRAF (V600E) Kinase Inhibitory Activity

A test compound (2.5 μl) dissolved in dimethyl sulfoxide (DMSO) was added to 37.5 μl of a reaction solution (25 mM HEPES (pH 7.5), 10 mM magnesium acetate, 1 mM dithiothreitol) containing BRAF (V600E) enzyme (30 ng) and recombinant type protein GST-MEK1 (K96R) 250 ng, and the mixture was incubated at room temperature for 10 min. ATP solution (10 μl) (2.5 μM ATP, 0.1 μCi [γ-$^{32}$P]ATP) was added to the obtained mixture, and the mixture was reacted at room temperature for 20 min. The reaction was quenched by adding 50 μL of ice-cooled 20% trichloroacetic acid (Wako Pure Chemical Industries, Ltd.). The reaction solution was allowed to stand at 4° C. for 30 min, and the acid-precipitable fraction was transferred to GF/C filter plate (Millipore Corporation) using cell harvester (PerkinElmer). The plate was dried at 45° C. for 60 min, and 40 μL of MicroScinti 0 (PerkinElmer) was added thereto. The radioactivity was measured using TopCount (PerkinElmer). The kinase inhibitory rate (%) of the test compound was calculated by the following formula:

Inhibitory rate(%)=(1−(count of test compound−blank)÷(control−blank))×100

The count of the solution reacted without addition of the compound was used as a "control", and the count of the solution without the compound and enzyme was used as a "blank". The inhibitory rate of the compounds of Examples 70, 319, 330, 398, 427 and 431 at 1 μM was not less than 90%.

SEQUENCE LISTING free text

[SEQ ID NO: 1]
Designed oligonucleotide primer to amplify DNA encoding human VEGFR2
[SEQ ID NO: 2]
Designed oligonucleotide primer to amplify DNA encoding human VEGFR2
[SEQ ID NO: 3]
Designed oligonucleotide primer to amplify DNA encoding human BRAF
[SEQ ID NO: 4]
Designed oligonucleotide primer to amplify DNA encoding human BARF
[SEQ ID NO: 5]
Designed oligonucleotide primer to introduce V600E mutation
[SEQ ID NO: 6]
Designed oligonucleotide primer to introduce V600E mutation

Industrial Applicability

The compounds (I)-(IV), a salt thereof and a prodrug thereof of the present invention show superior inhibitory activity on kinases such as vascular endothelial growth factor receptor and the like. Therefore, a clinically useful agent for the prophylaxis or treatment of diseases related to the action of vascular endothelial growth factor in the living body (e.g., cancer etc.) can be provided. Moreover, since compounds (I)-(IV), a salt thereof and a prodrug thereof of the present invention are also superior in efficacy expression, pharmacokinetics, solubility, interaction with other pharmaceutical products, safety and stability, they are useful as pharmaceutical agents.

This application is based on patent application Nos. 2006-213981, 2006-331230 and 2007-144072 filed in Japan, the contents of which are incorporated in full herein by this reference.

The invention claimed is:
1. A compound represented by the formula (II):

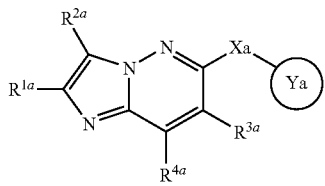

wherein
ring Ya is
(1) $C_{6-10}$ aryl optionally substituted by 1 to 3 substituents selected from
   (a) a halogen atom,
   (b) $C_{1-4}$ alkyl,
   (c) $C_{1-4}$ alkoxy,
   (d) amino optionally substituted by the substituents selected from
      (i) $C_{1-4}$ alkyl optionally substituted by a 5-membered aromatic heterocyclic group optionally substituted by 1 to 3 $C_{1-4}$ alkyl,
      (ii) $C_{1-4}$ alkyl-carbonyl optionally substituted by 1 to 3 substituents selected from
         (i') hydroxy,
         (ii') $C_{1-4}$ alkylsulfonyl, and
         (iii') a 6-membered aromatic heterocyclic group,
      (iii) $C_{2-4}$ alkenyl-carbonyl optionally substituted by $C_{6-10}$ aryl,
      (iv) $C_{2-4}$ alkynyl-carbonyl optionally substituted by $C_{6-10}$ aryl,
      (v) $C_{3-6}$ cycloalkyl-carbonyl,
      (vi) $C_{3-6}$ cycloalkenyl-carbonyl,
      (vii) $C_{6-10}$ aryl-carbonyl optionally substituted by 1 to 3 substituents selected from
         (i') a halogen atom,
         (ii') $C_{1-4}$ alkyl optionally substituted by 1 to 3 substituents selected from a halogen atom, cyano, hydroxy and $C_{3-6}$ cycloalkyl,
         (iii') $C_{3-6}$ cycloalkyl optionally substituted by cyano,
         (iv') $C_{1-4}$ alkoxy optionally substituted by 1 to 5 halogen atoms,
         (v') $C_{1-4}$ alkoxy-carbonyl, and
         (vi') a 5- or 6-membered heterocyclic group optionally substituted by cyano or oxo,
      (viii) 5- or 6-membered heterocyclyl-carbonyl containing, as ring-constituting atom, 1 to 3 heteroatoms selected from oxygen atom, sulfur atom and nitrogen atom besides carbon atoms, which is optionally substituted by 1 to 3 substituents selected from
         (i') a halogen atom,
         (ii') $C_{1-4}$ alkyl optionally substituted by 1 to 3 substituents selected from a halogen atom, cyano, hydroxy and $C_{1-4}$ alkoxy,
         (iii') $C_{6-10}$ aryl,
         (iv') $C_{6-10}$ aryl-$C_{1-4}$ alkyl,
         (v') $C_{1-4}$ alkoxy optionally substituted by $C_{1-4}$ alkoxy,
         (vi') $C_{1-4}$ alkylsulfonyl,
         (vii') $C_{1-4}$ alkyl-carbonyl, and
         (viii') oxo,
      (ix) aromatic fused heterocyclyl-carbonyl,
      (x) $C_{1-4}$ alkyl-aminocarbonyl,
      (xi) $C_{6-10}$ aryl-aminocarbonyl optionally substituted by $C_{1-4}$ alkyl optionally substituted by 1 to 3 halogen atoms,
      (xii) $C_{1-4}$ alkoxy-aminocarbonyl,
      (xiii) 5-membered heterocyclyl-aminocarbonyl optionally substituted by 1 to 3 substituents selected from $C_{1-4}$ alkyl and $C_{6-10}$ aryl, and
      (xiv) 5-membered aromatic heterocyclyl-sulfonyl optionally substituted by 1 to 3 $C_{1-4}$ alkyl,
   (e) $C_{1-4}$ alkyl-aminocarbonyl optionally having $C_{6-10}$ aryl,
   (f) 5-membered heterocyclyl-aminocarbonyl optionally substituted by 1 to 3 substituents selected from $C_{1-4}$ alkyl and $C_{6-10}$ aryl,
   (g) $C_{6-10}$ aryl-aminocarbonyl optionally substituted by $C_{1-4}$ alkyl optionally substituted by 1 to 3 substituents selected from a halogen atom and cyano,
   (h) carboxy, and
   (i) nitro,
(2) monocyclic aromatic heterocycle optionally substituted by 1 to 3 substituents selected from
   (a) a halogen atom, and
   (b) $C_{6-10}$ aryl-carbonylamino optionally substituted by $C_{1-4}$ alkyl optionally substituted by 1 to 3 halogen atoms, or
(3) fused aromatic heterocycle optionally substituted by 1 to 3 substituents selected from
   (a) $C_{1-4}$ alkyl, and
   (b) $C_{6-10}$ arylamino optionally substituted by $C_{1-4}$ alkyl optionally substituted by 1 to 3 halogen atoms;
Xa is —O—, —S—, —S(O)—, —S(O)$_2$— or —NH—;
$R^{1a}$ is
(1) amino,
(2) $C_{1-4}$ alkyl-carbonylamino optionally substituted by 1 to 3 substituents selected from
   (a) a halogen atom,
   (b) hydroxy,
   (c) $C_{1-4}$ alkoxy,
   (d) $C_{1-4}$ alkyl-carbonyloxy,
   (e) $C_{1-4}$ alkylamino,
   (f) di-$C_{1-4}$ alkylamino,
   (g) $C_{1-4}$ alkylsulfonyl, and
   (h) a 6-membered heterocyclic group optionally having 1 to 3 $C_{1-4}$ alkyl,
(3) $C_{2-4}$ alkenyl-carbonylamino optionally having $C_{1-4}$ alkoxy,
(4) $C_{2-4}$ alkynyl-carbonylamino,
(5) $C_{3-6}$ cycloalkyl-carbonylamino optionally substituted by 1 to 4 substituents selected from
   (a) a halogen atom,
   (b) hydroxy,
   (c) $C_{1-4}$ alkyl optionally having hydroxy,
   (d) $C_{1-4}$ alkoxy,
   (e) $C_{1-4}$ alkoxy-carbonyl, and
   (f) $C_{1-4}$ alkyl-carbonyloxy,
(6) $C_{3-6}$ cycloalkyl-$C_{1-4}$ alkyl-carbonylamino,
(7) 6-membered heterocyclyl-carbonylamino optionally substituted by 1 to 3 substituents selected from
   (a) a halogen atom,
   (b) cyano, and
   (c) $C_{1-4}$ alkyl optionally having 1 to 3 halogen atoms, (8) aminocarbonylamino optionally substituted by 1 or 2 substituents selected from
(a) $C_{1-4}$ alkyl optionally having 1 to 3 $C_{1-4}$ alkoxy optionally having 1 to 3 hydroxy, and
(b) $C_{1-4}$ alkoxy,
(9) $C_{1-4}$ alkoxy-carbonylamino optionally substituted by 1 to 3 halogen atoms,
(10) $C_{1-4}$ alkylsulfonylamino,
(11) $C_{3-6}$ cycloalkylsulfonylamino,
(12) $C_{6-10}$ arylamino, or
(13) heterocyclylamino optionally substituted by 1 to 3 substituents selected from
(a) a halogen atom, and
(b) $C_{1-4}$ alkylamino;
$R^{2a}$ is a hydrogen atom;
$R^{3a}$ is a hydrogen atom;
$R^{4a}$ is a hydrogen atom;
provided that
methyl [6-(phenylthio)imidazo[1,2-b]pyridazin-2-yl]carbamate and
methyl [6-(phenylsulfinyl)imidazo[1,2-b]pyridazin-2-yl]carbamate are excluded, or a salt thereof.

2. A compound selected from the group consisting of:
N-[2-chloro-5-({2-[(cyclopropylcarbonyl)amino]imidazo[1,2-b]pyridazin-6-yl}oxy)phenyl]-1,3-dimethyl-1H-pyrazole-5-carboxamide;
N-[3-({2-[(cyclopropylcarbonyl)amino]imidazo[1,2-b]pyridazin-6-yl}oxy)phenyl]-2,4-dimethyl-1,3-thiazole-5-carboxamide;
N-[3-({2-[(cyclopropylcarbonyl)amino]imidazo[1,2-b]pyridazin-6-yl}oxy)phenyl]-2,5-dimethyl-1,3-oxazole-4-carboxamide;
N-[3-({2-[(N,N-dimethylglycyl)amino]imidazo[1,2-b]pyridazin-6-yl}oxy)phenyl]-1,3-dimethyl-1H-pyrazole-5-carboxamide;
N-[3-({2-[(cyclopropylcarbonyl)amino]imidazo[1,2-b]pyridazin-6-yl}sulfanyl)phenyl]-1,3-dimethyl-1H-pyrazole-5-carboxamide;
N-[5-({2-[(cyclopropylcarbonyl)amino]imidazo[1,2-b]pyridazin-6-yl}oxy)-2-fluorophenyl]-1-ethyl-3-methyl-1H-pyrazole-4-carboxamide;
N-[3-({2-[(cyclopropylcarbonyl)amino]imidazo[1,2-b]pyridazin-6-yl}oxy)phenyl]benzamide;
N-[5-({2-[(cyclopropylcarbonyl)amino]imidazo[1,2-b]pyridazin-6-yl}oxy)-2-fluorophenyl]-1,3-dimethyl-1H-pyrazole-4-carboxamide;
N-[5-({2-[(cyclopropylcarbonyl)amino]imidazo[1,2-b]pyridazin-6-yl}oxy)-2-fluorophenyl]-1-ethyl-1H-pyrazole-5-carboxamide;
N-[5-({2-[(cyclopropylcarbonyl)amino]imidazo[1,2-b]pyridazin-6-yl}oxy)-2-fluorophenyl]-3-methoxy-1-methyl-1H-pyrazole-5-carboxamide;
N-[5-({2-[(cyclopropylcarbonyl)amino]imidazo[1,2-b]pyridazin-6-yl}oxy)-2-fluorophenyl]-3-ethyl-1-methyl-1H-pyrazole-5-carboxamide;
N-[2-chloro-5-({2-[(cyclopropylcarbonyl)amino]imidazo[1,2-b]pyridazin-6-yl}oxy)phenyl]-1-ethyl-3-methyl-1H-pyrazole-4-carboxamide;
N-[5-({2-[(cyclopropylcarbonyl)amino]imidazo[1,2-b]pyridazin-6-yl}oxy)-2-fluorophenyl]-1-methyl-1H-pyrazole-5-carboxamide;
N-[5-({2-[(cyclopropylcarbonyl)amino]imidazo[1,2-b]pyridazin-6-yl}oxy)-2-fluorophenyl]-2,4-dimethyl-1,3-oxazole-5-carboxamide;
N-[5-({2-[(cyclopropylcarbonyl)amino]imidazo[1,2-b]pyridazin-6-yl}oxy)-2-fluorophenyl]-2-ethyl-4-methyl-1,3-oxazole-5-carboxamide;
N-[3-({2-[(cyclopropylcarbonyl)amino]imidazo[1,2-b]pyridazin-6-yl}oxy)phenyl]-3-(trifluoromethyl)benzamide;
3-(1-cyano-1-methylethyl)-N-[5-({2-[(cyclopropylcarbonyl)amino]imidazo[1,2-b]pyridazin-6-yl}oxy)-2-methylphenyl]benzamide;
N-[3-({2-[(N,N-dimethylglycyl)amino]imidazo[1,2-b]pyridazin-6-yl}oxy)phenyl]-3-(trifluoromethyl)benzamide;
N-[3-({2-[(cyclopropylcarbonyl)amino]imidazo[1,2-b]pyridazin-6-yl}thio)phenyl]-3-(trifluoromethyl)benzamide; and
N-{6-[3-({[3-(trifluoromethyl)phenyl]carbamoyl}amino)phenoxy]imidazo[1,2-b]pyridazin-2-yl}cyclopropanecarboxamide, or a salt thereof.

3. A pharmaceutical agent comprising the compound of claim 1 or a prodrug thereof, and pharmacologically acceptable carrier.

4. The compound of claim 2, which is N-[2-chloro-5-({2-[(cyclopropylcarbonyl)amino]imidazo[1,2-b]pyridazin-6-yl}oxy)phenyl]-1,3-dimethyl-1H-pyrazole-5-carboxamide or a salt thereof.

5. The compound of claim 2, which is N-[3-({2-[(cyclopropylcarbonyl)amino]imidazo[1,2-b]pyridazin-6-yl}oxy)phenyl]-2,4-dimethyl-1,3-thiazole-5-carboxamide or a salt thereof.

6. The compound of claim 2, which is N-[3-({2-[(cyclopropylcarbonyl)amino]imidazo[1,2-b]pyridazin-6-yl}oxy)phenyl]-2,5-dimethyl-1,3-oxazole-4-carboxamide or a salt thereof.

7. The compound of claim 2, which is N-[3-({2-[(N,N-dimethylglycyl) amino]imidazo[1,2-b]pyridazin-6-yl}oxy)phenyl]-1,3-dimethyl-1H-pyrazole-5-carboxamide or a salt thereof.

8. The compound of claim 2, which is N-[3-({2-[(cyclopropylcarbonyl)amino]imidazo[1,2-b]pyridazin-6-yl}sulfanyl)phenyl]-1,3-dimethyl-1H-pyrazole-5-carboxamide or a salt thereof.

9. The compound of claim 2, which is N-[5-({2-[(cyclopropylcarbonyl)amino]imidazo[1,2-b]pyridazin-6-yl}oxy)-2-fluorophenyl]-1-ethyl-3-methyl-1H-pyrazole-4-carboxamide or a salt thereof.

10. The compound of claim 2, which is N-[3-({2-[(cyclopropylcarbonyl)amino]imidazo[1,2-b]pyridazin-6-yl}oxy)phenyl]benzamide or a salt thereof.

11. The compound of claim 2, which is N-[5-({2-[(cyclopropylcarbonyl)amino]imidazo[1,2-b]pyridazin-6-yl}oxy)-2-fluorophenyl]-1,3-dimethyl-1H-pyrazole-4-carboxamide or a salt thereof.

12. The compound of claim 2, which is N-[5-({2-[(cyclopropylcarbonyl)amino]imidazo[1,2-b]pyridazin-6-yl}oxy)-2-fluorophenyl]-1-ethyl-1H-pyrazole-5-carboxamide or a salt thereof.

13. The compound of claim 2, which is N-[5-({2-[(cyclopropylcarbonyl)amino]imidazo[1,2-b]pyridazin-6-yl}oxy)-2-fluorophenyl]-3-methoxy-1-methyl-1H-pyrazole-5-carboxamide or a salt thereof.

14. The compound of claim 2, which is N-[5-({2-[(cyclopropylcarbonyl)amino]imidazo[1,2-b]pyridazin-6-yl}oxy)-2-fluorophenyl]-3-ethyl-1-methyl-1H-pyrazole-5-carboxamide or a salt thereof.

15. The compound of claim 2, which is N-[2-chloro-5-({2-[(cyclopropylcarbonyl)amino]imidazo[1,2-b]pyridazin-6-yl}oxy)phenyl]-1-ethyl-3-methyl-1H-pyrazole-4-carboxamide or a salt thereof.

16. The compound of claim 2, which is N-[5-({2-[(cyclopropylcarbonyl)amino]imidazo[1,2-b]pyridazin-6-yl}oxy)-2-fluorophenyl]-1-methyl-1H-pyrazole-5-carboxamide or a salt thereof.

17. The compound of claim 2, which is N-[5-({2-[(cyclopropylcarbonyl)amino]imidazo[1,2-b]pyridazin-6-yl}oxy)-2-fluorophenyl]-2,4-dimethyl-1,3-oxazole-5-carboxamide or a salt thereof.

18. The compound of claim 2, which is N-[5-({2-[(cyclopropylcarbonyl)amino]imidazo[1,2-b]pyridazin-6-yl}oxy)-2-fluorophenyl]-2-ethyl-4-methyl-1,3-oxazole-5-carboxamide or a salt thereof.

19. The compound of claim 2, which is N-[3-({2-[(cyclopropylcarbonyl)amino]imidazo[1,2-b]pyridazin-6-yl}oxy)phenyl]-3-(trifluoromethyl)benzamide or a salt thereof.

20. The compound of claim 2, which is 3-(1-cyano-1-methylethyl)-N-[5-({2-[(cyclopropylcarbonyl)amino]imidazo[1,2-b]pyridazin-6-yl}oxy)-2-methylphenyl]benzamide or a salt thereof.

21. The compound of claim 2, which is N-[3-({2-[(N,N-dimethylglycyl)amino]imidazo[1,2-b]pyridazin-6-yl}oxy)phenyl]-3-(trifluoromethyl)benzamide or a salt thereof.

22. The compound of claim 2, which is N-[3-({2-[(cyclopropylcarbonyl)amino]imidazo[1,2-b]pyridazin-6-yl}thio)phenyl]-3-(trifluoromethyl)benzamide or a salt thereof.

23. The compound of claim 2, which is N-{6-[3-({[3-(trifluoromethyl)phenyl]carbamoyl}amino)phenoxy]imidazo[1,2-b]pyridazin-2-yl}cyclopropanecarboxamide or a salt thereof.

* * * * *